(12) United States Patent
Chestnut et al.

(10) Patent No.: US 10,745,695 B2
(45) Date of Patent: Aug. 18, 2020

(54) TAL-EFFECTOR ASSEMBLY PLATFORM, CUSTOMIZED SERVICES, KITS AND ASSAYS

(71) Applicants: LIFE TECHNOLOGIES CORPORATION, Carlsbad, CA (US); THERMO FISHER SCIENTIFIC GENEART GMBH, Regensburg (DE)

(72) Inventors: Jonathan Chestnut, Carlsbad, CA (US); Matthias Arnold, Regensburg (DE); Kevin Hoff, San Diego, CA (US)

(73) Assignees: LIFE TECHNOLOGIES CORPORATION, Carslbad, CA (US); THERMO FISHER SCIENTIFIC GENEART GMBH, Regensburg (DE)

( * ) Notice: Subject to any disclaimer, the term of this patent is extended or adjusted under 35 U.S.C. 154(b) by 0 days.

(21) Appl. No.: 15/951,938

(22) Filed: Apr. 12, 2018

(65) Prior Publication Data

US 2019/0112596 A1    Apr. 18, 2019

Related U.S. Application Data

(60) Division of application No. 14/811,363, filed on Jul. 28, 2015, now abandoned, which is a continuation of application No. 13/856,978, filed on Apr. 4, 2013, now abandoned.

(60) Provisional application No. 61/784,658, filed on Mar. 14, 2013, provisional application No. 61/644,975, filed on May 9, 2012, provisional application No. 61/620,228, filed on Apr. 4, 2012.

(51) Int. Cl.
| | |
|---|---|
| *C12N 15/10* | (2006.01) |
| *C12N 9/96* | (2006.01) |
| *C07K 14/195* | (2006.01) |
| *C12N 15/66* | (2006.01) |
| *C12N 9/90* | (2006.01) |

(52) U.S. Cl.
CPC ........ *C12N 15/1082* (2013.01); *C07K 14/195* (2013.01); *C12N 9/90* (2013.01); *C12N 9/96* (2013.01); *C12N 15/102* (2013.01); *C12N 15/1086* (2013.01); *C12N 15/1093* (2013.01); *C12N 15/66* (2013.01); *C12Y 599/01002* (2013.01)

(58) Field of Classification Search
None
See application file for complete search history.

(56) References Cited

U.S. PATENT DOCUMENTS

| | | | |
|---|---|---|---|
| 5,487,994 A | 1/1996 | Chandrasegaran | |
| 5,786,464 A | 7/1998 | Seed | |
| 5,888,732 A | 3/1999 | Hartley et al. | |
| 6,114,148 A | 9/2000 | Seed et al. | |
| 6,277,608 B1 | 8/2001 | Hartley et al. | |
| 7,119,255 B2 * | 10/2006 | Betts | C07K 14/415 800/287 |
| 7,176,029 B2 | 2/2007 | Bernard et al. | |
| 7,244,560 B2 | 7/2007 | Chestnut et al. | |
| 7,393,623 B2 | 7/2008 | Conroy et al. | |
| 7,670,823 B1 | 3/2010 | Hartley et al. | |
| 7,820,412 B2 | 10/2010 | Belshaw et al. | |
| 7,833,759 B2 | 11/2010 | Padgett et al. | |
| 7,838,210 B2 | 11/2010 | Ludwig et al. | |
| 8,030,066 B2 | 10/2011 | Chesnut et al. | |
| 8,034,598 B2 | 10/2011 | Miller | |
| 8,067,222 B2 | 11/2011 | Kerovuo et al. | |
| 2006/0127920 A1 | 6/2006 | Church et al. | |
| 2007/0141557 A1 | 6/2007 | Raab | |
| 2007/0231805 A1 | 10/2007 | Baynes et al. | |
| 2008/0145913 A1 | 6/2008 | Padgett | |
| 2008/0216185 A1 | 9/2008 | Chesnut et al. | |
| 2009/0324546 A1 | 12/2009 | Notka et al. | |
| 2010/0216648 A1 | 8/2010 | Staehler et al. | |
| 2010/0297642 A1 | 11/2010 | Liss et al. | |
| 2011/0119778 A1 | 5/2011 | Liss | |
| 2011/0124049 A1 | 5/2011 | Li et al. | |
| 2011/0145940 A1 * | 6/2011 | Voytas | C12N 15/102 800/13 |
| 2011/0301073 A1 | 12/2011 | Gregory et al. | |
| 2011/0311499 A1 | 12/2011 | Mougous et al. | |
| 2012/0270271 A1 | 10/2012 | Mougous | |

FOREIGN PATENT DOCUMENTS

| | | | |
|---|---|---|---|
| WO | WO2009/049359 | 4/2009 | |
| WO | WO2009/113794 | 9/2009 | |
| WO | WO2011/072246 | 6/2011 | |
| WO | WO-2011/102802 | 8/2011 | |
| WO | WO2011/146121 | 11/2011 | |
| WO | WO2011/154393 | 12/2011 | |
| WO | WO-2011154393 A1 * | 12/2011 | ......... A01K 67/0278 |
| WO | WO2013/152220 | 10/2013 | |

OTHER PUBLICATIONS

Aslanidis, et al., "Ligation-independent cloning of PCR products (LIC-PCR)" *Nucleic Acids Research*, vol. 18, No. 20, Oct. 25, 1990, 6069-6074.

Ayer, et al., "Mad proteins contain a dominant transcription repression domain", *Molecular and Cellular Biology*, vol. 16, No. 10, Oct. 1996, 5772-5781.

Babon, et al., "The use of resolvases T4 endonuclease VII and T7 endonuclease I in mutation detection", *Molecular Biotechnology*, vol. 23, No. 1, Jan. 2003, 73-81.

(Continued)

*Primary Examiner* — Tracy Vivlemore
*Assistant Examiner* — Sahana S Kaup
(74) *Attorney, Agent, or Firm* — Stephen G. Whiteside

(57) ABSTRACT

The invention generally relates to compositions and methods for designing and producing functional DNA binding effector molecules and associated customized services, tool kits and functional assays. In some aspects, the invention provides methods and tools for efficient assembly of customized TAL effector molecules. Furthermore, the invention relates to uses of TAL effector molecules and functional evaluation of such TAL by, for example, customized assays.

11 Claims, 74 Drawing Sheets

Specification includes a Sequence Listing.

(56) References Cited

OTHER PUBLICATIONS

Belfort, et al., "Homing endonucleases: keeping the house in order", *Nucleic Acids Research*, vol. 25, No. 17, Sep. 1, 1997, 3379-3388.
Bibikova, et al., "Stimulation of Homologous Recombination through Targeted Cleavage by Chimeric Nucleases", *Molecular and Cellular Biology*, vol. 21, No. 1, Jan. 2001, 289-297.
Boch, et al., "Breaking the Code of DNA Binding Specificity of TAL-Type III Effectors", *Science*, vol. 326, No. 5959, Oct. 29, 2009, 1509-1512.
Boch, et al., "Xanthomonas AvrBs3 Family-Type III Effectors: Discovery and Function", *Annual Reviews Phytopathology*, vol. 48, May 2010, 419-436.
Bultmann, et al., "Targeted transcriptional activation of silent oct4 pluripotency gene by combining desinger TALEs and inhibition of epigenetic modifiers" *Nucleic Acids Research*, vol. 40, No. 12, Mar. 2, 2012, 5368-5377.
Cermak, et al., "Efficient design and assembly of custom TALEN and other TAL effector-based constructs for DNA targeting", *Nucleic Acids Research*, vol. 39, No. 12, 2011, e82.
Christian, et al., "Targeting DNA Double-Strand Breaks with TAL Effector Nucleases", *Genetics*, vol. 186, No. 2, Oct. 1, 2010, 757-761.
Conrado, et al., "DNA-guided assembly of biosynthetic pathways promotes improved catalytic efficiency", *Nucleic Acids Research*, vol. 40, No. 4, Feb. 2012, 1879-1889.
Deng, et al., "Recognition of methylated DNA by TAL effectors", *Cell Research*, vol. 22, Sep. 4, 2012, 1502-1504.
Deng, et al., "Structural Basis for Sequence-Specific Recognition of DNA by TAL Effectors", *Science*, vol. 335, No. 6069, Feb. 10, 2012, 720-723.
Elliott, et al., "Intercellular trafficking and protein delivery by a herpesvirus structural protein", *Cell*, vol. 88, No. 2, Jan. 24, 1997, 223-233.
Engler, et al., "A One Pot, One Step, Precision Cloning Method with High Throughput Capability", *PLos One*, vol. 3, No. 11, Nov. 5, 2008, e3647 (9 pages).
Engler, et al., "Generation of Families of Construct Variants Using Golden Gate Shuffling", *Methods of Molecular Biology*, Chapter 11, vol. 729,, 2011, 167-181.
Engler, et al., "Golden Gate Shuffling: A One-Pot DNA Shuffling Method Based on Type IIs Restriction Enzymes", *PLos One*, May 14, 2009, e5553.
Fahraeus, et al., "Inhibition of pRb phosphorylation and cell-cycle progression by a 20-residue peptide from p16CDKN2/INK4A", *Current Biology*, vol. 6, No. 12, Dec. 1996, 84-91.
Hockemeyer, et al., "Efficient targeting of expressed and silent genes in human ESCs and iPSCs using zinc-finger nucleases", *Nature Biotechnology*, vol. 27, No. 9, Sep. 2009, 851-857.
Irion, et al., "Identification and targeting of the ROSA26 locus in human embryonic stem cells", *Nature Biotechnology*, vol. 25, No. 12, Dec. 2007, 1477-1482.
Kay, et al., "A Bacterial Effector Acts as a Plant Transcription Factor and Induces a Cell Size Regulator", *Science*, vol. 318, No. 5850, Oct. 26, 2007, 648-651.
Kay, et al., "How Xanthomonas type III effectors manipulate the host plant", *Current Opinion in Microbiology*, vol. 12, No. 1, Feb. 2009, 37-43.
Kim, et al., "Hybrid restriction enzymes: zinc finger fusions to Fok I cleavage domain", *Proceedings of the National Academy of Sciences*, vol. 93, No. 3, Feb. 6, 1996, 1156-1160.
Kotera, et al., "A high-throughput and single-tube recombination of crude PCR products using a DNA polymerase inhibitor and type IIS restricdtion enzyme", *Journal of Biotechnology*, vol. 137, 2008, 1-7.

Lackner, et al., "Complete Genome Sequence of Burkholderia rhizoxinica, an Endosymbiont of Rhizopus microspour", *Journal of Bacteriology*, vol. 193, No. 3, Feb. 2011, 783-784.
Li, et al., "Functional domains in Fok I restriction endonuclease", *Proceedings of the National Academy of Sciences*, vol. 89, No. 10, May 15, 1992, 4275-4279.
Lin, et al., "Identification, expression, and immunogenicity of Kaposi's sarcoma-associated herpesvirus-encoded small viral capsid antigen", *Journal of Virology*, vol. 71, No. 4, Apr. 1997, 3069-3076.
Lombardo, et al., "Site-specific integration and tailoring of cassette design for sustainable gene transfer", *Nature Methods*, vol. 8, No. 10, Oct. 2011, 861-869.
Margolin, et al., "Kruppel-associated boxes are potent transcriptional repression domains", *Proceedings of the National Academy of Sciences (PNAS)*, vol. 91, No. 10, May 10, 1994, 4509-4513.
Miller, et al., "A TALE nuclease architecture for efficient genome editing", *Nature Biotechnology*, vol. 29, No. 2, Feb. 2011, 143-148.
Morbitzer, et al., "Assembly of custom TALE-type DNA binding domains by modular cloning", *Nucleic Acids Research*, vol. 39, No. 13, Jul. 2011, 5790-5799.
Moscou, et al., "A Simple Cipher Governs DNA Recognition by TAL Effectors" *Science*, vol. 326, No. 5959, Oct. 29, 2009, 1501.
PCT/US2013/035316 "International Preliminary Report on Patentability and Written Opinion dated Oct. 7, 2014", dated Oct. 7, 2014, 9 Pages.
PCT/US2013/035316, "International Search Report and Written Opinion", dated Dec. 20, 2013, 1-13.
PCT/US2013/035316 "Partial International Search Report", dated Jun. 26, 2013, 1-3.
Roberts, et al., "REBASE: restriction enzymes and methyltransferases", *Nucleic Acids Research*, vol. 31, No. 1, Jan. 1, 2003, 418-420.
Romer, et al., "Plant Pathogen Recognition Mediated kby Promoter Activation of the Pepper Bs3 Resistance Gene", *Science*, vol. 318, 2007, 645-648.
Sakurai, "Efficient integration of transgenes into a defined locus in human embryonic stem cells", *Nucleic Acids Research*, vol. 38, No. 7, Apr. 2010, e96.
Sanjana, et al., "A transcription activator-like effector toolbox for genome engineering", *Nature Protocols*, vol. 7, No. 1, Jan. 2012, 171-192.
Sgouras, et al., "ERF: an ETS domain protein with strong transcriptional repressor activity, can suppress ets-associated tumorigenesis and is regulated by phosphorylation during cell cycle and mitogenic stimulation", *EMBO Journal*, vol. 14, No. 19, Oct. 2, 1995, 4781-4793.
Smith, et al., "Requirements for double-strand cleavage by chimeric restriction enzymes with zinc finger DNA-recognition domains", *Nucleic Acids Research*, vol. 28, No. 17, Sep. 1, 2000, 3361-3369.
Snowden, et al., "Gene-Specific Targeting of H3K9 Methylation Is Sufficient for Initiating Repression In Vivo", *Current Biology*, vol. 12, No. 24, Dec. 23, 2002, 2159-2166.
UNIPROT Consortium, "Sequence 771 AA".
Valton, et al., "Overcoming Transcription Activator-like Effector (TALE) DNA Binding Domain Sensitivity to Cytosine Methylation", *Journal of Biological Chemistry*, vol. 287, No. 46, Nov. 9, 2012, 38427-38432.
Weber, , "Assembly of Designer TAL Effectors by Golden Gate Cloning", *PLos One*, vol. 6, May 19, 2011, e19722.
Yin, et al., "Specific DNA-RNA Hybrid Recognition by TAL Effectors", *Cell Reports*, vol. 2, No. 4, Sep. 27, 2012, 707-713.
Zhang, et al., "Efficient construction of sequence-specific TAL effectors for modulating mammalian transcription", *Nature Biotechnology*, vol. 29, No. 2, Feb. 2011, 149-153.

* cited by examiner

FIG. 2B

```
  1 MDPIRSRTPS PARELLSGPQ PDGVQPTADR GVSPPAGGPL DGLPARRTMS
 51 RTRLPSPPAP SPAFSADSFS DLLRQFDPSL FNTSLFDSLP PFGAHHTEAA
101 TGEWDEVQSG LRAADAPPPT MRVAVTAARP PRAKPAPRRR AAQPSDASPA  1
151 AQVDLRTLGY SQQQEKIKP  KVRSTVAQHH EALVGHGFTH AHIVALSQHP
201 AALGTVAVKY QDMIAALPEA THEAIVGVGK QWSGARALIA LLTVAGELRG
251 PPLQLDTGQL LKIAKRGGVT AVEAVHAWRN ALTGAPLNLT PEQVVAIASN
301 IGGKQALETV QRLLPVLCQA HGLTPQQVVA IASHDGGKQA LETVQRLLPV
351 LCQAHGLTPE QVVAIASNIG GKQALETVQA LLPVLCQAHG LTPEQVVAIA
401 SHDGGKQALE TVQRLLPVLC QAHGLTPQQV VAIASHDGGK QALETVQRLL
451 PVLCQAHGLT PQQVVAIASH DGGKQALETV QRLLPVLCQA HGLTPQQVVA  2
501 IASNSGGKQA LETVQRLLPV LCQAHGLTPQ QVVAIASNSG GKQALETVQR
551 LLPVLCQAHG LTPQQVVAIA SNSGGKQALE TVQRLLPVLC QAHGLTPEQV
601 VAIASHDGGK QALETVQRLL PVLCQAHGLT PQQVVAIASN IGGKQALETV
651 QRLLPVLCQA HGLTPQQVVA IASNGGGRPA LESIVAQLSR PDPALAALTN
701 DHLVALACLG GRPALDAVKK GLPHAPALIK RTNRRIPERT SHRVADHAQV
751 VRVLGFFQCH SHPAQAFDDA MTQFGMSRHG LLQLFRRVGV TELEARSGTL  3
801 PPASQRWDRI LQASGMKRAK PSPTSTQTPD QASLHAFADS LERDLDAPSP
851 MHEGDQTRAS SRKRSRSDRA VTGPSAQQSF EVRVPEQRDA LHLPLLSWGV
901 KRPRTRIGGL LDPGTPMDAD LVASSTVVWE QDADPFAGTA DDFPAFNEEE
951 LAWLMELLPQ
```

FIG. 3A

```
   1 MGKPIPNPLL GLDSTGGMAP KKKRKVDGGV DLRTLGYSQQ QQEKIKPKVR
  51 STVAQHHEAL VGHGFTHAHI VALSQHPAAL GTVAVKYQDM IAALPEATHE
 101 AIVGVGKQWS GARALEALLT VAGELRGPPL QLDTGQLLKI AKRGGVTAVE
 151 AVHAWRNALT GAPLNLTPEQ VVAIASNIGG KQALETVQRL LPVLCQAHGL
 201 TPEQVVAIAS HDGGKQALET VQRLLPVLCQ AHGLTPEQVV AIASNIGGKQ
 251 ALETVQRLLP VLCQAHGLTP EQVVAIASHD GGKQALETVQ RLLPVLCQAH
 301 GLTPEQVVAI ASNGGKQAL ETVQRLLPVL CQAHGLTPEQ VVAIASNGGG
 351 KQALETVQRL LPVLCQAHGL TPEQVVAIAS NGGGKQALET VQRLLPVLCQ
 401 AHGLTPEQVV AIASNGGKQ VLCQAHGLTP EQVVAIASHD ETVQRLLPVL
 451 GGKQALETVQ RLLPVLCQAH GLTPEQVVAI ASNKGGKQAL ETVQRLLPVL
 501 CQAHGLTPEQ VVAIASNGGG KQALETVQRL LPVLCQAHGL TPEQVVAIAS
 551 NKGGKQALET VQRLLPVLCQ AHGLTPEQVV AIASNGGGKQ ALETVQRLLP
 601 VLCQAHGLTP EQVVAIASNG GGKQALETVQ RLLPVLCQAH GLTPEQVVAI
 651 ASHDGGKQAL ETVQRLLPVL CQAHGLTPEQ VVAIASNKGG KQALETVQRL
 701 LPVLCQAHGL TPEQVVAIAS NKGGKQALET VQRLLPVLCQ AHGLTPQQVV
 751 AIASNIGGRP ALESIVAQLS RPDPALAALT NDHLVALACL GGRPALDAVK
 801 KGLPHAPALI KRTNRRIPER TSHRVAGSQL VKSELEEKKS ELRHKLKYVP
 851 HEYIELIEIA RNSTQDRILE MKVMEFFMKV YGYRGKHLGG SRKPDGAIYT
 901 VGSPIDYGVI VDTKAYSGGY NLPIGQADEM QRYVEENQTR NKHINPNEWW
 951 KVYPSSVTEF KFLFVSGHFK GNYKAQLTRL NHITNCNGAV LSVEELLIGG
1001 EMIKAGTLTL EEVRRKFNNG EINF
```

FIG. 3B

SEQ ID NO: 1

CAGCTGGTGAAATCTGAGCTGGAGGAGAAGAAGTCTGAGCTGGAGGAGAAGAAGTCTGAGCTGGAGGAGAAGAAGTCTGAGCTGGATC
GAGATCGCCAGAAATAGCACCCAGGAGATCAATCCTGGAGATGAAGGTGATGAGTTCTTCATGAAGGTGTACGGCTACAGAGGAAAG
CACCTGGGAGGAGGCAGAAAACCTGACGGAGCCATTTATACAGTGGGCAGCCCTATCGATTATGGCGTGATCGTGGATACAAAGGCC
TACAGCGGAGGCTACAATCTGCCTATTGGACAGGCCGATGAGATCAGAGATACGTGGAGGAACCAGAGACCAGGAACAAGCACATC
AACCCTAACGAGTGGTGGAAGTGTACCCTTCTAGCGTGTACCCTAGCAACAAATTGTAATGGCGCCCGTGTCTGTGGAGGAGAATG
AAGGCCCAGCTGACCAGGCTGAACCTGACACTGACACTGGAGGAGGTGAGAAGAAAGTTCAACAACGGCGAGATCAACTTCTGA
ATTAAGGCCGGAACACTGACACTGGAGGAGGTGAGAAGAAAGTTCAACAACGGCGAGATCAACTTCTGA

SEQ ID NO: 2

CAGCTGGTGAAATCTGAGCTGGAGGAGAAGAAGTCTGAGCTGGAGGAGAAGAAGTCTGAGCTGGATC
GAGATTGCCAGAAATAGCACCCAGGAGATCAATCCTGGAGATGAAGGTGATGAGTTCTTCATGAAGGTGTACGGCTATAGAGGAGAG
CACCTGGGAGGAGGCAGAAAACCTGACGGAGCCATTTATACAGTGGGCAGCCCTATCGATTATGGCGTGATCGTGGATACAAAGGCC
TACAGCGGAGGCTACAATCTGCCTATTGGACAGGCCGATGAGATCAGAGATACGTGGAGGAACCAGAGACCAGGAACAAGCACATC
AACCCTAATGAGTGGTGGAAGTGTACCCTGAACAGAAAGACAAATTGTAATGGCGCCCGTGTCTGTGGAGGAGAATG
AAGGCCCAGCTGACCCGGCTGAACCTGACACTGGAGGAGGTGAGAAGAAAGTTCAACAACGGCGAGATCAACTTCTGA
ATTAAGGCCGGAACACTGACACTGGAGGAGGTGAGAAGAAAGTTCAACAACGGCGAGATCAACTTCTGA

SEQ ID NO: 3

CAGCTGGTGAAATCTGAGCTGGAGGAGAAGAAGTCTGAGCTGGAGGAGAAGAAGTCTGAGCTGGATC
GAGATTGCCAGAAATAGCACCCAGGAGATCAATCCTGGAGATGAAGGTGATGAGTTCTTCATGAAGGTGTACGGCTATAGAGGAGAG
CACCTGGGAGGAGGCAGAAAACCTGACGGAGCCATTTATACAGTGGGCAGCCCTATCGATTATGGCGTGATCGTGGATACAAAGGCC
TACAGCGGAGGCTACAATCTGCCTATTGGACAGGCCGATGAGATCAGAGATGAGAATCAGACCAGAGAACAGACAAGCACCTG
AACCCTAACGAATGAGTGGTGGAAGTGTACCCTAGCAGCGTGACCGAGTTCAAGTTTCTGTTTCTGTTTCTGTGGAGGAGAATG
AAGGCCCAGCTGACCAGGCTGAACCTGACACTGGAGGAGGTGAGAAGAAAGTTCAACAACGGCGAGATCAACTTCTGA
ATTAAGGCCGGAACACTGACACTGGAGGAGGTGAGAAGAAAGTTCAACAACGGCGAGATCAACTTCTGA

FIG. 6A

SEQ ID NO: 4

GCCCCTCCTACAGATGTGTCTCTGGGAGATGAGCTCCACCTGGAGAAGATGTGGCCATGGCCCACGCCGATGCCCTGGATGA
TTTTGATCTGGATATGCTGGGAGATGGCCGATTCTCCCTGGACCTGGATTTACACCTCACGATTCTGCCCCTTATGGAGCCCTGGATA
TGGCCGATTTTGAGTTCGAGCAGATGTTCACAGATGCCCTGGGCATCGACGAGTATGGCGGCTGA

SEQ ID NO: 5

CCTAAGAAAAAGCGGAAAGTGGAAGCCCTCTGGATCTGGCAGAGCCGATGCCCTGGATGATTTTGATCTGGATATGCTGGGAAGCGA
CGCCCTGGATGATTTCGATCTGGATATGCTCGGGATCTGGGATCTGACGCGCCCTGGATATGCTGGGATCTGGGATCTGACGCCCTGG
ATGATTTCGATCTGGACATGCTGATCAACAGCTGA

SEQ ID NO: 6

GACGACGCCAAGAGAGCCTGACAGCCTGGAGCAGAGAACACTGGTGACATTCAAGGATGTGTTCGTGGACTTCACCAGGGAGGAATGGAAA
CTGCTGGATACAGCCCAGCAGATCGTGTACAGAAATGTGGAGAACTACAAGAACCTGGTGTCTCTGGGCTACCAGCTGACA
AAGCCCTGATGTGATTCTGAGACTGGAGAAGGGCGAAGAACCTTGGCTGGTGAAAGAGAGATCCACTGA

FIG. 6B

MCS sequence

5'-CGTTTAAACAAGCTTGTCGACGGTACCGAATTCATCGATAGTACTCTCGAGGGATCCGAGCTCAAGATCT-3'
3'-GCAAATTTGTTCGAACAGCTGCCATGGCTTAAGTAGCTATCATGAGAGCTCCCTAGGCTCGAGTTCTAGA-3'

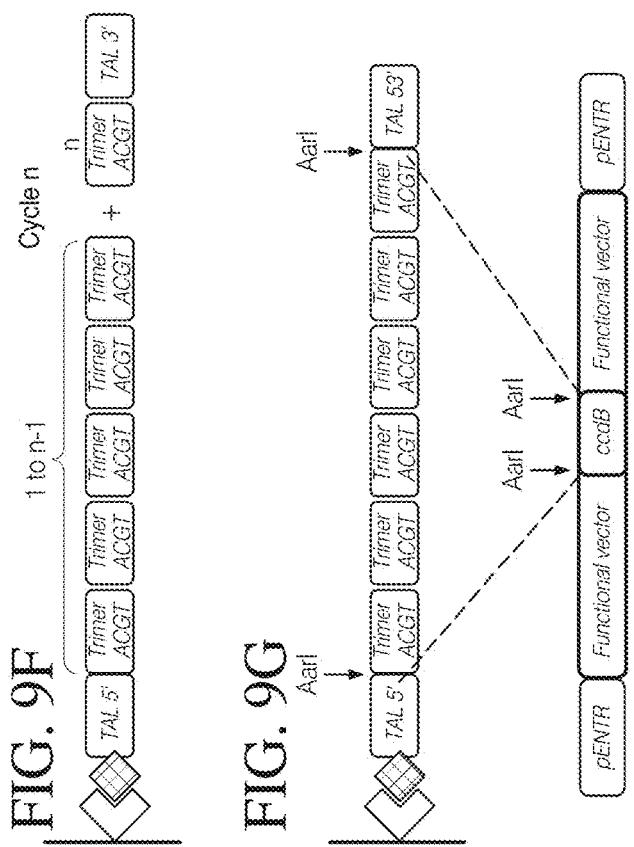
FIG. 9B
FIG. 9C
FIG. 9D
FIG. 9E
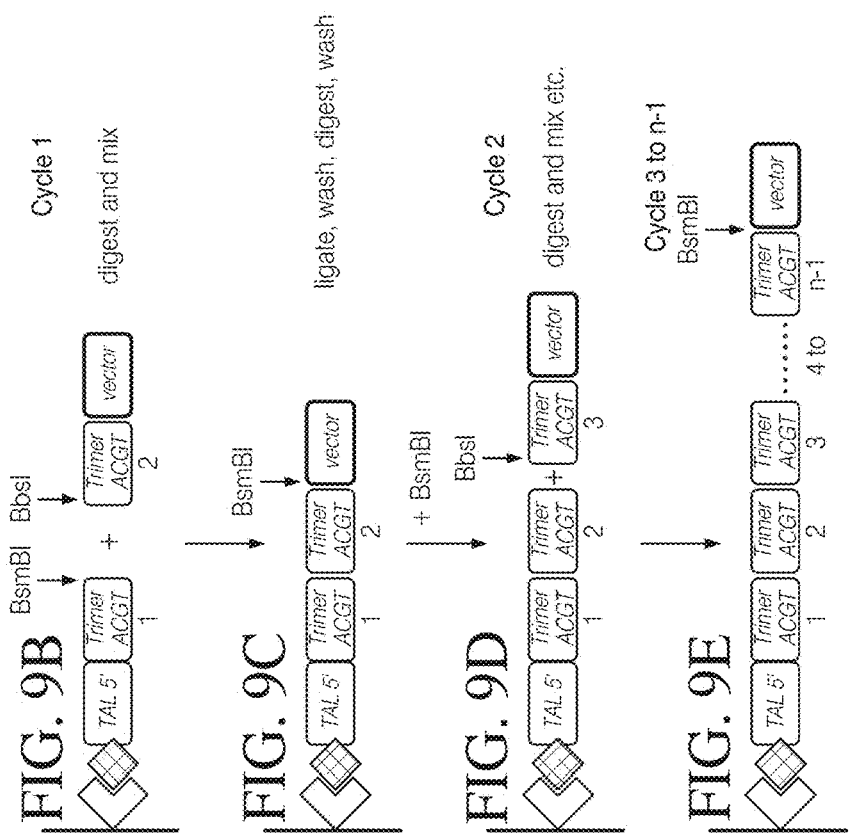
FIG. 9F
FIG. 9G

```
                                                                    NcoI
ccatggc ctg acc ccg gag  -  gcc agc  A   ggt  -  gcg ctg       gag acg  gtg  -  cag  gcc cat ggc
        L   T   P   E       A   S   N   G       A   L         E   T    V       Q    A   H   G
                                A                                   Esp3I ccatggc ctg acc ccg gag  -  gcc agc  T   ggt  -  gcg ctg       gag acg  gtg  -  cag  gcc cat ggc
        L   T   P   E       A   S   N   G       A   L         E   T    V       Q    A   H   G ccatggc ctg acc ccg gag  -  gcc agc  C   ggt  -  gcg ctg       gag acg  gtg  -  cag  gcc cat ggc
        L   T   P   E       A   S   H   G       A   L         E   T    V       Q    A   H   G ccatggc ctg acc ccg gag  -  gcc agc  G/A ggt  -  gcg ctg       gag acg  gtg  -  cag  gcc cat ggc
        L   T   P   E       A   S   N   G       A   L         E   T    V       Q    A   H   G
```

FIG. 12B

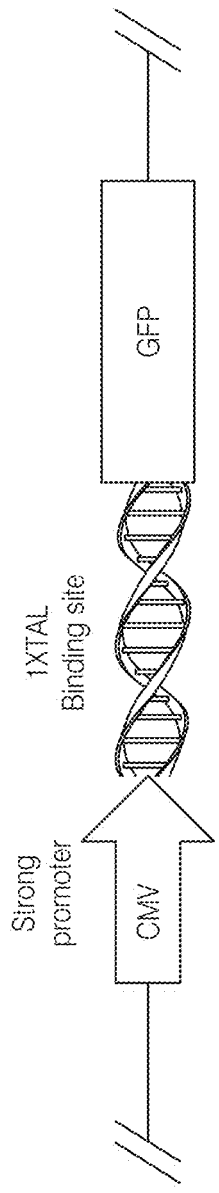
FIG. 16D
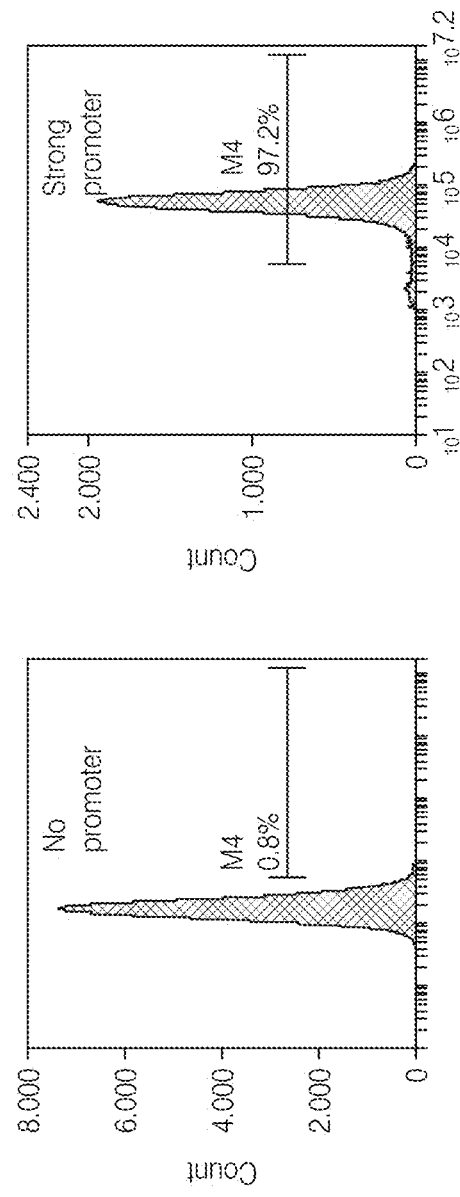
FIG. 16E
FIG. 16F

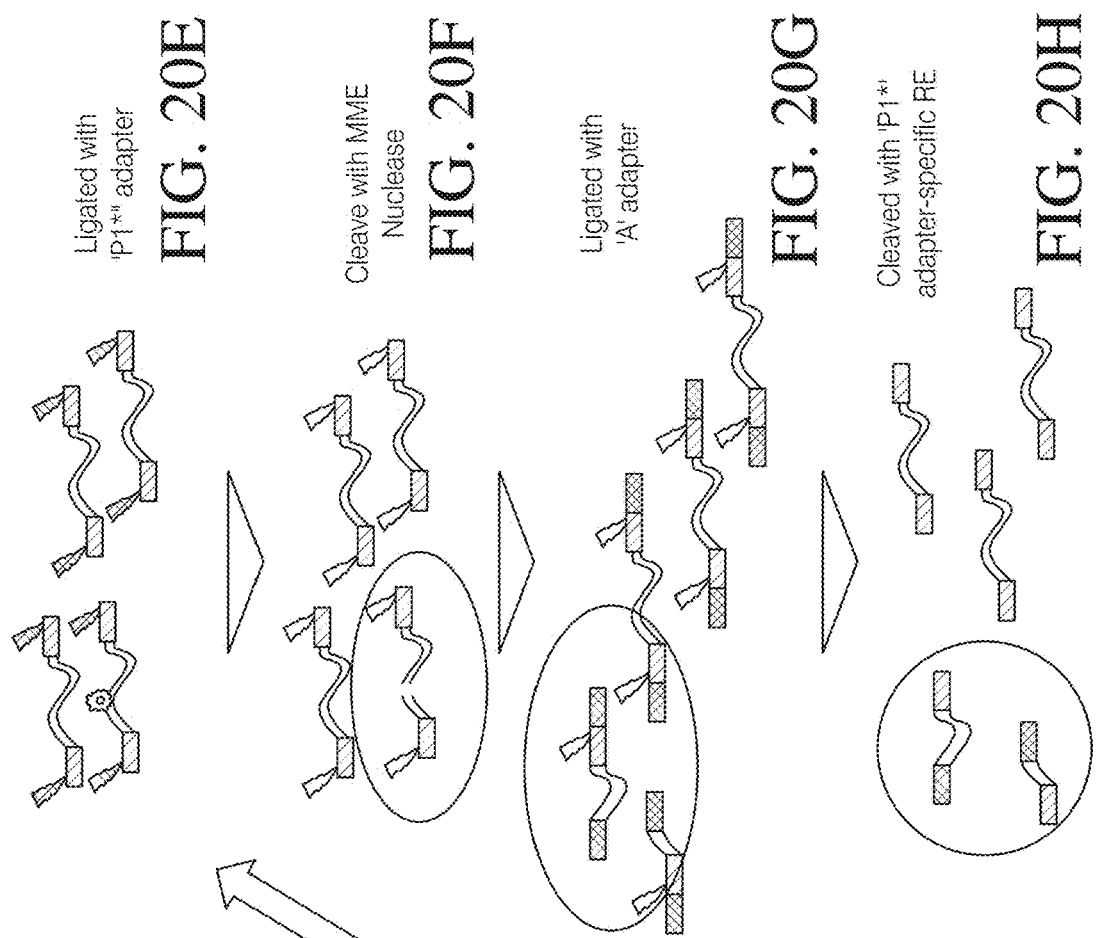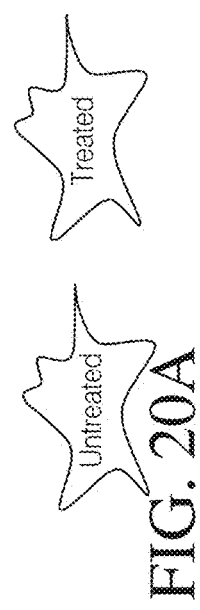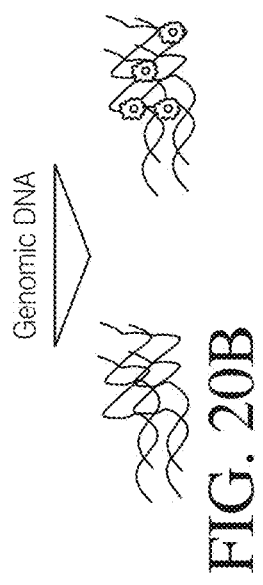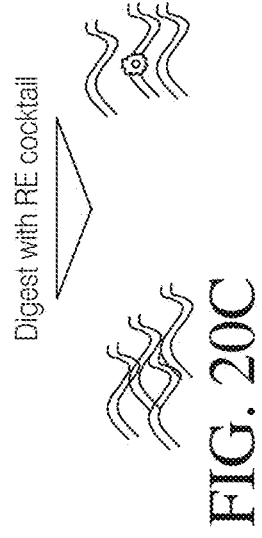

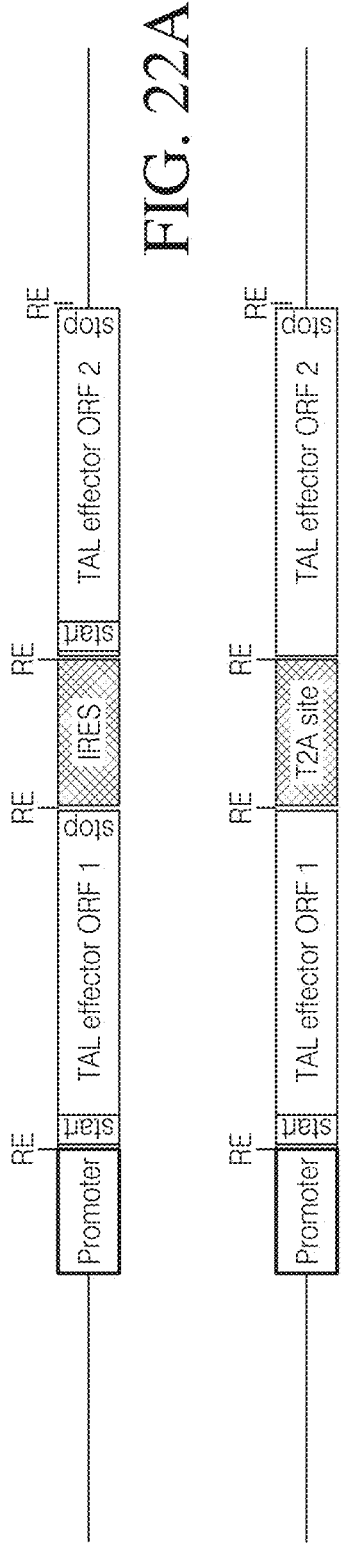
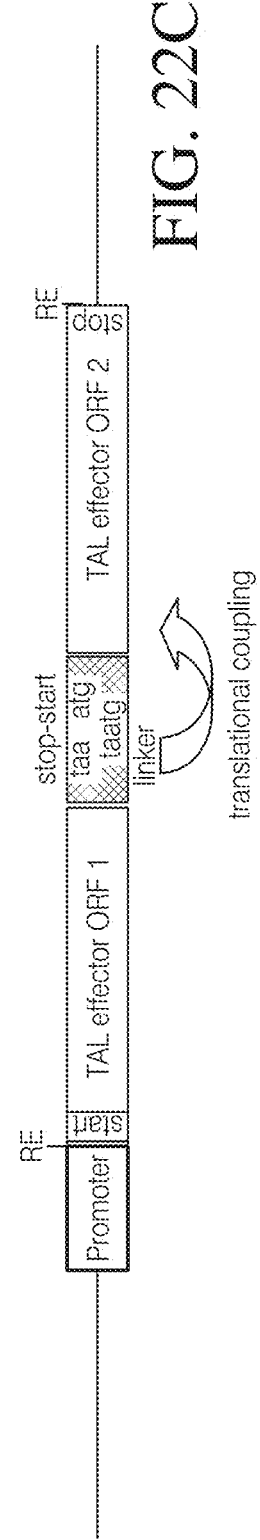
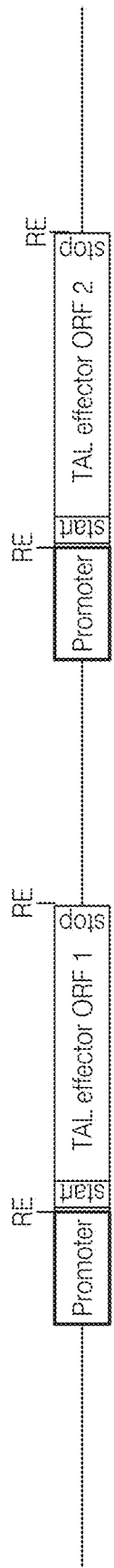
FIG. 22A
FIG. 22B
FIG. 22C
FIG. 22D
FIG. 22E

```
                                    1                                              50
YP_004022479 RBRH_01844    (1)   -MSTAFVDQDKQMANRLNLSPLERSTLEKQYGGATLAFISNKQNELAQI
YP_004030669 RBRH_01776    (1)   MPATSMHQEDKQSANGLNLSPLERIKIEKHYGGATLAFISNQHDELAQV
                Consensus  (1)    ATA DKQ AN LNLSPLER KIEK YGGA TLAFISN  ELAQI 51                                             100
YP_004022479 RBRH_01844   (50)   LSRADILKIASYDCAAHALQAVLDCGPMLGKRGFSQSDIVKIAGNIGGAQ
YP_004030669 RBRH_01776   (51)   LSRADILKIASYDCASQALQAVLDCGPMLGKRGFSPADIVKIAGNGGGAQ
                Consensus (51)   LSRADILKIASYDCAA ALQAVLDCGPMLGKRGFS ADIVKIAGN GGAQ 101                                            150
YP_004022479 RBRH_01844  (100)   ALQAVLDLESMLGTR--------------------------------GFSR
YP_004030669 RBRH_01776  (101)   ALSYSVLDVEPTLGKRGFSQVDVVKIAGGGAQALHTVLEIGPTLGERGFSR
                Consensus (101)  AL  AVLDLE  LGKR                               GFSR 151                                            200
YP_004022479 RBRH_01844  (119)   DIAKIAGNIGGAQTLQAVLDLESAFKERGFSQADIVKIAGNIGGAQALY
YP_004030669 RBRH_01776  (151)   GTVTIAGNGGGAQALQAVLDLEPTLRERGFNQADIVKIAGNGGAQALQ
                Consensus (151)   DI  IAGN GGAQ LQAVLDLE   RERGF QADIVKIAGN GGAQAL 201                                            250
YP_004022479 RBRH_01844  (169)   SVLDVEPTLGKR-----------------------------------
YP_004030669 RBRH_01776  (201)   AVLDVEPAIGKRGFSRVDIAKIAGGGAQALQAVLGLEPTLRKRGFHPTDI
                Consensus (201)  AVLDVEP LGKR 251                                            300
YP_004022479 RBRH_01844  (181)   ------------------------GFSRADIVKIAGNIGGAQAHTVL
YP_004030669 RBRH_01776  (251)   IKIAGNNGGAQALQAVLDLELMLRERGFSQADIVKMASNIGGAQAVL
                Consensus (251)                            GFS ADIVKIA N GGAQAL  VL 301                                            350
YP_004022479 RBRH_01844  (205)   DLEPALGKRGFSRIDIVKIAANGGAQALHAVLDIGPTLRECGFSQATIA
YP_004030669 RBRH_01776  (301)   NLEPALCERGFSQPDIVKMAGNSGGAQALQAVLDLELAFRERGFSQADIV
                Consensus (301)   LEPAL  RGFS  DIVKIAAN GGAQAL AVLDL   RE GFSQA I 351                                            400
YP_004022479 RBRH_01844  (255)   KIAGNIGGAQALQVLDIGPALGKRGFSQATIAKIAGNIGGAQALTVL
YP_004030669 RBRH_01776  (351)   KMASNIGGAQALQAVLDLEPALHERGFSQANIVKMAGNSGGAQALQAVL
                Consensus (351)  KIA NIGGAQALQ VLDL PAL  RGFSQA I KIAGN GGAQALQ VLD 401                                            450
YP_004022479 RBRH_01844  (305)   EPALCERGFSQATIAKMAGNGGAQIQTVLDLEPLLKKDFQADIIK
YP_004030669 RBRH_01776  (401)   ELVFRERGFSQPEIVKMAGNIGGAQALHTVLDLELAFRERGVRQADIVK
                Consensus (401)  LE  ERGFSQ  I MAGN GGAQAL TVLDLE A R R RQADIIK 451                                            500
YP_004022479 RBRH_01844  (355)   IASNDGGAQALQAVIEHGPTLR-------------------------
YP_004030669 RBRH_01776  (451)   IVGNIGGAQALQAVFELEPTLRERGFNQATIVKIAANGGGAQALYSVLDV
                Consensus (451)  I GN GGAQALQAV E  PTLR 501                                            550
YP_004022479 RBRH_01844  (377)   -------------------------------QHSFNLADIVKMAG
YP_004030669 RBRH_01776  (501)   EPTLDKRGFSRVDIVKIAGGGAQALHTAFELEPTLRKRGFNPTDIVKIAG
                Consensus (501)                                 GFN  DIVKIAG 551                                            600
YP_004022479 RBRH_01844  (391)   NIGGAQALQAVLDLKRVMDHEFSCPDIVKMAGNIGGAQAVLSLGPA
YP_004030669 RBRH_01776  (551)   NKGGAQALQAVLELEPALRERGFNQATIVKMAGNSGGAQALYSVLDVEPA
                Consensus (551)  N GGAQALQAVLDL P L E GF Q IVKMAGN GGAQAL AVL L PA
```

```
  1 MPATSMHQED KQSANGLNLS PLERIKIEKH YGGGATLAFI SNQHDELAQV
 51 LSRADILKIA SYDCAAQALQ AVLDCGPMLG KRGFSRADIV RIAGNGGGAQ
101 ALYSVLDVEP TLGKRGFSQV DVVKIAGGGA QALHTVLEIG PTLGERGFSR
151 GDIVTIAGNN GGAQALQAVL ELEPTLRERG FNQADIVKIA GNGGGAQALQ
201 AVLDVEPALG KRGFSRVDIA KIAGGGAQAL QAVLGLEPTL RKRGFHPTDI
251 IKIAGNNGGA QALQAVLDLE LMLRERGFSQ ADIVKMASNI GGAQALQAVL
301 NLEPALCERG FSQPDIVKMA GNSGGAQALQ AVLDLELAFR ERGFSQADIV
351 KMASNIGGAQ ALQAVLELEP ALHERGFSQA NIVKMAGNSG GAQALQAVLD
401 LELVFRERGF SQPEIVEMAG NIGGAQALHT VLDLELAFRE RGVRQADIVK
451 IVGNNGGAQA LQAVFELEPT LRERGFNQAT IVKIAANGGG AQALYSVLDV
501 EPTLDKRGFS RVDIVKIAGG GAQALHTAFE LEPTLRKRGF NPTDIVKIAG
551 NKGGAQALQA VLELEPALRE RGFNQATIVK MAGNAGGAQA LYSVLDVEPA
601 LRERGFSQPE IVKIAGNIGG AQALHTVLEL EPTLHKRGFN PTDIVKIAGN
651 SGGAQALQAV LELEPAFRER GFGQPDIVKM ASNIGGAQAL QAVLELEPAL
701 RERGFSQPDI VEMAGNIGGA QALQAVLELE PAFRERGFSQ SDIVKIAGNI
751 GGAQALQAVL ELEPTLRESD FRQADIVNIA GNDGSTQALK AVIEHGPRLR
801 QRGFNRASIV KIAGNSGGAQ ALQAVLKHGP TLDERGFNLT NIVKIAGNGG
851 GAQALKAVIE HGPTLQQRGF NLTDIVEMAG KGGGAQALKA VLEHGPTLRQ
901 RGFNLIDIVE MASNTGGAQA LKTVLEHGPT LRQRDLSLID IVEIASNGGA
951 QALKAVLKYG PVLMQAGRSN EEIVHVAARR GGAGRIRKMV ALLLERQ
```

```
Position         1        10        20       30 33
                 ↓         ↓ ⇓⇓       ↓        ↓  ↓ SEQ ID NO.
Marine Org A-1   FRTEGIVQMVSHGGGSKNLVAVQANYAALTGLG  198
Marine Org A-2   FRTEDIVQMVSHDGGSKNLVAVQANYAALTGLG  199
Marine Org A-3   FRTEDIVQMVSHDGGSKNLAAIIDKSTALTGLG  200
Marine Org A-4   FRTEDIVQMVSNNGGSKNLAAIIDKSTALKGLG  201
Marine Org A-5   FRTEDIVQMVSHGGGSKNLEVVQANYAALTGLG  202
Marine Org A-6   FRTEGIVQMVSHGGGSKNLVAVQANYAALTGLG  203
Marine Org A-7   FRTEDIVQMVSHDGGSKNLAAMIDKYTALKDLG  204
Marine Org A-8   FRTEDIVQMVSHDGGSKNLAAIIDKSTALKGLG  205
Marine Org A-9   FLTEDIVQMVSHDGGSKNLEVVQASIDTLTELK  206
Consensus        FRTEDIVQMVSHDGGSKNL AVQA Y ALTGLG
```

FIG. 28

```
Position         1        10        20       30 33
                 ↓         ↓ ⇓⇓       ↓        ↓  ↓ SEQ ID NO.
Marine Org B-1   LEPKDIVSIASHGGATQAITTLLNKWDDLRDKG  207
Marine Org B-2   LEPKDIVSIASNNGATQAIATTLAKWDSLIAKG  208
Marine Org B-3   LQPKDIVSIASHGGATQAITTLLNRWGDLRAKE  209
Marine Org B-4   LEPKDIVSIASHDGATQAITTLLEKWDELRAKE  210
Marine Org B-5   LEPKDIVSIASHIGANQTITTLLNKWGALIDLE  211
Marine Org B-6   LEPKDIVSIASHGGANKAITTLLEKWAALRAKE  212
Consensus        LEPKDIVSIASHGGATQAITTLLNKWDDLRAKG
```

FIG. 29

| Position | 1 | 10 | 20 | 30 | 35 | SEQ ID NO. |
|---|---|---|---|---|---|---|
| AvrXa27-1 | LTPDQVVAIASN-GGKQALETVQRLLPVLCQAHG- | | | | | 213 |
| AvrXa27-2 | LTPAQVVAIASNIGGKQALETVQRLLPVLCRAHG- | | | | | 214 |
| BBP1 | LTPQQVVAIAANTGGKQAIGAITTQLPILRAAPLN | | | | | 215 |
| BBP2 | LSPEQVVAIASNNGGKQALEAVKAQLLELRAAPYE | | | | | 216 |
| BBP3 | LSTGQVVAIASNGGGRQALEAVREQLLALRAAPYE | | | | | 217 |
| BBP4 | LSTEQVVIANSIGGKQALEAVKVQLPVLRAVPYE | | | | | 218 |
| BBP5 | LSTEQVVAIASNNGGKQALEAVKTQLLALRTVPYE | | | | | 219 |
| BBP6 | LSPEQVVAIASNNGGKQALEAVRALLPVLRVAPYE | | | | | 220 |
| Hax3-1 | LTPEQVVAIASNIGGKQALETVQRLLPVLCQAHG- | | | | | 221 |
| Hax3-2 | LTPQQVVAIASHDGGKQALETVQRLLPVLCQAHG- | | | | | 222 |
| PSI07-1 | LTPQQVVAIAANTGGKQAIGAITTQLPILRAAPYE | | | | | 223 |
| PSI07-2 | LSTEQVVAIASNNGGKQALEAVKAQLLVLRAAPYG | | | | | 224 |
| PSI07-3 | LSPEQVVAIASNNGGKPALEAVKAQLLELRAAPYE | | | | | 225 |
| Tal5a-1 | LTPNQLVAIANNGGKQALETVQRLLPVLCQDHG- | | | | | 226 |
| Tal5a-2 | LTPDQVVAIASHDGGKQALETVQRLLPVLCQAHG- | | | | | 227 |
| Tal 11a-1 | LTPDQVVAIASNIGGKQALETVQRLLPVLCQAHG- | | | | | 228 |
| Tal 11a-2 | LTPAQVVAIASNIGGKQALETVQRLLPVLCQAHG- | | | | | 229 |
| Tal 11a-3 | LTLDQVVAIASNGGSKQALETVQRLLPVLCQAHG- | | | | | 230 |
| Marine Org B-1 | LEPKDIVSIASHGGATQAITTLNKWDDLRDKG-- | | | | | 207 |
| Marine Org B-2 | LEPKDIVSIASNNGATQAIATLLAKWDSLIAKG-- | | | | | 208 |
| Marine Org B-3 | LQPKDIVSIASHGGATQAITTLNRWGDLRAKE-- | | | | | 209 |
| Marine Org B-4 | LEPKDIVSIASHDGATQAITTLLEKWDELRAKG-- | | | | | 210 |
| Marine Org B-5 | LEPKDIVSIASHIGANQTITTLNKWGALIDLE-- | | | | | 211 |
| Marine Org B-6 | LEPKDIVSIASHGGANKAITTLEKWAALRAKE-- | | | | | 212 |
| Consensus | LTP QVVAIASN GGKQALETV  LPVLR A | | | | | |

```
MGKPIPNPLL GLDSTGGMAP KKKRKVDGQV DLRTLGYSQQ QQEKIKPKVR   50
STVAQHHEAL VGHGFTHAHI VALSQHPAAL GTVAVKYQDM IAALPEATHE  100
AIVGVGKQWS GARALEALLT VAGELRGPPL QLDTGQLLKI AKRGGVTAVE  150
AVHAWRNALT GAPLNLTPEQ VVAIASNNGG KQALETVQRL LPVLCQAHGL  200
TPEQVVAIAS VQRLLPVLCQ AHGLTPEQVV AIASNNGGKQ ALETVQRLLP  250
VLCQAHGLTP EQVVAIASNN GGKQALETVQ RLLPVLCQAH GLTPEQVVAI  300
ASHDGGKQAL ETVQRLLPVL CQAHGLTPEQ VVAIASHDGG KQALETVQRL  350
LPVLCQAHGL TPEQVVAIAS NNGGKQALET VQRLLPVLCQ AHGLTPEQVV  400
AIASNNGGKQ ALETVQRLLP VLCQAHGLTP EQVVAIASNI GGKQALETVQ  450
RLLPVLCQAH GLTPEQVVAI ASNNGGKQAL ETVQRLLPVL CQAHGLTPEQ  500
VVAIASHDGG KQALETVQRL LPVLCQAHGL TPEQVVAIAS HDGGKQALET  550
VQRLLPVLCQ AHGLTPEQVV AIASNNGGKQ ALETVQRLLP VLCQAHGLTP  600
EQVVAIASHD GGKQALETVQ RLLPVLCQAH GLTPEQVVAI ASNIGGKQAL  650
ETVQRLLPVL CQAHGLTPEQ VVAIASNNGG KQALETVQRL LPVLCQAHGL  700
TPEQVVAIAS NGGKQALET VQRLLPVLCQ AHGLTPQQVV AIASNNGGRP  750
ALESIVAQLS RPDPALAALT NDHLVALACL GGRPALDAVK KGLPHAPALI  800
KRTNRRIPER TSHRVADHAQ VVRVLGFFQC HSHPAQAFDD AMTQFGMSRH  850
GLLQLFRRVG VTELEARSGT LPPASQRWDR ILQGGGVTMA KMAFTLADRV  900
TEEMLADKAA LVVEVVEENY HDAPIVGIAV VNERGRFFLR PETALADPQF  950
VAWLGDETKK KSMFDSKRAA VALKWKGIEL CGVSFDLLLA AYLLDPAQGV 1000
DDVAAAAKMK QYEAVRPDEA VYGKGAKRAV PDEPVLAEHL VRKAAAIWEL 1050
ERPFLDELRR NEQDRLLVEL EQPLSSILAE MEFAGVKVDT KRLEQMGKEL 1100
AEQLGTVEQR IYELAGQEFN INSPKQLGVI LFEKLQLPVL KKTKTGYSTS 1150
ADVLEKLAPY HEIVENILHY RQLGKLQSTY IEGLLKVVRP DTKKVHTIFN 1200
QALTQTGRLS STEPNLQNIP IRLEEGRKIR QAFVPSESDW LIFAADYSQI 1250
ELRVLAHIAE DDNLMEAFRR DLDIHTKTAM DIFQVSEDEV TPNMRRQAKA 1300
VNFGIVYGIS DYGLAQNLNI SRKEAAEFIE RYFQSFPGVK RYMENIVQEA 1350
KQKGYVTTLL HRRRYLPDIT SRNFNVRSFA ERMAMNTPIQ GSAADIIKKA 1400
MIDLNARLKE ERLQAHLLLQ VHDELILEAP KEEMERLCRL VPEVMEQAVT 1450
LRVPLKVDYR YGSTWYDAK*
```

FIG. 35

SEQUENCE LISTING

```
<160> NUMBER OF SEQ ID NOS: 234

<210> SEQ ID NO 1
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cagctggtga aatctgagct ggaggagaag aagtctgagc tgagacacaa gctgaagtac      60
gtgcctcacg agtacatcga gctgatcgag atcgccagaa atagcaccca ggatagaatc     120
ctggagatga aggtgatgga gttcttcatg aaggtgtacg gctacagagg aaagcacctg     180
ggaggaagca gaaaacctga cggagccatt tatacagtgg gcagccctat cgattatggc     240
gtgatcgtgg atacaaaggc ctacagcgga ggctacaatc tgcctattgg acaggccgat     300
gagatgcaga gatacgtgga ggagaaccag accaggaaca agcacatcaa ccctaacgag     360
tggtggaagg tgtacccttc tagcgtgacc gagttcaagt tcctgtttgt gagcggccac     420
ttcaagggca attataaggc ccagctgacc aggctgaacc acatcacaaa ttgtaatggc     480
gccgtgctgt ctgtggagga actgctgatt ggaggagaga tgattaaggc cggaacactg     540
acactggagg aggtgagaag aaagttcaac aacggcgaga tcaacttctg a              591

<210> SEQ ID NO 2
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 2

```
cagctggtga aatctgagct ggaggagaag aagtctgagc tgagacacaa gctgaagtac      60
gtgcctcacg agtacatcga gctgatcgag attgccagaa accccaccca ggatagaatc     120
ctggagatga aggtgatgga gttcttcatg aaggtgtacg gctatagagg agagcacctg     180
ggaggaagca gaaaacctga cggagccatt tatacagtgg gcagccctat cgattatggc     240
gtgatcgtgg atacaaaggc ctacagcgga ggctacaatc tgcctattgg acaggccgat     300
gagatgcaga gatacgtgaa ggagaaccag acccggaaca agcacatcaa ccctaatgag     360
tggtggaagg tgtaccctag cagcgtgacc gagttcaagt ttctgtttgt gagcggccac     420
ttcaagggca attataaggc ccagctgacc cggctgaaca gaaagacaaa ttgtaatggc     480
gccgtgctgt ctgtggagga actgctgatt ggaggagaga tgattaaggc cggaacactg     540
acactggagg aggtgagaag aaagttcaac aacggcgaga tcaacttctg a              591
```

<210> SEQ ID NO 3
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
cagctggtga aatctgagct ggaggagaag aagtctgagc tgagacacaa gctgaagtac      60
gtgcctcacg agtacatcga gctgatcgag attgccagaa accccaccca ggatagaatc     120
ctggagatga aggtgatgga gttcttcatg aaggtgtacg gctatagagg agagcacctg     180
ggaggaagca gaaaacctga cggagccatt tatacagtgg gcagccctat cgattatggc     240
gtgatcgtgg atacaaaggc ctacagcgga ggctacaatc tgcctattgg acaggccgat     300
gagatggaga gatacgtgga ggagaatcag accagagaca agcacctgaa ccctaacgaa     360
tggtggaagg tgtaccctag cagcgtgacc gagttcaagt ttctgtttgt gagcggccac     420
ttcaagggca attataaggc ccagctgacc aggctgaacc acatcacaaa ttgtaatggc     480
gccgtgctgt ctgtggagga actgctgatt ggaggagaga tgattaaggc cggaacactg     540
acactggagg aggtgagaag aaagttcaac aacggcgaga tcaacttctg a              591
```

<210> SEQ ID NO 4
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
gcccctccta cagatgtgtc tctgggagat gagctccacc tggatggaga agatgtggcc      60
atggcccacg ccgatgccct ggatgatttt gatctggata tgctgggaga tggcgattct     120
cctggacctg gatttacacc tcacgattct gccccttatg agccctggga tatggccgat     180
tttgagttcg agcagatgtt cacagatgcc ctgggcatcg acgagtatgg cggctga        237
```

<210> SEQ ID NO 5
<211> LENGTH: 207
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 5
cctaagaaaa agcggaaagt ggaagcctct ggatctggca gagccgatgc cctggatgat    60
tttgatctgg atatgctggg aagcgacgcc ctggatgatt tcgatctgga tatgctggga   120
tctgacgccc tggatgattt cgatctggat atgctgggat ctgacgccct ggatgatttc   180
gatctggaca tgctgatcaa cagctga                                       207

<210> SEQ ID NO 6
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gacgacgcca agagcctgac agcctggagc agaacactgg tgacattcaa ggatgtgttc    60
gtggacttca ccaggagga atggaaactg ctggatacag cccagcagat cgtgtacaga   120
aatgtgatgc tggagaacta caagaacctg gtgtctctgg ctaccagct gacaaagcct   180 gatgtgattc tgagactgga agggcgaa gaaccttggc tggtggaaag agagatccac    240
tga                                                                 243

<210> SEQ ID NO 7
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid
<220> FEATURE:
<223> OTHER INFORMATION: see specification as filed for detailed
      description of substitutions and preferred embodiments

<400> SEQUENCE: 7

Leu Thr Pro Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala His Ile Val Ala Leu Ser Gln His Pro Ala Ala Leu Gly Thr Val
1               5                   10                  15

Ala Val

<210> SEQ ID NO 9
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Asn Ala Leu Thr Gly Ala Pro Leu Asn
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Thr Gly Gln Leu Leu Lys Ile Ala Lys Arg Gly Gly Val Thr Ala
1               5                   10                  15

Val

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Gly Glu Leu Arg Gly Pro Pro Leu Gln Leu Asp Thr Gly Gln Leu
1               5                   10                  15

Leu

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Ile Ala Lys Arg Gly Gly Val Thr Ala Val Glu Ala Val His Ala
1               5                   10                  15

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Asp Leu Arg Thr Leu Gly Tyr Ser Gln Gln Gln Gln
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Val Asp Leu Cys Thr Leu Gly Tyr Ser Gln Gln Gln Gln
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Ala Leu Val Gly His Gly Phe Thr His Ala His Ile
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gln Gln Gln Gln Glu Lys Ile Lys Pro Lys Val Arg
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Thr Val Ala Gln His His Glu Ala Leu Val Gly His
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Leu Thr Asn Asp His Leu Val Ala Leu Ala Cys Leu Gly
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Arg Pro Ala Leu Asp Ala Val Lys Lys Gly Leu Pro His Ala Pro
1               5                   10                  15

<210> SEQ ID NO 20
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Leu Phe Arg Arg Val Gly Val Thr Glu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Arg Arg Ile Pro Glu Arg Thr Ser His
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Arg Val Pro Glu Gln Arg Asp Ala Leu His
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Asp Asp Phe Pro Ala Phe Asn Glu Glu Glu
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Ala Trp Leu Met Glu Leu Leu Pro Gln
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu His Ala Phe Ala Asp Ser Leu Glu Arg Asp Leu
```

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Ala Pro Ser Pro Met His Glu Gly Asp Gln Thr
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Thr Leu Pro Pro Ala Ser Gln Arg Trp
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Met Ala Pro Lys Lys Lys Arg Lys Val Asp Gly Gly
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gly Ser Pro Lys Lys Lys Arg Lys Val Asp Ala Pro Pro
1               5                   10

<210> SEQ ID NO 30
<211> LENGTH: 4034
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300

-continued

```
gtttgatgcc tggcagttta tggcgggcgt cctgcccgcc accctccggg ccgttgcttc     360
acaacgttca aatccgctcc cggcggattt gtcctactca ggagagcgtt caccgacaaa     420
caacagataa aacgaaaggc ccagtcttcc gactgagcct ttcgttttat ttgatgcctg     480
gcagttccct actctcgcgt taacgctagc atggatgttt cccagtcac gacgttgtaa      540
aacgacggcc agtcttaagc tcgggcccca ataatgatt ttattttgac tgatagtgac      600
ctgttcgttg caacaaattg atgagcaatg ctttttttata atgccaactt tgtacaaaaa    660
agcaggctgc ggccgcgcca ccatgggaaa acctattcct aatcctctgc tgggcctgga     720
ttctaccgga ggcatggccc taagaaaaa gcggaaggtg gacggcggag tggacctgag     780
aacactggga tattctcagc agcagcagga gaagatcaag cccaaggtga gatccacagt     840
ggcccagcac cacgaagccc tggtgggaca cggatttaca cacgcccaca ttgtggccct     900
gtctcagcac cctgccgccc tgggaacagt ggccgtgaaa tatcaggata tgattgccgc     960
cctgcctgag gccacacacg aagccattgt gggagtggga aaacagtggt ctggagccag     1020
agccctggaa gccctgctga cagtggccgg agaactgaga ggacctcctc tgcagctgga    1080
tacaggacag ctgctgaaga ttgccaaaag gggcggagtg accgcggtgg aagccgtgca    1140
cgcctggaga aatgccctga caggagcccc tctgaacct tgcaggtgcc ggaattgcca     1200
gctggggcgc cctctggtaa ggttgggaag ccctgcaaag taaactggat ggctttcttg     1260
ccgccaagga tctgatggcg cagggatca agctctgatc aagagacagg atgaggatcg      1320
tttcgcatgc agttcaaagt gtatacctac aaacgtgaaa gccgttatcg tctgtttgtg     1380
gatgtgcaga gcgatattat tgatacccccg ggtcgtcgta tggtgattcc gctggcctct    1440
gcgcgtctgc tgtctgataa agtgagccgt gagctgtatc cggtggtgca tattggtgat    1500
gaaagctggc gtatgatgac caccgatatg gcgagcgtgc cggtgagcgt gattggcgaa     1560
gaagtggcgg atctgagcca tcgtgaaaac gatatcaaaa acgcgattaa cctgatgttt    1620
tggggcattt aataaatgtc aggctcccctt atacacagcc agtctgcagt cacctgcgga    1680
tagcattgtg gcccagctgt ctagacctga tcctgccctg gccgccctga caaatgatca     1740
cctggtggcc ctggcctgtc tgggaggcag acctgccctg gatgccgtga aaaaggact     1800
gcctcacgcc cctgccctga tcaagagaac aaatagaaga atccccgagc ggacctctca    1860
cagagtggcc gatcacgccc aggtggtgag agtgctggga ttttttcagt gtcactctca     1920
ccctgcccag gcctttgatg atgccatgac acagtttggc atgagcagac acggactgct    1980
gcagctgttt agaagagtgg gagtgacaga actggaggcc agatccggaa ccctgcctcc    2040
tgcctctcag agatgggata ggattctgca gggttcccgt ttaaacaagc ttgtcgacgg    2100
taccgaattc atcgatagta ctctcgaggg atccgagctc aagatcttag ctaagtagac    2160
ccagctttct tgtacaaagt tggcattata agaaagcatt gcttatcaat ttgttgcaac    2220
gaacaggtca ctatcagtca aaataaaatc attatttgcc atccagctga tatcccctat    2280
agtgagtcgt attacatggt catagctgtt cctggcagc tctggcccgt gtctcaaaat     2340
ctctgatgtt acattgcaca agataaaaat atatcatcat gaacaataaa actgtctgct    2400
tacataaaca gtaatacaag gggtgttatg agccatattc aacgggaaac gtcgaggccg    2460
cgattaaatt ccaacatgga tgctgattta tatgggtata aatgggctcg cgataatgtc    2520
gggcaatcag gtgcgacaat ctatcgcttg tatgggaagc ccgatgcgcc agagttgttt    2580
ctgaaacatg gcaaaggtag cgttgccaat gatgttacag atgagatggt cagactaaac    2640
tggctgacgg aatttatgcc tcttccgacc atcaagcatt ttatccgtac tcctgatgat    2700
```

-continued

```
gcatggttac tcaccactgc gatccccgga aaaacagcat tccaggtatt agaagaatat    2760
cctgattcag gtgaaaatat tgttgatgcg ctggcagtgt tcctgcgccg gttgcattcg    2820
attcctgttt gtaattgtcc ttttaacagc gatcgcgtat ttcgtctcgc tcaggcgcaa    2880
tcacgaatga ataacggttt ggttgatgcg agtgattttg atgacgagcg taatggctgg    2940
cctgttgaac aagtctggaa agaaatgcat aaacttttgc cattctcacc ggattcagtc    3000
gtcactcatg gtgatttctc acttgataac cttattttg acgagggaa attaataggt      3060 tgtattgatg ttggacgagt cggaatcgca gaccgatacc aggatcttgc catcctatgg    3120
aactgcctcg gtgagttttc tccttcatta cagaaacggc ttttcaaaa atatggtatt     3180 gataatcctg atatgaataa attgcagttt catttgatgc tcgatgagtt tttctaatca    3240
gaattggtta attggttgta acactggcag agcattacgc tgacttgacg ggacggcgca    3300
agctcatgac caaatccct  taacgtgagt tacgcgtcgt tccactgagc gtcagacccc     3360
gtagaaaaga tcaaggatc  ttcttgagat ccttttttc tgcgcgtaat ctgctgcttg      3420
caaacaaaaa accaccgct accagcggtg gtttgtttgc cggatcaaga gctaccaact     3480 cttttttccga aggtaactgg cttcagcaga gcgcagatac caaatactgt ccttctagtg   3540
tagccgtagt taggccacca cttcaagaac tctgtagcac cgcctacata cctcgctctg    3600
ctaatcctgt taccagtggc tgctgccagt ggcgataagt cgtgtcttac cgggttggac    3660
tcaagacgat agttaccgga taaggcgcag cggtcgggct gaacgggggg ttcgtgcaca    3720
cagcccagct tggagcgaac gacctacacc gaactgagat acctacagcg tgagcattga    3780
gaaagcgcca cgcttcccga agggagaaag gcggacaggt atccggtaag cggcagggtc    3840
ggaacaggag agcgcacgag ggagcttcca gggggaaacg cctggtatct ttatagtcct    3900
gtcgggtttc gccacctctg acttgagcgt cgatttttgt gatgctcgtc aggggggcgg    3960
agcctatgga aaaacgccag caacgcggcc ttttacggt  tcctggcctt tgctggcct    4020 tttgctcaca tgtt                                                      4034
```

<210> SEQ ID NO 31
<211> LENGTH: 4349
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
ctttcctgcg ttatcccctg attctgtgga taaccgtatt accgcctttg agtgagctga    60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagttta tggcgggcgt cctgcccgcc accctccggg ccgttgcttc   360
acaacgttca aatccgctcc cggcggattt gtcctactca ggagagcgtt caccgacaaa   420
caacagataa aacgaaaggc ccagtcttcc gactgagcct ttcgttttat ttgatgcctg   480
gcagttccct actctcgcgt taacgctagc atggatgttt tcccagtcac gacgttgtaa   540
aacgacggcc agtcttaagc tcgggcccca ataatgatt  ttattttgac tgatagtgac    600
ctgttcgttg caacaaattg atgagcaatg ctttttata atgccaactt tgtacaaaaa     660
```

```
agcaggctgc ggccgcgcca ccatgggaaa acctattcct aatcctctgc tgggcctgga    720
ttctaccgga ggcatggccc ctaagaaaaa gcggaaggtg gacggcggag tggacctgag    780
aacactggga tattctcagc agcagcagga gaagatcaag cccaaggtga gatctacagt    840
ggcccagcac cacgaagccc tggtgggaca cggatttaca cacgcccaca ttgtggccct    900
gtctcagcac cctgccgccc tgggaacagt ggccgtgaaa tatcaggata tgattgccgc    960
cctgcctgag gccacacacg aagccattgt gggagtggga aaacagtggt ctggagccag   1020
agccctggaa gccctgctga cagtggccgg agaactgaga ggacctcctc tgcagctgga   1080
tacaggacag ctgctgaaga ttgccaaaag gggcggagtg accgcggtgg aagccgtgca   1140
cgcctggaga aatgccctga caggagcccc tctgaaccct gcaggtgcc ggaattgcca    1200 gctgggcgc cctctggtaa ggttgggaag ccctgcaaag taaactggat ggctttcttg    1260
ccgccaagga tctgatggcg caggggatca agctctgatc aagagacagg atgaggatcg   1320
tttcgcatgc agttcaaagt gtataccctac aaacgtgaaa gccgttatcg tctgtttgtg   1380
gatgtgcaga gcgatattat tgatacccccg ggtcgtcgta tggtgattcc gctggcctct   1440
gcgcgtctgc tgtctgataa agtgagccgt gagctgtatc cggtggtgca tattggtgat   1500
gaaagctggc gtatgatgac caccgatatg gcgagcgtgc cggtgagcgt gattggcgaa   1560
gaagtggcgg atctgagcca tcgtgaaaac gatatcaaaa acgcgattaa cctgatgttt   1620
tggggcattt aataaatgtc aggctcccctt atacacagcc agtctgcagt cacctgcgga   1680
tagcattgtg gcccagctgt ctagacctga tcctgccctg ccgccctga caaatgatca    1740 cctggtggcc ctggcctgtc tgggaggcag acctgccctg gatgccgtga aaaaggact    1800 gcctcacgcc cctgccctga tcaagagaac aaatagaaga atccccgagc ggacctctca   1860
cagagtggcc ggatcccagc tggtgaaatc tgagctggag gagaagaagt ctgagctgag   1920
acacaagctg aagtacgtgc ctcacgagta catcgagctg atcgagatcg ccagaaatag   1980
cacccaggat agaatcctgg agatgaaggt gatggagttc ttcatgaagg tgtacggcta   2040
cagaggaaag cacctgggag gaagcagaaa acctgacgga gccatttata cagtgggcag   2100
ccctatcgat tatggcgtga tcgtggatac aaaggcctac agcggaggct acaatctgcc   2160
tattggacag gccgatgaga tgcagagata cgtggaggag aaccagacca ggaacaagca   2220
catcaaccct aacgagtggt ggaaggtgta cccttctagc gtgaccgagt tcaagttcct   2280
gtttgtgagc ggccacttca agggcaatta taaggcccag ctgaccaggc tgaaccacat   2340 cacaaaattgt aatggcgccg tgctgtctgt ggaggaactg ctgattggag agagatgat    2400 taaggccgga acactgacac tggaggaggt gagaagaaag ttcaacaacg gcagatcaa    2460 cttctgaaag cttacccagc tttcttgtac aaagttggca ttataagaaa gcattgctta   2520
tcaatttgtt gcaacgaaca ggtcactatc agtcaaaata aaatcattat ttgccatcca   2580
gctgatatcc cctatagtga gtcgtattac atggtcatag ctgtttcctg gcagctctgg   2640
cccgtgtctc aaaatctctg atgttacatt gcacaagata aaaatatatc atcatgaaca   2700
ataaaactgt ctgcttacat aaacagtaat acaaggggtg ttatgagcca tattcaacgg   2760
gaaacgtcga ggccgcgatt aaattccaac atggatgctg atttatatgg gtataaatgg   2820
gctcgcgata atgtcgggca atcaggtgcg acaatctatc gcttgtatgg gaagcccgat   2880
gcgccagagt tgtttctgaa acatggcaaa ggtagcgttg ccaatgatgt tacagatgag   2940
atggtcagac taaactggct gacggaattt atgcctcttc cgaccatcaa gcattttatc   3000
```

```
cgtactcctg atgatgcatg gttactcacc actgcgatcc ccggaaaaac agcattccag    3060
gtattagaag aatatcctga ttcaggtgaa aatattgttg atgcgctggc agtgttcctg    3120
cgccggttgc attcgattcc tgtttgtaat tgtccttttt acagcgatcg cgtatttcgt    3180
ctcgctcagg cgcaatcacg aatgaataac ggtttggttg atgcgagtga ttttgatgac    3240
gagcgtaatg gctggcctgt tgaacaagtc tggaaagaaa tgcataaact tttgccattc    3300
tcaccggatt cagtcgtcac tcatggtgat ttctcacttg ataaccttat ttttgacgag    3360
gggaaattaa taggttgtat tgatgttgga cgagtcggaa tcgcagaccg ataccaggat    3420
cttgccatcc tatggaactg cctcggtgag ttttctcctt cattacagaa acggcttttt    3480
caaaaatatg gtattgataa tcctgatatg aataaattgc agtttcattt gatgctcgat    3540
gagttttcct aatcagaatt ggttaattgg ttgtaacact ggcagagcat tacgctgact    3600
tgacgggacg gcgcaagctc atgaccaaaa tcccttaacg tgagttacgc gtcgttccac    3660
tgagcgtcag accccgtaga aaagatcaaa ggatcttctt gagatccttt ttttctgcgc    3720
gtaatctgct gcttgcaaac aaaaaaacca ccgctaccag cggtggtttg tttgccggat    3780
caagagctac caactctttt tccgaaggta actggcttca gcagagcgca gataccaaat    3840
actgtccttc tagtgtagcc gtagttaggc caccacttca agaactctgt agcaccgcct    3900
acatacctcg ctctgctaat cctgttacca gtggctgctg ccagtggcga taagtcgtgt    3960
cttaccgggt tggactcaag acgatagtta ccggataagg cgcagcggtc gggctgaacg    4020
gggggttcgt gcacacagcc cagcttggag cgaacgacct acaccgaact gagataccta    4080
cagcgtgagc attgagaaag cgccacgctt cccgaaggga gaaaggcgga caggtatccg    4140
gtaagcggca gggtcggaac aggagagcgc acgagggagc ttccagggggg aaacgcctgg    4200 tatctttata gtcctgtcgg gtttcgccac ctctgacttg agcgtcgatt tttgtgatgc    4260
tcgtcagggg ggcggagcct atggaaaaac gccagcaacg cggccttttt acggttcctg    4320
gccttttgct ggccttttgc tcacatgtt                                      4349
```

<210> SEQ ID NO 32
<211> LENGTH: 5054
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta ggcgggcgt cctgcccgcc accctccggg ccgttgcttc      360
acaacgttca aatccgctcc cggcggattt gtcctactca ggagagcgtt caccgacaaa    420
caacagataa aacgaaaggc ccagtcttcc gactgagcct tcgttttat ttgatgcctg      480 gcagttccct actctcgcgt taacgctagc atggatgttt cccagtcac gacgttgtaa     540 aacgacggcc agtcttaagc tcgggcccca ataatgatt ttattttgac tgatagtgac     600
ctgttcgttg caacaaattg atgagcaatg ctttttttata atgccaactt tgtacaaaaa    660
```

-continued

| | |
|---|---|
| agcaggctgc ggccgcgcca ccatgggaaa acctattcct aatcctctgc tgggcctgga | 720 |
| ttctaccatg gaccctatta gaagcagaac accctctcca gccagagaac tgctgtctgg | 780 |
| acctcagcct gatggagtgc agcctacagc cgatagagga gtgtctcctc ctgccggagg | 840 |
| acctctggat ggactgcctg cccggagaac aatgagcaga acaagactgc cttctcctcc | 900 |
| agccccatct cctgccttt ctgccgattc ttttagcgac ctgctgagac agtttgaccc | 960 |
| cagcctgttt aataccagcc tgttcgatag cctgcctcct tttggagccc accacacaga | 1020 |
| ggccgccaca ggcgaatggg atgaagtgca gtctggactg agagccgccg atgcccctcc | 1080 |
| tcctacaatg agagtggccg tgacagccgc cagacctcct agagccaaac ctgcccctag | 1140 |
| aaggagagcc gcccagcctt ctgatgcctc tcctgccgcc caggtggacc tgagaacact | 1200 |
| gggatattct cagcagcagc aggagaagat caagcccaag gtgaggtcta cagtggccca | 1260 |
| gcaccacgaa gccctggtgg gacacggatt tacacacgcc cacattgtgg ccctgtctca | 1320 |
| gcaccctgcc gccctgggaa cagtggccgt gaaatatcag gatatgattg ccgccctgcc | 1380 |
| tgaggccaca cacgaagcca ttgtgggagt gggaaaacag tggtctggag ccagagccct | 1440 |
| ggaagccctg ctgacagtgg ccggagaact gagaggacct cctctgcagc tggatacagg | 1500 |
| acagctgctg aagattgcca aaaggggcgg agtgaccgcg gtggaagccg tgcacgcctg | 1560 |
| gagaaatgcc ctgacaggag cccctctgaa cccttgcagg tgccggaatt gccagctggg | 1620 |
| gcgccctctg gtaaggttgg gaagccctgc aaagtaaact ggatggcttt cttgccgcca | 1680 |
| aggatctgat ggcgcagggg atcaagctct gatcaagaga caggatgagg atcgtttcgc | 1740 |
| atgcagttca aagtgtatac ctacaaacgt gaaagccgtt atcgtctgtt tgtggatgtg | 1800 |
| cagagcgata ttattgatac ccctggtcgt cgtatggtga ttccgctggc ctctgcgcgt | 1860 |
| ctgctgtctg ataaagtgag ccgtgagctg tatccggtgg tgcatattgg tgatgaaagc | 1920 |
| tggcgtatga tgaccaccga tatggcgagc gtgccggtga gcgtgattgg cgaagaagtg | 1980 |
| gcggatctga gccatcgtga aaacgatatc aaaaacgcga ttaacctgat gttttggggc | 2040 |
| atttaataaa tgtcaggctc ccttatacac agccagtctg cagtcacctg cggatagcat | 2100 |
| tgtggcccag ctgtctagac ctgatcctgc cctggccgcc ctgacaaatg atcacctggt | 2160 |
| ggccctggcc tgtctgggag gcagacctgc cctggatgcc gtgaaaaaag gactgcctca | 2220 |
| cgccctgcc ctgatcaaga gaacaaatag aagaatcccc gagcggacct ctcacagagt | 2280 |
| ggccgatcac gcccaggtgg tgagagtgct gggatttttt cagtgtcact ctcaccctgc | 2340 |
| ccaggccttt gatgatgcca tgacacagtt tggcatgagc agacacggac tgctgcagct | 2400 |
| gtttagaaga gtgggagtga cagaactgga ggccagaagc ggaacactgc ctccagcctc | 2460 |
| tcagagatgg gatagaattc tgcaggccag cggaatgaag agagccaaac cttctcctac | 2520 |
| cagcacccag acacctgatc aggccagcct gcacgccttt gccgattctc tggaacggga | 2580 |
| tctggacgcc ccttctccta tgcacgaagg agatcagaca agagccagca gcagaaagag | 2640 |
| aagcaggtct gatagagccg tgacaggacc ttctgcccag cagtcttttg aagtgagagt | 2700 |
| gcctgaacag agagatgccc tgcatctgcc tctgctgtct tggggagtga aaagacctag | 2760 |
| aacaagaatc ggaggactgc tggacccggg aacacctatg gatgccgatc tggtggcctc | 2820 |
| ttctacagtg gtgtgggaac aggatgccga tccttttgcc ggaacagccg atgatttccc | 2880 |
| tgcctttaat gaggaagaac tggcctggct gatggaactg ctgcctcagg gatccgcccc | 2940 |
| tcctacagat gtgtctctgg gagatgagct ccacctggat ggagaagatg tggccatggc | 3000 |
| ccacgccgat gccctggatg attttgatct ggatatgctg ggagatggcg attctcctgg | 3060 |

```
acctggattt acacctcacg attctgcccc ttatggagcc ctggatatgg ccgattttga    3120
gttcgagcag atgttcacag atgccctggg catcgacgag tatggcggct gaaagcttac    3180
ccagctttct tgtacaaagt tggcattata agaaagcatt gcttatcaat ttgttgcaac    3240
gaacaggtca ctatcagtca aaataaaatc attatttgcc atccagctga tatccctat    3300
agtgagtcgt attacatggt catagctgtt tcctggcagc tctggcccgt gtctcaaaat    3360
ctctgatgtt acattgcaca agataaaaat atatcatcat gaacaataaa actgtctgct    3420
tacataaaca gtaatacaag gggtgttatg agccatattc aacgggaaac gtcgaggccg    3480
cgattaaatt ccaacatgga tgctgattta tgggtata aatgggctcg cgataatgtc     3540
gggcaatcag gtgcgacaat ctatcgcttg tatgggaagc ccgatgcgcc agagttgttt    3600
ctgaaacatg gcaaaggtag cgttgccaat gatgttacag atgagatggt cagactaaac    3660
tggctgacgg aatttatgcc tcttccgacc atcaagcatt ttatccgtac tcctgatgat    3720
gcatggttac tcaccactgc gatccccgga aaaacagcat tccaggtatt agaagaatat    3780
cctgattcag gtgaaaatat tgttgatgcg ctggcagtgt tcctgcgccg gttgcattcg    3840
attcctgttt gtaattgtcc ttttaacagc gatcgcgtat ttcgtctcgc tcaggcgcaa    3900
tcacgaatga ataacggttt ggttgatgcg agtgattttg atgacgagcg taatggctgg    3960
cctgttgaac aagtctggaa agaaatgcat aaacttttgc cattctcacc ggattcagtc    4020
gtcactcatg gtgatttctc acttgataac cttattttg acgaggggaa attaataggt     4080
tgtattgatg ttggacgagt cggaatcgca gaccgatacc aggatcttgc catcctatgg    4140
aactgcctcg gtgagttttc tccttcatta cagaaacggc ttttttcaaaa atatggtatt   4200
gataatcctg atatgaataa attgcagttt catttgatgc tcgatgagtt tttctaatca    4260
gaattggtta attggttgta acactggcag agcattacgc tgacttgacg ggacggcgca    4320
agctcatgac caaaatccct taacgtgagt tacgcgtcgt tccactgagc gtcagacccc    4380
gtagaaaaga tcaaggatc ttcttgagat cctttttttc tgcgcgtaat ctgctgcttg     4440
caaacaaaaa aaccaccgct accagcggtg gtttgtttgc cggatcaaga gctaccaact    4500
ctttttccga aggtaactgg cttcagcaga gcgcagatac caaatactgt ccttctagtg    4560
tagccgtagt taggccacca cttcaagaac tctgtagcac cgcctacata cctcgctctg    4620
ctaatcctgt taccagtggc tgctgccagt ggcgataagt cgtgtcttac cgggttggac    4680
tcaagacgat agttaccgga taaggcgcag cggtcgggct gaacgggggg ttcgtgcaca    4740
cagcccagct tggagcgaac gacctacacc gaactgagat acctacagcg tgagcattga    4800
gaaagcgcca cgcttcccga agggagaaag gcggacaggt atccggtaag cggcagggtc    4860
ggaacaggag agcgcacgag ggagcttcca ggggggaaacg cctggtatct ttatagtcct    4920
gtcgggtttc gccacctctg acttgagcgt cgatttttgt gatgctcgtc agggggggcgg   4980
agcctatgga aaaacgccag caacgcggcc ttttacggt tcctggcctt ttgctggcct      5040
tttgctcaca tgtt                                                      5054
```

<210> SEQ ID NO 33
<211> LENGTH: 4891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

-continued

```
ctttcctgcg ttatccctg attctgtgga taaccgtatt accgcctttg agtgagctga      60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt cccagtcac gacgttgtaa    540 aacgacggcc agtcttaagc tcgggcccca ataatgatt ttattttgac tgatagtgac    600
ctgttcgttg caacaaattg atgagcaatg cttttttata atgccaactt tgtacaaaaa    660
agcaggctgc ggccgcgcca ccatgggaaa acctattcct aatcctctgc tgggcctgga    720
ttctaccatg gaccctatta gaagcagaac accctctcca gccagagaac tgctgtctgg    780
acctcagcct gatggagtgc agcctacagc cgatagagga gtgtctcctc ctgccggagg    840
acctctggat ggactgcctg cccggagaac aatgagcaga acaagactgc cttctcctcc    900
agccccatct cctgcctttt ctgccgattc ttttagcgac ctgctgagac agtttgaccc    960
cagcctgttt aataccagcc tgttcgatag cctgcctcct tttggagccc accacacaga   1020
ggccgccaca ggcgaatggg atgaagtgca gtctggactg agagccgccg atgcccctcc   1080
tcctacaatg agagtggccg tgacagccgc cagacctcct agagccaaac ctgcccctag   1140
aaggagagcc gcccagcctt ctgatgcctc tcctgccgcc caggtggacc tgagaacact   1200
gggatattct cagcagcagc aggagaagat caagcccaag gtgaggtcta cagtggccca   1260
gcaccacgaa gccctggtgg acacggatt tacacacgcc cacattgtgg ccctgtctca   1320
gcaccctgcc gccctgggaa cagtggccgt gaaatatcag gatatgattg ccgccctgcc   1380
tgaggccaca cacgaagcca ttgtgggagt gggaaaacag tggtctggag ccagagccct   1440
ggaagccctg ctgacagtgg ccggagaact gagaggacct cctctgcagc tggatacagg   1500
acagctgctg aagattgcca aaaggggcgg agtgaccgcg gtggaagccg tgcacgcctg   1560
gagaaatgcc ctgacaggag ccctctgaa cccttgcagg tgccggaatt gccagctggg   1620
gcgccctctg gtaaggttgg gaagccctgc aaagtaaact ggatggcttt cttgccgcca   1680
aggatctgat ggcgcagggg atcaagctct gatcaagaga caggatgagg atcgtttcgc   1740
atgcagttca aagtgtatac ctacaaacgt gaaagccgtt atcgtctgtt tgtggatgtg   1800
cagagcgata ttattgatac ccctggtcgt cgtatggtga ttccgctggc ctctgcgcgt   1860
ctgctgtctg ataaagtgag ccgtgagctg tatccggtgg tgcatattgg tgatgaaagc   1920
tggcgtatga tgaccaccga tatgcgagcg tgccggtga gcgtgattgg cgaagaagtg   1980
gcggatctga gccatcgtga aaacgatatc aaaaacgcga ttaacctgat gttttgggc   2040 atttaataaa tgtcaggctc ccttatacac agccagtctg cagtcacctg cggatagcat   2100
tgtggcccag ctgtctagac ctgatcctgc cctggccgcc ctgacaaatg atcacctggt   2160
ggccctggcc tgtctgggag cagacctgcc cctggatgcc gtgaaaaaag gactgcctca   2220
cgcccctgcc ctgatcaaga gaacaaatag aagaatcccc gagcggacct ctcacagagt   2280
ggccgatcac gcccaggtgg tgagagtgct gggatttttt cagtgtcact ctcaccctgc   2340
```

```
ccaggccttt gatgatgcca tgacacagtt tggcatgagc agacacggac tgctgcagct    2400
gtttagaaga gtgggagtga cagaactgga ggccagaagc ggaacactgc ctccagcctc    2460
tcagagatgg gatagaatcc tgcaggccag cggaatgaag agagccaaac cttctcctac    2520
cagcacccag acacctgatc aggccagcct gcacgccttt gccgattctc tggaaaggga    2580
tctggacgcc ccttctccta tgcacgaagg agatcagaca gagccagca gcagaaagag    2640
aagcaggtct gatagagccg tgacaggacc ttctgcccag cagtcttttg aagtgagagt    2700
gcctgaacag agagatgccc tgcatctgcc tctgctgtct ggggagtga aaagacctag    2760
aacaagaatc ggaggactgc tggaccccgg gacacctatg gatgccgatc tggtggcctc    2820
ttctacagtg gtgtgggaac aggatgccga tccttttgcc ggaacagccg atgatttccc    2880
tgcctttaat gaggaagaac tggcctggct gatggaactg ctgcctcagg gttcccgttt    2940
aaacaagctt gtcgacggta ccgaattcat cgatagtact ctcgagggat ccgagctcaa    3000
gatctagcta agtagaccca gctttcttgt acaaagttgg cattataaga aagcattgct    3060
tatcaatttg ttgcaacgaa caggtcacta tcagtcaaaa taaaatcatt atttgccatc    3120
cagctgatat cccctatagt gagtcgtatt acatggtcat agctgtttcc tggcagctct    3180
ggcccgtgtc tcaaaatctc tgatgttaca ttgcacaaga taaaaatata tcatcatgaa    3240
caataaaact gtctgcttac ataaacagta atacaagggg tgttatgagc catattcaac    3300
gggaaacgtc gaggccgcga ttaaattcca acatggatgc tgatttatat gggtataaat    3360
gggctcgcga taatgtcggg caatcaggtg cgacaatcta tcgcttgtat gggaagcccg    3420
atgcgccaga gttgtttctg aaacatggca aaggtagcgt tgccaatgat gttacagatg    3480
agatggtcag actaaactgg ctgacggaat ttatgcctct tccgaccatc aagcatttta    3540
tccgtactcc tgatgatgca tggttactca ccactgcgat ccccggaaaa acagcattcc    3600
aggtattaga agaatatcct gattcaggtg aaaatattgt tgatgcgctg gcagtgttcc    3660
tgcgccggtt gcattcgatt cctgtttgta attgtccttt taacagcgat cgcgtatttc    3720
gtctcgctca ggcgcaatca cgaatgaata cggtttggt tgatgcgagt gattttgatg    3780
acgagcgtaa tggctggcct gttgaacaag tctggaaaga atgcataaa cttttgccat    3840
tctcaccgga ttcagtcgtc actcatggtg atttctcact tgataacctt atttttgacg    3900
aggggaaatt aataggttgt attgatgttg gacgagtcgg aatcgcagac cgataccagg    3960
atcttgccat cctatggaac tgcctcggtg agttttctcc ttcattacag aaacggcttt    4020
ttcaaaaata tggtattgat aatcctgata tgaataaatt gcagtttcat ttgatgctcg    4080
atgagttttt ctaatcagaa ttggttaatt ggttgtaaca ctggcagagc attacgctga    4140
cttgacggga cggcgcaagc tcatgaccaa aatcccttaa cgtgagttac gcgtcgttcc    4200
actgagcgtc agacccgta gaaaagatca aggatcttc ttgagatcct ttttttctgc    4260
gcgtaatctg ctgcttgcaa acaaaaaaac caccgctacc agcggtggtt tgtttgccgg    4320
atcaagagct accaactctt tttccgaagg taactggctt cagcagagcg cagataccaa    4380
atactgtcct tctagtgtag ccgtagttag gccaccactt caagaactct gtagcaccgc    4440
ctacatacct cgctctgcta atcctgttac cagtggctgc tgccagtggc gataagtcgt    4500
gtcttaccgg gttggactca agacgatagt taccggataa ggcgcagcgg tcgggctgaa    4560
cggggggttc gtgcacacag cccagcttgg agcgaacgac ctacaccgaa ctgagatacc    4620
tacagcgtga gcattgagaa agcgccacgc ttcccgaagg gagaaaggcg gacaggtatc    4680
cggtaagcgg cagggtcgga acaggagagc gcacgaggga gcttccaggg ggaaacgcct    4740
```

```
ggtatcttta tagtcctgtc gggtttcgcc acctctgact tgagcgtcga ttttgtgat      4800 gctcgtcagg ggggcggagc ctatggaaaa acgccagcaa cgcggccttt ttacggttcc     4860
tggccttttg ctggccttt gctcacatgt t                                     4891
```

<210> SEQ ID NO 34
<211> LENGTH: 5408
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
ctttcctgcg ttatccctg attctgtgga taaccgtatt accgcctttg agtgagctga       60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca atccgctcc cggcggattt gtcctactca ggagagcgtt caccgacaaa     420
caacagataa aacgaaaggc ccagtcttcc gactgagcct ttcgttttat ttgatgcctg     480
gcagttccct actctcgcgt taacgctagc atggatgttt tcccagtcac gacgttgtaa     540
aacgacggcc agtcttaagc tcgggcccca ataatgatt ttatttgac tgatagtgac     600 ctgttcgttg caacaaattg atgagcaatg cttttttata atgccaactt tgtacaaaaa     660
agcaggctgc ggccgcgcca ccatgggaaa acctattcct aatcctctgc tgggcctgga     720
ttctaccatg gaccctatta gaagcagaac accctctcca gccagagaac tgctgtctgg     780
acctcagcct gatggagtgc agcctacagc cgatagagga gtgtctcctc ctgccggagg     840
acctctggat ggactgcctg cccggagaac aatgagcaga acaagactgc cttctcctcc     900
agccccatct cctgcctttt ctgccgattc ttttagcgac ctgctgagac agtttgaccc     960
cagcctgttt aataccagcc tgttcgatag cctgcctcct ttggagccc accacacaga    1020 ggccgccaca ggcgaatggg atgaagtgca gtctggactg agagccgccg atgcccctcc    1080
tcctacaatg agagtggccg tgacagccgc cagacctcct agagccaaac ctgcccctag    1140
aaggagagcc gcccagcctt ctgatgcctc tcctgccgcc caggtggacc tgagaacact    1200
gggatattct cagcagcagc aggagaagat caagcccaag gtgaggtcta cagtggccca    1260
gcaccacgaa gccctggtgg acacggatt tacacacgcc cacattgtgg ccctgtctca    1320
gcaccctgcc gccctgggaa cagtggccgt gaaatatcag gatatgattg ccgccctgcc    1380
tgaggccaca cacgaagcca ttgtgggagt gggaaaacag tggtctggag ccagagccct    1440
ggaagccctg ctgacagtgg ccggagaact gagaggacct cctctgcagc tggatacagg    1500
acagctgctg aagattgcca aaggggcgg agtgaccgcg gtggaagccg tgcacgcctg    1560
gagaaatgcc ctgacaggag cccctctgaa cccttgcagg tgccggaatt gccagctggg    1620
gcgccctctg gtaaggttgg aagccctgc aaagtaaact ggatggcttt cttgccgcca    1680
aggatctgat ggcgcagggg atcaagtctc gatcaagaga caggatgagg atcgtttcgc    1740
atgcagttca aagtgtatac ctacaaacgt gaaagccgtt atcgtctgtt tgtggatgtg    1800
cagagcgata ttattgatac ccctggtcgt cgtatggtga ttccgctggc ctctgcgcgt    1860
```

```
ctgctgtctg ataaagtgag ccgtgagctg tatccggtgg tgcatattgg tgatgaaagc    1920
tggcgtatga tgaccaccga tatggcgagc gtgccggtga gcgtgattgg cgaagaagtg    1980
gcggatctga gccatcgtga aaacgatatc aaaaacgcga ttaacctgat gttttggggc    2040
atttaataaa tgtcaggctc ccttatacac agccagtctg cagtcacctg cggatagcat    2100
tgtggcccag ctgtctagac ctgatcctgc cctggccgcc ctgacaaatg atcacctggt    2160
ggccctggcc tgtctgggag gcagacctgc cctggatgcc gtgaaaaaag gactgcctca    2220
cgcccctgcc ctgatcaaga gaacaaatag aagaatcccc gagcggacct ctcacagagt    2280
ggccgatcac gcccaggtgg tgagagtgct gggattttt cagtgtcact ctcaccctgc      2340
ccaggccttt gatgatgcca tgacacagtt tggcatgagc agacacggac tgctgcagct    2400
gtttagaaga gtgggagtga cagaactgga ggccagaagc ggaacactgc ctccagcctc    2460
tcagagatgg gatagaattc tgcaggccag cggaatgaag agagccaaac cttctcctac    2520
cagcacccag acacctgatc aggccagcct gcacgccttt gccgattctc tggaacggga    2580
tctggacgcc ccttctccta tgcacgaagg agatcagaca gagccagca gcagaaagag     2640 aagcaggtct gatagagccg tgacaggacc ttctgcccag cagtcttttg aagtgagagt    2700
gcctgaacag agagatgccc tgcatctgcc tctgctgtct ggggagtga aaagacctag     2760 aacaagaatc ggaggactgc tggaccctgg aacacctatg gatgccgatc tggtggcctc    2820
ttctacagtg gtgtgggaac aggatgccga tccttttgcc ggaacagccg atgatttccc    2880
tgcctttaat gaggaagaac tggcctggct gatggaactg ctgcctcagg gatcccagct    2940
ggtgaaatct gagctggagg agaagaagtc tgagctgaga cacaagctga agtacgtgcc    3000 tcacagagtac atcgagctga tcgagatcgc cagaaatagc acccaggata gaatcctgga    3060
gatgaaggtg atggagttct tcatgaaggt gtacggctac agaggaaagc acctgggagg    3120
aagcagaaaa cctgacggag ccatttatac agtgggcagc cctatcgatt atggcgtgat    3180
cgtggataca aaggcctaca gcggaggcta caatctgcct attggacagg ccgatgagat    3240
gcagagatac gtggaggaga accagaccag gaacaagcac atcaacccta acgagtggtg   3300
gaaggtgtac ccttctagcg tgaccgagtt caagttcctg tttgtgagcg ccacttcaa     3360 gggcaattat aaggcccagc tgaccaggct gaaccacatc acaaattgta atggcgccgt    3420
gctgtctgtg gaggaactgc tgattggagg agagatgatt aaggccggaa cactgacact    3480
ggaggaggtg agaagaaagt caacaacgg cgagatcaac ttctgaaagc ttacccagct    3540
ttcttgtaca aagttggcat tataagaaag cattgcttat caatttgttg caacgaacag    3600
gtcactatca gtcaaaataa aatcattatt tgccatccag ctgatatccc ctatagtgag    3660
tcgtattaca tggtcatagc tgtttcctgg cagctctggc ccgtgtctca aaatctctga    3720
tgttacattg cacaagataa aaatatatca tcatgaacaa taaaactgtc tgcttacata    3780
aacagtaata caagggggt tatgagccat attcaacggg aaacgtcgag ccgcgatta     3840 aattccaaca tggatgctga tttatatggg tataaatggg ctcgcgataa tgtcgggcaa    3900
tcaggtgcga caatctatcg cttgtatggg aagcccgatg cgccagagtt gtttctgaaa    3960
catggcaaag gtagcgttgc caatgatgtt acagatgaga tggtcagact aaactggctg    4020
acggaattta tgcctcttcc gaccatcaag cattttatcc gtactcctga tgatgcatgg    4080
ttactcacca ctgcgatccc cggaaaaaca gcattccagg tattagaaga atatcctgat    4140
tcaggtgaaa atattgttga tgcgctggca gtgttcctgc gccggttgca ttcgattcct    4200
```

| | | |
|---|---|---|
| gtttgtaatt gtccttttaa cagcgatcgc gtatttcgtc tcgctcaggc gcaatcacga | 4260 | |
| atgaataacg gtttggttga tgcgagtgat tttgatgacg agcgtaatgg ctggcctgtt | 4320 | |
| gaacaagtct ggaaagaaat gcataaactt ttgccattct caccggattc agtcgtcact | 4380 | |
| catggtgatt tctcacttga taaccttatt tttgacgagg ggaaattaat aggttgtatt | 4440 | |
| gatgttggac gagtcggaat cgcagaccga taccaggatc ttgccatcct atggaactgc | 4500 | |
| ctcggtgagt tttctccttc attacagaaa cggcttttc aaaaatatgg tattgataat | 4560 | |
| cctgatatga ataaattgca gtttcatttg atgctcgatg agttttcta atcagaattg | 4620 | |
| gttaattggt tgtaacactg gcagagcatt acgctgactt gacgggacgg cgcaagctca | 4680 | |
| tgaccaaaat cccttaacgt gagttacgcg tcgttccact gagcgtcaga ccccgtagaa | 4740 | |
| aagatcaaag gatcttcttg agatcctttt tttctgcgcg taatctgctg cttgcaaaca | 4800 | |
| aaaaaaccac cgctaccagc ggtggtttgt ttgccggatc aagagctacc aactcttttt | 4860 | |
| ccgaaggtaa ctggcttcag cagagcgcag ataccaaata ctgtccttct agtgtagccg | 4920 | |
| tagttaggcc accacttcaa gaactctgta gcaccgccta catacctcgc tctgctaatc | 4980 | |
| ctgttaccag tggctgctgc cagtggcgat aagtcgtgtc ttaccgggtt ggactcaaga | 5040 | |
| cgatagttac cggataaggc gcagcggtcg ggctgaacgg ggggttcgtg cacacagccc | 5100 | |
| agcttggagc gaacgaccta caccgaactg agatacctac agcgtgagca ttgagaaagc | 5160 | |
| gccacgcttc ccgaagggag aaaggcggac aggtatccgg taagcggcag gtcggaaca | 5220 | |
| ggagagcgca cgagggagct tccaggggga aacgcctggt atctttatag tcctgtcggg | 5280 | |
| tttcgccacc tctgacttga gcgtcgattt ttgtgatgct cgtcagggg gcggagccta | 5340 | |
| tggaaaaacg ccagcaacgc ggcctttta cggttcctgg cctttgctg gcctttgct | 5400 | |
| cacatgtt | 5408 | |

<210> SEQ ID NO 35
<211> LENGTH: 5024
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

| | | |
|---|---|---|
| ctttcctgcg ttatcccctg attctgtgga taaccgtatt accgcctttg agtgagctga | 60 | |
| taccgctcgc cgcagccgaa cgaccgagcg cagcgagtca gtgagcgagg aagcggaaga | 120 | |
| gcgcccaata cgcaaaccgc ctctccccgc gcgttggccg attcattaat gcagctggca | 180 | |
| cgacaggttt cccgactgga aagcgggcag tgagcgcaac gcaattaata cgcgtaccgc | 240 | |
| tagccaggaa gagtttgtag aaacgcaaaa aggccatccg tcaggatggc cttctgctta | 300 | |
| gtttgatgcc tggcagttta tggcgggcgt cctgcccgcc accctccggg ccgttgcttc | 360 | |
| acaacgttca atccgctcc cggcggattt gtcctactca ggagagcgtt caccgacaaa | 420 | |
| caacagataa acgaaaggc ccagtcttcc gactgagcct ttcgttttat ttgatgcctg | 480 | |
| gcagttccct actctcgcgt taacgctagc atggatgttt tcccagtcac gacgttgtaa | 540 | |
| aacgacggcc agtcttaagc tcgggcccca ataatgatt ttattttgac tgatagtgac | 600 | |
| ctgttcgttg caacaaattg atgagcaatg ctttttata atgccaactt tgtacaaaaa | 660 | |
| agcaggctgc ggccgcgcca ccatgggaaa acctattcct aatcctctgc tgggcctgga | 720 | |
| ttctaccatg gaccctatta gaagcagaac accctctcca gccagagaac tgctgtctgg | 780 | |

| | |
|---|---|
| acctcagcct gatggagtgc agcctacagc cgatagagga gtgtctcctc ctgccggagg | 840 |
| acctctggat ggactgcctg cccggagaac aatgagcaga acaagactgc cttctcctcc | 900 |
| agccccatct cctgccttt ctgccgattc ttttagcgac ctgctgagac agtttgaccc | 960 |
| cagcctgttt aataccagcc tgttcgatag cctgcctcct tttggagccc accacacaga | 1020 |
| ggccgccaca ggcgaatggg atgaagtgca gtctggactg agagccgccg atgcccctcc | 1080 |
| tcctacaatg agagtggccg tgacagccgc cagacctcct agagccaaac ctgcccctag | 1140 |
| aaggagagcc gcccagcctt ctgatgcctc tcctgccgcc caggtggacc tgagaacact | 1200 |
| gggatattct cagcagcagc aggagaagat caagcccaag gtgaggtcta cagtggccca | 1260 |
| gcaccacgaa gccctggtgg acacggatt tacacacgcc cacattgtgg ccctgtctca | 1320 |
| gcaccctgcc gccctgggaa cagtggccgt gaaatatcag gatatgattg ccgccctgcc | 1380 |
| tgaggccaca cacgaagcca ttgtgggagt gggaaaacag tggtctggag ccagagccct | 1440 |
| ggaagccctg ctgacagtgg ccggagaact gagaggacct cctctgcagc tggatacagg | 1500 |
| acagctgctg aagattgcca aaggggcgg agtgaccgcg gtggaagccg tgcacgcctg | 1560 |
| gagaaatgcc ctgacaggag cccctctgaa cccttgcagg tgccggaatt gccagctggg | 1620 |
| gcgccctctg gtaaggttgg gaagccctgc aaagtaaact ggatggcttt cttgccgcca | 1680 |
| aggatctgat ggcgcagggg atcaagctct gatcaagaga caggatgagg atcgtttcgc | 1740 |
| atgcagttca aagtgtatac ctacaaacgt gaaagccgtt atcgtctgtt tgtggatgtg | 1800 |
| cagagcgata ttattgatac ccctggtcgt cgtatggtga ttccgctggc ctctgcgcgt | 1860 |
| ctgctgtctg ataaagtgag ccgtgagctg tatccggtgg tgcatattgg tgatgaaagc | 1920 |
| tggcgtatga tgaccaccga tatggcgagc gtgccggtga gcgtgattgg cgaagaagtg | 1980 |
| gcggatctga gccatcgtga aaacgatatc aaaaacgcga ttaacctgat gttttggggc | 2040 |
| atttaataaa tgtcaggctc ccttatacac agccagtctg cagtcacctg cggatagcat | 2100 |
| tgtggcccag ctgtctagac ctgatcctgc cctggccgcc ctgacaaatg atcacctggt | 2160 |
| ggccctggcc tgtctgggag gcagacctgc cctggatgcc gtgaaaaaag gactgcctca | 2220 |
| cgcccctgcc ctgatcaaga gaacaaatag aagaatcccc gagcggacct ctcacagagt | 2280 |
| ggccgatcac gcccaggtgg tgagagtgct gggattttt cagtgtcact ctcaccctgc | 2340 |
| ccaggccttt gatgatgcca tgacacagtt tggcatgagc agacacggac tgctgcagct | 2400 |
| gtttagaaga gtgggagtga cagaactgga ggccagaagc ggaacactgc ctccagcctc | 2460 |
| tcagagatgg gatagaattc tgcaggccag cggaatgaag agagccaaac cttctcctac | 2520 |
| cagcacccag acacctgatc aggccagcct gcacgccttt gccgattctc tggaacggga | 2580 |
| tctggacgcc ccttctcctc tgcacgaagg agatcagaca agagccagca gcagaaagag | 2640 |
| aagcaggtct gatagagccg tgacaggacc ttctgcccag cagtcttttg aagtgagagt | 2700 |
| gcctgaacag agagatgccc tgcatctgcc tctgctgtct tggggagtga aaagacctag | 2760 |
| aacaagaatc ggaggactgc tggaccctgg aacacctatg gatgccgatc tggtggcctc | 2820 |
| ttctacagtg gtgtgggaac aggatgccga tccttttgcc ggaacagccg atgatttccc | 2880 |
| tgcctttaat gaggaagaac tggcctggct gatggaactg ctgcctcagg gatcccctaa | 2940 |
| gaaaaagcgg aaagtggaag cctctggatc tggcagagcc gatgccctgg atgattttga | 3000 |
| tctggatatg ctgggaagcg acgccctgga tgatttcgat ctggatatgc tgggatctga | 3060 |
| cgccctggat gatttcgatc tggatatgct gggatctgac gccctggatg atttcgatct | 3120 |
| ggacatgctg atcaacagct gaaagcttac ccagctttct tgtacaaagt tggcattata | 3180 |

| | |
|---|---|
| agaaagcatt gcttatcaat ttgttgcaac gaacaggtca ctatcagtca aaataaaatc | 3240 |
| attatttgcc atccagctga tatccctat agtgagtcgt attacatggt catagctgtt | 3300 |
| tcctggcagc tctggcccgt gtctcaaaat ctctgatgtt acattgcaca agataaaaat | 3360 |
| atatcatcat gaacaataaa actgtctgct tacataaaca gtaatacaag gggtgttatg | 3420 |
| agccatattc aacgggaaac gtcgaggccg cgattaaatt ccaacatgga tgctgattta | 3480 |
| tatgggtata aatgggctcg cgataatgtc gggcaatcag gtgcgacaat ctatcgcttg | 3540 |
| tatgggaagc ccgatgcgcc agagttgttt ctgaaacatg gcaaaggtag cgttgccaat | 3600 |
| gatgttacag atgagatggt cagactaaac tggctgacgg aatttatgcc tcttccgacc | 3660 |
| atcaagcatt ttatccgtac tcctgatgat gcatggttac tcaccactgc gatccccgga | 3720 |
| aaaacagcat tccaggtatt agaagaatat cctgattcag gtgaaaatat tgttgatgcg | 3780 |
| ctggcagtgt tcctgcgccg gttgcattcg attcctgttt gtaattgtcc ttttaacagc | 3840 |
| gatcgcgtat ttcgtctcgc tcaggcgcaa tcacgaatga ataacggttt ggttgatgcg | 3900 |
| agtgattttg atgacgagcg taatggctgg cctgttgaac aagtctggaa agaaatgcat | 3960 |
| aaacttttgc cattctcacc ggattcagtc gtcactcatg gtgatttctc acttgataac | 4020 |
| cttatttttg acgaggggaa attaataggt tgtattgatg ttggacgagt cggaatcgca | 4080 |
| gaccgatacc aggatcttgc catcctatgg aactgcctcg gtgagttttc tccttcatta | 4140 |
| cagaaacggc ttttttcaaaa atatggtatt gataatcctg atatgaataa attgcagttt | 4200 |
| catttgatgc tcgatgagtt tttctaatca gaattggtta ttggttgta acactggcag | 4260 |
| agcattacgc tgacttgacg ggacggcgca agctcatgac caaaatccct taacgtgagt | 4320 |
| tacgcgtcgt tccactgagc gtcagacccc gtagaaaaga tcaaaggatc ttcttgagat | 4380 |
| ccttttttc tgcgcgtaat ctgctgcttg caaacaaaaa aaccaccgct accagcggtg | 4440 |
| gtttgtttgc cggatcaaga gctaccaact cttttccga aggtaactgg cttcagcaga | 4500 |
| gcgcagatac caaatactgt ccttctagtg tagccgtagt taggccacca cttcaagaac | 4560 |
| tctgtagcac cgcctacata cctcgctctg ctaatcctgt taccagtggc tgctgccagt | 4620 |
| ggcgataagt cgtgtcttac cgggttggac tcaagacgat agttaccgga taaggcgcag | 4680 |
| cggtcgggct gaacggggggg ttcgtgcaca gcccagct tggagcgaac gacctacacc | 4740 |
| gaactgagat acctacagcg tgagcattga gaaagcgcca cgcttcccga agggagaaag | 4800 |
| gcggacaggt atccggtaag cggcagggtc ggaacaggag agcgcacgag ggagcttcca | 4860 |
| gggggaaacg cctggtatct ttatagtcct gtcgggtttc gccacctctg acttgagcgt | 4920 |
| cgattttgt gatgctcgtc aggggggcgg agcctatgga aaaacgccag caacgcggcc | 4980 |
| tttttacggt tcctggcctt ttgctggcct tttgctcaca tgtt | 5024 |

<210> SEQ ID NO 36
<211> LENGTH: 4659
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

| | |
|---|---|
| ctttcctgcg ttatcccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |

```
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt cccagtcac gacgttgtaa    540 aacgacggcc agtcttaagc tcgggcccca ataatgatt ttattttgac tgatagtgac    600
ctgttcgttg caacaaattg atgagcaatg cttttttata atgccaactt tgtacaaaaa    660
agcaggctgc ggccgcgcca ccatgggaaa acctattcct aatcctctgc tgggcctgga    720
ttctaccgac cctattagaa gcagaacacc ttctccagcc agagagctgc tgtctggacc    780
tcagcctgat ggagtgcagc ctacagccga taggagtg tctcctcctg ccggaggacc    840
tctggatgga ctgcctgccc ggagaacaat gagcagaaca agactgcctt ctcctccagc    900
cccatctcct gccttttctg ccgattcttt tagcgacctg ctgagacagt ttgacccag    960 cctgttaat accagcctgt tcgatagcct gcctccttt ggagcccacc acacagaggc    1020
cgccacaggc gaatgggatg aagtgcagtc tggactgaga gccgccgatg cccctcctcc    1080
tacaatgaga gtgccgtga cagccgccag acctcctaga gccaaacctg ccctagaag    1140 gagagccgcc cagccttctg atgcctctcc tgccgcccag gtggatctga aacactggg    1200 atattctcag cagcagcagg agaagatcaa gcccaaggtg agatctacag tggcccagca    1260
ccacgaagcc ctggtgggac acggatttac acacgcccac attgtggccc tgtctcagca    1320
ccctgccgcc ctgggaacag tggccgtgaa atatcaggat atgattgccg ccctgcctga    1380
ggccacacac gaagccattg tgggagtggg aaaacagtgg tctggagcca gagccctgga    1440
agccctgctg acagtggccg gagaactgag aggacctcct ctgcagctgg atacaggaca    1500
gctgctgaag attgccaaaa ggggcggagt gaccgcggtg gaagccgtgc acgcctggag    1560
aaatgccctg acaggagccc ctctgaaccc ttgcaggtgc cggaattgcc agctggggcg    1620
ccctctggta aggttgggaa gccctgcaaa gtaaactgga tggcttttctt gccgccaagg    1680 atctgatggc gcaggggatc aagctctgat caagagacag gatgaggatc gtttcgcatg    1740
cagttcaaag tgtataccta caaacgtgaa agccgttatc gtctgttgt ggatgtgcag    1800 agcgatatta ttgataccc gggtcgtcgt atggtgattc cgctggcctc tgcgcgtctg    1860
ctgtctgata aagtgagccg tgagctgtat ccggtggtgc atattggtga tgaaagctgg    1920
cgtatgatga ccaccgatat ggcgagcgtg ccggtgagcg tgattggcga agaagtggcg    1980
gatctgagcc atcgtgaaaa cgatatcaaa acgcgattac acctgatgtt tgggcatt    2040 taataaatgt caggctccct tatacacagc cagtctgcag tcacctgcgg atagcattgt    2100
ggcccagctg tctagacctg atcctgccct ggccgccctg acaaatgatc acctggtggc    2160
cctggcctgt ctgggaggca gacctgccct ggatgccgtg aaaaaggac tgcctcacgc    2220 ccctgccctg atcaagagaa caaatagaag aatccccgag cggacctctc acagagtggc    2280
cgatcacgcc caggtggtga gagtgctggg attttttcag tgtcactctc accctgccca    2340
ggcctttgat gatgccatga cacagtttgg catgagcaga cacggactgc tgcagctgtt    2400
tagaagagtg ggagtgacag aactggaggc cagatctggt accctgcctc ctgcctctca    2460
gagatgggat agaattctgc agctgaagct gctgtctagc attgaacagg cctgccccaa    2520
```

```
gaagaagaga aaagtggacg acgccaagag cctgacagcc tggagcagaa cactggtgac    2580
attcaaggat gtgttcgtgg acttcaccag ggaggaatgg aaactgctgg atacagccca    2640
gcagatcgtg tacagaaatg tgatgctgga gaactacaag aacctggtgt ctctgggcta    2700
ccagctgaca aagcctgatg tgattctgag actggagaag ggcgaagaac cttggctggt    2760
ggaaagagag atccactgaa agcttaccca gctttcttgt acaaagttgg cattataaga    2820
aagcattgct tatcaatttg ttgcaacgaa caggtcacta tcagtcaaaa taaaatcatt    2880
atttgccatc cagctgatat cccctatagt gagtcgtatt acatggtcat agctgtttcc    2940
tggcagctct ggcccgtgtc tcaaaatctc tgatgttaca ttgcacaaga taaaaatata    3000
tcatcatgaa caataaaact gtctgcttac ataaacagta atacaagggg tgttatgagc    3060
catattcaac gggaaacgtc gaggccgcga ttaaattcca acatggatgc tgatttatat    3120
gggtataaat gggctcgcga taatgtcggg caatcaggtg cgacaatcta tcgcttgtat    3180
gggaagcccg atgcgccaga gttgtttctg aaacatggca aaggtagcgt tgccaatgat    3240
gttacagatg agatggtcag actaaactgg ctgacggaat ttatgcctct tccgaccatc    3300 aagcattta tccgtactcc tgatgatgca tggttactca ccactgcgat ccccggaaaa    3360
acagcattcc aggtattaga agaatatcct gattcaggtg aaaatattgt tgatgcgctg    3420
gcagtgttcc tgcgccggtt gcattcgatt cctgtttgta attgtccttt taacagcgat    3480
cgcgtatttc gtctcgctca ggcgcaatca cgaatgaata cggtttggt tgatgcgagt    3540 gattttgatg acgagcgtaa tggctggcct gttgaacaag tctggaaaga aatgcataaa    3600
cttttgccat tctcaccgga ttcagtcgtc actcatggtg atttctcact tgataacctt    3660 attttgacgaggggaaatt aataggttgt attgatgttg gacgagtcgg aatcgcagac    3720
cgataccagg atcttgccat cctatggaac tgcctcggtg agttttctcc ttcattacag    3780
aaacggcttt ttcaaaaata tggtattgat aatcctgata tgaataaatt gcagtttcat    3840
ttgatgctcg atgagttttt ctaatcagaa ttggttaatt ggttgtaaca ctggcagagc    3900
attacgctga cttgacggga cggcgcaagc tcatgaccaa atcccttaa cgtgagttac    3960 gcgtcgttcc actgagcgtc agaccccgta gaaaagatca aaggatcttc ttgagatcct    4020
ttttttctgc gcgtaatctg ctgcttgcaa acaaaaaaac caccgctacc agcggtggtt    4080
tgtttgccgg atcaagagct accaactctt tttccgaagg taactggctt cagcagagcg    4140
cagataccaa atactgtcct tctagtgtag ccgtagttag gccaccactt caagaactct    4200
gtagcaccgc ctacatacct cgctctgcta atcctgttac cagtggctgc tgccagtggc    4260
gataagtcgt gtcttaccgg gttggactca agacgatagt taccggataa ggcgcagcgg    4320
tcgggctgaa cggggggttc gtgcacacag cccagcttgg agcgaacgac ctacaccgaa    4380
ctgagatacc tacagcgtga gcattgagaa agcgccacgc ttcccgaagg gagaaaggcg    4440
gacaggtatc cggtaagcgg cagggtcgga acaggagagc gcacgaggga gcttccaggg    4500
ggaaacgcct ggtatcttta tagtcctgtc gggtttcgcc acctctgact tgagcgtcga    4560
tttttgtgat gctcgtcagg gggcggagc ctatggaaaa acgccagcaa cgcggccttt    4620
ttacggttcc tggccttttg ctggcctttt gctcacatg                          4659
```

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Phe Ser Gln Ala Asp Ile Val Lys Ile Ala Gly Asn
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Ala Gln Ala Leu Gln Ala Val Leu Asp Leu Glu Pro
1               5                   10

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Gly Ala Gln Ala Leu Gln Ala Val Leu Asp Leu Glu Pro Ala Leu
1               5                   10                  15

Arg Glu Arg Gly
            20

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Arg Thr Glu Asp Ile Val Gln Met Val Ser
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Ser Lys Asn Leu Ala Ala Val Gln Ala
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Ser Lys Asn Leu Glu Ala Val Gln Ala
1               5                   10

```
<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Glu Pro Lys Asp Ile Val Ser Ile Ala Ser
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Ala Thr Gln Ala Ile Thr Thr Leu Leu Asn Lys Trp
1               5                   10

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Asp, Ser, Ala or Glu

<400> SEQUENCE: 45

Gly Ala Thr Gln Ala Ile Thr Thr Leu Leu Asn Lys Trp Asp Xaa Leu
1               5                   10                  15

Arg Ala Lys Gly
            20

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Asp, Ser, Ala or Glu

<400> SEQUENCE: 46

Gly Ala Thr Gln Ala Ile Thr Thr Leu Leu Asn Lys Trp Gly Xaa Leu
1               5                   10                  15

Arg Ala Lys Gly
            20

<210> SEQ ID NO 47
<211> LENGTH: 997
<212> TYPE: PRT
<213> ORGANISM: Burkholderia rhizoxinica

<400> SEQUENCE: 47
```

-continued

```
Met Pro Ala Thr Ser Met His Gln Glu Asp Lys Gln Ser Ala Asn Gly
1               5                   10                  15

Leu Asn Leu Ser Pro Leu Glu Arg Ile Lys Ile Glu Lys His Tyr Gly
            20                  25                  30

Gly Gly Ala Thr Leu Ala Phe Ile Ser Asn Gln His Asp Glu Leu Ala
            35                  40                  45

Gln Val Leu Ser Arg Ala Asp Ile Leu Lys Ile Ala Ser Tyr Asp Cys
        50                  55                  60

Ala Ala Gln Ala Leu Gln Ala Val Leu Asp Cys Gly Pro Met Leu Gly
65                  70                  75                  80

Lys Arg Gly Phe Ser Arg Ala Asp Ile Val Arg Ile Ala Gly Asn Gly
                85                  90                  95

Gly Gly Ala Gln Ala Leu Tyr Ser Val Leu Asp Val Glu Pro Thr Leu
            100                 105                 110

Gly Lys Arg Gly Phe Ser Gln Val Asp Val Val Lys Ile Ala Gly Gly
        115                 120                 125

Gly Ala Gln Ala Leu His Thr Val Leu Glu Ile Gly Pro Thr Leu Gly
        130                 135                 140

Glu Arg Gly Phe Ser Arg Gly Asp Ile Val Thr Ile Ala Gly Asn Asn
145                 150                 155                 160

Gly Gly Ala Gln Ala Leu Gln Ala Val Leu Glu Leu Glu Pro Thr Leu
            165                 170                 175

Arg Glu Arg Gly Phe Asn Gln Ala Asp Ile Val Lys Ile Ala Gly Asn
                180                 185                 190

Gly Gly Gly Ala Gln Ala Leu Gln Ala Val Leu Asp Val Glu Pro Ala
            195                 200                 205

Leu Gly Lys Arg Gly Phe Ser Arg Val Asp Ile Ala Lys Ile Ala Gly
        210                 215                 220

Gly Gly Ala Gln Ala Leu Gln Ala Val Leu Gly Leu Glu Pro Thr Leu
225                 230                 235                 240

Arg Lys Arg Gly Phe His Pro Thr Asp Ile Ile Lys Ile Ala Gly Asn
                245                 250                 255

Asn Gly Gly Ala Gln Ala Leu Gln Ala Val Leu Asp Leu Glu Leu Met
            260                 265                 270

Leu Arg Glu Arg Gly Phe Ser Gln Ala Asp Ile Val Lys Met Ala Ser
        275                 280                 285

Asn Ile Gly Gly Ala Gln Ala Leu Gln Ala Val Leu Asn Leu Glu Pro
    290                 295                 300

Ala Leu Cys Glu Arg Gly Phe Ser Gln Pro Asp Ile Val Lys Met Ala
305                 310                 315                 320

Gly Asn Ser Gly Gly Ala Gln Ala Leu Gln Ala Val Leu Asp Leu Glu
            325                 330                 335

Leu Ala Phe Arg Glu Arg Gly Phe Ser Gln Ala Asp Ile Val Lys Met
                340                 345                 350

Ala Ser Asn Ile Gly Gly Ala Gln Ala Leu Gln Ala Val Leu Glu Leu
            355                 360                 365

Glu Pro Ala Leu His Glu Arg Gly Phe Ser Gln Ala Asn Ile Val Lys
    370                 375                 380

Met Ala Gly Asn Ser Gly Gly Ala Gln Ala Leu Gln Ala Val Leu Asp
385                 390                 395                 400

Leu Glu Leu Val Phe Arg Glu Arg Gly Phe Ser Gln Pro Glu Ile Val
                405                 410                 415

Glu Met Ala Gly Asn Ile Gly Gly Ala Gln Ala Leu His Thr Val Leu
```

```
                420             425             430
Asp Leu Glu Leu Ala Phe Arg Glu Arg Gly Val Arg Gln Ala Asp Ile
            435                 440                 445
Val Lys Ile Val Gly Asn Asn Gly Ala Gln Ala Leu Gln Ala Val
        450                 455                 460
Phe Glu Leu Glu Pro Thr Leu Arg Glu Arg Gly Phe Asn Gln Ala Thr
465                 470                 475                 480
Ile Val Lys Ile Ala Ala Asn Gly Gly Ala Gln Ala Leu Tyr Ser
                485                 490                 495
Val Leu Asp Val Glu Pro Thr Leu Asp Lys Arg Gly Phe Ser Arg Val
            500                 505                 510
Asp Ile Val Lys Ile Ala Gly Gly Ala Gln Ala Leu His Thr Ala
        515                 520                 525
Phe Glu Leu Glu Pro Thr Leu Arg Lys Arg Gly Phe Asn Pro Thr Asp
            530                 535                 540
Ile Val Lys Ile Ala Gly Asn Lys Gly Ala Gln Ala Leu Gln Ala
545                 550                 555                 560
Val Leu Glu Leu Glu Pro Ala Leu Arg Glu Arg Gly Phe Asn Gln Ala
                565                 570                 575
Thr Ile Val Lys Met Ala Gly Asn Ala Gly Gly Ala Gln Ala Leu Tyr
                580                 585                 590
Ser Val Leu Asp Val Glu Pro Ala Leu Arg Glu Arg Gly Phe Ser Gln
            595                 600                 605
Pro Glu Ile Val Lys Ile Ala Gly Asn Ile Gly Gly Ala Gln Ala Leu
        610                 615                 620
His Thr Val Leu Glu Leu Glu Pro Thr Leu His Lys Arg Gly Phe Asn
625                 630                 635                 640
Pro Thr Asp Ile Val Lys Ile Ala Gly Asn Ser Gly Gly Ala Gln Ala
                645                 650                 655
Leu Gln Ala Val Leu Glu Leu Glu Pro Ala Phe Arg Glu Arg Gly Phe
                660                 665                 670
Gly Gln Pro Asp Ile Val Lys Met Ala Ser Asn Ile Gly Gly Ala Gln
            675                 680                 685
Ala Leu Gln Ala Val Leu Glu Leu Glu Pro Ala Leu Arg Glu Arg Gly
        690                 695                 700
Phe Ser Gln Pro Asp Ile Val Glu Met Ala Gly Asn Ile Gly Gly Ala
705                 710                 715                 720
Gln Ala Leu Gln Ala Val Leu Glu Leu Glu Pro Ala Phe Arg Glu Arg
                725                 730                 735
Gly Phe Ser Gln Ser Asp Ile Val Lys Ile Ala Gly Asn Ile Gly Gly
            740                 745                 750
Ala Gln Ala Leu Gln Ala Val Leu Glu Leu Glu Pro Thr Leu Arg Glu
        755                 760                 765
Ser Asp Phe Arg Gln Ala Asp Ile Val Asn Ile Ala Gly Asn Asp Gly
770                 775                 780
Ser Thr Gln Ala Leu Lys Ala Val Ile Glu His Gly Pro Arg Leu Arg
785                 790                 795                 800
Gln Arg Gly Phe Asn Arg Ala Ser Ile Val Lys Ile Ala Gly Asn Ser
                805                 810                 815
Gly Gly Ala Gln Ala Leu Gln Ala Val Leu Lys His Gly Pro Thr Leu
            820                 825                 830
Asp Glu Arg Gly Phe Asn Leu Thr Asn Ile Val Lys Ile Ala Gly Asn
                835                 840                 845
```

Gly Gly Gly Ala Gln Ala Leu Lys Ala Val Ile Glu His Gly Pro Thr
            850                 855                 860

Leu Gln Gln Arg Gly Phe Asn Leu Thr Asp Ile Val Glu Met Ala Gly
865                 870                 875                 880

Lys Gly Gly Ala Gln Ala Leu Lys Ala Val Leu Glu His Gly Pro
                885                 890                 895

Thr Leu Arg Gln Arg Gly Phe Asn Leu Ile Asp Ile Val Glu Met Ala
            900                 905                 910

Ser Asn Thr Gly Gly Ala Gln Ala Leu Lys Thr Val Leu Glu His Gly
            915                 920                 925

Pro Thr Leu Arg Gln Arg Asp Leu Ser Leu Ile Asp Ile Val Glu Ile
            930                 935                 940

Ala Ser Asn Gly Gly Ala Gln Ala Leu Lys Ala Val Leu Lys Tyr Gly
945                 950                 955                 960

Pro Val Leu Met Gln Ala Gly Arg Ser Asn Glu Glu Ile Val His Val
                965                 970                 975

Ala Ala Arg Arg Gly Gly Ala Gly Arg Ile Arg Lys Met Val Ala Leu
            980                 985                 990

Leu Leu Glu Arg Gln
            995

<210> SEQ ID NO 48
<211> LENGTH: 771
<212> TYPE: PRT
<213> ORGANISM: Burkholderia rhizoxinica

<400> SEQUENCE: 48

Met Ser Thr Ala Phe Val Asp Gln Asp Lys Gln Met Ala Asn Arg Leu
1               5                   10                  15

Asn Leu Ser Pro Leu Glu Arg Ser Lys Ile Glu Lys Gln Tyr Gly Gly
            20                  25                  30

Ala Thr Thr Leu Ala Phe Ile Ser Asn Lys Gln Asn Glu Leu Ala Gln
        35                  40                  45

Ile Leu Ser Arg Ala Asp Ile Leu Lys Ile Ala Ser Tyr Asp Cys Ala
50                  55                  60

Ala His Ala Leu Gln Ala Val Leu Asp Cys Gly Pro Met Leu Gly Lys
65                  70                  75                  80

Arg Gly Phe Ser Gln Ser Asp Ile Val Lys Ile Ala Gly Asn Ile Gly
                85                  90                  95

Gly Ala Gln Ala Leu Gln Ala Val Leu Asp Leu Glu Ser Met Leu Gly
            100                 105                 110

Lys Arg Gly Phe Ser Arg Asp Asp Ile Ala Lys Met Ala Gly Asn Ile
            115                 120                 125

Gly Gly Ala Gln Thr Leu Gln Ala Val Leu Asp Leu Glu Ser Ala Phe
        130                 135                 140

Arg Glu Arg Gly Phe Ser Gln Ala Asp Ile Val Lys Ile Ala Gly Asn
145                 150                 155                 160

Asn Gly Gly Ala Gln Ala Leu Tyr Ser Val Leu Asp Val Glu Pro Thr
                165                 170                 175

Leu Gly Lys Arg Gly Phe Ser Arg Ala Asp Ile Val Lys Ile Ala Gly
            180                 185                 190

Asn Thr Gly Gly Ala Gln Ala Leu His Thr Val Leu Asp Leu Glu Pro
        195                 200                 205

Ala Leu Gly Lys Arg Gly Phe Ser Arg Ile Asp Ile Val Lys Ile Ala

```
                210                 215                 220
Ala Asn Asn Gly Gly Ala Gln Ala Leu His Ala Val Leu Asp Leu Gly
225                 230                 235                 240

Pro Thr Leu Arg Glu Cys Gly Phe Ser Gln Ala Thr Ile Ala Lys Ile
                245                 250                 255

Ala Gly Asn Ile Gly Gly Ala Gln Ala Leu Gln Met Val Leu Asp Leu
                260                 265                 270

Gly Pro Ala Leu Gly Lys Arg Gly Phe Ser Gln Ala Thr Ile Ala Lys
        275                 280                 285

Ile Ala Gly Asn Ile Gly Gly Ala Gln Ala Leu Gln Thr Val Leu Asp
        290                 295                 300

Leu Glu Pro Ala Leu Cys Glu Arg Gly Phe Ser Gln Ala Thr Ile Ala
305                 310                 315                 320

Lys Met Ala Gly Asn Asn Gly Gly Ala Gln Ala Leu Gln Thr Val Leu
                325                 330                 335

Asp Leu Glu Pro Ala Leu Arg Lys Arg Asp Phe Arg Gln Ala Asp Ile
                340                 345                 350

Ile Lys Ile Ala Gly Asn Asp Gly Gly Ala Gln Ala Leu Gln Ala Val
        355                 360                 365

Ile Glu His Gly Pro Thr Leu Arg Gln His Gly Phe Asn Leu Ala Asp
        370                 375                 380

Ile Val Lys Met Ala Gly Asn Ile Gly Gly Ala Gln Ala Leu Gln Ala
385                 390                 395                 400

Val Leu Asp Leu Lys Pro Val Leu Asp Glu His Gly Phe Ser Gln Pro
                405                 410                 415

Asp Ile Val Lys Met Ala Gly Asn Ile Gly Gly Ala Gln Ala Leu Gln
                420                 425                 430

Ala Val Leu Ser Leu Gly Pro Ala Leu Arg Glu Arg Gly Phe Ser Gln
        435                 440                 445

Pro Asp Ile Val Lys Ile Ala Gly Asn Thr Gly Gly Ala Gln Ala Leu
        450                 455                 460

Gln Ala Val Leu Asp Leu Glu Leu Thr Leu Val Glu His Gly Phe Ser
465                 470                 475                 480

Gln Pro Asp Ile Val Arg Ile Thr Gly Asn Arg Gly Gly Ala Gln Ala
                485                 490                 495

Leu Gln Ala Val Leu Ala Leu Glu Leu Thr Leu Arg Glu Arg Gly Phe
                500                 505                 510

Ser Gln Pro Asp Ile Val Lys Ile Ala Gly Asn Ser Gly Gly Ala Gln
        515                 520                 525

Ala Leu Gln Ala Val Leu Asp Leu Glu Leu Thr Phe Arg Glu Arg Gly
        530                 535                 540

Phe Ser Gln Ala Asp Ile Val Lys Ile Ala Gly Asn Asp Gly Gly Thr
545                 550                 555                 560

Gln Ala Leu His Ala Val Leu Asp Leu Glu Arg Met Leu Gly Glu Arg
                565                 570                 575

Gly Phe Ser Arg Ala Asp Ile Val Asn Val Ala Gly Asn Asn Gly Gly
                580                 585                 590

Ala Gln Ala Leu Lys Ala Val Leu Glu His Glu Ala Thr Leu Asn Glu
        595                 600                 605

Arg Gly Phe Ser Arg Ala Asp Ile Val Lys Ile Ala Gly Asn Gly Gly
        610                 615                 620

Gly Ala Gln Ala Leu Lys Ala Val Leu Glu His Glu Ala Thr Leu Asp
625                 630                 635                 640
```

-continued

```
Glu Arg Gly Phe Ser Arg Ala Asp Ile Val Arg Ile Ala Gly Asn Gly
                645                 650                 655

Gly Gly Ala Gln Ala Leu Lys Ala Val Leu Glu His Gly Pro Thr Leu
            660                 665                 670

Asn Glu Arg Gly Phe Asn Leu Thr Asp Ile Val Glu Met Ala Ala Asn
        675                 680                 685

Ser Gly Gly Ala Gln Ala Leu Lys Ala Val Leu Glu His Gly Pro Thr
    690                 695                 700

Leu Arg Gln Arg Gly Leu Ser Leu Ile Asp Ile Val Glu Ile Ala Ser
705                 710                 715                 720

Asn Gly Gly Ala Gln Ala Leu Lys Ala Val Leu Lys Tyr Gly Pro Val
                725                 730                 735

Leu Met Gln Ala Gly Arg Ser Asn Glu Glu Ile Val His Val Ala Ala
            740                 745                 750

Arg Arg Gly Gly Ala Gly Arg Ile Arg Lys Met Val Ala Pro Leu Leu
        755                 760                 765

Glu Arg Gln
    770

<210> SEQ ID NO 49
<211> LENGTH: 997
<212> TYPE: PRT
<213> ORGANISM: Burkholderia rhizoxinica

<400> SEQUENCE: 49

Met Pro Ala Thr Ser Met His Gln Glu Asp Lys Gln Ser Ala Asn Gly
1               5                   10                  15

Leu Asn Leu Ser Pro Leu Glu Arg Ile Lys Ile Glu Lys His Tyr Gly
            20                  25                  30

Gly Gly Ala Thr Leu Ala Phe Ile Ser Asn Gln His Asp Glu Leu Ala
        35                  40                  45

Gln Val Leu Ser Arg Ala Asp Ile Leu Lys Ile Ala Ser Tyr Asp Cys
    50                  55                  60

Ala Ala Gln Ala Leu Gln Ala Val Leu Asp Cys Gly Pro Met Leu Gly
65                  70                  75                  80

Lys Arg Gly Phe Ser Arg Ala Asp Ile Val Arg Ile Ala Gly Asn Gly
                85                  90                  95

Gly Gly Ala Gln Ala Leu Tyr Ser Val Leu Asp Val Glu Pro Thr Leu
            100                 105                 110

Gly Lys Arg Gly Phe Ser Gln Val Asp Val Val Lys Ile Ala Gly Gly
        115                 120                 125

Gly Ala Gln Ala Leu His Thr Val Leu Glu Ile Gly Pro Thr Leu Gly
    130                 135                 140

Glu Arg Gly Phe Ser Arg Gly Asp Ile Val Thr Ile Ala Gly Asn Asn
145                 150                 155                 160

Gly Gly Ala Gln Ala Leu Gln Ala Val Leu Glu Leu Glu Pro Thr Leu
                165                 170                 175

Arg Glu Arg Gly Phe Asn Gln Ala Asp Ile Val Lys Ile Ala Gly Asn
            180                 185                 190

Gly Gly Gly Ala Gln Ala Leu Gln Ala Val Leu Asp Val Glu Pro Ala
        195                 200                 205

Leu Gly Lys Arg Gly Phe Ser Arg Val Asp Ile Ala Lys Ile Ala Gly
    210                 215                 220

Gly Gly Ala Gln Ala Leu Gln Ala Val Leu Gly Leu Glu Pro Thr Leu
```

```
            225                 230                 235                 240

Arg Lys Arg Gly Phe His Pro Thr Asp Ile Ile Lys Ile Ala Gly Asn
                245                 250                 255

Asn Gly Gly Ala Gln Ala Leu Gln Ala Val Leu Asp Leu Glu Leu Met
                260                 265                 270

Leu Arg Glu Arg Gly Phe Ser Gln Ala Asp Ile Val Lys Met Ala Ser
                275                 280                 285

Asn Ile Gly Gly Ala Gln Ala Leu Gln Ala Val Leu Asn Leu Glu Pro
                290                 295                 300

Ala Leu Cys Glu Arg Gly Phe Ser Gln Pro Asp Ile Val Lys Met Ala
305                 310                 315                 320

Gly Asn Ser Gly Gly Ala Gln Ala Leu Gln Ala Val Leu Asp Leu Glu
                325                 330                 335

Leu Ala Phe Arg Glu Arg Gly Phe Ser Gln Ala Asp Ile Val Lys Met
                340                 345                 350

Ala Ser Asn Ile Gly Gly Ala Gln Ala Leu Gln Ala Val Leu Glu Leu
                355                 360                 365

Glu Pro Ala Leu His Glu Arg Gly Phe Ser Gln Ala Asn Ile Val Lys
                370                 375                 380

Met Ala Gly Asn Ser Gly Gly Ala Gln Ala Leu Gln Ala Val Leu Asp
385                 390                 395                 400

Leu Glu Leu Val Phe Arg Glu Arg Gly Phe Ser Gln Pro Glu Ile Val
                405                 410                 415

Glu Met Ala Gly Asn Ile Gly Gly Ala Gln Ala Leu His Thr Val Leu
                420                 425                 430

Asp Leu Glu Leu Ala Phe Arg Glu Arg Gly Val Arg Gln Ala Asp Ile
                435                 440                 445

Val Lys Ile Val Gly Asn Asn Gly Gly Ala Gln Ala Leu Gln Ala Val
                450                 455                 460

Phe Glu Leu Glu Pro Thr Leu Arg Glu Arg Gly Phe Asn Gln Ala Thr
465                 470                 475                 480

Ile Val Lys Ile Ala Ala Asn Gly Gly Gly Ala Gln Ala Leu Tyr Ser
                485                 490                 495

Val Leu Asp Val Glu Pro Thr Leu Asp Lys Arg Gly Phe Ser Arg Val
                500                 505                 510

Asp Ile Val Lys Ile Ala Gly Gly Gly Ala Gln Ala Leu His Thr Ala
                515                 520                 525

Phe Glu Leu Glu Pro Thr Leu Arg Lys Arg Gly Phe Asn Pro Thr Asp
                530                 535                 540

Ile Val Lys Ile Ala Gly Asn Lys Gly Gly Ala Gln Ala Leu Gln Ala
545                 550                 555                 560

Val Leu Glu Leu Glu Pro Ala Leu Arg Glu Arg Gly Phe Asn Gln Ala
                565                 570                 575

Thr Ile Val Lys Met Ala Gly Asn Ala Gly Gly Ala Gln Ala Leu Tyr
                580                 585                 590

Ser Val Leu Asp Val Glu Pro Ala Leu Arg Glu Arg Gly Phe Ser Gln
                595                 600                 605

Pro Glu Ile Val Lys Ile Ala Gly Asn Ile Gly Gly Ala Gln Ala Leu
                610                 615                 620

His Thr Val Leu Glu Leu Glu Pro Thr Leu His Lys Arg Gly Phe Asn
625                 630                 635                 640

Pro Thr Asp Ile Val Lys Ile Ala Gly Asn Ser Gly Gly Ala Gln Ala
                645                 650                 655
```

Leu Gln Ala Val Leu Glu Leu Glu Pro Ala Phe Arg Glu Arg Gly Phe
            660                 665                 670

Gly Gln Pro Asp Ile Val Lys Met Ala Ser Asn Ile Gly Ala Gln
            675                 680                 685

Ala Leu Gln Ala Val Leu Glu Leu Glu Pro Ala Leu Arg Glu Arg Gly
690                 695                 700

Phe Ser Gln Pro Asp Ile Val Glu Met Ala Gly Asn Ile Gly Ala
705                 710                 715                 720

Gln Ala Leu Gln Ala Val Leu Glu Leu Glu Pro Ala Phe Arg Glu Arg
            725                 730                 735

Gly Phe Ser Gln Ser Asp Ile Val Lys Ile Ala Gly Asn Ile Gly Gly
            740                 745                 750

Ala Gln Ala Leu Gln Ala Val Leu Glu Leu Glu Pro Thr Leu Arg Glu
            755                 760                 765

Ser Asp Phe Arg Gln Ala Asp Ile Val Asn Ile Ala Gly Asn Asp Gly
            770                 775                 780

Ser Thr Gln Ala Leu Lys Ala Val Ile Glu His Gly Pro Arg Leu Arg
785                 790                 795                 800

Gln Arg Gly Phe Asn Arg Ala Ser Ile Val Lys Ile Ala Gly Asn Ser
            805                 810                 815

Gly Gly Ala Gln Ala Leu Gln Ala Val Leu Lys His Gly Pro Thr Leu
            820                 825                 830

Asp Glu Arg Gly Phe Asn Leu Thr Asn Ile Val Lys Ile Ala Gly Asn
            835                 840                 845

Gly Gly Gly Ala Gln Ala Leu Lys Ala Val Ile Glu His Gly Pro Thr
            850                 855                 860

Leu Gln Gln Arg Gly Phe Asn Leu Thr Asp Ile Val Glu Met Ala Gly
865                 870                 875                 880

Lys Gly Gly Gly Ala Gln Ala Leu Lys Ala Val Leu Glu His Gly Pro
            885                 890                 895

Thr Leu Arg Gln Arg Gly Phe Asn Leu Ile Asp Ile Val Glu Met Ala
            900                 905                 910

Ser Asn Thr Gly Gly Ala Gln Ala Leu Lys Thr Val Leu Glu His Gly
            915                 920                 925

Pro Thr Leu Arg Gln Arg Asp Leu Ser Leu Ile Asp Ile Val Glu Ile
            930                 935                 940

Ala Ser Asn Gly Gly Ala Gln Ala Leu Lys Ala Val Leu Lys Tyr Gly
945                 950                 955                 960

Pro Val Leu Met Gln Ala Gly Arg Ser Asn Glu Ile Val His Val
            965                 970                 975

Ala Ala Arg Arg Gly Gly Ala Gly Arg Ile Arg Lys Met Val Ala Leu
            980                 985                 990

Leu Leu Glu Arg Gln
        995

<210> SEQ ID NO 50
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Ile, Asn, Thr, Asp, Arg, Ser, Gly, Lys or Ala

```
<220> FEATURE:
<221> NAME/KEY: MOD_RES
<222> LOCATION: (28)..(28)
<223> OTHER INFORMATION: Ala or Thr
<220> FEATURE:
<223> OTHER INFORMATION: see specification as filed for detailed
      description of substitutions and preferred embodiments

<400> SEQUENCE: 50

Phe Ser Gln Ala Asp Ile Val Lys Ile Ala Gly Asn Xaa Gly Gly Ala
1               5                   10                  15

Gln Ala Leu Gln Ala Val Leu Asp Leu Glu Pro Xaa Leu Arg Glu Arg
            20                  25                  30

Gly

<210> SEQ ID NO 51
<211> LENGTH: 8
<212> TYPE: PRT
<213> ORGANISM: Burkholderia sp.

<400> SEQUENCE: 51

Leu Asn Leu Ser Pro Leu Glu Arg
1               5

<210> SEQ ID NO 52
<211> LENGTH: 7
<212> TYPE: PRT
<213> ORGANISM: Burkholderia sp.

<400> SEQUENCE: 52

Thr Leu Ala Phe Ile Ser Asn
1               5

<210> SEQ ID NO 53
<211> LENGTH: 33
<212> TYPE: PRT
<213> ORGANISM: Burkholderia sp.

<400> SEQUENCE: 53

Tyr Gly Pro Val Leu Met Gln Ala Gly Arg Ser Asn Glu Glu Ile Val
1               5                   10                  15

His Val Ala Ala Arg Arg Gly Gly Ala Gly Arg Ile Arg Lys Met Val
            20                  25                  30

Ala

<210> SEQ ID NO 54
<211> LENGTH: 5
<212> TYPE: PRT
<213> ORGANISM: Burkholderia sp.

<400> SEQUENCE: 54

Leu Leu Glu Arg Gln
1               5

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Ser Pro Glu Asp Ile Val Ala Ile Ala Ser
```

```
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Phe Thr Pro Glu Asp Ile Val Ala Ile Ala Ser
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Thr Pro Ala Asp Ile Val Ala Ile Ala Ser
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Ser Pro Ala Gln Val Val Ala Ile Ala Ser
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Thr Pro Ala Gln Ile Val Lys Ile Ala Ser
1               5                   10

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (3)..(3)
<223> OTHER INFORMATION: Ala or Lys
<220> FEATURE:
<221> NAME/KEY: MOD_RES
<222> LOCATION: (4)..(4)
<223> OTHER INFORMATION: Ile or Met
<220> FEATURE:
```

```
<221> NAME/KEY: MOD_RES
<222> LOCATION: (5)..(5)
<223> OTHER INFORMATION: Ala or Val
<220> FEATURE:
<221> NAME/KEY: MOD_RES
<222> LOCATION: (6)..(6)
<223> OTHER INFORMATION: Ser or Gly

<400> SEQUENCE: 60

Xaa Val Xaa Xaa Xaa Xaa
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly or Ala
<220> FEATURE:
<221> NAME/KEY: MOD_RES
<222> LOCATION: (3)..(3)
<223> OTHER INFORMATION: Ala, Lys or Ser
<220> FEATURE:
<221> NAME/KEY: MOD_RES
<222> LOCATION: (4)..(4)
<223> OTHER INFORMATION: Gln or Lys
<220> FEATURE:
<221> NAME/KEY: MOD_RES
<222> LOCATION: (5)..(5)
<223> OTHER INFORMATION: Ala or Asn
<220> FEATURE:
<221> NAME/KEY: MOD_RES
<222> LOCATION: (6)..(6)
<223> OTHER INFORMATION: Leu or Ile

<400> SEQUENCE: 61

Gly Xaa Xaa Xaa Xaa Xaa
1               5

<210> SEQ ID NO 62
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid
<220> FEATURE:
<223> OTHER INFORMATION: see specification as filed for detailed
      description of substitutions and preferred embodiments

<400> SEQUENCE: 62

Phe Ser Pro Glu Asp Ile Val Ala Ile Ala Ser Xaa Xaa Gly Gly Ala
1               5                   10                  15

Gln Ala Leu Glu Ala Val Leu Asp Leu Glu Pro Ala Leu Arg Glu Arg
            20                  25                  30

Gly

<210> SEQ ID NO 63
<211> LENGTH: 33
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid
<220> FEATURE:
<223> OTHER INFORMATION: see specification as filed for detailed
      description of substitutions and preferred embodiments

<400> SEQUENCE: 63

Leu Ser Pro Glu Asp Ile Val Lys Ile Ala Gly Xaa Xaa Gly Gly Lys
1               5                   10                  15

Gln Ala Leu Gln Ala Val Leu Glu Leu Glu Pro Val Leu Cys Glu Arg
            20                  25                  30

Gly

<210> SEQ ID NO 64
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid
<220> FEATURE:
<223> OTHER INFORMATION: see specification as filed for detailed
      description of substitutions and preferred embodiments

<400> SEQUENCE: 64

Leu Thr Thr Glu Gln Ile Val Ala Met Ala Ser Xaa Xaa Gly Gly Ala
1               5                   10                  15

Lys Ala Leu Glu Ala Val Leu Asp Leu Glu Pro Ala Leu Arg Glu Arg
            20                  25                  30

His Gly

<210> SEQ ID NO 65
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid
<220> FEATURE:
<223> OTHER INFORMATION: see specification as filed for detailed
      description of substitutions and preferred embodiments

<400> SEQUENCE: 65

Phe Ser Pro Glu Asp Ile Val Ala Ile Ala Ser Xaa Xaa Gly Gly Ala
1               5                   10                  15

Gln Ala Leu Glu Ala Val Leu Asp Leu Glu Pro Ala Leu Arg Glu Arg
            20                  25                  30

His Gly Glu
        35

<210> SEQ ID NO 66
<211> LENGTH: 33
<212> TYPE: PRT
<213> ORGANISM: Artificial Sequence
<220> FEATURE:
```

-continued

<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid
<220> FEATURE:
<223> OTHER INFORMATION: see specification as filed for detailed
      description of substitutions and preferred embodiments

<400> SEQUENCE: 66

Phe Thr Pro Glu Asp Ile Val Lys Ile Ala Gly Xaa Xaa Gly Gly Lys
1               5                   10                  15

Gln Ala Leu Glu Ala Val Leu Asp Leu Glu Pro Val Leu Arg Glu Arg
            20                  25                  30

Gly

<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
atcgtagctg ttgat                                                    15

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 68
atcgnancng ttgat                                                    15

<210> SEQ ID NO 69
<211> LENGTH: 579
<212> TYPE: PRT
<213> ORGANISM: Planomicrobium okeanokoites

<400> SEQUENCE: 69

Met Val Ser Lys Ile Arg Thr Phe Gly Trp Val Gln Asn Pro Gly Lys
1               5                   10                  15

Phe Glu Asn Leu Lys Arg Val Val Gln Val Phe Asp Arg Asn Ser Lys
            20                  25                  30

Val His Asn Glu Val Lys Asn Ile Lys Ile Pro Thr Leu Val Lys Glu
        35                  40                  45

Ser Lys Ile Gln Lys Glu Leu Val Ala Ile Met Asn Gln His Asp Leu
    50                  55                  60

Ile Tyr Thr Tyr Lys Glu Leu Val Gly Thr Gly Thr Ser Ile Arg Ser

```
            65                  70                  75                  80
        Glu Ala Pro Cys Asp Ala Ile Ile Gln Ala Thr Ile Ala Asp Gln Gly
                        85                  90                  95

Asn Lys Lys Gly Tyr Ile Asp Asn Trp Ser Ser Asp Gly Phe Leu Arg
                        100                 105                 110

Trp Ala His Ala Leu Gly Phe Ile Glu Tyr Ile Asn Lys Ser Asp Ser
                        115                 120                 125

Phe Val Ile Thr Asp Val Gly Leu Ala Tyr Ser Lys Ser Ala Asp Gly
                        130                 135                 140

Ser Ala Ile Glu Lys Glu Ile Leu Ile Glu Ala Ile Ser Ser Tyr Pro
        145                 150                 155                 160

Pro Ala Ile Arg Ile Leu Thr Leu Leu Glu Asp Gly Gln His Leu Thr
                        165                 170                 175

Lys Phe Asp Leu Gly Lys Asn Leu Gly Phe Ser Gly Glu Ser Gly Phe
                        180                 185                 190

Thr Ser Leu Pro Glu Gly Ile Leu Leu Asp Thr Leu Ala Asn Ala Met
                        195                 200                 205

Pro Lys Asp Lys Gly Glu Ile Arg Asn Asn Trp Glu Gly Ser Ser Asp
                        210                 215                 220

Lys Tyr Ala Arg Met Ile Gly Gly Trp Leu Asp Lys Leu Gly Leu Val
        225                 230                 235                 240

Lys Gln Gly Lys Lys Glu Phe Ile Ile Pro Thr Leu Gly Lys Pro Asp
                        245                 250                 255

Asn Lys Glu Phe Ile Ser His Ala Phe Lys Ile Thr Gly Glu Gly Leu
                        260                 265                 270

Lys Val Leu Arg Arg Ala Lys Gly Ser Thr Lys Phe Thr Arg Val Pro
                        275                 280                 285

Lys Arg Val Tyr Trp Glu Met Leu Ala Thr Asn Leu Thr Asp Lys Glu
                        290                 295                 300

Tyr Val Arg Thr Arg Arg Ala Leu Ile Leu Glu Ile Leu Ile Lys Ala
        305                 310                 315                 320

Gly Ser Leu Lys Ile Glu Gln Ile Gln Asp Asn Leu Lys Lys Leu Gly
                        325                 330                 335

Phe Asp Glu Val Ile Glu Thr Ile Glu Asn Asp Ile Lys Gly Leu Ile
                        340                 345                 350

Asn Thr Gly Ile Phe Ile Glu Ile Lys Gly Arg Phe Tyr Gln Leu Lys
                        355                 360                 365

Asp His Ile Leu Gln Phe Val Ile Pro Asn Arg Gly Val Thr Lys Gln
                        370                 375                 380

Leu Val Lys Ser Glu Leu Glu Lys Lys Ser Glu Leu Arg His Lys
        385                 390                 395                 400

Leu Lys Tyr Val Pro His Glu Tyr Ile Glu Leu Ile Glu Ile Ala Arg
                        405                 410                 415

Asn Ser Thr Gln Asp Arg Ile Leu Glu Met Lys Val Met Glu Phe Phe
                        420                 425                 430

Met Lys Val Tyr Gly Tyr Arg Gly Lys His Leu Gly Gly Ser Arg Lys
                        435                 440                 445

Pro Asp Gly Ala Ile Tyr Thr Val Gly Ser Pro Ile Asp Tyr Gly Val
                        450                 455                 460

Ile Val Asp Thr Lys Ala Tyr Ser Gly Gly Tyr Asn Leu Pro Ile Gly
        465                 470                 475                 480

Gln Ala Asp Glu Met Gln Arg Tyr Val Glu Glu Asn Gln Thr Arg Asn
                        485                 490                 495
```

```
Lys His Ile Asn Pro Asn Glu Trp Trp Lys Val Tyr Pro Ser Ser Val
            500                 505                 510

Thr Glu Phe Lys Phe Leu Phe Val Ser Gly His Phe Lys Gly Asn Tyr
            515                 520                 525

Lys Ala Gln Leu Thr Arg Leu Asn His Ile Thr Asn Cys Asn Gly Ala
            530                 535                 540

Val Leu Ser Val Glu Glu Leu Leu Ile Gly Gly Glu Met Ile Lys Ala
545                 550                 555                 560

Gly Thr Leu Thr Leu Glu Glu Val Arg Arg Lys Phe Asn Asn Gly Glu
            565                 570                 575

Ile Asn Phe

<210> SEQ ID NO 70
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gcttttttat actaa                                                      15

<210> SEQ ID NO 71
<211> LENGTH: 34
<212> TYPE: PRT
<213> ORGANISM: Xanthomonas campestris

<400> SEQUENCE: 71

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 72
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72 ctgaccccccg aacaggtggt ggccattgcc agcaacatcg gcggcaagca ggccctggaa    60
accgtgcaga gactgctgcc cgtgctgtgc caggcccatg gc                       102

<210> SEQ ID NO 73
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
ttgactccag aacaggtggt ggctattgct tccaatattg gggggaaaca ggccctggaa    60
actgtgcagc gcctgctgcc agtgctgtgc caggctcacg ga                      102

<210> SEQ ID NO 74
```

```
<210> SEQ ID NO 74
<211> LENGTH: 19
<212> TYPE: DNA
<213> ORGANISM: Homo sapiens

<400> SEQUENCE: 74
ttatctcaca ggtaaaact                                               19

<210> SEQ ID NO 75
<211> LENGTH: 19
<212> TYPE: DNA
<213> ORGANISM: Homo sapiens

<400> SEQUENCE: 75
tctagtcccc aatttatat                                               19

<210> SEQ ID NO 76
<211> LENGTH: 19
<212> TYPE: DNA
<213> ORGANISM: Homo sapiens

<400> SEQUENCE: 76
tctagccaga gtcttgcat                                               19

<210> SEQ ID NO 77
<211> LENGTH: 19
<212> TYPE: DNA
<213> ORGANISM: Homo sapiens

<400> SEQUENCE: 77
tcagccccag tccattacc                                               19

<210> SEQ ID NO 78
<211> LENGTH: 19
<212> TYPE: DNA
<213> ORGANISM: Homo sapiens

<400> SEQUENCE: 78
tgactgcaat ttgcatctt                                               19

<210> SEQ ID NO 79
<211> LENGTH: 19
<212> TYPE: DNA
<213> ORGANISM: Homo sapiens

<400> SEQUENCE: 79
tgaacatgaa tctcagggc                                               19

<210> SEQ ID NO 80
<211> LENGTH: 19
<212> TYPE: DNA
<213> ORGANISM: Mus sp.

<400> SEQUENCE: 80
tcgtgatctg caactccag                                               19

<210> SEQ ID NO 81
<211> LENGTH: 19
<212> TYPE: DNA
<213> ORGANISM: Mus sp.

<400> SEQUENCE: 81
tgcccagaag actcccgcc                                               19
```

```
<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala or Thr
<220> FEATURE:
<221> NAME/KEY: MOD_RES
<222> LOCATION: (5)..(5)
<223> OTHER INFORMATION: Ala or Thr

<400> SEQUENCE: 82

Gly Gly Xaa Gln Xaa Leu
1               5

<210> SEQ ID NO 83
<211> LENGTH: 6
<212> TYPE: PRT
<213> ORGANISM: Unknown
<220> FEATURE:
<223> OTHER INFORMATION: Description of Unknown:  Marine organism A
      TAL repeat structure peptide

<400> SEQUENCE: 83

Gly Gly Ser Lys Asn Leu
1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Thr or Asn
<220> FEATURE:
<221> NAME/KEY: MOD_RES
<222> LOCATION: (4)..(4)
<223> OTHER INFORMATION: Asn or Lys
<220> FEATURE:
<221> NAME/KEY: MOD_RES
<222> LOCATION: (5)..(5)
<223> OTHER INFORMATION: Ala or Thr

<400> SEQUENCE: 84

Gly Ala Xaa Xaa Xaa Ile
1               5

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any of the twenty naturally occurring amino
      acids
<220> FEATURE:
<221> NAME/KEY: MOD_RES
<222> LOCATION: (8)..(8)
<223> OTHER INFORMATION: Any of the twenty naturally occurring amino
      acids
```

```
<220> FEATURE:
<223> OTHER INFORMATION: see specification as filed for detailed
      description of substitutions and preferred embodiments

<400> SEQUENCE: 85

Gly Gly Ala Gln Ala Leu Xaa Xaa Val Leu Leu
1               5                   10

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Gly Ala Gln Ala Leu
1               5

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tacacgtttc gtgttcgga                                                19

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Lys Pro Ile Pro Asn Pro Leu Leu Gly Leu Asp Ser Thr
1               5                   10

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Gly Gly Val Thr Met
1               5

<210> SEQ ID NO 90
<211> LENGTH: 34
<212> TYPE: PRT
<213> ORGANISM: Unknown
<220> FEATURE:
<223> OTHER INFORMATION: Description of Unknown: Naturally
      occurring cassette polypeptide

<400> SEQUENCE: 90

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
```

His Gly

<210> SEQ ID NO 91
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Gly, Ile, Asp, Thr, Asn, Lys or absent

<400> SEQUENCE: 91

Leu Thr Pro Asp Gln Val Val Ala Ile Ala Ser Asn Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 92
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Ile, Asn, His or Tyr
<220> FEATURE:
<221> NAME/KEY: MOD_RES
<222> LOCATION: (13)..(13)
<223> OTHER INFORMATION: Gly, Ile, Asp, Thr, Asn, Lys or absent

<400> SEQUENCE: 92

Leu Thr Pro Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asp, Ala, Glu, Gln or Asn
<220> FEATURE:
<221> NAME/KEY: MOD_RES
<222> LOCATION: (11)..(11)
<223> OTHER INFORMATION: Ser, Ala or Asn

<400> SEQUENCE: 93

Leu Thr Pro Xaa Gln Val Val Ala Ile Ala Xaa
1               5                   10

<210> SEQ ID NO 94
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pro or Gln
<220> FEATURE:
<221> NAME/KEY: MOD_RES
<222> LOCATION: (7)..(7)
<223> OTHER INFORMATION: Glu or Gly

<400> SEQUENCE: 94

Gly Gly Lys Xaa Ala Leu Xaa
1               5

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala or Thr
<220> FEATURE:
<221> NAME/KEY: MOD_RES
<222> LOCATION: (5)..(5)
<223> OTHER INFORMATION: Ala or Thr
<220> FEATURE:
<221> NAME/KEY: MOD_RES
<222> LOCATION: (7)..(8)
<223> OTHER INFORMATION: Any amino acid except Glu or Gly
<220> FEATURE:
<221> NAME/KEY: MOD_RES
<222> LOCATION: (10)..(10)
<223> OTHER INFORMATION: Leu, Phe or Ile
<220> FEATURE:
<223> OTHER INFORMATION: see specification as filed for detailed
      description of substitutions and preferred embodiments

<400> SEQUENCE: 95

Gly Gly Xaa Gln Xaa Leu Xaa Xaa Val Xaa
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(8)
<223> OTHER INFORMATION: Any amino acid except Glu or Gly
<220> FEATURE:
<223> OTHER INFORMATION: see specification as filed for detailed
      description of substitutions and preferred embodiments

<400> SEQUENCE: 96

Gly Gly Ala Gln Ala Leu Xaa Xaa Val Leu
1               5                   10

<210> SEQ ID NO 97
<211> LENGTH: 10
<212> TYPE: PRT
<213> ORGANISM: Burkholderia sp.
```

```
<400> SEQUENCE: 97

Gly Gly Ala Gln Ala Leu Gln Ala Val Leu
1               5                   10

<210> SEQ ID NO 98
<211> LENGTH: 6
<212> TYPE: PRT
<213> ORGANISM: Burkholderia sp.

<400> SEQUENCE: 98

Gly Gly Ala Gln Ala Leu
1               5

<210> SEQ ID NO 99
<211> LENGTH: 6
<212> TYPE: PRT
<213> ORGANISM: Unknown
<220> FEATURE:
<223> OTHER INFORMATION: Description of Unknown:  Marine organism A
      TAL repeat structure peptide

<400> SEQUENCE: 99

Ile Val Gln Met Val Ser
1               5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Thr or Asn
<220> FEATURE:
<221> NAME/KEY: MOD_RES
<222> LOCATION: (4)..(4)
<223> OTHER INFORMATION: Gln or Lys
<220> FEATURE:
<221> NAME/KEY: MOD_RES
<222> LOCATION: (5)..(5)
<223> OTHER INFORMATION: Ala or Thr

<400> SEQUENCE: 100

Gly Ala Xaa Xaa Xaa Ile
1               5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pro or Gln

<400> SEQUENCE: 101

Gly Gly Lys Xaa Ala Leu
1               5

<210> SEQ ID NO 102
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala or Thr
<220> FEATURE:
<221> NAME/KEY: MOD_RES
<222> LOCATION: (5)..(5)
<223> OTHER INFORMATION: Ala or Thr

<400> SEQUENCE: 102

Gly Gly Xaa Gln Xaa Leu
1               5

<210> SEQ ID NO 103
<211> LENGTH: 9
<212> TYPE: PRT
<213> ORGANISM: Unknown
<220> FEATURE:
<223> OTHER INFORMATION: Description of Unknown:  Marine organism
      TAL repeat structure peptide

<400> SEQUENCE: 103

Pro Lys Asp Ile Val Ser Ile Ala Ser
1               5

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys or Arg

<400> SEQUENCE: 104

Gly Gly Xaa Gln Ala Leu
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala or Val
<220> FEATURE:
<221> NAME/KEY: MOD_RES
<222> LOCATION: (7)..(7)
<223> OTHER INFORMATION: Ser or Asn

<400> SEQUENCE: 105

Gln Val Val Xaa Ile Ala Xaa
1               5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 106

Cys Cys Pro Gly Cys Cys
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Pro Lys Lys Lys Arg Lys Val
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Pro Lys Lys Lys Arg Lys Val Glu
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Pro Lys Lys Lys Arg Lys Val Asp
1               5

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Ser Ala Phe Ala Pro
1               5

<210> SEQ ID NO 111
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111 tgaccccga acaggtggtg gccattgcca gcaacatcgg cggcaagcag gccctggaaa      60
ccgtgcagag actgctgccc gtgctgtgcc aggcccatgg                          100

<210> SEQ ID NO 112

```
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
tgactccaga acaggtggtg gctattgctt ccaatattgg ggggaaacag gccctggaaa      60
ctgtgcagcg cctgctgcca gtgctgtgcc aggctcacgg                          100

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tcttctgcac cggtatgcg                                                  19

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tattctggga cgttgtacg                                                  19

<210> SEQ ID NO 115
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
attcaggtac                                                            10

<210> SEQ ID NO 116
<211> LENGTH: 33
<212> TYPE: PRT
<213> ORGANISM: Xanthomonas oryzae

<400> SEQUENCE: 116

Leu Thr Pro Asp Gln Val Val Ala Ile Ala Ser Asn Gly Gly Lys Gln
1               5                   10                  15

Ala Leu Glu Thr Val Gln Arg Leu Leu Pro Val Leu Cys Gln Ala His
            20                  25                  30

Gly

<210> SEQ ID NO 117
<211> LENGTH: 34
<212> TYPE: PRT
<213> ORGANISM: Xanthomonas oryzae

<400> SEQUENCE: 117

Leu Thr Pro Ala Gln Val Val Ala Ile Ala Ser Asn Ile Gly Gly Lys
1               5                   10                  15
```

Gln Ala Leu Glu Thr Val Gln Arg Leu Leu Pro Val Leu Cys Arg Ala
            20                  25                  30

His Gly

<210> SEQ ID NO 118
<211> LENGTH: 34
<212> TYPE: PRT
<213> ORGANISM: Xanthomonas campestris

<400> SEQUENCE: 118

Leu Thr Pro Gln Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 119
<211> LENGTH: 35
<212> TYPE: PRT
<213> ORGANISM: Ralstonia solanacearum

<400> SEQUENCE: 119

Leu Thr Pro Gln Gln Val Val Ala Ile Ala Ala Asn Thr Gly Gly Lys
1               5                   10                  15

Gln Ala Leu Gly Ala Ile Thr Thr Gln Leu Pro Ile Leu Arg Ala Ala
            20                  25                  30

Pro Tyr Glu
        35

<210> SEQ ID NO 120
<211> LENGTH: 35
<212> TYPE: PRT
<213> ORGANISM: Ralstonia solanacearum

<400> SEQUENCE: 120

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Val Leu Arg Ala Ala
            20                  25                  30

Pro Tyr Gly
        35

<210> SEQ ID NO 121
<211> LENGTH: 35
<212> TYPE: PRT
<213> ORGANISM: Ralstonia solanacearum

<400> SEQUENCE: 121

Leu Ser Pro Glu Gln Val Val Ala Ile Ala Ser Asn Asn Gly Gly Lys
1               5                   10                  15

Pro Ala Leu Glu Ala Val Lys Ala Gln Leu Leu Glu Leu Arg Ala Ala
            20                  25                  30

Pro Tyr Glu
        35

<210> SEQ ID NO 122
<211> LENGTH: 34
<212> TYPE: PRT
<213> ORGANISM: Xanthomonas oryzae

<400> SEQUENCE: 122

```
Leu Thr Pro Asn Gln Leu Val Ala Ile Ala Asn Asn Gly Gly Lys
1               5                   10                  15

Gln Ala Leu Glu Thr Val Gln Arg Leu Pro Val Leu Cys Gln Asp
            20                  25                  30

His Gly
```

<210> SEQ ID NO 123
<211> LENGTH: 34
<212> TYPE: PRT
<213> ORGANISM: Xanthomonas oryzae

<400> SEQUENCE: 123

```
Leu Thr Pro Asp Gln Val Val Ala Ile Ala Ser His Asp Gly Gly Lys
1               5                   10                  15

Gln Ala Leu

<400> SEQUENCE: 127

```
Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Ala Ala Gln Pro
130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285

Leu Thr Pro Glu Gln Val Val Ala Ile Ala Ser Asn Ile Gly Gly Lys
290                 295                 300

Gln Ala Leu Glu Thr Val Gln Arg Leu Leu Pro Val Leu Cys Gln Ala
305                 310                 315                 320

His Gly Leu Thr Pro Gln Gln Val Val Ala Ile Ala Ser His Asp Gly
                325                 330                 335

Gly Lys Gln Ala Leu Glu Thr Val Gln Arg Leu Leu Pro Val Leu Cys
            340                 345                 350

Gln Ala His Gly Leu Thr Pro Glu Gln Val Val Ala Ile Ala Ser Asn
        355                 360                 365

Ile Gly Gly Lys Gln Ala Leu Glu Thr Val Gln Ala Leu Leu Pro Val
370                 375                 380

Leu Cys Gln Ala His Gly Leu Thr Pro Glu Gln Val Val Ala Ile Ala
385                 390                 395                 400

Ser His Asp Gly Gly Lys Gln Ala Leu Glu Thr Val Gln Arg Leu Leu
                405                 410                 415
```

```
Pro Val Leu Cys Gln Ala His Gly Leu Thr Pro Gln Gln Val Val Ala
            420                 425                 430

Ile Ala Ser His Asp Gly Gly Lys Gln Ala Leu Glu Thr Val Gln Arg
        435                 440                 445

Leu Leu Pro Val Leu Cys Gln Ala His Gly Leu Thr Pro Gln Gln Val
450                 455                 460

Val Ala Ile Ala Ser His Asp Gly Gly Lys Gln Ala Leu Glu Thr Val
465                 470                 475                 480

Gln Arg Leu Leu Pro Val Leu Cys Gln Ala His Gly Leu Thr Pro Gln
                485                 490                 495

Gln Val Val Ala Ile Ala Ser Asn Ser Gly Gly Lys Gln Ala Leu Glu
            500                 505                 510

Thr Val Gln Arg Leu Leu Pro Val Leu Cys Gln Ala His Gly Leu Thr
        515                 520                 525

Pro Gln Gln Val Val Ala Ile Ala Ser Asn Ser Gly Gly Lys Gln Ala
530                 535                 540

Leu Glu Thr Val Gln Arg Leu Leu Pro Val Leu Cys Gln Ala His Gly
545                 550                 555                 560

Leu Thr Pro Gln Gln Val Val Ala Ile Ala Ser Asn Ser Gly Gly Lys
                565                 570                 575

Gln Ala Leu Glu Thr Val Gln Arg Leu Leu Pro Val Leu Cys Gln Ala
            580                 585                 590

His Gly Leu Thr Pro Glu Gln Val Val Ala Ile Ala Ser His Asp Gly
        595                 600                 605

Gly Lys Gln Ala Leu Glu Thr Val Gln Arg Leu Leu Pro Val Leu Cys
610                 615                 620

Gln Ala His Gly Leu Thr Pro Glu Gln Val Val Ala Ile Ala Ser Asn
625                 630                 635                 640

Ile Gly Gly Lys Gln Ala Leu Glu Thr Val Gln Arg Leu Leu Pro Val
                645                 650                 655

Leu Cys Gln Ala His Gly Leu Thr Pro Gln Gln Val Val Ala Ile Ala
            660                 665                 670

Ser Asn Gly Gly Gly Arg Pro Ala Leu Glu Ser Ile Val Ala Gln Leu
        675                 680                 685

Ser Arg Pro Asp Pro Ala Leu Ala Ala Leu Thr Asn Asp His Leu Val
690                 695                 700

Ala Leu Ala Cys Leu Gly Gly Arg Pro Ala Leu Asp Ala Val Lys Lys
705                 710                 715                 720

Gly Leu Pro His Ala Pro Ala Leu Ile Lys Arg Thr Asn Arg Arg Ile
                725                 730                 735

Pro Glu Arg Thr Ser His Arg Val Ala Asp His Ala Gln Val Val Arg
            740                 745                 750

Val Leu Gly Phe Phe Gln Cys His Ser His Pro Ala Gln Ala Phe Asp
        755                 760                 765

Asp Ala Met Thr Gln Phe Gly Met Ser Arg His Gly Leu Leu Gln Leu
770                 775                 780

Phe Arg Arg Val Gly Val Thr Glu Leu Glu Ala Arg Ser Gly Thr Leu
785                 790                 795                 800

Pro Pro Ala Ser Gln Arg Trp Asp Arg Ile Leu Gln Ala Ser Gly Met
                805                 810                 815

Lys Arg Ala Lys Pro Ser Pro Thr Ser Thr Gln Thr Pro Asp Gln Ala
            820                 825                 830
```

Ser Leu His Ala Phe Ala Asp Ser Leu Glu Arg Asp Leu Asp Ala Pro
835                 840                 845

Ser Pro Met His Glu Gly Asp Gln Thr Arg Ala Ser Ser Arg Lys Arg
850                 855                 860

Ser Arg Ser Asp Arg Ala Val Thr Gly Pro Ser Ala Gln Gln Ser Phe
865                 870                 875                 880

Glu Val Arg Val Pro Glu Gln Arg Asp Ala Leu His Leu Pro Leu Leu
                885                 890                 895

Ser Trp Gly Val Lys Arg Pro Arg Thr Arg Ile Gly Leu Leu Asp
                900                 905                 910

Pro Gly Thr Pro Met Asp Ala Asp Leu Val Ala Ser Ser Thr Val Val
                915                 920                 925

Trp Glu Gln Asp Ala Asp Pro Phe Ala Gly Thr Ala Asp Asp Phe Pro
930                 935                 940

Ala Phe Asn Glu Glu Glu Leu Ala Trp Leu Met Glu Leu Leu Pro Gln
945                 950                 955                 960

<210> SEQ ID NO 128
<211> LENGTH: 1024
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Gly Lys Pro Ile Pro Asn Pro Leu Leu Gly Leu Asp Ser Thr Gly
1               5                   10                  15

Gly Met Ala Pro Lys Lys Arg Lys Val Asp Gly Gly Val Asp Leu
                20                  25                  30

Arg Thr Leu Gly Tyr Ser Gln Gln Gln Glu Lys Ile Lys Pro Lys
                35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
                100                 105                 110

Arg Ala Leu Glu Ala Leu Leu Thr Val Ala Gly Glu Leu Arg Gly Pro
            115                 120                 125

Pro Leu Gln Leu Asp Thr Gly Gln Leu Leu Lys Ile Ala Lys Arg Gly
        130                 135                 140

Gly Val Thr Ala Val Glu Ala Val His Ala Trp Arg Asn Ala Leu Thr
145                 150                 155                 160

Gly Ala Pro Leu Asn Leu Thr Pro Glu Gln Val Val Ala Ile Ala Ser
                165                 170                 175

Asn Ile Gly Gly Lys Gln Ala Leu Glu Thr Val Gln Arg Leu Leu Pro
                180                 185                 190

Val Leu Cys Gln Ala His Gly Leu Thr Pro Glu Gln Val Val Ala Ile
            195                 200                 205

Ala Ser His Asp Gly Gly Lys Gln Ala Leu Glu Thr Val Gln Arg Leu
        210                 215                 220

Leu Pro Val Leu Cys Gln Ala His Gly Leu Thr Pro Glu Gln Val Val
225                 230                 235                 240

```
Ala Ile Ala Ser Asn Ile Gly Gly Lys Gln Ala Leu Glu Thr Val Gln
                245             250                 255

Arg Leu Leu Pro Val Leu Cys Gln Ala His Gly Leu Thr Pro Glu Gln
            260                 265                 270

Val Val Ala Ile Ala Ser His Asp Gly Gly Lys Gln Ala Leu Glu Thr
        275                 280                 285

Val Gln Arg Leu Leu Pro Val Leu Cys Gln Ala His Gly Leu Thr Pro
    290                 295                 300

Glu Gln Val Val Ala Ile Ala Ser Asn Lys Gly Gly Lys Gln Ala Leu
305                 310                 315                 320

Glu Thr Val Gln Arg Leu Leu Pro Val Leu Cys Gln Ala His Gly Leu
                325                 330                 335

Thr Pro Glu Gln Val Val Ala Ile Ala Ser Asn Gly Gly Gly Lys Gln
            340                 345                 350

Ala Leu Glu Thr Val Gln Arg Leu Leu Pro Val Leu Cys Gln Ala His
        355                 360                 365

Gly Leu Thr Pro Glu Gln Val Val Ala Ile Ala Ser Asn Gly Gly Gly
    370                 375                 380

Lys Gln Ala Leu Glu Thr Val Gln Arg Leu Leu Pro Val Leu Cys Gln
385                 390                 395                 400

Ala His Gly Leu Thr Pro Glu Gln Val Val Ala Ile Ala Ser Asn Gly
                405                 410                 415

Gly Gly Lys Gln Ala Leu Glu Thr Val Gln Arg Leu Leu Pro Val Leu
            420                 425                 430

Cys Gln Ala His Gly Leu Thr Pro Glu Gln Val Val Ala Ile Ala Ser
        435                 440                 445

His Asp Gly Gly Lys Gln Ala Leu Glu Thr Val Gln Arg Leu Leu Pro
    450                 455                 460

Val Leu Cys Gln Ala His Gly Leu Thr Pro Glu Gln Val Val Ala Ile
465                 470                 475                 480

Ala Ser Asn Lys Gly Gly Lys Gln Ala Leu Glu Thr Val Gln Arg Leu
                485                 490                 495

Leu Pro Val Leu Cys Gln Ala His Gly Leu Thr Pro Glu Gln Val Val
            500                 505                 510

Ala Ile Ala Ser Asn Gly Gly Gly Lys Gln Ala Leu Glu Thr Val Gln
        515                 520                 525

Arg Leu Leu Pro Val Leu Cys Gln Ala His Gly Leu Thr Pro Glu Gln
    530                 535                 540

Val Val Ala Ile Ala Ser Asn Lys Gly Gly Lys Gln Ala Leu Glu Thr
545                 550                 555                 560

Val Gln Arg Leu Leu Pro Val Leu Cys Gln Ala His Gly Leu Thr Pro
                565                 570                 575

Glu Gln Val Val Ala Ile Ala Ser Asn Gly Gly Gly Lys Gln Ala Leu
            580                 585                 590

Glu Thr Val Gln Arg Leu Leu Pro Val Leu Cys Gln Ala His Gly Leu
        595                 600                 605

Thr Pro Glu Gln Val Val Ala Ile Ala Ser Asn Gly Gly Gly Lys Gln
    610                 615                 620

Ala Leu Glu Thr Val Gln Arg Leu Leu Pro Val Leu Cys Gln Ala His
625                 630                 635                 640

Gly Leu Thr Pro Glu Gln Val Val Ala Ile Ala Ser His Asp Gly Gly
                645                 650                 655
```

Lys Gln Ala Leu Glu Thr Val Gln Arg Leu Leu Pro Val Leu Cys Gln
                660                 665                 670

Ala His Gly Leu Thr Pro Glu Gln Val Val Ala Ile Ala Ser Asn Lys
        675                 680                 685

Gly Gly Lys Gln Ala Leu Glu Thr Val Gln Arg Leu Leu Pro Val Leu
690                 695                 700

Cys Gln Ala His Gly Leu Thr Pro Glu Gln Val Val Ala Ile Ala Ser
705                 710                 715                 720

Asn Lys Gly Gly Lys Gln Ala Leu Glu Thr Val Gln Arg Leu Leu Pro
            725                 730                 735

Val Leu Cys Gln Ala His Gly Leu Thr Pro Gln Gln Val Val Ala Ile
                740                 745                 750

Ala Ser Asn Ile Gly Gly Arg Pro Ala Leu Glu Ser Ile Val Ala Gln
                755                 760                 765

Leu Ser Arg Pro Asp Pro Ala Leu Ala Ala Leu Thr Asn Asp His Leu
        770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gln Leu Val Lys
                820                 825                 830

Ser Glu Leu Glu Glu Lys Lys Ser Glu Leu Arg His Lys Leu Lys Tyr
        835                 840                 845

Val Pro His Glu Tyr Ile Glu Leu Ile Glu Ile Ala Arg Asn Ser Thr
    850                 855                 860

Gln Asp Arg Ile Leu Glu Met Lys Val Met Glu Phe Phe Met Lys Val
865                 870                 875                 880

Tyr Gly Tyr Arg Gly Lys His Leu Gly Gly Ser Arg Lys Pro Asp Gly
                885                 890                 895

Ala Ile Tyr Thr Val Gly Ser Pro Ile Asp Tyr Gly Val Ile Val Asp
                900                 905                 910

Thr Lys Ala Tyr Ser Gly Gly Tyr Asn Leu Pro Ile Gly Gln Ala Asp
        915                 920                 925

Glu Met Gln Arg Tyr Val Glu Glu Asn Gln Thr Arg Asn Lys His Ile
    930                 935                 940

Asn Pro Asn Glu Trp Trp Lys Val Tyr Pro Ser Ser Val Thr Glu Phe
945                 950                 955                 960

Lys Phe Leu Phe Val Ser Gly His Phe Lys Gly Asn Tyr Lys Ala Gln
                965                 970                 975

Leu Thr Arg Leu Asn His Ile Thr Asn Cys Asn Gly Ala Val Leu Ser
            980                 985                 990

Val Glu Glu Leu Leu Ile Gly Gly Glu Met Ile Lys Ala Gly Thr Leu
        995                 1000                1005

Thr Leu Glu Glu Val Arg Arg Lys Phe Asn Asn Gly Glu Ile Asn
    1010                1015                1020

Phe

<210> SEQ ID NO 129
<211> LENGTH: 43
<212> TYPE: DNA
<213> ORGANISM: Artificial Sequence
<220> FEATURE:
<223> OTHER INFORMATION: Description of Artificial Sequence: Synthetic
    oligonucleotide

```
<220> FEATURE:
<221> NAME/KEY: modified_base
<222> LOCATION: (10)..(34)
<223> OTHER INFORMATION: a, c, t, g, unknown or other

<400> SEQUENCE: 129
gcatactcgn nnnnnnnnnn nnnnnnnnnn nnnncgagta tgc                    43

<210> SEQ ID NO 130
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(34)
<223> OTHER INFORMATION: a, c, t, g, unknown or other

<400> SEQUENCE: 130
gaccatccgn nnnnnnnnnn nnnnnnnnnn nnnncggatg gtc                    43

<210> SEQ ID NO 131
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
aatacggcta gc                                                      12

<210> SEQ ID NO 132
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
cgtgtgaaag gc                                                      12

<210> SEQ ID NO 133
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cgtttaaaca agcttgtcga cggtaccgaa ttcatcgata gtactctcga gggatccgag  60
ctcaagatct                                                         70

<210> SEQ ID NO 134
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
agatcttgag ctcggatccc tcgagagtac tatcgatgaa ttcggtaccg tcgacaagct  60
```
tgtttaaacg                                                                70

<210> SEQ ID NO 135
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 135
nnnnatgcag tatgtcatgg tacgt                                               25

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tcgtaccatg acatactgca t                                                   21

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(25)
<223> OTHER INFORMATION: a, c, t, g, unknown or other

<400> SEQUENCE: 137
tcgtaccatg acatactgca tnnnn                                               25

<210> SEQ ID NO 138
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
caattcgcgc taacttacat taattgcgtt gcgctcactg cccgctttcc agtcgggaaa         60
cctgtcgtgc cagctgcatt aatgaatcgg ccaacgcgcg gggagaggcg gtttgcgtat        120
tgggcgccag ggtggttttt cttttcacca gtgagacggg caacagctga ttgcccttca        180
ccgcctggcc ctgagagagt tgcagcaagc ggtccacgct ggtttgcccc agcaggcgaa        240
aatcctgttt gatggtggtt gacggcggga tataacatga gctgtcttcg gtatcgtcgt        300
atcccactac cgagatatcc gcaccaacgc gcagcccgga ctcggtaatg gcgcgcattg        360
cgcccagcgc catctgatcg ttggcaacca gcatcgcagt gggaacgatg ccctcattca        420
gcatttgcat ggtttgttga aaaccggaca tggcactcca gtcgccttcc cgttccgcta        480
tcggctgaat ttgattgcga gtgagatatt tatgccagcc agccagacgc agacgcgccg        540

```
agacagaact taatgggccc gctaacagcg cgatttgctg gtgacccaat gcgaccagat    600
gctccacgcc cagtcgcgta ccgtcttcat gggagaaaat aatactgttg atgggtgtct    660
ggtcagagac atcaagaaat aacgccggaa cattagtgca ggcagcttcc acagcaatgg    720
catcctggtc atccagcgga tagttaatga tcagcccact gacgcgttgc gcagaagat     780 tgtgcaccgc cgctttacag gcttcgacgc cgcttcgttc taccatcgac accaccacgc    840
tggcacccag ttgatcggcg cgagatttaa tcgccgcgac aatttgcgac ggcgcgtgca    900
gggccagact ggaggtggca acgccaatca gcaacgactg tttgcccgcc agttgttgtg    960
ccacgcggtt gggaatgtaa ttcagctccg ccatcgccgc ttccactttt tcccgcgttt    1020
tcgcagaaac gtggctggcc tggttcacca                                    1050
```

<210> SEQ ID NO 139
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other

<400> SEQUENCE: 139
cgtctcnnnn nn                                                       12

<210> SEQ ID NO 140
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other

<400> SEQUENCE: 140
nnnnnngaga cg                                                       12

<210> SEQ ID NO 141
<211> LENGTH: 19
<212> TYPE: DNA
<213> ORGANISM: Xanthomonas sp.
<220> FEATURE:
<221> NAME/KEY: CDS
<222> LOCATION: (8)..(19)

<400> SEQUENCE: 141 ccatggc ctg acc ccg gag                                             19
        Leu Thr Pro Glu
          1

<210> SEQ ID NO 142
<211> LENGTH: 4
<212> TYPE: PRT
<213> ORGANISM: Xanthomonas sp.

<400> SEQUENCE: 142

Leu Thr Pro Glu
1

```
<210> SEQ ID NO 143
<211> LENGTH: 15
<212> TYPE: DNA
<213> ORGANISM: Xanthomonas sp.
<220> FEATURE:
<221> NAME/KEY: CDS
<222> LOCATION: (1)..(15)

<400> SEQUENCE: 143 gcc agc aat att ggt                                    15
Ala Ser Asn Ile Gly
1               5

<210> SEQ ID NO 144
<211> LENGTH: 5
<212> TYPE: PRT
<213> ORGANISM: Xanthomonas sp.

<400> SEQUENCE: 144

Ala Ser Asn Ile Gly
1               5

<210> SEQ ID NO 145
<211> LENGTH: 15
<212> TYPE: DNA
<213> ORGANISM: Xanthomonas sp.
<220> FEATURE:
<221> NAME/KEY: CDS
<222> LOCATION: (1)..(15)

<400> SEQUENCE: 145 gcg ctg gag acg gtg                                    15
Ala Leu Glu Thr Val
1               5

<210> SEQ ID NO 146
<211> LENGTH: 5
<212> TYPE: PRT
<213> ORGANISM: Xanthomonas sp.

<400> SEQUENCE: 146

Ala Leu Glu Thr Val
1               5

<210> SEQ ID NO 147
<211> LENGTH: 12
<212> TYPE: DNA
<213> ORGANISM: Xanthomonas sp.
<220> FEATURE:
<221> NAME/KEY: CDS
<222> LOCATION: (1)..(12)

<400> SEQUENCE: 147 cag gcc cat ggc                                        12
Gln Ala His Gly
1

<210> SEQ ID NO 148
<211> LENGTH: 4
<212> TYPE: PRT
<213> ORGANISM: Xanthomonas sp.

<400> SEQUENCE: 148

Gln Ala His Gly
1

<210> SEQ ID NO 149
```

```
<211> LENGTH: 15
<212> TYPE: DNA
<213> ORGANISM: Xanthomonas sp.
<220> FEATURE:
<221> NAME/KEY: CDS
<222> LOCATION: (1)..(15)

<400> SEQUENCE: 149 gcc agc aat ggc ggt                                                15
Ala Ser Asn Gly Gly
1               5

<210> SEQ ID NO 150
<211> LENGTH: 5
<212> TYPE: PRT
<213> ORGANISM: Xanthomonas sp.

<400> SEQUENCE: 150

Ala Ser Asn Gly Gly
1               5

<210> SEQ ID NO 151
<211> LENGTH: 15
<212> TYPE: DNA
<213> ORGANISM: Xanthomonas sp.
<220> FEATURE:
<221> NAME/KEY: CDS
<222> LOCATION: (1)..(15)

<400> SEQUENCE: 151 gcc agc cac gat ggt                                                15
Ala Ser His Asp Gly
1               5

<210> SEQ ID NO 152
<211> LENGTH: 5
<212> TYPE: PRT
<213> ORGANISM: Xanthomonas sp.

<400> SEQUENCE: 152

Ala Ser His Asp Gly
1               5

<210> SEQ ID NO 153
<211> LENGTH: 15
<212> TYPE: DNA
<213> ORGANISM: Xanthomonas sp.
<220> FEATURE:
<221> NAME/KEY: CDS
<222> LOCATION: (1)..(15)

<400> SEQUENCE: 153 gcc agc aat agc ggt                                                15
Ala Ser Asn Ser Gly
1               5

<210> SEQ ID NO 154
<211> LENGTH: 5
<212> TYPE: PRT
<213> ORGANISM: Xanthomonas sp.

<400> SEQUENCE: 154

Ala Ser Asn Ser Gly
1               5

<210> SEQ ID NO 155
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tactgtcctc cgag                                                       14

<210> SEQ ID NO 156
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tatgcgggtc tctt                                                       14

<210> SEQ ID NO 157
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
aacgtcccag aata                                                       14

<210> SEQ ID NO 158
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
acaggacccg cata                                                       14

<210> SEQ ID NO 159
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tattctggga cgtt                                                       14

<210> SEQ ID NO 160
<211> LENGTH: 33
<212> TYPE: PRT
<213> ORGANISM: Burkholderia rhizoxinica

<400> SEQUENCE: 160

Phe Ser Arg Ala Asp Ile Val Arg Ile Ala Gly Asn Gly Gly Gly Ala
1               5                   10                  15

Gln Ala Leu Tyr Ser Val Leu Asp Val Glu Pro Thr Leu Gly Lys Arg
            20                  25                  30

Gly
```

<210> SEQ ID NO 161
<211> LENGTH: 33
<212> TYPE: PRT
<213> ORGANISM: Burkholderia rhizoxinica

<400> SEQUENCE: 161

```
Phe Asn Gln Ala Thr Ile Val Lys Ile Ala Ala Asn Gly Gly Gly Ala
1               5                   10                  15

Gln Ala Leu Tyr Ser Val Leu Asp Val Glu Pro Thr Leu Asp Lys Arg
            20                  25                  30

Gly
```

<210> SEQ ID NO 162
<211> LENGTH: 33
<212> TYPE: PRT
<213> ORGANISM: Burkholderia rhizoxinica

<400> SEQUENCE: 162

```
Phe Ser Arg Gly Asp Ile Val Thr Ile Ala Gly Asn Asn Gly Gly Ala
1               5                   10                  15

Gln Ala Leu Gln Ala Val Leu Glu Leu Glu Pro Thr Leu Arg Glu Arg
            20                  25                  30

Gly
```

<210> SEQ ID NO 163
<211> LENGTH: 33
<212> TYPE: PRT
<213> ORGANISM: Burkholderia rhizoxinica

<400> SEQUENCE: 163

```
Phe Asn Gln Ala Asp Ile Val Lys Ile Ala Gly Asn Gly Gly Gly Ala
1               5                   10                  15

Gln Ala Leu Gln Ala Val Leu Asp Val Glu Pro Ala Leu Gly Lys Arg
            20                  25                  30

Gly
```

<210> SEQ ID NO 164
<211> LENGTH: 33
<212> TYPE: PRT
<213> ORGANISM: Burkholderia rhizoxinica

<400> SEQUENCE: 164

```
Phe Asn Pro Thr Asp Ile Val Lys Ile Ala Gly Asn Lys Gly Gly Ala
1               5                   10                  15

Gln Ala Leu Gln Ala Val Leu Glu Leu Glu Pro Ala Leu Arg Glu Arg
            20                  25                  30

Gly
```

<210> SEQ ID NO 165
<211> LENGTH: 33
<212> TYPE: PRT
<213> ORGANISM: Burkholderia rhizoxinica

<400> SEQUENCE: 165

```
Phe His Pro Thr Asp Ile Ile Lys Ile Ala Gly Asn Asn Gly Gly Ala
1               5                   10                  15

Gln Ala Leu Gln Ala Val Leu Asp Leu Glu Leu Met Leu Arg Glu Arg
            20                  25                  30

Gly

<210> SEQ ID NO 166
<211> LENGTH: 33
<212> TYPE: PRT
<213> ORGANISM: Burkholderia rhizoxinica

<400> SEQUENCE: 166

Phe Ser Gln Ala Asp Ile Val Lys Met Ala Ser Asn Ile Gly Gly Ala
1               5                   10                  15

Gln Ala Leu Gln Ala Val Leu Asn Leu Glu Pro Ala Leu Cys Glu Arg
            20                  25                  30

Gly

<210> SEQ ID NO 167
<211> LENGTH: 33
<212> TYPE: PRT
<213> ORGANISM: Burkholderia rhizoxinica

<400> SEQUENCE: 167

Phe Ser Gln Pro Asp Ile Val Lys Met Ala Gly Asn Ser Gly Gly Ala
1               5                   10                  15

Gln Ala Leu Gln Ala Val Leu Asp Leu Glu Leu Ala Phe Arg Glu Arg
            20                  25                  30

Gly

<210> SEQ ID NO 168
<211> LENGTH: 33
<212> TYPE: PRT
<213> ORGANISM: Burkholderia rhizoxinica

<400> SEQUENCE: 168

Phe Ser Gln Ala Asp Ile Val Lys Met Ala Ser Asn Ile Gly Gly Ala
1               5                   10                  15

Gln Ala Leu Gln Ala Val Leu Glu Leu Glu Pro Ala Leu His Glu Arg
            20                  25                  30

Gly

<210> SEQ ID NO 169
<211> LENGTH: 33
<212> TYPE: PRT
<213> ORGANISM: Burkholderia rhizoxinica

<400> SEQUENCE: 169

Phe Ser Gln Ala Asn Ile Val Lys Met Ala Gly Asn Ser Gly Gly Ala
1               5                   10                  15

Gln Ala Leu Gln Ala Val Leu Asp Leu Glu Leu Val Phe Arg Glu Arg
            20                  25                  30

Gly

<210> SEQ ID NO 170
<211> LENGTH: 33
<212> TYPE: PRT
<213> ORGANISM: Burkholderia rhizoxinica

<400> SEQUENCE: 170

Phe Ser Gln Pro Glu Ile Val Glu Met Ala Gly Asn Ile Gly Gly Ala
1               5                   10                  15

Gln Ala Leu His Thr Val Leu Asp Leu Glu Leu Ala Phe Arg Glu Arg
            20                  25                  30

Gly

<210> SEQ ID NO 171
<211> LENGTH: 33
<212> TYPE: PRT
<213> ORGANISM: Burkholderia rhizoxinica

<400> SEQUENCE: 171

Val Arg Gln Ala Asp Ile Val Lys Ile Val Gly Asn Asn Gly Gly Ala
1               5                   10                  15

Gln Ala Leu Gln Ala Val Phe Glu Leu Glu Pro Thr Leu Arg Glu Arg
            20                  25                  30

Gly

<210> SEQ ID NO 172
<211> LENGTH: 33
<212> TYPE: PRT
<213> ORGANISM: Burkholderia rhizoxinica

<400> SEQUENCE: 172

Phe Asn Gln Ala Thr Ile Val Lys Met Ala Gly Asn Ala Gly Gly Ala
1               5                   10                  15

Gln Ala Leu Tyr Ser Val Le

Gly

<210> SEQ ID NO 176
<211> LENGTH: 33
<212> TYPE: PRT
<213> ORGANISM: Burkholderia rhizoxinica

<400> SEQUENCE: 176

Phe Ser Gln Pro Asp Ile Val Glu Met Ala Gly Asn Ile Gly Gly Ala
1               5                   10                  15

Gln Ala Leu Gln Ala Val Leu Glu Leu Glu Pro Ala Phe Arg Glu Arg
            20                  25                  30

Gly

<210> SEQ ID NO 177
<211> LENGTH: 33
<212> TYPE: PRT
<213> ORGANISM: Burkholderia rhizoxinica

<400> SEQUENCE: 177

Phe Ser Gln Ser Asp Ile Val Lys Ile Ala Gly Asn Ile Gly Gly Ala
1               5                   10                  15

Gln Ala Leu Gln Ala Val Leu Glu Leu Glu Pro Thr Leu Arg Glu Ser
            20                  25                  30

Asp

<210> SEQ ID NO 178
<211> LENGTH: 33
<212> TYPE: PRT
<213> ORGANISM: Burkholderia rhizoxinica

<400> SEQUENCE: 178

Phe Ser Gln Ser Asp Ile Val Lys Ile Ala Gly Asn Ile Gly Gly Ala
1               5                   10                  15

Gln Ala Leu Gln Ala Val Leu Asp Leu Glu Ser Met Leu Gly Lys Arg
            20                  25                  30

Gly

<210> SEQ ID NO 179
<211> LENGTH: 33
<212> TYPE: PRT
<213> ORGANISM: Burkholderia rhizoxinica

<400> SEQUENCE: 179

Phe Ser Arg Asp Asp Ile Ala Lys Met Ala Gly Asn Ile Gly Gly Ala
1               5                   10                  15

Gln Thr Leu Gln Ala Val Leu Asp Leu Glu Ser Ala Phe Arg Glu Arg
            20                  25                  30

Gly

<210> SEQ ID NO 180
<211> LENGTH: 33
<212> TYPE: PRT
<213> ORGANISM: Burkholderia rhizoxinica

<400> SEQUENCE: 180

Phe Ser Gln Ala Asp Ile Val Lys Ile Ala Gly Asn Asn Gly Gly Ala
1               5                   10                  15

Gln Ala Leu Tyr Ser Val Leu Asp Val Glu Pro Thr Leu Gly Lys Arg
            20                  25                  30

<210> SEQ ID NO 181
<211> LENGTH: 33
<212> TYPE: PRT
<213> ORGANISM: Burkholderia rhizoxinica

<400> SEQUENCE: 181

Phe Ser Arg Ala Asp Ile Val Lys Ile Ala Gly Asn Thr Gly Ala
1               5                   10                  15
Gln Ala Leu His Thr Val Leu Asp Leu Glu Pro Ala Leu Gly Lys Arg
            20                  25                  30
Gly

<210> SEQ ID NO 182
<211> LENGTH: 33
<212> TYPE: PRT
<213> ORGANISM: Burkholderia rhizoxinica

<400> SEQUENCE: 182

Phe Ser Arg Ile Asp Ile Val Lys Ile Ala Ala Asn Asn Gly Gly Ala
1               5                   10                  15
Gln Ala Leu His Ala Val Leu Asp Leu Gly Pro Thr Leu Arg Glu Cys
            20                  25                  30
Gly

<210> SEQ ID NO 183
<211> LENGTH: 33
<212> TYPE: PRT
<213> ORGANISM: Burkholderia rhizoxinica

<400> SEQUENCE: 183

Phe Ser Gln Ala Thr Ile Ala Lys Ile Ala Gly Asn Ile Gly Gly Ala
1               5                   10                  15
Gln Ala Leu Gln Met Val Leu Asp Leu Gly Pro Ala Leu Gly Lys Arg
            20                  25                  30
Gly

<210> SEQ ID NO 184
<211> LENGTH: 33
<212> TYPE: PRT
<213> ORGANISM: Burkholderia rhizoxinica

<400> SEQUENCE: 184

Phe Ser Gln Ala Thr Ile Ala Lys Ile Ala Gly Asn Ile Gly Gly Ala
1               5                   10                  15
Gln Ala Leu Gln Thr Val Leu Asp Leu Glu Pro Ala Leu Cys Glu Arg
            20                  25                  30
Gly

<210> SEQ ID NO 185
<211> LENGTH: 33
<212> TYPE: PRT
<213> ORGANISM: Burkholderia rhizoxinica

<400> SEQUENCE: 185

Phe Ser Gln Ala Thr Ile Ala Lys Met Ala Gly Asn Asn Gly Gly Ala
1               5                   10                  15
Gln Ala Leu Gln Thr Val Leu Asp Leu Glu Pro Ala Leu Arg Lys Arg

-continued

```
                    20                  25                  30

Asp

<210> SEQ ID NO 186
<211> LENGTH: 33
<212> TYPE: PRT
<213> ORGANISM: Burkholderia rhizoxinica

<400> SEQUENCE: 186

Phe Arg Gln Ala Asp Ile Ile Lys Ile Ala Gly Asn Asp Gly Gly Ala
1               5                   10                  15

Gln Ala Leu Gln Ala Val Ile Glu His Gly Pro Thr Leu Arg Gln His
            20                  25                  30

Gly

<210> SEQ ID NO 187
<211> LENGTH: 33
<212> TYPE: PRT
<213> ORGANISM: Burkholderia rhizoxinica

<400> SEQUENCE: 187

Phe Asn Leu Ala Asp Ile Val Lys Met Ala Gly Asn Asn Gly Gly Ala
1               5                   10                  15

Gln Ala Leu Gln Ala Val Leu Asp Leu Lys Pro Val Leu Asp Glu His
            20                  25                  30

Gly

<210> SEQ ID NO 188
<211> LENGTH: 33
<212> TYPE: PRT
<213> ORGANISM: Burkholderia rhizoxinica

<400> SEQUENCE: 188

Phe Ser Gln Pro Asp Ile Val Lys Met Ala Gly Asn Ile Gly Gly Ala
1               5                   10                  15

Gln Ala Leu Gln Ala Val Leu Ser Leu Gly Pro Ala Leu Arg Glu Arg
            20                  25                  30

Gly

<210> SEQ ID NO 189
<211> LENGTH: 33
<212> TYPE: PRT
<213> ORGANISM: Burkholderia rhizoxinica

<400> SEQUENCE: 189

Phe Ser Gln Pro Asp Ile Val Lys Ile Ala Gly Asn Thr Gly Gly Ala
1               5                   10                  15

Gln Ala Leu Gln Ala Val Leu Asp Leu Glu Leu Thr Leu Val Glu His
            20                  25                  30

Gly

<210> SEQ ID NO 190
<211> LENGTH: 33
<212> TYPE: PRT
<213> ORGANISM: Burkholderia rhizoxinica

<400> SEQUENCE: 190

Phe Ser Gln Pro Asp Ile Val Arg Ile Thr Gly Asn Arg Gly Gly Ala
1               5                   10                  15
```

```
Gln Ala Leu Gln Ala Val Leu Ala Leu Glu Leu Thr Leu Arg Glu Arg
            20                  25                  30

Gly

<210> SEQ ID NO 191
<211> LENGTH: 33
<212> TYPE: PRT
<213> ORGANISM: Burkholderia rhizoxinica

<400> SEQUENCE: 191

Phe Ser Gln Pro Asp Ile Val Lys Ile Ala Gly Asn Ser Gly Gly Ala
1               5                   10                  15

Gln Ala Leu Gln Ala Val Leu Asp Leu Glu Leu Thr Phe Arg Glu Arg
            20                  25                  30

Gly

<210> SEQ ID NO 192
<211> LENGTH: 33
<212> TYPE: PRT
<213> ORGANISM: Burkholderia rhizoxinica

<400> SEQUENCE: 192

Phe Ser Gln Ala Asp Ile Val Lys Ile Ala Gly Asn Asp Gly Gly Thr
1               5                   10                  15

Gln Ala Leu His Ala Val Leu Asp Leu Glu Arg Met Leu Gly Glu Arg
            20                  25                  30

Gly

<210> SEQ ID NO 193
<211> LENGTH: 33
<212> TYPE: PRT
<213> ORGANISM: Burkholderia rhizoxinica

<400> SEQUENCE: 193

Phe Ser Arg Ala Asp Ile Val Asn Val Ala Gly Asn Asn Gly Gly Ala
1               5                   10                  15

Gln Ala Leu Lys Ala Val Leu Glu His Glu Ala Thr Leu Asn Glu Arg
            20                  25                  30

Gly

<210> SEQ ID NO 194
<211> LENGTH: 33
<212> TYPE: PRT
<213> ORGANISM: Burkholderia rhizoxinica

<400> SEQUENCE: 194

Phe Ser Arg Ala Asp Ile Val Lys Ile Ala Gly Asn Gly Gly Gly Ala
1               5                   10                  15

Gln Ala Leu Lys Ala Val Leu Glu His Glu Ala Thr Leu Asp Glu Arg
            20                  25                  30

Gly

<210> SEQ ID NO 195
<211> LENGTH: 33
<212> TYPE: PRT
<213> ORGANISM: Burkholderia rhizoxinica

<400> SEQUENCE: 195

Phe Ser Arg Ala Asp Ile Val Arg Ile Ala Gly Asn Gly Gly Gly Ala
1               5                   10                  15
```

Gln Ala Leu Lys Ala Val Leu Glu His Gly Pro Thr Leu Asn Glu Arg
            20                  25                  30

Gly

<210> SEQ ID NO 196
<211> LENGTH: 33
<212> TYPE: PRT
<213> ORGANISM: Burkholderia rhizoxinica

<400> SEQUENCE: 196

Phe Asn Leu Thr Asp Ile Val Glu Met Ala Ala Asn Ser Gly Gly Ala
1               5                   10                  15

Gln Ala Leu Lys Ala Val Leu Glu His Gly Pro Thr Leu Arg Gln Arg
            20                  25                  30

Gly

<210> SEQ ID NO 197
<211> LENGTH: 32
<212> TYPE: PRT
<213> ORGANISM: Burkholderia rhizoxinica

<400> SEQUENCE: 197

Leu Ser Leu Ile Asp Ile Val Glu Ile Ala Ser Asn Gly Gly Ala Gln
1               5                   10                  15

Ala Leu Lys Ala Val Leu Lys Tyr Gly Pro Val Leu Met Gln Ala Gly
            20                  25                  30

<210> SEQ ID NO 198
<211> LENGTH: 33
<212> TYPE: PRT
<213> ORGANISM: Unknown
<220> FEATURE:
<223> OTHER INFORMATION: Description of Unknown: Marine organism A
      TAL repeat structure peptide

<400> SEQUENCE: 198

Phe Arg Thr Glu Gly Ile Val Gln Met Val Ser His Gly Gly Gly Ser
1               5                   10                  15

Lys Asn Leu Val Ala Val Gln Ala Asn Tyr Ala Ala Leu Thr Gly Leu
            20                  25                  30

Gly

<210> SEQ ID NO 199
<211> LENGTH: 33
<212> TYPE: PRT
<213> ORGANISM: Unknown
<220> FEATURE:
<223> OTHER INFORMATION: Description of Unknown: Marine organism A
      TAL repeat structure peptide

<400> SEQUENCE: 199

Phe Arg Thr Glu Asp Ile Val Gln Met Val Ser His Asp Gly Gly Ser
1               5                   10                  15

Lys Asn Leu Val Ala Val Gln Ala Asn Tyr Ala Ala Leu Thr Gly Leu
            20                  25                  30

Gly

<210> SEQ ID NO 200
<211> LENGTH: 33
<212> TYPE: PRT
<213> ORGANISM: Unknown

```
<220> FEATURE:
<223> OTHER INFORMATION: Description of Unknown:  Marine organism A
      TAL repeat structure peptide

<400> SEQUENCE: 200

Phe Arg Thr Glu Asp Ile Val Gln Met Val Ser His Asp Gly Gly Ser
1               5                   10                  15

Lys Asn Leu Ala Ala Ile Ile Asp Lys Ser Thr Ala Leu Thr Gly Leu
            20                  25                  30

Gly

<210> SEQ ID NO 201
<211> LENGTH: 33
<212> TYPE: PRT
<213> ORGANISM: Unknown
<220> FEATURE:
<223> OTHER INFORMATION: Description of Unknown:  Marine organism A
      TAL repeat structure peptide

<400> SEQUENCE: 201

Phe Arg Thr Glu Asp Ile Val Gln Met Val Ser Asn Asn Gly Gly Ser
1               5                   10                  15

Lys Asn Leu Ala Ala Ile Ile Asp Lys Ser Thr Ala Leu Lys Gly Leu
            20                  25                  30

Gly

<210> SEQ ID NO 202
<211> LENGTH: 33
<212> TYPE: PRT
<213> ORGANISM: Unknown
<220> FEATURE:
<223> OTHER INFORMATION: Description of Unknown:  Marine organism A
      TAL repeat structure peptide

<400> SEQUENCE: 202

Phe Arg Thr Glu Asp Ile Val Gln Met Val Ser His Gly Gly Gly Ser
1               5                   10                  15

Lys Asn Leu Glu Val Val Gln Ala Asn Tyr Ala Ala Leu Thr Gly Leu
            20                  25                  30

Gly

<210> SEQ ID NO 203
<211> LENGTH: 33
<212> TYPE: PRT
<213> ORGANISM: Unknown
<220> FEATURE:
<223> OTHER INFORMATION: Description of Unknown:  Marine organism A
      TAL repeat structure peptide

<400> SEQUENCE: 203

Phe Arg Thr Glu Gly Ile Val Gln Met Val Ser His Gly Gly Gly Ser
1               5                   10                  15

Lys Asn Leu Val Ala Val Gln Ala Asn Tyr Ala Ala Leu Thr Gly Leu
            20                  25                  30

Gly

<210> SEQ ID NO 204
<211> LENGTH: 33
<212> TYPE: PRT
<213> ORGANISM: Unknown
<220> FEATURE:
<223> OTHER INFORMATION: Description of Unknown:  Marine organism A
      TAL repeat structure peptide
```

-continued

```
<400> SEQUENCE: 204

Phe Arg Thr Glu Asp Ile Val Gln Met Val Ser His Asp Gly Gly Ser
1               5                   10                  15

Lys Asn Leu Ala Ala Met Ile Asp Lys Tyr Thr Ala Leu Lys Asp Leu
            20                  25                  30

Gly

<210> SEQ ID NO 205
<211> LENGTH: 33
<212> TYPE: PRT
<213> ORGANISM: Unknown
<220> FEATURE:
<223> OTHER INFORMATION: Description of Unknown: Marine organism A
      TAL repeat structure peptide

<400> SEQUENCE: 205

Phe Arg Thr Glu Asp Ile Val Gln Met Val Ser His Asp Gly Gly Ser
1               5                   10                  15

Lys Asn Leu Ala Ala Ile Ile Asp Lys Ser Thr Ala Leu Lys Gly Leu
            20                  25                  30

Gly

<210> SEQ ID NO 206
<211> LENGTH: 33
<212> TYPE: PRT
<213> ORGANISM: Unknown
<220> FEATURE:
<223> OTHER INFORMATION: Description of Unknown: Marine organism A
      TAL repeat structure peptide

<400> SEQUENCE: 206

Phe Leu Thr Glu Asp Ile Val Gln Met Val Ser His Asp Gly Gly Ser
1               5                   10                  15

Lys Asn Leu Glu Val Val Gln Ala Ser Tyr Asp Thr Leu Thr Glu Leu
            20                  25                  30

Lys

<210> SEQ ID NO 207
<211> LENGTH: 33
<212> TYPE: PRT
<213> ORGANISM: Unknown
<220> FEATURE:
<223> OTHER INFORMATION: Description of Unknown: Marine organism B
      TAL repeat structure peptide

<400> SEQUENCE: 207

Leu Glu Pro Lys Asp Ile Val Ser Ile Ala Ser His Gly Gly Ala Thr
1               5                   10                  15

Gln Ala Ile Thr Thr Leu Leu Asn Lys Trp Asp Asp Leu Arg Asp Lys
            20                  25                  30

Gly

<210> SEQ ID NO 208
<211> LENGTH: 33
<212> TYPE: PRT
<213> ORGANISM: Unknown
<220> FEATURE:
<223> OTHER INFORMATION: Description of Unknown: Marine organism B
      TAL repeat structure peptide

<400> SEQUENCE: 208
```

```
Leu Glu Pro Lys Asp Ile Val Ser Ile Ala Ser Asn Asn Gly Ala Thr
1               5                  10                 15

Gln Ala Ile Ala Thr Leu Leu Ala Lys Trp Asp Ser Leu Ile Ala Lys
            20                 25                 30

Gly

<210> SEQ ID NO 209
<211> LENGTH: 33
<212> TYPE: PRT
<213> ORGANISM: Unknown
<220> FEATURE:
<223> OTHER INFORMATION: Description of Unknown:  Marine organism B
      TAL repeat structure peptide

<400> SEQUENCE: 209

Leu Gln Pro Lys Asp Ile Val Ser Ile Ala Ser His Gly Gly Ala Thr
1               5                  10                 15

Gln Ala Ile Thr Thr Leu Leu Asn Arg Trp Gly Asp Leu Arg Ala Lys
            20                 25                 30

Glu

<210> SEQ ID NO 210
<211> LENGTH: 33
<212> TYPE: PRT
<213> ORGANISM: Unknown
<220> FEATURE:
<223> OTHER INFORMATION: Description of Unknown:  Marine organism B
      TAL repeat structure peptide

<400> SEQUENCE: 210

Leu Glu Pro Lys Asp Ile Val Ser Ile Ala Ser His Asp Gly Ala Thr
1               5                  10                 15

Gln Ala Ile Thr Thr Leu Leu Glu Lys Trp Asp Glu Leu Arg Ala Lys
            20                 25                 30

Gly

<210> SEQ ID NO 211
<211> LENGTH: 33
<212> TYPE: PRT
<213> ORGANISM: Unknown
<220> FEATURE:
<223> OTHER INFORMATION: Description of Unknown:  Marine organism B
      TAL repeat structure peptide

<400> SEQUENCE: 211

Leu Glu Pro Lys Asp Ile Val Ser Ile Ala Ser His Ile Gly Ala Asn
1               5                  10                 15

Gln Thr Ile Thr Thr Leu Leu Asn Lys Trp Gly Ala Leu Ile Asp Leu
            20                 25                 30

Glu

<210> SEQ ID NO 212
<211> LENGTH: 33
<212> TYPE: PRT
<213> ORGANISM: Unknown
<220> FEATURE:
<223> OTHER INFORMATION: Description of Unknown:  Marine organism B
      TAL repeat structure peptide

<400> SEQUENCE: 212

Leu Glu Pro Lys Asp Ile Val Ser Ile Ala Ser His Gly Gly Ala Asn
1               5                  10                 15
```

```
Lys Ala Ile Thr Thr Leu Leu Glu Lys Trp Ala Ala Leu Arg Ala Lys
            20                  25                  30
Glu

<210> SEQ ID NO 213
<211> LENGTH: 33
<212> TYPE: PRT
<213> ORGANISM: Xanthomonas oryzae

<400> SEQUENCE: 213

Leu Thr Pro Asp Gln Val Val Ala Ile Ala Ser Asn Gly Gly Lys Gln
1               5                   10                  15
Ala Leu Glu Thr Val Gln Arg Leu Leu Pro Val Leu Cys Gln Ala His
            20                  25                  30
Gly

<210> SEQ ID NO 214
<211> LENGTH: 34
<212> TYPE: PRT
<213> ORGANISM: Xanthomonas oryzae

<400> SEQUENCE: 214

Leu Thr Pro Ala Gln Val Val Ala Ile Ala Ser Asn Ile Gly Gly Lys
1               5                   10                  15
Gln Ala Leu Glu Thr Val Gln Arg Leu Leu Pro Val Leu Cys Arg Ala
            20                  25                  30
His Gly

<210> SEQ ID NO 215
<211> LENGTH: 35
<212> TYPE: PRT
<213> ORGANISM: Unknown
<220> FEATURE:
<223> OTHER INFORMATION: Description of Unknown: Blood-borne
      pathogen TAL binding cassette peptide

<400> SEQUENCE: 215

Leu Thr Pro Gln Gln Val Val Ala Ile Ala Ala Asn Thr Gly Gly Lys
1               5                   10                  15
Gln Ala Leu Gly Ala Ile Thr Thr Gln Leu Pro Ile Leu Arg Ala Ala
            20                  25                  30
Pro Leu Asn
        35

<210> SEQ ID NO 216
<211> LENGTH: 35
<212> TYPE: PRT
<213> ORGANISM: Unknown
<220> FEATURE:
<223> OTHER INFORMATION: Description of Unknown: Blood-borne
      pathogen TAL binding cassette peptide

<400> SEQUENCE: 216

Leu Ser Pro Glu Gln Val Val Ala Ile Ala Ser Asn Asn Gly Gly Lys
1               5                   10                  15
Gln Ala Leu Glu Ala Val Lys Ala Gln Leu Leu Glu Leu Arg Ala Ala
            20                  25                  30
Pro Tyr Glu
        35

<210> SEQ ID NO 217
```

```
<211> LENGTH: 35
<212> TYPE: PRT
<213> ORGANISM: Unknown
<220> FEATURE:
<223> OTHER INFORMATION: Description of Unknown: Blood-borne
      pathogen TAL binding cassette peptide

<400> SEQUENCE: 217

Leu Ser Thr Gly Gln Val Val Ala Ile Ala Ser Asn Gly Gly Arg
1               5                   10                  15

Gln Ala Leu Glu Ala Val Arg Glu Gln Leu Leu Ala Leu Arg Ala Ala
            20                  25                  30

Pro Tyr Glu
        35

<210> SEQ ID NO 218
<211> LENGTH: 35
<212> TYPE: PRT
<213> ORGANISM: Unknown
<220> FEATURE:
<223> OTHER INFORMATION: Description of Unknown: Blood-borne
      pathogen TAL binding cassette peptide

<400> SEQUENCE: 218

Leu Ser Thr Glu Gln Val Val Ile Ala Asn Ser Ile Gly Gly Lys
1               5                   10                  15

Gln Ala Leu Glu Ala Val Lys Val Gln Leu Pro Val Leu Arg Ala Val
            20                  25                  30

Pro Tyr Glu
        35

<210> SEQ ID NO 219
<211> LENGTH: 35
<212> TYPE: PRT
<213> ORGANISM: Unknown
<220> FEATURE:
<223> OTHER INFORMATION: Description of Unknown: Blood-borne
      pathogen TAL binding cassette peptide

<400> SEQUENCE: 219

Leu Ser Thr Glu Gln Val Val Ala Ile Ala Ser Asn Asn Gly Gly Lys
1               5                   10                  15

Gln Ala Leu Glu Ala Val Lys Thr Gln Leu Leu Ala Leu Arg Thr Val
            20                  25                  30

Pro Tyr Glu
        35

<210> SEQ ID NO 220
<211> LENGTH: 35
<212> TYPE: PRT
<213> ORGANISM: Unknown
<220> FEATURE:
<223> OTHER INFORMATION: Description of Unknown: Blood-borne
      pathogen TAL binding cassette peptide

<400> SEQUENCE: 220

Leu Ser Pro Glu Gln Val Val Ala Ile Ala Ser Asn Asn Gly Gly Lys
1               5                   10                  15

Gln Ala Leu Glu Ala Val Arg Ala Leu Leu Pro Val Leu Arg Val Ala
            20                  25                  30

Pro Tyr Glu
        35
```

```
<210> SEQ ID NO 221
<211> LENGTH: 34
<212> TYPE: PRT
<213> ORGANISM: Xanthomonas campestris

<400> SEQUENCE: 221

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 222
<211> LENGTH: 34
<212> TYPE: PRT
<213> ORGANISM: Xanthomonas campestris

<400> SEQUENCE: 222

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 223
<211> LENGTH: 35
<212> TYPE: PRT
<213> ORGANISM: Ralstonia solanacearum

<400> SEQUENCE: 223

Leu Thr Pro Glu Gln Val Val Ala Ile Ala Ala Asn Thr Gly Gly Lys
1               5                   10                  15

Gln Ala Leu Gly Ala Ile Thr Thr Gln Leu Pro Ile Leu Arg Ala Ala
            20                  25                  30

Pro Tyr Glu
        35

<210> SEQ ID NO 224
<211> LENGTH: 35
<212> TYPE: PRT
<213> ORGANISM: Ralstonia solanacearum

<400> SEQUENCE: 224

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Val Leu Arg Ala Ala
            20                  25                  30

Pro Tyr Gly
        35

<210> SEQ ID NO 225
<211> LENGTH: 35
<212> TYPE: PRT
<213> ORGANISM: Ralstonia solanacearum

<400> SEQUENCE: 225

Leu Ser Pro Glu Gln Val Val Ala Ile Ala Ser Asn Asn Gly Gly Lys
1               5                   10                  15

Pro Ala Leu Glu Ala Val Lys Ala Gln Leu Leu Glu Leu Arg Ala Ala
            20                  25                  30
```

Pro Tyr Glu
        35

<210> SEQ ID NO 226
<211> LENGTH: 34
<212> TYPE: PRT
<213> ORGANISM: Xanthomonas oryzae

<400> SEQUENCE: 226

Leu Thr Pro Asn Gln Leu Val Ala Ile Ala Asn Asn Asn Gly Gly Lys
1               5

His Gly

<210> SEQ ID NO 231
<211> LENGTH: 1102
<212> TYPE: PRT
<213> ORGANISM: Xanthomonas oryzae

<400> SEQUENCE: 231

Met Asp Pro Ile Arg Ser Arg Thr Pro Ser Pro Ala Arg Glu Leu Leu
1 5 10 15

Pro Gly Pro Gln Pro Asp Arg Val Gln Pro Thr Ala Asp Arg Gly Gly
20 25 30

Ala Pro Pro Ala Gly Gly Pro Leu Asp Gly Leu Pro Ala Arg Arg Thr
35 40 45

Met Ser Arg Thr Arg Leu Pro Ser Pro Pro Ala Pro Ser Pro Ala Phe
50 55 60

Ser Ala Gly Ser Phe Ser Asp Leu Leu Arg Gln Phe Asp Pro Ser Leu
65 70 75 80

Leu Asp Thr Ser Leu Leu Asp Ser Met Pro Ala Val Gly Thr Pro His
85 90 95

Thr Ala Ala Ala Pro Ala Glu Cys Asp Glu Val Gln Ser Gly Leu Arg
100 105 110

Ala Ala Asp Asp Pro Pro Pro Thr Val Arg Val Ala Val Thr Ala Arg
115 120 125

Pro Pro Arg Ala Lys Pro Ala Pro Arg Arg Arg Ala Ala Gln Pro Ser
130 135 140

Asp Ala Ser Pro Ala Ala Gln Val Asp Leu Arg Thr Leu Gly Tyr Ser
145 150 155 160

Gln Gln Gln Gln Glu Lys Ile Lys Pro Lys Val Arg Ser Thr Val Ala
165 170 175

Gln His His Glu Ala Leu Val Gly His Gly Phe Thr His Ala His Ile
180 185 190

Val Ala Leu Ser Gln His Pro Ala Ala Leu Gly Thr Val Ala Val Thr
195 200 205

Tyr Gln Asp Ile Ile Arg Ala Leu Pro Glu Ala Thr His Glu Asp Ile
210 215 220

Val Gly Val Gly Lys Gln Trp Ser Gly Ala Arg Ala Leu Glu Ala Leu
225 230 235 240

Leu Thr Glu Ala Gly Glu Leu Arg Gly Pro Pro Leu Gln Leu Asp Thr
245 250 255

Gly Gln Leu Leu Lys Ile Ala Lys Arg Gly Gly Val Thr Ala Val Glu
260 265 270

Ala Val His Ala Trp Arg Asn Ala Leu Thr Gly Ala Pro Leu Asn Leu
275 280 285

Thr Pro Asp Gln Val Val Ala Ile Ala Ser Asn Ile Gly Gly Asn Gln
290 295 300

Ala Leu Glu Thr Val Gln Arg Leu Leu Pro Val Leu Cys Gln Ala His
305 310 315 320

Gly Leu Thr Pro Asp Gln Val Val Ala Ile Ala Ser His Gly Gly Gly
325 330 335

Lys Gln Ala Leu Glu Thr Val Gln Arg Leu Leu Pro Val Leu Cys Gln
340 345 350

Ala His Gly Leu Thr Pro Asp Gln Val Val Ala Ile Ala Ser Asn Ile

```
            355                 360                 365
Gly Gly Lys Gln Ala Leu Ala Thr Val Gln Arg Leu Leu Pro Val Leu
370                 375                 380
Cys Gln Asp His Gly Leu Thr Pro Asp Gln Val Val Ala Ile Ala Ser
385                 390                 395                 400
His Gly Gly Gly Lys Gln Ala Leu Glu Thr Val Gln Arg Leu Leu Pro
                405                 410                 415
Val Leu Cys Gln Asp His Gly Leu Thr Pro Asp Gln Val Val Ala Ile
                420                 425                 430
Ala Ser Asn Ile Gly Gly Lys Gln Ala Leu Glu Thr Val Gln Arg Leu
                435                 440                 445
Leu Pro Val Leu Cys Gln Asp His Gly Leu Thr Pro Asp Gln Val Val
        450                 455                 460
Ala Ile Ala Ser Asn Ile Gly Gly Lys Gln Ala Leu Glu Thr Val Gln
465                 470                 475                 480
Arg Leu Leu Pro Val Leu Cys Gln Asp His Gly Leu Thr Pro Asp Gln
                485                 490                 495
Val Val Ala Ile Ala Ser Asn Asn Gly Gly Lys Gln Ala Leu Glu Thr
            500                 505                 510
Val Gln Arg Leu Leu Pro Val Leu Cys Gln Thr His Gly Leu Thr Pro
        515                 520                 525
Asp Gln Val Val Ala Ile Ala Asn His Asp Gly Lys Gln Ala Leu
530                 535                 540
Glu Thr Val Gln Arg Leu Leu Pro Val Leu Cys Gln Asp His Gly Leu
545                 550                 555                 560
Thr Pro Asp Gln Val Val Ala Ile Ala Ser Asn Ile Gly Gly Lys Gln
                565                 570                 575
Ala Leu Ala Thr Val Gln Arg Leu Leu Pro Val Leu Cys Gln Ala His
                580                 585                 590
Gly Leu Thr Pro Asp Gln Val Val Ala Ile Ala Ser His Asp Gly Gly
            595                 600                 605
Lys Gln Ala Leu Glu Thr Val Gln Arg Leu Leu Pro Val Leu Cys Gln
        610                 615                 620
Asp His Gly Leu Thr Pro Asp Gln Val Val Ala Ile Ala Ser Asn Asn
625                 630                 635                 640
Gly Gly Lys Gln Ala Leu Glu Thr Val Gln Arg Leu Leu Pro Val Leu
                645                 650                 655
Cys Gln Asp His Gly Leu Thr Pro Ala Gln Val Val Ala Ile Ala Asn
                660                 665                 670
His Gly Gly Gly Lys Gln Ala Leu Glu Thr Val Gln Arg Leu Leu Pro
            675                 680                 685
Val Leu Cys Gln Asp His Gly Leu Thr Pro Val Gln Val Val Ala Ile
        690                 695                 700
Ala Ser Asn Ser Gly Gly Lys Gln Ala Leu Glu Thr Val Gln Arg Leu
705                 710                 715                 720
Leu Pro Val Leu Cys Gln Asp His Gly Leu Thr Pro Val Gln Val Val
                725                 730                 735
Ala Ile Ala Ser Asn Gly Gly Lys Gln Ala Leu Ala Thr Val Gln
                740                 745                 750
Arg Leu Leu Pro Val Leu Cys Gln Asp His Gly Leu Thr Pro Val Gln
            755                 760                 765
Val Val Ala Ile Ala Ser His Asp Gly Gly Lys Gln Ala Leu Glu Thr
        770                 775                 780
```

Val Gln Arg Leu Leu Pro Val Leu Cys Gln Asp His Gly Leu Thr Pro
785                 790                 795                 800

Asp Gln Val Val Ala Ile Ala Ser Asn Gly Gly Lys Gln Ala Leu Glu
            805                 810                 815

Ser Ile Val Ala Gln Leu Ser Arg Pro Asp Pro Ala Leu Ala Ala Leu
        820                 825                 830

Thr Asn Asp His Leu Val Ala Leu Ala Cys Leu Gly Gly Arg Pro Ala
    835                 840                 845

Leu Asp Ala Val Lys Lys Gly Leu Pro His Ala Pro Glu Leu Ile Arg
850                 855                 860

Arg Ile Asn Arg Arg Ile Pro Glu Arg Thr Ser His Arg Val Ala Asp
865                 870                 875                 880

Leu Ala His Val Val Arg Val Leu Gly Phe Phe Gln Ser His Ser His
            885                 890                 895

Pro Ala Gln Ala Phe Asp Asp Ala Met Thr Gln Phe Gly Met Ser Arg
        900                 905                 910

His Gly Leu Ala Gln Leu Phe Arg Arg Val Gly Val Thr Glu Leu Glu
    915                 920                 925

Ala Arg Tyr Gly Thr Leu Pro Pro Ala Ser Gln Arg Trp Asp Arg Ile
930                 935                 940

Leu Gln Ala Ser Gly Met Lys Arg Val Lys Pro Ser Pro Thr Ser Ala
945                 950                 955                 960

Gln Thr Pro Asp Gln Ala Ser Leu His Ala Phe Ala Asp Ser Leu Glu
            965                 970                 975

Arg Asp Leu Asp Ala Pro Ser Pro Met His Glu Gly Asp Gln Thr Arg
        980                 985                 990

Ala Ser Ser Arg Lys Arg Ser Arg Ser Asp Arg Ala Val Thr Gly Pro
    995                 1000                1005

Ser Thr  Gln Gln Ser Phe Glu  Val Arg Val Pro Glu  Gln Gln Asp
    1010               1015                1020

Ala Leu  His Leu Pro Leu Ser  Trp Arg Val Lys Arg  Pro Arg Thr
    1025               1030                1035

Arg Ile  Gly Gly Gly Leu Pro  Asp Pro Gly Thr Pro  Ile Ala Ala
    1040               1045                1050

Asp Leu  Ala Ala Ser Ser Thr  Val Met Trp Glu Gln  Asp Ala Ala
    1055               1060                1065

Pro Phe  Ala Gly Ala Ala Asp  Asp Phe Pro Ala Phe  Asn Glu Glu
    1070               1075                1080

Glu Leu  Ala Trp Leu Met Glu  Leu Leu Pro Gln Ser  Gly Ser Val
    1085               1090                1095

Gly Gly  Thr Ile
    1100

<210> SEQ ID NO 232
<211> LENGTH: 1469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu

-continued

```
                20                  25                  30
Arg Thr Leu Gly Tyr Ser Gln Gln Gln Glu Lys Ile Lys Pro Lys
                35                  40                  45

Val Arg Ser Thr Val Ala Gln His Glu Ala Leu Val Gly His Gly
                50                  55                  60

Phe Thr His Ala His Ile Val Ala Leu Ser Gln His Pro Ala Ala Leu
 65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
                100                 105                 110

Arg Ala Leu Glu Ala Leu Leu Thr Val Ala Gly Glu Leu Arg Gly Pro
                115                 120                 125

Pro Leu Gln Leu Asp Thr Gly Gln Leu Leu Lys Ile Ala Lys Arg Gly
                130                 135                 140

Gly Val Thr Ala Val Glu Ala Val His Ala Trp Arg Asn Ala Leu Thr
145                 150                 155                 160

Gly Ala Pro Leu Asn Leu Thr Pro Glu Gln Val Val Ala Ile Ala Ser
                165                 170                 175

Asn Asn Gly Gly Lys Gln Ala Leu Glu Thr Val Gln Arg Leu Leu Pro
                180                 185                 190

Val Leu Cys Gln Ala His Gly Leu Thr Pro Glu Gln Val Val Ala Ile
                195                 200                 205

Ala Ser Val Gln Arg Leu Leu Pro Val Leu Cys Gln Ala His Gly Leu
                210                 215                 220

Thr Pro Glu Gln Val Val Ala Ile Ala Ser Asn Asn Gly Gly Lys Gln
225                 230                 235                 240

Ala Leu Glu Thr Val Gln Arg Leu Leu Pro Val Leu Cys Gln Ala His
                245                 250                 255

Gly Leu Thr Pro Glu Gln Val Val Ala Ile Ala Ser Asn Asn Gly Gly
                260                 265                 270

Lys Gln Ala Leu Glu Thr Val Gln Arg Leu Leu Pro Val Leu Cys Gln
                275                 280                 285

Ala His Gly Leu Thr Pro Glu Gln Val Val Ala Ile Ala Ser His Asp
                290                 295                 300

Gly Gly Lys Gln Ala Leu Glu Thr Val Gln Arg Leu Leu Pro Val Leu
305                 310                 315                 320

Cys Gln Ala His Gly Leu Thr Pro Glu Gln Val Val Ala Ile Ala Ser
                325                 330                 335

His Asp Gly Gly Lys Gln Ala Leu Glu Thr Val Gln Arg Leu Leu Pro
                340                 345                 350

Val Leu Cys Gln Ala His Gly Leu Thr Pro Glu Gln Val Val Ala Ile
                355                 360                 365

Ala Ser Asn Asn Gly Gly Lys Gln Ala Leu Glu Thr Val Gln Arg Leu
                370                 375                 380

Leu Pro Val Leu Cys Gln Ala His Gly Leu Thr Pro Glu Gln Val Val
385                 390                 395                 400

Ala Ile Ala Ser Asn Asn Gly Gly Lys Gln Ala Leu Glu Thr Val Gln
                405                 410                 415

Arg Leu Leu Pro Val Leu Cys Gln Ala His Gly Leu Thr Pro Glu Gln
                420                 425                 430

Val Val Ala Ile Ala Ser Asn Ile Gly Gly Lys Gln Ala Leu Glu Thr
                435                 440                 445
```

```
Val Gln Arg Leu Leu Pro Val Leu Cys Gln Ala His Gly Leu Thr Pro
    450                 455                 460

Glu Gln Val Val Ala Ile Ala Ser Asn Asn Gly Gly Lys Gln Ala Leu
465                 470                 475                 480

Glu Thr Val Gln Arg Leu Leu Pro Val Leu Cys Gln Ala His Gly Leu
                485                 490                 495

Thr Pro Glu Gln Val Val Ala Ile Ala Ser His Asp Gly Gly Lys Gln
            500                 505                 510

Ala Leu Glu Thr Val Gln Arg Leu Leu Pro Val Leu Cys Gln Ala His
        515                 520                 525

Gly Leu Thr Pro Glu Gln Val Val Ala Ile Ala Ser His Asp Gly Gly
    530                 535                 540

Lys Gln Ala Leu Glu Thr Val Gln Arg Leu Leu Pro Val Leu Cys Gln
545                 550                 555                 560

Ala His Gly Leu Thr Pro Glu Gln Val Val Ala Ile Ala Ser Asn Asn
                565                 570                 575

Gly Gly Lys Gln Ala Leu Glu Thr Val Gln Arg Leu Leu Pro Val Leu
            580                 585                 590

Cys Gln Ala His Gly Leu Thr Pro Glu Gln Val Val Ala Ile Ala Ser
        595                 600                 605

His Asp Gly Gly Lys Gln Ala Leu Glu Thr Val Gln Arg Leu Leu Pro
    610                 615                 620

Val Leu Cys Gln Ala His Gly Leu Thr Pro Glu Gln Val Val Ala Ile
625                 630                 635                 640

Ala Ser Asn Ile Gly Gly Lys Gln Ala Leu Glu Thr Val Gln Arg Leu
                645                 650                 655

Leu Pro Val Leu Cys Gln Ala His Gly Leu Thr Pro Glu Gln Val Val
            660                 665                 670

Ala Ile Ala Ser Asn Asn Gly Gly Lys Gln Ala Leu Glu Thr Val Gln
        675                 680                 685

Arg Leu Leu Pro Val Leu Cys Gln Ala His Gly Leu Thr Pro Glu Gln
    690                 695                 700

Val Val Ala Ile Ala Ser Asn Gly Gly Gly Lys Gln Ala Leu Glu Thr
705                 710                 715                 720

Val Gln Arg Leu Leu Pro Val Leu Cys Gln Ala His Gly Leu Thr Pro
                725                 730                 735

Gln Gln Val Val Ala Ile Ala Ser Asn Asn Gly Gly Arg Pro Ala Leu
            740                 745                 750

Glu Ser Ile Val Ala Gln Leu Ser Arg Pro Asp Pro Ala Leu Ala Ala
        755                 760                 765

Leu Thr Asn Asp His Leu Val Ala Leu Ala Cys Leu Gly Gly Arg Pro
    770                 775                 780

Ala Leu Asp Ala Val Lys Lys Gly Leu Pro His Ala Pro Ala Leu Ile
785                 790                 795                 800

Lys Arg Thr Asn Arg Arg Ile Pro Glu Arg Thr Ser His Arg Val Ala
                805                 810                 815

Asp His Ala Gln Val Val Arg Val Leu Gly Phe Phe Gln Cys His Ser
            820                 825                 830

His Pro Ala Gln Ala Phe Asp Asp Ala Met Thr Gln Phe Gly Met Ser
        835                 840                 845

Arg His Gly Leu Leu Gln Leu Phe Arg Arg Val Gly Val Thr Glu Leu
    850                 855                 860
```

-continued

```
Glu Ala Arg Ser Gly Thr Leu Pro Pro Ala Ser Gln Arg Trp Asp Arg
865                 870                 875                 880

Ile Leu Gln Gly Gly Val Thr Met Ala Lys Met Ala Phe Thr Leu
                885                 890                 895

Ala Asp Arg Val Thr Glu Glu Met Leu Ala Asp Lys Ala Ala Leu Val
            900                 905                 910

Val Glu Val Val Glu Glu Asn Tyr His Asp Ala Pro Ile Val Gly Ile
        915                 920                 925

Ala Val Val Asn Glu Arg Gly Arg Phe Phe Leu Arg Pro Glu Thr Ala
    930                 935                 940

Leu Ala Asp Pro Gln Phe Val Ala Trp Leu Gly Asp Glu Thr Lys Lys
945                 950                 955                 960

Lys Ser Met Phe Asp Ser Lys Arg Ala Ala Val Ala Leu Lys Trp Lys
                965                 970                 975

Gly Ile Glu Leu Cys Gly Val Ser Phe Asp Leu Leu Leu Ala Ala Tyr
            980                 985                 990

Leu Leu Asp Pro Ala Gln Gly Val Asp Asp Val Ala Ala Ala Ala Lys
        995                 1000                1005

Met Lys Gln Tyr Glu Ala Val Arg Pro Asp Glu Ala Val Tyr Gly
    1010                1015                1020

Lys Gly Ala Lys Arg Ala Val Pro Asp Glu Pro Val Leu Ala Glu
    1025                1030                1035

His Leu Val Arg Lys Ala Ala Ile Trp Glu Leu Glu Arg Pro
    1040                1045                1050

Phe Leu Asp Glu Leu Arg Arg Asn Glu Gln Asp Arg Leu Leu Val
    1055                1060                1065

Glu Leu Glu Gln Pro Leu Ser Ser Ile Leu Ala Glu Met Glu Phe
    1070                1075                1080

Ala Gly Val Lys Val Asp Thr Lys Arg Leu Glu Gln Met Gly Lys
    1085                1090                1095

Glu Leu Ala Glu Gln Leu Gly Thr Val Glu Gln Arg Ile Tyr Glu
    1100                1105                1110

Leu Ala Gly Gln Glu Phe Asn Ile Asn Ser Pro Lys Gln Leu Gly
    1115                1120                1125

Val Ile Leu Phe Glu Lys Leu Gln Leu Pro Val Leu Lys Lys Thr
    1130                1135                1140

Lys Thr Gly Tyr Ser Thr Ser Ala Asp Val Leu Glu Lys Leu Ala
    1145                1150                1155

Pro Tyr His Glu Ile Val Glu Asn Ile Leu His Tyr Arg Gln Leu
    1160                1165                1170

Gly Lys Leu Gln Ser Thr Tyr Ile Glu Gly Leu Leu Lys Val Val
    1175                1180                1185

Arg Pro Asp Thr Lys Lys Val His Thr Ile Phe Asn Gln Ala Leu
    1190                1195                1200

Thr Gln Thr Gly Arg Leu Ser Ser Thr Gly Pro Asn Leu Gln Asn
    1205                1210                1215

Ile Pro Ile Arg Leu Glu Glu Gly Arg Lys Ile Arg Gln Ala Phe
    1220                1225                1230

Val Pro Ser Glu Ser Asp Trp Leu Ile Phe Ala Ala Asp Tyr Ser
    1235                1240                1245

Gln Ile Glu Leu Arg Val Leu Ala His Ile Ala Glu Asp Asp Asn
    1250                1255                1260

Leu Met Glu Ala Phe Arg Arg Asp Leu Asp Ile His Thr Lys Thr
```

```
                    1265                1270                1275

Ala Met Asp Ile Phe Gln Val Ser Glu Asp Val Thr Pro Asn
        1280                1285                1290

Met Arg Arg Gln Ala Lys Ala Val Asn Phe Gly Ile Val Tyr Gly
    1295                1300                1305

Ile Ser Asp Tyr Gly Leu Ala Gln Asn Leu Asn Ile Ser Arg Lys
    1310                1315                1320

Glu Ala Ala Glu Phe Ile Glu Arg Tyr Phe Gln Ser Phe Pro Gly
    1325                1330                1335

Val Lys Arg Tyr Met Glu Asn Ile Val Gln Glu Ala Lys Gln Lys
    1340                1345                1350

Gly Tyr Val Thr Thr Leu Leu His Arg Arg Tyr Leu Pro Asp
        1355                1360                1365

Ile Thr Ser Arg Asn Phe Asn Val Arg Ser Phe Ala Glu Arg Met
    1370                1375                1380

Ala Met Asn Thr Pro Ile Gln Gly Ser Ala Ala Asp Ile Ile Lys
    1385                1390                1395

Lys Ala Met Ile Asp Leu Asn Ala Arg Leu Lys Glu Glu Arg Leu
    1400                1405                1410

Gln Ala His Leu Leu Leu Gln Val His Asp Glu Leu Ile Leu Glu
    1415                1420                1425

Ala Pro Lys Glu Glu Met Glu Arg Leu Cys Arg Leu Val Pro Glu
    1430                1435                1440

Val Met Glu Gln Ala Val Thr Leu Arg Val Pro Leu Lys Val Asp
    1445                1450                1455

Tyr Arg Tyr Gly Ser Thr Trp Tyr Asp Ala Lys
    1460                1465

<210> SEQ ID NO 233
<211> LENGTH: 9
<212> TYPE: PRT
<213> ORGANISM: Unknown
<220> FEATURE:
<223> OTHER INFORMATION: Description of Unknown: 'LAGLIDADG' family
      peptide

<400> SEQUENCE: 233

Leu Ala Gly Leu Ile Asp Ala Asp Gly
1               5

<210> SEQ ID NO 234
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (12)..(13)
<223> OTHER INFORMATION: This region may encompass "His Asp," "Asn Ile,"
      "Asn Lys," or "Asn Gly"

<400> SEQUENCE: 234

Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly
```

TAL-EFFECTOR ASSEMBLY PLATFORM, CUSTOMIZED SERVICES, KITS AND ASSAYS

CROSS-REFERENCE TO RELATED APPLICATIONS

This application is a divisional of U.S. patent application Ser. No. 14/811,363, filed Jul. 28, 2015, which is continuation of U.S. patent application Ser. No. 14/856,978, filed Apr. 4, 2013, now abandoned, which claims the benefit of priority to U.S. Provisional Patent Application No. 61/784,658 filed Mar. 14, 2013; U.S. Provisional Patent Application No. 61/644,975 filed May 9, 2012 and U.S. Provisional Patent Application No. 61/620,228 filed Apr. 4, 2012, which disclosures are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Nov. 11, 2019, is named LT00652DIV_SL.txt and is 189,133 bytes in size.

FIELD OF THE INVENTION

The invention generally relates to compositions and methods for designing and producing functional DNA binding effector molecules and associated customized services, tool kits and functional assays. In some aspects, the invention provides methods and tools for efficient assembly of customized TAL effector molecules. Furthermore, the invention relates to uses of TAL effector molecules and functional evaluation of such TAL by, for example, customized assays.

BACKGROUND

Transcription activator-like (TAL) effectors represent a class of DNA binding proteins secreted by plant-pathogenic bacteria of the species, such as *Xanthomonas* and *Ralstonia*, via their type III secretion system upon infection of plant cells. Natural TAL effectors specifically have been shown to bind to plant promoter sequences thereby modulating gene expression and activating effector-specific host genes to facilitate bacterial propagation (Römer, P., et al., Plant pathogen recognition mediated by promoter activation of the pepper Bs3 resistance gene. Science 318, 645-648 (2007); Boch, J. & Bonas, U. *Xanthomonas* AvrBs3 family-type III effectors: discovery and function. Annu. Rev. Phytopathol. 48, 419-436 (2010); Kay, S., et al. U. A bacterial effector acts as a plant transcription factor and induces a cell size regulator. Science 318, 648-651 (2007); Kay, S. & Bonas, U. How *Xanthomonas* type III effectors manipulate the host plant. Curr. Opin. Microbiol. 12, 37-43 (2009).) Natural TAL effectors are generally characterized by a central repeat domain and a carboxyl-terminal nuclear localization signal sequence (NLS) and a transcriptional activation domain (AD). The central repeat domain typically consists of a variable amount of between 1.5 and 33.5 amino acid repeats that are usually 33-35 residues in length except for a generally shorter carboxyl-terminal repeat referred to as half-repeat. The repeats are mostly identical but differ in certain hypervariable residues. DNA recognition specificity of TAL effectors is mediated by hypervariable residues typically at positions 12 and 13 of each repeat—the so-called repeat variable diresidue (RVD) wherein each RVD targets a specific nucleotide in a given DNA sequence. Thus, the sequential order of repeats in a TAL protein tends to correlate with a defined linear order of nucleotides in a given DNA sequence. The underlying RVD code of some naturally occurring TAL effectors has been identified, allowing prediction of the sequential repeat order required to bind to a given DNA sequence (Boch, J. et al. Breaking the code of DNA binding specificity of TAL-type III effectors. Science 326, 1509-1512 (2009); Moscou, M. J. & Bogdanove, A. J. A simple cipher governs DNA recognition by TAL effectors. Science 326, 1501 (2009)). Further, TAL effectors generated with new repeat combinations have been shown to bind to target sequences predicted by this code. It has been shown that the target DNA sequence generally start with a 5' thymine base to be recognized by the TAL protein.

The modular structure of TALs allows for combination of the DNA binding domain with effector molecules such as nucleases. In particular, TAL effector nucleases allow for the development of new genome engineering tools known.

Zinc-finger nucleases (ZFN) and meganucleases are examples of other genome engineering tools. ZFNs are chimeric proteins consisting of a zinc-finger DNA-binding domain and the a nuclease domain. One example of a nuclease domain is the non-specific cleavage domain from the type IIS restriction endonuclease FokI (Kim, Y G; Cha, J., Chandrasegaran, S. Hybrid restriction enzymes: zinc finger fusions to Fok I cleavage domain Proc. Natl. Acad. Sci. USA. 1996 Feb. 6; 93(3):1156-60) typically separated by a linker sequence of 5-7 bp. A pair of the FoId cleavage domain is generally required to allow for dimerization of the domain and cleavage of a non-palindromic target sequence from opposite strands. The DNA-binding domains of individual $Cys_2His_2$ ZFNs typically contain between 3 and 6 individual zinc-finger repeats and can each recognize between 9 and 18 base pairs.

One problem associated with ZNFs is the possibility of off-target cleavage which may lead to random integration of donor DNA or result in chromosomal rearrangements or even cell death which still raises concern about applicability in higher organisms (Zinc-finger Nuclease-induced Gene Repair With Oligodeoxynucleotides: Wanted and Unwanted Target Locus Modifications Molecular Therapy vol. 18 no. 4, 743-753 (2010)).

Another group of genomic engineering proteins are sequence-specific rare cutting endonucleases with recognition sites exceeding 12 bp—so-called meganucleases or homing endonucleases. The large DNA recognition sites of 12 to 40 base pairs usually occur only once in a given genome and meganucleases (such as, e.g., I-SceI) are therefore considered the most specific restriction enzymes in nature and have been used to modify all sorts of genomes from plants or animals. One example of a meganuclease is PI-SceI, which belongs to the LAGLIDADG (SEQ ID NO: 233) family of homing endonucleases. However, the repertoire of naturally occurring meganucleases is limited and decreases the probability of finding a specific enzyme for a defined genomic target sequence. Meganucleases are therefore engineered to modify their recognition sequence. To develop tailored meganucleases with new recognition sites, two main approaches have been adopted: random mutagenesis of residues in the binding domain and subsequent selection of functional variants or fusing other enzyme domains to meganuclease half-sites to create chimeric meganucleases.

There is a need to improve these tools to (1) make them more flexible and reliable, (2) develop new means to predict and rationally design new binders, (3) tailor and modify effector activities and (4) efficiently assemble, test and deliver the engineered molecules.

SUMMARY OF THE INVENTION

The invention relates to compositions and methods which may be used for genetic engineering and altering the structure and/or function of nucleic acid molecules (e.g., nucleic acid molecules located within cells). In some aspects, the invention relates, in part, to compositions and methods for in vivo genetic manipulation (e.g., involving homologous recombination) and the alteration of gene expression (e.g., gene activation, repression, modulation, etc.).

Furthermore, the invention includes methods, compositions and tools to design and efficiently assemble nucleic acid molecules. In particular the described methods and vectors are useful for assembling nucleic acid molecules encoding TAL effectors and TAL effector fusion proteins but can also be used to assemble other nucleic acid sequences encoding complex or modular protein functions or fusions.

In some embodiments, the invention includes linear nucleic acid molecules (e.g., linear vectors), such as those comprising one or more (e.g., two or more, three or more or all four) of the following: (a) a region encoding an N-terminal portion of a TAL effector, (b) a region encoding a C-terminal portion of a TAL effector, (c) at least one recombination site, and (d) at least one covalently bound topoisomerase, as well as methods for producing and using such nucleic acid molecules. In many instances, the topoisomerase will be located at one or both of the termini of the linear nucleic acid molecule. Also, in many instance, the covalently bound topoisomerase will be located within 100 (e.g., from about 2 to about 90, from about 5 to about 90, from about 10 to about 90, from about 15 to about 90, from about 20 to about 90, from about 25 to about 90, from about 30 to about 90, from about 2 to about 40, from about 5 to about 40, from about 10 to about 40, from about 15 to about 40, from about 2 to about 25, from about 5 to about 25, etc.) nucleotides of a recombination site.

In some more specific embodiments, the invention includes linear nucleic acid molecules, such as those comprising: (a) a region encoding an N-terminal portion of a TAL effector, (b) a region encoding a C-terminal portion of a TAL effector, and (c) at least one covalently bound topoisomerase, as well as methods for producing and using such nucleic acid molecules.

In many instances, linear nucleic acid molecules of the invention will have a sequence which is complementary to a sequence generated by a Type IIS restriction endonuclease. Thus, the invention also includes methods for generating one or more nucleic acid segments which contain overhangs at one or both termini generated by digestion with a Type IIS restriction endonuclease, followed by contacting one or more nucleic acid segments with one or more linear nucleic acid molecules under conditions which allow for covalent joining of the digested nucleic acid segment with the one or more linear nucleic acid molecules.

Linear nucleic acid molecules, such as those described above, may be circularized. In many instances, circularization will result in the addition of nucleic acid to the linear nucleic acid molecules (e.g., the addition of an "insert"). Further, in some instances when the nucleic acid molecules are circularized and contain TAL repeats (i.e., more than one TAL nucleic acid binding cassette) located between the termini of the linear nucleic acid molecules, the circularized nucleic acid molecules will encode TAL effectors capable of binding to specified nucleic acid sequences. In other instances, the circularized nucleic acid molecules (e.g., vectors) may contain coding sequences for one or more component of TAL effectors.

When a vector, or other nucleic acid molecule, is circularized, it may be circularized by covalently linkage of one or both strands of one or both ends by the action of a ligase or topoisomerase. Further, a circularized vector may be contains one or more nicks in one or both strands. As an example, nicks may be located in one strand at one or both junctions where an insert is added to the vector. The presence of one or more nicks will generally result in a relaxed supercoil structure of the circularized vector. Further, nicks may be repaired in vitro via the use of, for example, ligases. Nicks may also be repaired in vivo (within a cell) via cellular repair mechanisms.

In many instance, linear nucleic acid molecules of the invention will be molecules such as vectors. Thus, linear nucleic acid molecules of the invention may contain one or more origin of replication. Such origins of replication may allow for replication in particular cell types, such as prokaryotic cells (e.g., *Escherichia coli, Synechococcus* species, etc.) and eukaryotic cells (e.g., *Chlamydomonas reinhardtii*, human cells, mouse cells, sf9 cells, etc.).

Further, linear nucleic acid molecules of the invention may comprise one or more recombination site. In some instances, such recombination sites are selected from the group consisting of (a) att sites (e.g., attB, attP, attL, and attR sites), (b) lox sites (e.g., loxP, loxP511, etc.), and (c) frt sites.

Topoisomerases suitable for use with the invention vary greatly but will typically have the ability to covalently join at least one strand of two nucleic acid termini. Thus, linear nucleic acid molecules of the invention may comprise at least one covalently bound topoisomerase which is a Type IA, Type IB, Type IIA, and/or Type II topoisomerase. In some instances, the covalently bound topoisomerase is a Vaccinia virus topoisomerase. The invention also includes methods for generating linear nucleic acid molecules with one or more covalently bound topoisomerase.

Linear nucleic acid molecule of the invention may have two blunt termini or an overhang (e.g., a 5' and/or a 3' overhang) on at least one terminus. Further, the lengths of overhangs, when present, may vary greatly but will often be between one and ten (e.g., from about 1 to about 6, from about 2 to about 6, from about 3 to about 6, from about 1 to about 4, etc.) nucleotides in length.

In some specific instances, the overhang on linear nucleic acid molecules of the invention will be a single thymine or uridine. Typically, such overhangs will be 5' overhangs present on one or both termini. Termini such as this will often be useful in what is referred to as TA cloning. TA cloning makes use of the generation of a polymerase chain reaction (PCR) product produced using a non-proofreading polymerase having a tendency to leave 3' terminal adenines at the termini of the resulting PCR products. Thus, the invention includes the use of linear nucleic acid molecules of the invention in TA cloning procedures.

The invention also includes methods for preparing TAL effector libraries, as well as the libraries themselves and methods for using such libraries. In some aspects, such methods comprise (a) connecting a population of TAL nucleic acid binding cassettes encoding TAL subunits that individually bind adenine, guanine, thymidine, or cytosine base binders, when the base is present in a nucleic acid molecule (e.g., to generate a TAL repeat) and (b) introducing the connected TAL nucleic acid binding cassettes (e.g., a TAL repeat) generated in (a) into a vector to generate a TAL effector library. Such libraries will often encode TAL effectors which bind to different nucleotide sequences.

The AT/CG ratio of nucleic acids in differs between organisms, within the genome of the same organism, and in different locations within a genome of the same organism. For example, a eukaryotic organism will often have a different AT/CG ratio in nucleic acid which forms the nuclear genome and the mitochondrial genome. Thus, when generating a TAL effector library designed to bind to nucleic acid of (1) a particular genome or (2) a region or regions (e.g., promoter regions) of a particular genome, the nucleic acid binding site may be "biased" towards the generation of binding domains for the desired target. Thus, the invention includes method for generating TAL effector libraries wherein TAL nucleic acid binding cassettes that encode adenine, guanine, thymidine, and cytosine binders are either all present in equimolar amounts or not all present in equimolar amounts. In specific instances, TAL nucleic acid binding cassettes that encode adenine and thymine binders are present in equimolar amounts and represent from about 51% to about 75% (e.g., from about 51% to about 70%, from about 51% to about 65%, from about 51% to about 60%, from about 51% to about 55%, from about 55% to about 65%, etc.) of the total TAL nucleic acid binding cassettes present. In other specific instances, TAL nucleic acid binding cassettes that encode cytosine and guanine binders are present in equimolar amounts and represent from about 51% to about 75% (e.g., from about 51% to about 70%, from about 51% to about 65%, from about 51% to about 60%, from about 51% to about 55%, from about 55% to about 65%, etc.) of the total TAL nucleic acid binding cassettes present. Thus, the invention includes methods for generating TAL effector libraries comprising TAL nucleic acid binding cassettes with nucleic acid recognition having an AT/CG ratio biased in favor of the genome or region of a genome for which binding activity is sought.

In some instances, these TAL effector libraries will not be bound to a fusion partner but nucleic acid binding activity can be assessed and a fusion partner, if desired, can be added later to form a TAL effector fusion. In many instances, TAL effector libraries of the invention will encode TAL effector fusions.

In some instances, TAL effector fusions of the invention will have transcriptional activation activity. In other instances, TAL effector fusions of the invention will inhibit transcription. Transcriptional inhibition may be conferred by a number of different mechanisms, including blocking of a binding site for transcriptional activators.

Vector suitable for use in compositions of the invention include viral vectors (e.g., lentiviral vectors, adenoviral vectors, etc.).

The invention also includes methods for identifying TAL effectors that bind to specified nucleotide sequences, as well as TAL effectors identified by such methods. In some instances, such methods comprise (a) connecting a population TAL nucleic acid binding cassettes which individually encode TAL repeats that bind to one of the bases adenine, guanine, thymidine, and cytosine, when the base is present in a nucleic acid molecule, (b) introducing the connected TAL nucleic acid binding cassettes generated in (a) into a vector to generate a TAL effector library, wherein the library contains TAL effectors which bind to different nucleotide sequences, (c) introducing the TAL effector library into a cell under conditions which allow for the expression of TAL effectors, and (d) screening the cells generated in (c) to identify cells in which at least one cellular parameter is altered by expression of a TAL effector. In some instances, the cellular parameter is TAL effector induced transcriptional activation of a non-TAL effector gene. Further, cells used in the practice of this aspect of the invention may contain nucleic acid comprising a promoter operably linked to a reporter (e.g., lacZ, green fluorescent protein, etc.). Such cells may be used in methods wherein the cellular parameter is transcriptional activation of the reporter.

The invention further includes novel transcription activator-like (TAL) repeats and TAL repeat amino acid sequences, as well as other components of TAL proteins. As described herein, TAL homologs were identified by amino acid sequence based bioinformatic searches using known TAL amino acid sequences. Once a prospective TAL protein was identified, the amino sequence of the proteins was then analyzed for TAL repeats and other features.

In many instances, proteins which contain TAL repeats described herein will bind nucleic acid (e.g., DNA in a sequence specific manner). Assays for measuring sequence specific nucleic acid binding activity and characteristics of such proteins are described elsewhere herein.

In some aspects, provided herein are embodiments of further TAL repeat structures, including TAL effector (TALE) molecules containing repeat sequences, as well as further amine- and carboxyl-terminal sequences flanking a repeated region. These further TAL repeats as well as the flanking regions, independently can be incorporated into TAL fusion proteins, nucleic acids encoding such fusion proteins. The invention further includes vectors comprising the nucleic acids encoding TAL repeats and TAL fusion proteins, host cells comprising the vectors, and kits containing for practicing various embodiments of the invention.

The invention includes, in part, non-naturally occurring proteins (e.g., fusion proteins such as non-naturally occurring fusion proteins) which contain one or more TAL repeats (e.g., TAL repeats with sequence specific nucleic acid binding activity). In the some embodiments such non-naturally occurring proteins comprising (a) an amine terminal region (e.g., an amine terminal region of between from about 25 and to about 500 amino acids, from about 50 and to about 500 amino acids, from about 75 and to about 500 amino acids, from about 100 and to about 500 amino acids, from about 150 and to about 500 amino acids, from about 50 and to about 250 amino acids, etc.), (b) a carboxyl terminal region of between 25 and 500 amino acids (e.g., a carboxyl terminal region of between from about 25 and to about 500 amino acids, from about 50 and to about 500 amino acids, from about 75 and to about 500 amino acids, from about 100 and to about 500 amino acids, from about 150 and to about 500 amino acids, from about 50 and to about 250 amino acids, etc.), and (c) a central region containing five or more (e.g., from about 5 to about 25, from about 5 to about 20, from about 5 to about 18, from about 10 to about 30, from about 10 to about 25, from about 15 to about 25, etc.) amino acid segments which confer upon the non-naturally occurring protein sequence specific nucleic acid binding activity. In some embodiments, all of or one or more of the individual amino acid segments in which form the central region are between from about 30 and to about 38 amino acids, from about 30 and to about 37 amino acids, from about 30 and to about 36 amino acids, from about 30 and to about 35 amino acids, from about 33 and to about 35 amino acids, etc., in length.

The amino acid segments which form the central region may contain one or more amino acid sequence at least 80%, 85%, 90%, 95%, or identical to one or more of the following amino acid sequences: (1) FSQADIVKIAGN (SEQ ID NO:37), (2) GGAQALQAVLDLEP (SEQ ID NO:38), (3)

GGAQALQAVLDLEPALRERG (SEQ ID NO:39), (4) FRTEDIVQMVS (SEQ ID NO:40), (5) GGSKNLAAVQA (SEQ ID NO:41), (6) GGSKNLEAVQA (SEQ ID NO:42), (7) LEPKDIVSIAS (SEQ ID NO:43), (8) GATQAIT-TLLNKW (SEQ ID NO:44), (9) GATQAITTLLNKWDX-LRAKG (SEQ ID NO:45), and (10) GATQAITTLLNK-WGXLRAKG (SEQ ID NO:46). In some instances, X in the above sequences may independently be one of the following amino acids: aspartic acid, serine, alanine, or glutamic acid. The invention also includes peptides and proteins which comprise the above amino acid sequences, as well as nucleic acid molecules which encode such amino acid sequences.

A number of TAL proteins are known in the art. Thus, in some specific aspects, the invention does not include proteins which are in the prior art.

In many instances, proteins of the invention and, in appropriate instances, subcomponents thereof are not identical to an amino acid sequence of a TAL protein which naturally occurs in a bacterium of the genera *Burkholderia, Xanthomonas* or *Ralstonia*. In specific embodiments, the invention does not include non-naturally occurring proteins in which at least one (e.g., one, two, three, four, five, six, etc. or all) of the amino acid segments is identical to an amino acid sequence of a TAL protein which naturally occurs in a bacterium of the genera *Burkholderia, Xanthomonas* or *Ralstonia*. In some instances, the invention does not include one or more amino acid segments identical to an amino acid sequence of a TAL protein, with the exception of the RVD sequence, which naturally occurs in a bacterium of one of the more of the genera *Burkholderia, Xanthomonas* or *Ralstonia*.

In additional specific embodiments, the invention does not include non-naturally occurring proteins comprising at least one (e.g., one, two, three, four, five, six, etc. or all) amino acid segment identical to either an amino acid sequence shown in FIG. 30 or one of the first eighteen amino acid sequences shown in FIG. 30. However, in some embodiments, the invention does include proteins which contain any sequence shown in FIG. 30 (as well as any other amino acid sequence found in nature or otherwise known) in combination with other sequences (e.g., TAL repeat sequences provided herein).

The invention also includes non-naturally occurring proteins (e.g., fusion proteins) comprising a region containing five or more amino acid segments (in some instances, collectively referred to as "TAL repeats") which confer upon the non-naturally occurring protein sequence specific nucleic acid binding activity. In some instances, each of the five or more amino acid segments has a length of 32-35 amino acids (e.g., some amino acid segments having a length of 33 amino acids and others having a length of 35 amino acids). In additional instances, at least one of the of the five or more amino acid segments has isoleucine residue at position 6. In further additional instances, amino acid 12 or amino acids 12 and 13 of at least one of the of the five or more amino acid segments confers upon the renders the amino acid segment the ability to recognize a single base in a nucleic acid molecule. In some instances, at least one of the five or more amino acid segments comprises at amino acid positions 14-19 an amino acid sequence having at least 80%, 85%, 90%, or 95% identical to an amino acid sequence selected from the group consisting of: (a) GG(A or T)Q(A or T)L (SEQ ID NO: 82), (b) GGSKNL (SEQ ID NO: 83), and (c) GA(T or N)(N or K)(A or T)I (SEQ ID NO: 84).

In additional embodiments, non-naturally occurring proteins (e.g., a fusion proteins) of the invention, as well as individual TAL repeats of the invention, comprises at amino acid positions 14-23 of at least one TAL repeat a sequence having at least 80%, 85%, 90%, or 95% identical to GGAQALX$_1$X$_2$VLL (SEQ ID NO: 85), where X$_1$ and X$_2$ are independently any of the twenty of the commonly occurring amino acids found in proteins. In some instances, X$_1$ and X$_2$ are not E or G. In additional embodiments, non-naturally occurring proteins of the invention comprise at amino acid positions 14-19 at least one TAL repeat sequence having at least 80% identical to GGAQAL (SEQ ID NO: 86).

As described elsewhere herein, the invention includes non-naturally occurring proteins which are fusion proteins. In many instances, these non-naturally occurring fusion proteins comprise a sequence specific nucleic acid binding activity and at least a second activity other than sequence specific nucleic acid binding activity. In certain embodiments, the second activity may be one of the following: an activator activity (e.g., a transcriptional activation activity), a repressor activity (e.g., a transcriptional repression activity), a nuclease activity, a topoisomerase activity, a gyrase activity, a ligase activity, a glycosylase activity, an acetylase activity, a deacetylase activity, an integrase activity, a transposase activity, a methylase activity, a demethylase activity, a methyl-transferase activity, a kinase activity, a recombinase activity, a phosphatase activity, a sulphurilase activity, a polymerase activity, a fluorescent activity.

In some instances, the second activity is a nuclease activity. Further, such nuclease may comprise a FokI nuclease cleavage domain, a FokI nuclease cleavage domain mutant KKR Sharkey, or a FokI nuclease cleavage domain mutant ELD Sharkey. Further, the second activity may be conferred, for example, by a VP16, VP32 or VP64 transcriptional activator domain(s) or a KRAB transcriptional repressor domain.

The invention also comprises nucleic acid molecules (e.g., vectors) which encode proteins described herein, as well as host cells comprising such nucleic acid molecules.

The invention further comprises methods of regulating expression of a target gene. In some instances, methods of the invention comprise contacting a cell with a nucleic acid molecule which encodes a non-naturally occurring fusion protein described herein under conditions which allow for intracellular expression of the non-naturally occurring fusion protein.

Alignments of protein sequences were carried out and consensus sequences were generated using VectorNTI Advance, version 11.5.1, using the default settings (Life Technologies, Carlsbad, Calif.). The software scores amino acids in terms of identity and in terms of similarity. Similarity is defined as set forth in TABLE 1. A "strong" designation depicts a strong similarity while a "weak" designation depicts a weak similarity. Those designated as "strong" are depicted in the figures in the same manner as identical amino acids.

TABLE 1

| Amino Acid | Strong | Weak |
|---|---|---|
| A | GS | CTV |
| C |  | AS |
| D | E | GHKNQRS |
| E | D | HKNQRS |
| F | WY | HILM |

TABLE 1-continued

| Amino Acid | Strong | Weak |
|---|---|---|
| G | A | DNS |
| H | Y | DEFKNQR |
| I | LMV | F |
| K | R | DEHNQST |
| L | IMV | F |
| M | ILV | F |
| N | Q | DEGHKRST |
| P |  | ST |
| Q | N | DEHKRS |
| R | K | DEHNQ |
| S | AT | CDEGKNPQ |
| T | S | AKNPV |
| V | ILM | AT |
| W | FY |  |
| Y | FHW |  |

The invention also includes methods for genomic engineering and site specific integration of a nucleic acid molecule of interest and various assay formats and surrogate reporter systems to evaluate TAL effector activity. Also the invention provides for methods to enrich, select or isolate cells that have been modified by a TAL effector such as, e.g., a TAL effector nuclease.

Furthermore, the invention comprises methods to fine-tune the activity of TAL effector proteins in a target host cell.

The invention may be more fully understood by reference to the following drawings.

DESCRIPTION OF THE FIGURES

FIGS. 1A-1B and FIGS. 2A-2B show a work flow for a modular web-based platform for providing TAL-specific services to customers. FIG. 1A shows one example of a how a customer portal can be organized to allow for automatic processing of orders related to TAL effectors and related services. After login to the portal, the customer enters a specific nucleic acid sequence to be targeted by a requested TAL effector molecule and provides or selects additional product specifications. In addition, the customer can select optional services from a menu or enter inquiries or additional comments. Product specifications and requested services are then processed via an internal system based on design and assembly programs and databases to identify optimal assembly criteria. TAL effector molecules are then assembled based on de novo synthesized nucleic acid molecules and/or available libraries or parts. FIG. 1A discloses SEQ ID NO: 115.

FIG. 1B shows an example of a possible modular organization of such web-based platform that includes workflows directed to TAL services. The platform consists at least of (i) a web interface (module 1) for input and storage of customer- and project-specific information and for information exchange between customer and service provider; a Design Engine (module 2) which integrates software and database information to determine TAL design and generated an assembly strategy and (iii) a manufacture unit (module 3) comprising means and material to synthesize, assemble, express and analyse TAL constructs wherein at least some steps of the workflow may be supported by a Laboratory Information Management System (LIMS).

FIG. 2A is a schematic drawing of the modular structure of a representative naturally occurring TAL protein. This protein is composed of an amino terminal end (N), a central array comprising a variable number of 34-amino acid repeats indicated by ovals with hypervariable residues at positions 12 and 13 that determine base preference, and a carboxyl terminal end (C) comprising a nuclear localization signal (NLS) and a transcription activator (AD) domain. FIG. 2A discloses SEQ ID NO: 90.

FIG. 2B shows an amino acid alignment of TAL nucleic acid binding cassettes from five different protein. Two repeats are from the AvrXa27 protein of *Xanthomonas oryzae* (GenBank: AAY54168.1) (SEQ ID NOS 116-117, respectively, in order of appearance), two repeats are from the Hax3 protein of *Xanthomonas campestris* (GenBank: AAY43359.1) (SEQ ID NOS 71 and 118, respectively, in order of appearance), three repeats are from the PS107 protein of *Ralstonia solanacearum* (YP 003750492.1) (SEQ ID NOS 119-121, respectively, in order of appearance), two repeats are from the Tal5a protein of *Xanthomonas oryzae* (GenBank: AEQ96609.1) (SEQ ID NOS 122-123, respectively, in order of appearance), and three repeats are from the Tal11a protein of *Xanthomonas oryzae* (GenBank: AEQ98467.1) (SEQ ID NOS 124-126, respectively, in order of appearance). Identical amino acids are shown as white letters on black background and non-identical amino acids are shown as black letters on white background.

FIG. 3A shows the amino acid sequence of the wild-type Hax3 protein (960 amino acids total) of *Xanthomonas campestris* (GenBank AAY43359.1) (SEQ ID NO: 127). The 288 amino acid region labeled "1" is the amino flanking region of the TAL repeat region, which is labeled "2". The 291 amino acid carboxyl terminal flanking region of the TAL repeat region is labeled "3". The first TAL repeat of the repeat region is shown boxed. Further, amino acids 153, 289, and 683 are labeled for reference.

FIG. 3B shows a TAL effector construct (SEQ ID NO: 128) designed to bind to the following nucleotide sequence: TACACGTTTCGTGTTCGGA (SEQ ID NO: 87). The labels are as follows: (1) V5 epitope, (2) nuclear localization signal, (3) amino flanking region of the TAL repeat region, (4) TAL repeat region, (5) carboxyl terminal flanking region of the TAL repeat region, (6) two amino acid linker, and (7) a wild-type FokI nuclease coding sequence. The first TAL repeat of the repeat region is shown boxed.

FIG. 4A is a plate assay where TAL effectors translated in cell-free environment are bound to DNA probes containing a TAL target site on Nickel-coated plates. An intercalating agent is added to allow for detection of specifically bound DNA molecules. Fluorescence read-out allows for comparison of binding specificity of different TAL-DNA interactions.

FIG. 4C is an alternative binding assay using paramagnetic Nickel-beads. Equal amounts of TAL protein were covalently coupled to activated DYNABEADS® and incubated with a 5-fold molar excess (Sample 1) and equimolar amount (Sample 2) of plasmid DNA for 1 hour. Beads were then separated from supernatant, washed once with PBS with Mg2+ and resuspended in equal volumes H2O. Resuspended beads were further diluted and total DNA was quantified by qPCR with plasmid specific primers and SYBR® Green against known dilutions of plasmid DNA (Std. 1 ng-Std. 0.001 ng). Samples were set up and quantified in triplicates.

FIG. 4E is a Gel shift assay where target-site containing DNA is shifted in the presence of sufficient amounts of a specifically binding TAL protein.

FIG. 4F shows an example of a TAL effector binding assay where TAL binding to a predicted binding site correlates with an increase in fluorescent signals. A customized TAL effector protein translated in vitro (e.g., from a plasmid or PCR fragment containing a promoter region) is incubated with a set of oligonucleotides. A first oligonucleotide (sense) (SEQ ID NO: 129) carries a TAL binding site and terminal ends that can form a stem-loop structure. One end of said oligonucleotide is attached to a fluorophore (star symbol) whereas the other end is attached to a quencher molecule (sphere symbol) so that the fluorophore signal is quenched in the stem-loop conformation. The second oligonucleotide (antisense) (SEQ ID NO: 130) is designed to hybridize with the first oligonucleotide (where labeling is optional). At least a portion of the first and second oligonucleotides in the pool are present in an annealed open state where the fluorophore signal is not quenched. Binding of a specific TAL effector protein to the TAL binding site stabilizes the annealed open conformation thereby shifting the equilibrium which results in a signal increase. In contrast a signal increase cannot be measured in the absence of TAL effector binding. FIG. 4D discloses SEQ ID NOS 129-130, 129-130 and 129-130, respectively, in order of appearance.

FIGS. 6A and 6B show various effector fusion open reading frames sequence-optimized for expression in mammalian hosts: SEQ ID NO: 1: codon-optimized sequence encoding FokI nuclease cleavage domain; SEQ ID NO: 2: codon-optimized sequence encoding FokI nuclease cleavage domain mutant KKR Sharkey; SEQ ID NO: 3: codon-optimized sequence encoding FokI nuclease cleavage domain mutant ELD Sharkey; SEQ ID NO: 4: codon-optimized sequence encoding VP16 activator; SEQ ID NO: 5 codon-optimized sequence encoding VP64 activator composed of a tetramer sequence representing the VP16 core motif; SEQ ID NO: 6: codon-optimized sequence encoding KRAB repressor.

FIG. 7B discloses SEQ ID NOS 131-132, respectively, in order of appearance.

FIG. 8A discloses SEQ ID NOS 133-134, respectively, in order of appearance. FIG. 8B shows the vector map for pENTR221 TATLTATL vp16 activator. FIG. 8C shows the vector map for pENTR221 Truncated TAL MCS.

FIG. 9A shows the different modules required for solid-phase assembly from trimer building blocks: 16 starter modules comprising a TAL 5' flanking region attached to an anchor and 16 different trimer modules representing all triplet combinations starting with a T-binding cassette, 64 elongation modules representing all triplet combinations of A-, G-, C- and T-binding cassettes, and 64 completion modules representing all triplet combination fused to a TAL 3' flanking region.

FIGS. 9B to 9G illustrate one possible method of assembling TAL effector sequences on solid-phase. Following immobilization of a starter module on a solid phase via a molecular anchor (FIG. 9B) the module is cleaved with a first type IIS enzyme (BsmBI in this example) to generate a single-strand overhang at the 3' end. A first elongation module is selected from the library and cleaved with a second type IIS enzyme (BbsI in this example) to generate an overhang at the 5' end. Cleaved starter module and first elongation module are then mixed and ligated on the solid phase (FIG. 9C). After a washing step an overhang is generated at the 3' end of the ligation product using the first type IIS enzyme, and a second elongation module comprising a compatible 5' overhang is added and ligated (FIG. 9D). Digestion and ligation cycles are repeated until a chain of n−1 modules has been assembled (FIG. 9E). The last step performed on the solid phase adds a completion module which provides the 3' flanking TAL sequences (FIG. 9F). Finally the TAL effector sequence is released from the solid phase by cleavage with a third type IIS enzyme (AarI in this example) which generates the compatible ends for insertion in a capture or functional vector (FIG. 9G).

FIG. 10D shows a topoisomerase adapted vector format of a type which can be used for insertion of one or more nucleic acid segments, resulting in the generation of a circularized molecule. FIGS. 10E and 10F show two vector formats which contain recombination sites and can be used for the insertion of nucleic acid segments at either two (FIG. 10E) or one (FIG. 10F) location. Labels are as follows: "Rec#", recombination sites with specificities which vary with the number; "SM", selectable marker (e.g., positive or negative selectable markers); "ori", origin or replication; "Tag", a tag sequence (e.g., an affinity tag); "Coding Sequence", an amino acid coding sequence formatted so as to result in the generation of a fusion protein when a another coding sequence is located between Rec1 and Rec2 is transcribed and translated; and the arrows represent promoters.

FIG. 11A discloses SEQ ID NO: 138.

FIG. 12A discloses SEQ ID NOS 139-140, respectively, in order of appearance.

FIG. 12B shows four partial TAL nucleic acid binding cassette coding sequences and encoded amino acids. Dashes represent omitted sequence data. NcoI and Esp3I cut sites are shown in the upper most nucleotide sequence in boxes. The two codon coding sequences encode the amino acids that determine base recognition in each of the four TAL cassettes are shown in boxes. Also, bases recognized by each TAL cassette are shown above the codons coding sequences. FIG. 12B discloses SEQ ID NOS 141, 143, 145, 147, 142, 144, 146, 148, 141, 149, 145, 147, 142, 150, 146, 148, 141, 151, 145, 147, 142, 152, 146, 148, 141, 153, 145, 147, 142, 154, 146 and 148, respectively, in order of appearance.

FIG. 13A shows a genetic inverter system that was created to test whether a TAL effector binds DNA in *E. coli*, in which the induction of AvrBs3 constructs by addition of arabinose is predicted to inhibit GFP expression (Des. GFP, destabilized GFP; Alt. TAL-trun, alternate truncations). FIG. 13B indicates that three AvrBs3 C-terminal truncation constructs expressed as fusions to thioredoxin show proper molecular weight in an SDS-PAGE analysis. FIG. 13C indicates that reporter strain expressing AvrBs3 constructs show significantly decreased fluorescence relative to control strains. (pTrc-UPA, promoter with an UPA20 target sequence).

FIG. 15B discloses SEQ ID NO: 155.

In FIG. 16A a reporter construct harboring a Tet-responsive binding site was used as negative control to demonstrate TAL specificity. The TAL repressor was constructed by replacing the C-terminal activation domain of AvrBs3 with a KRAB domain. The reporter constructs express GFP or LacZ from a full-length CMV promoter harboring TAL DNA binding sequence or TET binding sequence as a control. Cell cultures co-transfected with the indicated combinations of plasmids were analyzed in a microscope for GFP expression (left). The repression activity of TAL-KRAB was demonstrated to be target-site specific. Furthermore β-galactosidase reporter activity was measured 72 hours post-transfection. The figure is graphed as the percentage of the signal to the pcDNA3 control transfection. Co-expression of AvrB3-Krab was more efficient in the presence of two copies of TAL DNA binding sites and comparable with Tet-mediated repression.

FIG. 16B shows an example for the establishment of TAL responsive stable cell lines. A single copy of the TAL responsive reporter cassette was integrated into the genome of FLP-IN™-293 cells. The GFP reporter is driven from a full-length CMV promoter harboring a TAL DNA binding sequence. Cell of parental stable FLP-In cells and cells with CMV-GFP cassette were analyzed by flow cytometry.

FIGS. 16C to 16J show down regulation of chromosomal genes by engineered TALs. A TAL-KRAB repressor was co-transfected with a RFP expression plasmid as a transfection control into FLP-IN™ stable cell line harboring a CMV-1×TAL-GFP reporter cassette. pcDNA3 empty vector and Tet repressor were used as negative control. siRNA targeting GFP and control siRNA were co-transfected with RFP expression plasmid. Cell population gated by RFP positive cells was analyzed by flow cytometry 72 hours post transfection.

FIG. 19 discloses SEQ ID NOS 156-159, respectively, in order of appearance.

FIGS. 20A to 20H show an example of sequence mapping of TAL effector nuclease mediated genomic lesions. This approach takes advantage of mismatch-detecting enzymes (MME) such as that from *Perkinsus marinas*, Cel1, Res1 or similar to identify modifications in the genome. A) Starting with treated and untreated cell populations, the genomic DNA is purified (B) and cleaved with a cocktail of restriction enzymes that result in an average fragment size of 100 base pairs (C). This can also be achieved using mechanical and enzymatic shearing techniques. D) Those populations are mixed, melted and allowed to cross-hybridize resulting in a mismatch at the point of the lesion where the strand from the treated cell anneals with that from the untreated cell. E) The fragments are then adapted using modified Ion PGM 'P1*' adapter containing a very rare restriction site at its 5' end. This restriction site would ideally be a rare-cutting type IIS restriction enzyme to be compatible with ION TORRENT™ sequencing primer design. F) After clean up, the mismatch (indicating the lesion to be identified) is cleaved by treatment with an MME. G) The population containing new non-adapted ends is then ligated with 'A' adapter which does not contain the rare site in 'P1*'. H) The entire population is then treated with the rare cutting enzyme to release the 'A' adapter ligated the modified 'P1*' adapter. This leaves a population of fragments appended with the 'P1*' adapter on each end (non-lesion) and fragments with the 'P1*' adapter on one end and 'A' ligated to the lesion site. This population would then be subjected to PGM sequencing using 'P1*' to anchor the fragments to the beads and 'A' to identify the genomic lesion sites.

FIGS. 22A to 22E show different vectors suitable for co-expression of TAL effector pairs wherein TAL effector open reading frames (ORF) are under control of the same promoter and either separated by an IRES (FIG. 22A), a T2A cleavage site (FIG. 22B), a translational coupler sequence (FIG. 22C) or an intein (FIG. 22D), or wherein TAL effector ORFs are expressed from different expression cassettes on the same vector (FIG. 22E).

FIG. 25A and FIG. 25B show an amino acid alignment between two coding region-derived protein sequences and consensus sequence regions at identical or strongly similar positions thereof; the proteins are RBRH_01844 of *Burkholderia rhizoxinica* HKI 454 (GenBank Accession No. YP_004022479) (SEQ ID NO: 48) and RBRH_01776 of the same species (GenBank Accession No. YP_004030669) (SEQ ID NO: 49). For the protein sequences, identical and strongly similar amino acids are shown as white text against a black background while weakly similar amino acids are shown as black text against a white background. The boxed consensus sequence regions at the amine and carboxyl termini of the full length amino acid sequences are regions that flank the TAL repeat region. The underlined regions in the consensus sequence near the amine and carboxyl termini may represent TAL repeats or TAL repeat-like sequences. TAL repeat-like sequences such as these could assist in the formation of the corrected structure or nucleic acid binding activity of terminal TAL repeats or the TAL repeat region generally.

FIG. 26 shows the coding region-derived amino acid sequence of protein RBRH_01776 of *Burkholderia rhizoxinica* (SEQ ID NO:47; GenBank Accession No. YP_004030669). The white text on a black background at the amine and carboxyl termini of the full length amino acid sequence depicts regions that flank the TAL repeat region. The underlined regions near the amine and carboxyl termini may represent TAL repeats or TAL repeat-like sequences. The individual TAL repeats are shown in alternating bold, italic text and plain text. The amino acid pairs shown in boxes are repeat variable diresidue (RVD) sequences within TAL repeats.

FIG. 27 shows an amino acid alignment of TAL repeat structures of the two *Burkholderia* proteins; those repeat structures designated *Burkholderia* 1-18 are from protein RBRH_01776 of *Burkholderia rhizoxinica* HKI 454 (GenBank Accession No. YP_004030669) (SEQ ID NOS 160-177, respectively, in order of appearance) and those repeat structures designated *Burkholderia* A-T are from protein RBRH_01844 of the same species (GenBank Accession No. YP_004022479) (SEQ ID NOS 178-197, respectively, in order of appearance). Identical or similar amino acids are shown as white letters on black background and non-identical amino acids are shown as black letters on white background. The sequences are assigned sequence identification numbers in FIG. 26. The symbols ⇊ designate the repeat variable diresidue at amino acid positions 12 and 13.

FIG. 28 shows an amino acid alignment of TAL repeat structures from a protein of an unidentified marine organism (referred to as Marine Organism A, GenBank Accession No. EBN19409) (SEQ ID NOS 198-206, respectively, in order of appearance). Identical or similar amino acids are shown as white letters on black background and non-identical amino acids are shown as black letters on white background. The sequences are assigned sequence identification numbers in FIG. 27. The symbols ⇊ designate the repeat variable diresidue at amino acid positions 12 and 13.

FIG. 29 shows an amino acid alignment of TAL repeat structures from a protein of an unidentified marine organism (referred to as Marine Organism B, GenBank Accession No. ECG96325) (SEQ ID NOS 207-212, respectively, in order of appearance). Identical or similar amino acids are shown as white letters on black background and non-identical amino acids are shown as black letters on white background. The sequences are assigned sequence identification numbers in FIG. 28. The symbols ⇊ designate the repeat variable diresidue at amino acid positions 12 and 13.

FIG. 30 shows an amino acid alignment of TAL nucleic acid binding cassettes from seven different proteins. Two repeats are from the AvrXa27 protein of *Xanthomonas oryzae* (GenBank Accession No. AAY54168.1) (SEQ ID NOS 213-214, respectively, in order of appearance), two repeats are from the Hax3 protein of *Xanthomonas campestris* (GenBank Accession No. AAY43359.1) (SEQ ID NOS 221-222, respectively, in order of appearance), three repeats are from the PSI07 protein of *Ralstonia solanacearum* (Accession No. YP_003750492.1) (SEQ ID NOS 223-225, respectively, in order of appearance), two repeats are from the Tal5a protein of *Xanthomonas oryzae* (Accession No. AEQ96609.1) (SEQ ID NOS 226-227, respectively, in order of appearance), three repeats are from the Tal11a protein of *Xanthomonas oryzae* (GenBank Accession No. AEQ98467.1 (SEQ ID NOS 228-230, respectively, in order of appearance), six repeats are from an unidentified blood-borne pathogen protein (BBP) (GenBank Accession No. CCA82456) (SEQ ID NOS 215-220, respectively, in order of appearance), and six repeats from Marine Organism B from FIG. 28 (SEQ ID NOS 207-212, respectively, in order of appearance). Identical and similar amino acids are shown as white letters on black background and non-identical amino acids are shown as black letters on white background. The symbols ⇊ designate the repeat variable diresidue at amino acid positions 12 and 13.

Figure 31A:
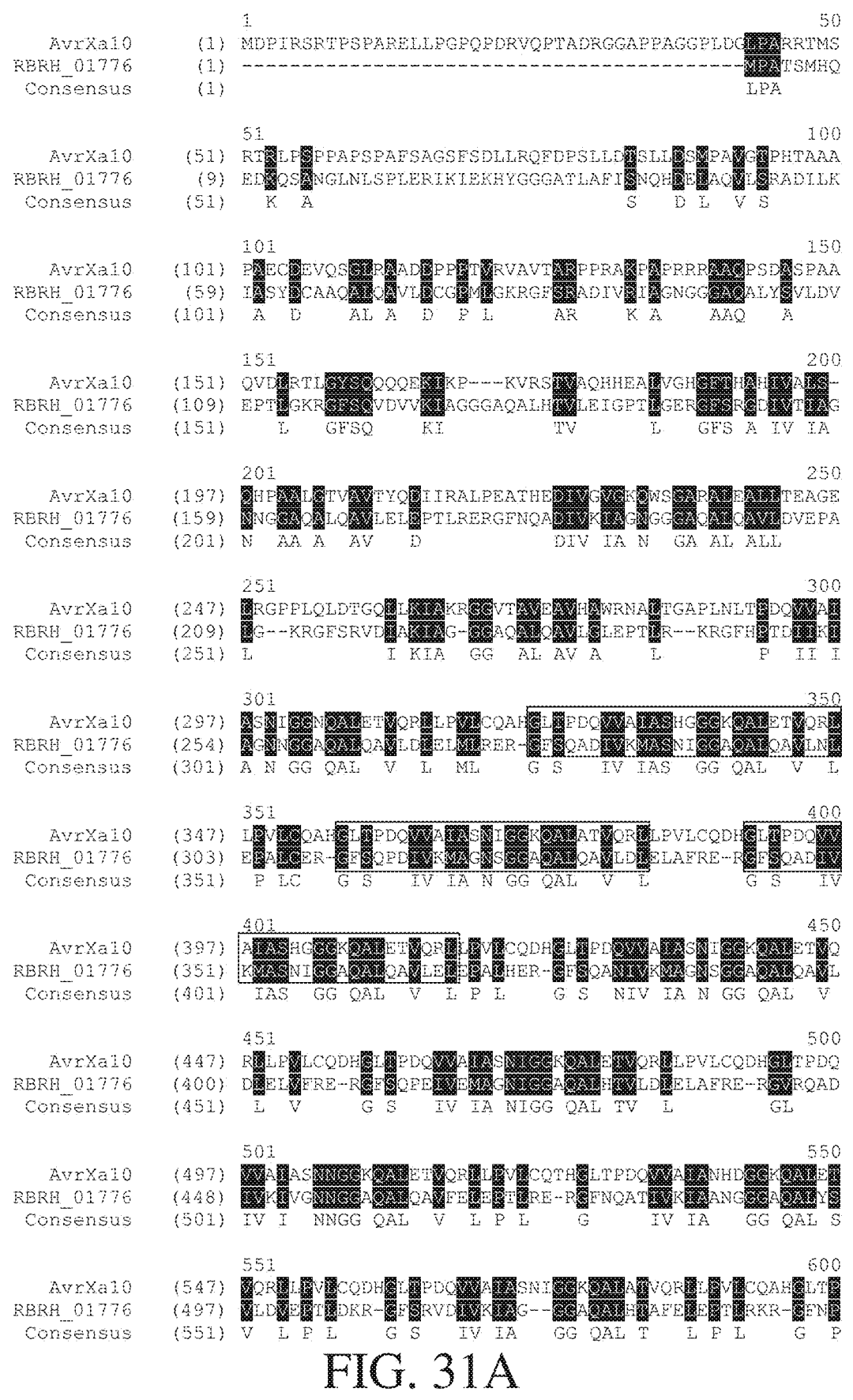
Figure 31B:
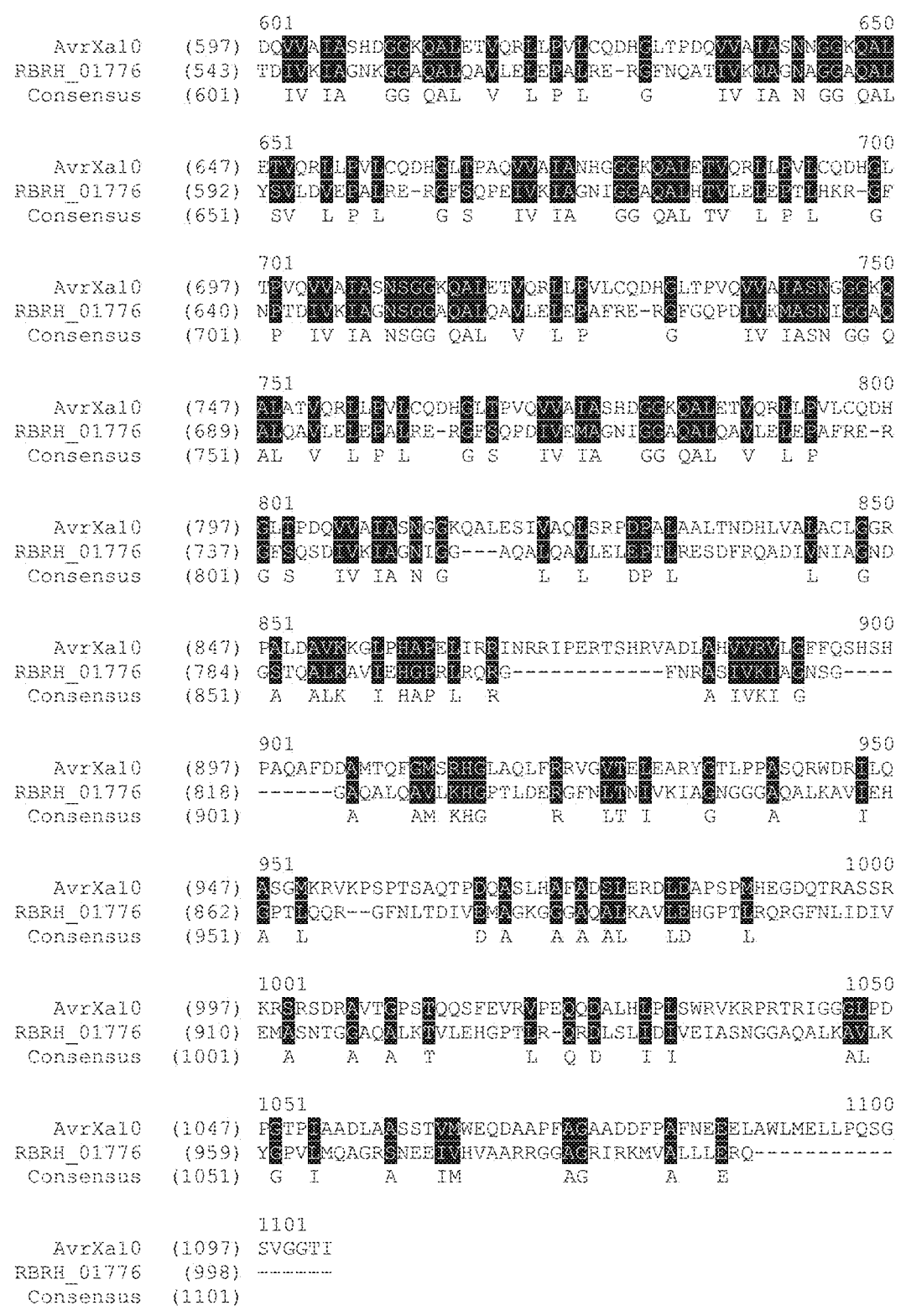

FIG. 31A and FIG. 31B show an amino acid alignment between the AvrXa10 protein of *Xanthomonas oryzae* (GenBank Accession No. AAA92974) (SEQ ID NO: 231) and a coding region-derived amino acid sequence of protein RBRH_01776 of *Burkholderia rhizoxinica* (GenBank Accession No. YP_004030669) (SEQ ID NO: 47). Identical and strongly similar amino acids are shown as white text against a black background. Weakly similar amino acids are shown as black text against a white background. Three roughly 26 amino acid sequences are also enclosed in open boxes as shown in FIG. 31A. These boxes are included to show exemplary amino acid sequences which are fairly highly conserved between the two proteins represented therein.

FIG. 32A illustrates how a dimer library can be arranged to allow for co-assembly of 4 building blocks each into two capture vectors using a minimum set of building blocks. FIG. 32B shows how a universal TAL assembly kit relying on a collection of dimer building blocks may be arranged.

FIG. 33A shows the promoter region of the endogenous sox2 gene with transcription factor- and TAL-binding sites indicated. FIG. 33B shows the activation of Sox2 promoter via targeting of TAL FLVP64 activator fusion proteins to binding sites 4643 or/and 655. FIG. 33C shows the repression of the Sox2 promoter via targeting of TAL KRAB repressor and TAL MCS fusion proteins to binding site 4643. HeLa cells were transfected the indicated TAL effectors expression plasmids and then the mRNA levels of sox2 were evaluated by TaqMan assay 72 hours post transfection and normalized to β-actin.

FIG. 34A shows an embodiment, wherein TAL nuclease expression vector(s) are co-delivered to a target host cell with a surrogate reporter containing a tse2 gene fused to target binding site for the TAL nuclease and a tsi2 gene placed out of frame. Cells not expressing functional TAL nuclease pairs will be killed by Tse2 expression. However, in the presence of functional TAL nuclease double strand breaks are introduced into the target cleavage site a portion of which will be repaired by NHEJ putting the tsi2 gene into the correct reading frame. The Tsi2 antidote protein will be released via T2A-mediated auto-cleavage and rescue cells from Tse2-associated toxicity. FIG. 34B shows an embodiment where a vector set for coexpression of two TALE FokI nuclease cleavage half domains each of which is connected in a separate vector to either Tse2 or Tsi2 via a T2A self cleavage site is delivered into a target host cell. As nuclease-mediated modification of cells depends on the coexpression of both TAL nuclease cleavage half domains and the survival of cells depends on expression of Tsi2, only cells with balanced Tse2 and Tsi2 expression levels will survive and grow.

FIG. 35 shows the amino acid sequence of a TAL polymerase fusion protein (SEQ ID NO: 232), referred to as TAL-Bst1.0. The first boxed sequence shows a V5 epitope (amino acids 1 through 15, bold italicized sequence) and a nuclear localization signal (NLS) (amino acids 16 through 29). A 136 amino acid N-terminal region of a TAL effector (Hax3) is shown as amino acids 30 through 165. The first complete and last partial TAL repeats are shown in double lined boxes (amino acids 166 through 748). A 135 amino acid N-terminal region of a TAL effector (also Hax3) is shown as amino acids 749 through 883. A linker sequence (GGGVTM) (SEQ ID NO: 89) is shown as amino acids 884 through 889. A portion of a DNA polymerase I from *Bacillus stearothermophilus* (Bst1.0) is shown as amino acids 890 to 1469. The DNA polymerase contains both an exonuclease activity as well as a 5'-3' DNA polymerase activity (amino acid sequences not delineated).

FIG. 36A shows an exemplary TAL effector sequence with 24 cassettes where sequencing is performed with a set of forward and reverse primers binding 5' and 3' of the TAL repeat coding region (e.g., within the TAL N- and C-terminus, respectively) and at least one additional primer specifically binding to a cassette within the center or near the center of the series of assembled TAL effector cassettes. The at least one additional primer can be designed to bind in the 5' portion of the TAL effector sequence reading forward or can be designed to bind in the 3' portion of the TAL effector sequence reading backward (reverse primer). For larger TAL effector sequences two additional primers reading forward and backward may be used. FIG. 36B shows how a cassette allocated to a specific position within the series of assembled cassettes (in this example position 16) may be designed to allow specific binding of an additional primer. Based on the repetitive structure all cassettes may contain at least one homologous region (indicated by a vertical bar in each cassette) with an identical nucleotide composition. Such homologous region should have a size sufficient to allow for specific primer binding. For example the homologous region may contain at least 10, 11, 12, 13, 14, 15, 16, 17, 18, 19, 20, 21, 22, 23, 24, 25, 26, 27, 28, 29, 30 or more than 30 nucleotides. At least one cassette of each binding category (A-, G-, C, T-binder) allocated to a defined position (here position 16 within the 24 cassettes) is designed such that the nucleotide composition within the homologous region differs from the same region within all other cassettes in all other positions. The nucleotide composition within the homologous region may differ by at least 3 or 4 nucleotides (indicated by vertical lines in the hatched homologous region of cassette No. 16) from the nucleotide composition of the same region in all other cassettes to allow stable binding of a sequencing primer to the target sequence within the selected cassette. The skilled person will understand that the number of differing nucleotides depends on the length of the homologous region available for primer binding and the length and melting temperature of the sequencing primer. The differing nucleotides are preferably located at the 3'-end of the primer to prevent unspecific binding. To generate cassettes with unique nucleotide composition, silent mutations may be introduced without changing the encoded amino acid sequence. As described elsewhere herein such modifications may for example be introduced based on the degeneracy of the genetic code using alternative codons.

DETAILED DESCRIPTION OF THE INVENTION

Definitions

Figure 1A:
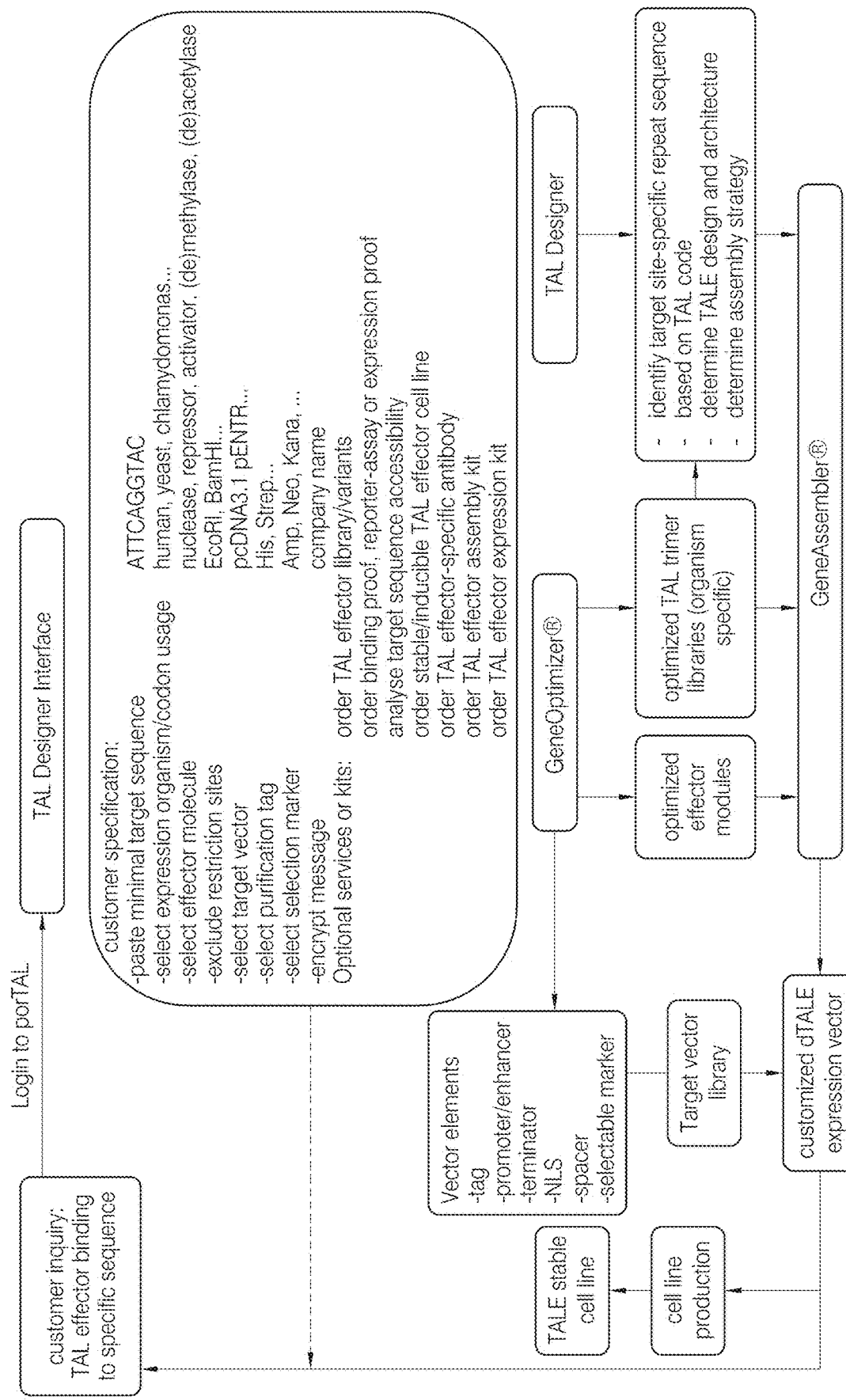

As used herein "TAL nucleic acid binding cassette" (also referred to as a "TAL cassette") refers to nucleic acid that encodes a polypeptide which allows for a protein that the polypeptide is present in to bind a single base pair (e.g., A, T, C, or G) of a nucleic acid molecule. In most instances, proteins will contain more than one polypeptide encoded by a TAL nucleic acid binding cassettes. The individual amino acid sequences of the encoded multimers are referred to as "TAL repeats". In many instances, TAL repeats will be between twenty-eight and forty amino acids in length and (for the amino acids present) will share at least 60% (e.g., at least about 65%, at least about 70%, at least about 75%, at least about 80%, from about 60% to about 95%, from about 65% to about 95%, from about 70% to about 95%, from about 75% to about 95%, from about 80% to about 95%, from about 85% to about 95%, from about 60% to about 90%, from about 60% to about 85%, from about 65% to about 90%, from about 70% to about 90%, from about 75% to about 90%, etc.) identity with the following thirty-four amino acid sequence:

```
                                          (SEQ ID NO: 7)
LTPDQVVAIA SXXGGKQALE TVQRLLPVLC QAHG
```

As explained in addition detail elsewhere herein, the two Xs at positions twelve and thirteen in the above sequence represent amino acid which also TAL nucleic acid binding cassettes to recognize a specific base in an nucleic acid molecule.

In many instances, the final TAL repeat present at the carboxyl terminus of a series of repeats series will often be a partial TAL repeat in that the carboxyl terminal end may be missing (e.g., roughly the amino terminal 15 to 20 amino acids of this final TAL repeat).

Nucleotide and amino acid sequence may be compared to each other by a number of means. For example a number of publicly available computer programs may be used to compare sequences.

In sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, as described below for the BLASTN (nucleic acids) and BLASTP (proteins) programs, or alternative parameters can be designated. The sequence comparison algorithm then calculates the percent sequence identities for the test sequences relative to the reference sequence, based on the program parameters. Alignment of sequences for comparison can also be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis., USA).

One algorithm suitable for determining percent sequence identity and sequence similarity are the BLAST and BLAST 2.0 algorithms, which are described in Altschul et al., Nucl. Acids Res. 25:3389-3402 (1977) and Altschul et al., J Mol. Biol. 215:403-410 (1990), respectively. Software for performing BLAST analyses is publicly available through the National Center for Biotechnology Information (see http://blast.ncbi.nlm.nih.gov/Blast.cgi). In some instances, amino acid sequence comparisons as performed using the algorithm designated blastp (protein-protein BLAST) with the default settings.

As used herein "TAL effector" refers to proteins composed of more than one TAL repeat and is capable of binding to nucleic acid in a sequence specific manner. In many instances, TAL effectors will contain at least six (e.g., at least 8, at least 10, at least 12, at least 15, at least 17, from about 6 to about 25, from about 6 to about 35, from about 8 to about 25, from about 10 to about 25, from about 12 to about 25, from about 8 to about 22, from about 10 to about 22, from about 12 to about 22, from about 6 to about 20, from about 8 to about 20, from about 10 to about 22, from about 12 to about 20, from about 6 to about 18, from about 10 to about 18, from about 12 to about 18, etc.) TAL repeats. In some instances, a TAL effector may contain 18 or 24 or 17.5 or 23.5 TAL nucleic acid binding cassettes. In additional instances, a TAL effector may contain 15.5, 16.5, 18.5, 19.5, 20.5, 21.5, 22.5 or 24.5 TAL nucleic acid binding cassettes. TAL effectors will generally have at least one polypeptide region which flanks the region containing the TAL repeats. In many instances, flanking regions will be present at both the amino and carboxyl termini of the TAL repeats.

As used herein "TAL effector fusion" refers to a TAL effector connected to another polypeptide or protein to which it is not naturally associated with in nature. In many instances, the non-TAL component of the TAL effector fusion will confer a functional activity (e.g., an enzymatic activity) upon the fusion protein. The one or more connected polypeptides or proteins may have functions equal to or different from the TAL effector. For example, a TAL effector fusion may also have binding activity or may have an activity that directly or indirectly triggers nucleic acid modification, such as, e.g., an enzymatic activity.

In one aspect, the function of a TAL effector may be embodied by the binding activity per se. Specific binding of a TAL effector to a target sequence may, e.g., block the sequence or repress downstream events or may allow for detection of a sequence or recruit other molecules. In many instances TAL effectors also include proteins wherein the TAL repeat is operatively linked with at least one other activity. TAL effectors engineered to bind specific DNA targets can be designed according to rational criteria applying known TAL code rules, computerized algorithms for processing information in a database storing information of existing RVD designs and binding data. Functional TAL effectors can further be selected from rationally designed libraries in directed evolution approaches described elsewhere herein.

TAL effectors may be fused to DNA modifying enzymes capable of modifying the genetic material of a cell by, for example, cleavage, covalent interaction, water-mediated interaction or the like. The TAL fusion partner may be any DNA interacting or modifying protein such as, for example, an activator or a repressor, a nuclease, a topoisomerase, a gyrase, a ligase, a glycosylase, an acetylase, a deacetylase, an integrase, a transposase, a methylase, a demethylase, a methyl-transferase, a homing endonuclease, a kinase, a recombinase, a ligase, a phosphatase, a sulphurilase or an inhibitor of the one or more activities of one or more of such TAL fusion partners.

As used herein a TAL binding site or target binding site refers to any order of bases in a given nucleic acid sequence that can be recognized and bound by a TAL effector. Such binding site can be provided either in the context of double-stranded DNA or alternatively in the context of a DNA-RNA hybrid, wherein the DNA strand determines binding specificity. If the binding site is provided in the context of double-stranded DNA it can be methylated or unmethylated.

As used herein the term "nucleic acid molecule" refers to a covalently linked sequence of nucleotides or bases (e.g., ribonucleotides for RNA and deoxyribonucleotides for DNA but also include DNA/RNA hybrids where the DNA is in separate strands or in the same strands) in which the 3' position of the pentose of one nucleotide is joined by a phosphodiester linkage to the 5' position of the pentose of the next nucleotide. Nucleic acid molecule may be single- or double-stranded or partially double-stranded. Nucleic acid molecule may appear in linear or circularized form in a supercoiled or relaxed formation with blunt or sticky ends and may contain "nicks". Nucleic acid molecule may be composed of completely complementary single strands or of partially complementary single strands forming at least one mismatch of bases. Nucleic acid molecule may further comprise two self-complementary sequences that may form a double-stranded stem region, optionally separated at one end by a loop sequence. The two regions of nucleic acid molecule which comprise the double-stranded stem region are substantially complementary to each other, resulting in self-hybridization. However, the stem can include one or more mismatches, insertions or deletions. Nucleic acid molecules may comprise chemically, enzymatically, or metabolically modified forms of nucleic acid molecules or combinations thereof. Chemically synthesized nucleic acid molecules may refer to nucleic acids typically less than or equal to 150 nucleotides long (e.g., between 5 and 150, between 10 and 100, between 15 and 50 nucleotides in length) whereas enzymatically synthesized nucleic acid molecules may encompass smaller as well as larger nucleic acid molecules as described elsewhere in the application. Enzymatic synthesis of nucleic acid molecules may include stepwise processes using enzymes such as polymerases, ligases, exonucleases, endonucleases or the like or a combination thereof. Thus, the invention provides, in part, compositions and combined methods relating to the enzymatic assembly of chemically synthesized nucleic acid molecules.

Nucleic acid molecule also refers to short nucleic acid molecules, often referred to as, for example, primers or probes. Primers are often referred to as single stranded starter nucleic acid molecules for enzymatic assembly reactions whereas probes may be typically used to detect at least partially complementary nucleic acid molecules. A nucleic acid molecule has a "5'-terminus" and a "3'-terminus" because nucleic acid molecule phosphodiester linkages occur between the 5' carbon and 3' carbon of the pentose ring of the substituent mononucleotides. The end of a nucleic acid molecule at which a new linkage would be to a 5' carbon is its 5' terminal nucleotide. The end of a nucleic acid molecule at which a new linkage would be to a 3' carbon is its 3' terminal nucleotide. A terminal nucleotide or base, as used herein, is the nucleotide at the end position of the 3'- or 5'-terminus. A nucleic acid molecule sequence, even if internal to a larger nucleic acid molecule (e.g., a sequence region within a nucleic acid molecule), also can be said to have 5'- and 3'-ends.

A "wild-type sequence" as used herein refers to any given sequence (e.g., an isolated sequence) that can be used as template for subsequent reactions or modifications. As understood by the skilled artisan, a wild-type sequence may include a nucleic acid sequence (such as DNA or RNA or combinations thereof) or an amino acid sequence or may be composed of different chemical entities. In some embodiments, the wild-type sequence may refer to an in silico sequence which may be the sequence information as such or sequence data that can be stored in a computer readable medium in a format that is readable and/or editable by a mechanical device. A wild-type sequence (reflecting a given order of nucleotide or amino acid symbols) can be entered, e.g., into a customer portal via a web interface. In most instances, the sequence initially provided by a customer would be regarded as wild-type sequence in view of downstream processes based thereon—irrespective of whether the sequence itself is a natural or modified sequence, i.e., it was modified with regard to another wild-type sequence or is completely artificial.

In some instances wild-type sequence may also refer to a physical molecule such as a nucleic acid molecule (such as RNA or DNA or combinations thereof) or a protein, polypeptide or peptide composed of amino acids. Methods to obtain a wild-type sequence by chemical, enzymatic or other means are known in the art. In one embodiment, a physical nucleic acid wild-type sequence may be obtained by PCR amplification of a corresponding template region or may be synthesized de novo based on assembly of synthetic oligonucleotides. A wild-type sequence as used herein can encompass naturally occurring as well as artificial (e.g., chemically or enzymatically modified) parts or building blocks. A wild-type sequence can be composed of two or multiple sequence parts. A wild-type sequence can be, e.g., a coding region, an open reading frame, an expression cassette, an effector domain, a repeat domain, a promoter/enhancer or terminator region, an untranslated region (UTR) but may also be a defined sequence motif, e.g., a binding, recognition or cleavage site within a given sequence. A wild-type sequence can be both, DNA or RNA of any length and can be linear, circular or branched and can be either single-stranded or double stranded.

"Optimization" of a sequence as used herein shall include all aspects of sequence modification of a given wild-type sequence to improve or prepare the sequence for a specific purpose or application. Optimization can be performed in silico, e.g., by computer-implemented methods using specific algorithms or software. A given wild-type sequence may be completely optimized (e.g., over its entire length). Alternatively, only parts or domains of the sequence may be subject to an optimization process. In some instances optimization includes modification of a physical molecule e.g., by replacing, inserting or deleting one or more elements in the sequence. By way of example a protein sequence or function can be optimized by modification of the underlying nucleic acid sequence. This can be achieved by molecular methods known in the art such as mutation, shuffling or recombination approaches or by de novo synthesis of modified sequence parts.

Optimization of a wild-type sequence may include silent codon changes to replace non- or less preferred codons by more preferred codons without modifying the encoded amino acid sequence. Codon-optimization may for example impact expression yields, solubility, protein activity, protein folding or other functions of an expression product. Optimization of the codon bias of a wild-type sequence is often employed to allow for optimal expression of a given gene in a homologous or heterologous host. For example, a gene originally derived from plant, virus, bacteria, yeast etc. may be adapted to the preferred codon usage of mammalian cells to achieve optimal expression yields in a mammalian host and vice versa. Apart from codon usage certain sequence motifs such as splice sites, cis-active inhibitory RNA motifs (often referred to as CRS or INS), internal poly-adenylation signal sequences such as, e.g., AUUUA, or silencing motifs may have to be eliminated to allow for heterologous expression. Furthermore, specific motifs triggering expression can be fused to (e.g., 5' or 3'-UTR regions) or inserted (such as, e.g., modification of the intragenic CpG dinucleotide content) in a sequence to modulate expression or activity of an expression product in a specific host.

In genetic engineering selectable markers are widely used as reporter systems to evaluate the success of cloning strategies or cell transduction efficiency. Various selection marker genes are known in the art often encoding antibiotic resistance function for selection in prokaryotic (e.g. against ampicillin, kanamycin, tetracycline, chloramphenicol, zeocin, spectinomycin/streptomycin) or eukaryotic cells (e.g. geneticin, neomycin, hygromycin, puromycin, blasticidin, zeocin) under selective pressure. Other marker systems allow for screening and identification of wanted or unwanted cells such as the well-known blue/white screening system used in bacteria to select positive clones in the presence of X-gal or fluorescent reporters such as green or red fluorescent proteins expressed in successfully transduced host cells. Another class of selection markers most of which are only functional in prokaryotic systems relates to counter selectable marker genes often also referred to as "death genes" which express toxic gene products that kill producer cells. Examples of such genes include sacB, rpsL(strA), tetAR, pheS, thyA, gata-1, or ccdB, the function of which is described in Reyrat et al. Counterselectable Markers: Untapped Tools for Bacterial Genetics and Pathogenesis. Infect Immun. 66(9): 4011-4017 (1998).

A "counter selectable" marker (also referred to herein a "negative selectable marker") or marker gene as used herein refers to any gene or functional variant thereof that allows for selection of wanted vectors, clones, cells or organisms by eliminating unwanted elements. These markers are often toxic or otherwise inhibitory to replication under certain conditions which often involve exposure to a specific substrates or shift in growth conditions. Counter selectable marker genes are often incorporated into genetic modification schemes in order to select for rare recombination or cloning events that require the removal of the marker or to selectively eliminate plasmids or cells from a given population. They have been used for the selection of transformed bacteria or to identify mutants in genetic engineering and are likewise appropriate for use in certain aspects of the invention. Such selectable marker genes help to significantly boost cloning efficiency by reducing the background in cloning experiments represented by uncut or recircularized empty background vectors lacking an insert. Negative selection requires a loss of the marker function which may be achieved by different strategies. In a first embodiment the toxic function may, e.g., be destroyed by insertion of a DNA fragment or gene of interest into either the open reading frame (ORF) of the marker gene or into/prior to the regulatory region (e.g. promoter region) thereby interfering with marker gene expression ("insertion strategy"). Alternatively, a DNA fragment or gene of interest may be inserted thereby completely replacing the marker gene ("replacement strategy"). Whereas most of the embodiments described elsewhere herein refer to the replacement strategy it is understood by the skilled person that vectors used in methods of the invention can be adapted to use the insertion strategy instead. In both cases cloning vectors which carry the DNA fragment or gene of interest within or instead of the selectable marker ORF will allow bacterial growth and selection of positive clones (i.e. carrying the desired insert) whereas cells obtaining the marker gene expression construct will die and automatically be sorted out.

One example of a negative selectable marker system widely used in bacterial cloning methods is the CcdA/CCdB Type II Toxin-antitoxin system. The system encodes two proteins: the 101 amino acid (11.7 kDa) CcdB toxin which inhibits cell proliferation by forming a complex with the GyrA subunit of DNA gyrase, a bacterial topoisomerase II, and the 72 amino acid CcdA antidote (8.7 kDa) which prevents the toxic effect by forming a tight complex with CcdB. The CcdA/CCdB system is located on the F-plasmid and functions in plasmid maintenance in E. coli by killing those daughter cells that have not inherited a copy of the F-plasmid at cell division which is also referred to as "post-segregational killing" (Bernard and Couturier. Mol. Gen. Genet. 226, 297-304 (1991); Salmon et al. Mol. Gen. Genet. 244, 530-538 (1994)). In order to use this system for cloning purposes the CcdB encoding gene can be inserted into cloning or expression vectors to kill bacteria which have not received a recombinant vector carrying a gene or DNA molecule of interest. One example where the ccd selection system has been successfully employed is the Gateway® Technology offered by Invitrogen/Life Technologies (Carlsbad, Calif.) which relies on replacement of the ccdB gene by a DNA fragment or gene of interest via site-specific homologous recombination and is described in more detail elsewhere herein.

In certain instances it may be required to amplify or propagate a vector carrying a negative selectable marker gene. In toxin-sensitive bacteria this may be achieved by using an inducible marker gene expression cassette. Another possibility is the provision of a host strain which is resistant to the toxic effects of the marker protein. For example, to allow for propagation of vectors carrying a ccdB gene, host strains have been genetically engineered to carry a CcdA expression cassette which guarantees survival of bacteria receiving a ccdB-containing vector. Such ccdB Survival™ strain is offered by Invitrogen/Life Technologies (Carlsbad, Calif.). Furthermore, CcdA expression host strains are described in U.S. Pat. No. 7,176,029 which is incorporated by reference in its entirety herein.

Another example of a selection system that relies on toxin-antitoxin interaction is the Tse2/Tsi2 system. The two components are derived from the type-6-secretion system (T6SS) which was shown to be used by Pseudomonas aeruginosa to inject type VI secretion exported 1-3 effector proteins (Tse1, Tse2 and Tse3) into the periplasmic space of neighbored competing Gram-negative bacteria thereby inhibiting target cell proliferation (Hood et al. Cell Host Microbe. 7(1):25-37 (2010)). However, to avoid self-intoxication by Tse2 part of which also remains in the cyotsol of P. aeruginosa, the cytosolic type VI secretion immunity 2 protein (Tsi2) which neutralizes the toxic effects of Tse2 must be present in the cell. Tse2 has been shown to inhibit essential cellular processes in a broad spectrum of organisms including prokaryotic (e.g. E. coli, Burkholderia thailandensis) or eukaryotic cells (e.g. S. cerevisiae, HeLa cells) which makes it an attractive universal selection marker. A Tse2 encoding expression cassette (containing a tse2 gene operationally linked to a regulatory sequence) can therefore be inserted into cloning vectors to allow counter selection of positive clones containing inserted DNA fragments or a gene of interest whereas those cells which have received a Tse2 expressing plasmid will be sorted out. As described above, the Tse2 expression cassette can be adapted to allow either insertion or replacement of one or more DNA fragments or a gene of interest. Various vectors allowing for inducible or constitutive expression of the tse2 gene (or truncated or mutated versions thereof) as counter selectable marker for recombinational, TOPO, TA- or restriction enzyme cleavage-mediated cloning are described in U.S. Patent Publication No. 2012/0270271 which is incorporated by reference in its entirety herein.

In certain instances it may be required to amplify or propagate a vector carrying a tse2 gene in a host cell. In Tse2 sensitive cells, this can be achieved by either making Tse2 expression inducible or by providing an antidote to confer immunity upon Tse2 expressing cells. The antidote can be any expression product capable of interfering with the cytotoxic activity of Tse2, including but not limited to Tse2 antisense constructs, Tse2 binding aptamers and Tse2 binding polypeptides. In one embodiment an inducible Tsi2 expression cassette can be included in the vector containing a Tse2 expression cassette. Another possibility is the co-expression with a Tsi2 coding vector or the provision of a host strain expressing the Tsi2 antidote to render a cell immune towards Tse2 expression. In certain embodiments it may be required to use a host cell which has been genetically engineered to carry a Tsi2 expression cassette chromosomally integrated or on an extrachromosomal element. Different embodiments providing suitable Tse2 antidotes or recombinant Tse2 expressing immune host cells are described in U.S. Patent Publication No. 2011/0311499 which is incorporated by reference in its entirety herein.

Any of the vectors used in embodiments of the invention (including cloning vectors, expression vectors, capture vectors, viral vectors or functional vectors) can be modified to carry counter selectable marker genes such as ccdB or tse2 or functional variants thereof. In certain instances it may be preferred to use a sequence-optimized version of a selectable marker gene such as, e.g., a ccdB gene or a tse2 gene adapted to the preferred codon usage of E. coli. To achieve improved expression of a selectable marker gene in a specific host cell, procedures of sequence and/or codon optimization as described above may be pursued.

A "vector" as used herein is a nucleic acid molecule that can be used as a vehicle to transfer genetic material into a cell. A vector can be a plasmid, a virus or bacteriophage, a cosmid or an artificial chromosome such as, e.g., yeast artificial chromosomes (YACs) or bacterial artificial chromosomes (BAC). In most instances a vector refers to a DNA molecule harboring at least one origin of replication, a multiple cloning site (MCS) and one or more selection markers. A vector is typically composed of a backbone region and at least one insert or transgene region or a region designed for insertion of a DNA fragment or transgene such as a MCS. The backbone region often contains an origin of replication for propagation in at least one host and one or more selection markers. In most instances a vector contains additional features. Such additional features may include natural or synthetic promoters, genetic markers, antibiotic resistance cassettes or selection markers (e.g., toxins such as ccdB or tse2), epitopes or tags for detection, manipulation or purification (e.g., V5 epitope, c-myc, hemagglutinin (HA), FLAG™, polyhistidine (His), glutathione-S-transferase (GST), maltose binding protein (MBP)), scaffold attachment regions (SARs) or reporter genes (e.g., green fluorescent protein (GFP), red fluorescence protein (RFP), luciferase, β-galactosidase etc.). In most instances vectors are used to isolate, multiply or express inserted DNA fragments in a target host. A vector can for example be a cloning vector, an expression vector, a functional vector, a capture vector, a co-expression vector (for expression of more than one open reading frame), a viral vector or an episome (i.e., a nucleic acid capable of extrachromosomal replication) etc.

A "cloning vector" as used herein includes any vector that can be used to delete, insert, replace or assemble one or more nucleic acid molecules. In some instances a cloning vector may contain a counter selectable marker gene (such as, e.g., ccdB or tse2) that can be removed or replaced by another transgene or DNA fragment. In some instances a cloning vector may be referred to as donor vector, entry vector, shuttle vector, destination vector, target vector, functional vector or capture vector. Cloning vectors typically contain a series of unique restriction enzyme cleavage sites (e.g., type II or type IIS) for removal, insertion or replacement of DNA fragments. Alternatively, DNA fragments can be replaced or inserted by TOPO® Cloning or recombination as, e.g., employed in the GATEWAY® Cloning System offered by Invitrogen/Life Technologies (Carlsbad, Calif.) and described in more detail elsewhere herein. A cloning vector that can be used for expression of a transgene in a target host may also be referred to as expression vector. In some instances a cloning vector is engineered to obtain a TAL nucleic acid binding cassette, a TAL repeat, a TAL effector or a TAL effector fusion.

An "expression vector" is designed for expression of a transgene and generally harbors at least one promoter sequence that drives expression of the transgene. Expression as used herein refers to transcription of a transgene or transcription and translation of an open reading frame and can occur in a cell-free environment such as a cell-free expression system or in a host cell. In most instances expression of an open reading frame or a gene results in the production of a polypeptide or protein. An expression vector is typically designed to contain one or more regulatory sequences such as enhancer, promoter and terminator regions that control expression of the inserted transgene. Suitable expression vectors include, without limitation, plasmids and viral vectors. Vectors and expression systems for various applications are available from commercial suppliers such as Novagen (Madison, Wis.), Clontech (Palo Alto, Calif.), Stratagene (La Jolla, Calif.), and Life Technologies Corp. (Carlsbad, Calif.). In some instances an expression vector is engineered for expression of a TAL nucleic acid binding cassette, a TAL repeat, a TAL effector or a TAL effector fusion.

A "capture vector" as used herein is a vector suitable for assembly of TAL cassettes. A capture vector contains a region for TAL cassette insertion that is typically flanked by restriction cleavage sites such as type IIS cleavage sites. The capture vector may contain a counter selectable marker gene such as, e.g., ccdB or tse2. Different capture vectors can be used for assembly of different TAL cassettes. In some instances, all required TAL cassettes may be assembled into a single capture vector. In other instances, at least two capture vectors may be used to assemble all required TAL cassettes. For example, for the assembly of n TAL cassettes, 1-n/2 cassettes may be assembled into a first capture vector and (n/2+1)-n TAL cassettes may be assembled into a second capture vector and both capture vectors may be combined in a subsequent reaction to assemble the TAL cassettes of the first capture vector and the TAL cassettes of the second capture vector into a third vector or third capture vector. In another example, three capture vectors may be used wherein each of the three capture vectors carries one third of the total amount of TAL cassettes to be assembled. In yet another example the amount of TAL cassettes assembled into each capture vector may be different. For example, capture vectors 1, 2, 3 and 4 may comprise 12 cassettes, 6 cassettes, 4 cassettes and 2 cassettes respectively, which may further be combined stepwise or in parallel reactions into 24 cassettes.

A "functional vector" as used herein refers to a vector that contains either a TAL effector sequence or a TAL effector fusion sequence (with or without TAL nucleic acid binding cassettes and/or TAL repeats, respectively). For example, a functional vector can carry the flanking N- and C-termini of a TAL effector, wherein the sequence between the termini contains a counter selectable marker (such as, e.g., ccdB or tse2) that can be removed or replaced by TAL cassettes via type IIS cleavage. In many instances a functional vector contains an effector fusion domain, such as, e.g., a DNA binding or enzymatic activity. A functional vector may, e.g., carry a TAL effector fusion encoding a nuclease, an activator, a repressor or may contain a multiple cloning site. In certain aspects a functional vector may be an expression vector. In some instances a functional vector maybe a topoisomerase-adapted vector or a GATEWAY® Entry Clone.

A "viral vector" generally relates to a genetically-engineered noninfectious virus containing modified viral nucleic acid sequences. In most instances a viral vector contains at least one viral promoter and is designed for insertion of one or more transgenes or DNA fragments. In some instances a viral vector is delivered to a target host together with a helper virus providing packaging or other functions. In many instances viral vectors are used to stably integrate transgenes into the genome of a host cell. A viral vector may be used for delivery and/or expression of transgenes.

Viral vectors may be derived from bacteriophage, baculoviruses, tobacco mosaic virus, vaccinia virus, retrovirus (avian leukosis-sarcoma, mammalian C-type, B-type viruses, D type viruses, HTLV-BLV group, lentivirus, spumavirus), adenovirus, parvovirus (e.g., adenoassociated viruses), coronavirus, negative strand RNA viruses such as orthomyxovirus (e.g., influenza virus) or sendai virus, rhabdovirus (e.g., rabies and vesicular stomatitis virus), paramyxovirus (e.g., measles and Sendai), positive strand RNA viruses such as picornavirus and alphavirus (such as Semliki Forest virus), and double-stranded DNA viruses including adenovirus, herpes virus (e.g., Herpes Simplex virus types 1 and 2, Epstein-Barr virus, cytomegalovirus), and poxvirus (e.g., vaccinia, fowlpox and canarypox). Other viruses include without limitation Norwalk virus, togavirus, flavivirus, reoviruses, papovavirus, hepadnavirus, and hepatitis virus. For example common viral vectors used for gene delivery are lentiviral vectors based on their relatively large packaging capacity, reduced immunogenicity and their ability to stably transduce with high efficiency a large range of different cell types. Such lentiviral vectors can be "integrative" (i.e., able to integrate into the genome of a target cell) or "non-integrative" (i.e., not integrated into a target cell genome). Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

"Regulatory sequence" as used herein refers to nucleic acid sequences that influence transcription and/or translation initiation and rate, stability and/or mobility of a transcript or polypeptide product. Regulatory sequences include, without limitation, promoter sequences or control elements, enhancer sequences, response elements, protein recognition sites, inducible elements, protein binding sequences, transcriptional start sites, termination sequences, polyadenylation sequences, introns, 5' and 3' untranslated regions (UTRs) and other regulatory sequences that can reside within coding sequences, such as splice sites, inhibitory sequence elements (often referred to as CNS or INS such known from some viruses), secretory signals, Nuclear Localization Signal (NLS) sequences, inteins, translational coupler sequences, protease cleavage sites as described in more detail elsewhere herein. A 5' untranslated region (UTR) is transcribed, but not translated, and is located between the start site of the transcript and the translation initiation codon and may include the +1 nucleotide. A 3' UTR can be positioned between the translation termination codon and the end of the transcript. UTRs can have particular functions such as increasing mRNA message stability or translation attenuation. Examples of 3' UTRs include, but are not limited to polyadenylation signals and transcription termination sequences. Regulatory sequences may be universal or host- or tissue-specific.

A "promoter" as used herein is a transcription regulatory sequence which is capable of directing transcription of a nucleic acid segment (e.g., a transgene comprising, for example, an open reading frame) when operably connected thereto. A promoter is a nucleotide sequence which is positioned upstream of the transcription start site (generally near the initiation site for RNA polymerase II). A promoter typically comprises at least a core, or basal motif, and may include or cooperate with at least one or more control elements such as upstream elements (e.g., upstream activation regions (UARs)) or other regulatory sequences or synthetic elements. A basal motif constitutes the minimal sequence necessary for assembly of a transcription complex required for transcription initiation. In many instances, such minimal sequence includes a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

The choice of a promoter to be included in an expression vector depends upon several factors, including without limitation efficiency, selectability, inducibility, desired expression level, and cell or tissue specificity. For example, tissue-, organ- and cell-specific promoters that confer transcription only or predominantly in a particular tissue, organ, and cell type, respectively, can be used. In some instances, promoters that are essentially specific to seeds ("seed-preferential promoters") can be useful. In many instances, constitutive promoters are used that can promote transcription in most or all tissues of a specific species. Other classes of promoters include, but are not limited to, inducible promoters, such as promoters that confer transcription in response to external stimuli such as chemical agents, developmental stimuli, or environmental stimuli. Inducible promoters may be induced by pathogens or stress like cold, heat, UV light, or high ionic concentrations or may be induced by chemicals. Examples of inducible promoters are the eukaryotic metallothionein promoter, which is induced by increased levels of heavy metals; the prokaryotic lacZ promoter, which is induced in response to isopropyl-β-D-thiogalacto-pyranoside (IPTG); and eukaryotic heat shock promoters, which are induced by raised temperature. Numerous additional bacterial and eukaryotic promoters suitable for use with the invention are known in the art and described in re, e.g., in Sambrook et al., Molecular Cloning, A Laboratory Manual (2nd ed. 1989; 3rd ed., 2001); Kriegler, Gene Transfer and Expression: A Laboratory Manual (1990); and Ausubel et al., Current Protocols in Molecular Biology. Bacterial expression systems for expressing the ZFP are available in, e.g., *E. coli, Bacillus* sp., and *Salmonella* (Palva et al. Secretion of interferon by *Bacillus subtilis*. Gene 22:229-235 (1983)). Kits for such expression systems are commercially available. Eukaryotic expression systems for mammalian cells, yeast, and insect cells are well known by those of skill in the art and are also commercially available.

Common promoters for prokaryotic protein expression are e.g., lac promoter or trc and tac promoter (IPTG induction), tetA promoter/operator (anhydrotetracyclin induction), PPBAD promoter (L-arabinose induction), rhaPBAD promoter (L-rhamnose induction) or phage promoters such as phage promoter pL (temperature shift sensitive), T7, T3, SP6, or T5.

Common promoters for mammalian protein expression are, e.g., Cytomegalovirus (CMV) promoter, SV40 promoter/enhancer, Vaccinia virus promoter, Viral LTRs (MMTV, RSV, HIV etc.), E1B promoter, promoters of constitutively expressed genes (actin, GAPDH), promoters of genes expressed in a tissue-specific manner (albumin, NSE), promoters of inducible genes (Metallothionein, steroid hormones).

Numerous promoter for expression of nucleic acids in plants are known and may be used in the practice of the invention. Such promoter may be constitutive, regulatable, and/or tissue-specific (e.g., seed specific, stem specific, leaf specific, root specific, fruit specific, etc.). Exemplary promoters which may be used for plant expression include the Cauliflower mosaic virus 35S promoter and promoter for the following genes: the ACT11 and CAT3 genes from *Arabidopsis*, the gene encoding stearoyl-acyl carrier protein desaturase from *Brassica napus* (GenBank No. X74782), and the genes encoding GPCJ (GenBank No. X15596) and GPC2 (GenBank No. U45855) from maize. Additional promoters include the tobamovirus subgenomic promoter, the cassaya vein mosaic virus (CVMV) promoter (which exhibits high transcriptional activity in vascular elements, in leaf mesophyll cells, and in root tips), the drought-inducible promoter of maize, and the cold, drought, and high salt inducible promoter from potato. A number of additional promoters suitable for plant expression are found in U.S. Pat. No. 8,067,222, the disclosure of which is incorporated herein by reference.

Heterologous expression in chloroplast of microalgae such as, e.g., *Chlamydomonas reinhardtii* can be achieved using, for example, the psbA promoter/5' untranslated region (UTR) in a psbA-deficient genetic background (due to psbA/D1-dependent auto-attenuation) or by fusing the strong 16S rRNA promoter to the 5' UTR of the psbA and atpA genes to the expression cassette as, for example, disclosed in Rasala et al., "Improved heterologous protein expression in the chloroplast of *Chlamydomonas reinhardtii* through promoter and 5' untranslated region optimization", Plant Biotechnology Journal, Volume 9, Issue 6, pages 674-683, (2011).

The promoter used to direct expression of a TAL effector encoding nucleic acid depends on the particular application. For example, a strong constitutive promoter is typically used for expression and purification of TAL-effector fusion proteins. In contrast, when a TAL effector nuclease fusion protein is administered in vivo for gene regulation, it may be desirable to use either a constitutive or an inducible promoter, depending on the particular use of the TAL effector nuclease fusion protein and other factors. In addition, a promoter suitable for administration of a TAL effector nuclease fusion protein can be a weak promoter, such as HSV thymidine kinase or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard. Tight control of gene expression in mammalian cells by tetracycline-responsive promoters. Proc. Natl. Acad. Sci. USA 89:5547 (1992); Oligino et al. Drug inducible transgene expression in brain using a herpes simplex virus vector. Gene Ther. 5:491-496 (1998); Wang et al. Positive and negative regulation of gene expression in eukaryotic cells with an inducible transcriptional regulator. Gene Ther. 4:432-441 (1997); Neering et al. Transduction of primitive human hematopoietic cells with recombinant adenovirus vectors. Blood 88:1147-1155 (1996); and Rendahl et al., Regulation of gene expression in vivo following transduction by two separate rAAV vectors Nat. Biotechnol. 16:757-761 (1998)). The MNDU3 promoter can also be used, and is preferentially active in CD34+ hematopoietic stem cells.

By "host" is meant a cell or organism that supports the replication of a vector or expression of a protein or polypeptide encoded by a vector sequence. Host cells may be prokaryotic cells such as E. coli, or eukaryotic cells such as yeast, fungal, protozoal, higher plant, insect, or amphibian cells, or mammalian cells such as CHO, HeLa, 293, COS-1, and the like, e.g., cultured cells (in vitro), explants and primary cultures (in vitro and ex vivo), and cells in vivo.

As used herein, the phrase "recombination proteins" includes excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Examples of recombination proteins include Cre, Int, IHF, Xis, Flp, Fis, Hin, Gin, Phi-C31, Cin, Tn3 resolvase, TndX, XerC, XerD, TnpX, Hjc, SpCCE1, and ParA.

A used herein, the phrase "recombination site" refers to a recognition sequence on a nucleic acid molecule which participates in an integration/recombination reaction by recombination proteins. Recombination sites are discrete sections or segments of nucleic acid on the participating nucleic acid molecules that are recognized and bound by a site-specific recombination protein during the initial stages of integration or recombination. For example, the recombination site for Cre recombinase is loxP which is a 34 base pair sequence comprised of two 13 base pair inverted repeats (serving as the recombinase binding sites) flanking an 8 base pair core sequence (see FIG. 1 of Sauer, B. Site-specific recombination: developments and applications. Curr. Opin. Biotech. 5:521-527 (1994)). Other examples of recognition sequences include the attB, attP, attL, and attR sequences described herein, and mutants, fragments, variants and derivatives thereof, which are recognized by the recombination protein lambda phage Integrase and by the auxiliary proteins integration host factor (IHF), Fis and excisionase (lamda phage is).

As used herein, the phrase "recognition sequence" refers to a particular sequence to which a protein, chemical compound, DNA, or RNA molecule (e.g., restriction endonuclease, a modification methylase, or a recombinase) recognizes and binds. In the present invention, a recognition sequence will usually refer to a recombination site. For example, the recognition sequence for Cre recombinase is loxP which is a 34 base pair sequence comprising two 13 base pair inverted repeats (serving as the recombinase binding sites) flanking an 8 base pair core sequence (see FIG. 1 of Sauer, B. Current Opinion in Biotechnology 5:521-527 (1994)). Other examples of recognition sequences are the attB, attP, attL, and attR sequences which are recognized by the recombinase enzyme lamda phage Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS and excisionase (lamda phage is). (See Landy, Current Opinion in Biotechnology 3:699-707 (1993).)

Throughout this document, unless the context requires otherwise, the words "comprise," "comprises" and "comprising" or "contain", "contains" or "containing" will be understood to imply the inclusion of a stated step or element or group of steps or elements but not the exclusion of any other step or element or group of steps or elements.

A Modular TAL Designer Portal and Customized Services

Gene assembly and shuffling methods and related compositions, kits and protocols including those described herein may be useful for anyone skilled in the art to assemble or clone available DNA fragments. However, in certain instances it may be useful to order gene synthesis and/or related services from a commercial supplier, e.g., when a DNA sequence (e.g., a template for PCR amplification) is not available, a project is complex or the skilled artisan is not sufficiently equipped to perform certain experiments or production steps. In some instances, gene synthesis services may be offered online via an order portal. In one aspect, orders may be placed via a web-based platform designed to provide customized gene synthesis services and/or specific products to customers. Gene synthesis services may include at least one or a combination of the following: design, optimization, synthesis, assembly, purification, mutagenesis, recombination, cloning, screening, expression, and/or analysis of nucleic acid molecules but may also include related services such as protein services, cell line construction and testing, manufacturing, kit development or product composition, assay design and/or development, comparative analyses, detection or screening, project design and/or advisory service. Gene synthesis services may include in vitro as well as in vivo processes or applications. In some aspects, gene synthesis services may include methods and compositions related to DNA binding molecules. In some embodiments the web-based platform may include means to offer services or products related to DNA binding effector molecules, such as, for example, TAL effectors.

Thus, in part, the invention relates to a web-based order portal for gene synthesis services which includes services related to DNA binding molecules, such as, e.g., TALs, zinc-finger nucleases or meganucleases. In one aspect, the order portal includes services related to TAL proteins which may include customized services or products as well as catalogue products. FIG. 1A and Example 1 provide one illustration of how such customer portal can be organized and how a customer can place an order with a service provider offering TAL-related services via a web-based platform.

In some embodiments of the invention, the web-based order portal may have a modular organization. In certain embodiments the portal may include at least one of the following: (i) a first module or web interface ("module 1"), (ii) a second module or design engine ("module 2"), and (iii) a third module or manufacture unit ("module 3"). Modules 1, 2 and 3 as used herein shall be understood to represent specific functions as described in more detail below and it should therefore be understood by the skilled in the art that the respective functions may also be organized in a different way, e.g., in less or more than 3 modules or under a different terminology. For example, in certain instances, some of the functions described herein under module 2 be included in module 1 or 3 or vice versa or at least one of the modules or several functions thereof may be incorporated in another module; e.g., module 2 per se may be part of module 1 etc. Other hierarchies or organizations of the described functions are therefore included in the invention.

Module 1 may serve as a platform for information exchange between customer and service provider, to enter and store project-related and customer-specific information, and/or place an order. In some embodiments, module 1 provides at least one of the following features: means to enter and save customer information such as, e.g., contact data, shipping address, billing information, customer ID, discount options etc.; means to select and order items from menus or lists, means to enter and save customer project specifications, or means to enter a description of material provided by a customer. Module 1 may further include pricing information for catalogue products or customized projects. In many instances, products or services may be designed and constructed based upon anticipated customer needs and intended for sale, for example, as a "catalogue product". However, in some instances the design and construction of deliverables such as synthetic genes will be customized according to individual specifications.

Figure 1B:
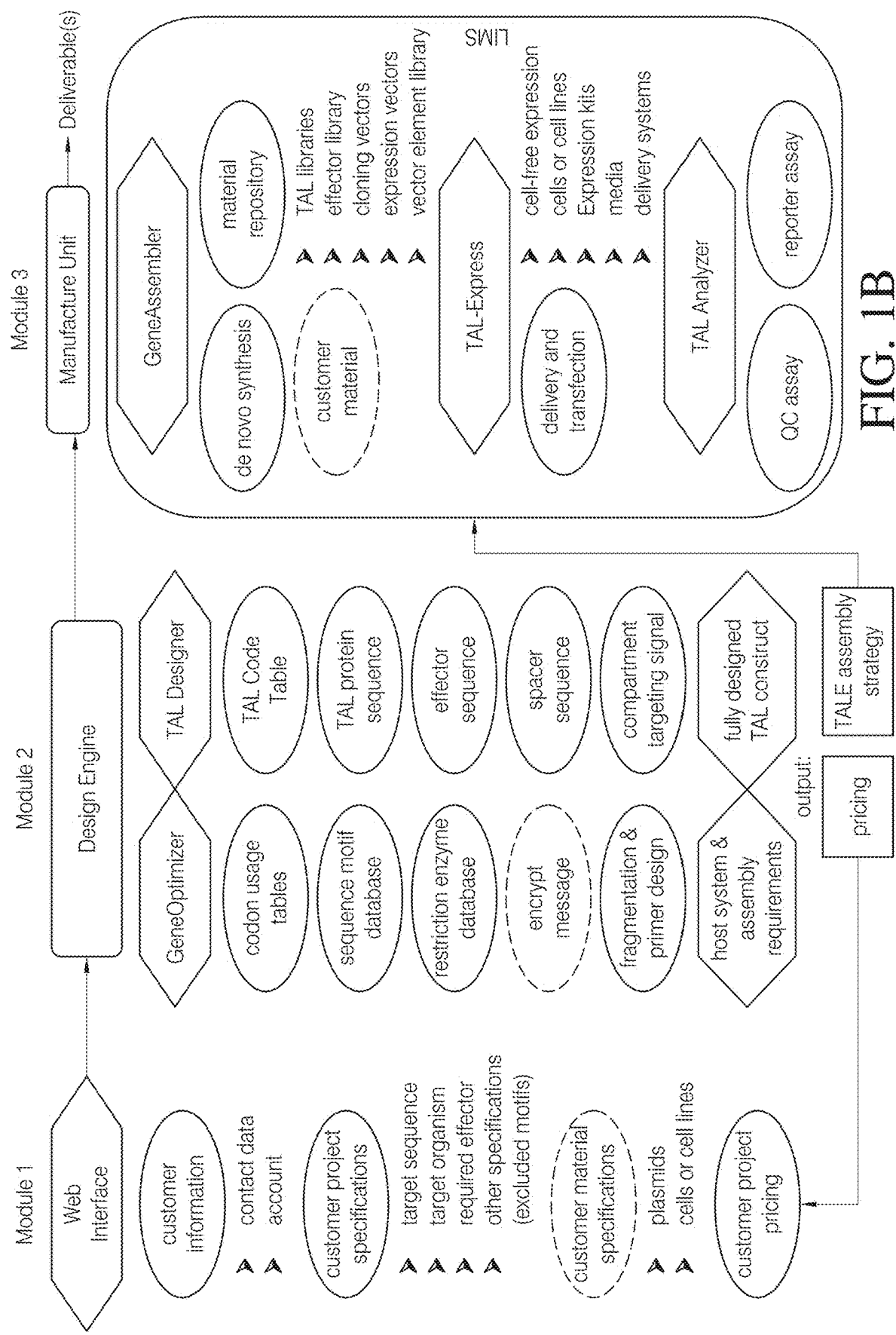

One example of how module 1 can be organized, for example, to provide customized services related to DNA binding molecules such as TALs is illustrated in FIG. 1B. In this example, customer information contains at least customer contact data and account-related information. Customer can enter project specifications such as a target sequence, a target organism, an effector function and can add additional specifications such as, for example, excluded motifs, cloning requirements and the like. In certain instances customer may provide material such as, for example, a plasmid or cells. In such case, customer may be asked to enter material specifications to describe the provided material.

The information stored or exchanged via module 1 may further be used, analyzed and/or processed by module 2. Module 2 may at least contain information, components or means required for sequence and/or assembly design and may include or provide at least one of the following: database or access to database such as e.g., codon usage tables, sequence motif database, vector database, restriction enzyme database, effector sequence database, parts and/or devices database, code rules, host specifications, etc.; sequence analysis and optimization tools, means to perform sequence fragmentation, means for oligonucleotide design, means for encrypting a watermark or information in a sequence, means to develop an assembly strategy. One example of how module 2 can be organized is illustrated in FIG. 1B. In some examples, module 2 is capable of generating an assembly strategy. For example the output of module 2 may contain an assembly strategy for a customized gene. In certain instances, the output may comprise an assembly strategy for a DNA binding molecule such as a TAL effector as defined in more detail elsewhere herein. If a synthetic gene is to be designed module 2 may comprise means to optimize the sequence of said gene. For this purpose it may be required to use information from proprietary or open source database such as, for example, codon usage tables, or programs identifying suitable restriction enzymes for production or identifying inhibitory sequence motifs that may be excluded or programs taking into account host-specific requirements. Module 2 may further include means to edit a sequence or decompose a sequence into smaller parts to allow for optimal synthesis, assembly and/or production of a molecule. It may further include means to design oligonucleotides for synthesis. In some embodiments, module 2 may include a multi-parameter software taking into account optimization and production requirements in parallel, such as, for example, a GENEOPTIMIZER® program as described in more detail elsewhere herein.

If a molecule representing a specific function is to be designed, the design may include database or information or rules specific to said molecule function. For example, if a DNA binding molecule is to be designed, module 2 may include at least a binding code table allocating amino acids to specific nucleotides. In some embodiments, module 2 may be organized to include information or rules related to TAL design (e.g., a TAL designer tool). Such "TAL designer" tool may include at least one of the following: one or more (e.g., from about 2 to about 30, from about 4 to about 30, from about 8 to about 30, from about 10 to about 30, from about 15 to about 30, from about 5 to about 50, etc.) TAL code tables as described elsewhere herein, means to apply TAL code rules, means to identify and select TAL effector related sequences, parts, domains etc. from a library or database; means to generate a TAL effector construct sequence or parts thereof and means to generate an assembly strategy for said construct. In certain instances it may be advantageous to include specific motifs in a TAL sequence such as for example a specific compartment targeting signal sequence where a TAL is to be targeted to a defined compartment within a cell. The TAL designer may receive the relevant information from a respective database. It may further be useful to consider species-specific requirements. For example, a given compartment targeting signal may only be active in a limited amount of species and may therefore be inappropriate for certain hosts. The TAL designer tool may therefore include means to analyze a TAL design or TAL sequence for host compatibility. In one embodiment, the TAL designer may be equipped with a tool that can generate a model of a protein or protein domain such as, e.g., a protein folding program providing a three-dimensional model of a folded protein or structural data of said protein. In some embodiments, the tool can generate a model of a protein in nucleic acid-bound and/or nucleic acid-free conformation. Such data could be used to evaluate the binding specificity of TALs, the stability of protein-DNA or protein-protein interaction and/or structural properties of engineered TAL repeats or TAL effector proteins. The tool may therefore include means to analyze these data and identify accessible and/or inaccessible domains or residues within a TAL effector. The results of such analysis may serve to indicate whether the engineered protein or domain would be suitable for a specific application. For example, if the protein model suggests that an effector domain is not sufficiently exposed or shows a constrained conformation, it may be required to include a flexible linker (e.g., a Gly-Ser linker) or insert, delete, modify, extend, truncate or shift certain sequence elements as, for example, spacer sequences between domains. The TAL designer may further comprise means to edit a modeled protein sequence (e.g., replace certain amino acid residues by others) to modify the structure, function, binding specificity or activity of a protein. The editing function may be provided as a separate program or may be incorporated in other programs, for example, as part of the protein modeling tool. Such function may allow for in silico analysis and modification of engineered TAL proteins resulting in an edited protein or amino acid sequence that can be back-translated into a nucleic acid sequence to obtain a template for synthesis. Features specific for TAL design or incorporated in the TAL designer may be linked with those features relevant for general gene design. For example, the TAL designer may also access database information related to sequence optimization.

In one aspect of the invention module 2 may further include a tool capable of designing a DNA binding molecule based on sequence information. The sequence information may for example comprise a specific target site, such as a TAL binding site and may be obtained from a customer or some other source such as a database or from the literature. In one aspect of the invention such tool may provide at least one of the following: (i) means to analyze sequence information, (ii) means to access database information and select items or rules therefrom, (iii) means to translate the rules into a protein design, (iv) means to back-translate the protein sequence into a nucleic acid sequence and/or (v) means to feed the information into a production system. The function of sequence dependent design of a binding entity may be provided as a separate program or may be incorporated in other programs, for example, as part of the TAL designer.

In one aspect, the invention relates to a TAL designer tool which is capable of generating an assembly strategy for a two-step TAL assembly process and which (i) provides access to a TAL repeat database and selects the required monomer building blocks; (ii) provides access to a vector database and selects an effector sequence in combination with a target vector sequence; (iii) defines the required triplets by allocation of the respective positions on a carrier (e.g., a 96 well plate); (iv) determines the assembly strategy of the capture vectors (allocation of the required triplets, wherein the terminal overhangs define their position within the capture vectors); (v) generates the complete nucleic acid sequence of the TAL repeat domain; (vi) generates the nucleic acid sequences of both capture vectors; (vii) generates the nucleic acid sequence of the TAL effector open reading frame (ATG to Stop); (viii) allows for importation of the sequences generated in one or more of steps (v) to (vii) into a database controlling a production process, and (ix) optionally generates a .gb file of the final TAL functional vector sequence. The steps may be performed in the given order or may be performed in a different order. In one aspect, the TAL designer tool may be presented by an excel-based program.

In some instances, module 2 may also provide means to transform individual steps of a working process into pricing information. For example, the final pricing of a customized project may depend on the amount and/or complexity of steps required to produce a deliverable, the time to perform the service, the costs of material, reagents or equipment used or employed to perform the services. For such purpose, module 2 may, for example, include means to process information from lists of standardized items or stock keeping units (SKUs). In some instances, some of the information and/or results obtained from module 2 maybe re-directed to module 1. For example, pricing information related to a customer project generated in the context of project design may become accessible through the web interface of module 1. In some instances, information and/or results generated by the means and methods described in module 2 maybe fed into or retrieved by a third module such as a manufacture or production unit. In some embodiments, the sequence information and/or design and/or assembly strategy generated in module 2 can be translated into a production workflow operated by module 3. Thus, the invention includes processing of results or information obtained from module 2 by a manufacture or production unit.

Module 3 may at least contain one of the following: (i) means to synthesize nucleic acid molecules, (ii) means to assemble nucleic acid molecules, (iii) means to clone or transfer nucleic acid molecules, (iv) one or more material repositories, (v) means to sequence nucleic acid molecules, (vi) means to cultivate, propagate, and/or manipulate cells, (vii) means to analyze data, (viii) means to store biological material, (ix) a laboratory information management system. It is to be understood that the aforementioned means or the process steps performed by a production or manufacture unit can be performed in a different order or can be separated between different sub-modules or production entities which may be controlled or regulated together, separately or sequentially or may be interconnected. For example, means to synthesize or assembly nucleic acid molecules may be timely and/or locally separated from means to manipulate cells.

In some embodiments, module 3 contains means to synthesize nucleic acid molecules. Synthesis of nucleic acid molecules is usually based on a combination of organic chemistry and molecular biological techniques. In one aspect, nucleic acid molecules such as genes, gene fragments, parts, vectors, plasmids, domains, variants, libraries etc. may be synthesized "de novo", without the need for a template such as e.g., a given DNA template. De novo synthesis may, for example, include chemical synthesis of oligonucleotides which can be combined and assembled to obtain larger nucleic acid molecules, as, for example, described in Example 3. In another aspect, nucleic acid molecules may be obtained by template-dependent methods known in the art such as, for example, by PCR amplification, mutagenesis, recombination or the like. In yet another aspect, pre-synthesized parts may be combined and connected to obtain novel nucleic acid molecules. For example, nucleic acid parts or building blocks may be taken from a library or material repository. In some embodiments at least one step in the synthesis or assembly process may be conducted on a solid support or solid phase or in a microfluidic environment. Gene synthesis services used in the method of the invention can relate to any of the above described approaches or combinations thereof. In another aspect, one or more of the synthesis or assembly steps may be performed on solid supports or in solution as required. In yet another aspect, de novo synthesized nucleic acid molecules may be combined with template-derived nucleic acid molecules or may be combined with already available or pre-synthesized parts.

FIG. 1B illustrates an example of how module 3 (composed of different sub-modules) may be organized to allow for manufacture of DNA binding molecules such as TALs. In one aspect, module 3 may contain a "GeneAssembler" module that coordinates nucleic acid synthesis and assembly according to the assembly strategy developed in module 2. A GeneAssembler module may have access to one or more material repositories which may contain, for example, reagents for gene synthesis, standardized parts, vectors, plasmids, nucleic acid libraries, cloning tools, enzymes and/or enzyme cocktails and where required, means to store customer material and/or synthesis or assembly derivatives. In some embodiments, the at least one material repository contains material related to TAL assembly such as TAL libraries or repeat domain building blocks (e.g., monomers, dimers, trimers etc.), effector domains (e.g., nucleases, activators, repressors, (de)methylases, (de)acetylases etc.) or variants thereof (e.g., mutated or truncated), TAL cloning or expression vectors etc. TAL-related tools or parts as described elsewhere herein may be taken from a repository or may be synthesized de novo and may be combined and/or assembled with other parts obtained from a material repository or synthesized de novo or provided by customer. For example, a TAL repeat domain may be assembled from a TAL trimer library, may be combined with a de novo synthesized effector domain and may be cloned into a vector provided by the customer. However, all other combinations of available and de novo synthesized parts are possible and included in the concept of the invention. In certain instances, de novo synthesized parts or parts obtainable from a repository may be combined to produce a novel catalogue product, such as a vector (e.g., a TAL GATEWAY® vector) or a composition. In yet another embodiment, the service provider may develop an assembly strategy for a customer and compose a customized toolkit from repository parts and provide it to the customer for assembly (see, e.g., FIG. 7B).

A GeneAssembler module as used herein may employ different assembly tools and strategies and may incorporate in vitro and/or in vivo assembly approaches. For example, assembly may be performed using the inventive methods, compositions and/or tools described elsewhere herein. In some embodiments, a GeneAssembler module may employ at least one of the following assembly strategies: type II conventional cloning, type IIS-mediated or "Golden Gate" cloning (see, e.g., Engler, C., R. Kandzia, and S. Marillonnet. A one pot, one step, precision cloning method with high throughput. capability. PLos One 3:e3647 (2008.).; Kotera, I., and T. Nagai. A high-throughput and single-tube recombination of crude PCR products using a DNA polymerase inhibitor and type IIS restriction enzyme. J Biotechnol 137:1-7. (2008); Weber, E., R. Gruetzner, S. Werner, C. Engler, and S. Marillonnet. Assembly of Designer TAL Effectors by Golden Gate Cloning. PloS One 6:e19722 (2011)), GATEWAY® recombination, TOPO® cloning, exonuclease-mediated assembly (Aslanidis and de Jong (Ligation-independent cloning of PCR products (LIC-POR); Nucleic Acids Research, Vol. 18, No. 20 6069 (1990)), homologous recombination, non-homologous end joining or a combination thereof. Modular type IIS based assembly strategies are, e.g., disclosed in PCT Publication WO 2011/154147 the disclosure of which is included herein by reference. A GeneAssembler module may further comprise means for error correction of nucleic acid molecules.

Error correction can be performed either prior to assembly, between assembly steps or after assembly as required. One issue associated with nucleic acid synthesis, including chemical synthesis of nucleic acids, is errors in the sense that occasionally synthesized nucleic acids contain an incorrect base.

Consider the following hypothetical. Nucleic acid molecules are generated with one error in every 100 nucleotides and a nucleic acid molecule of 2000 nucleotides is assembled. This means that there will be, on average, 20 errors per molecule. Errors in proteins coding regions can result in frame shifts, amino acid substitutions, or premature stop codons. In order to obtain a coding sequence which encodes a specified amino acid sequence two options are: (1) Sequencing a large number of nucleic acid molecules to identify ones without errors OR (2) correct errors, then confirm sequence of a smaller number of molecules.

Error correction can be performed by any number of methods. Some such methods employ DNA binding enzymes which are capable of recognizing sequence errors or mismatches. For example, error correction methods may be based on mismatch endonucleases known in the art (e.g., MutS, CelI, ResI, Vsr, or *Perkinsus marinus* nuclease PA3, T4 endonuclease VII or T7 endonuclease I).

Another method of error correction is set out in the following work flow. In the first step, nucleic acid molecules of a length smaller than that of the full-length desired nucleotide sequence (i.e., "nucleic acid molecule fragments" of the full-length desired nucleotide sequence) are obtained. Each nucleic acid molecule is intended to have a desired nucleotide sequence that comprises a part of the full length desired nucleotide sequence. Each nucleic acid molecule may also be intended to have a desired nucleotide sequence that comprises an adapter primer for PCR amplification of the nucleic acid molecule, a tethering sequence for attachment of the nucleic acid molecule to a DNA microchip, or any other nucleotide sequence determined by any experimental purpose or other intention. The nucleic acid molecules may be obtained in any of one or more ways, for example, through synthesis, purchase, etc.

In the optional second step, the nucleic acid molecules are amplified to obtain more of each nucleic acid molecule. The amplification may be accomplished by any method, for example, by PCR. Introduction of additional errors into the nucleotide sequences of any of the nucleic acid molecules may occur during amplification.

In the third step, the amplified nucleic acid molecules are assembled into a first set of molecules intended to have a desired length, which may be the intended full length of the desired nucleotide sequence. Assembly of amplified nucleic acid molecules into full-length molecules may be accomplished in any way, for example, by using a PCR-based method.

In the fourth step, the first set of full-length molecules is denatured. Denaturation renders single-stranded molecules from double-stranded molecules. Denaturation may be accomplished by any means. In some embodiments, denaturation is accomplished by heating the molecules.

In the fifth step, the denatured molecules are annealed. Annealing renders a second set of full-length, double-stranded molecules from single-stranded molecules. Annealing may be accomplished by any means. In some embodiments, annealing is accomplished by cooling the molecules.

In the sixth step, the second set of full-length molecules are reacted with one or more endonucleases to yield a third set of molecules intended to have lengths less than the length of the complete desired gene sequence. The endonucleases cut one or more of the molecules in the second set into shorter molecules. The cuts may be accomplished by any means. Cuts at the sites of any nucleotide sequence errors are particularly desirable, in that assembly of pieces of one or more molecules that have been cut at error sites offers the possibility of removal of the cut errors in the final step of the process. In an exemplary embodiment, the molecules are cut with T7 endonuclease I, E. coli endonuclease V, and Mung Bean endonuclease in the presence of manganese. In this embodiment, the endonucleases are intended to introduce blunt cuts in the molecules at the sites of any sequence errors, as well as at random sites where there is no sequence error.

In the last step, the third set of molecules is assembled into a fourth set of molecules, whose length is intended to be the full length of the desired nucleotide sequence. Because of the late-stage error correction enabled by the provided method, the set of molecules is expected to have many fewer nucleotide sequence errors than can be provided by methods in the prior art.

The process set out above is also set out in U.S. Pat. No. 7,704,690, the disclosure of which is incorporated herein by reference.

Another process for effectuating error correction in chemically synthesized nucleic acid molecules is by a commercial process referred to as ErrASE™ (Novici Biotech). Error correction methods and reagent suitable for use in error correction processes are set out in U.S. Pat. Nos. 7,838,210 and 7,833,759, U.S. Patent Publication No. 2008/0145913 A1 (mismatch endonucleases), and PCT Publication WO 2011/102802 A1, the disclosures of which are incorporated herein by reference.

Exemplary mismatch endonucleases include endonuclease VII (encoded by the T4 gene 49), T7 endonuclease I, ResI endonuclease, CelI endonuclease, and SP endonuclease or methyl-directed endonucleases such as MutH, MutS or MutL. The skilled person will recognize that other methods of error correction may be practiced in certain embodiments of the invention such as those described, for example, in U.S. Patent Publication Nos. 2006/0127920 AA, 2007/0231805 AA, 2010/0216648 A1, 2011/0124049 A1 or U.S. Pat. No. 7,820,412, the disclosures of which are incorporated herein by reference.

Another schematic of an error correction method is shown in FIG. 7.

Synthetically generate nucleic acid molecules typically have error rate of about 1 base in 300-500 bases). Further, in many instances, greater than 80% of errors are single base frameshift deletions and insertions. Also, less than 2% of error result from the action of polymerases when high fidelity PCR amplification is employed. In many instances, mismatch endonuclease (MME) correction will be performed using fixed protein:DNA ratio.

In another embodiment, error correction may be performed indirectly, e.g., by selecting correct nucleic acid molecules or eliminating incorrect nucleic acid molecules from a mixture or library of nucleic acid molecules. In one aspect the correction may include negative selection of frameshift mutations and may for example employ frame-dependent reporter expression to identify correct constructs such as, e.g., disclosed in published U.S. Patent Publication No. 2010/0297642 AA, the disclosure of which is included herein by reference. A GeneAssembler module may further contain sequencing means to determine the sequence of synthesized or assembled nucleic acid molecules. Sequencing may be applied to fragments and/or full-length genes. A GeneAssembler module should be equipped with all devices required to perform the described workflows including reagents and material (e.g., chemicals, enzymes, solvents, media, cells, consumables etc.), machines (e.g., oligonucleotide synthesizer, PCR-cycler, sequencer, incubator, clone picker, HPLC) and/or computer programs and analysis tools.

In one aspect of the invention, protein expression may be performed by the service provider as part of the service. In another aspect, the customer may order a construct and an expression kit and the expression may be performed by the customer. In cases where customer requests expression or protein services, module 3 may further contain an "Express" module. Where protein services are directed to TALs, a respective TAL-Express module may be provided which may at least include means for delivery of TAL constructs, means for TAL expression, means to cultivate and manipulate TAL host cells, means for protein extraction or purification and/or reporter systems. In some embodiments, TAL-Express offers different vectors or delivery systems to transfect host cells or target TALs to specific compartments. In particular, TAL-Express may employ the delivery systems or expression systems as described elsewhere herein. Furthermore, a TAL-Express module may include different expression systems or host cells such as bacteria, algae, yeast, fungi, plant, mammalian or human cells or cell cultures.

In cases where expression is performed by customer a TAL construct may be delivered together with an expression kit. Different expression systems or kits are known in the art and may be chosen from the service provider's order portal or catalogue such as bacterial expression strains or expression kits (e.g., BL21star™ based Champion™ pET Expression System from Life Technologies (Carlsbad, Calif.), algae expression kits (e.g., GeneArt® Chlamydomonas Engineering Kit, GeneArt® Synechococcus Engineering Kit), or mammalian cell lines allowing for stable integration of an ordered construct and efficient expression from a transcriptionally active genomic locus (e.g., FLP-In™ or Jump-In mammalian cells). In some instances, customer may want to order delivery tools from service provider to deliver an ordered construct into a certain cell type. For example, TAL constructs may be efficiently delivered to non-dividing or diving mammalian cells by using an adenoviral-based expression system (e.g., ViraPower™ Adenoviral Gateway® Expression Kit offered by Life Technologies (Carlsbad, Calif.)).

In some instances, a cell-free TAL expression may be employed. Cell-free protein production can be accomplished with several kinds and species of cell extracts such as E. coli lysates (e.g., Expressway™ Maxi Cell-Free E. coli Expression System), rabbit reticulocyte lysates (RRL), wheat germ extracts, insects cell (such as SF9 or SF21) lysates, or extracts with human translation machinery. For such purpose, service provider may offer a selection of cell-free expression kits to be ordered together with the gene synthesis service. However, in certain embodiments, cell-free expression may also be employed by service provider in the context of protein services.

In another aspect, module 3 may contain means to analyse the function or structure or correctness of deliverables or manufacture intermediates. Respective analyses may be routinely performed by service provider for quality control (QC) purposes. For example, where a synthetic gene has been manufactured for a customer, QC analysis would at least include evaluation of sequence correctness, e.g., by sequencing of said gene. In certain instances, where TAL services are offered, module 3 may include a "TAL Analyzer" module that performs additional experiments or analyses to validate the manufactured products. A TAL Analyser may e.g., include reporter assays to analyse TAL repeat integrity, TAL binding specificity, TAL function, TAL structure, TAL activity, effector activity, TAL expression etc. In particular, TAL Analyzer may employ the reporter assays and analysis tools as described elsewhere herein. Different options for reporter-based analysis of TAL constructs may be provided. In a first embodiment, a reporter kit may be provided as catalogue product and may be ordered by customer together with TAL services. In another embodiment, a reporter-based analysis of TAL function etc. may be offered as extra service. In such case, the reporter assay or analysis would be performed by the service provider and customer would obtain the results of the assay. In a third embodiment, customer may order a customized reporter assay for TAL analysis developed by service provider. Different options may be combined and offered for selection in the order portal.

Optionally, some or all of the steps or workflows summarized in module 3 may be controlled or interconnected by a software-based Laboratory Information Management System (LIMS) that offers features to support laboratory operations. Such features may include workflow and data tracking and may provide data exchange interfaces connecting workflows of different modules or production steps. A LIMS may further integrate data mining or assay data management and may provide numerous software functions such as, e.g., the reception and log in of a sample and its associated customer data; the assignment, scheduling, and tracking of the sample (e.g., via a barcode) and the associated workload; the processing and quality control associated with the sample and the utilized equipment, the storage of data associated with the sample and/or the inspection, approval, and compilation of the sample data for reporting and/or further analysis.

Deliverables resulting from the methods and processes summarized in module 3 will be shipped or transferred to customer. Deliverables may include material such as nucleic acid molecules, proteins, cells, kits or compositions. Deliverables may further include data such as sequence information, service reports, assay results or QC documents which may either be shipped together with material, separately or may be provided, e.g., via email, or a web interface (e.g., the interface of module 1).

TAL Effector Sequence Design

The methods and compositions described herein can be applied to any modular DNA binding effector molecule but may be particularly useful for engineered TAL effector systems. In one aspect, the invention relates to the generation of engineered TAL effectors with improved nucleic acid binding cassettes wherein the cassettes have been optimized for (i) increased expression in a target host and/or (ii) increased specificity for a defined target sequence. In another aspect, the invention relates to the generation of engineered effector fusions wherein the effector fusions can be optimized for (i) increased expression in a target host and/or (ii) increased activity towards a defined target sequence. Thus, in one aspect, the invention includes methods of designing TAL effector proteins and TAL effector coding nucleic acid sequences for optimal performance in downstream applications.

In certain embodiments of the invention the selected TAL effector nucleic acid sequence or a portion thereof may be subject to a sequence optimization process prior to synthesis. The optimization process can be directed to the nucleic acid sequence encoding the TAL binding domain or the nucleic acid sequence encoding the TAL effector fusion or can include sequence optimization of both moieties and if applicable, can include optimization of additional spacer, adapter, linker or tag sequences contributing to the TAL effector entity. The optimization of different parts of the TAL effector nucleic acid sequence can occur either sequentially or simultaneously. Different computational approaches for sequence modification are known in the art and may be employed to optimize a given nucleotide sequence in terms of (1) efficient assembly and/or (2) improved performance in a given host.

To design a nucleotide sequence for optimal assembly, a full-length sequence may be broken down into a defined number of smaller fragments with optimal hybridization properties by means of an algorithm taking into account parameters such as melting temperature, overlap regions, self-hybridization, absence or presence of cloning sites and the like. In certain aspects of the invention, it may be desired to use an optimization strategy that takes into account multiple different parameters simultaneously including assembly- as well as expression-related sequence properties. Algorithms for designing codon-optimized coding sequences are known in the art. One example of a comprehensive multiparameter approach that may be used in the current invention for optimized sequence design is the GENEOPTIMIZER® technology described in U.S. Patent Publication No. 2007/0141557 AA, the disclosure of which is incorporated herein by reference In certain embodiments of the invention, it may be desirable to optimize the TAL effector nucleic acid sequence for improved performance in a given homologous or heterologous host, to trigger, e.g., expression yield, activity or solubility. In this context codon optimization was proven to be an efficient tool to increase expression yields in many different species such as, e.g., plants including algae such, bacteria, yeast, insect cells or mammalian cells (such as human cells), etc. By codon optimization is meant to replace codons by synonymous codons wherein the term "synonymous codon" as used herein refers to a codon having a different nucleotide sequence than another codon but encoding the same amino acid as that other codon. The codon usage of a given gene or gene fragment may e.g., be adapted to the codon choice of the organism in which it shall be expressed. The codon usage can vary significantly for different expression systems including the most widely used viral (retro- and lentiviral, AAV, Adeno, Baculo, Sindbis, Vaccinia), bacterial (e.g., *E. coli, B. subtilis, L. lactis*), yeast (e.g., *S. cerevisiae, S. pombe, P. pastoris*), fungal (e.g., *A. niger, A. oryzae, A. awamori, Fusarium, Trichoderma* sp, *Penicillium* sp.), insect (e.g., *Spodoptera frugiperda* Sf9, Sf21, *Drosophila melanogaster* S2; *Trichoplusia ni* High Five™), plant (e.g., *Agrobacterium tumefaciens, Nicotiana tobaccum*), algae (e.g., *P. tricornutum., C. reinhardtii, Synechococcus elongates, Chlorella vulgaris*), mammalian (e.g., CHO, 3T3 cells) or human (e.g., H1299, 293, PERC6, cells) expression systems. Genomic codon usage tables for various species are available in the codon usage database at http://www.kazusa.or.jp/codon/ including codon usage tables for chloroplasts and mitochondria. Two exemplary codon usage tables reflecting the genomic codon usage of *C. reinhardtii* (TABLE 2) and the chloroplast codon usage of *C. reinhardtii* (TABLE 3) are shown below:

TABLE 2

Genomic Codon Usage of *C. reinhardtii*
Fields: Triplet - Frequency: per Thousand - (. . . Number)

| | | | | | | | |
|---|---|---|---|---|---|---|---|
| UUU | 5.0 (2110) | UCU | 4.7 (1992) | UAU | 2.6 (1085) | UGU | 1.4 (601) |
| UUC | 27.1 (11411) | UCC | 16.1 (6782) | UAC | 22.8 (9579) | UGC | 13.1 (5498) |
| UUA | 0.6 (247) | UCA | 3.2 (1348) | UAA | 1.0 (441) | UGA | 0.5 (227) |
| UUG | 4.0 (1673) | UCG | 16.1 (6763) | UAG | 0.4 (183) | UGG | 13.2 (5559) |
| CUU | 4.4 (1869) | CCU | 8.1 (3416) | CAU | 2.2 (919) | CGU | 4.9 (2071) |
| CUE | 13.0 (5480) | CCC | 29.5 (12409) | CAC | 17.2 (7252) | CGC | 34.9 (14676) |
| CUA | 2.6 (1086) | CCA | 5.1 (2124) | CAA | 4.2 (1780) | CGA | 2.0 (841) |
| CUG | 65.2 (27420) | CCG | 20.7 (8684) | CAG | 36.3 (15283) | CGG | 11.2 (4711) |
| AUU | 8.0 (3360) | ACU | 5.2 (2171) | AAU | 2.8 (1157) | AGU | 2.6 (1089) |
| AUC | 26.6 (11200) | ACC | 27.7 (11663) | AAC | 28.5 (11977) | AGC | 22.8 (9590) |
| AUA | 1.1 (443) | ACA | 4.1 (1713) | AAA | 2.4 (1028) | AGA | 0.7 (287) |
| AUG | 25.7 (10796) | ACG | 15.9 (6684) | AAG | 43.3 (18212) | AGG | 2.7 (1150) |
| GUU | 5.1 (2158) | GCU | 16.7 (7030) | GAU | 6.7 (2805) | GGU | 9.5 (3984) |
| GUC | 15.4 (6496) | GCC | 54.6 (22960) | GAC | 41.7 (17519) | GGC | 62.0 (26064) |
| GUA | 2.0 (857) | GCA | 10.6 (4467) | GAA | 2.8 (1172) | GGA | 5.0 (2084) |
| GUG | 46.5 (19558) | GCG | 44.4 (18688) | GAG | 53.5 (22486) | GGG | 9.7 (4087) |

TABLE 3

Chloroplast Codon Usage of *C. reinhardtii*
Fields: Triplet - Frequency: per Thousand - (. . . Number)

| | | | | | | | |
|---|---|---|---|---|---|---|---|
| UUU | 33.4 (894) | UCU | 17.0 (455) | UAU | 24.6 (657) | UGU | 7.6 (203) |
| UUC | 17.1 (456) | UCC | 2.8 (74) | UAC | 10.0 (266) | UGC | 1.5 (39) |
| UUA | 77.7 (2078) | UCA | 22.0 (588) | UAA | 2.9 (78) | UGA | 0.1 (3) |
| UUG | 4.3 (114) | UCG | 4.0 (107) | UAG | 0.4 (12) | UGG | 13.5 (361) |
| CUU | 14.3 (383) | CCU | 15.5 (414) | CAU | 10.1 (270) | CGU | 32.4 (866) |
| CUC | 1.0 (28) | CCC | 3.4 (90) | CAC | 8.8 (235) | CGC | 4.1 (110) |
| CUA | 6.4 (170) | CCA | 23.6 (630) | CAA | 38.4 (1026) | CGA | 3.4 (90) |
| CUG | 3.7 (99) | CCG | 2.4 (63) | CAG | 4.1 (110) | CGG | 0.5 (14) |
| AUU | 51.4 (1374) | ACU | 24.4 (651) | AAU | 42.1 (1126) | AGU | 16.0 (428) |
| AUC | 8.2 (219) | ACC | 5.1 (135) | AAC | 17.7 (472) | AGC | 5.4 (144) |
| AUA | 6.9 (184) | ACA | 32.4 (865) | AAA | 69.1 (1847) | AGA | 5.3 (143) |
| AUG | 22.3 (596) | ACG | 3.9 (103) | AAG | 6.2 (167) | AGG | 0.9 (23) |
| GUU | 29.3 (783) | GCU | 34.0 (908) | GAU | 25.3 (676) | GGU | 44.0 (1177) |
| GUC | 2.5 (68) | GCC | 5.9 (159) | GAC | 9.8 (263) | GGC | 6.4 (172) |
| GUA | 26.0 (696) | GCA | 20.7 (554) | GAA | 41.1 (1098) | GGA | 8.6 (229) |
| GUG | 5.6 (149) | GCG | 3.3 (88) | GAG | 5.7 (152) | GGG | 3.7 (99) |

Thus, in one aspect, the invention relates to optimized TAL effector expression constructs and methods to achieve the best possible design for a given target host. An increase in gene expression may be achieved, for example, by replacing non-preferred or less preferred codons by more preferred codons or non-preferred codons by more preferred and less-preferred codons with regard to a specific host system thereby taking advantage of the degenerate genetic code without modifying the encoded amino acid sequence. Methods of producing synthetic genes with improved codon usage are, e.g., described in U.S. Pat. Nos. 6,114,148 and 5,786,464 the disclosures of which is incorporated herein by reference. Alternatively, it may be sufficient to only modify or randomize the initial 5'codons of a given sequence or open reading frame as, e.g., described in WO2009/113794. In another embodiment, the codon adaptation strategy may be such as to modify codons that are over- or underrepresented in genomic sequences, eliminate only random codons or certain motifs (such as, e.g., AGG in viral sequences) and harmonize the distribution of other codons over the entire sequence. For example the GC content may be harmonized to allow for correct folding of complex, modular or repetitive protein motifs. Also, a combination of different optimization strategies may be ideal to achieve the best effect for a given TAL or TAL effector sequence. In some methods of the invention, codon optimization can be applied to (i) the TAL cassettes and/or (ii) TAL repeats as a whole, and/or (iii) the N- and C-terminal flanking regions and/or (iv) effector fusion encoding sequences. However, in certain aspects it may in addition be useful to optimize other upstream or downstream located sequences.

In some embodiments of the invention at least all sequences expressed in a target host have been subject to codon-optimization. In certain aspects of the invention it may, however, be useful to optimize or de-optimize only one or two of the above listed domains or only a proportion thereof. For example in certain embodiments of the invention, one or more of the sequences to be expressed have been codon-optimized by at least 20%, 25%, 30%, 35%, 40%, 45%, 50%, 55%, 60%, 65%, 70%, 75%, 80%, 85%, 90%, 95%, 99% or more with regard to a given target host system. In one embodiment the host system is an algae system and one or more sequences to be expressed have been optimized based on the codon usage preferences listed in TABLES 2 or 3. In one embodiment a TAL effector sequences reflects the codon usage of one or more algal chloroplasts.

In another aspect of the invention, it may be useful to decrease the number of optimized codons in a given sequence as a means for lowering expression levels. For example, it may be useful to decrease expression level of a certain expression product as compared to another expression product in order to balance interaction or activity of both products. In another aspect, different optimization strategies can be applied e.g., to different gene products expressed together in a host cell. For example, a functional vector comprising a TAL effector and more than one effector fusion sequences may be designed such that one of the effector sequences has been optimized for increased expression whereas another effector sequence has been de-optimized to limit expression levels. Optimization can thus be used to trigger a defined production ratio of expressed gene products thereby modulating their activity. This strategy may for example be particularly useful where TALs are being used as scaffolds to arrange enzyme activities for a given biosynthetic pathway on a DNA template—as described in more detail elsewhere herein. In such cases, it may be required that different enzymes are subject to different codon optimization strategies to achieve different expression levels or a rational expression balance for the best possible interplay.

In another aspect of the invention, a multi-organisms optimization or de-optimization approach may be applied as, e.g., codons may be selected to allow for (i) expression in more than one specific host organism or (ii) expression in one organisms but not in another or (iii) a blend of optimized codons for improved expression in two or more organisms). For example, a codon choice may be used that allows for a TAL effector to be efficiently expressed in yeast and algae but not in E. coli or in another example a codon choice may be used to allow for expression in mammalian as well as insect systems. Thus, in some embodiments, the invention relates to engineered TAL effector sequences exhibiting a codon choice that is compatible with a first species and at least a second species wherein the TAL effector sequence can be expressed at detectable levels in the first and at least the second species. In another embodiment, the invention relates to an engineered TAL effector sequence exhibiting a codon choice that is compatible with a first species but is not compatible with at least a second species wherein the TAL effector sequence can be expressed at detectable levels in the first species but cannot be expressed at detectable levels in at least a second species.

Apart from translational effects, codon usage may influence multiple levels of RNA metabolism and has also been shown to influence transcriptional regulation. For example, the expression of a gene can be modulated by modifying the number of CpG dinucleotides in the open reading frame as described in U.S. Patent Publication No. 2009/0324546 AA, the disclosure of which is incorporated herein by reference. In this context it was demonstrated that an increase of the intragenic CpG content can further augment expression yields as compared to a "conventionally codon-optimized" gene mainly by triggering de novo transcription rates whereas a decrease of the intragenic CpG content has the contrary effect. Thus, in one aspect the invention relates to TAL effector sequences wherein at least (i) the TAL repeat domain and/or (ii) the N- and C-terminal flanking regions and/or (iii) effector encoding sequences comprise an increased CpG dinucleotide content to increase expression or a decreased intragenic CpG dinucleotide content to decrease expression.

The above described strategies may further be combined to modulate the immunogenicity of gene products. It may for example be desired to minimize the immunogenicity of a TAL effector for therapeutic application in a mammalian or human host. For example, PCT Publication WO 2009/049359 A1, the disclosure of which is included herein by reference, discloses methods of modulating the quality of an immune response to a target antigen in a mammal wherein the quality is modulated by replacing at least one codon of the polynucleotide with a synonymous codon that has a higher or lower preference of usage by the mammal to confer the immune response than the codon it replaces. The ranking of codons mediating increased expression is not necessarily identical with the ranking of codons mediating an increased immune response. Thus, in a further aspect of the invention, replacement by synonymous codons may be applied to change the immunogenicity of a heterologous DNA binding effector molecule such as zinc-finger nuclease, meganucleases or TAL effector molecules in a target host system by replacing codons with a higher ranking to confer an immune response by synonymous codons with a lower ranking to confer a lower immune response in a mammalian or human host.

Thus, the invention relates, in part, to DNA binding effector molecules optimized for increased expression in mammalian organisms which at the same time having decreased immunogenicity in said mammalian host. In one embodiment, the invention relates to a DNA binding effector sequence wherein at least one of (i) the DNA binding domain sequence or (ii) at least one effector domain sequence has been codon-optimized for expression in mammalian cells and wherein the codon-optimization takes into account selecting synonymous codons that have a lower immune response preference, wherein at least one codon may be replaced according to the following scheme to decrease immunogenicity of the optimized sequence: GCT by GCG or GCA or GCC; GCC by GCG or GCA; CGA by AGG or CGG; CGC by AGG or CGG; CGT by AGG or CGG; AGA by AGG or CGG; AAC by AAT; GAC by GAT; TGC by TGT; ATC by ATA or ATT; ATT by ATA; CTG by CTA or CTT or TTG or TTA; CTC by CTA or CTT or TTG or TTA; CTA by TTG or TTA; CTT by TTG or TTA; TTG by TTA; TTT by TTC; CCC by CCT; TCG by TCT or TCA or TCC or AGC or AGT; TCT by AGC or AGT; TCA by AGC or AGT; TCC by AGC or AGT; ACG by ACC or ACA or ACT; ACC by ACA or ACT; ACA by ACT; TAC by TAT; GAA by GAG; GGA by GGC or GGT or GGG; CCC by CCA or CCG; CCT by CCA or CCG; GTG by GTT or GTA; GTC by GTT or GTA; GTT by GTA.

A DNA binding effector sequence optimized as described above, wherein the DNA binding effector is a zinc-finger nuclease, a TAL effector, a TAL epigenetic modifier or a meganuclease.

In specific embodiments, an optimized open reading frame may be combined with an algorithm to encrypt a secret message into the open reading frame as described in U.S. Patent Publication No. 2011/0119778 AA the disclosure of which is incorporated herein by reference. Such message may allow the identification or tracking of certain synthetic nucleic acid molecules encoding DNA binding effector molecules. In certain aspects of the invention the encrypted message may be included in the TAL effector sequence and may serve to identify transfected or genetically engineered cells such as mammalian cells, yeast cells, algae or microalgae or other engineered plants, plant seeds or crops. In some embodiments, the encrypted message is included in either the TAL binding domain or at least one effector domain encoding sequence. The message can be inserted without changing the amino acid sequence of the effector domain making use of the degenerate genetic code as described e.g., in U.S. Patent Publication No. 2011/0119778 AA the disclosure of which is incorporated herein by reference. Thus, the invention also relates to DNA binding effector molecules such as zinc-finger nucleases, meganucleases, TAL effectors or TAL epigenetic modifier encoding sequences containing an encrypted message. Furthermore the invention relates to TAL effector construct wherein at least part of the TAL effector sequence has been codon-adapted to an algae, plant or mammalian expression system and the effector fusion harbors a secret massage encrypted according to the method as described in U.S. Patent Publication No. 2011/0119778 AA.

Engineered TAL Effectors

The TAL Code.

Figure 2A:
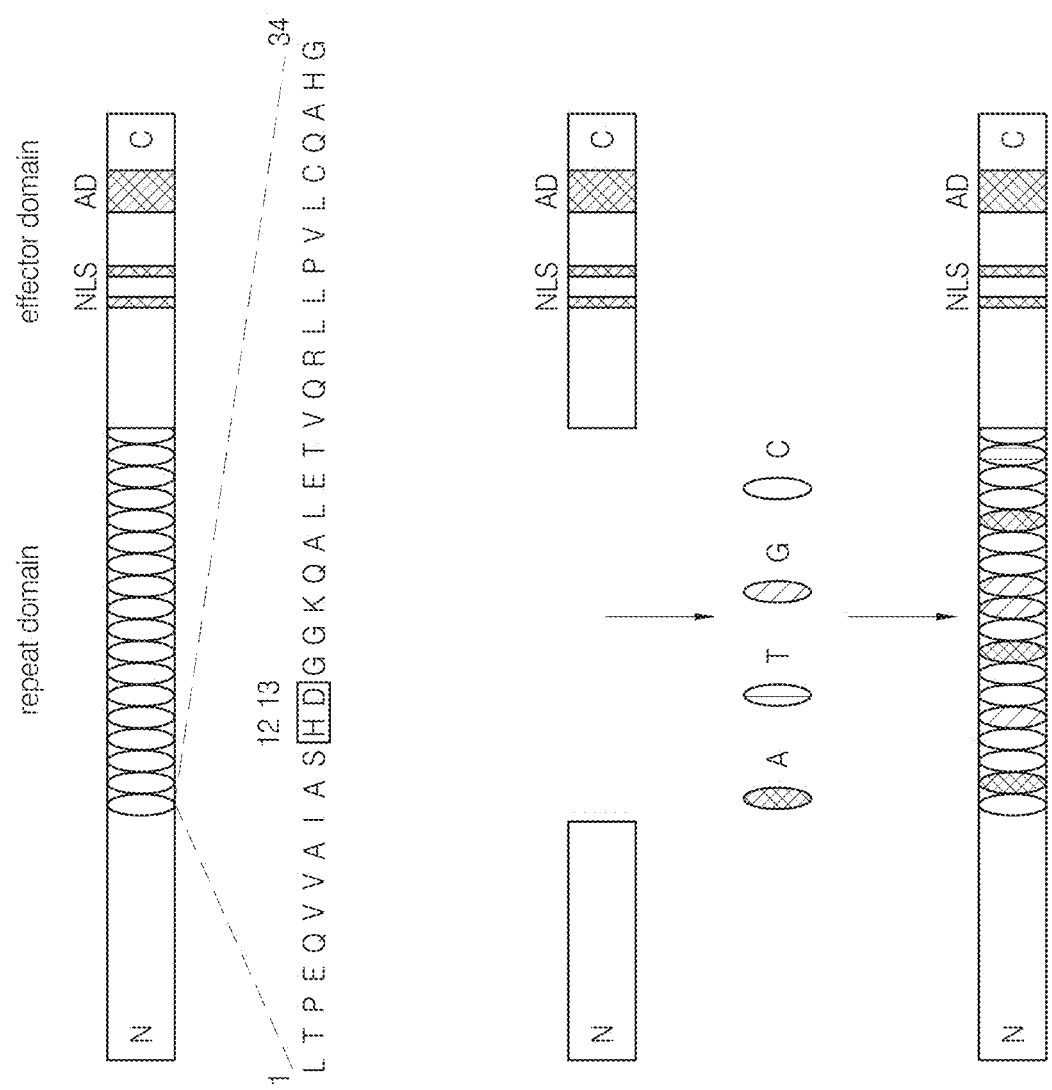

Natural TAL effectors are usually composed of an amino-terminal moiety (N-terminus), a central array comprising multiple amino acid repeats with hypervariable RVD that determine base preference and a carboxyl-terminal portion (C-terminus) comprising a nuclear localization signal (NLS) and a transcription activator (AD) domain the latter of which can be replaced by any effector domain. In many instances, the central amino acid repeats are between 32 and 35 amino acids in length, with amino acid variations at positions 12 and 13 determining base specificity of the particular repeat. Based on the modular TAL structure the central repeats can be synthesized separately to be assembled into a given TAL (see. FIG. 2A) which allows for efficient genetic engineering of TAL effectors with novel function.

As noted above, a distinctive characteristic of TAL effectors is a central repeat domain containing between 1.5 and 33.5 TAL cassettes that are usually around 34 residues in length (the C-terminal cassette is generally shorter and referred to as a "half repeat"). A typical sequence of a naturally occurring cassette is LTPEQVVAIASHDGG-KQALE TVQRLLPVLCQAHG (SEQ ID NO: 90), with hypervariable residues at positions 12 and 13.

Figure 2B:
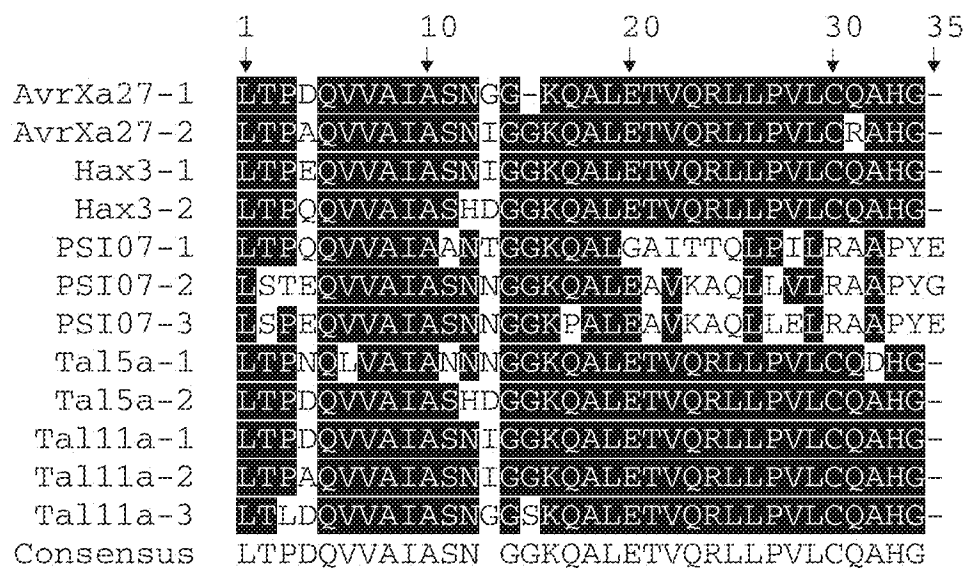

The amino acid sequences of TAL repeats can vary to some extent within the same protein and between proteins. An alignment of TAL repeats from proteins obtained from different bacteria is shown in FIG. 2B. The repeats contain several conserved regions. TAL repeats of the invention may contain one or more of the amino acid sequences set out in TABLE 4.

TABLE 4

TAL Amino Acid Sequences

LTPDQVVAIASN1GGKQALETVQRLLPVLCQAHG (SEQ ID NO: 91)

LTPDQVVAIAS21GGKQALETVQRLLPVLCQAHG (SEQ ID NO: 92)

LTP3QVVAIA4 (SEQ ID NO: 93)

GGK5AL6 (SEQ ID NO: 94)

Legend:
"1" is G, I, D, T, N, K, or no amino acid
"2" is I, N, H, or Y
"3" is D, A, E, Q, or N
"4" is S, A, or N
"5" is P or Q
"6" is E or G The primary amino acid sequence of a TAL repeat domain dictates the nucleotide sequence to which it binds. The crystal structure of a TAL effector bound to DNA suggests that each TAL cassette comprises two alpha helices and a short RVD-containing loop where the second residue of the RVD at position 13 makes sequence-specific DNA contacts while the first residue of the RVD at position 12 stabilizes the RVD-containing loop (Deng, D et al., Structural Basis for Sequence-Specific Recognition of DNA by TAL Effectors". Science 335 (6069): 720-723 (2012)). Target sites of TAL effectors also tend to include a T flanking the 5' base targeted by the first repeat and this appears to be due to a contact between this T and a conserved Tryptophan in the region N-terminal of the central cassettes. Because the specific relationship between the TAL amino acid sequence and the target binding site, target sites can be predicted for TAL effectors, and TAL effectors also can be engineered and generated for the purpose of binding to particular nucleotide sequences.

TAL effectors have been shown to bind to DNA duplexes as well as DNA-RNA hybrids, wherein binding is in each case believed to be determined by the DNA forward strand (Yin et al. Specific DNA-RNA Hybrid Recognition by TAL Effectors. Cell Reports 2, 707-713 (2012)). Therefore, as used herein a target site or TAL binding site can be provided in the context of a DNA double strand or a DNA-RNA hybrid.

Thus, the invention relates, in part, to TAL effectors wherein each TAL nucleic acid binding cassette is responsible for recognizing one base pair in the target DNA sequence (wherein the target DNA sequence may be provided in the context of a double stranded DNA or a DNA-RNA hybrid molecule), and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; I-IN for recognizing G; NA for recognizing G; SN for recognizing G or A; and YG for recognizing T. Each DNA binding cassette can comprise a RVD that determines recognition of a base pair in the target DNA sequence, wherein each DNA binding cassette is responsible for recognizing one base pair in the target DNA sequence, and wherein the RVD comprises one or more of: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T, wherein * represents a gap in the second position of the RVD; HG for recognizing T; H* for recognizing T, wherein * represents a gap in the second position of the RVD; and IG for recognizing T.

In certain instances it may be required to target a methylated nucleic acid sequence or a methylated chromatin region of a cell. DNA is usually methylated by DNA methyltransferase at the C5 position of cytosine often in the context of a CpG dinucleotide motif resulting in 5-methyl-cytosine (mC). It has been found that between 60% and 90% of all CpGs are methylated in mammalian and plant somatic or pluripotent cells whereas most unmethylated CpGs are grouped in clusters referred to as CpG islands which are present in the 5' regulatory regions of many genes. DNA methylation is important for regulation of gene transcription and genes with high levels of mC in their promoter region are transcriptionally silent. It was found that methylated DNA can be specifically recognized by TAL effectors via RVDs NG and N* (Deng et al. Recognition of methylated DNA by TAL effectors. Cell Research 22: 1502-1504 (2012); Valton et al. Overcoming TALE DNA Binding Domain Sensitivity to Cytosine Methylation. J. Biol. Chem. 287: 38427-38432 (2012)). NG usually recognizes T whereas N* binds both, T and C. It was shown that both RVDs additionally bind mC. Thus, whereas N* may be included in TAL effectors in those instances where both cytosine variants (mC and C) are to be recognized, NG (which recognizes only mC but not C) may be used to distinguish methylated from un-methylated sequences. Thus, the invention further relates, in part, to TAL effectors wherein each TAL nucleic acid binding cassette is responsible for recognizing one base pair in the target DNA sequence, and wherein the RVD comprises one or more of: NG or N* for recognizing mC.

The invention thus includes TAL effectors that recognize methylated nucleic acids, as well as methods for bringing TAL effector fusion proteins with various biological activities in contact with such nucleic acids. Exemplary activities include methylation and demythylation activities. The invention thus includes compositions and methods for altering the methylation state of nucleic acids. In one aspect, the invention includes methods for altering the methylation state of nucleic acid molecules in cells comprising contacting the cells with one or more nucleic acid molecules encoding non-naturally occurring fusion protein comprising an artificial transcription activator-like (TAL) effector repeat domain, for example, of contiguous repeat units 33 to 35 amino acids in length and a methylation state modification activity (e.g., methylation or demethylation), wherein the repeat domain is engineered for recognition of a predetermined nucleotide sequence, wherein the fusion protein recognizes the predetermined nucleotide sequence, and wherein the fusion protein is expressed in the cells.

The invention thus includes methods for altering the methylation state of specific regions of nucleic acid molecules, for example, in cells. This includes the conversion of hemimethylated nucleic acids to fully methylated or fully demethylated nucleic acids. Thus, the invention includes methods for converting hemimethylated nucleic acids to fully methylated or fully demethylated nucleic acids, as well as compositions of matter for performing such methods.

Exemplary methylases that may be used in the practice of the invention are described elsewhere herein.

In some aspects, TAL cassettes may be assembled from single cassettes or monomers and a library of monomers may be provided representing at least four different categories wherein at least one category encodes an RVD to bind A, at least one category encodes an RVD to bind G, at least one category encodes an RVD to bind C and at least one category encodes an RVD to bind T, wherein the RVDs binding A, G, C or T may be chosen from the aforementioned list.

The target site bound by a TAL effector or TAL effector fusion can meet at least one of the following criteria: (i) is a minimum of 15 bases long and is oriented from 5' to 3' with a T immediately preceding the site at the 5' end; (ii) does not have a T in the first (5') position or an A in the second position; (iii) ends in T at the last (3') position and does not have a G at the next to last position; and (iv) has a base composition of 0-63% A, 11-63% C, 0-25% G, and 2-42% T.

In another aspect, an engineered TAL effector may be designed to incorporate a nucleic acid encoding a variant 0th DNA binding cassette with specificity for A, C, or G, thus eliminating the requirement for T at position −1 of the target site.

TAL Repeat Structures—*Burkholderia*-Derived

*Burkholderia* TAL-Like Amino Acid Sequences: Hypothetical protein RBRH_01844 of *Burkholderia rhizoxinica* HKI 454 has the following amino acid sequence in which standard one-letter amino acid abbreviations are used (GenBank Accession No. YP_004022479.1) (SEQ ID NO:48).

```
  1 mstafvdqdk qmanrlnlsp lerskiekqy ggattlafis nkqnelaqil sradilkias
 61 ydcaahalqa vldcgpmlgk rgfsqsdivk iagniggaqa lqavldlesm lgkrgfsrdd
121 iakmagnigg aqtlqavldl esafrergfs qadivkiagn nggaqalysv ldveptlgkr
181 gfsradivki agntggaqal htvldlepal gkrgfsridi vkiaanngga qalhavldlg
241 ptlrecgfsq atiakiagni ggaqalqmvl dlgpalgkrg fsqatiakia gniggaqalq
301 tvldlepalc ergfsqatia kmagnnggaq alqtvldlep alrkrdfrqa diikiagndg
361 gaqalqavie hgptlrqhgf nladivkmag niggaqalqa vldlkpvlde hgfsqpdivk
421 magniggaqa lqavlslgpa lrergfsqpd ivkiagntgg aqalqavldl eltlvehgfs
481 qpdivritgn rggaqalqav laleltlrer gfsqpdivki agnsggaqal qavldleltf
541 rergfsqadi vkiagndggt qalhavldle rmlgergfsr adivnvagnn ggaqalkavl
601 eheatlnerg fsradivkia gnggaqalk avleheatld ergfsradiv riagngggaq
661 alkavlehgp tlnergfnlt divemaansg gaqalkavle hgptlrqrgl slidiveias
721 nggaqalkav lkygpvlmqa grsneeivhv aarrggagri rkmvapller q
```

Hypothetical protein RBRH_01776, also of *Burkholderia rhizoxinica* HKI 454, has the following amino acid sequence (GenBank Accession No. YP_004030669) (SEQ ID NO:49).

```
  1 mpatsmhqed kqsanglnls plerikiekh ygggatlafi snqhdelaqv lsradilkia
 61 sydcaaqalq avldcgpmlg krgfsradiv riagngggaq alysvldvep tlgkrgfsqv
```

-continued

```
121dvvkiaggga qalhtvleig ptlgergfsr gdivtiagnn ggaqalqavl eleptlrerg

181fnqadivkia gngggaqalq avldvepalg krgfsrvdia kiagggaqal qavlgleptl

241rkrgfhptdi ikiagnngga qalqavldle lmlrergfsq adivkmasni ggaqalqavl

301nlepalcerg fsqpdivkma gnsggaqalq avldlelafr ergfsqadiv kmasniggaq

361alqavlelep alhergfsqa nivkmagnsg gaqalqavld lelvfrergf sqpeivemag

421niggaqalht vldlelafre rgvrqadivk ivgnnggaqa lqavfelept lrergfnqat

481ivkiaanggg aqalysvldv eptldkrgfs rvdivkiagg gaqalhtafe leptlrkrgf

541nptdivkiag nkggaqalqa vlelepalre rgfnqativk magnaggaqa lysvldvepa

601lrergfsqpe ivkiagnigg aqalhtvlel eptlhkrgfn ptdivkiagn sggaqalqav

661lelepafrer gfgqpdivkm asniggaqal qavlelepal rergfsqpdi vemagnigga

721qalqavlele pafrergfsq sdivkiagni ggaqalqavl eleptlresd frqadivnia

781gndgstqalk aviehgprlr qrgfnrasiv kiagnsggaq alqavlkhgp tldergfnlt

841nivkiagngg gaqalkavie hgptlqqrgf nltdivemag kgggaqalka vlehgptlrq

901rgfnlidive masntggaqa lktvlehgpt lrqrdlslid iveiasngga qalkavlkyg

961pvlmqagrsn eeivhvaarr ggagrirkmv alllerq
```

Figure 25B:
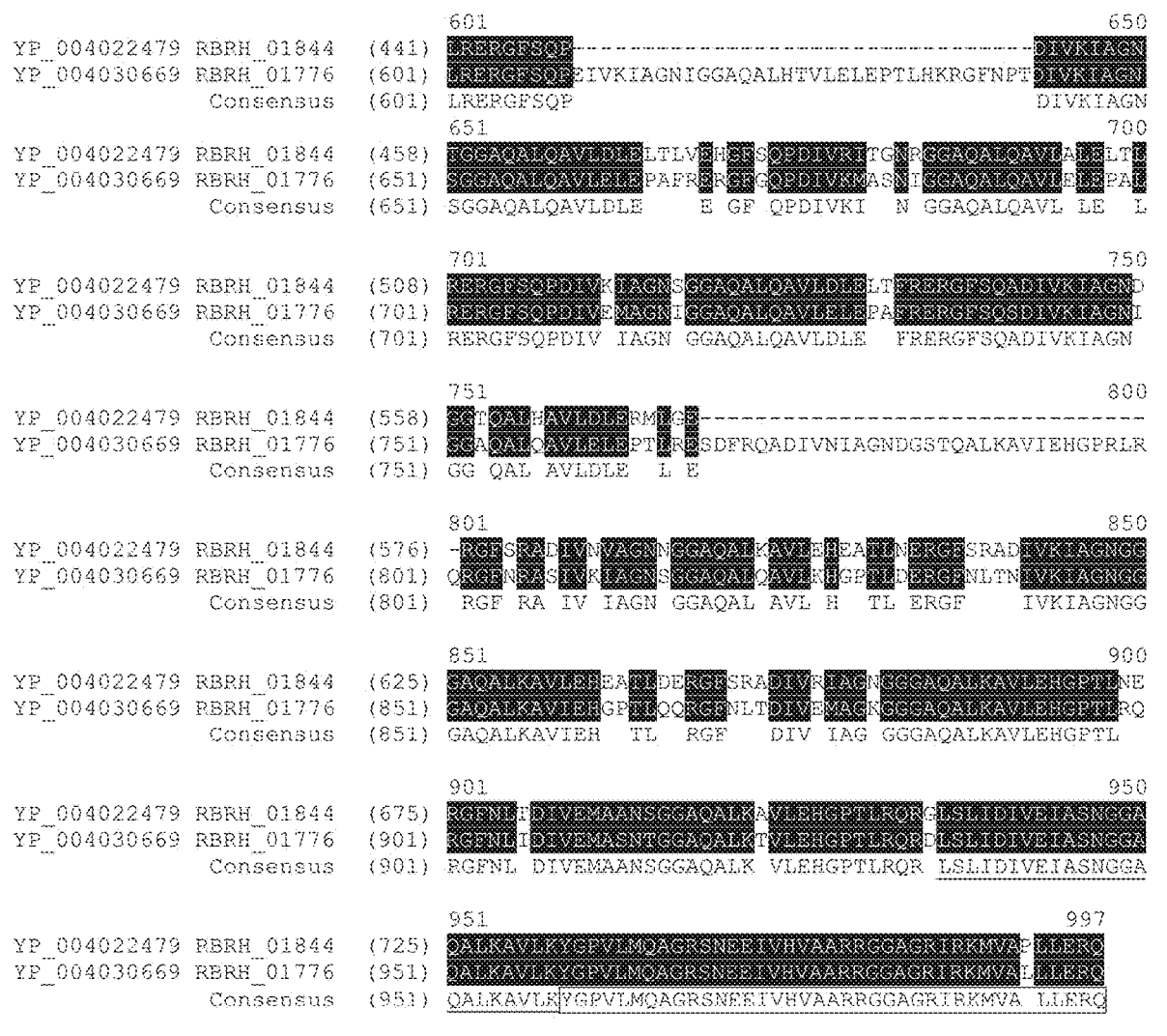

FIGS. 25A and 25B show an amino acid sequence alignment between the amino acid sequences of the two proteins represented. Also included in FIGS. 25A and 25B is a consensus sequence of identical or strongly similar positions thereof. The proteins have related and short N and C termini, indicating that the sequences represent the complete sequences of the proteins. As shown in FIG. 26 for the RBRH_01776 protein, a TAL repeat region begins at amino acid 51 and ends at amino acid 958 and is composed of individual repeats of 33 amino acids. Most of the TAL repeat regions shown have a recognizable repeat variable diresidue sequence (boxed) beginning with an "N." A partial TAL repeat precedes the indicated carboxyl flanking region.

As further discussed below, individual repeated sequences of *Burkholderia* proteins tend to contain 33 amino acids and contain more homology to each other than to known TAL repeat sequences. The conservation of repeat length, and of several amino acid residue positions (including nucleotide binding RVDs at positions 12 and 13) with known TAL repeat sequences suggest that these proteins are expressed and functional and do not represent pseudo genes. The proteins are believed to have nucleic acid binding activity, in part, due to their similarity to known TALEs and TALE repeats.

Based upon the *Burkholderia* sequences, TAL repeats were characterized as set out in FIG. 27. *Burkholderia* repeat sequences nos. 1-18 are from the RBRH_01776 protein and repeat sequences A-T are from the RBRH_01844 protein. The white letters on a black background show identical and strongly similar amino acids as noted in TABLE 1 and the text describing this table.

The double arrow ⇊ symbol in FIG. 27, as well as other figures herein, represents the two amino acids that have recognition properties for particular deoxyribonucleotides, i.e., the RVD or repeat variable diresidue sequence as described earlier herein. Those amino acid diresidues at positions 12 and 13 for the *Burkholderia* repeat sequences above are as follows: NA, ND, NG, NI, NK, NN, NR, NS, NT, and N-. Based on correlations between such repeat variable diresidues and their cognizant deoxyribonucleotides, the *Burkholderia* RVD's appear to have specificity for binding as follows: NA for recognizing guanine, ND for recognizing cytidine, NG for recognizing thymine, NI for recognizing adenine, NK for recognizing guanine, NN for recognizing guanine or adenine, NR may lack specificity, NS for recognizing any deoxyribonucleotide, NT for recognizing any deoxyribonucleotide with a strong preference for adenine and guanine, and N- for recognizing cytidine or thymine, where - represents a gap in the second position of the RVD.

The *Burkholderia* repeat sequences contain several conserved regions. In one aspect, the repeat sequence comprises the sequence GG(A/T)Q(A/T)L$X_1X_2$V(L/F/I) (SEQ ID NO: 95) immediately after the repeat variable diresidue at positions 12 and 13, i.e., at positions 14-23, where "$X_1$" and "$X_2$" are other than E or G and may be the same or different. The parenthesis (A/T) means that either amino acid A or T may be in the indicated position. Similarly, the parenthesis (L/F/I) means that either amino acid L or F or I may be in the indicated position. In another aspect, $X_1$ is Q, H, Y or K; and $X_2$ is A, T, S, or M. In another aspect, an amino acid sequence at positions 14-23 of a *Burkholderia* repeat sequence is GGAQAL$X_1X_2$VL (SEQ ID NO: 96) where "$X_1$" and "$X_2$" are other than E or G and may be the same or different, or $X_1$ is Q, H, Y or K; and $X_2$ is A, T, S, or M. In another aspect, an amino acid sequence at positions 14-23 of a *Burkholderia* repeat sequence is GGAQALQAVL (SEQ ID NO: 97), or a sequence having 70%, 80% or 90% identity thereto. Positions are in reference to the repeat variable diresidue at positions 12 and 13 identified above in FIG. 27 as ⇊.

In another aspect, the repeat sequence for *Burkholderia* comprises the sequence GGAQAL (SEQ ID NO: 98) at positions 14-19, or a sequence having 80% identity thereto. In another aspect, the repeat sequence for *Burkholderia* comprises I at position 6. Position 6 distinguishes the above cited *Burkholderia* repeat sequences from those of *Ralstonia* and *Xanthomonas* repeat sequences in that that position is V or L in the *Ralstonia* and *Xanthomonas* sequences.

Further, in some aspects of a *Burkholderia* repeat sequence, position 5 is other than Q, position 6 is other than V or L, position 8 is other than A or V, or position 26 is other than L. Positions are in reference to the repeat variable diresidue at positions 12 and 13 identified above in FIG. 27 as ⇊.

In some aspects of a *Burkholderia* repeat sequence, position 1 is F, V, or L, position 2 is S or N, position 3 is Q or R, position 4 is A, P, or T, position 5 is D or T, position 6 is an I, position 7 is V or A, position 8 is K or R, position 9 is I or M, position 10 is A, position 11 is G, position 24 is D or E, position 25 is L, V, or H, position 26 is E or G, position 27 is P or L, position 28 is A or T, position 29 is L or F, position 30 is R or G, position 31 is E or K, position 32 is R or position 33 is G. Positions are in reference to the repeat variable diresidue at positions 12 and 13 identified above in FIG. 27 as ⇓⇓.

In some aspects of a *Burkholderia* repeat sequence, position 1 is F, V, or L, position 2 is S, N, H, R or G, position 3 is Q, R, P or L, position 4 is A, P, T, G, S, I or D, position 5 is D, T, N or E, position 6 is an I, position 7 is V, A or I, position 8 is K, R, T, E or N, position 9 is I, M or V, position 10 is A, V, or T, position 11 is G, A or S, position 24 is D, E, N, S, or A, position 25 is L, V, or H, position 26 is E, G, or K, position 27 is P, L, S, R, or A, position 28 is A, T, V, or M, position 29 is L or F, position 30 is R, G, C, D, H, V, or N, position 31 is E, K, or Q, position 32 is R, S, C, or H, or position 33 is G or D.

In one aspect of repeat sequences, the repeat has a consensus protein sequence FSQADIVKIAGNX₃GGAQALQAVLDLEPX₄LRERG (SEQ ID NO: 50) where "X₃" represents a DNA base recognition residue such as I, N, T, D, R, S, G, K or A, and where "X₄" represents A or T, or a sequence having 60%, 70%, 80% or 90% identity thereto.

Amine and Carboxyl Regions Flanking *Burkholderia* TAL Repeats:

The amine and carboxyl termini of *Burkholderia* proteins are naturally shorter than even truncated TALEs described herein for *Xanthomonas* or *Ralstonia* species.

The amine terminal region of the RBRH_01844 TAL effector has two candidate repeat structures roughly at amino acids 18-50 and 51-82 (based on partial sequence homology to the repeated sequences) thereby providing for a number of possible combinations for the amine-terminal sequence flanking the repeated sequences of an engineered TAL effector. For example, all 82 amino acids may be present (i.e., no truncations), amino acids 1-17 may be present, and/or amino acids 51-82 may be present in the amine flanking region, or any combination thereof. Further, truncations from either end of the amine flanking sequence can generate altered amine flanking regions for use in engineered constructs. Restriction sites may be introduced as needed into any location of a nucleic acid encoding the amine flanking region to facilitate cloning procedures. Further, a restriction site can be engineered into this region such that it will be relatively straightforward to make any desirable modifications to the protein structure. For example, compatible restriction sites can be included such that the genes can be cloned into the existing VP16/64 activator and FokI nuclease vectors, as described elsewhere herein. Further, amine flanking sequences or truncated amine flanking sequences used for *Xanthomonas*-type TAL repeat constructs may be engineered to flank *Burkholderia* TAL repeats in an engineered construct.

In an aspect, the amine terminal region flanking the repeat regions of both proteins represented in FIGS. 25A and 25B contains the conserved amino acid sequences LNLSPLER (SEQ ID NO: 51) and TLAFISN (SEQ ID NO: 52). The invention includes proteins comprising one or both of these amino sequences, as well as proteins containing amino acid sequences at least 80%, 85%, or 90% identical or strongly similar to one or both of these sequences.

As stated herein, nucleic acid target sites of TAL effectors tend to include a thymine base flanking the 5' base targeted by the first repeat of the effector; this appears to be due to a contact between the thymine and a conserved tryptophan residue in the amine flanking region N-terminal to the repeated sequences. In contrast to this pattern, which was essentially based on TALEs from *Xanthomonas*, there is no tryptophan (W) residue in the N terminal (or any) region of the *Burkholderia* proteins, which suggests that a 5' thymine in the DNA binding site is not required.

Figure 27:
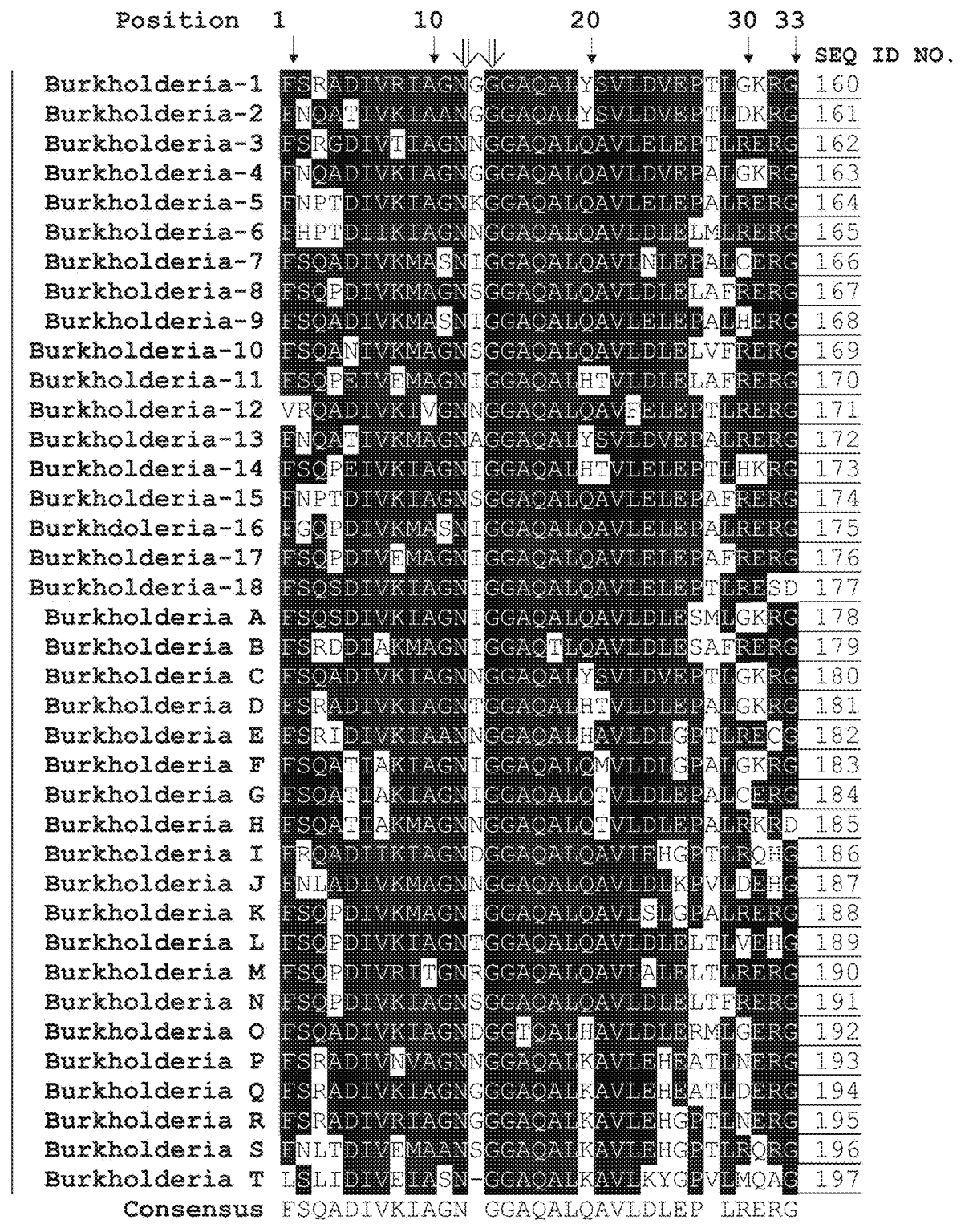

The sequence from amino acid 710 to 741 of the RBRH_01844 amino acid sequence shown in FIG. 2A is shown in FIG. 27 as line T, and may or may not be a functional repeat in the sense that it binds a base in a nucleic acid molecule. In any event, the sequence of this protein demonstrates a relatively short C-terminal region of 29 or 61 residues. Further, truncations from either end of the carboxyl flanking sequence can generate altered carboxyl flanking regions for use in engineered constructs. Further, restriction sites may be introduced as needed into a nucleic acid encoding the carboxyl flanking region to facilitate cloning procedures and/or to make any desirable modifications to the protein structure carboxyl to the repeated sequence. For example, compatible restriction sites can be included such that the genes can be cloned into the existing VP16/64 activator and FokI nuclease vectors. Further, carboxyl flanking sequences or truncated carboxyl flanking sequences used for *Xanthomonas*-type TAL repeat constructs may be engineered to flank *Burkholderia* TAL repeats in an engineered construct.

In an aspect, the carboxyl terminal region flanking the repeat regions of both proteins represented in FIGS. 25A and 25B contains the conserved amino acid sequences YGPVLMQAGRSNEEIVHVAARRGGAGRIRKMVA (SEQ ID NO: 53) and LLERQ (SEQ ID NO: 54). The invention includes proteins comprising one or both of these amino sequences, as well as proteins containing amino acid sequences at least 80%, 85%, or 90% identical or strongly similar to one or both of these sequences.

The short flanking regions of *Burkholderia* TAL effectors can obviate the need to use TALE amine or carboxyl truncations as described earlier. Further, the particularly compact structure of *Burkholderia* TAL effectors contributes to shorter vector molecules, smaller plasmids that are more efficiently introduced into cells, and to smaller proteins that are generally more highly expressed.

TAL Repeat Structures—Marine Organism-Based

Further TAL repeat structures are found in marine organisms designated herein as "Marine Organism A" and "Marine Organism B." The organisms from which these TAL repeat sequences were derived have not been identified and sequence alignment based searches of the available amino acid sequence data yielded provided no additional information related to the identification of these organisms.

FIG. 28 shows an alignment and a consensus sequence for repeats from Marine Organism A. The repeat variable diresidues at positions 12 and 13 of Marine Organism A are sequences known to recognize particular bases in DNA, i.e., the diresidue HG recognizes T, HD recognizes C, and NN recognizes G or A.

A conserved six amino acid sequence of GGSKNL (SEQ ID NO: 83), at positions 14-19, immediately follows the repeat variable diresidue sequence. Another conserved sequence is IVQMVS (SEQ ID NO: 99), at positions 6-11. The isoleucine at position 6 is invariant among Marine Organism A1-A9 repeats; that position 6 is also isoleucine and invariant in *Burkholderia* repeats but that position has not been found to be isoleucine in *Xanthomonas* or *Ralstonia* species thus far. The invention includes proteins which contain the amino acid features referred to above (e.g., the sequences: GGSKNL (SEQ ID NO: 83) and/or IVQMVS (SEQ ID NO: 99)).

FIG. 29 provides an alignment and a consensus sequence for repeats from Marine Organism B. The repeat variable diresidues at positions 12 and 13 of Marine Organism B are sequences known to recognize particular bases in DNA, i.e., the diresidue HG recognizes T, HD recognizes C, HI recognizes C, and NN recognizes G or A.

The six amino acid sequence immediately following the repeat variable diresidue sequence at positions 14-19 has a sequence GA(T/N)(Q/K)(A/T)I (SEQ ID NO: 100). This sequence differs from that of TABLE 4 (GGK(P/Q)AL) (SEQ ID NO: 101), and from that of Burkholderia repeats (GG(A/T)Q(A/T)L (SEQ ID NO: 102), and from Marine Organism A (GGSKNL) (SEQ ID NO: 83). Another conserved sequence is PKDIVSIAS (SEQ ID NO: 103), at positions 3-11. The isoleucine at position 6 is again invariant, similar to that of Marine Organism A and that of Burkholderia; position 6 has not been found to be isoleucine in Xanthomonas or Ralstonia species thus far. The invention includes proteins which contain the amino acid features referred to above (e.g., the sequences: GA(T/N)(Q/K)(A/T)I (SEQ ID NO: 100) and/or PKDIVSIAS (SEQ ID NO: 103)).

TAL Repeat Structures—Blood Borne Pathogen-Based

Further TAL repeat structures are found in a blood-borne pathogen designated herein as "BBP." Based upon amino acid sequence alignment of the protein which contains the TAL repeats, this organism is likely a strain of Ralstonia solanacearum.

FIG. 30 provides an alignment for six repeats from BBP, further compared with a number of repeats of proteins from Xanthomonas, Ralstonia and Marine Organism B. A consensus sequence is provided for repeat structures from these four organisms.

The repeat variable diresidues at positions 12 and 13 of the blood-borne pathogen are sequences that recognize particular bases in nucleic acids (e.g., the diresidue NG recognizes thymine, NN recognizes guanine or adenine, NT recognizes any deoxyribonucleotide with preference for adenine and guanine, and SI is thought to recognize adenine or cytosine).

The six amino acid sequence immediately following the repeat variable diresidue sequence for blood-borne pathogen repeats, at positions 14-19, has a sequence GG(K/R)QAL (SEQ ID NO: 104). Further, position 6 is a valine. Another fairly conserved sequence is QVV(A/V)IA(S/N) (SEQ ID NO: 105), at positions 5-11. The invention includes proteins which contain the amino acid features referred to above (e.g., the sequences: GG(K/R)QAL (SEQ ID NO: 104) and/or QVV(A/V)IA(S/N) (SEQ ID NO: 105)).

Using TAL Repeat Sequences in Engineered Constructs:

A TAL effector fusion construct may be designed as described herein to contain Burkholderia flanking and/or repeated sequences or to contain marine organism repeated sequences. That is, in one aspect, at least one of the amine flanking region, the repeated sequence, and the carboxyl flanking region of a construct may be substantially based on a Burkholderia sequence as provided herein while remaining sequences of a construct may be substantially based on Xanthomonas or Ralstonia sequences.

Further, when the amine or carboxyl flanking regions of an engineered TAL protein are prepared, these flanking regions may contain portions of one or both flanking regions set out in FIG. 25A and/or FIG. 25B. In some embodiments, one or both flanking regions of the engineered protein may contain an amino acid region comprising from about 10 to about 30 amino acids, about 10 to about 40 amino acids, about 15 to about 40 amino acids, about 15 to about 30 amino acids, about 15 to about 20 amino acids, about 10 to about 20 amino acids, etc., identical or strongly similar to an amino acid sequence shown in FIG. 25A and/or FIG. 25B.

In another aspect, a repeated sequence may be substantially based on a marine organism repeated sequence as provided herein while carboxyl or amine flanking sequences may be substantially based on a Xanthomonas, a Ralstonia, or a Burkholderia sequence, for example.

Summary of Tal Protein Homologs:

TABLE 5 shows positional amino acid sequence variations derived from fifty-one naturally occurring TAL repeats and repeats from proteins believed to be TAL protein homologs. The numbering in TABLE 5 corresponds to individual positions in TAL repeats in which positions 12 and 13 designate the repeat variable diresidue which recognizes particular deoxyribonucleotides. The numbers next to the amino acid designations indicate the number of TAL repeats that contain that particular amino acid in that location. For example, at position 1, phenylalanine was found 26 times, leucine was found 24 times, and valine was found 1 time.

TABLE 5

| | TAL Repeat Variations | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Repeat Position | F 26 L 24 V 1 | S 17 T 11 R 9 E 5 N 5 G 1 H 1 L 1 Q 1 | P 22 T 13 Q 13 R 2 L 1 | E 16 A 10 K 6 P 5 D 4 T 3 Q 3 G 2 N 1 S 1 | D 26 Q 18 E 2 G 2 T 2 N 1 | I 33 V 17 L 1 | V 50 I 1 | A 17 K 14 Q 9 S 6 E 2 R 1 T 1 V 1 | I 34 M 17 | A 41 V 10 | S 32 G 14 A 3 N 2 | | | G 51 | G 44 A 6 S 1 | A 18 K 17 S 9 T 4 N 2 R 1 | Q 40 K 10 P 1 |

| | 18 | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|---|
| Repeat Position | A 41 N 9 T 1 | L 45 I 6 | E 18 Q 13 A 5 T 5 V 3 Y 3 G 2 H 2 | A 29 T 17 S 3 V 2 | V 39 L 6 I 5 M 1 | L 23 Q 14 K 5 I 4 R 2 T 2 F 1 | D 12 E 12 A 10 R 9 N 4 T 3 V 1 | L 24 K 9 Q 8 N 4 V 4 R 1 S 1 | E 18 L 18 W 6 Y 6 S 3 | P 27 L 9 A 5 D 4 T 4 G 2 | A 22 V 13 T 7 E 3 D 2 I 2 M 1 S 1 | L 46 F 5 | R 25 C 10 T 6 K 3 G 2 H 2 I 2 D 1 | E 15 A 11 Q 8 G 7 K 4 D 3 R 1 T 1 V 1 | R 17 A 15 L 10 K 5 V 2 D 1 S 1 | G 28 H 9 P 9 E 3 D 1 K 1 | -33 G 9 Y 8 L 1 | -42 E 7 N 1 G 1 |

When assessing the data of TABLE 5, several factors should be considered, including the following:
1. All TAL repeats within a TAL protein (1) may not be functional and/or (2) may exhibit otherwise unfavorable DNA binding activity (e.g., binding affinity which is too high or too low for optimal DNA functional interaction). Since TAL proteins tend to recognize multiple bases, a TAL protein may interface with DNA correctly even where one or more repeat is non-functional.
2. A single amino acid alteration may result in TAL repeat becoming non-functional but this non-functionality may be corrected by a one or more amino acid alteration(s) at another location within or external to the TAL repeat.
3. The data presented in TABLE 5 is derived from a subset of known and predicted TAL proteins.
4. A TAL repeat modification that results in enhanced DNA binding activity may confer a selective disadvantage to a host cell because it could result in functional activity (e.g., transcriptional activation) which is either "leaky" or difficult to "off-regulate".

Some of the amino acids in particular positions of TABLE 5 are well conserved and others are much less conserved. As examples, amino acid positions 1, 6, 7, 9, 10, 14, 15, 17, 18, 19, and 29 are well conserved. Using amino acid position 1 for purposes of illustration, three amino acids have been found: Phenylalanine, leucine, and valine. Further, valine is seen only once. These data suggest that having a valine at in position 1 of a TAL repeat is not optimal. Further, amino acids with exhibiting low conservation include positions 2, 4, 8, 16, 20, 23, 24, 25, 26, 27, 28, 30, 31, 32, 33, 34, and 35, with amino acids positions 34 and 35 optionally being deleted.

In general, a degree of amino acid conservation is seen in the region of TAL repeats on the amine terminal side of positions 12 and 13. Further, amino acid alterations within TAL repeats are expected to alter TAL protein DNA binding activity. TABLE 6 shows amino acids found at individual repeat locations that were identified on the amino-terminal side of the RVD where an amino acid appeared more than once.

TABLE 6

TAL Repeat N-Terminal Amino Acid Variations

| 1 | 2 | 3 | 4 | 5 | 6 | 7 | 8 | 9 | 10 | 11 |
|---|---|---|---|---|---|---|---|---|----|----|
| F, L | S, T, R, E, N | P, T, Q, R | E, A, K, P, D, T, Q, G | D, Q, E, G, T | I, V | V | A, K, Q, S, E | I, M | A, V | S, G, A, N |

Thus, an aspect of the invention includes TAL repeats, as well as TAL proteins that contain such TAL repeats, that contain amino acids shown in TABLE 6 at the indicated locations. For purposes of illustration, the invention includes TAL repeats that contain one or more of the following amino acid sequences:

F S P E D I V A I A S,  (SEQ ID NO: 55)

F T P E D I V A I A S,  (SEQ ID NO: 56)

L T P A D I V A I A S,  (SEQ ID NO: 57)

L S P A Q V V A I A S,  (SEQ ID NO: 58)
and

L T P A Q I V K I A S.  (SEQ ID NO: 59)

An aspect of the invention may further include TAL repeats that contain phenylalanine or leucine at position 1, isoleucine or valine at position 6, valine at position 7, isoleucine or methionine at position 9, and/or alanine or valine position 10.

A degree of amino acid conservation is also found immediately flanking the repeat variable diresidue sequences at positions 12 and 13 of the repeats, that is from positions 6-11 and 14-19. For example, TABLE 7 shows amino acids found at individual repeat locations that were identified on the amino-terminal side of the RVD at positions 6-11 and on the carboxyl-terminal side of the RVD at positions 14-19 where an amino acid appeared more than once.

TABLE 7

| TAL Repeat Amino Acid Variations Immediately Flanking the Repeat Variable Diresidue Sequences (i.e., positions 12 and 13 designated /// below) | | | | | | | | | | | | |
|---|---|---|---|---|---|---|---|---|---|---|---|---|
| 6 | 7 | 8 | 9 | 10 | 11 | /// | /// | 14 | 15 | 16 | 17 | 18 | 19 |
| I, V | V | A, K, Q, S, E | I, M | A, V | S, G, A, N | /// | /// | G | G, A | A, K, S, T, N | Q, K | A, N | L, I |

Thus, an aspect of the invention includes TAL repeats, as well as TAL proteins that contain such TAL repeats, that contain amino acids shown in TABLE 7 at the indicated locations. For purposes of illustration, the invention includes TAL repeats that contain one or more of the following amino acid sequences: (I/V)V(A/K)(I/M)(A/V)(S/G) (SEQ ID NO: 60) at positions 6-11, and G(G/A)(A/K/S)(Q/K)(A/N)(L/I) (SEQ ID NO: 61) at positions 14-19, where (_/_) indicates that either amino acid could occur at that position.

An aspect of the invention includes TAL repeats that contain one or more of the following: glycine at position 14, glycine or alanine at position 15, glutamine or lysine at position 17, alanine or asparagine at position 18, leucine or isoleucine at position 19, alanine, threonine, serine, or valine at position 21, valine, leucine, or isoleucine at position 22, leucine, lysine, or phenylalanine at position 25, alanine, valine or threonine at position 28, and leucine or phenylalanine at position 29.

The following amino acid sequence represents a TAL repeat composed of the most commonly identified amino acids found at each position: F S P E D I V A I A S $X_5$ $X_6$ G G A Q A L E A V L D L E P A L R E R G (SEQ ID NO: 62), where $X_5$ and $X_6$ are repeat variable diresidue sequences.

Additional variations containing common variations of amino acids are as follows:

(SEQ ID NO: 63)
L S P E D I V K I A G $X_5$ $X_6$ G G K Q A L Q A V L E
L E P V L C E R G, where $X_5$ and $X_6$ are repeat variable diresidue sequences at positions 12 and 13, L T T E Q I V A M A S $X_5$ $X_6$ G G A K A L E A V L D L E P A L R E R H G (SEQ ID NO: 64), where $X_5$ and $X_6$ are repeat variable diresidue sequences at positions 12 and 13, F S P E D I V A I A S $X_5$ $X_6$ G G A Q A L E A V L D L E P A L R E R H G E (SEQ ID NO: 65), where $X_5$ and $X_6$ are repeat variable diresidue sequences at positions 12 and 13, or F T P E D I V K I A G $X_5$ $X_6$ G G K Q A L E A V L D L E P V L R E R G (SEQ ID NO: 66), where $X_5$ and $X_6$ are repeat variable diresidue sequences at positions 12 and 13.

In some instances, particular TAL repeats may be non-functional in the sense that these repeats do not recognize one or more base in a specific location in a nucleic acid molecule. As an example, consider the situation where a protein contains 15 TAL repeats and TAL repeats 1 through 8 and 10-15 recognize specific, ordered bases in a nucleic acid molecule. Further, assuming that the binding sequence for this protein is as follows: ATCGT AGCTG TTGAT (SEQ ID NO: 67). In an instance where TAL repeat number 9 recognizes no base, as long as structural properties of the TAL repeat region are maintained, the protein would be expected to still bind the 15 nucleotide recognition sequence. Further, so long as the recognition sequence is long enough, unless duplication events have occurred, the sequence will occur rarely in the genome.

The invention thus includes proteins which contain TAL repeats where a portion of the TAL repeats are non-functional in that they do not recognize one or more base in a specific location in a nucleic acid molecule, as well as nucleic acids which encode such proteins and methods for using such proteins and nucleic acids. In particular, the invention includes proteins which contain one or more (e.g., one, two, three, four, five, six, seven, eight, etc.) non-functional TAL repeats. Proteins of the invention may contain from about 1 to about 10, from about 1 to about 10, from about 2 to about 10, from about 3 to about 10, from about 4 to about 10, from about 1 to about 6, from about 1 to about 5, from about 1 to about 4, from about 2 to about 4, from about 2 to about 3, etc., non-functional TAL repeats.

The invention also includes proteins which contain TAL repeats which recognize more than one (e.g., one, two, three, four, five, six, seven, eight, etc.) nucleotide sequence. For purposes of illustration, a single TAL repeat regions may be designed which recognizes each of the following nucleotide sequences: ATCGN ANCNG TTGAT (SEQ ID NO: 68), where N is any base. A single TAL repeat may be designed where repeat numbers 5, 7, and 9 are not specific for any base but do not disrupt the ability of a protein containing these non-functional repeats from binding the nucleotide sequence.

Non-functionality of a TAL repeat may be conferred by the RVD sequence of flanking amino acid sequences. For example, the RVD may not recognize a base. Also, one or both regions flanking the RVD may have a secondary structure which renders the TAL repeat non-functional.

The invention further includes methods for using one or more proteins which contain TAL repeats for interacting with multiple locations in a cellular genome. One application advantage of a TAL repeat containing protein with "loose" structure recognition is that proteins can be designed which bind to more than one location in a genome. In some instances, these locations may be engineered to contain a recognition sequence, the recognition sequences may be naturally present in the genome, or a combination of engineered and naturally occurring sequences may be used. In particular, the invention includes methods comprising (1) engineering a cell to contain a sequence at a specific genomic location which is recognized by a TAL repeat and (2) and introducing into or expressing within the cell a protein containing the TAL repeat wherein the TAL repeat recognizes both the sequence introduced into the cellular genome and a sequence which occurs naturally within the genome.

The invention includes proteins which contain the above sequences and variations thereof, for example, as indicated herein, as well as methods for designing, screening, and producing such proteins, further including nucleic acid molecules which encode such proteins.

TAL Truncations.

Naturally occurring TAL effectors from bacteria have been identified. In many instances, these proteins are believed to have functional activity in plant cells. It has been found that modification of naturally occurring TAL effectors can alter TAL effector fusion activities, especially activity in various types of cells. As an example, it has been shown that by using truncated flanking regions of naturally occurring TAL effectors, TAL effectors fusion proteins can be generated with altered activities within mammalian cells (see, e.g., PCT Publication WO 2011/146121, the disclosure of which is incorporated herein by reference, and Miller et al., Nat. Biotechnol., 29:143-148 (2011)). Thus, the invention provides TAL effectors and TAL effectors fusions with functional activities (e.g., sequence specific DNA binding activities, sequence specific nuclease activities, sequence specific transcription activation activities, etc.) in various cell types (e.g., plant cells, animal cells, mammalian cells, human cells, human liver cells, etc.).

One mechanism for alter functional activities of TAL effectors and TAL effectors fusions is by alteration of the amino and carboxyl regions which flank the TAL repeats. In certain embodiments, either of the amino flanking region or the carboxyl flanking region are altered. In additional embodiments, both the amino flanking region and the carboxyl flaking region are altered. In many instances, the TAL effectors and TAL effectors fusions will be altered in a manner so as to provide higher functional activities in a particular cell type.

Using the Hax3 amino acid sequence shown in FIG. 3A as a point of reference, specific alterations to the amino flanking region of the TAL repeat include the deletions up to amino acids 10, 25, 50, 65, 75, 90, 110, 115, 148, 152, 161, 175, 182, 195, 202, etc. up to the beginning of the TAL repeat region. In some embodiments, amino flanking regions may be from about 10 to about 400 amino acids, from about 50 to about 400 amino acids, from about 100 to about 400 amino acids, from about 150 to about 400 amino acids, from about 152 to about 400 amino acids, from about 200 to about 400 amino acids, from about 10 to about 300 amino acids, from about 10 to about 288 amino acids, from about 10 to about 200 amino acids, from about 10 to about 100 amino acids, from about 10 to about 75 amino acids, from about 10 to about 50 amino acids, from about 50 to about 300 amino acids, from about 50 to about 200 amino acids, from about 90 to about 300 amino acids, from about 90 to about 200 amino acids, from about 100 to about 300 amino acids, from about 100 to about 200 amino acids, etc., in length.

By "carboxyl flanking region" and "amino flanking region", when used in the context of TAL repeats, is meant either naturally occurring flanking regions or derivatives thereof. A "derivative", as used with respect to TAL flanking regions refers to truncations of naturally occurring flanking regions and amino acid segments of at least 20 amino acids which share at least 90% amino acid sequence identity with a naturally occurring TAL flanking region from a species in either of the following genera: *Xathamonas* or *Ralstonia*. Thus, carboxyl and amino flanking regions include truncations and will generally include at least 10 amino acids of a naturally occurring TAL effector (e.g., Hax3) flanking region. Heterologous amino acid segments not normally associated with natural TAL effectors (e.g., a V5 epitope) do not fall within the scope of carboxyl and amino flanking regions. Thus, as an example, amino acid segments 1, 2, 6 and 7 in FIG. 3B are not carboxyl and amino flanking regions as the terms are used with respect to a TAL repeat.

In some instances, TAL effectors and TAL effector fusions of the invention will contain one or more of the sequences set out in TABLE 8 and/or not one or more of the sequences set out in TABLE 9.

TABLE 8

| | |
|---|---|
| AHIVALSQHPAALGTVAV | SEQ ID NO: 8 |
| RNALTGAPLN | SEQ ID NO: 9 |
| DTGQLLKIAKRGGVTAV | SEQ ID NO: 10 |
| AGELRGPPLQLDTGQLL | SEQ ID NO: 11 |
| KIAKRGGVTAVEAVHA | SEQ ID NO: 12 |

TABLE 9

| | |
|---|---|
| VDLRTLGYSQQQQ | SEQ ID NO: 13 |
| VDLCTLGYSQQQQ | SEQ ID NO: 14 |
| EALVGHGFTHAHI | SEQ ID NO: 15 |
| SQQQQEKIKPKVR | SEQ ID NO: 16 |
| STVAQHHEALVGH | SEQ ID NO: 17 |

Again, using the Hax3 amino acid sequence shown in FIG. 3A as a point of reference, specific alterations to the carboxyl flanking region of the TAL repeat include the deletions up to amino acids 10, 25, 50, 65, 75, 90, 110, 115, 148, 152, 161, 175, 182, 195, 202, 250, etc. from the end of the TAL repeat region. In some embodiments, carboxyl flanking regions may be from about 10 to about 400 amino acids, from about 50 to about 400 amino acids, from about 100 to about 400 amino acids, from about 150 to about 400 amino acids, from about 152 to about 400 amino acids, from about 200 to about 400 amino acids, from about 10 to about 300 amino acids, from about 10 to about 282 amino acids, from about 10 to about 200 amino acids, from about 10 to about 100 amino acids, from about 10 to about 75 amino acids, from about 10 to about 50 amino acids, from about 50 to about 300 amino acids, from about 50 to about 200 amino acids, from about 90 to about 300 amino acids, from about 90 to about 200 amino acids, from about 100 to about 300 amino acids, from about 100 to about 200 amino acids, etc., in length.

In some instances, TAL effectors and TAL effectors fusions of the invention will contain one or more of the sequences set out in TABLE 10 and/or not one or more of the sequences set out in TABLE 11.

TABLE 10

| | |
|---|---|
| ALTNDHLVALACLG | SEQ ID NO: 18 |
| GRPALDAVKKGLPHAP | SEQ ID NO: 19 |
| QLFRRVGVTE | SEQ ID NO: 20 |
| NRRIPERTSH | SEQ ID NO: 21 |
| VRVPEQRDALH | SEQ ID NO: 22 |

TABLE 11

| | |
|---|---|
| ADDFPAFNEEE | SEQ ID NO: 23 |
| LAWLMELLPQ | SEQ ID NO: 24 |
| LHAFADSLERDL | SEQ ID NO: 25 |
| DAPSPMHEGDQT | SEQ ID NO: 26 |
| GTLPPASQRW | SEQ ID NO: 27 |

The total size of TAL effector flanking regions (i.e., amino terminal and carboxyl terminal combined) may be in the ranges of from about 50 to about 1,000 amino acids, from about 100 to about 1,000 amino acids, from about 150 to about 1,000 amino acids, from about 200 to about 1,000 amino acids, from about 300 to about 1,000 amino acids, from about 100 to about 700 amino acids, from about 100 to about 500 amino acids, from about 150 to about 800 amino acids, from about 150 to about 500 amino acids, etc., amino acids. The amino flanking region and the carboxyl flanking region may be of about the same size or of different sizes. For example, either of flanking regions may be comprised of amino acids in a ratio of from 1:1 about to 3:1, from 1:1 about to 4:1, from 1:1 about to 2:1, from 1:1 about to 5:1, from 1:1 about to 6:1, etc., as compared to the other flanking region. As an example, if a hypothetical TAL effector has a 1:3 ratio of amino acids in the amino flanking region and the larger flanking region is the amino flanking region with 150 amino acid, then the carboxyl flanking region is 50 amino acids in length.

Flanking sequences may or may not be linked to polypeptide segments which have additional functional activities (e.g., heterologous functional activities) and/or elements (e.g., an affinity tag such as a V5 epitope).

TAL effector and TAL effector fusions may also be characterized by their properties (e.g., the ability to bind nucleic acid, an enzymatic activity, etc.). Further, activities may be measured in cells or outside of cells. In addition, when activities are measured intracellularly, these activities may vary with the type of cell. The invention provides TAL effectors and TAL effector fusion with specific functional activity characteristics. In many instances, such activities and activity levels will be functional characteristics of TAL proteins and, thus, will be a feature of these TAL protein compositions of matter.

Qualitative and Quantitative TAL Binding Assays

Extracellular TAL effector binding activity may be assessed by any number of means. TAL effector binding assays may be qualitative or quantitative. In a qualitative assay, TAL effector binding activity would normally be measured as either present or absent. In quantitative and semi-quantitative assays, the amount of binding is measured. Most assays used would be quantitative to some extent because such assays better discriminate between non-specific and specific binding. Also, qualitative binding assays allow for the identification of binding molecules with specific binding affinities. Such assays also allow for comparative assessment of binding activity. Usually, a standard is used to set a baseline, with weaker binder exhibiting lower binding activity and stringent binders exhibiting higher binding activity.

Figure 4A:
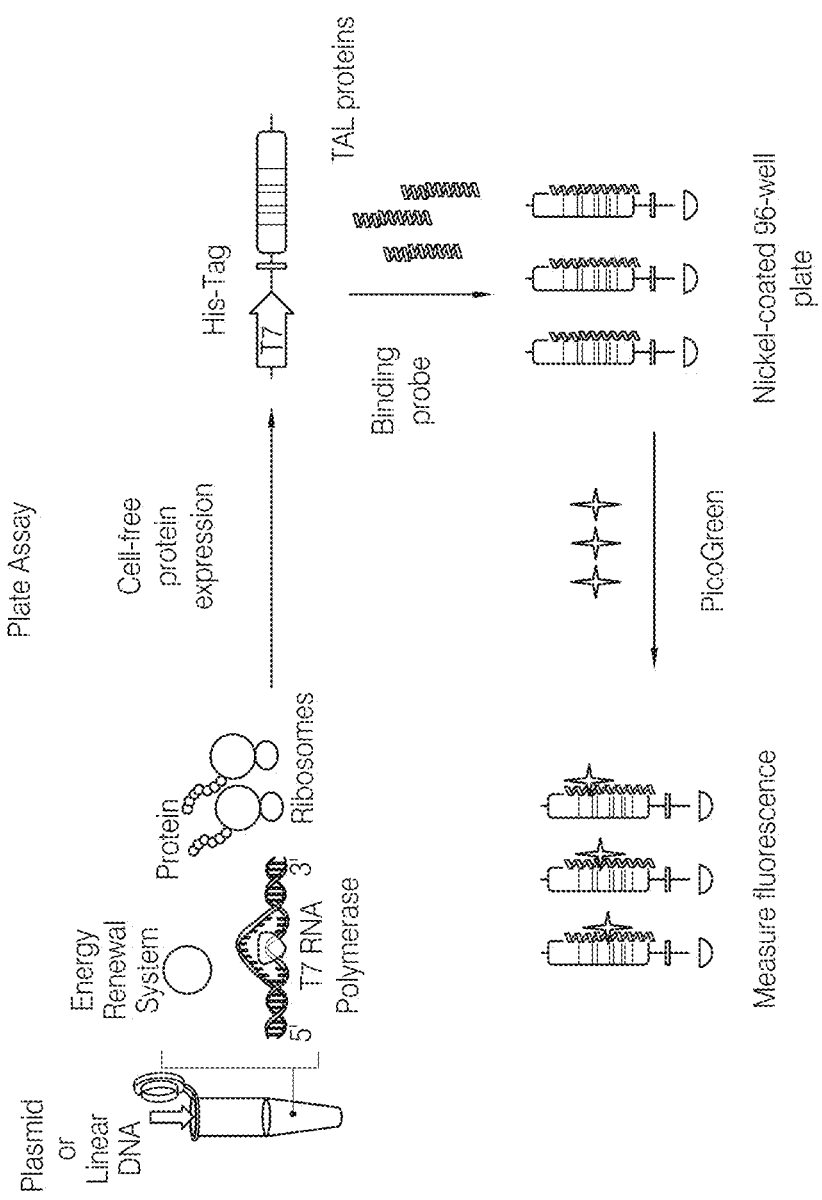
FIG. 4A to 4F show examples of TAL-binding assays suitable for evaluation of TAL binding specificity in vitro.
Figure 4B:
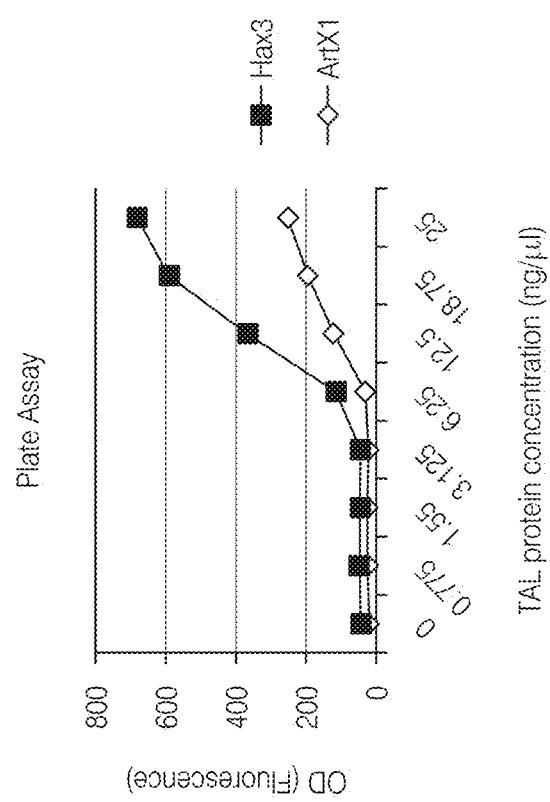
Figure 4C:
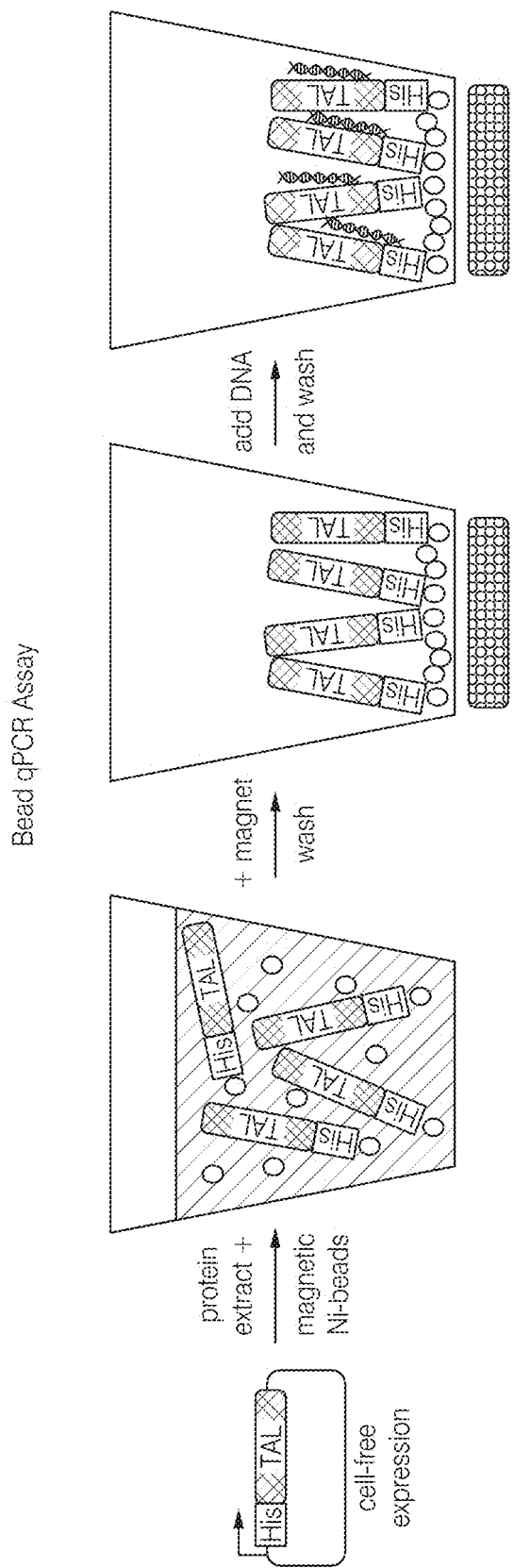
Figure 4D:
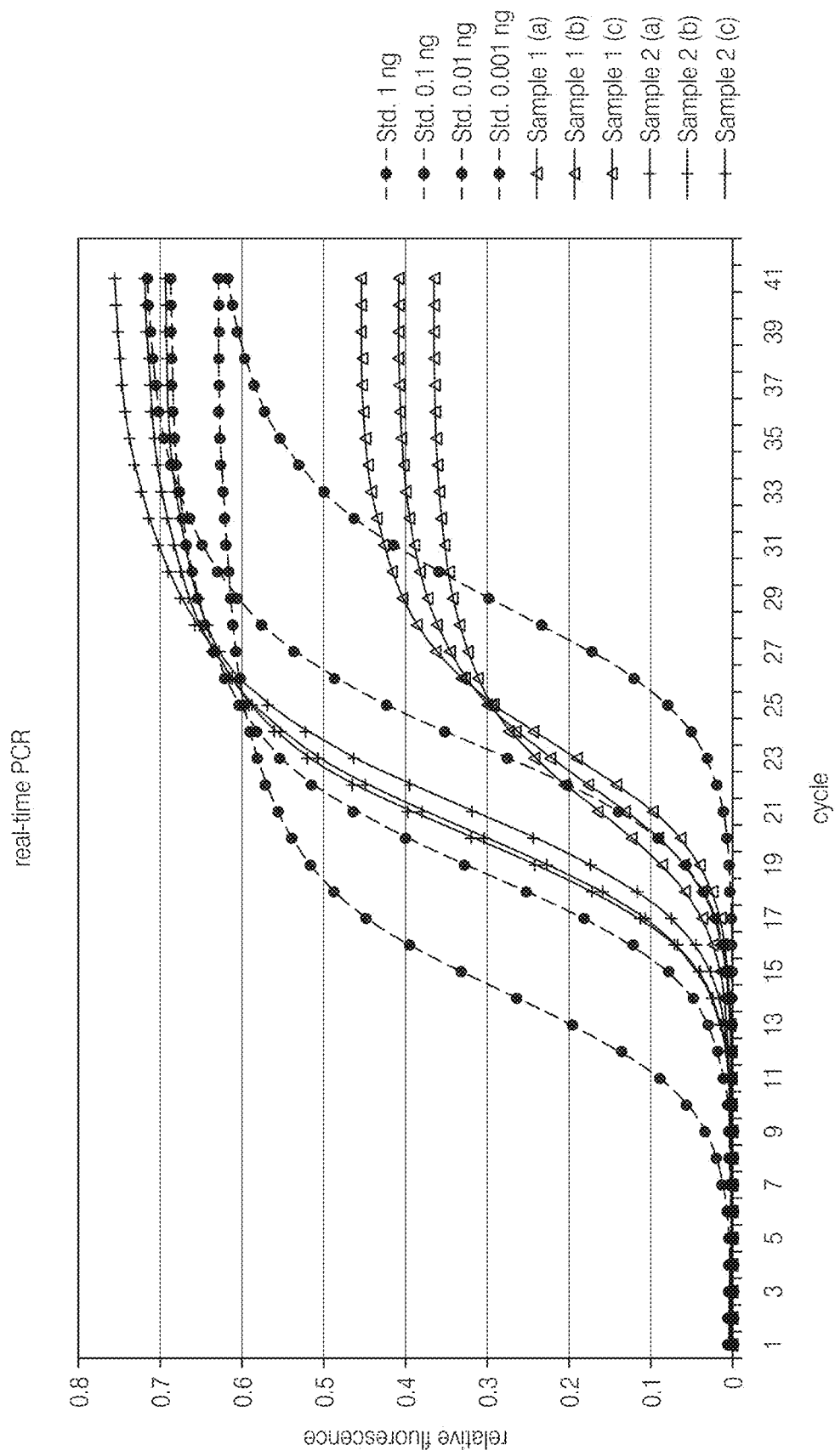

One type of qualitative binding assay is set out in Example 2 and FIGS. 4A and 4C.

The in vitro binding assay is sensitive, fast, easy to perform and can be applied to any TAL protein to demonstrate TAL binding specificity and. For this purpose, the TAL protein may be fused with a purification or detection tag (e.g., V5 epitope, c-myc, hemagglutinin (HA), FLAG™, polyhistidine (His), glutathione-S-transferase (GST), maltose binding protein (MBP)) and expressed, e.g., in a cell free system.

Efficient in vitro cell-free expression systems suitable for use in the assay without limitation are, e.g., an *E. coli* S30 fraction, a Rabbit Reticulocyte lysate, a wheat germ extract, a human cell extract or another expression system known in the art. A well known prokaryotic in vitro translation system is the *E. coli* crude extract (30S) where endogenous mRNA is removed by run-off translation and subsequent degradation. The *E. coli* system comprises user friendly translation apparatus and allows for convenient control of initiation.

A commonly used eukaryotic cell-free expression system is the rabbit reticulocyte lysate. Reticulocytes are immature red blood cells specialized for haemoglobin synthesis (Hb is 90% of protein content) lacking nuclei but comprising a complete translation machinery. Endogenous globin mRNA may be removed by treatment with $Ca^{2+-}$ dependent micrococcal nuclease, which is then inactivated by EGTA-chelation of $Ca^{2+-}$. Exogenous proteins are synthesized at a rate close to that observed in intact reticulocytes. Both capped (eukaryotic) and uncapped (viral) RNA are translated efficiently in this system. Kozak consensus and polyA signal are generally provided on the RNA. This system allows for synthesis of mainly full-length products.

Another common cell-free expression system which is a convenient alternative to rabbit reticulocyte lysate is the wheat germ extract, a system with low levels of endogenous mRNA and thus, low background which allows for high level synthesis of exogenous proteins of mammalian, viral or plant origin.

The obtained protein extract containing the TAL protein is added to a solid support, such as, e.g., a coated plate or coated beads. Two different embodiments of such assay are illustrated in FIGS. 4A and 4C. In some embodiments, the TAL protein is a His-tagged protein and is captured on a Nickel-coated support. However, also other suitable systems known in the art can be used to capture tagged proteins onto solid supports. One further example is the streptavidin-biotin system or the FlAsH system (Life Technologies Corp, Carlsbad) where proteins containing the tetracysteine motif Cys-Cys-Pro-Gly-Cys-Cys (SEQ ID NO: 106) are specifically bound by FlAsH or ReAsH arsenic reagents. In one embodiment, the TAL protein carries an N-terminal or C-terminal His-tag and is captured on Nickel-coated plates or Nickel-coated beads. The unbound protein is washed away and double stranded DNA targets ("binding probe") containing the predicted target site are then incubated with the bound protein. In a parallel reaction unrelated control DNA may be used. The DNA incubation may occur either prior to or after the protein binding step. Following incubation with binding probes the solid support may be washed again and the complexes are further incubated with a labeling dye such as e.g., an intercalating agent. Different reagents suitable for said purpose are known in the art and may include, e.g., PicoGreen®, YOPRO, SYBR® Green, Ethidium bromide (EthBr), EnhanCE or others. The labeled complexes may then be analyzed by measuring fluorescence or may be subject to real-time PCR analysis as, e.g., illustrated in FIG. 4B.

Thus, the invention relates, in part, to a TAL binding assay wherein the assay includes at least the following steps: (i) expression of a tagged TAL protein, (ii) binding of the TAL protein to a solid support, (iii) incubating the TAL protein with a DNA probe, (iv) incubating the complex with an intercalating fluorescent dye, and (v) detecting the bound DNA. Step (i) of the binding assay may further be performed in a cell-free expression system. In one embodiment, the binding of TAL protein in step (ii) is mediated by a protein tag such as a His-tag and the solid support may, e.g., be a Nickel-coated plate or Nickel-coated beads. In some instances, step (iii) may precede step (ii). In another embodiment, washing steps are performed after steps (ii) and/or (iii) and/or (iv). Furthermore the invention relates to a TAL binding kit comprising at least the following components: (i) a customized TAL expression vector, (ii) a solid support for TAL protein binding, (iii) one or more buffer systems, (iv) a specific binding probe, (v), an unspecific binding probe, (vii) an intercalating fluorescent dye.

The TAL binding kit may further comprise an extract for cell-free protein expression. Furthermore the customized TAL expression vector may comprise a sequence encoding a protein tag (e.g., a His-tag) to allow for expression of a tagged TAL protein. In another embodiment the TAL binding kit may further comprise one or more binding buffer and/or washing buffer systems.

TAL binding assays can be used to rapidly test TAL nuclease activity in vitro using crude TAL nuclease protein mixtures expressed in a cell free system. Qualitative assays essentially test parameters, such as the mechanics of target recognition, spacing, and cleavage of a synthetic linear template. In certain instances, it may be desired to further adjust the binding assay by making it more quantitative to allow a better approximation of enzyme kinetics which supports prediction of TAL nuclease activity at specific genomic loci in cells. Assignment of specific activity of a particular TAL nuclease pair to its synthetic target would allow prediction of relative activity in a cellular context may also be desirable. In an initial step, the concentration of TAL nuclease in a cell free expression mix (as described above) is quantified. This information may then used to develop a linear standard curve of activity from which enzyme kinetic data can be generated. Several TAL nuclease pairs may be evaluated an assigned specific activity values which are then compared to locus specific cleavage in cells as measured by a mismatch repair endonuclease assay (as described in detail elsewhere herein). Combining the information obtained from both analyses allows for a clear correlation between TAL nuclease pair specific activity in vitro and locus modulation efficiency in a cell under a controlled set of conditions. Thus the invention relates in part to a quantifiable in vitro assay to predict TAL nuclease activity in vivo. In one embodiment the quantifiable assay is characterized by at least the following steps:

1. Quantification of TAL nuclease concentration from a crude cell extract. Various methods may be used for quantifying TAL nuclease proteins from crude cell extract. For example, a TAL nuclease can be expressed with an affinity tag (e.g., a N-terminal or C-terminal tag, such as, e.g., a His-tag) and rapidly purified/enriched using an affinity purification resin (e.g., Ni-NTA or similar resins). Resulting protein fractions can then be quantified via standard protein assays. Alternatively, an in situ assay can be applied where the expressed TAL nuclease contains an N-terminal FlAsH tag. By adding the FlAsH reagent, fluorescence in a particular reaction can be read against a standard curve of purified, similarly tagged protein.

2. In vitro enzymatic determination of TAL nuclease activity. Following quantification of a panel of TAL nucleases, known amounts (e.g., equimolar amounts) of the respective TAL nuclease cleavage half domains may be incubated with a fixed molar amount of target template under standard conditions (at a given time, temperature, ionic strength). From such titrations, a range of concentrations is determined which yields a linear function of cleavage activity (% template cleaved) to TAL nuclease pair concentration. Based on the obtained cleavage-concentration ratio a unit measurement (e.g., 50% cleavage of x moles template equals 1 unit) may be assigned. At a suitable linear dynamic range (for instance one to two logs concentration), TAL nucleases can be expressed, quantified, normalized, and assayed at fixed concentration to measure specific activity (units/mass).

3. Correlation of TAL nuclease specific in vitro activity with endogenous locus modification activity in vivo. The panel of TAL nuclease pairs tested in step 1. may then ranked ordered according to the specific activities measured in vitro and subsequently tested in their specific host cell lines (as described elsewhere herein in detail). With the third step a relative correlation of determined in vitro activity to effective in vivo activity may be gained that allows for prediction of TAL nuclease functionality in the desired host.

A quantifiable assay according to the invention may be offered as part of a custom service by a TAL service provider. Alternatively, the assay may be offered in the context of a kit providing all reagents, protocols and analysis tools to allow expression, purification and measurements of one or more TAL nuclease pairs according to the three steps described above. Such kits may be aided by suitable programs or equations to perform required calculations (e.g., as specified under step 2.). There is a desire for quality testing of TAL nucleases prior to initiating potentially long and expensive experimental protocols in cells. Therefore, kits and assays according to the invention can help researchers to efficiently screen multiple TAL nuclease configurations to ensure their experimental protocol is based on the most optimal configuration.

Another binding assay is a sandwich assay employing a solid support with nucleic acid molecules with sequences recognized by a TAL effector. The TAL effector is then contacted with the solid support under conditions which allow for binding. After an incubation period, unbound TAL effector molecules are removed and the bound TAL effectors are quantified with a labeled anti-TAL effector antibody.

Figure 4E:
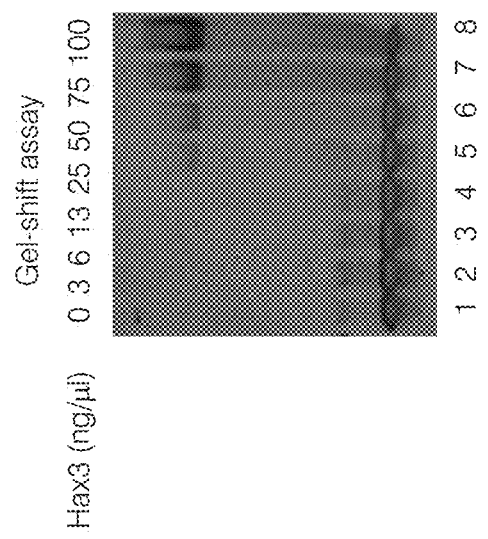

Another type of assays is referred to as a mobility shift DNA-binding assay (see, e.g., FIG. 4E). In one variation of this DNA-binding assay, nondenaturing polyacrylamide gel electrophoresis (PAGE) is used to provide simple, rapid, and sensitive detection of sequence-specific DNA-binding proteins.

For example, proteins that bind specifically to a labeled (e.g., end-labeled, nick translation labeled, etc.) DNA fragment retard the mobility of the fragment when the DNA fragment is subjected to electrophoresis. This results in discrete bands corresponding to the individual protein-DNA complexes and unbound DNA fragments. One advantage of this assay is that either purified proteins or extracts may be used. Also, data derived from such assays may be used to make quantitative determinations of the (1) affinity, (2) DNA binding protein concentration, (3) association rate constants, (4) dissociation rate constants, and (5) binding specificity of the subject DNA-binding proteins. Further, banding patterns may be used to identify bands which contain two TAL effectors bound to each nucleic acid molecule. This is so because such nucleic acid molecules will be retarded during PAGE more than nucleic acid molecules which are not bound by a TAL effector and nucleic acid molecules to which only one TAL effector is bound. TAL effectors which function as nucleases will often have functional activity upon dimerization of nuclease domains. Mobility shift assays allow for the measurement of TAL effectors with binding activities that allow for dimer formation.

Even protein-DNA complexes with short half-lives (<1 minute) are normally detected by mobility shift assays despite the fact that electrophoresis takes significant amounts of time. This is so because kinetic stability is typically not required for detection of protein-DNA complexes. Further, the sensitivity of these assays is often in the femtomole range.

Figure 4F:
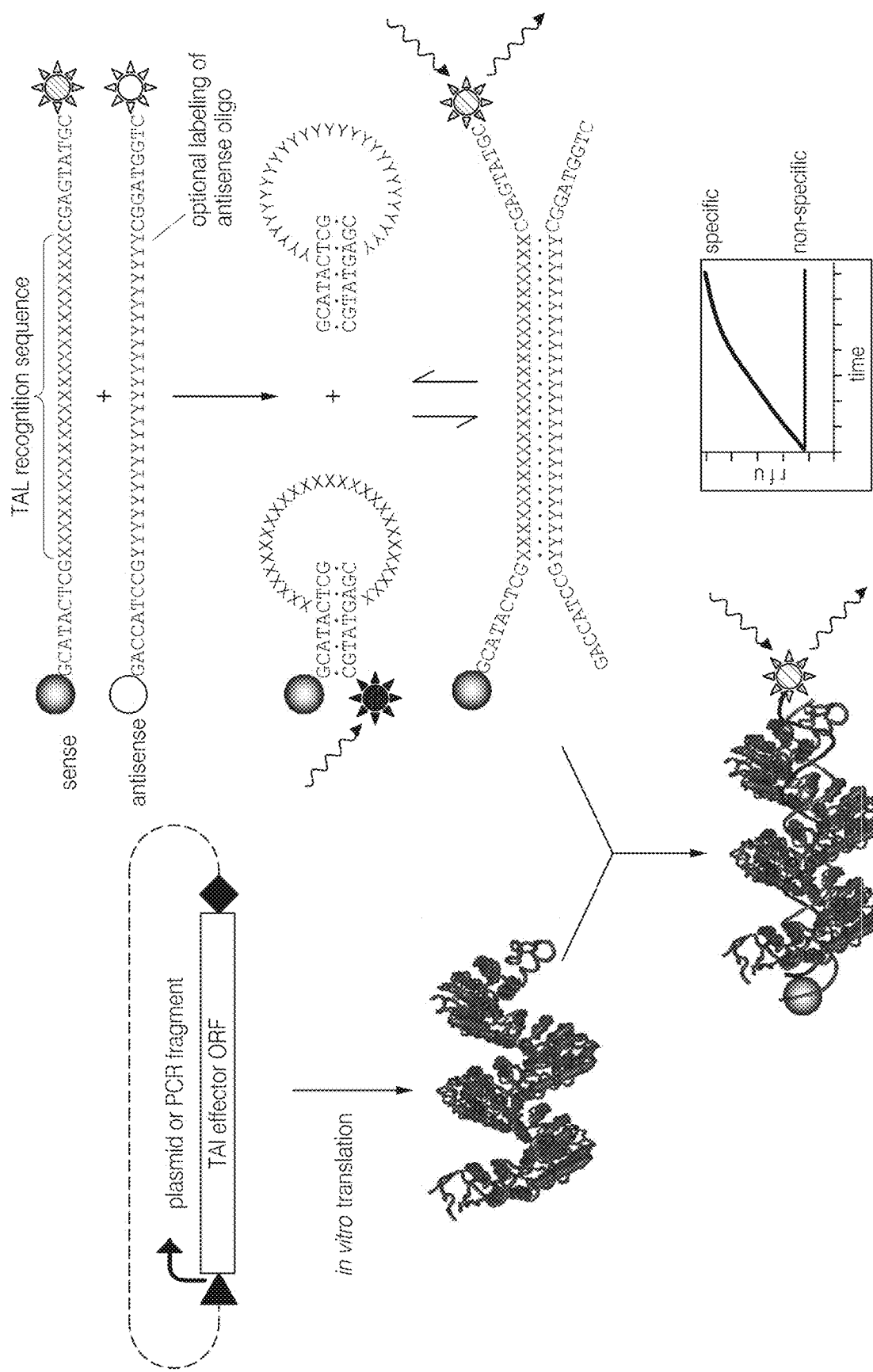

The invention further relates to another assay format that is suitable to confirm specific DNA binding of customized TAL effector proteins in vitro. The suggested system can be used in a high throughput setting and can be performed as "one-pot" reaction including in vitro transcription and/or translation of a given TAL effector protein followed by on-line detection of TAL DNA binding. One embodiment of this assay is illustrated in FIG. 4F. The open reading frame encoding a TAL effector that is to be tested may, e.g., be provided in a plasmid or as PCR fragment flanked by a promoter (e.g., a T7 promoter) or as RNA molecule and may be subject to in vitro transcription and/or in vitro translation, e.g., according to one of the methods described above (e.g. using wheat germ or *E. coli* lysate).

The in vitro translated TAL effector protein is incubated with a pair of oligonucleotides (sense & antisense) harboring a specific TAL binding site (see FIG. 4F). At least one of both oligonucleotides is designed to contain terminal sequences that are not required for TAL effector binding and are able to hybridize and form an intramolecular stem-loop structure. The TAL binding site may comprise at least between 4 and 10, between 8 and 15, between 12 and 20, between 15 and 26, between 20 and 30 nucleotides. For example, the TAL binding site may comprise 19 or 25 nucleotides. In some aspects the TAL binding site may start with a "T". In some instances the terminal sequences not required for TAL effector binding may comprise between 4 and 7, between 5 and 9, between 8 and 15, between 10 and 20 nucleotides. An optimal length of the terminal sequences may be determined depending on the length and/or composition of the TAL binding site, e.g., by computer-assisted means. In one embodiment, one end of the first oligonucleotide (e.g., sense) may be attached to a reporter fluorophore (e.g., FAM), whereas the other end may be attached to a non-fluorescent quencher moiety (e.g., BHQ-1).

Any fluorophore labels known in the art can be used in the invention and may be chosen according to their excitation and emission spectra. Suitable fluorophores include without limitation FAM, TET, CAL Fluor Gold 540, HEX, JOE, VIC, CAL Fluor Orange 560, Cy3, NED, Quasar 570, Oyster 556, TMR, CAL Fluor Red 590, ROX, LC red 610, CAL Fluor Red 610, Texas red, LC red 640, CAL Fluor Red 635, Cy5, LC red 670, Quasar 670, Oyster 645, LC red 705, Cy5.5 etc. For contact quenching any non-fluorescent quencher can serve as acceptor of energy from the fluorophore. Quencher molecules that can be used in the invention include without limitation DDQ-I, Dabcyl, Eclipse, Iowa Black FQ, BHQ-1, QSY-7, BHQ-2, DDQ-II, Iowa Black RQ, QSY-21, BHQ-3, etc.

When the oligonucleotide forms a stem-loop the fluorophore and quencher moiety are brought into close proximity, allowing energy from the fluorophore to be transferred directly to the quencher through contact quenching. This molecular beacon will initially be in equilibrium between its closed stem-loop conformation that allows for quenching of the signal and an open state where the stem-loop structure dissociates thereby separating the fluorophore and the quencher from each other. In the open conformation sense and antisense oligonucleotides hybridize to form a double strand structure that allows for signaling of the free fluorophore. With an increasing amount of TAL effector protein binding to the oligonucleotide pair the open state confirmation will be stabilized and dominate in the population which leads to a measurable signal increase over time.

Thus in one aspect, the invention relates to an assay for analysis of TAL effector binding wherein the assay contains at least (i) a TAL effector protein, (ii) a first oligonucleotide that contains a TAL binding site and terminal sequences capable of forming a stem-loop structure, wherein one end of the oligonucleotide is associated with a fluorophore molecule and the other end of the oligonucleotide is associated with a quenching molecule, (iii) a second oligonucleotide with a sequence that is capable of annealing to said first oligonucleotide, wherein a measurable signal is obtained when at least a portion of the first and second oligonucleotides are annealed, and wherein binding of the TAL effector protein to the TAL binding site favors annealing of the first and second oligonucleotides.

As negative control, a parallel binding reaction with an unrelated pair of oligonucleotides may be performed. As the signal strength depends on the ratio of oligonucleotides present in a stem-loop or open conformation, the assay allows for quantitative evaluation of TAL effector binding. The method of the invention may also be performed with the following variations: In a first alternative embodiment, a quenching effect may be achieved in the open conformation when a fluorophore is attached, e.g., to the 3' end of the sense oligonucleotide and the quencher is attached to the 5' end of the antisense oligonucleotide (or vice versa). In this case TAL effector binding would lead to a decreasing signal. In another alternative embodiment, fluorescence resonance energy transfer (FRET) can be used to track oligonucleotide conformation. FRET is a distance-dependent interaction between the electronic excited states of two dye molecules in which excitation is transferred from a donor molecule to an acceptor molecule without emission of a photon. This interaction only occurs when donor and acceptor molecules are in close proximity.

Thus, the invention also relates to an assay for analysis of TAL effector binding wherein the assay contains at least (i) a TAL effector protein, (ii) a first oligonucleotide that contains a TAL binding site and terminal sequences capable of forming a stem-loop structure, wherein one terminal end of the oligonucleotide is associated with a first FRET molecule (donor or acceptor), (iii) a second oligonucleotide with a sequence that is capable of annealing to said first oligonucleotide, wherein one terminal end of the second oligonucleotide is associated with a second FRET molecule (donor if first FRET molecule is an acceptor and acceptor if first FRET molecule is a donor), wherein a measurable FRET signal is obtained when at least a portion of the first and second oligonucleotides are annealed, and wherein binding of the TAL effector protein to the TAL binding site favors annealing of the first and second oligonucleotides. In an alternative embodiment, FRET acceptor and donor molecules can be attached to both ends of one oligonucleotide. In this case TAL effector binding would lead to a decreasing FRET signal. For the design of annealing fluorescent oligonucleotides using FRET, fluorophore-quencher pairs that have sufficient spectral overlap should be chosen. Different donor/acceptor pairs known in the art can be used in this assay including, e.g., Fluorescein/Tetramethylrhodamine, IAEDANS/Fluorescein, EDANS/Dabcyl, Fluorescein/Fluorescein, BODIPY FL/BODIPY FL, Fluorescein/QSY 7, QSY 9 dyes etc. In most applications, the donor and acceptor dyes are different, in which case FRET can be detected by the appearance of sensitized fluorescence of the acceptor or by quenching of donor fluorescence. When the donor and acceptor are the same, FRET can be detected by the resulting fluorescence depolarization.

In certain instances, in vitro translation of the TAL effector protein may be observed real-time by using fluorescent reagents that are capable of interacting with the translated protein and change their fluorescent properties upon binding. Such fluorescent reagents may, e.g., include small molecules, interacting with a protein tag (such as, e.g., His-tag), fluorescently labeled aptamers or fluorophore/quencher or FRET systems coupled to antibodies, single chain antibodies or aptamers or anticalins which may bind to conserved domains of the TAL effector proteins. For example, the reagents may be designed to bind pairwise to adjacent loops in the TAL repeat domain which may lead to quenching/FRET signaling thereby changing the signal obtained in the unbound state.

Additional methods suitable for use in the practice of the invention for detecting the sequence-specific binding of proteins to nucleic acids, including nitrocellulose filter binding, DNaseI foot printing, methylation protection, and methylation interference.

In many instances it will be desirable to employ in vivo assays of TAL function. This will likely be so when, for example, one wishes to use a TAL effector or TAL effector fusion in a particular cell. In vivo assays may fall into two categories based upon either inhibition and activation.

Inhibition assays are useful for, for example, detecting intracellular TAL effector or TAL effector fusion binding activity. An inhibition assay may be designed in which a TAL effector binding site is located, for example, between a promoter and a reporter gene. The reporter may be regulatable of constitutive and TAL effector binding activity may be measured by the suppression of transcription (e.g., suppression of reporter protein or mRNA production). Further, differential measurement of transcriptional suppression may be used to assay the TAL binding strength (e.g., affinity of a TAL effector for a specific nucleotides sequence). Thus, the invention includes, in part, methods for screening the binding activity of TAL effectors, these methods comprising the following:

(a) generating nucleic acid molecules encoding a population of TAL effectors or TAL effector fusions with identical TAL repeats but differing in the amino flanking region and/or the carboxyl flanking region;

(b) introducing the nucleic acid molecules into cells (e.g., a mammalian cell such as 293, HeLa, CHO, etc., cells) containing a TAL effector binding site located between a promoter and a gene (e.g., a reporter gene) under conditions suitable for expression of the encoded TAL effectors or TAL effector fusions; and (c) comparing cellular expression levels of the gene either (i) in the same cells before or after TAL effector expression or (ii) in different cells which express the TAL effectors and do not express the TAL effectors.

An activation assay is one in which an activity of TAL effectors or TAL effector fusions other than nucleic acid binding activity is measured. One example is where nucleic acid molecules are generated encoding a population of TAL effector fusions wherein the fusion partner is a transcriptional activator (e.g., VP16, VP64, etc.) are screened to determine transcriptional activation activity of population members. Thus, the invention includes, in part, methods for screening TAL effector fusions for transcriptional activation activity, these method comprising:

(a) generating nucleic acid molecules encoding a population of TAL effector fusions with identical TAL repeats but differing in the amino flanking region and/or the carboxyl flanking region;

(b) introducing the nucleic acid molecules into cells (e.g., a mammalian cell such as 293, HeLa, CHO, etc., cells) containing a TAL effector binding site located between a promoter and a gene (e.g., a reporter gene) under conditions suitable for expression of the TAL effector fusions; and (c) comparing cellular expression levels of the gene either (i) in the same cells before or after TAL effector fusion expression or (ii) in different cells which express the TAL effector fusions and do not express the TAL effector fusions.

The population of TAL effector fusions may, e.g., be TAL effector fusions with modified or truncated N- and or/C-terminal flanking regions. Fully assembled TAL effector proteins comprising at least a central repeat domain and an amino- and carboxyl-terminal domain may comprise more than 800 amino acid residues. In some instances it may be beneficial to identify the minimal terminal ends required for TAL effector binding in order to reduce the size of engineered TAL effectors or large TAL effector fusions. TAL effectors with truncated N- and/or C-terminal ends have been demonstrated to be functional in the context of fusion proteins including the truncated TAL effector nucleases described in this document. One strategy to identify minimal functional N- and C-terminal domains of TAL effectors is described in Zhang et al. ("Efficient construction of sequence-specific TAL effectors for modulating mammalian transcription". Nat. Biotechnol. 2011 February; 29(2):149-53.). The authors used a program to predict the secondary structure of TAL N- and C-termini and introduced truncations at predicted loop regions. However, the development of novel engineered TAL effectors with tailored TAL repeats for any given DNA target sequence may require a more systematic approach to identify minimal and/or optimal N-terminal and C-terminal domains which support TAL binding activity.

Figure 5:
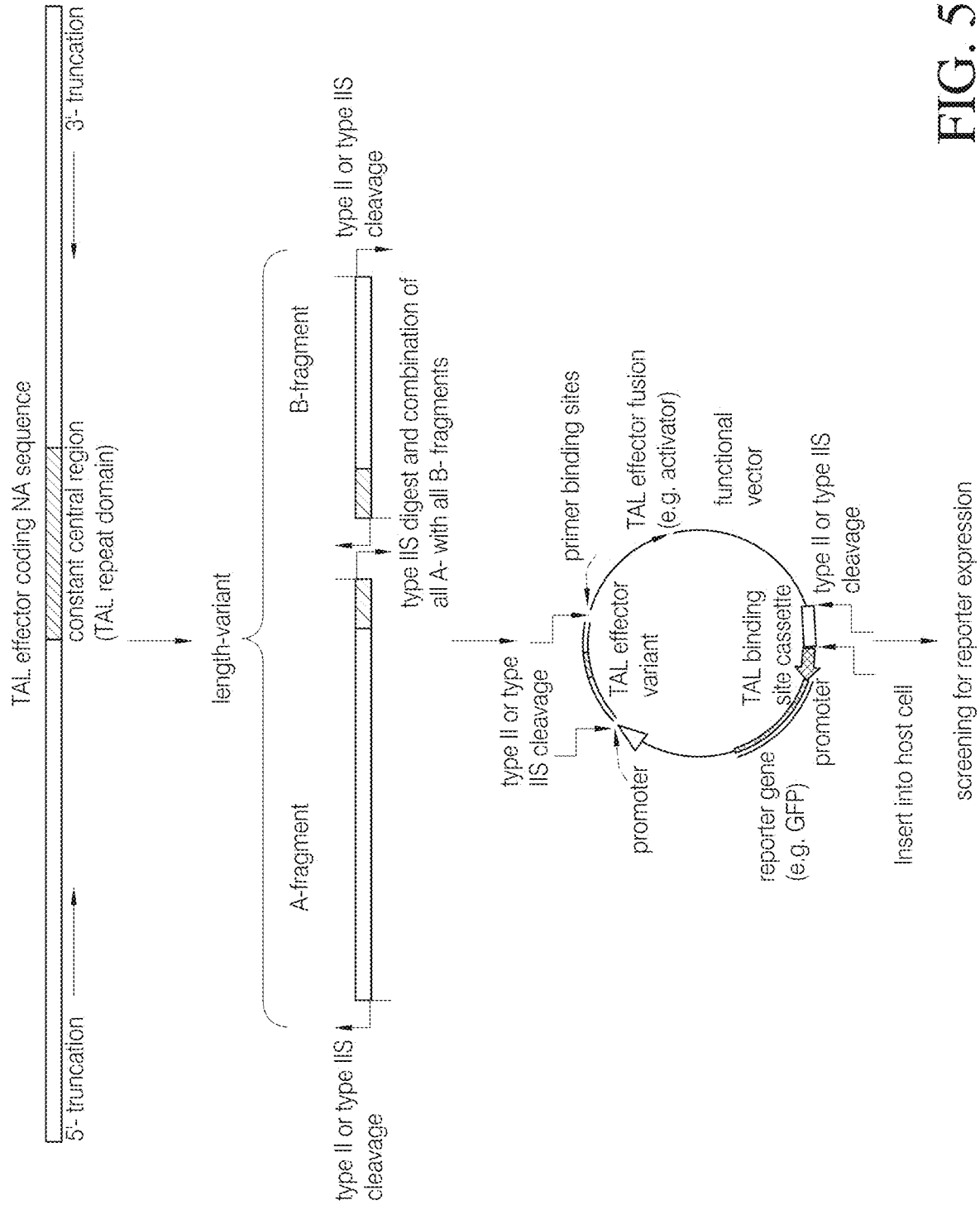
FIG. 5 shows a method and assay to identify truncated TAL effector variants with binding activity. A series of DNA fragments encoding truncated versions of TAL N- and C-termini are generated. Each 5' DNA fragment (A-fragment) contains a nucleic acid sequence encoding a truncated TAL N-terminus and the 5' moiety of the central repeat domain whereas each 3' fragment (B-fragment) contains a nucleic acid sequence encoding a truncated TAL C-terminus and the 3' moiety of the central repeat domain. The resulting length variants are equipped with terminal restriction sites and are combined in a cleavage-ligation reaction to obtain all possible combinations of A- and B-fragments. The obtained length variants are inserted into a linearized target vector downstream of a promoter allowing for expression of the variants in a host cell and upstream of a fusion domain (e.g., an activator domain) to obtain a TAL effector fusion protein. Furthermore, the target vector carries one or more specific TAL binding sites for the TAL effector variants associated with a reporter gene operatively linked with a promoter region. The resulting truncation library is then inserted into host cells allowing for expression of the various TAL effector truncations. Only the functional truncated variants will bind to the TAL binding site(s) in the vector and induce detectable reporter gene expression allowing to identify those cells carrying a functional truncated TAL effector. Selected host cells may be replicated and nucleic acid sequences of identified candidates can be obtained via sequencing of the 5' and 3' ends using specific primer binding sites in the vector flanking the TAL effector insertion site.

In one aspect the invention includes a strategy to identify functional TAL truncations from a truncation library. A library that contains all possible combinations of TAL N- and C-terminal truncations flanking a given central repeat domain can be obtained by a method comprising at least the following steps: (1) generating a series of A-fragments each encoding at least part of a TAL N-terminus and a 5' moiety of a TAL repeat domain; (2) generating a series of B-fragments each encoding at least part of a TAL C-terminus and a 3' moiety of a TAL repeat domain; (3) cleaving the plurality of A-fragments and B-fragments to obtain compatible overhangs that allow for (i) combination of any A-fragment with any B-fragment and (ii) directed insertion of the resulting combinations of A- and B-fragments into a target vector and (4) ligating the combinations of A- and B-fragments into said target vector to obtain a vector library. Optionally, the method may further comprise inserting the vector library into a host cell (see FIG. 5).

The series of A-fragments and B-fragments representing step-wise truncations of TAL N- and C-termini may be generated either by de novo gene synthesis as described elsewhere herein or may be obtained by template-dependent PCR. For example truncations of the N-terminus may be introduced using a series of primer pairs wherein a forward primer binds inside the N-terminus encoding region and a reverse primer binds within the central repeat domain coding region of a TAL effector template DNA. Step-wise truncations may occur amino acid-wise (every primer is shifted by one codon) or may be performed in larger steps (e.g., each primer is shifted by 5 to 10 or more amino acids). In one embodiment the A- and B-fragments are designed to contain type II or type IIS cleavage sites at the 5' and 3' ends. In one embodiment, the 3' ends of the A-fragments and the 5' ends of the B-fragments contain type IIS cleavage sites whereas the 5' ends of the A-fragments and the 3'ends of the B-fragments may contain either type II or type IIS cleavage sites. For example, when A- and B-fragments are generated by PCR, the cleavage sites may be introduced via terminal amplification primers. In some embodiments, the overhangs resulting from type IIS cleavage at the 3' ends of the A-fragments may be compatible with the overhangs resulting from type IIS cleavage at the 5' ends of the B-fragments but may not be compatible with the overhangs resulting from cleavage at the 5' ends of the A-fragments. Likewise, the overhangs resulting from type IIS cleavage at the 5' ends of the B-fragments may be compatible with the overhangs resulting from type IIS cleavage at the 3' ends of the A-fragments but may not be compatible with the overhangs resulting from cleavage at the 3' ends of the B-fragments. This strategy may be used to avoid combinations of an A-fragment with another A-fragment or of a B-fragment with another B-fragment thereby excluding nonsense combinations from the library.

The obtained library of A-fragments with B-fragments collectively referred to as "length variants" may be inserted into a target vector (e.g., a functional vector) under control of a promoter region that allows for expression in the target host. The vector may be designed to provide a coding sequence for a TAL effector fusion downstream of the inserted length variants so that a library of TAL effector fusion proteins is expressed. The fusion domain may, e.g., be an activator domain, a repressor domain, a nuclease domain or any other suitable domain. Furthermore, the vector may contain a reporter gene cassette in proximity to one or more TAL binding sites that can be bound by functional length variants of the TAL effector fusion proteins (see FIG. 5).

Thus the invention also relates to a vector containing at least the following elements: (i) a TAL effector insertion site for insertion of a TAL effector sequence flanked by type II or IIS cleavage sites, (ii) a promoter region upstream of the insertion site, (iii) a sequence encoding a TAL effector fusion domain downstream of the TAL effector insertion site, (iv) at least one selection marker, (v) one or more insertion sites for one or more copies of a TAL binding site flanked by type II or IIS cleavage sites, (vi) a reporter gene cassette composed of at least a promoter region and a reporter open reading frame, optionally, at least one primer binding site flanking the TAL effector insertion site. One or more copies of TAL binding sites may, e.g., be provided in the form of annealed oligonucleotides designed to have terminal overlaps that are compatible with the overhangs generated by type H or type IIS cleavage in the target vector. The aforementioned vector is not limited to the testing of truncated TAL effector proteins but can be used as binding reporter system, e.g., in a high throughput setting to validate binding of engineered TAL effector proteins to a predicted binding site in vivo. As reporter gene, any gene may be used that allows for identification of cells harbouring a functional TAL effector protein. Reporter genes that may be used in the vector system include without limitation gfp, rfp, luciferase or a resistance marker gene suitable for a given host as described elsewhere in this document.

In an alternative embodiment, TAL effector fusion variants may be provided in a first vector and the reporter gene expression cassette and the TAL binding site(s) may be provided in a second vector. Furthermore, the invention relates to a library of vectors wherein each vector carries a truncated variant of a TAL effector sequence.

The library of vectors containing the different length variants may be inserted into host cells to allow for expression of the TAL effector fusion proteins. Thus, in one aspect the invention also relates to a host cell library and the use thereof to identify functional TAL effector truncations. Suitable methods for host transformation or transfection are described elsewhere herein. In certain instances it may be desirable to stably transfect host cells with the library, e.g., by using integration systems that provide recombinases such as, e.g., Cre, Flp or PhiC31 to integrate one copy of a vector in a defined genomic region (see, e.g., FLP-IN™ or JUMP-IN™ from Life Technologies (Carlsbad, Calif.). In certain instances it may be advantageous use an inducible promoter for regulated TAL effector expression. Following expression of the TAL effector fusion library, only the functional truncated variants will bind to the target binding sites and modulate the expression of the reporter gene by the activity of the fusion domain. Detection of reporter gene activity can be used to identify host cells carrying a functional TAL effector fusion protein. In one embodiment the reporter gene may be a fluorescent gene such as, e.g., gfp or rfp and the effector fusion domain may be an activator domain (e.g., VP64).

The invention thus provides methods for integrating expression constructs (e.g., nucleic acid molecules which encode TAL effectors) into the genome of a cell. As noted above, integration systems which employ recombinases may be used in such methods. Other methods (e.g., homologous recombination may also be used).

Genome integration may be random or site specific. When random integration is employed, cells that have potentially integrated nucleic acid into their genome may be screened for nucleic acid expression (e.g., selectable marker expression, mRNA levels, etc.). Thus, insert expression levels may be sued to identify cells which have incorporated nucleic acid in a region of the genome which allows for suitable expression levels (e.g., regions of open chromatin structure in eukaryotic cells).

When site specific integration is used with the goal of expression of inserted nucleic acid, then generally it will be desirable to insert the nucleic acid in a site which allows for expression. Further, such sites vary with factors such as, for example, the organism, the cell type, and stage of development. Examples of site-specific integration sites which may be used include the human PPP1R12C (e.g., in the intronic region between exons 1 and 2), AAVS1 and CCR5 (e.g., in the region overlapping the intron between exons 2 and 3 and the exon 3 coding region) loci as described in more detail elsewhere herein.

The invention also provides cell lines which are designed for site specific integration of exogenous nucleic acid into their genomes. These cell lines may be contain one or more recombination or pseudo recombination site in their genome, Typically, such sites will be selected or structured in such a manner as to allow for insertion of nucleic acids (see, e.g., Chesnut et al., U.S. Patent Publication No. 2008/0216185 A1, the disclosure of which is incorporated herein by reference).

In some embodiments, recombination sites will be introduced into the genome. Such introduction may be site specific or random. Further, cell which have random acquired recombination sites may then be screened to determine whether one or more recombination sites have been introduced in a location suitable for a particular purpose (e.g., transcription of a coding sequence integrated at the locus). Site specific recombination sites may introduced specifically at locations known to be suitable for a particular purpose.

In additional embodiments, where integration of nucleic acid into specific regions of a genome is desired, sites with functional homology to site-specific recombination sites (pseudo recombination sites) can be identified and used. These sites may be used to target the insertion of nucleic acids to a desired region. Pseudo recombination sites which may be used for this purpose include, but are not limited to, those recognized by the recombinases phiC31, R4, phi80, P22, P2, 186, P4 and P1. A large number of genomes have been sequenced. These sequence data may be searched to identify pseudo recombination sites and determine whether they are potentially suitable for a particular purpose. Thus, the invention includes bioinformatic screening to identify pseudo recombination sites for site specific integration of nucleic acids into genomes.

In another embodiment the reporter gene may be a resistance gene and cells carrying a functional TAL effector fusion will survive under selective pressure. When a resistance marker gene is used as reporter it may be possible to select for better binders by increasing the selective pressure. Upon binding of a functional truncated TAL effector variant to the TAL binding site reporter expression (e.g., GFP) would be induced by binding of the activator domain to the upstream promoter region. The resulting green cells carrying functional truncated TAL effector variants can be easily selected and the truncated sequence can be identified by sequencing via flanking primer binding sites. At least one control vector should be included in the screening (e.g., containing a full-length or tested truncated variant) to ensure binding of the repeat domain to the predicted TAL binding site(s).

Reporter constructs suitable for use with the invention are described elsewhere herein. Further, such reporters may be used to isolate cells by, for example, fluorescent activated cell sorting (FACS) based upon expression activation level. In addition, nucleic acid molecule encoding TAL effectors and TAL effector fusions may then be isolated from cells after the cells have been screened for TAL activity. Thus, the methods include screening method for identifying functional activities of TAL effectors and TAL effector fusions and isolating nucleic acid molecules which encode these proteins. In particular, these methods include isolation methods which allow for the isolation of individual which have been shown to encode proteins having specific functional activities and/or specific levels of a particular functional activity.

TAL Nucleases.

TAL effectors may for example be fused with sequences encoding nuclease activities. For example, the TAL effector fusion-encoding nucleic acid sequences are sequences encoding a nuclease or a portion of a nuclease, typically a non-specific cleavage domain from a type IIS restriction nuclease such as FokI (Kim et al. (1996) *Proc. Natl. Acad. Sci. USA* 93:1156-1160). The FokI endonuclease was first isolated from the bacterium *Flavobacterium okeanokoites*. This type IIS nuclease has two separate domains, the N-terminal DNA binding domain and C-terminal DNA cleavage domain. The DNA binding domain functions for recognition of a non-palindromic sequence 5'-GGATG-3'/5'-CATCC-3' while the catalytic domain cleaves double-stranded DNA non-specifically at a fixed distance of 9 and 13 nucleotides downstream of the recognition site. FokI exists as an inactive monomer in solution and becomes an active dimer following the binding to its target DNA and in the presence of some divalent metals. As a functional complex, two molecules of FokI each binding to a double stranded DNA molecule dimerize through the DNA catalytic domain for the effective cleavage of DNA double strands. Thus, as noted below, TAL effector fusions employing enzymes such as FokI will typically be introduced into cells and expressed as pairs. In many instances, these pairs will bind different nucleotide sequences, spaced in a manner to allow for dimerization of the FokI fusion components.

Other useful nucleases may include, for example, HhaI, HindIII, NotI, BbvC1, EcoRI, BgII, and AlwI. The fact that some nucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers dimerize to create a functional enzyme. By requiring DNA binding to activate the nuclease, a highly site-specific restriction enzyme can be created. A sequence-specific TAL effector nuclease can recognize a particular sequence within a preselected target nucleotide sequence present in a host. Thus, in some embodiments, a target nucleotide sequence can be scanned for nuclease recognition sites, and a particular nuclease can be selected based on the target sequence. In other cases, a TAL effector nuclease can be engineered to target a particular cellular sequence. A nucleotide sequence encoding the desired TAL effector nuclease can be inserted into any suitable expression vector, and can be linked to one or more expression control sequences. For example, a nuclease coding sequence can be operably linked to a promoter sequence that will lead to constitutive expression of the nuclease in the species of plant to be transformed. Alternatively, a nuclease coding sequence can be operably linked to a promoter sequence that will lead to conditional expression (e.g., expression under certain nutritional conditions).

The cleavage domain portion of the fusion proteins disclosed herein can be obtained from any endo- or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. No. 5,487,994; as well as Li et al. ("Functional domains in Fok I restriction endonuclease") *Proc. Natl. Acad. Sci. USA* 89:4275-4279. Thus, in one embodiment, fusion proteins comprise the cleavage domain (or cleavage half-domain) from at least one Type IIS restriction enzyme.

Accordingly, for the purposes of the present disclosure, the portion of the FokI enzyme used in the disclosed fusion proteins is considered a cleavage half-domain. A cleavage domain or cleavage half-domain can be any portion of a protein that retains cleavage activity, or that retains the ability to multimerize (e.g., dimerize) to form a functional cleavage domain. Thus, for targeted double-stranded cleavage and/or targeted replacement of cellular sequences using TAL-FokI fusions, two fusion proteins, each comprising a FokI cleavage half-domain, can be used to reconstitute a catalytically active cleavage domain.

Multiple parameters may influence the catalytic activity of nuclease fusion proteins such as TAL effector FokI fusions.

For purposes of amino acid sequence reference, the FokI amino acid sequence found in GenBank accession number AAA24934 is used herein and set out below (SEQ ID NO: 69):

```
  1 MVSKIRTFGW VQNPGKFENL KRVVQVFDRN SKVHNEVKNI KIPTLVKESK IQKELVAIMN
 61 QHDLIYTYKE LVGTGTSIRS EAPCDAIIQA TIADQGNKKG YIDNWSSDGF LRWAHALGFI
```

```
121 EYINKSDSFV ITDVGLAYSK SADGSAIEKE ILIEAISSYP PAIRILTLLE DGQHLTKFDL

181 GKNLGFSGES GFTSLPEGIL LDTLANAMPK DKGEIRNNWE GSSDKYARMI GGWLDKLGLV

241 KQGKKEFIIP TLGKPDNKEF ISHAFKITGE GLKVLRRAKG STKFTRVPKR VYWEMLATNL

301 TDKEYVRTRR ALILEILIKA GSLKIEQIQD NLKKLGFDEV IETIENDIKG LINTGIFIEI

361 KGRFYQLKDH ILQFVIPNRG VTKQLVKSEL EEKKSELRHK LKYVPHEYIE LIEIARNSTQ

421 DRILEMKVME FFMKVYGYRG KHLGGSRKPD GAIYTVGSPI DYGVIVDTKA YSGGYNLPIG

481 QADEMQRYVE ENQTRNKHIN PNEWWKVYPS SVTEFKFLFV SGHFKGNYKA QLTRLNHITN

541 CNGAVLSVEE LLIGGEMIKA GTLTLEEVRR KFNNGEINF
```

FokI nuclease cleavage domains with increased cleavage activity consisting of two amino acid mutations S418P and K441E and referred to as "Sharkey" were generated employing a directed evolution strategy as described in Guo et al., (2010) ("Directed Evolution of an Enhanced and Highly Efficient FokI Cleavage Domain for Zinc Finger Nucleases"; *Journal of Molecular Biology* 400 (1): 96) and U.S. Pat. No. 8,034,598, the disclosure of which is included herein by reference. Other mutations were shown to improve dimer enzyme specificity or enzyme activity either alone or in combination. Some of the mutations resulting in modified FokI cleavage domain activity are without limitation: KKR (E490K, I538K, H537R), ELD (Q486E, I499L, N496D), RR (R487D, N496D, D483R, H537R). Thus the methods and compositions disclosed herein also relate in part to TAL effector fusions comprising an engineered FokI cleavage half-domain, wherein the engineered cleavage half-domain comprises a mutation in one or more wild-type amino acid residues 483, 486, 487, 490, 496, 499, 537, 538, or combinations thereof, and wherein the engineered cleavage half-domain forms an obligate heterodimer with a wild-type cleavage half-domain or a second engineered cleavage half-domain.

Furthermore, the invention relates in part to TAL effector nuclease fusion proteins and optimized sequences encoding such proteins. In particular the invention includes TAL effectors with codon-optimized nuclease sequences or nuclease cleavage domains such as those encoded by SEQ ID NOs: 1 to 3 (see FIG. 6A).

Additional restriction enzymes also contain separable binding and cleavage domains, and these are contemplated by the present disclosure. See, for example, Roberts et al. (2003) *Nucleic Acids Res.* 31:418-420. Examples of Type IIS Restriction Enzymes suitable for use with the invention include the following, many of which are Type IIS enzymes: AarI, BsrBI, SspD5I, AceIII, BsrDI, Sth132I, AciI, BstF5I, StsI, AloI, BtrI, TspDTI, BaeI, BtsI, TspGWI, Bbr7I, CdiI, Tth111iI, BbvI, CjePI, UbaPI, BbvII, DrdII, BsaI, BbvCI, EciI, BsmBI, BccI, Eco31I, Bce83I, Eco57I, BceAI, Eco57MI, BcefI, Esp3I, BcgI, FauI, BciVI, FinI, BfiI, FokI, BinI, GdiII, BmgI, GsuI, Bpu10I, HgaI, BsaXI, Hin4II, BsbI, HphI, BscAI, Ksp632I, BscGI, MboII, BseRI, MlyI, BseYI, MmeI, BsiI, MnlI, BsmI, Pfl1108I, BsmAI, PleI, BsmFI, PpiI, Bsp24I, PsrI, BspGI, RleAI, BspMI, SapI, BspNCI, BsrI, or SimI.

The disclosed TAL effectors with nuclease function can be used to cleave DNA at a region of interest in cellular chromatin (e.g., at a desired or predetermined site in a genome, for example, in a gene, either mutant or wild-type). For such targeted DNA cleavage, TAL repeats are engineered to bind a target site at or near the predetermined cleavage site, and a fusion protein comprising the engineered TAL binding domain and a cleavage domain is expressed in a cell. Upon binding of the TAL repeat to the target site, the DNA is typically cleaved near the target site by the cleavage domain. For targeted cleavage using a TAL effector nuclease fusion protein, the binding site can encompass the cleavage site, or the near edge of the binding site can be 1, 2, 3, 4, 5, 6, 10, 25, 50 or more nucleotides (or any integral value between 1 and 50 nucleotides) from the cleavage site. The exact location of the binding site, with respect to the cleavage site, will depend upon the particular cleavage domain, and the length of any linker. Thus, the methods described herein can employ an engineered TAL effector nuclease fusion. In these cases, the TAL effector fusion is engineered to bind to a target sequence, at or near which cleavage is desired. Once introduced into a cell the TAL effector fusion binds to the target sequence and cleaves at or near the target sequence.

The exact site of cleavage depends on the nature of the cleavage domain and/or the presence and/or nature of linker sequences between the binding and cleavage domains. Optimal levels of cleavage can also depend on both the distance between the binding sites of the two fusion proteins (See, for example, Smith et al. (2000) *Nucleic Acids Res.* 28:3361-3369; Bibikova et al. (2001) *Mol. Cell. Biol.* 21:289-297) and the length of the linker in each fusion protein. In certain embodiments, the cleavage domain comprises two cleavage half-domains, both of which are part of a single polypeptide comprising a TAL cassette, a first cleavage half-domain and a second cleavage half-domain. The cleavage half-domains can have the same amino acid sequence or different amino acid sequences, so long as they function to cleave the DNA.

Further, the TAL repeats bind to target sequences which are typically disposed in such a way that, upon binding of the TAL effector fusion proteins, the two cleavage half-domains are presented in a spatial orientation to each other that allows reconstitution of a cleavage domain (e.g., by dimerization of the half-domains), thereby positioning the half-domains relative to each other to form a functional cleavage domain, resulting in cleavage of cellular chromatin in a region of interest. Generally, cleavage by the reconstituted cleavage domain occurs at a site located between the two target sequences.

The two fusion proteins can bind in the region of interest in the same or opposite polarity, and their binding sites (i.e., target sites) can be separated by any number of nucleotides, e.g., from 0 to 200 nucleotides or any integral value in between. In certain embodiments, the binding sites for two fusion proteins, each comprising a TAL effector and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native FokI results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for many applications, including targeted recombination and targeted mutagenesis cleavage within a range of nucleotides is generally sufficient, and cleavage between particular base pairs is not required.

TAL effector fusion(s) can be delivered to cells as polypeptides and/or polynucleotides as described elsewhere herein. For example, two polynucleotides, each comprising sequences encoding one of the aforementioned polypeptides, can be introduced into a cell. Alternatively, a single polynucleotide comprising sequences encoding both fusion polypeptides may be introduced into a cell, for example using one of the vectors shown in FIG. 22.

TAL Activators.

Figure 18A:
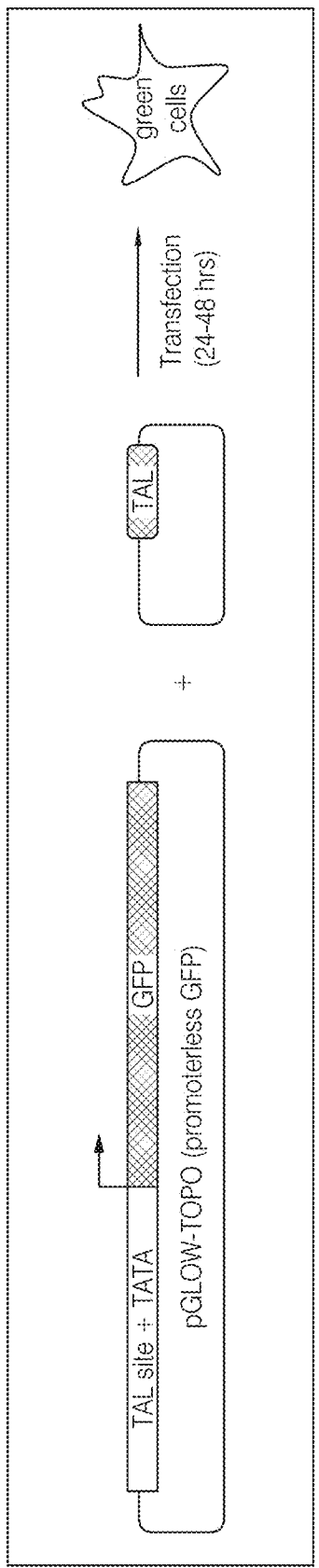
FIG. 18A shows a TAL effector mammalian transient activation assay designed to assess the ability of a custom TAL activator to bind and stimulate transcription at a target site tissue culture cells. pGLOW-TOPO® is a promoterless GFP vector that expresses very low or undetectable levels of GFP when introduced into tissue culture cells. A specific TAL binding site is fused in front of a minimal promoter (e.g., by PCR), and the resulting product is then topoisomerase cloned into the GFP vector. Co-transfection of this plasmid and the custom TAL activator leads to expression of GFP, which can be detected by various methods such as fluorescence microscopy or flow cytometry.
Figure 18B:
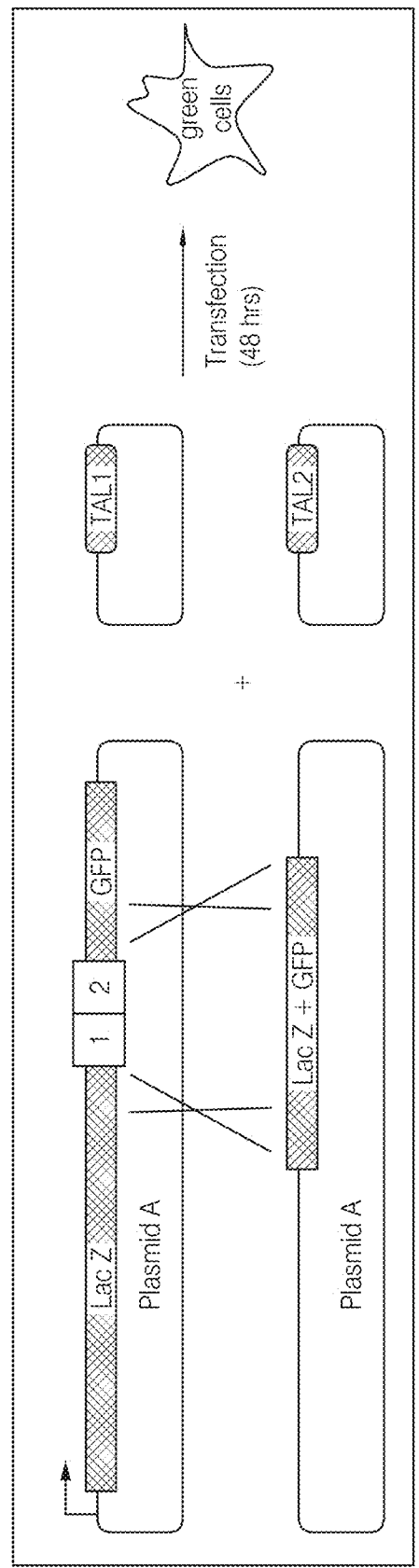
FIG. 18B shows a transient cleavage and repair assay designed to assess the ability of a custom TAL nuclease pair to bind and cleave a plasmid bearing a specific target site in tissue culture cells. Plasmid A is a cleavage target that fuses LacZ, two custom TAL nuclease binding sites separated by a spacer of approximately 16 bp, and a GFP fragment containing a 5' truncation sufficient to render the expressed protein non-functional. Plasmids C and D express custom TAL nucleases 1 and 2 that bind to DNA sequences 1 and 2 on Plasmid A. The nuclease domains of each TAL nuclease then dimerize and generate a double strand DNA break on Plasmid A. Plasmid B consists of the 3' end of LacZ fused in frame to GFP. Plasmid B does not contain a promoter and therefore does not express GFP. Generation of a double strand break between sequences 1 and 2 on Plasmid A stimulates recombination between homologous sequences on Plasmids A and B and leads to the expression of a functional LacZ-GFP fusion protein which can be detected by various methods such as fluorescence microscopy or flow cytometry.
Figure 33A:
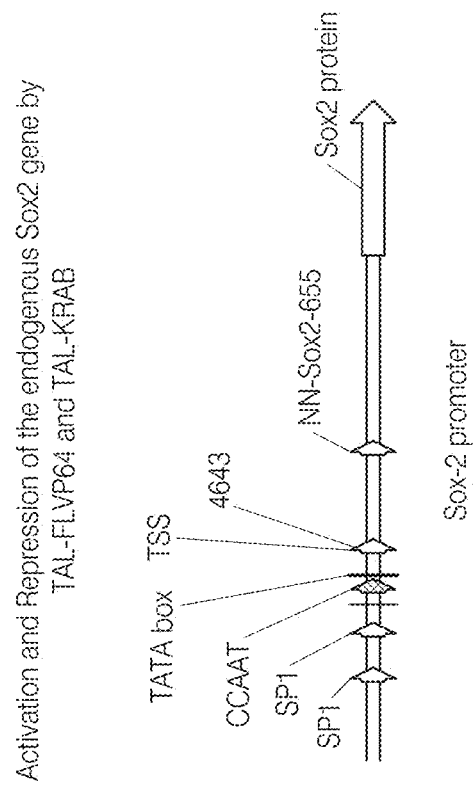
FIGS. 33A to 33C show the activation and repression of the endogenous sox2 gene in HeLa cells using TAL activator and TAL repressor proteins.
Figure 33B:
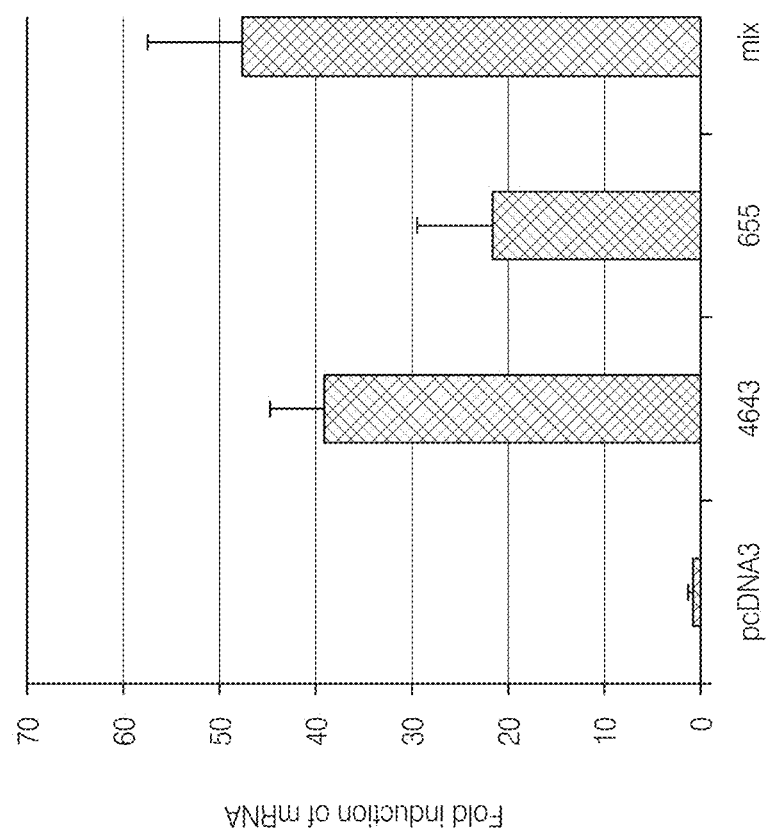

TAL effector fusions engineered, assembled or used by the methods or in compositions described herein may further relate to polypeptides or proteins with activator activity. Activation domains that may be fused to engineered TAL effectors are for example herpes simplex virus protein 16 (VP16) (Sadowski et al., "GAL4-VP16 is an unusually potent transcriptional activator", Nature. 1988 Oct. 6; 335 (6190):563-4., the engineered VP64 activator containing four copies of the VP16 core motif (Beerli et al., "Toward controlling gene expression at will: specific regulation of the erbB-2/HER-2 promoter by using polydactyl zinc finger proteins constructed from modular building blocks." Proc. Natl. Acad. Sci U.S.A. 1998 Dec. 8; 95(25):14628-33.), nuclear factor-KB subunit p65 (Liu et al., "Regulation of an endogenous locus using a panel of designed zinc finger proteins targeted to accessible chromatin regions. Activation of vascular endothelial growth factor A." J. Biol. Chem. 2001 Apr. 6; 276(14):11323-34.), VP32, VP48, VP80 or other activation domains known in the art. Thus the invention relates, in part, to TAL effector activator fusion proteins and optimized sequences encoding such proteins. In particular, the invention includes TAL effectors with codon-optimized activator domains such as those encoded by SEQ ID NOs: 4 and 5 (see FIG. 6B). Successful activation of gene expression by TAL activator fusion proteins has been demonstrated by the inventors in the context of various reporter assay systems (FIGS. 15 and 18A) and for the endogenous sox2 gene in HeLa cells (FIG. 33B). In this experiment, the promoter region of the sox2 gene which encodes a transcription factor for maintaining pluripotent stem cells was targeted by TAL FLVP64 activator fusion proteins. Two different TAL binding domains were designed to bind to the 4643 and 655 sites in the Sox2 promoter region (FIG. 33A) and fused to the VP64 activation domain. HeLa cells were then transfected with empty vector (pcDNA3), either of the 4643 or 655 specific TAL VP64 activators or a mixture of both fusion proteins. The mRNA levels of Sox2 were evaluated by Taqman assay 72 hours post transfection and normalized to β-actin and fold-induction of Sox2 mRNA was determined. As shown in FIG. 33B Sox2 expression could be significantly increased by TAL VP64 targeted to the 655 site whereas the expression boost was even more substantial when the 4643 site was bound. Further, a synergistic effect on Sox2 gene expression was observed when both TAL VP64 proteins were present in the transfected cells. These experiments illustrate the ability of designed TAL activator fusion proteins to efficiently activate endogenous gene expression.

TAL Repressors.

TAL effector fusions engineered, assembled or used by the methods or in compositions described herein may further relate to polypeptides or proteins with repressor activity. Repressor domains that may be fused to engineered TAL effectors are for example Krüppel associated box proteins KRAB, a transcriptional repression module responsible for the DNA binding-dependent gene silencing activity of hundreds of vertebrate zinc finger proteins (Margolin et al. "Krüppel-associated boxes are potent transcriptional repression domains." Proc Natl Acad Sci USA. 1994 May 10; 91(10):4509-13.), mSin3 interaction domain SID (Ayer et al. "Mad proteins contain a dominant transcription repression domain." Mol Cell Biol. 1996 October; 16(10):5772-81.), ERF repressor domain ERD (Sgouras et al. "ERF: an ETS domain protein with strong transcriptional repressor activity, can suppress ets-associated tumorigenesis and is regulated by phosphorylation during cell cycle and mitogenic stimulation." EMBO J. 1995 Oct. 2; 14(19):4781-93.), histone methyltransferase HMT (Snowden et al. "Gene-specific targeting of H3K9 methylation is sufficient for initiating repression in vivo." Curr Biol. 2002 Dec. 23; 12(24):2159-66.), Gfi-1 (growth factor independent 1 transcription repressor), repressor element 1 (RE1) silencing transcription factor REST or other repressor domains known in the art. Thus the invention relates in part to TAL effector repressor fusion proteins and optimized sequences encoding such proteins. In particular the invention includes TAL effectors with codon-optimized repressor domains such as those encoded by SEQ ID NO: 6 (FIG. 6B).

Figure 33C:
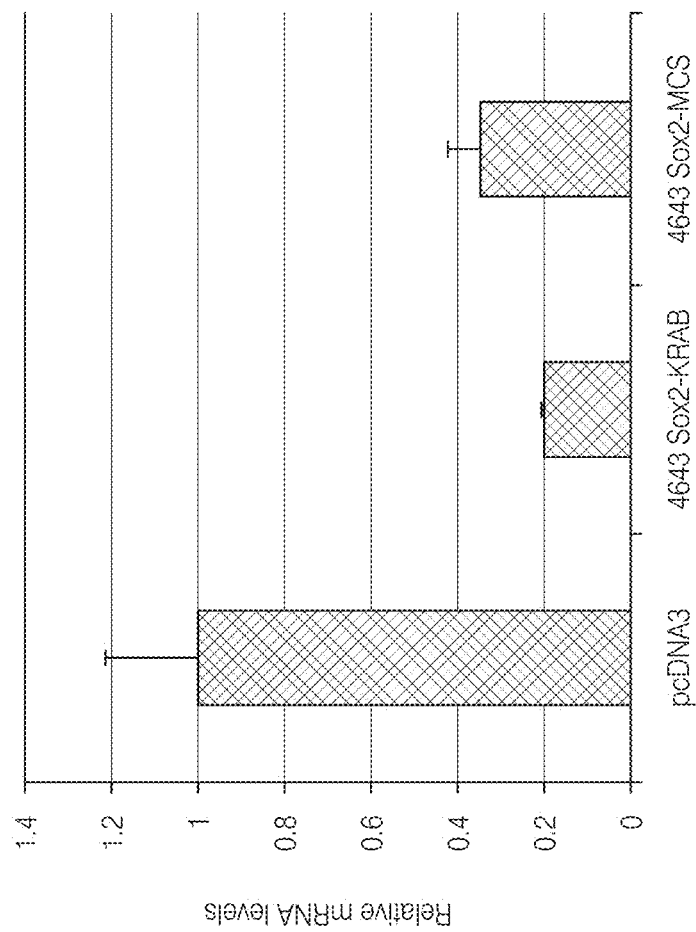

Successful repression of gene expression by TAL repressor fusion proteins has been demonstrated by the inventors in the context of various reporter assay systems (FIGS. 15 and 16) and for the endogenous sox2 gene in HeLa cells (FIG. 33C). In this experiment, HeLa cells were transfected with either an empty vector (pcDNA3.1), a TAL MCS expression plasmid targeting the 4643 site in the promoter region of the sox2 gene in the absence of a repressor function or a TAL KRAB repressor fusion protein directed to the 4643 site. Relative mRNA levels of sox2 were evaluated by Taqman assay 72 hours post transfection and normalized to β-actin. As shown in FIG. 33C, a significant repression of Sox2 expression was achieved by the binding of the TAL effector to the 4643 site, whereas an even stronger downregulation was observed in the presence of the KRAB repressor fusion. This example demonstrates the functionality of TAL effectors and TAL repressor fusion proteins for endogenous gene knock-down applications.

Furthermore, in certain instances TAL effectors may be fused with other effector functions such as a methylase (e.g., DNA-MT), a demethylase (e.g., MDB2b), an acetylase (histone acetylase HAT) or a deacetylase (e.g., histone deacetylase HDAC). Thus the invention relates in part to TAL effectors with chromatin modifying function and optimized sequences encoding such proteins. In particular the invention includes TAL effectors with codon-optimized sequences encoding methylase, demethylase, acetylase or deacetylase activities.

TAL Epigenetic Modifiers.

In one aspect the invention relates to TAL epigenetic modifiers paired with transcriptional activators. Activation or up-regulation of endogenous genes is a key application for TAL effectors. As knowledge of eukaryotic cellular pathways increases, combinations of knock-out, down-regulation, and up-regulation of particular genes in a pathway will be key to modulating production of a specific product or the inducement of a particular phenotype in response to extracellular stimuli. Up-regulation of silenced genes poses a unique challenge since many genes are silenced by virtue of epigenetic modification such as methylation, acetylation and sequestration of the promoter region in heterochromatin. A solution to this problem is provided by a method where a TAL is fused with an epigenetic modifier such as e.g., a deacetylase or a demethlyase, etc. and the modifier is combined with a specific activation domain in the same molecule such as for example, VP16, VP64, etc.

Combination of these activities in one molecule would, e.g., allow demethylation of a methylated promoter region by the activity of the epigenetic modifier and subsequent activation of the promoter by the fused activator moiety in an efficient manner. Thus, the invention includes, in part, a TAL epigenetic modifier operationally linked with a transcriptional activator domain. In particular, the invention includes a TAL effector fusion protein composed of at least a TAL effector (i.e., one or more TAL cassettes flanked by N- and C-terminal domains) (BD) or a modified version thereof, a spacer sequence(s) of a defined length, an epigenetic modifier (EM) or a modified variant thereof, a specific activation domain (AD) or a modified variant thereof and a nuclear localization signal (NLS). In one aspect of the invention, the modified version of the TAL effector can be a truncated binding domain wherein either the N-terminus or the C-terminus or both termini have been truncated. In one aspect of the invention the epigenetic modifier can be a deacetylase, a demethylase, or a truncated or mutated variant thereof. In another aspect, the activation domain may be a natural or synthetic activation domain. For example, the activation domain may be VP16 or an array of two, three, four, five, six, seven or eight repeats of the VP16 minimal core motif as defined elsewhere herein. In one aspect, the activation domain may be VP32, VP48 or VP64 or VP80 or modified versions derived therefrom. The invention further includes different architectures of the TAL epigenetic modifiers wherein the fused moieties can be connected in different orders.

Thus, in one aspect the invention relates to a functional vector containing a nucleic acid sequence encoding a TAL epigenetic modifier, wherein the vector contains at least nucleic acid sequences encoding (i) a TAL effector (BD), (ii) an epigenetic modifier (EM), (iii) an activator domain (AD), (iv) a nuclear localization signal (NLS), and (v) one or more spacer sequences(s).

In certain instances one or more of the TAL cassettes in the TAL effector (BD) may contain RVD specifically recognizing methylated sequences as described elsewhere herein. In one embodiment the RVD NG may be used to recognize mC where binding to C shall be excluded. In yet another embodiment RVD N* may be used where binding to both, mC and C is required.

The invention includes a vector, as described above, wherein the elements (i) to (v) are arranged in any of the following orders: 5'-BDsEMsADsNLS-3' or 5'-BDsAD-sEMsNLS-3' or 5'-EMsBDsADsNLS-3' or 5'-EMsADsBD-sNLS-3' or 5'-ADsBDsEMsNLS-3' or 5'-ADsEMsBDsNLS-3' or 5'-NLSsBDsEMsAD-3' or 5'-NLSsBDsADsEM-3' or 5'-NLSsEMsBDsAD-3' or 5'-NLSsEMsADsBD-3' or 5'-NLSsADsBDsEM-3' or 5'-NLSsADsEMsBD-3' or 5'-BDssNLSEMsAD-3' or 5'-BDsNLSsADsEM-3' or 5'-EMsNLSBDsAD-3' or 5'-EMsNLSsADsBD-3' or 5'-ADsNLSsBDsEM-3' or 5'-ADsNLSsEMsBD-3' or 5'-BDsEMsNLSsAD-3' or 5'-BDsADsNLSsEM-3' or 5'-EMsBDsNLSsAD-3' or 5'-EMsADsNLSsBD-3' or 5'-ADsBDsNLSsEM-3' or 5'-ADsEMsNLSsBD-3'.

The invention further relates to a vector as described above wherein (i) the TAL cassettes and/or TAL repeats or (ii) the flanking N- and/or C-terminal domains are truncated or modified. For example, the TAL effector may contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 33, 35 or more cassettes. Further, the number of amino acids encoded by each cassette may differ in the number of amino acids and may consist of 34, 35 or less than 34 amino acid residues. The N-terminal and/or C-terminal domains may be truncated by 10, 25, 50, 65, 75, 90, 110, 115, 148, 152, 161, 175, 182, 195, 202 or more amino acid residues etc. In another aspect of the invention, at least one of the domains in the above described vector may be linked with a sequence encoding a tag, such as a purification or detection tag as disclosed elsewhere herein. The vector as described above maybe a GATEWAY® vector or a topoisomerase-adapted vector or a vector as described elsewhere herein. Furthermore, the invention also relates in part, to a host cell transformed or transfected with the above described vector and a fusion protein expressed from the above described vector.

Nuclear Localization Signal.

DNA binding molecules, such as TAL effectors and TAL effector fusions, may be designed for optimal function in different species or may be directed to different compartments within a cell. In some instances, it may be required to target a DNA binding molecule to a cell nucleus. This can be achieved, for example, by using a nuclear localization signal (NLS). The C-terminal domain of wild-type TALs usually harbors an NLS to efficiently target the TAL to the nucleus of plant cells. However, when constructing new or modified DNA binding molecules it may be desirable to use a species-specific or engineered NLS. For example if a truncated TAL repeat domain is to be used lacking parts of the C-terminal domain that would naturally harbor the NLS, a modified or heterologous NLS may be incorporated in the truncated molecule. It may also be required to change the location of an NLS within a protein to achieve optimal accessibility and/or activity. Different NLS are known in the art and may either be species-specific or compatible with several species. Typically, a NLS consists of one or more short sequences of positively charged lysines or arginines exposed on the protein surface. Different nuclear localized proteins may share the same NLS. In some of the TAL effectors described herein, the original NLS found in the Hax3 TAL effector is included. However, in certain embodiments of the invention the natural TAL NLS may be replaced by a heterologous NLS to optimize efficiency of nuclear import. A classical NLS suitable for practicing the invention may, e.g., include SV40 T-Antigen monopartite NLS, C-myc monopartite NLS or nucleoplasmin bipartite NLS or modified or evolved versions recognized by importin-α thereof but may also include non classical NLS known in the art most of which are recognized directly by specific receptors of the importin β family without the intervention of an importin a-like protein. In one aspect of the invention truncated TAL vectors in which the original Hax3 NLSs have been removed may be equipped with a slightly modified SV40 NLS sequence for efficient nuclear targeting. The core motif of the SV40 NLS is typically PKKKRKV (SEQ ID NO: 107) or PKKKRKVE (SEQ ID NO: 108). In a first variant, two glycines were added to the NLS on either site to provide a flexible linker to increase accessibility of the NLS if located at different positions between the fused domains. Furthermore, an aspartate residue was inserted right after the core motif to increase activity yielding sequence GGMAPKKKRKVDGG (SEQ ID NO: 28). In another variant a glycine-serine linker was attached upstream of the core motif yielding sequence QGSPKKKRKVDAPP (SEQ ID NO: 29). Other variations can be introduced on either sites of the core motifs to increase activity or accessibility within the folded protein. Furthermore, an NLS sequence can be located at different positions within a TAL effector such as e.g., N-terminal or C-terminal of the repeat domain.

Thus, the invention relates in part to TAL effectors or TAL epigenetic modifiers containing a heterologous NLS different from the original NLS of the TAL protein. Furthermore, the invention relates to TAL effectors or TAL epigenetic modifiers containing a heterologous NLS different from the original NLS of the TAL protein, wherein the TAL domain is a truncated TAL domain. Furthermore, the invention relates to TAL effectors or TAL epigenetic modifiers containing a heterologous NLS different from the original NLS of the TAL protein, wherein the TAL domain is a truncated TAL domain and the NLS is located at the N-terminus of the TAL domain or at the C-terminus of the TAL domain or between the TAL domain and the effector domain or between the TAL domain and the epigenetic modifier or between the epigenetic modifier and the activator domain. In some embodiments, the invention relates to a truncated TAL effector comprising an NLS with core motif PKKKRKVD (SEQ ID NO: 109), wherein at least one side of the core motif is flanked by a flexible linker sequence.

Organelle Targeting of TAL Effectors.

Nuclear localization signals as described elsewhere herein allow for targeting of TAL effector fusions to nuclei of various host cells. However, in some instances it may be required to target TAL effectors to organelles other than the nucleus, such as, e.g., mitochondria or plant chloroplasts. Typical targeting signals that may direct polypeptides to these organelles are listed in the following TABLE 12:

TABLE 12

| Organelle | Typical signal location within polypeptide | Nature of Signal |
|---|---|---|
| Mitochondrium | N-terminal | 3 to 5 nonconsecutive Arg or Lys residues, often with Ser and Thr; no Glu or Asp |
| Chloroplast | N-terminal | Generally rich in Ser, Thr, and small hydrophobic residues, typically poor in Glu and Asp |
| Nucleus | Internal | Core motif of 5 basic residues, or two smaller clusters of basic residues separated by approx. 10 amino acids |

Specific targeting can be triggered by various mechanisms. In a first posttranslational mechanism, the import machinery of an organelle selects proteins by recognition of a transit peptide or specific localization signals. In a second co-translational mechanism, the signal sequence in the nascent polypeptide binds signal recognition particles (SRPs), which represses further translation and targets this entire RNA-ribosome-nascent polypeptide complex to the endoplasmatic reticulum, where protein translation resumes. In a third mRNA-based mechanism the untranslated mRNA is localized by an RNA-binding protein associated with a molecular motor or the target membrane, and translation is initiated after mRNA localization. All three mechanisms have been shown to contribute to organelle targeting in both, mammals and algae such as, e.g., *Chlamydomonas* (Uniacke and Zerges, "Chloroplast protein targeting involves localized translation in *Chlamydomonas*" *Proc. Natl. Acad. Sci. USA* 2009, vol. 106 no. 5, p. 1439-1444).

In certain instances, it may be required to target a TAL effector or TAL effector fusion to the genome of mitochondria or chloroplasts of plants for genomic engineering. In some instances, it may be required to target TAL effectors to the chloroplast genome of algae or microalgae. A TAL effector that is to be targeted to the chloroplast genome may, e.g., be expressed in the algae nucleus, translated in the cytosol and then directed to the chloroplast lumen via a signal sequence in the TAL effector fusion protein. In some aspects, the invention relates to a TAL effector or TAL effector fusion harboring a signal sequence which allows for chloroplast targeting. In one embodiment the signal sequence is located in the N-terminal domain of the TAL effector or TAL effector fusion. In some aspects, the signal sequence may be multipartite. For example the signal sequence may be accompanied by an ER retention signal in cases where the first step in targeting polypeptides to plastids requires passage of that polypeptide into the ER. In some aspects, at least one part of the signal sequence may be rich in serine and/or threonine residues. Furthermore, at least one part of the signal sequence may comprise small hydrophobic residues. In addition, at least one part of the signal sequence may be poor in glutamate and/or aspartate residues. In one embodiment the signal sequence may encode the amino acid motif ASAFAP (SEQ ID NO: 110). The signal sequence may be derived from a natural signal sequence or may be an artificial sequence or composed of several signal sequences. In some embodiments, the signal sequence may contain between 4 and 10, between 8 and 20, between 15 and 40, between 20 and 50 amino acid residues.

For expression of a TAL effector or TAL effector fusion protein in algae, the TAL effector coding sequence containing a chloroplast targeting signal may, e.g., be cloned in a suitable expression vector for microalgae such as, e.g., the pChlamy 1 Vector which is part of the "GENEART® *Chlamydomonas* Engineering Kits" offered by Life Technologies Corp. (Carlsbad, Calif.). In some embodiments, an algae expression vector should harbor one or more of the following features: an algae promoter (e.g., hybrid Hsp70A-RbcS2 promoter), an untranslated region for increased mRNA stability (e.g., Cop1 3'-UTR), a versatile multiple cloning site for simplified cloning of the TAL effector or TAL effector fusion, a resistance gene (e.g., aph7 gene driven by the β2-tubulin promoter for hygromycin selection), an *E. coli* selection marker (e.g., ampicillin, kanamycin etc.) and an origin for maintenance (e.g., pUC ori). To achieve stable expression of the TAL effector or TAL effector fusion, the expression vector is then transformed into algae by methods known in the art (e.g., electroporation). Following random integration into the algae nuclear genome, the TAL effector or TAL effector fusion will be expressed in the cytosol and will be delivered to the chloroplast by means of the signal sequence.

Alternatively TAL effector function can be delivered to chloroplasts by direct expression of TAL effector sequences in the chloroplast compartment. For direct expression in chloroplasts the TAL effector encoding sequence and/or sequences encoding fused domains may be codon optimized. In one embodiment genes to be expressed in chloroplasts are codon optimized by using preferably codons containing adenine or uracil nucleotides in the third position. Since heterologous proteins expressed in algae may be subject to protease degradation, e.g., by ATP-dependent proteases, the TAL effector design may further include elimination of potential protease cleavage sites. The TAL effector or TAL effector fusion coding sequence is then cloned into a suitable expression vector that carries additional elements required for expression by the chloroplast machinery such as, e.g., a suitable promoter, 5' and 3' UTRs and a marker gene for selection of transformed cells. For example, a suitable expression vector may contain at least a chloroplast promoter (e.g., psbA or atpA promoter) and a chloroplast terminator (e.g., rbcL terminator) for driving expression of the TAL effector, a marker gene (e.g., bacterial gene aadA conferring spectinomycin and streptomycin resistance) and flanking sequences (e.g., from the psbA gene) for homologous integration into the chloroplast DNA. The expression vector may be delivered to the chloroplast by a plastid transformation procedure known as biolistics using gold carrier particles from Seashell Technology (La Jolla, Calif.) or by other methods known in the art (see, e.g., Radakovits et al. "Genetic Engineering of Algae for Enhanced Biofuel Production"; Eukaryotic Cell 2010, 9(4): 486.). The TAL effector sequence will then be inserted into the chloroplast genome by homologous recombination mediated by the flanking sequences.

Fluorescent and Other Detectably Tagged TAL Proteins.

TAL effectors of the invention can be fused to various functional effector molecules as described above to fulfill specific tasks when delivered to a given host cell. In certain instances it may be desired to either determine (i) where a TAL effector is located in a cell or (ii) how much of a TAL effector is present. Such tracking may help to ensure that a customized TAL effector is delivered to the predicted place of action at sufficient amounts to fulfill its function. For this purpose TAL effectors can be labeled with a fluorescent or other detectable (e.g., luminescent) portion which allows detection of the TAL effector, e.g., by in vivo imaging. Any fluorescent or other detectable portion or protein known in the art can be used to tag a TAL protein. In a first aspect, a fluorescent moiety may be attached to a TAL effector protein e.g. by providing a fluorescently labeled antibody specifically binding to a TAL or its fused effector function. In another aspect, a fluorescent or other detectable moiety can be directly fused at the amino- or carboxyl-terminal ends of a TAL effector or a TAL effector fusion protein. The location of the fluorescent or other detectable moiety within the fusion protein will mainly depend on the provided effector function and the folding requirements of the fused domains. In a specific embodiment, a gene encoding a fluorescent or other detectable protein may be inserted in a TAL effector expression vector so that a TAL fluorescent/detectable fusion protein will be expressed following delivery of such expression vector to a target host cell. Any fluorescent or other detectable protein suitable for in vivo tracking may be used for that purpose including but not limited to green fluorescent protein (GFP) or enhanced green fluorescent protein (EGFP), red fluorescent protein (RFP), blue fluorescent protein (BFP), cyan fluorescent protein (CFP), yellow fluorescent protein (YFP), violet-excitable green fluorescent protein (Sapphire) or luciferase. A sequence encoding a fluorescent or other detectable protein may be inserted upstream or downstream of a TAL repeat region or upstream or downstream of the effector coding region depending on functional and folding requirements of the provided domains. The gene sequence encoding the fluorescent or other detectable protein may be a wild-type or a codon-optimized synthetic sequence as described in more detail elsewhere herein. Such fluorescent or other detectable tag may be fused to any TAL effector function described herein including a separate TAL domain, a TAL nuclease or nuclease cleavage half domain, a TAL activator, a TAL repressor, a TAL epigenetic modifier, a TAL polymerase, a TAL scaffold etc. For example, each TAL nuclease cleavage half domain of a TAL nuclease pair may be fused to the same or a different fluorescent or other detectable protein. Use of a different fluorescent protein for each TAL nuclease cleavage half domain may be used to determine whether expression and localization of both domains within a cell is equally balanced. TAL fluorescent or other detectable protein fusions may be used to help to better understand TAL effector function and activity in vivo and may serve to improve and optimize TAL effector design for various applications including the methods and applications described herein.

Methods, Vectors and Kits for Assembly of TAL Effectors

Assembly of DNA Binding Effector Molecules and TAL Effectors and Customized Toolkits.

With the advent of the synthetic biology era, homologous recombination has become combined with multiple nucleic acid assembly technologies. Currently, commercially available assembly kits allow piecing together PCR-amplified or pre-cloned DNA fragments in vivo or in vitro in a single step in a pre-determined and seamless manner. Although these approaches work efficiently with up to 10 fragments that share common ends (and in some cases with fragments without end-terminal homology), many are not robust enough to be used in complex DNA shuffling cloning. Thus, there is a need for novel DNA shuffling assembly strategies and methods and kits based thereon to allow for efficient high throughput assembly and cloning of customized DNA binding effector molecules, such as TAL effectors.

A rapid subcloning nucleic acid transfer strategy which allows for the transfer of nucleic acid segments from one vector into another vector by type IIS assembly has been proposed referred to as "Golden Gate" cloning (Engler, C., R. Kandzia, and S. Marillonnet. 2008. A one pot, one step, precision cloning method with high throughput capability. PLos One 3:e3647.; Kotera, I., and T. Nagai. 2008. A high-throughput and single-tube recombination of crude PCR products using a DNA polymerase inhibitor and type IIS restriction enzyme. J Biotechnol 137:1-7.; Weber, E., R. Gruetzner, S. Werner, C. Engler, and S. Marillonnet. 2011. Assembly of Designer TAL Effectors by Golden Gate Cloning. *PloS One* 6:e19722.). The principles of this type IIS assembly strategy are based on the ability of type IIS restriction enzymes to cut outside of their recognition site. Two or more DNA fragments can be designed to be flanked by a type IIS restriction site such that digestion of the fragments removes the recognition sites of the Type IIs enzymes and generates ends with complementary three or four nucleotide overhangs that can be ligated seamlessly, generating a junction that lacks the recognition sites. A DNA shuffling approach based upon type IIS assembly also has been proposed (Engler, C., R. Gruetzner, R. Kandzia, and S. Marillonnet, 2009. Golden gate shuffling: a one-pot DNA shuffling method based on type IIS restriction enzymes. *PLoS One* 4:e5553.; Engler, C., and S. Marillonnet. 2011. Generation of families of construct variants using golden gate shuffling. *Methods Mol Biol* 729:167-81.). The strategy, which permits the generation of libraries of recombinant genes by combining in one reaction several fragment sets prepared from different parental templates, is also useful for building highly repetitive nucleic acid molecules, such as, e.g., TAL effectors (Weber, E., R. Gruetzner, S. Werner, C. Engler, and S. Marillonnet. 2011. Assembly of Designer TAL Effectors by Golden Gate Cloning. *PloS One* 6:e19722.).

Figure 7A:
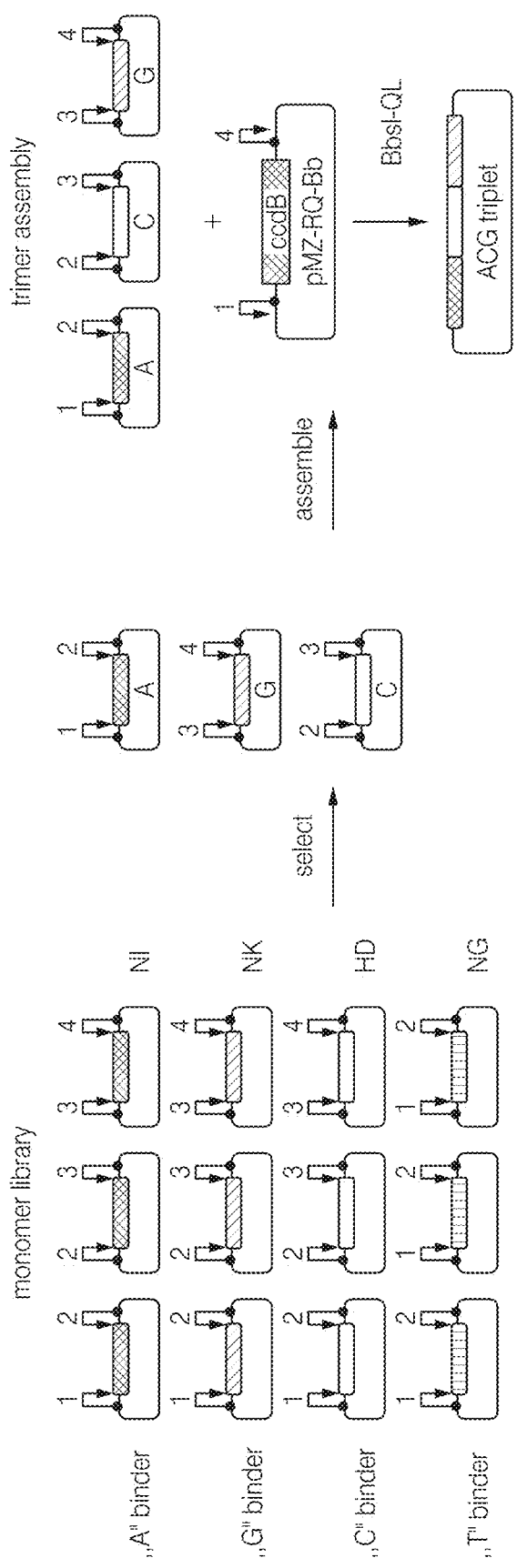
FIG. 7A shows one example of how a trimer repeat library can be assembled from repeat monomers. Selected building blocks from a monomer library with at least one repeat for each base and variants thereof providing individual overhangs upon type IIS cleavage are assembled in random combinations into a capture vector containing a counter selectable marker. Cleavage sites are indicated by numbers. Equal numbers represent resulting compatible overhangs.

Different strategies have been described in the literature to assemble TAL effectors starting with monomeric building blocks (cassettes). One method relies on PCR amplification of the starting material (e.g., TAL cassettes) to attach type IIS cleavage site containing adapter sequences providing the required individual overhangs (Zhang, F. et al. Efficient construction of sequence-specific TAL effectors for modulating mammalian transcription. *Nat. Biotechnol.* 29, 149-153 (2011)). This method involves several rounds of PCR and ligation to assemble individual cassettes into 12 cassette TAL effectors. One disadvantage of this method is that it is labor intensive and, thus, is not well suited for high throughput applications. Other approaches tried to avoid intermediate PCR steps to limit upfront work by assembling many (up to ten or twenty) cassettes simultaneously into a given target vector (Morbitzer, R., Elsaesser, J., Hausner, J. & Lahaye, T. Assembly of custom TALE-type DNA binding domains by modular cloning. *Nucleic Acids Res.* 39:5790-5799 (2011)). Although the successful parallel insertion of up to 10 fragments by type IIS assembly has been reported, the efficiency and reliability of this method decreases with increasing numbers of individual fragments. Thus, such method may not be optimal in many high-throughput settings. By making use of type IIS assembly, the inventors have developed an efficient assembly strategy for TAL nucleic acid binding cassettes starting from a library of TAL cassette trimers randomly assembled from monomer building blocks which is suitable for the construction in a manufacturing setting (FIG. 7A). The construction of a large trimer library (i.e., a collection of individual constructs each carrying a characterized triplett of TAL nucleic acid binding cassettes) allows for convenient high throughput TAL assembly processes. This is so because once a trimer library is generated, only a few steps need be performed with limited amounts of larger parts to generate various TAL effectors with different numbers of cassettes and recognizing different nucleotides sequences. By using the trimer library as starting material for all higher order assembly steps, two sets of only 3 or 4 trimer TAL cassettes are required to assemble TAL effectors with 18 or 24 cassettes, respectively. The parallel assembly of only 3 or 4 DNA fragments is a very reliable process with a high probability of picking a correct clone which avoids tedious screening procedures and repetition of experiments.

Furthermore the trimer library is based on an innovative design of the underlying TAL cassettes. A TAL cassette library usually contains at least four different categories of cassettes (e.g., NI, NK, HD, NG etc.) wherein all cassettes of one category bind a specific nucleotide (either A or G or C or T) (see FIG. 7A). One of the four cassettes or an additional cassette may be designed to bind either both mC and C or specifically bind mC only as described elsewhere herein. In addition, each category of cassettes may contain at least one shorter cassette encoding a so-called half-repeat. In some embodiments, the cassettes are designed such that one or more cassettes of a category can be recycled, i.e., they can be allocated to different positions of a TAL effector thereby reducing the total amount of cassettes that have to be synthesized. For example, a TAL effector with an array of 17.5 or 23.5 repeats can be assembled from a library that contains less than 24 different cassettes per category (e.g., 23, 22, 21, 20, 19, 18, 17, 16, 15, 14, 13, 12, 11 or 10). In one example, a library of cassettes that reflects categories NI, NK, HD and NG contains as few as 11 different cassettes per category resulting in a total of 44 (11×4) cassettes required to assemble all possible combinations of 17.5 or 23.5 repeats of a TAL effector with 4 cassettes (one per category) representing the half-repeats at positions 18 or 24 and 40 cassettes (10 per category) representing all other positions. Those cassettes encoding the 17.5 and 23.5 half-repeats, as well as other half repeats, may provide a 3' overhang that allows only direct assembly with a compatible overhang of a capture vector but with no other cassette of the library. In some instances the half repeat encoding cassette may already be part of a capture vector.

Thus, in one aspect the invention relates to a library of cassettes for assembly of a TAL effector with between 6 and 25 cassette positions (e.g., 18 or 24 positions), wherein the library of cassettes contains at least four different categories of cassettes with all cassettes of one category binding a specific nucleotide and wherein each cassette can be allocated to one or more distinct positions of the between 6 and 25 cassette positions (e.g. $A_1$-$A_{25}$, $G_1$-$G_{25}$, $C_1$-$C_{25}$, $T_1$-$T_{25}$), and wherein the one or more distinct positions are determined by complementary overhangs between cassettes.

Furthermore the invention relates to embodiments of the above library of cassettes, wherein the complementary overhangs are generated by type IIS cleavage and/or at least one cassette in each category encodes a half repeat and/or wherein at least 2, 3, 4, 5, 6, 7, 8 or 9 cassettes of each category can be allocated to more than one distinct position of the between 6 and 24 cassette positions. The invention further relates to the use of the above library for assembly of a TAL effector or TAL effector fusion. In certain instances the TAL effector may comprise 18 cassette positions. In other instances the TAL effector may comprise 24 cassette positions. Furthermore, the invention includes use of the above library for the assembly of a trimer library. In one embodiment, the nucleotide overhangs between different cassettes are designed to reflect an optimal sequence diversity. In some instances this may be a maximum sequence diversity. This can, e.g., be achieved by shifting the borders between cassettes by one or more nucleotides which may result in cassettes of different lengths. For example to generate an optimal overlap sequence between cassette A and cassette B, the border between both cassettes is shifted by one or more nucleotides in either direction resulting in one of both cassettes with a shorter nucleotide sequence and the other one with a longer nucleotide sequence. Thus, the invention further relates to a library of cassettes for assembly of TAL effectors wherein the library comprises standard and non-standard cassettes and wherein a standard cassette contains n×3 nucleotides encoding n residues, wherein n is a number between 10 and 35, and wherein a non-standard cassette contains n×3−x or n×3+x nucleotides, wherein x is a number between 1 and 7, between 5 and 10, between 8 and 15, between 12 and 30 or between 30 and 50. For example a standard cassette may consist of 34 residues encoded by 34×3=102 nucleotides whereas a non-standard cassette may consist of either 34×3−x (=less than 102 nucleotides) or 34×3+x (=more than 102 nucleotides). This strategy allows for generation of overhangs between cassettes with maximum diversity in nucleotide composition to improve efficiency of the assembly step.

Figure 7B:
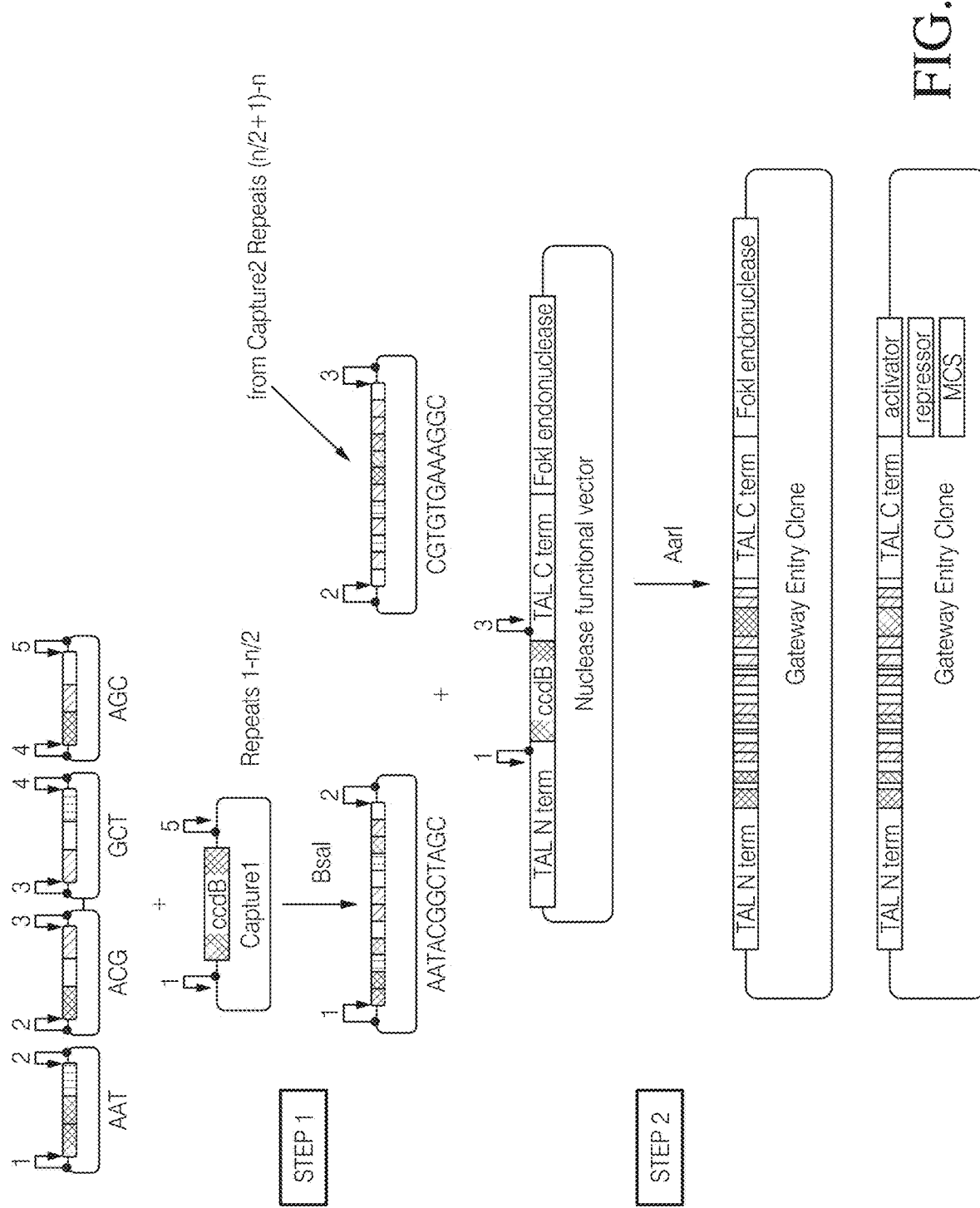
FIG. 7B illustrates the construction of a TAL effector fusion by a two-step assembly process. Two sets of 4 trimer building blocks arranged in capture vectors are assembled into a target vector via compatible type IIS restriction enzyme cleavage sites thereby replacing a negative selection marker gene. The target vector may already contain the flanking TAL effector N- and C-terminal ends and an effector fusion sequence or a multiple cloning site (MCS).

Furthermore, the invention relates to a two-step method for assembling a functional vector comprising a TAL effector composed of n TAL cassettes wherein the method starts with a library of TAL cassette trimers comprising all possible combinations of three cassettes wherein each cassette is capable of specifically binding one nucleotide said method being characterized by the following steps: (i) in a first step performing a first reaction wherein cassettes 1 to n/2 are concurrently cloned in a first capture vector using n/6 trimers, performing at least a second reaction wherein cassettes (n/2+1) to n are concurrently cloned in a second capture vector using n/6 trimers, wherein in the first capture vector cassettes 1 to n/2 are flanked by a first and a second type IIS cleavage site and in the second capture vector cassettes (n/2+1) to n are flanked by a second and a third cleavage site, and wherein the first, second, and third cleavage sites provide different overhangs when cleaved with one or more restriction enzymes and (ii) performing a third reaction wherein at least cassettes 1 to n/2 and cassettes (n/2+1) to n are released from the at least first and second capture vector in the presence of one or more, preferably the same type IIS restriction enzyme and are cloned in directed order via compatible ends of the first, second and third cleavage sites into a functional vector that provides overhangs compatible with the first and the third cleavage site (FIG. 7B). In one embodiment, the functional vector may be provided in a linearized form. In another embodiment, the functional vector may be provided in a closed circular form and may be cleaved together with the at least first and second capture vector in the same reaction. In yet another embodiment, the at least first and second capture vector and the functional vector are cleaved by the same type IIS restriction enzyme.

The two-step method may further be characterized in that the at least two reactions of step (i) are performed in parallel. Furthermore, in some embodiment, no PCR step is involved in either of steps (1) or (2). The assembly reaction in step (i) and/or step (ii) may be performed in the presence of a ligase such as, e.g., a T4 or Taq ligase. In some instances, at least one overhang in the reactions in step (i) and/or step (ii) may be generated by one of the following restriction enzymes: BbsI, BsmBI, BsaI, AarI, BtgZI, or SapI. In many instances at least one of the first capture vector, the second capture vector and/or the functional vector contain a counter selectable marker gene. In one embodiment the counter selectable marker gene may be a toxin gene such as, e.g., ccdB or tse2.

Example 3 describes various embodiments of the two-step assembly method outlined above. In certain instances it may be required to sequence-verify intermediate and/or final assembly products to ensure sequence correctness and functionality in downstream applications such as, e.g., expression experiments.

One first protocol that may be used to produce functional TAL effector fusions based on the two-step assembly method therefore involves a first sequence evaluation of TAL repeat subsets in capture vectors obtained from assembly step (i) to allow selection of correct sequences for subsequent assembly step (ii), followed by a second sequence evaluation of the final TAL effector fusion and a final plasmid preparation for downstream applications. A standard lab workflow for the two-step assembly of a TAL effector fusion according to such first protocol may therefore be characterized by the following steps: Day 1: step (i) assembly of TAL repeat subsets in capture vectors followed by transformation of the reactions into chemically or electro-competent bacteria (such as, e.g., E. coli) via heat shock- or electroporation-based methods, respectively, and plating on selective media; Day 2: colony PCR ("cPCR") for quick identification of clones carrying capture vectors with assembled TAL repeat subsets of correct length followed by inoculation of selective media cultures cultures with selected cfu ("colony-forming units"); Day 3: plasmid preparation from (typically overnight) cultures and sequencing of TAL repeat subsets or parts thereof; Day 4: step (ii) assembly of TAL effector fusions from sequence-verified TAL repeat subsets followed by transformation into competent bacteria and plating on selective media; Day 5: cPCR to identify clones carrying assembled TAL effector fusions followed by inoculation of selective media cultures culture(s) with selected cfu; Day 6: plasmid preparation from (typically overnight) culture(s) and sequencing of TAL effector fusions or parts thereof. The skilled person understands that cPCR can be replaced by other screening protocols known in the art (e.g., by growing each colony in selective media culture, subsequent plasmid preparation, digestion of the plasmid with restriction enzyme(s) that excises the insert, followed by separation by agarose gel electrophoresis) to identify positive clones. Further information on related cloning techniques and underlying protocols can be obtained, e.g., from Russell D W, Sambrook J (2001). Molecular cloning: a laboratory manual. Cold Spring Harbor, N.Y.: Cold Spring Harbor Laboratory. Thus, starting with trimers selected from a trimer library the two-step assembly method resulting in pig-amounts of sequence-verified TAL effector fusion plasmid may be performed within six days if sequence evaluation is performed after each assembly step (see TABLE 13 first protocol). A detailed description of an embodiment according to such first protocol is provided in Example 3a.

High Speed TAL Assembly.

In certain instances it may be desirable to reduce production time for customized TAL effector fusions thereby achieving shorter delivery times which may be of particular interest for customers ordering TAL-related services from a service provider as described elsewhere herein. Furthermore, a higher automation level of assembly processes can be achieved by reduction of required method steps resulting in less hands-on time. Thus, to minimize production time for customized TAL effector fusions, the inventors have further optimized the assembly procedure resulting in a second protocol. A lab workflow for the two-step assembly of a TAL effector fusion according to such second protocol may therefore be characterized by the following steps: Day 1: step (i) assembly of TAL repeat subsets in capture vectors followed by transformation of the reactions into competent bacteria (as outlined in the first protocol), and subsequent growth of pooled transformants in selective media cultures; Day 2: plasmid preparation from (typically overnight) cultures followed by step (ii) assembly of TAL effector fusions from purified pools of capture vectors containing non sequence-verified TAL repeat subsets followed by transformation into competent bacteria and plating on selective media; Day 3: cPCR to identify clones carrying assembled TAL effector fusions of correct length followed by inoculation of selective media culture(s) with selected cfu; Day 4: plasmid preparation from (typically overnight) culture(s) and sequencing of TAL effector fusions or parts thereof. The workflow according to such second protocol is summarized in TABLE 13. The findings that μg-amounts of correctly assembled TAL effector fusions can be obtained within four days using the two-step assembly workflow according to the second protocol indicate that step (i) assembly of intermediate TAL repeat subsets is particularly efficient allowing subsequent processing via step (ii) assembly without prior screening and pre-selection of correctly assembled capture vectors. Thus, whereas step (ii) assembly according to the first protocol is performed using pre-selected capture vectors with assembled TAL repeat subsets isolated from single cfu, step (ii) assembly according to the second protocol is performed with a pool of capture vectors with assembled TAL repeat subsets resulting from step (i) assembly without prior screening and clone selection.

Thus, the invention further relates to a second two-step method for assembling a functional vector comprising a TAL effector composed of n TAL cassettes wherein the method starts with a library of TAL cassette trimers comprising all possible combinations of three cassettes wherein each cassette is capable of specifically binding one nucleotide said method being characterized by at least the following steps: (i) in a first step performing a first reaction wherein cassettes 1 to n/2 are concurrently cloned in a first capture vector using n/6 trimers, performing at least a second reaction wherein cassettes (n/2+1) to n are concurrently cloned in a second capture vector using n/6 trimers, wherein in the first capture vector cassettes 1 to n/2 are flanked by a first and a second type IIS cleavage site and in the second capture vector cassettes (n/2+1) to n are flanked by a second and a third cleavage site, and wherein the first, second, and third cleavage sites provide different overhangs when cleaved with one or more restriction enzymes and (ii) performing a third reaction wherein at least cassettes 1 to n/2 and cassettes (n/2+1) to n are released from the at least first and second capture vector in the presence of one or more, preferably the same type IIS restriction enzyme and are cloned in directed order via compatible ends of the first, second and third cleavage sites into a functional vector that provides overhangs compatible with the first and the third cleavage site, and wherein the third reaction is performed using a pool of isolated first capture vectors at least a portion thereof carrying assembled TAL repeat subsets obtained from the first reaction and a pool of isolated second capture vectors at least a portion thereof carrying assembled TAL repeat subsets resulting from the second reaction. In one embodiment according to the second protocol the functional vector may be provided in a linearized form. In another embodiment the functional vector may be provided in a closed circular form and may be cleaved together with the at least first and second capture vector in the same reaction. In another embodiment the at least first and second capture vector and the functional vector are cleaved by the same type IIS restriction enzyme. A detailed description of an embodiment according to such second protocol is provided in Example 3b.

The two-step method according to the second protocol may further be characterized in that the at least two reactions of step (i) are performed in parallel. Furthermore, in some embodiment, no PCR step is involved in either of steps (i) or (ii). The assembly reaction in step (i) and/or step (ii) may be performed in the presence of a ligase such as, e.g., a T4 or Taq ligase. In some instances, at least one overhang in the reactions in step (i) and/or step (ii) may be generated by one of the following restriction enzymes: BbsI, BsmBI, BsaI, AarI, BtgZI, or SapI. In many instances at least one of the first capture vector, the second capture vector and/or the functional vector contain a counter selectable marker gene. In one embodiment the counter selectable marker gene may be a toxin gene such as, e.g., ccdB or tse2 as described elsewhere herein.

In efforts to further optimize and speed-up the assembly process the inventors have developed a third protocol according to which the production of TAL effector fusions can be achieved within three days. A lab workflow for the two-step assembly of a TAL effector fusion according to such third protocol may therefore be characterized by the following steps: Day 1: step (i) assembly of TAL repeat subsets in capture vectors followed by step (ii) assembly and subsequent transformation of the reactions into competent bacteria (as outlined in the first protocol), and plating on selective media; Day 2: cPCR to identify clones carrying assembled TAL effector fusions of correct length followed by inoculation of selective media culture(s) with selected cfu; Day 3: plasmid preparation from (typically overnight) culture(s) and sequencing of TAL effector fusions or parts thereof. The workflow according to such third protocol is summarized in TABLE 13. The findings that μg-amounts of correctly assembled TAL effector fusions can be obtained within three days using the two-step assembly workflow according to the third protocol indicate that the reaction products obtained from step (i) assembly (i.e., capture vectors containing TAL repeat subsets) can be directly used in step (ii) assembly without prior amplification (i.e. transformation and growth in selective media culture) and isolation (i.e., plasmid preparation) of assembled capture vectors. Thus, whereas according to the second protocol step (ii) assembly is performed with isolated pools of capture vectors carrying TAL repeat subsets resulting from step (i) assembly, step (ii) assembly according to the third protocol is performed using the reaction mixture from step (i) assembly or portions thereof (containing capture vectors with assembled TAL repeat subsets) without prior amplification and isolation of assembled capture vectors.

Thus, the invention further relates to a third two-step method for assembling a functional vector comprising a TAL effector composed of n TAL cassettes wherein the method starts with a library of TAL cassette trimers comprising all possible combinations of three cassettes wherein each cassette is capable of specifically binding one nucleotide said method being characterized by the following steps: (i) in a first step performing a first reaction wherein cassettes 1 to n/2 are concurrently cloned in a first capture vector using n/6 trimers, performing at least a second reaction wherein cassettes (n/2+1) to n are concurrently cloned in a second capture vector using n/6 trimers, wherein in the first capture vector cassettes 1 to n/2 are flanked by a first and a second type IIS cleavage site and in the second capture vector cassettes (n/2+1) to n are flanked by a second and a third cleavage site, and wherein the first, second, and third cleavage sites provide different overhangs when cleaved with one or more restriction enzymes and (ii) performing a third reaction wherein at least cassettes 1 to n/2 and cassettes (n/2+1) to n are released from the at least first and second capture vector in the presence of one or more, preferably the same type IIS restriction enzyme and are cloned in directed order via compatible ends of the first, second and third cleavage sites into a functional vector that provides overhangs compatible with the first and the third cleavage site and wherein the third reaction is performed using the reaction mixture from the first reaction or a portion thereof containing first capture vectors with assembled TAL repeat subsets and the reaction mixture from the second reaction or a portion thereof containing second capture vectors with assembled TAL repeat subsets. In one embodiment, according to the third protocol the functional vector may be provided in a linearized form. In another embodiment, the functional vector may be provided in a closed circular form and may be cleaved together with the at least first and second capture vector in the same reaction. In an additional embodiment, the at least first and second capture vector and the functional vector are cleaved by the same type IIS restriction enzyme. A detailed description of an embodiment according to such second protocol is provided in Example 3c.

The two-step method according to the third protocol may further be characterized in that the at least two reactions of step (i) are performed in parallel. Furthermore, in some embodiment, no PCR step is involved in either of steps (i) or (ii). The assembly reaction in step (i) and/or step (ii) may be performed in the presence of a ligase such as, e.g., a T4 or Taq ligase. In some instances, at least one overhang in the reactions in step (i) and/or step (ii) may be generated by one of the following restriction enzymes: BbsI, BsmBI, BsaI, AarI, BtgZI, or SapI. In many instances at least one of the first capture vector, the second capture vector and/or the functional vector contain a counter selectable marker gene. In one embodiment the counter selectable marker gene may be a toxin gene such as, e.g., ccdB or tse2 as described elsewhere herein.

TABLE 13

| Days | First Protocol | Second Protocol | Third Protocol |
| --- | --- | --- | --- |
| Day 1 | step (i) assembly transformation | step (i) assembly transformation inoculate culture | step (i) assembly step (ii) assembly transformation |
| Day 2 | cPCR inoculate culture | prepare plasmid DNA step (ii) assembly transformation | cPCR inoculate culture |
| Day 3 | prepare plasmid DNA sequence subparts select correct clones | cPCR inoculate culture | prepare plasmid DNA sequence final construct select correct clone |
| Day 4 | step (ii) assembly transformation | prepare plasmid DNA sequence final construct select correct clone | — |
| Day 5 | cPCR inoculate culture | — | — |
| Day 6 | prepare plasmid DNA sequence final construct select correct clone | — | — |

Whereas the first protocol has been shown to be most efficient (both, for 18-mer and 24-mer assembly) in terms of the number of correct cfu per experiment, the third protocol allows for significantly reduced production times but has a lower cloning efficiency resulting in a lower amount of correct cfu per experiment which may be compensated by the amount of screened colonies. The second protocol combines the positive features of both, a high efficiency (i.e. number of correct cfu screened) with a shorter production time. The protocol chosen for assembly will generally depend on the underlying conditions and project requirements. For example, in cases where capture vectors carrying TAL repeat subsets are to be used separately or recycled in other assembly reactions, a method according to the first protocol may be most appropriate. A method according to the first or second protocol may also be preferred where sequencing capacities are limited and production time is less critical. In other cases where short production/delivery times are of paramount importance or where assembly steps are performed on automated or high throughput platforms, the second or in particular third protocol may be most appropriate. In certain instances, various protocols may be combined or adapted or performed in parallel to achieve an optimal combination of efficiency and speed. For example, the first protocol may be used as backup for the second protocol and the second protocol may be used as backup for the third protocol in case where colonies screened following step (ii) assembly do not contain correct sequences.

Apart from the assembly of TAL effector fusions, the protocols according to the invention can likewise be used for the step-wise assembly of any other DNA molecule from multiple subfragments. Currently, such subfragments are mostly assembled according to first protocol embodiments via consecutive assembly reactions, each followed by a selection step. Using assembly strategies according to the second or third protocol—or possibly combining even multiple step (i) and step(ii) assembly reactions can significantly reduce—all but the final selection steps could be dropped.

Thus, the invention further relates, in part, to a two-step method for assembling a DNA molecule from multiple DNA subfragments n wherein the method starts either from n vectors each carrying a single subfragment or from a library of subfragments wherein each vector in said library carries m subfragments with m<n, said method being characterized by the following steps: (i) in a first step performing a first reaction wherein a first amount of subfragments are concurrently cloned in a first cloning or capture vector, performing at least a second reaction wherein at least a second amount of subfragments are concurrently cloned in a second cloning or capture vector, wherein the first and last subfragment in the first cloning or capture vector are flanked by a first and a second type IIS cleavage site and the first and last subfragment in the second cloning or capture vector are flanked by a second and a third cleavage site, and wherein the first, second, and third cleavage sites provide different overhangs when cleaved with one or more restriction enzymes and (ii) performing a third reaction wherein the at least first and second amounts of subfragments are released from the at least first and second cloning or capture vector in the presence of one or more, preferably the same type IIS restriction enzyme and are cloned in directed order via compatible ends of the first, second and third cleavage sites into a target vector (e.g. an expression vector) that provides overhangs compatible with the first and the third cleavage site. In one embodiment, the third reaction is performed using a pool of isolated first cloning or capture vectors obtained from the first reaction and a pool of isolated second cloning or capture vectors resulting from the second reaction wherein at least a portion of the pool of isolated first cloning or capture vectors contains a correctly assembled first amount of subfragments and at least a portion of the pool of isolated second cloning or capture vectors carries a correctly assembled second amount of subfragments. In another embodiment, the third reaction is performed using the reaction mixture from the first reaction or a portion thereof containing first capture vectors with a correctly assembled first amount of subfragments and the reaction mixture from the second reaction or a portion thereof containing second capture vectors with a correctly assembled second amount of subfragments. In one embodiment, the target vector may be provided in a linearized form. In another embodiment, the target vector may be provided in a closed circular form and may be cleaved together with the at least first and second cloning or capture vector in the same reaction. In an additional embodiment, the at least first and second cloning or capture vector and the target vector are cleaved by the same type IIS restriction enzyme. The efficient assembly method of the invention allows for two or more subfragments to be cloned concurrently into each cloning or capture vector or target vector. In certain instances subfragment subsets derived from two, three, four, five or six cloning or capture vectors may be assembled concurrently into the same target vector in one step (ii) assembly reaction. Likewise, two, three, four, five or six subfragments may be cloned in each cloning or capture vector in a step (i) assembly reaction and the amount of subfragments cloned in each cloning or capture vector may be equal or different. For example, a first cloning or capture vector may carry three subfragments, whereas a second and a fourth cloning or capture vector may carry four subfragments each as described below (see e.g. TABLEs 14 or 15). In certain embodiments, the at least two reactions of step (i) assembly are performed in parallel. Furthermore, in some embodiments, no PCR step is involved in either of steps (i) or (ii). The assembly reaction in step (i) and/or step (ii) may be performed in the presence of a ligase such as, e.g., a T4 or Taq ligase. In some instances, at least one overhang in the reactions in step (i) and/or step (ii) may be generated by one of the following restriction enzymes: BbsI, BsmBI, BsaI, AarI, BtgZI, or SapI. In many instances, at least one of the first or second cloning or capture vectors and/or the target vector may contain a counter selectable marker gene. In one embodiment, the counter selectable marker gene may be a toxin gene such as, e.g., ccdB or tse2 as described elsewhere herein.

The functional vector may be designed to contain at least the TAL N-terminal and C-terminal domains or truncated versions thereof and a counter selectable marker gene. In addition, the functional vector may contain at least one effector fusion such as, e.g., a fusion with activator, repressor, nuclease, acetylase, de-acetylase, methylase, demethylase activity (see, e.g., FIG. 7C) or a effector fusion insertion site or multiple cloning site (MCS) as shown in FIG. 8A. In one embodiment the functional vector is a GATEWAY® entry clone comprising att recombination sites (see, e.g., FIGS. 8A-8C). In the functional vector, the TAL effector sequence may be cloned 5' or 3' to the effector fusion sequence or effector insertion sequence. In certain instances, the functional vector may have a sequence selected from the group of SEQ ID NOs: 30, 31, 32, 33, 34, 35, or 36.

In certain instances, the two-step assembly method may be used to assemble TAL effector fusions wherein the functional vector encodes a FokI nuclease cleavage domain or a truncated FokI nuclease cleavage domain. In some embodiments, the FokI nuclease cleavage domain may carry at least one of the following mutations: E490K, I538K, H537R, Q486E, I499L, N496D, R487D, N496D, D483R, H537R Furthermore, the functional vector used in the two-step method may carry at least one sequence that is codon-optimized with regard to a target host including but not limited to the TAL cassettes, TAL repeat, the TAL N-terminal and/or C-terminal coding sequences, the TAL effector or the TAL effector fusion sequence.

In yet another embodiment the above two step method for assembling a functional vector may rely on tetramers or may combine trimers and tetramers with dimers etc. TABLE 14 shows examples of how different library building blocks may be combined to assemble TAL effectors with n repeats.

TABLE 14

| n (no. of repeats) | first capture vector | second capture vector |
|---|---|---|
| 24 | 4 trimers (12 cassettes) | 4 trimers (12 cassettes) |
| 24 | 3 tetramers (12 cassettes) | 3 tetramers (12 cassettes) |
| 21 | 4 trimers (12 cassettes) | 3 trimers (9 cassettes) |
| 20 | 2 tetramers and 1 dimer (10 cassettes) | 2 tetramers and 1 dimer (10 cassettes) |
| 18 | 3 trimers (9 cassettes) | 3 trimers (9 cassettes) |
| 18 | 3 tetramers (12 cassettes) | 2 trimers (6 cassettes) |
| 16 | 2 tetramers (8 cassettes) | 2 tetramers (8 cassettes) |
| 12 | 4 trimers | — |
| 12 | 3 trimers (9 cassettes) | 1 trimer (3 cassettes) |
| 12 | 2 tetramers (8 cassettes) | |
| 30 | 4 tetramers (16 cassettes) | 2 tetramers and 2 trimers (14 cassettes) |
| 28 | 2 tetramers and 2 trimers (14 cassettes) | 2 tetramers and 2 trimers (14 cassettes) |

The skilled artisan will understand that in cases where a given number of n repeats cannot be assembled in 2 capture vectors, a third or fourth capture vector may be used as indicated in the following example in TABLE 15:

TABLE 15

| n (no. of repeats) | first capture vector | second capture vector | third capture vector |
|---|---|---|---|
| 35 | 3 tetramers (12 cassettes) | 3 tetramers (12 cassettes) | 2 tetramers and 1 trimer (11 cassettes) |
| 17 | 3 trimers (9 cassettes) | 2 trimers (6 cassettes) | 1 dimer (2 cassettes) |

Solid Phase TAL Assembly.

Figure 9A:
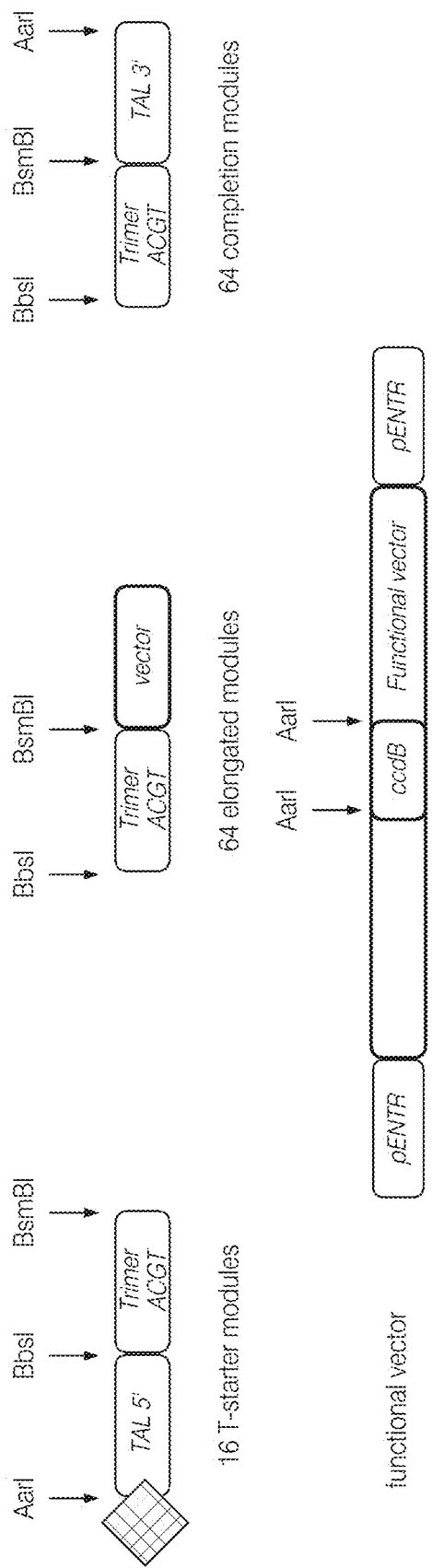
FIG. 9A shows an alternative method of assembling TAL effector encoding nucleic acid molecules by solid phase elongation based on a TAL trimer library.

The invention further relates to a method for assembling TAL effector molecules on a solid phase. The method allows for assembly of multiple different TAL effector molecules in a parallel, high-throughput and template-independent manner by using predesigned double stranded nucleic acid building blocks as illustrated in FIG. 9. TAL effector assembly on solid phase can be performed using single cassettes or may be performed using trimer or tetramer libraries described above. The building blocks may comprise one cassette encoding a single TAL repeat or they may comprise two or more cassettes encoding two or more TAL repeats. In some embodiments, a library of different modules is presented that contains at least three categories of modules: starter modules, elongation modules and completion modules. As illustrated in FIG. 9A, starter modules may be designed to comprise a TAL effector 5' flanking region attached to an anchor that can be immobilized on a solid phase and at least one TAL cassette. The anchor may, e.g., be a biotin anchor and may be bound to a streptavidin-coated surface. In one embodiment the at least one cassette is a T-binding cassette. In other embodiments the at least one cassette may be a A-, G- or C-binding cassette. In some instances starter molecules may comprise more than one TAL cassette. For example the starter modules may comprise a trimer or tetramer of cassettes as described above. In such case the library of starter modules may comprise all possible combinations of trimers or tetramers of A-, G-, C- and T-binding cassettes etc. In FIG. 9A, sixteen different starter modules are provided comprising all possible trimer combinations starting with a T-binding cassette. Elongation modules are used to sequentially elongate the nucleic acid chain immobilized on the solid phase. Like the starter modules the elongation modules may consist of one or more cassettes. In some embodiments, the elongation modules comprise more than one cassette such as, e.g., trimers or tetramers. A library of trimers would consist of 64 elongation modules whereas a library of tetramers would consist of 256 elongation modules to represent all possible combinations of A-, G-, C- and T-binding cassettes. The last cassette may be provided by a completion module that may further carry TAL effector 3' flanking regions. The completion module may likewise comprise one or more TAL effector cassettes.

Thus the invention relates to a library of TAL assembly modules, that contains three different categories of at least partially double stranded DNA building blocks:

(i) starter modules comprising a modification by which they can be immobilized on a solid phase, 5' TAL flanking sequences and one or more TAL cassettes wherein the starter module contains at least one first type IIS cleavage site flanking the 5' TAL sequences and at least one second type IIS cleavage site flanking the 3' end of the TAL cassettes.

(ii) elongation modules comprising one or more TAL cassettes wherein the 5' and 3' ends of the TAL cassette sequence are flanked by a third and a fourth type IIS cleavage site, and (iii) completion modules comprising at least one or more TAL cassettes and 3' TAL flanking sequences wherein the completion module contains at least a fifth type IIS cleavage site flanking the 5' end of the TAL cassettes and a sixth type IIS cleavage site flanking the 3' ends of the 3' TAL flanking sequences.

In some instances the solid phase assembly of TAL effector molecules may start with the immobilization of a starter molecule on a solid support followed by repeated cycles of type IIS-mediated cleavage and ligation of selected elongation modules as described in FIG. 9B-9G thereby sequentially elongating the TAL effector sequence. In the last cycle a completion module may be added to provide the 3' TAL flanking sequences. After completion of the modular assembly, the full-length TAL effector sequence comprising a defined number of TAL cassettes may be released from the solid support and cloned into a functional vector via terminal type IIS cleavage sites.

Thus, the invention further relates to a method for the manufacture of a nucleic acid molecule encoding a TAL effector or TAL effector fusion comprising the steps of a) providing a double-stranded starter module which has a modification by which it is immobilized on a surface, wherein the starter module comprises at least 5' TAL flanking sequences fused to one or more TAL cassettes and, at least a first recognition site for a first type IIS enzyme to generate a single-stranded overhang at the 5' end of the starter module, and a second recognition site for a second type IIS enzyme to generate a single-stranded overhang at the 3' end of the starter module, and which starter module is provided with a single-stranded overhang at the 3' end following cleavage with the second type IIS enzyme, b) providing a first double-stranded elongation module wherein the elongation module comprises one or more TAL cassettes and at least a third recognition site for a third type IIS enzyme to generate a single-stranded overhang at the 5' end of the elongation module and a fourth recognition site for a fourth type IIS enzyme to generate a single-stranded overhang at the 3' end of the elongation module, and which elongation module comprises a single-stranded overhang at the 5' end following cleavage with the third type IIS enzyme, wherein said single-stranded overhang at the 5' end is complementary to the single-stranded overhang at the 3' end of the starter module c) ligating the starter module and the first elongation module via their overhangs generating a first ligation product, d) cutting the ligation product with the fourth type IIS restriction enzyme to generate a single-stranded overhang at the 3' end of the first elongation module.

e) providing a second double-stranded elongation module that comprises a single-stranded overhang at the 5' end following cleavage with the third type IIS enzyme, wherein said single-stranded overhang at the 5' end is complementary to the single-stranded overhang at the 3' end of the first elongation module f) ligating the second elongation module and the first ligation product via their overhangs generating a second ligation product, g) optionally, repeating steps d) to 0 until a desired number of further elongation cassettes has been added, h) providing a double-stranded completion module comprising at least 3' TAL flanking sequences fused to one or more TAL cassettes and, at least a fifth recognition site for a fifth type IIS enzyme to generate a single-stranded overhang at the 5'end of the completion module and a sixth recognition site for a sixth type IIS enzyme to generate a single-stranded overhang at the 3' end of the completion module, and which completion module is provided with a single-stranded overhang at the 5' end following cleavage with the fifth type IIS enzyme, i) ligating the completion module and the final elongation module of the immobilized ligation product via their overhangs generating a final ligation product, and j) releasing the final ligation product via cleavage with the first and sixth type IIS enzymes.

In one embodiment, the first type IIS enzyme may be the same as the sixth type IIS enzyme and the second type IIS enzyme may be the same as the fourth type IIS enzyme. In most instances the at least first cassette of the starter module in step a) may be a T-binding cassette. In some embodiments, the starter modules, the elongation modules and the completion modules comprise three or four TAL cassettes.

Vectors for Assembly of TAL Effector Constructs

Nucleic acids which encode TAL effectors and TAL effector fusions may be constructed, propagated, and used to generate TAL proteins by a considerable number of methods, including Type IIS restriction enzyme assembly systems, as described elsewhere here.

In many instances, nucleic acids which encode TAL effectors and TAL effector fusions may either be integrated in cellular nucleic acid (e.g., a chromosome, etc.) or contained within a vector (e.g., a plasmid, a lentiviral vector, etc.).

Nucleic acid molecules encoding TAL proteins may have any number of components. As an example, TAL effector fusions will typically contain the following regions: (1) A region with two or more TAL repeats, (2) polypeptide regions flanking the TAL repeat region, and (3) a fusion partner. Some examples of additional regions which may be present include: (1) A linker region (e.g., a linker which connect the fusion partner to the TAL effector) and (2) a tag region (e.g., an affinity purification tag). Examples of nucleic acids which encode TAL fusion proteins are shown in the lower portion of FIG. 7B Vectors which contain TAL coding sequences can be generated by any number of methods. In some instances, TAL cassette nucleic acid may be chemically synthesized, then either individually connected to or inserted into other nucleic acid molecules (e.g., a vector) or connected to other TAL cassettes then connected to or inserted into other nucleic acid molecules (e.g., a vector). Methods for the construction of nucleic acid segments encoding TAL repeats is described elsewhere herein.

Figure 7C:
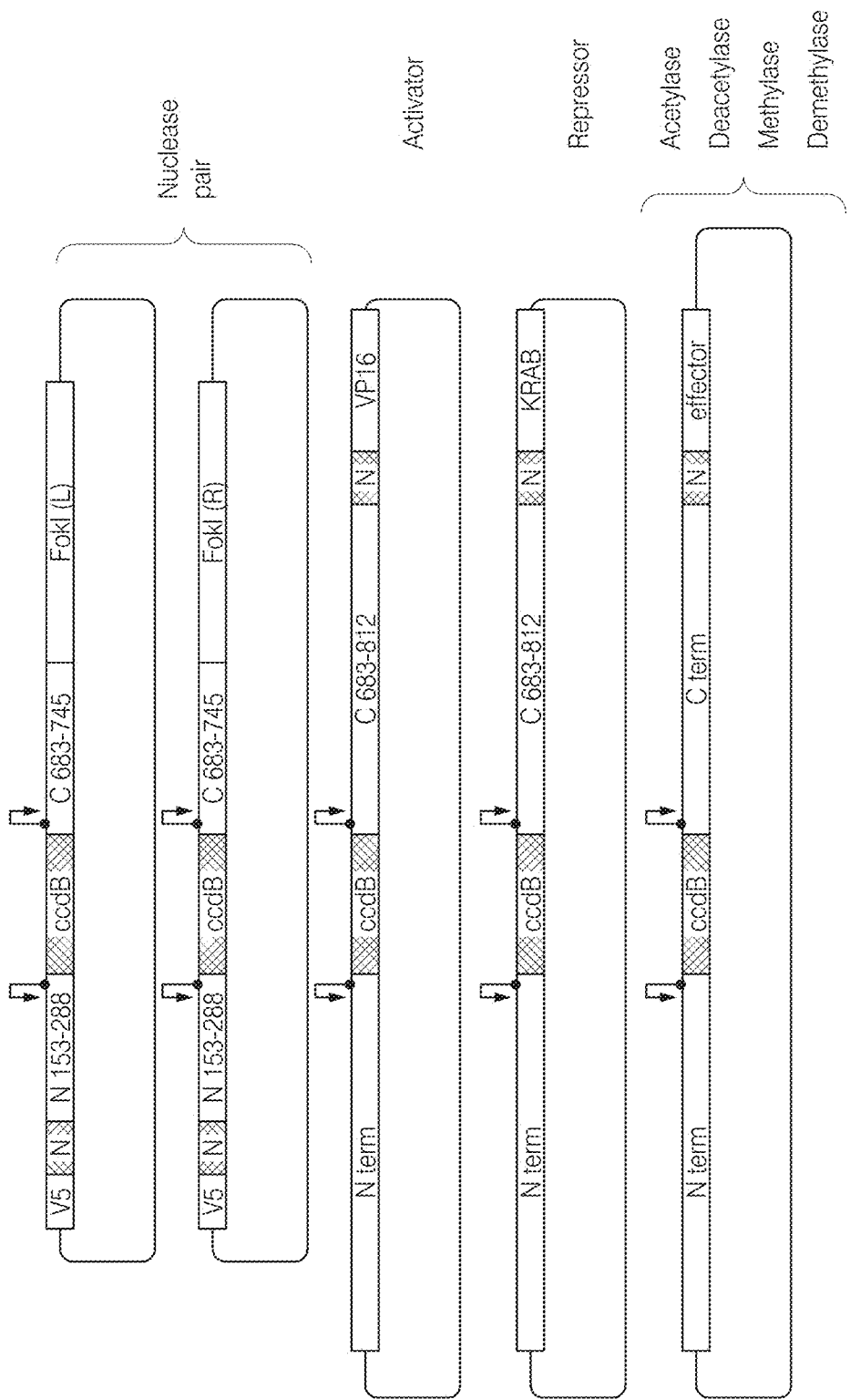
FIG. 7C shows target vectors for the construction of various TAL effector fusions. Examples for different effector functions are provided (VP16, activator; KRAB, repressor, FokI R and L, dimerizing nuclease cleavage domains); TAL effector nucleases active as dimers can be provided in a vector pair with each vector comprising the sequence for a nuclease monomer. Some of the vectors contain truncated versions of N- or C-terminal TAL ends described in more detail elsewhere herein.
Figure 8A:
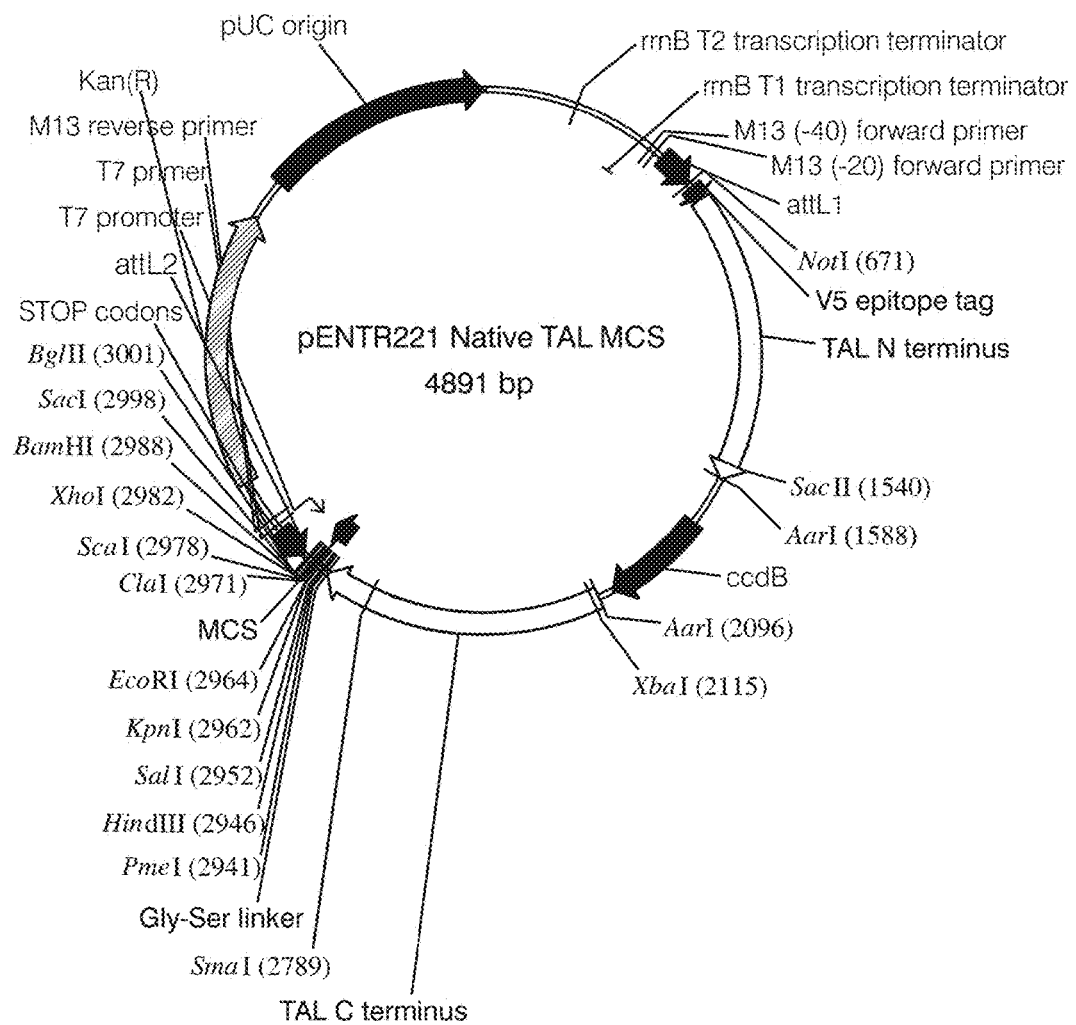
FIGS. 8A to 8C show vector maps of different TAL Gateway entry vectors. Vector features: NLS, nuclear localization signal; Kan(R), kanamycin resistance gene; attL1 and attL2, recombination sites (allow recombinational cloning of the gene of interest from an entry clone (Landy, A. Dynamic, structural, and regulatory aspects of lambda site-specific recombination". Ann. Rev. Biochem. 1989; 58:913-49. Review); pENTR-funct-vec-for and pENTR-funct-vec-rev, primer binding sites; rrnB T1 and T2 transcription terminators (protect the cloned gene from expression by vector-encoded promoters, thereby reducing possible toxicity (Orosz et al. Analysis of the complex transcription termination region of the *Escherichia coli* rrnB gene. Eur. J. Biochem. 201(3):653-9 (1991)); T7 promoter/priming site (allows in vitro transcription in the sense orientation and sequencing through the insert; M13 Forward (−20) priming site (allows sequencing in the sense orientation); V5 epitope Gly-Lys-Pro-Ile-Pro-Asn-Pro-Leu-Leu-Gly-Leu-Asp-Ser-Thr (SEQ ID NO: 88) (allows detection of the recombinant fusion protein by the Anti-V5 antibodies (Southern et al. Identification of an epitope on the P and V proteins of simian virus 5 that distinguishes between two isolates with different biological characteristics. 0.1 Gen Virol. 72 (Pt 7):1551-7 (1991)); pUC origin (allows high-copy number replication and growth in *E. coli*); Gly-Ser linker (flexible peptide linker to prevent steric hindrance between domains unique restriction enzyme cleavage sites are indicated for each vector).
Figure 8B:
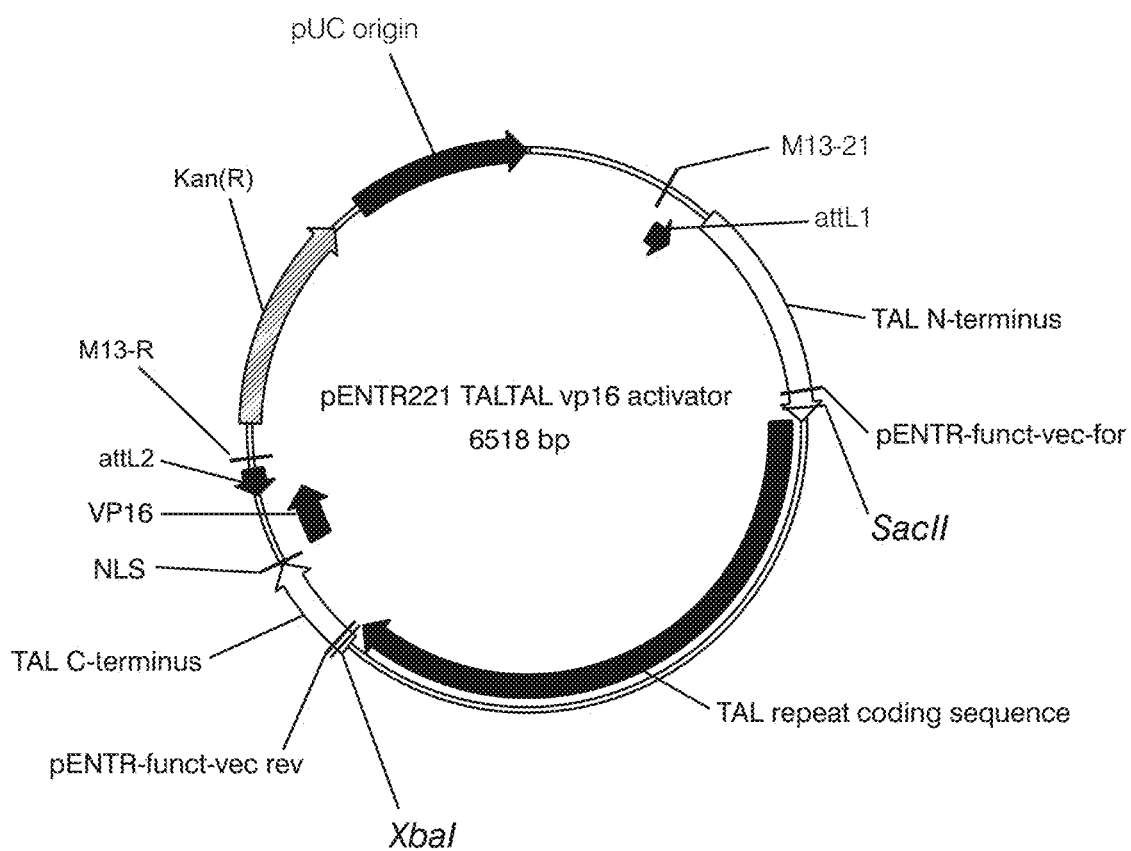
Figure 8C:
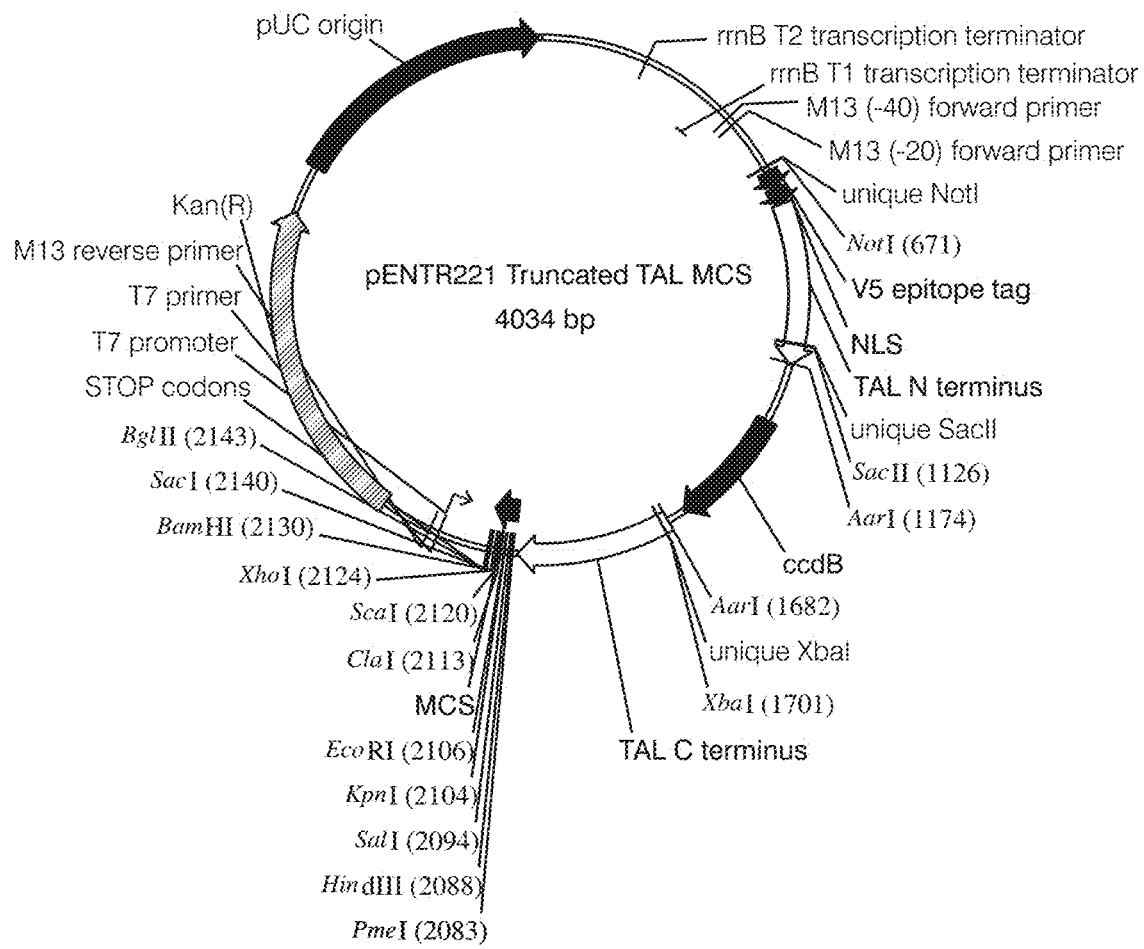

A series of closed, circular nucleic acid molecule into which TAL cassettes and TAL repeats may be inserted are shown in FIG. 7C. This figure shows vectors which may be used to generate (1) a TAL effector-FokI fusion nuclease pair, (2) a TAL effector-VP16, (3) a TAL effector-KRAB domain fusion, and (4) a TAL effector-effector protein (e.g., acetylase, deacetylase, methylase, demethylase, kinase, phosphatase, etc.) fusion. In each instance, the starting nucleic acid molecule is digested with a restriction enzyme that cuts at a site which differs from the recognition site (e.g., a Type II restriction enzymes such as a Type IIS enzymes). The results is excision of ccdB (or alternatively tse2) coding sequence from the vector and the formation of a linear vector. This vector may have any of the following: (1) two blunt termini, (2) two termini with overhanging ends (e.g., two 5' overhangs, two 3' overhangs, or a 5' and a 3' overhang), one blunt terminus and on overhanging terminus (a 5' or a 3' overhang).

Termini may be linked by any number of methods. Ligases (e.g., T4 DNA ligase) and topoisomerases are examples of enzymes which may be used to covalently connect one or both strands of different termini to each other. Ligases may be used, for example, to covalently connect both strands of both termini of a vector with both strands of both termini of another nucleic acid molecule (e.g., an insert) to generate an un-nicked, closed, circular nucleic acid molecule. As a specific example (see FIG. 10A), one terminus of the vector and one terminus of the other nucleic acid molecule may have complementary overhangs and the two other termini of both molecules may be blunt. In such a case, the complementarity of the overhanging termini may be used to direct to orientation by which the two nucleic acid molecules are connected to each other (e.g., so that the insert molecule go into the vector molecules in the same orientation).

Topoisomerase are categorized as type I, including type IA and type IB topoisomerase, which cleave a single strand of a double stranded nucleic acid molecule, and type II topoisomerase (gyrase), which cleave both strands of a nucleic acid molecule. Type IA and IB topoisomerases cleave one strand of a double-stranded nucleotide molecule. Cleavage of a double-stranded nucleotide molecule by type IA topoisomerases generates a 5' phosphate and a 3' hydroxyl at the cleavage site, with the type IA topoisomerase covalently binding to the 5' terminus of a cleaved strand. In comparison, cleavage of a double-stranded nucleotide molecule by type IB topoisomerases generates a 3' phosphate and a 5' hydroxyl at the cleavage site, with the type IB topoisomerase covalently binding to the 3' terminus of a cleaved strand. Type I and type II topoisomerases, as well as catalytic domains and mutant forms thereof, are useful for generating double-stranded recombinant nucleic acid molecules.

Type IA topoisomerases include *E. coli* topoisomerase I, *E. coli* topoisomerase III, eukaryotic topoisomerase II, archeal reverse gyrase, yeast topoisomerase III, *Drosophila* topoisomerase III, human topoisomerase III, *Streptococcus pneumoniae* topoisomerase III, and the like, including other type IA topoisomerases. *E. coli* topoisomerase III, which is a type IA topoisomerase that recognizes, binds to and cleaves the sequence 5'-GCAACTT-3', can be particularly useful in methods of the invention.

Type IB topoisomerases include the nuclear type I topoisomerases present in all eukaryotic cells and those encoded by Vaccinia and other cellular poxviruses. The eukaryotic type IB topoisomerases are exemplified by those expressed in yeast, *Drosophila* and mammalian cells, including human cells. Viral type IB topoisomerases are exemplified by those produced by the vertebrate poxviruses (Vaccinia, Shope fibroma virus, ORF virus, fowlpox virus, and *Molluscum contagiosum* virus), and the insect poxvirus (*Amsacta moorei* entomopoxvirus).

Type II topoisomerases include, for example, bacterial gyrase, bacterial DNA topoisomerase IV, eukaryotic DNA topoisomerase II, and T-even phage encoded DNA topoisomerases. Like the type IB topoisomerases, the type II topoisomerases have both cleaving and ligating activities. In addition, like type IB topoisomerase, substrate double-stranded nucleic acid molecules can be prepared such that the type II topoisomerase can form a covalent linkage to one strand at a cleavage site. For example, calf thymus type II topoisomerase can cleave a substrate double-stranded nucleic acid molecule containing a 5' recessed topoisomerase recognition site positioned three nucleotides from the 5' end, resulting in dissociation of the three nucleotide sequence 5' to the cleavage site and covalent binding the of the topoisomerase to the 5' terminus of the double-stranded nucleic acid molecule. Furthermore, upon contacting such a type II topoisomerase-charged double-stranded nucleic acid molecules with a second nucleotide sequence containing a 3' hydroxyl group, the type II topoisomerase can ligate the sequences together, and then is released from the recombinant nucleic acid molecule. As such, type II topoisomerases may be incorporated into compositions of the invention and also are useful for performing methods of the invention.

The invention includes methods for generating double-stranded nucleic acid molecules molecule with topoisomerase covalently linked at least one terminus. As an example, a double-stranded nucleic acid molecule with the following sequence at a terminus:

```
CCCTTATT-3' Terminus

GGGAATAA-5' Terminus
``` may be contact with a Vaccinia topoisomerase (a Type IB topoisomerase) under conditions suitable to generate the following terminus:

```
CCCTT-3' Terminus

GGGAATAA-5' Terminus
``` with topoisomerase covalently bound to the 3' phosphate. After nicking of the double-stranded nucleic acid molecule, the ATT segment will no longer be covalently bound and will tend to dissociate from the double-stranded nucleic acid molecule, leaving an overhanging sequence of 3'-TAA-5'.

The invention thus includes (1) nucleic acid molecules which contain one or more (e.g., one, two, three, four, five, six, from about one to about two, from about one, to about five, etc.) topoisomerase recognition sites, (2) nucleic acid molecules which contain one or more bound (e.g., covalently bound) topoisomerase, (3) methods for producing nucleic acid molecules of (1) and (2), and (4) methods for connecting nucleic acid molecules of (1) and (2), to other nucleic acid molecules.

Figure 10A:
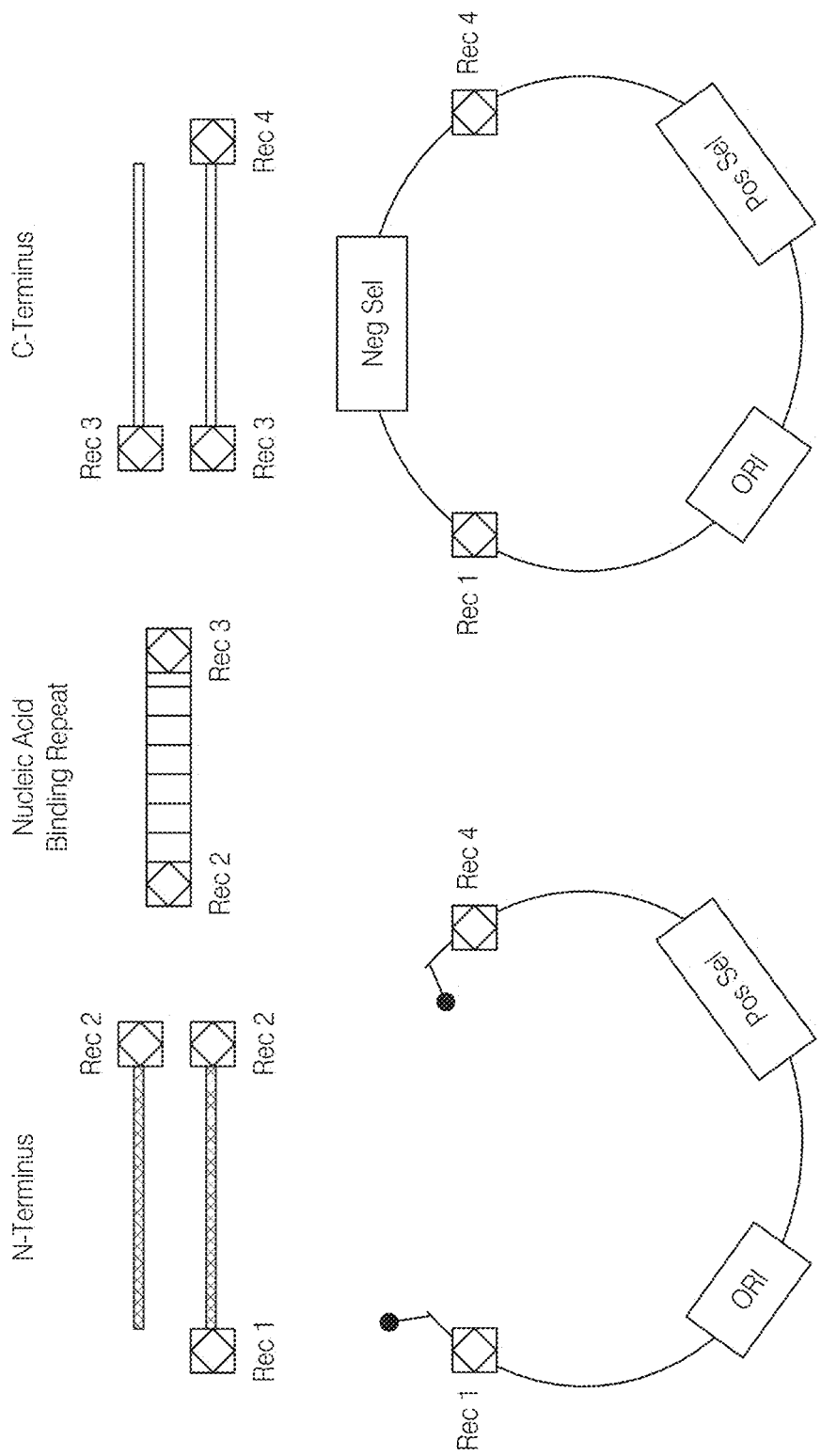
FIG. 10A shows (1) three types of amino acid coding sequences, labeled "N-Terminus", "Nucleic Acid Binding Repeat", and "C-Terminus", (2) topoisomerase adapted linear vector (lower left) and a closed circular vector. The boxes with diamond shapes in them represent recombination sites (e.g., GATEWAY™ sites) with different recombination specificities indicated by "Rec. No." Covalently bound topoisomerase proteins are represented at the termini of the linear vector by the closed circle connected to the vector by a solid line. "ORI" refers to an origin of replication, "Pos Sel" refers to a positive selectable marker, and "Neg Sel" refers to a negative selectable marker.
Figure 10B:
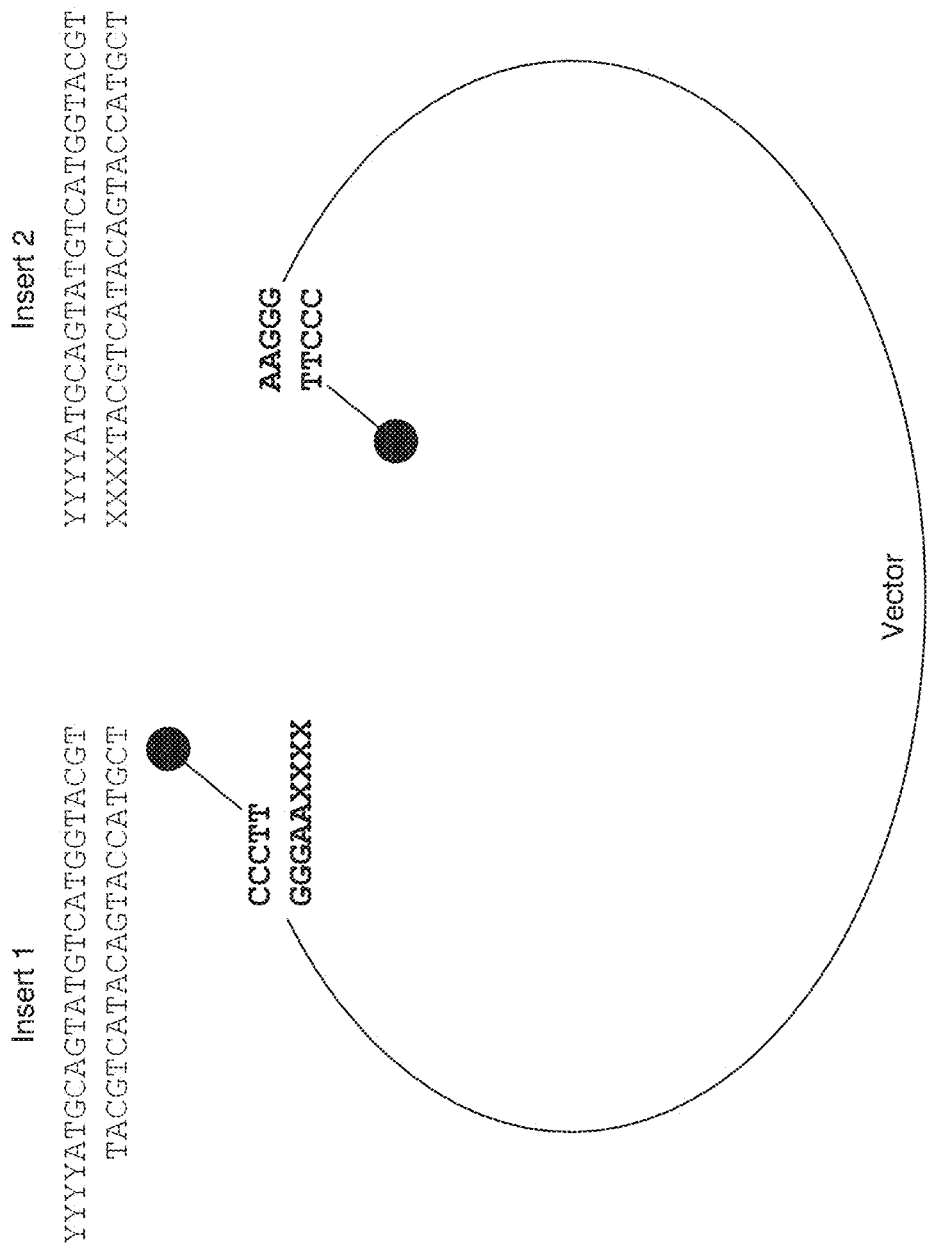
FIG. 10B shows a linear vector containing topoisomerase covalently bound at both ends. Also shown are two types of inserts (labeled "Insert 1" (SEQ ID NOS 135-136, respectively, in order of appearance) and "Insert 2" (SEQ ID NOS 135 and 137, respectively, in order of appearance), each with sequence identity at one end with one terminus of the vector.
Figure 10C:
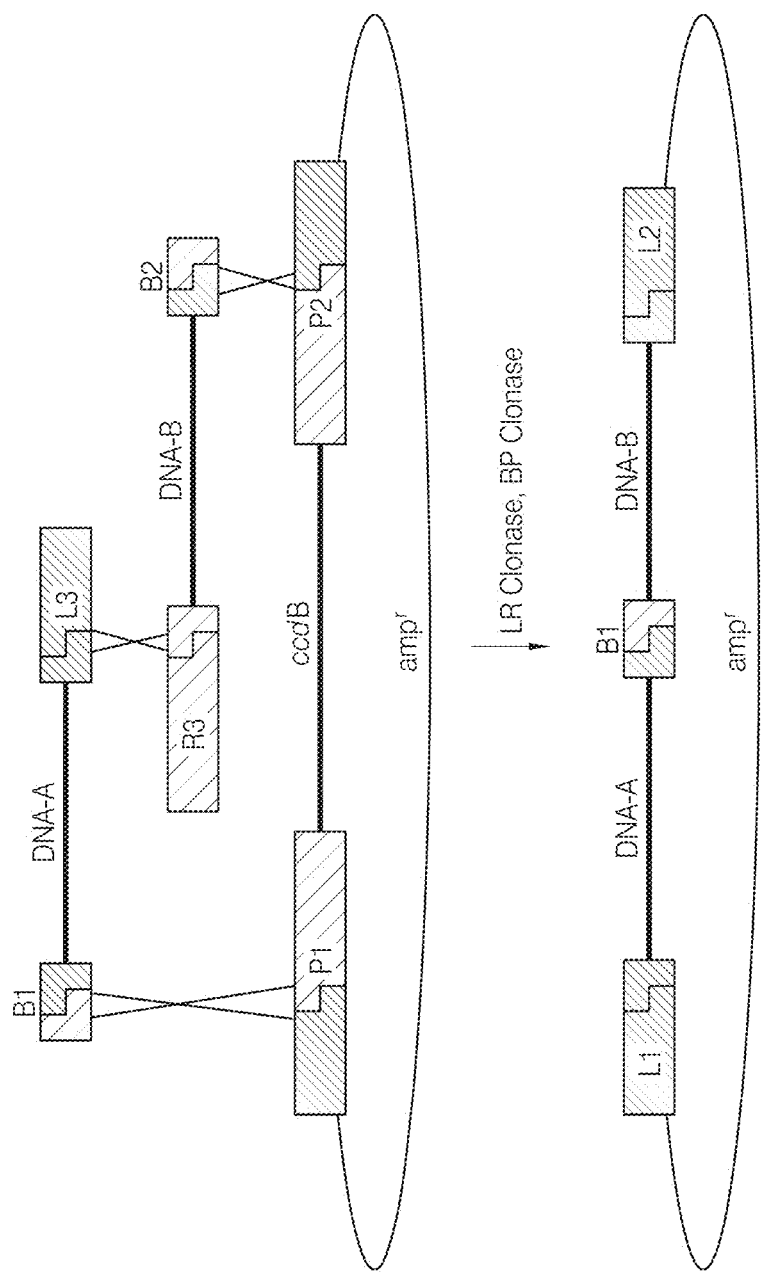
FIG. 10C shows a GATEWAY™ recombination reaction series in which two nucleic acid segments (labeled "DNA-A" and "DNA-B") are introduced into a circular nucleic acid molecule while a ccdB (or alternatively tse2) gene is excised from the circular nucleic acid molecule. The attB, attP, attL, and attR sites are each identified by single letter identifiers (e.g., B, P, L, and R). The numbers (i.e., 1, 2, and 3) following the letter att site type identifiers refer to recombination site specificities.
Figure 10F:
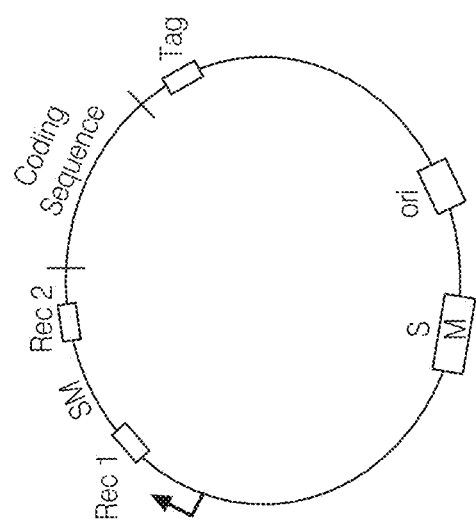
FIGS. 10D to 10F show three exemplary vector formats which may be used for assembly nucleic acids encoding TAL effectors and expression of TAL effector proteins and TAL fusions.
Figure 10E:
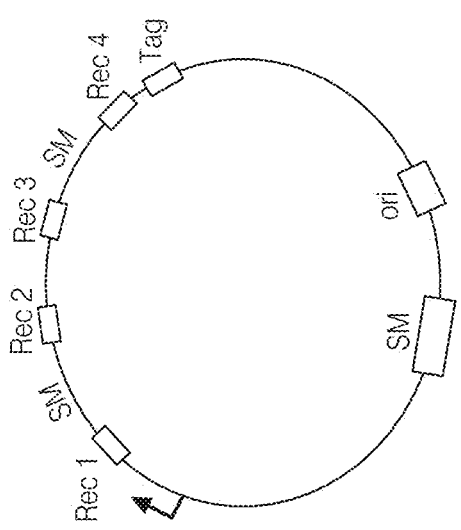
Figure 10D:
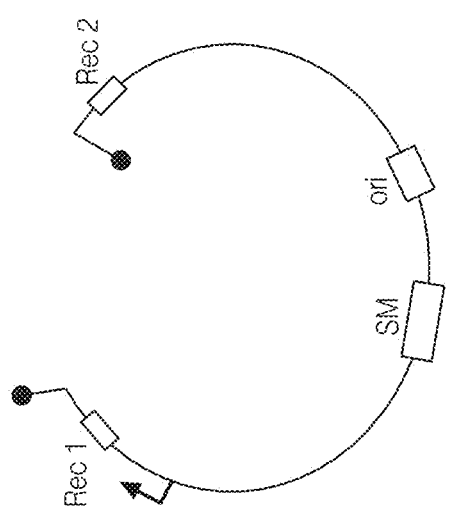

FIG. 10A shows one embodiment where topoisomerase is covalently bound to the 3' phosphate at both ends of the vector. When a compatible nucleic acid terminus (a terminus with a strand having a 5' hydroxyl) comes into contact with the topoisomerase adapted terminus, strands of each terminus are covalently connected to each other, resulting is a nick at or near the junction point. This nick may be repaired by any number of means but will normally be automatically repaired upon introduction into a cell by DNA repair mechanisms.

Two types of inserts are shown in FIG. 10A. Insert 1 is designed to hybridize with the vector by sequence complementarity of overhanging ends (with Y being bases that will pair with X bases). Insert 2 hybridizes to the vector also by sequence complementarity by a strand invasion mechanism whereby the single stranded 3' XXXX sequence of the vector hybridizes to the 5' YYYY sequence of Insert 2, resulting in a "flap" of Xs hanging off of Insert 2. Further, the 5' terminal Y of Insert 2 becomes covalently bound to the 3' T of the vector. This covalent bound stabilizes the association of the vector with Insert 2. As with nicks, the flap may be automatically removed by introduction of the assembly into a cell with functional DNA repair mechanisms, resulting in a junction where both strands are covalently bound to each other and complete hybridization of regional nucleotides (e.g., no mismatched bases).

Nucleic acid molecule of the invention and used in the practice of the invention may also contain recombination sites, also referred to as recombinational cloning site. Recombination sites suitable for use in the invention may be any nucleic acid that can serve as a substrate in a recombination reaction. Such recombination sites may be wild-type or naturally occurring recombination sites, or modified, variant, derivative, or mutant recombination sites. Examples of recombination sites for use in the invention include, but are not limited to, lambda phage recombination sites (such as attP, attB, attL, and attR and mutants or derivatives thereof) and recombination sites from other bacteriophage such as phi80, P22, P2, 186, P4 and P1 (including lox sites such as loxP and loxP511). Mutated att sites (e.g., attB, attP, attR and attL sites) are described in U.S. Patent Publication No. 2011/0275541, which is incorporated herein by reference. Other recombination sites having unique specificity (i.e., a first site will recombine with its corresponding site and will not recombine with a second site having a different specificity) are known to those skilled in the art and may be used to practice the present invention. Corresponding recombination proteins for these systems may be used in accordance with the invention with the indicated recombination sites. Other systems providing recombination sites and recombination proteins for use in the invention include the FLP/FRT system from *Saccharomyces cerevisiae*, the resolvase family (e.g., γδ, TndX, TnpX, Tn3 resolvase, Hin, Hjc, Gin, SpCCE1, ParA, and Cin), and IS231 and other *Bacillus thuringiensis* transposable elements. Other suitable recombination systems for use in the present invention include the XerC and XerD recombinases and the psi, dif and cer recombination sites in *E. coli*. Suitable recombination proteins and mutant, modified, variant, or derivative recombination sites for use in the invention include the GATEWAY® Cloning Technology and Multi-Site GATEWAY® Cloning Technology are available from Life Technologies Corp. (Carlsbad, Calif.)

Att site based recombination systems that may be used in conjunction with the present invention include those which rely on the following principles of operation. In the presence of a mixture of specific recombination proteins, attB site will recombine with attP sites, resulting in the generation of attL sites and attR sites. The reverse reaction may also occur in the presence of another mixture of specific recombination proteins. Further, att sites have been designed and may further be designed which have particular recombination specificities Representative examples of recombination sites which can be used in the practice of the invention include att sites referred to above. Att sites which specifically recombine with other att sites can be constructed by altering nucleotides in and near the 7 base pair overlap region. Thus, recombination sites suitable for use in the methods, compositions, and vectors of the invention include, but are not limited to, those with insertions, deletions or substitutions of one, two, three, four, or more nucleotide bases within the 15 base pair core region (GCTTTTTTATACTAA (SEQ ID NO:70)), which is identical in all four wild-type lambda att sites: attB, attP, attL and attR. Recombination sites suitable for use in the methods, compositions, and vectors of the invention also include those with insertions, deletions or substitutions of one, two, three, four, or more nucleotide bases within the 15 base pair core region referred to above and those which are at least 50% identical, at least 55% identical, at least 60% identical, at least 65% identical, at least 70% identical, at least 75% identical, at least 80% identical, at least 85% identical, at least 90% identical, or at least 95% identical to this 15 base pair core region.

The region defined by the sequence TTTATAC in the 15 base pair is referred to the seven base pair overlap region. The seven base pair overlap region is the cut site for the integrase protein and is the region where strand exchange takes place.

Altered att sites have been constructed which demonstrate that (1) substitutions made within the first three positions of the seven base pair overlap (TTTATAC) strongly affect the specificity of recombination, (2) substitutions made in the last four positions (TTTATAC) only partially alter recombination specificity, and (3) nucleotide substitutions outside of the seven by overlap, but elsewhere within the 15 base pair core region, do not affect specificity of recombination but do influence the efficiency of recombination. Thus, nucleic acid molecules and methods of the invention include those which comprising or employ one, two, three, four, five, six, eight, ten, or more recombination sites which affect recombination specificity, particularly one or more (e.g., one, two, three, four, five, six, eight, ten, twenty, thirty, forty, fifty, etc.) different recombination sites that may correspond substantially to the seven base pair overlap within the 15 base pair core region, having one or more mutations that affect recombination specificity. Particularly, such molecules may comprise a consensus sequence such as NNNATAC, wherein "N" refers to any nucleotide (i.e., may be A, G, T/U or C), as well as modified and non-standard nucleotides such as inosine. In some instances, if one of the first three nucleotides in the consensus sequence is a T/U, then at least one of the other two of the first three nucleotides is not a T/U. Exemplary seven base pair att site overlap regions suitable for with the invention are set out in TABLE 16.

TABLE 16

AAAATAC CAAATAC GAAATAC TAAATAC AACATAC CACATAC

GACATAC TACATAC AAGATAC CAGATAC GAGATAC TAGATAC

AATATAC CATATAC GATATAC TATATAC ACAATAC CCAATAC

TABLE 16-continued

```
GCAATAC TCAATAC ACCATAC CCCATAC GCCATAC TCCATAC

ACGATAC CCGATAC GCGATAC TCGATAC ACTATAC CCTATAC

GCTATAC TCTATAC AGAATAC CGAATAC GGAATAC TGAATAC

AGCATAC CGCATAC GGCATAC TGCATAC AGGATAC CGGATAC

GGGATAC TGGATAC AGTATAC CGTATAC GGTATAC TGTATAC

ATAATAC CTAATAC GTAATAC TTAATAC ATCATAC CTCATAC

GTCATAC TTCATAC ATGATAC CTGATAC GTGATAC TTGATAC

ATTATAC CTTATAC GTTATAC TTTATAC
```

Type IIS Topoisomerase Assembly Toolkit.

Based on type IIS restriction-mediated shuffling and topoisomerase mediated cloning the inventors have further developed a high throughput friendly DNA assembly kit suitable for assembling complex DNA binding effector molecules which provides a commercial solution, rich in consumables, for DNA shuffling cloning. In some aspects, the kit allows for rapid generation of intermediate cloning vectors that can be combined to generate the final full-length construct. One possible workflow of performing the invention is summarized in FIG. 11A of this document. In this example, a series of topoisomerase adapted donor vectors with symmetrical ends are built that differ only on the kind of type IIS restriction sites present at their ends. A design software tool selects a donor vector that is compatible with the nucleic acid sequence to be assembled. In other words, the corresponding type IIS restriction sites must be absent in the input sequence. The design software also generates the subsequences or sequence fragments that will appear in each entry clone (i.e., a donor vector with insert) based on compatibility of the adjacent ends. Thus, in some embodiments, the choice of topoisomerase adapted vector and the fragmentation of a given full-length sequence can be determined by a gene assembly algorithm that analyzes the input sequence, identifies non-cutter type IIS restriction enzymes, and recommends a subcloning strategy. One advantage of the invention is the symmetrical nature of the donor vector which does not impose limitations on the direction of the cloned sequence, virtually eliminating screening requirements. In an analogy with the MultiSite GATEWAY® technology (see, e.g., U.S. Pat. No. 8,030,066, the disclosure of which is incorporated herein by reference), the resulting entry clones carrying subfragments in unspecific orientation are combined with a target or destination vector (e.g., a functional vector) harboring compatible ends (e.g., flanking a counter selectable marker in the parental plasmid). An enzymatic mix composed of at least the corresponding type IIS restriction enzyme plus ligase is added, and after a brief incubation period an aliquot is transformed into competent cells. The resulting clone may for example be an expression vector.

Thus, in some embodiments, the invention comprises a product composed at least of: a web tool that (i) is capable of splitting a given wild-type sequence into smaller parts, (ii) develops an assembly strategy for the entry and expression clones based on cleavage sites absent in the wild-type sequence, (iii) designs the required oligonucleotides and (iv) indicates what kit should be used; and a series of kits (A, B, C, . . . N), each composed at least of (i) a linear topoisomerase-adapted (donor) vector, (ii) an enzyme mix comprising at least a DNA ligase and a type IIS cleavage enzyme, (iii) a (linearized) destination vector, and (iv) competent cells.

In another aspect, a customized kit differs from the series of different kits in the kind of type IIS restriction enzyme cleavage sites of the donor and destination vectors and the kind of type IIS restriction enzyme present in the enzyme mixture.

In one embodiment, the invention relates to a customized assembly kit as described above, wherein the destination vector is a functional TAL effector vector.

Figure 11A:
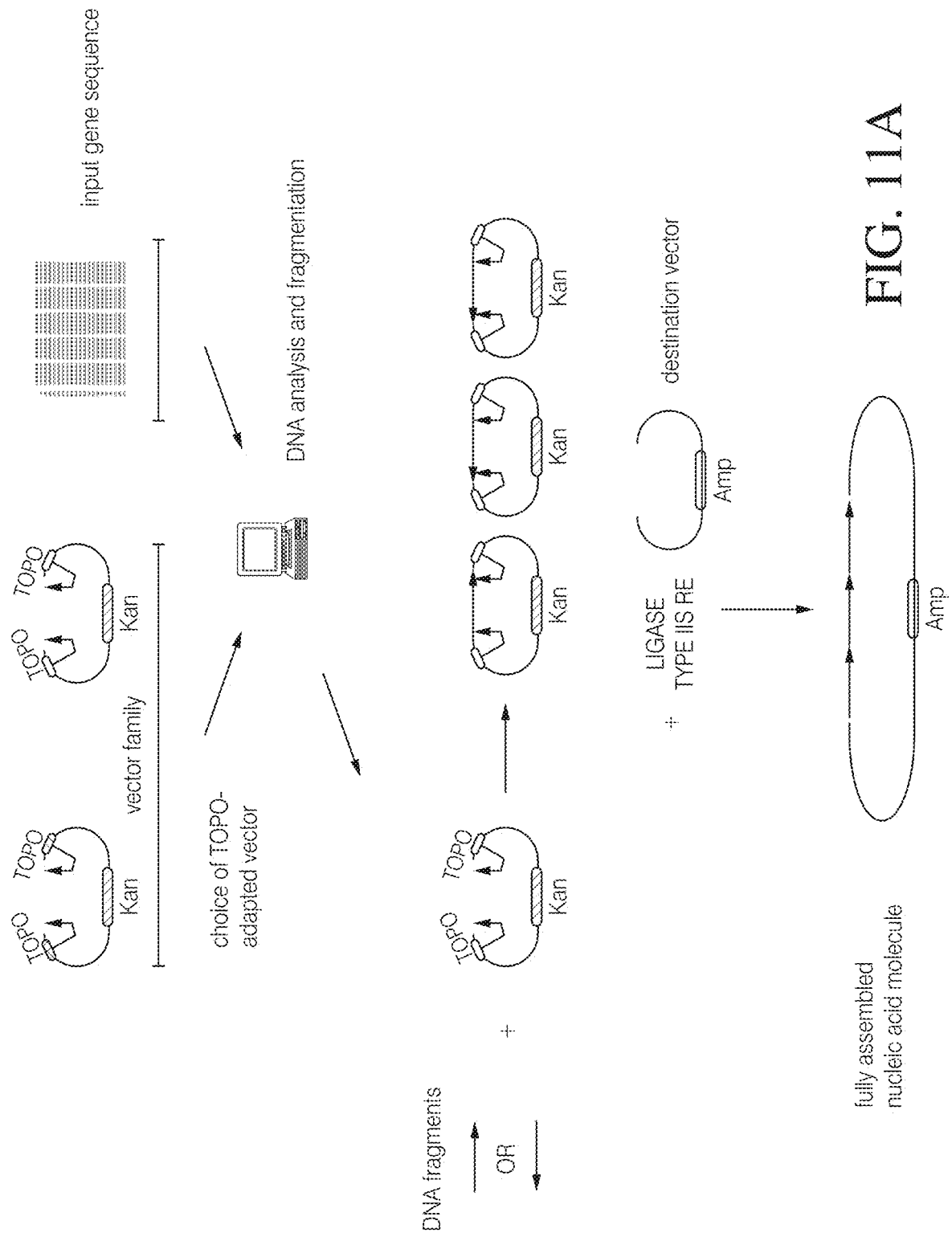
FIG. 11A shows an example of high throughput DNA assembly kit based on type IIS and topoisomerase mediated cloning. In this instance, a series of topoisomerase-adapted vectors containing symmetrical ends are designed that differ only in terminal type IIS restriction sites. Following analysis of an input sequence a design software tool selects a specific topoisomerase-adapted vector that is compatible with the nucleic acid sequence to be assembled and generates subfragments of the sequence. The subfragments obtained, e.g., by PCR are cloned into the selected topoisomerase-adapted vector in unspecific orientation. The resulting vector library is then combined with a target vector in the presence of an enzyme mix containing at least one type IIS restriction enzyme and a ligase, and the subfragments are assembled into the target vector in directed orientation due to their compatible ends.
Figure 11B:
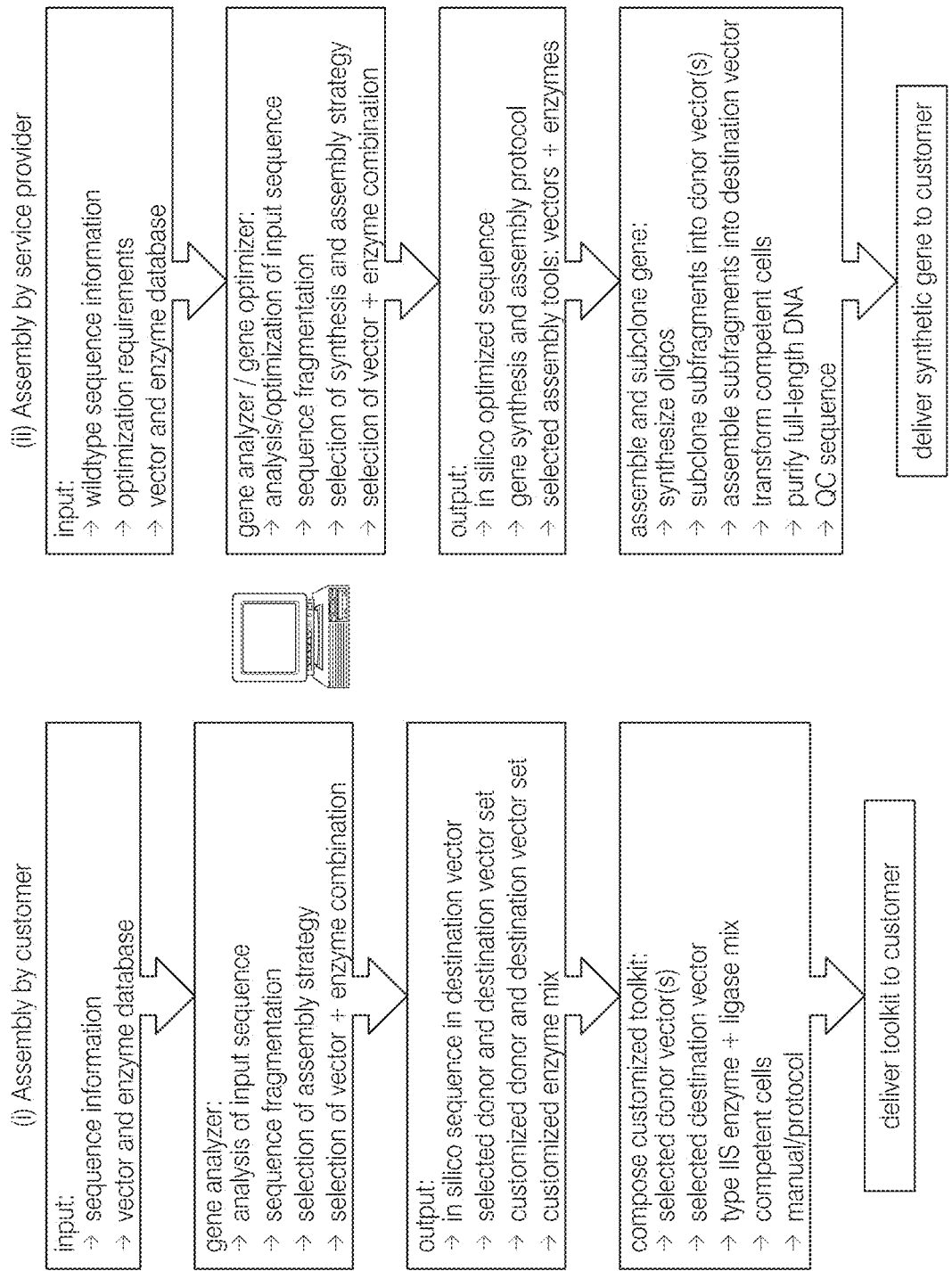
FIG. 11B illustrates two different exemplary workflows integrating a seamless cloning kit or the underlying assembly method in services offered by a service provider. In the left workflow an assembly strategy is developed by a service provider based on customer sequence information and the customer is provided with an individual toolkit comprising a selection of vectors (e.g., topoisomerase-adapted and target vectors), a ready-to-use enzyme mix, and competent cells together with an assembly protocol. The customer can use the kit to assemble available DNA fragments. The workflow on the right can be applied e.g., where no DNA template is available or customer requests an optimized or modified sequence. In this case, the service provider can integrate the vectors and assembly strategy illustrated in FIG. 7A into the internal manufacturing process to assemble de novo synthesized DNA fragments. The full-length synthetic gene is subjected to a quality control (QC) process and shipped to the customer.

Topoisomerase based assembly kits can be used by customers to assemble DNA subfragments that have been obtained, e.g., by PCR amplification, restriction digest or other methods known in the art (FIG. 11B, left chart). Thus, the invention relates, in part, to a first workflow for gene assembly including some or all of the following steps: (i) obtaining an input sequence from a customer and obtaining vector sequence information and restriction enzyme information from at least one database; (ii) analyzing the input sequence at least for absent cleavage sites, generating subfragments of the sequence by computer-aided means; generating an assembly strategy by computer-aided means and selecting vector and enzyme combinations from at least one database; (iii) composing a customized toolkit comprising at least (a) one or more topoisomerase-adapted donor vectors with flanking type IIS recognition sites, (b) a destination vector with a selectable marker sequence, (c) an enzyme mix containing at least one type IIS enzyme and a ligase and (d) competent cells; and (iv) shipping the customized toolkit to the customer for assembly.

In cases where no DNA template is available or customer requests an optimized or modified sequence, a gene synthesis service provider can integrate the vectors and assembly methods illustrated in FIG. 11A into the internal manufacturing process to assemble de novo synthesized and optionally optimized and/or modified genes which are then cloned, purified and subjected to a quality control (QC) process before the final synthetic gene is delivered to a customer. Thus, the invention relates, in part, to a second workflow for gene assembly including some or all of the following steps: (i) obtaining an input sequence from a customer and, optionally a request for sequence optimization, and obtaining vector sequence information and restriction enzyme information from at least one database; (ii) analyzing the input sequence at least for absent cleavage sites, optionally optimizing the input sequence by computer-aided means, generating subfragments of the sequence by computer-aided means, generating an assembly strategy by computer-aided means and selecting vector and enzyme combinations from at least one database; (iii) synthesizing the subfragments from overlapping oligonucleotides; (iv) cloning the subfragments into one or more topoisomerase-adapted donor vectors with flanking type IIS recognition sites; (v) assembling the subfragments simultaneously into at least one destination vector; (vi) transforming competent cells, and (vii) deliver purified and QC analysed synthetic gene to the customer.

The invention also relates to embodiments of either of the above workflows wherein the destination vector is a functional vector containing at least the N- and C-terminal flanking sequences of a TAL effector and, optionally an effector fusion sequence, and wherein the subfragments are TAL nucleic acid binding cassettes and/or TAL repeats.

Universal TAL Assembly Kit.

Apart from customized vector services or web-aided toolkits as described above, a universal TAL assembly kit may be an interesting alternative for customers who prefer doing most of the work themselves using standardized parts. In such instances, all components required for TAL effector assembly would be delivered in kit format by a service provider and assembly performed by customer according to the provided protocol. A universal TAL assembly kit that can be used for the assembly of various TAL effector fusions with any desired binding specificity. As described elsewhere herein, a TAL effector may contain a variable amount of repeats (typically between 1.5 and 33.5). The advantage of a smaller amount of repeats is the reduced complexity of assembly steps whereas a larger amount of repeats may be more reliable in terms of binding efficiency and specificity. The amount of repeats to be assembled by means of a universal assembly kit should therefore be in a reasonable range resulting in reliable binding without making correct assembly an experimental challenge. A smaller amount of repeats (such as, e.g., 6, 8 or 10 repeats) may be assembled by a two-step assembly method according to one of the protocols described herein using monomeric cassette building blocks, i.e., one cassette per building block. For example, three cassettes may be assembled into two capture vectors each and the two resulting trimers subsequently combined into a functional vector. Likewise, five cassettes may be assembled into each capture vector and the resulting 5-mers combined into a 10-mer repeat in the functional vector. In cases where larger arrays are to be assembled, a repeat library containing pre-synthesized combinations of two or more cassettes may be useful to limit the amount of fragments to be assembled per step and the amount of parallel assembly reactions.

A universal assembly kit of the invention may therefore contain a ready to use TAL cassette library, i.e., a collection of building blocks containing a specific combination of two, three or four or even more TAL cassettes. One embodiment of the invention described herein provides for trimer or tetramer libraries to assemble arrays of about 17.5 or 23.5 or even more repeats. Whereas trimer or tetramer libraries may be preferred in high-throughput assembly settings as described above, a library containing fewer building blocks may be a better starting point for a universal and well-arranged assembly kit. To provide a complete collection of triplet combinations of binding cassettes representing all possible positions within a 17.5 or a 23.5 repeat containing TAL effector, a trimer library would require a huge amount of individual constructs (512 clones in Example 3) which may be difficult to store and/or handle in a kit system. In contrast, using a library based on TAL repeat dimers would reduce the amount of required building blocks per kit without limiting the possibility to assemble all combinations of TAL nucleic acid binding cassettes. Whereas such dimer library can be provided to customer in a well-arranged format, the kit provider benefits from less manufacture work or reproduction of fewer components per kit which makes the kit more cost-efficient.

the cassettes of the kit may contain the following RVDs: NI for A, NK for G, HD for C and NG for T. As described elsewhere herein, alternative RVDs may be chosen as some bases are bound by different RVDs whereas some RVDs bind different bases (e.g., methylated versus non-methylated cytosine). The combination of each of the cassettes into pairs results in 16 distinct combinations (NI-NI, NI-NK, NI-HD, NI-NG, NK-NK, NK-HD, NK-NG, HD-HD, HD-NI, HD-NK, HD-NG, NG-NG, NG-NI, NG-NK, NG-HD). To allow for directed assembly into each possible position within a given repeat array each pair is flanked by a 5'region containing at least a first type IIS restriction enzyme cleavage sites at the and by a 3' region containing at least a second type IIS restriction enzyme cleavage site which generate unique protruding ends after cleavage. In one embodiment the 5' and 3' regions of each cassette pair have identical cleavage recognition sites but produce different single stranded overhangs upon cleavage to allow for directional assembly. Typically, the cassette pairs with cleavable 5' and 3' regions are inserted into plasmids to be stored as individual dimer building blocks. A selected set of building blocks can then be assembled into a capture vector by simultaneous cleavage according to the "Golden Gate" cloning strategy as described elsewhere herein to connect each cassette pair with a compatible overhang of another pair or with a compatible overhang of the respective capture vector.

Figure 32A:
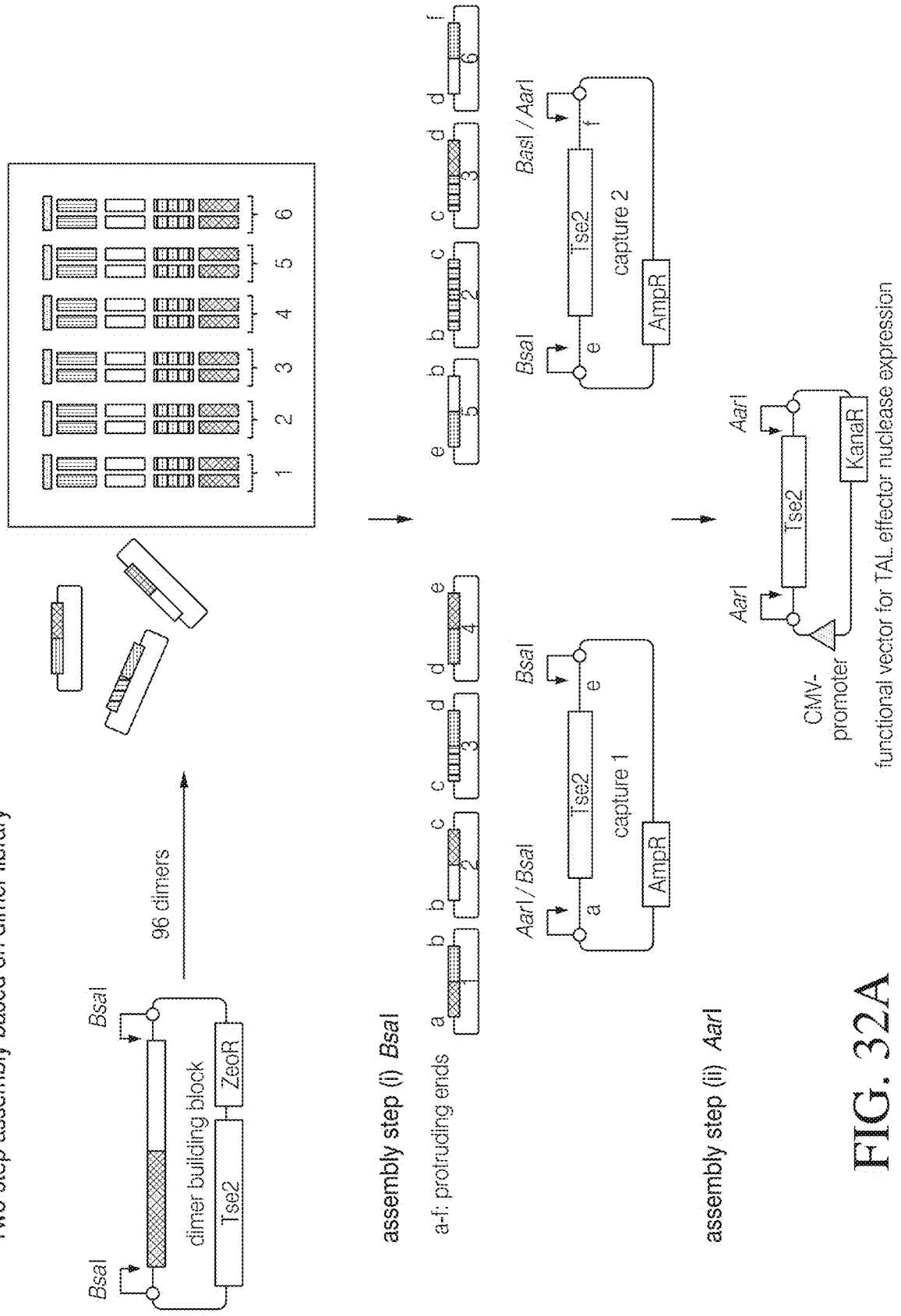
FIG. 32A and FIG. 32B show an exemplary kit and method for type IIS-mediated assembly of a TAL effector nuclease based on a dimer library of TAL cassette building blocks.

FIG. 32A shows an example of how a collection of dimer building blocks can be organized to allow for the assembly of a 16-repeat TAL array. In this example, a library of 96 TAL repeat dimer blocks, i.e., a collection of 96 purified plasmids each containing a pair of TAL binding cassettes is provided for two step-assembly of a TAL effector fusion. In a first step, 4 selected dimer pairs are assembled into each of the two capture vectors via BsaI-mediated cleavage. In the second step, the resulting 8-mers are combined into a functional expression vector encoding a nuclease function via AarI-mediated cleavage. As indicated in FIG. 32A and shown in TABLE 17 below, 6 variants of each of the 16 dimers are sufficient to represent all required compatible ends for co-assembly of four selected cassette pairs into each capture vector to generate a 16-repeat array. The outside dimer building blocks (variants 1, 4, 5 and 6 in the example of FIG. 32A) provide protruding ends that must be compatible with the ends of the first and second capture vectors and can therefore not be recycled at other positions. However, the internal building blocks (variants 2 and 3 in the example of FIG. 32A) can be allocated to positions 2 and 3 of both capture vectors, respectively, thereby reducing the amount of variants per vector to 6 (instead of 8) which results in a total amount of 6×16=96 required dimer building blocks. The compatibility of the protruding ends of each variant is shown in TABLE 17:

TABLE 17

| letters a to f represent individual overhangs generated on the 5' or 3' terminal ends of each building block or capture vector | | | | | |
|---|---|---|---|---|---|
| Variant 1 | Variant 2 | Variant 3 | Variant 4 | Variant 5 | Variant 6 |
| 5'-a-----b-3' | 5'-b-----c-3' | 5'-c-----d-3' | 5'-d-----e-3' | 5'-e-----b-3' | 5'-d-----f-3' |

A dimer library of the invention contains at least four different categories of cassettes each of which allows for specific binding of a base via its defined RVD. For example, As discussed above, the complexity of each multimer library can be further reduced depending on the amount of repeats to be assembled. For example, a kit using a dimer library designed for the assembly of 12 repeats may only require 5×16=80 dimer building blocks if three dimers are assembled into each capture vector. A kit with 5×16=80 dimer building blocks may also be used to co-assemble 5 dimers into a 10-repeat array in only one assembly step. In an alternative embodiment, more repeats can be assembled from a dimer library in the first step if a third capture vector is available. In such case, three dimers would be assembled into each capture vector in the first step and the resulting hexamers would be combined into the functional vector. Many different combinations are feasible. However, it should be taken into account that more parallel reactions may be less user-friendly and the assembly may become more error-prone with an increasing amount of fragments to be co-assembled in each step. Thus, for the assembly of larger arrays (e.g., requiring more than three capture vectors in a first assembly step), the use of a trimer or tetramer library as discussed above may be preferred to limit the amount of reactions. Also the assembly of many large fragments should be avoided as the efficiency decreases with fragment length.

The number of variants per dimer building block that are required to assemble a given amount of repeats depends on the assembly strategy. To calculate a minimum set of variants the number of capture vectors in a first assembly step and the number of building blocks co-assembled into each capture vector must be taken into account. The principle of the underlying calculation is demonstrated in TABLE 18 below.

TABLE 18

| CAS | $BB_{CV1}$ | $BB_{CV2}$ $(CV2_{Int})$ | $BB_{CV3}$ $(CV3_{Int})$ | $BB_{tot}$ | $n = BB_{tot} - (CV2_{Int} + CV3_{Int})$ | n × 16 |
|---|---|---|---|---|---|---|
| 24 | 4 | 4 (2) | 4 (2) | 12 | =12 − (2 + 2) = 8 | 128 |
| 22 | 4 | 4 (2) | 3 (1) | 11 | =11 − (2 + 1) = 8 | 128 |
| 20 | 4 | 3 (1) | 3 (1) | 10 | =10 − (1 + 1) = 8 | 128 |
| 18 | 3 | 3 (1) | 3 (1) | 9 | =9 − (1 + 1) = 7 | 112 |
| 16 | 4 | 4 (2) | 0 | 8 | =8 − (2 + 0) = 6 | 96 |
| 14 | 4 | 3 (1) | 0 | 7 | =7 − (1 + 0) = 6 | 96 |
| 12 | 3 | 3 (1) | 0 | 6 | =6 − (1 + 0) = 5 | 80 |
| 10 | 3 | 2 (0) | 0 | 5 | =5 − (0 + 0) = 5 | 80 |

The first column CAS indicates the total amount of required TAL binding cassettes to be assembled. $BB_{CV1}$, $BB_{CV2}$ and $BB_{CV3}$ indicate how many building blocks are to be co-assembled into each of the three capture vectors whereas $BB_{tot}$ shows the total number of dimer building blocks required in this first assembly step. The numbers in parentheses ($CV2_{int}$ and $CV3_{int}$) indicate how many of the building blocks are internal building blocks and can therefore be recycled in the second and (if applicable) the third capture vectors. To calculate the number of variants required per dimer building block, the total amount of dimer building blocks can be reduced by the sum of building blocks that can be recycled in CV2 and CV3, which can be expressed by the formula: $n=BB_{tot1}-(CV2_{int}+CV3_{int})$. Examples how to calculate the amount of variants for different combinations are given for repeat arrays containing between 10 and 24 repeats which reflects a reasonable range that can be covered based on a dimer library in a two-step assembly process. Smaller repeat numbers can be assembled in one step, whereas for larger repeat numbers the above-described trimer or tetramer libraries may be more useful. Also where half-repeats are to be included or an odd number of repeats is to be assembled, these can e.g. be provided in the terminal building block or in a functional vector.

Thus, the invention relates, in part, to a collection of n×16 dimer building blocks, each of the 16 dimer building blocks carrying a defined pair of TAL binding cassettes wherein each TAL binding cassette is selected from one of at least four different categories of RVDs which each RVD binding preferably to a specific base in a target nucleic acid molecule with $n=BB_{tot}-(CV2_{int}+CV3_{int})$, wherein $BB_{tot}$ represents the total amount of dimer building blocks assembled into CV1, CV2 and optionally CV3; and $CV2_{int}$ and $CV3_{int}$ represent the amount of internal dimer building blocks assembled into CV2 and CV3 which do not have a protruding end compatible with one of the protruding ends of CV2 and CV3.

Figure 32B:
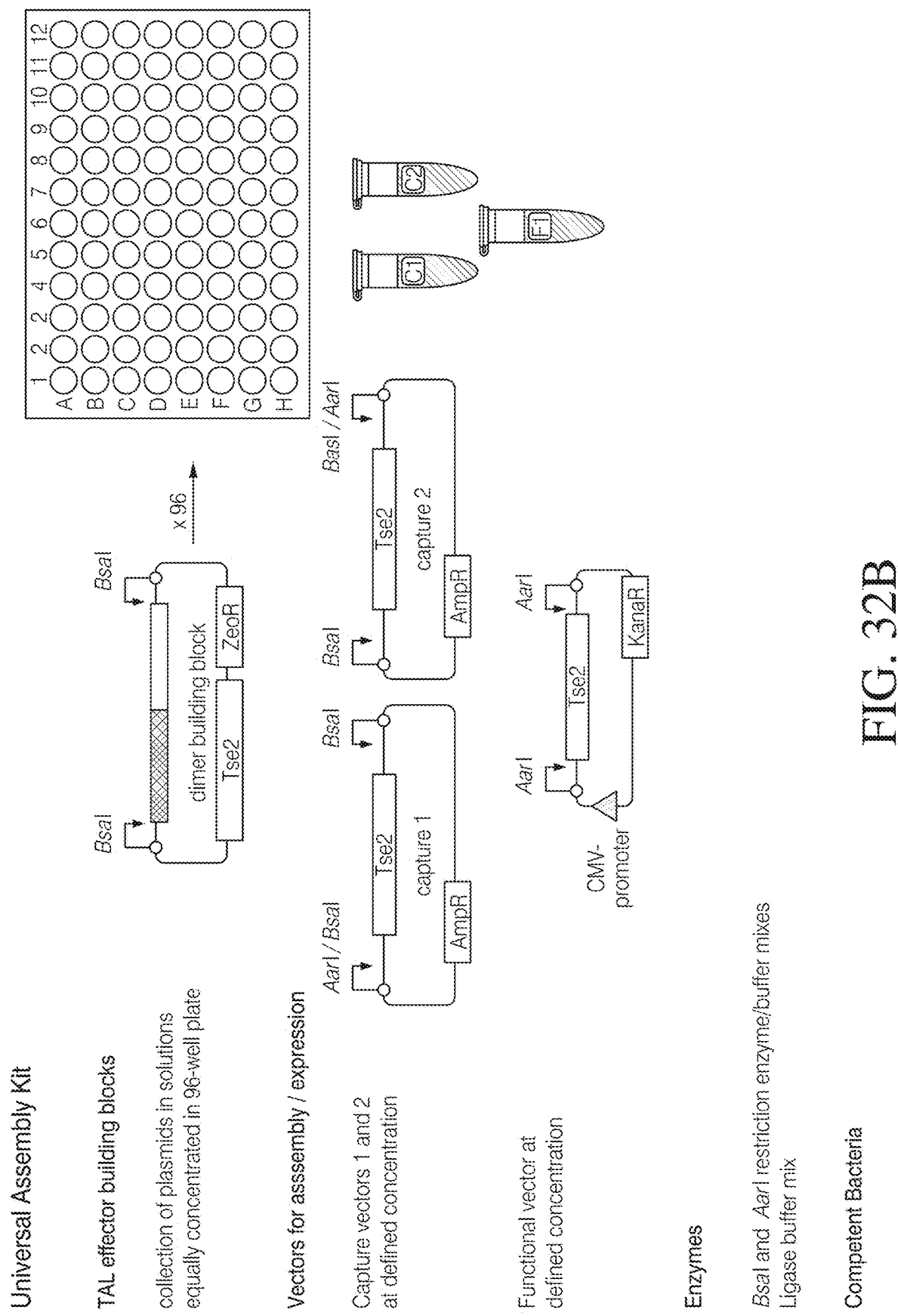

A universal assembly kit providing such collection of dimer building blocks as described above may further comprise the required amount of capture vectors for the envisaged assembly strategy and a functional vector for two-step assembly of a TAL effector fusion. One example of how a universal TAL assembly kit can be presented is shown in FIG. 32B. In this example the dimer library is arranged in a 96-well plate to allow for systematic pipetting of the required building blocks. In addition, the kit may contain two or more restriction enzymes, a ligase and respective buffer compositions required for type IIS-mediated assembly and optionally competent bacteria for transformation of assembled vectors. A universal assembly kit according to the embodiments of the invention can be used according to any one of the two-step assembly protocols described herein. The kit may be provided with one or more protocols and specific instructions including troubleshooting for each assembly approach.

A kit according to the embodiments of the invention may be furnished with one or more functional vectors. A functional vector provided in the kit may, e.g., carry a TAL effector fusion encoding a nuclease such as a FokI nuclease. Alternatively, a functional vector may carry an activator, a repressor, an epigenetic modifier or may contain a multiple cloning site for insertion of an effector function provided by the customer. In certain aspects, a functional vector provided with the kit may be an expression vector. The functional vector in the example of FIG. 32B provides an expression cassette under control of a CMV promoter and a polyA site for expression of assembled TAL effector FokI nuclease in mammalian cells. The functional vector in the kit may also be a topoisomerase-adapted vector or a GATEWAY® Entry Clone or any other functional vector described elsewhere herein.

In addition, some or all vectors included in the kit may contain a counter selectable marker gene. Any counter selectable marker gene that allows for selection of correctly assembled capture vectors or TAL effector fusions may be used for that purpose. In one embodiment, the selectable marker gene may be ccdB. In another embodiment, the selectable marker gene may be tse2 or a modified functional version thereof as described elsewhere herein. Vectors of the kit may carry the same or different selectable marker genes or may be furnished with one or more additional selection markers such as, e.g., an antibiotic resistance expression cassette. Providing kit-related vectors with toxic selection markers such as, e.g., tse2 may increase the success rate of correct assembly for customers using such kit and may also prevent commercial vector systems from being propagated and re-distributed by the customer in the absence of a commercially available antidote system (such as, e.g., a Tsi2 expressing host cell), which is essential for service provider to protect kit- or vector-associated revenues.

The universal assembly kit may further contain a control vector or a vector expressing a reporter gene which indicates successful assembly. In addition, the kit may be combined with a reporter vector or one of the functional assays of the invention described herein to evaluate TAL effector binding and/or activity of a fused effector function in vitro or in vivo.

Thus, the invention also relates to a TAL assembly kit for type IIS-mediated two-step assembly of a TAL effector characterized by at least a first assembly step in the presence of a first capture vector CV1, a second capture vector CV2 and optionally, a third capture vector CV3, wherein said kit contains at least:

(d) a collection of n×16 dimer building blocks, each of the 16 dimer building blocks carrying a defined pair of TAL binding cassettes wherein each TAL binding cassette is selected from one of at least four different categories of RVDs which each RVD binding preferably to a specific base in a target nucleic acid molecule with $n=BB_{tot}-(CV2_{int}+CV3_{int})$, wherein $BB_{tot}$ represents the total amount of dimer building blocks assembled into CV1, CV2 and optionally CV3; and $CV2_{int}$ and $CV3_{int}$ represent the amount of internal dimer building blocks assembled into CV2 and CV3 which do not have a protruding end compatible with one of the protruding ends of CV2 and CV3;

(e) at least a first capture vector CV1, a second capture vector CV2 and optionally, a third capture vector CV3; and (f) at least a first functional vector wherein said functional vector may contain one or more additional TAL binding cassettes or half cassettes.

The collection of dimer building blocks in (a) may be provided as circular plasmids either in solution or in lyophilized form. In one embodiment of the invention, the collection of dimer building blocks may be provided in a multi-well plate such as e.g. a 96-well plate either separate or as part of the kit. In certain embodiments of the invention, n is a number in the range of 5 to 8. The first, second and third capture vectors in (b) may contain one or more selectable markers. In yet another embodiment, at least one of the one or more selectable markers may be a counter selectable marker such as ccdB or tse2. The selectable marker may be flanked by one or more type IIS restriction enzyme cleavage sites. A second selectable marker may code for an antibiotic resistance.

The functional vector in (c) may encode an effector function such as a nuclease, a repressor, an activator or an epigenetic modifier activity. Alternatively, the functional vector may contain a region for insertion such as a multiple cleavage site for insertion of another fusion moiety.

In addition, a kit according to the invention may contain one or more of the following components:

(g) a first type IIS restriction enzyme and a buffer composition allowing for cleavage of a nucleic acid molecule containing a recognition site for said first type IIS restriction enzyme;

(h) a second type IIS restriction enzyme and a buffer composition allowing for cleavage of a nucleic acid molecule containing a recognition site for said second type IIS restriction enzyme;

(i) a ligase and a buffer composition allowing for ligation of assembled nucleic acid molecules;

(j) an aliquot of competent bacteria for transformation of assembled vectors such as, e.g., chemically competent or electro-competent E. coli;

(k) a control vector with a selectable marker gene or a reporter gene for validation of the assembly reaction; and (l) any one of a functional binding assays described herein.

In a specific embodiment, the first type IIS restriction enzyme of (d) may be BsaI and the second type IIS restriction enzyme may be AarI. In yet another embodiment, the ligase in (f) may be a T4 ligase. However, any other type IIS restriction enzyme or ligase suitable for using the kit according to one of the protocols of the invention can be included in the kit.

TAL QC and Functional Analyses

TAL Sequencing.

In another aspect, the invention relates to quality control of assembled TAL effector coding nucleic acid sequences. Due to the highly repetitive nature of TAL effector sequences, a quality control of assembled TAL repeats by sequencing from both ends is challenging. For example, if a TAL effector contains 24 cassettes it will not usually be a problem to sequence the first 10 or more repeats from the one end of a vector and the last 10 or more repeats from the other end of the vector by designing specific sequence primers to bind within the vector backbone and read in opposite directions. To guarantee complete sequencing of the entire 24 repeat domain encoded by approx. 2,450 nucleotides, at least one additional primer would have to be designed to bind to a target sequence located preferably near the center of the plurality of assembled cassettes. This can, however, only be realized if a specific primer binding site can be identified in at least one of the cassettes which is difficult due to the highly repetitive nucleotide sequence. One aspect of the invention provides a solution to this problem by making use of the degeneracy of the genetic code. By modifying the codon composition within one or more cassettes, specific primer binding sites can be provided without altering the encoded amino acid sequence.

Thus, in one embodiment the library of cassettes for TAL effector assembly contains at least one first cassette per category wherein the codon composition of said first cassette differs from the codon compositions of all other cassettes of the same category and wherein said cassette is allocated to only one distinct position in the series of cassettes and wherein said one distinct position is preferably a position in the center or close to the center of the total amount of cassette positions.

In another embodiment, the library of cassettes contains at least one second cassette per category wherein the codon composition of said second cassette differs from the codon composition of the first cassette and from the codon composition of all other cassettes of the same category and wherein said second cassette is allocated to only one distinct position in the series of cassettes and wherein said one distinct position is preferably a position in the center or close to the center of the total amount of cassette positions and is different from the position of the first cassette.

To generate cassettes with unique codon composition the codons can, e.g., be altered to use less preferred codons (e.g., the second best or third best codon instead of the best codon) according to a given codon usage table as illustrated by the following example:

A 34-amino acid repeat capable of binding to nucleotide "A" via RVD "NI" has the following amino acid sequence:

(SEQ ID NO: 71)
LTPEQVVAIASNIGGKQALETVQRLLPVLCQAHG

The same repeat sequence is encoded by all cassettes of the category "A" (cassette A1, A2, A3, A4, A5 etc.) which have been codon-optimized for expression in human hosts.

A cassette A10 may have the following nucleic acid sequence:
(SEQ ID NO: 72)
5'-CTGACCCCCGAACAGGTGGTGGCCATTGCCAGCAACATCGGCGGCAA

GCAGGCCCTGGAAACCGTGCAGAGACTGCTGCCCGTGCTGTGCCAGGCCC

ATGGC-3'

Another cassette A12 may have the following sequence:
(SEQ ID NO: 73)
5'-TTGACTCCAGAACAGGTGGTGGCTATTGCTTCCAATATTGGGGGAA

ACAGGCCCTGGAAACTGTGCAGCGCCTGCTGCCAGTGCTGTGCCAGGCT

CACGGA-3'

A comparison of the 34 codons in cassettes A10 and A12 reveals that A10 uses preferred codons (according to a human codon usage table) in 29 of 34 cases and uses less preferred codons in 5 cases whereas A12 uses preferred codons in only 15 cases and less preferred codons in 19 cases. By using more less-preferred codons in at least one of the cassettes of each category, individual primer binding sites can be generated at desired positions. The following alignment shows the different codon compositions of cassettes A10 (upper sequence) and A12 (lower sequence) and one possible primer binding site highlighted in bold.

encoding the members of the library may be operably linked to nucleic acid encoding additional activities. One method for doing this is to generate TAL effectors libraries and introduce the members of these libraries into vectors so that the TAL effector coding sequences are flanked by recombination sites (e.g., att sites). This allows for the library members to be readily transferred to other nucleic acid molecules (e.g., vectors) where they can become operably linked to nucleic acid encoding different additional activities. One recombinational cloning system described herein which can be used in such processes is the GATEWAY® system. Of course, non-recombinational cloning systems can also be used to operably link TAL effector library member to other nucleic acids, including standard restriction enzyme digestion, ligation methods.

FIG. 12B shows four nucleic acid segments which encode TAL nucleic acid binding repeats that recognize each of the four DNA bases. One methods for generating random TAL nucleic acid binding repeats involves starting with a linear vector which contains a coding region which encodes a partial first repeat (up to the Esp3I site). The linkage site for the first part TAL nucleic acid binding repeat can be designed so that a seamless connection occurs with the vector portion of the repeat. Linking may be facilitated by any number of means including the use of ligases and/or topoisomerases.

When generating TAL effector libraries conditions may be adjusted so that the libraries have certain characteristics. For example, the concentration ratio of repeating units to vector may be adjusted so as to arrive at a specified average number of repeats being present in each circularized vector. Of course, other methods may be used to achieve the same goal, including limiting the amount of time that ligation of repeats

```
TGACCCCCGAACAGGTGGTGGCCATTGCCAGCAACATCGGCGGCAAGCAGGCCCTGGAAA 61
||||  || |||||||||||||| |||||    ||| || || ||  ||||||||||||
TGACTCCAGAACAGGTGGTGGCTATTGCTTCCAATATTGGGGGAAACAGGCCCTGGAAA 61
                            ←-----------------
```

```
CCGTGCAGAGACTGCTGCCCGTGCTGTGCCAGGCCCATGG 101 (SEQ ID NO: 111)
|  ||||||  |  ||||||||| ||||||||||||||  ||  ||
CTGTGCAGCGCCTGCTGCCAGTGCTGTGCCAGGCTCACGG 101 (SEQ ID NO: 112)
```

In yet another embodiment, all cassettes of a category may vary in codon combination, e.g., when different ratios of preferred and non-preferred codons are used for each cassette. Cassettes with unique codon composition may further be incorporated into larger building blocks like trimers or tetramers as disclosed elsewhere herein. This strategy allows for robust sequencing of the center of larger TAL effectors.

Figure 12A:
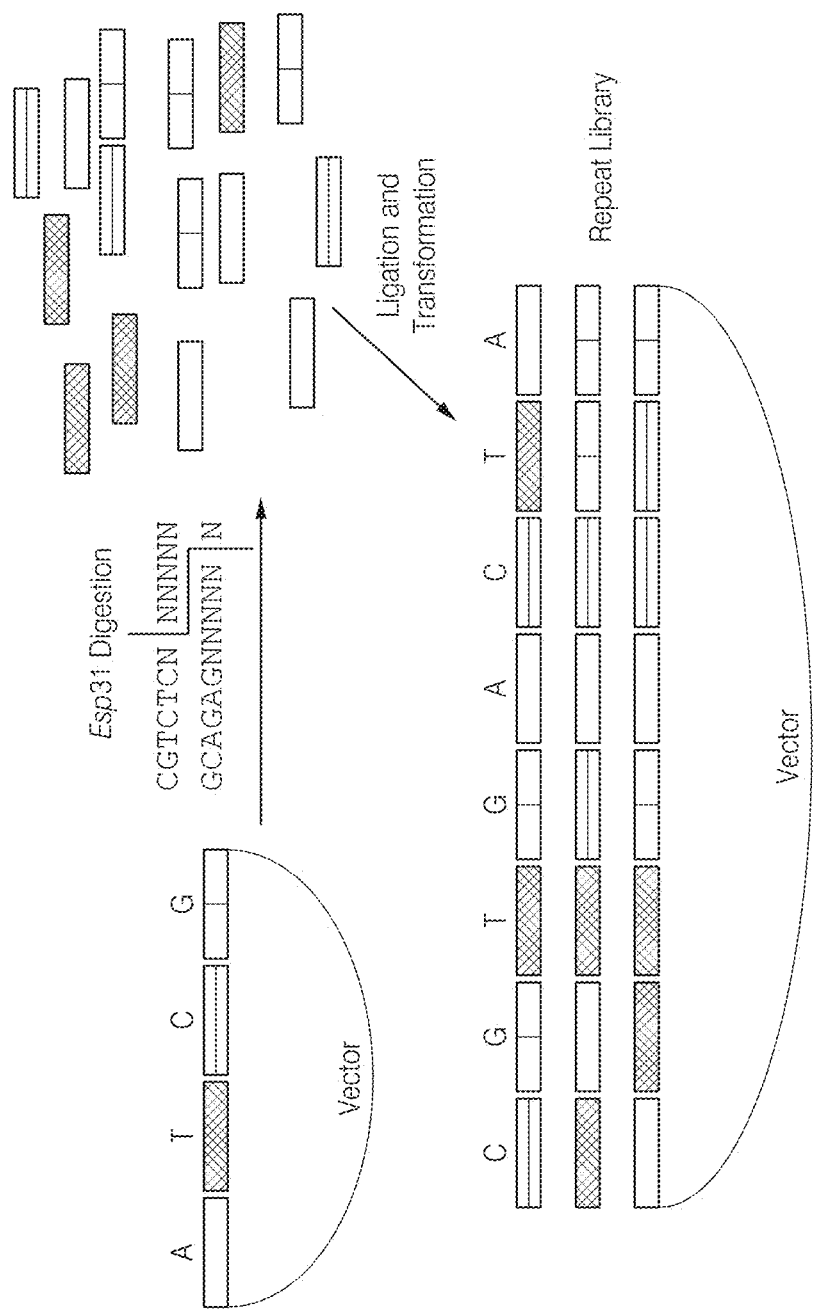
FIG. 12A shows one example of an assembly method for generating a random arrangement of TAL nucleic acid binding cassettes. Bases bound by each the various cassettes are indicated by the letters A, T, C, and G. Bases are indicated only for the top of the three Repeat Library members shown.

TAL Library Screening:

The invention also methods for generating and screening TAL effector libraries, as well as compositions comprising these libraries, and individual members of these libraries. A description of some embodiments of this aspect of the invention is shown in FIG. 12A. FIG. 12A shows a vector based approach in which TAL nucleic acid binding cassettes encoded by a vector are separated from the vector backbone and each other by digestion with a restriction enzyme (Esp3I in this instance) and then randomly assembled and introduced into a vector backbone to generate a library of nucleic acid binding cassettes which bind to different nucleic acid sequences. These libraries may contain TAL effectors in association with or without additional activities (e.g., transcriptional activation, nuclease, etc.). Further, libraries may be constructed in a manner in which nucleic acid segments is allowed to take place and size selection of either TAL nucleic acid binding cassettes or vectors which contain these cassettes. Thus, TAL effector libraries may be generated wherein at least 75% (e.g., at least 80%, 85%, 90%, 95%) of the individual library members comprise from about 5 to about 50, from about 10 to about 40, from about 10 to about 30, from about 10 to about 20, from about 10 to about 15, from about 12 to about 50, from about 12 to about 35, from about 12 to about 25, from about 12 to about 20, from about 15 to about 35, from about 15 to about 30, from about 15 to about 25, from about 15 to about 20, from about 17 to about 32, etc. TAL repeats.

Also, TAL effector libraries may be "biased" to increase the number of individual library members that will have binding specificity of nucleic acids with particular characteristics. As an example, AT/CG ratios vary with organism and regions of genomes within organisms. For example, if a TAL effector is sought which binds a nucleic acid region with a higher AT content than CG content, then the TAL effector library may be designed to reflect this. The invention thus includes TAL effector libraries which nucleic acid binding biases. In some embodiments, TAL effector libraries with have TAL repeats which are designed which contain from about 51% to about 80%, from about 55% to about 80%, from about 60% to about 80%, from about 51% to about 75%, from about 51% to about 70%, from about 51% to about 65%, from about 51% to about 60%, from about 55% to about 80%, from about 55% to about 70%, from about 55% to about 65%, from about 55% to about 60%, adenine and thymine binding repeats. In other embodiments, TAL effector libraries with have TAL repeats which are designed which contain from about 51% to about 80%, from about 55% to about 80%, from about 60% to about 80%, from about 51% to about 75%, from about 51% to about 70%, from about 51% to about 65%, from about 51% to about 60%, from about 55% to about 80%, from about 55% to about 70%, from about 55% to about 65%, from about 55% to about 60%, cytidine and guanidine binding repeats. The invention further includes methods for making such libraries, and compositions employed in such methods.

Screening of TAL effectors for binding activity can be performed by any number of methods. For purposes of illustration, the 5' region of a gene for which a TAL effector fusion activator is sought may be placed upstream from a reported gene (e.g., green fluorescent protein, beta-galactosidase, etc.). Library nucleic acid molecule may then be introduced into cells containing this reporter construct. The cells may then be screened to identify those in which the report is activated. The invention thus includes methods for identify TAL effectors with binding specificity for specific nucleotide sequences. Methods of this type have the following advantages: (1) In cases where the TAL effector format is functional within a particular cell type, only a single TAL effector library need be constructed for that cell type and (2) it may be possible to identify TAL effectors with different "strengths" of binding for the nucleic acid region. This is so because, when a reporter assay is used, signal strength may correlate with binding strength.

TAL effector libraries, as well as other nucleic acid molecules described herein (e.g., nucleic acid encoding TAL effector fusion proteins) may be inserted into any number of vector types, including lentiviral vectors, which allow for the delivery of one gene per cell.

Once introduced into cell, TAL effector libraries may be phenotypically screened by selection, cell sorting or reporter assay etc. Further, TAL effector library members may be "rescued" from cells by PCR. The targeted DNA sequence can be identified by sequencing the rescued TAL repeats and may be used, for example, to guide the BLAST search against genomic databases to identify potential candidate targets. TAL effector libraries can be used for cell-based phenotypic screening in a wide variety of areas, such as neurodegeneration, infectious disease, cancer, and stem cells. Phenotypic screening using randomized TAL effector libraries may be used to identify novel functional genes or new therapeutic targets.

Assay Systems for Evolved TAL Effectors.

The invention further includes assay systems and their use for functional evaluation of engineered TAL effector molecules that have been derived by the above described evolution approaches.

Figure 19:
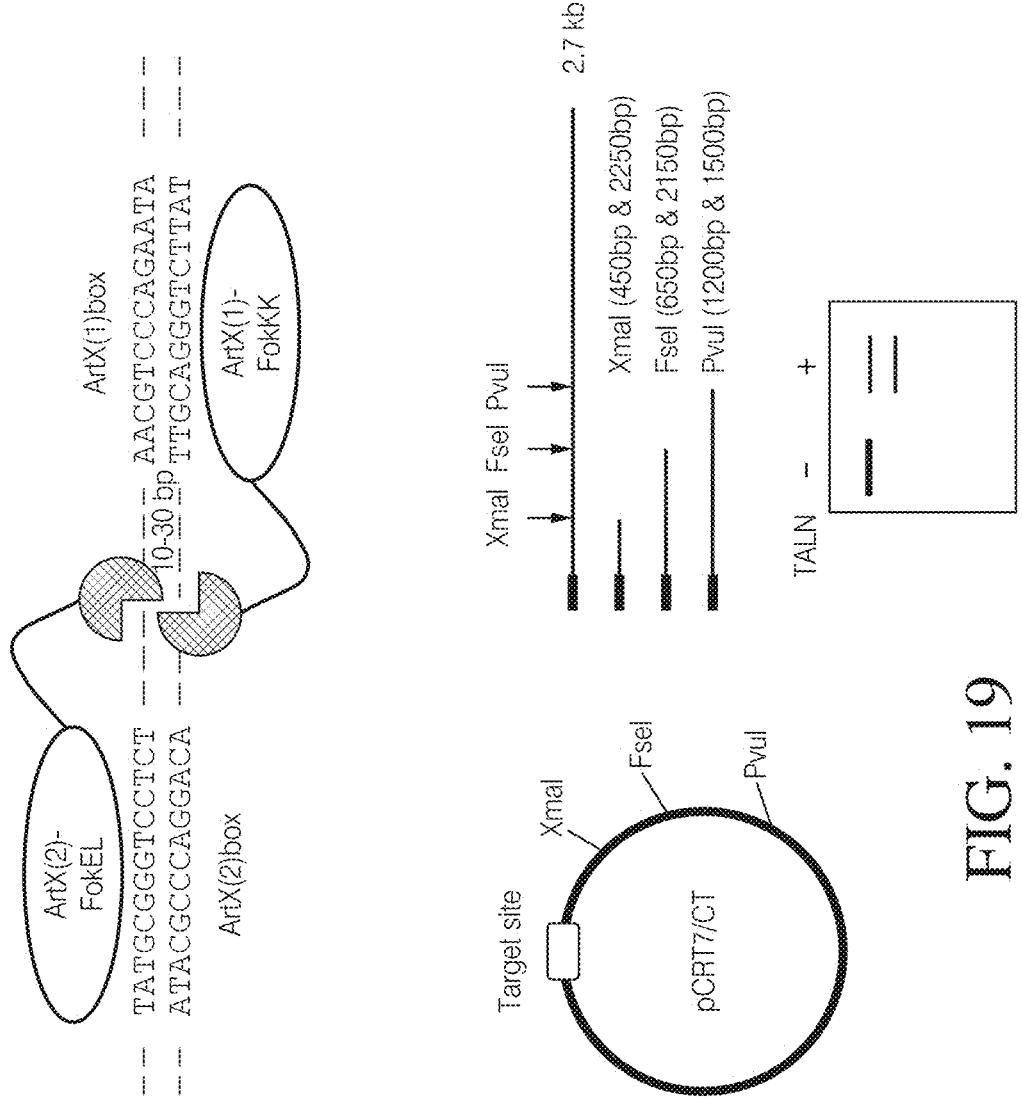
FIG. 19 shows an exemplary assay that can be used to demonstrate TAL nuclease-mediated DNA cleavage. TAL nucleases were synthesized using a rabbit reticulocyte in vitro transcription/translation system. The DNA target sites with different length spacers were cloned into pCRT7/CT vector by over-lapping PCR fragment. The pairs of nucleases expressed from in vitro transcription/translation system were incubated with the target plasmids or PCR amplicons spanning the target site. The digest products were resolved on an agarose gel to demonstrate successful cleavage.

Assays suitable to evaluate the function of TAL effector binding and/or activity of TAL effector fusions in different hosts are described in FIGS. 13-18 and 24. In these examples reporter systems and minimal genetic circuits were developed to analyse TAL effector function in E. coli (FIG. 13 and Example 4), in algae (FIG. 14 and Example 5) or in mammalian cell culture (FIGS. 15-18 and Examples 6, 7 and 8). Thus, the invention also relates to genetically engineered TAL responsive cell lines. Furthermore these examples demonstrate functionality of TAL effector activators (FIGS. 15 and 18A and FIG. 33B), TAL effector repressors (FIGS. 15 and 16, and FIG. 33C) and TAL effector nucleases in vivo (FIGS. 17 and 18B) and in vitro (FIG. 19).

Figure 24:
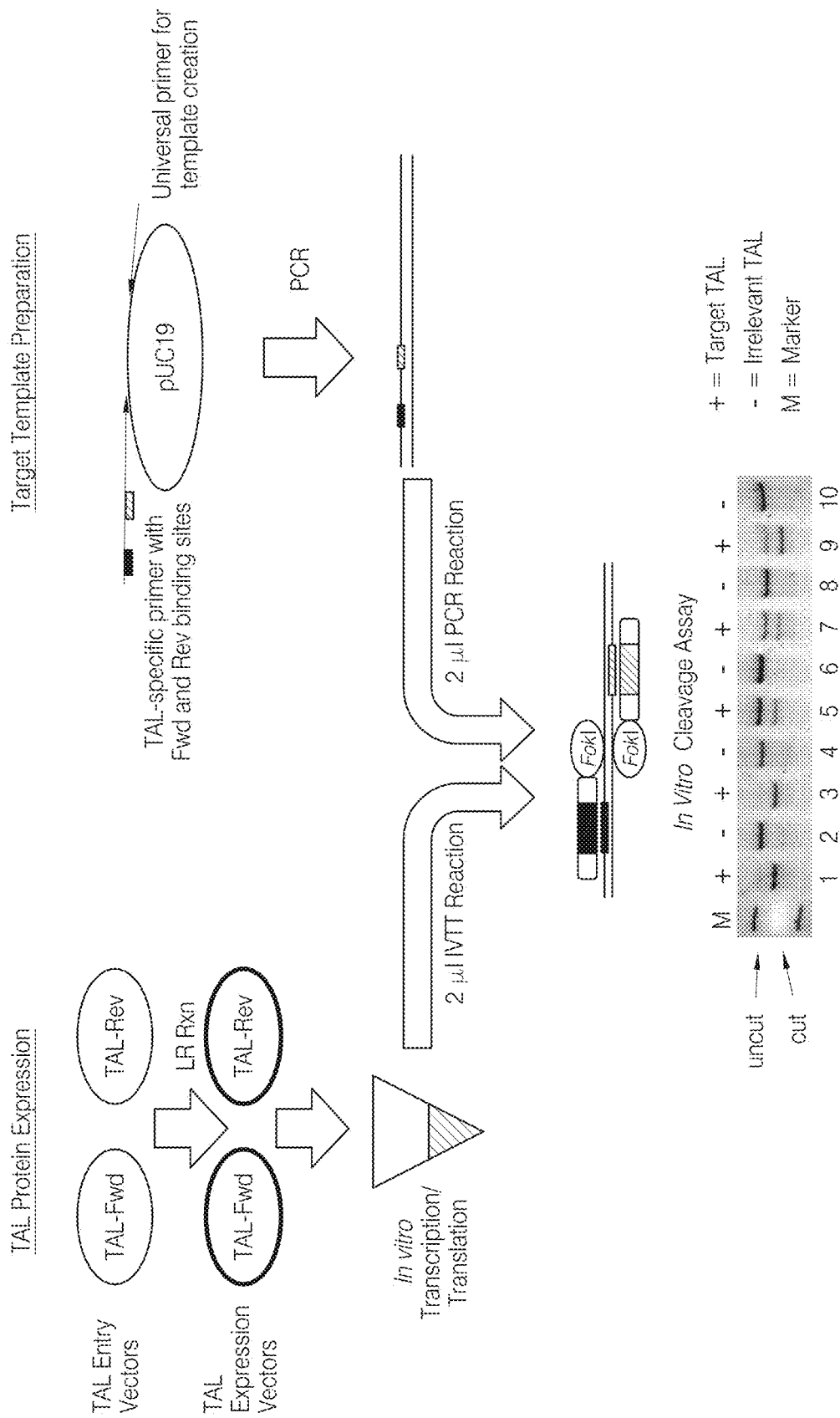
FIG. 24 shows an in vitro TAL nuclease cleavage assay and methods for preparing components used in the same. The left side of the figure diagrammatically shows the preparation of expressions vectors encoding TAL effector nuclease fusions. The expressions vectors labeled "TAL-Fwd" and "TAL-Rev" encode two domains of a FokI restriction endonuclease connected to TAL effectors which bind nucleic acid in a manner so as to bring the domains into the correct proximity for nuclease activity. These TAL effector nuclease fusion expression vectors are then transcribed and translated in vitro to produce two FokI-TAL effector fusions. The right side of the figure shows a pUC19 vector, primers and associated PCR reaction designed to generate amplification products which, upon hybridization, form a linear nucleic acid molecule with TAL effector fusion binding sites. These binding sites are positioned to bring TAL effector nuclease fusions together in a manner which results in cleavage of the nucleic acid between the TAL binding sites. The bottom center of the figure shows a gel of cleavage reaction mixtures.

The invention also includes in vitro nucleic acid cleavage assays for measuring TAL effector binding activity, which may be used, for example, TAL effector libraries. One exemplary work flow for such an assay is shown in FIG. 24. In this work flow, FokI TAL effector fusions are prepared by in vitro transcription and translation. These TAL effector fusions are then contacted with nucleic acid containing TAL effector binding sites positioned such that binding of the TAL effector fusions results in FokI endonuclease activity. The amount of cleavage product generated is then measure. In the work flow shown in FIG. 24, cleavage product generation is measured by gel electrophoresis.

The invention thus includes in vitro nucleic acid activity (e.g., nucleic acid cleavage, transcriptional activation, methylation, demethylation, etc.) assays for measuring TAL effector binding activity which involve (1) contacting one or more (e.g., one or two) TAL effectors with nucleic acid containing one or more (e.g., one or two) TAL effector binding site and (2) measuring TAL effector binding activity. In many instances, TAL effectors used in such assays will be TAL effector fusions and an activity associated with these fusions will be measured. As an example, TAL effector fusions which contain a transcriptional activation domain may be contacted with nucleic acid containing a TAL effector binding site and, optionally, a promoter under conditions where TAL effector fusion binding results in the activation of transcription. In such instances, TAL effector binding may be measured by measuring the amount of transcription product produced. Other in vitro assays may also be employed making use of the ability, for example, of TAL effector binding to block, for examples, a restriction site, a transcriptional activation site, a methylation site, or a demethylation site.

In many in vitro assays for TAL effector binding, the affinity of the TAL effector for a particular nucleic acid may be measured. The invention thus includes methods and compositions for comparing the binding affinity of two or more TAL effectors (e.g., a test TAL effector and a control TAL effector). With reference to the work flow shown in FIG. 24, assays will often be "graded" in nature. By this is meant that activities levels may be scored as effectively none, high or somewhere in between. For example, lanes 1 and 3 in FIG. 24 show nearly complete nucleic acid cleavage and lanes 5, 7 and 9 show differing levels of cleavage. Thus, the invention includes assays where a high level activity TAL effector control is used and the activity associated with other TAL effectors (test TAL effectors) are measured and compared to the control. In many instances, test TAL effectors may have activities, for example, between 0 and 100%, 10 and 60%, 10 and 100%, 60 and 100%, 80 and 100%, 50 and 90%, 40 and 80%, etc. of the activity of the control test TAL effector.

In other variations of the invention, a control TAL effector is used which has lower activity than at least some of the test TAL effectors. In such embodiments, the control TAL effector may represent an expected mid-level activity and test TAL effectors have activities which may vary above and below the activity of the control TAL effector. Using a control TAL effector activity adjusted to 100%, test TAL effectors may have activities which vary, for example, between 0 and 200%, 10 and 200%, 40 and 150%, 50 and 150%, 30 and 180%, 20 and 180%, etc. of the control TAL effector.

In one aspect, the invention relates to an assay for screening a library of TAL effector variants in *E. coli*. The library would be expressed in the presence of a second plasmid carrying an inducible marker gene and a TAL binding site. The marker gene can be a toxic gene, such as, e.g., ccdB or tse2—resulting in cell death upon successful expression. Expression of the marker gene can be induced, for example, by a temperature shift or can be induced by an inducible operon system known in the art such as arabinose, galactose, lactose or the like.

In instances where the TAL effector has, e.g., nuclease activity, the assay can be set up to analyse two different TAL effector functions: in a first embodiment the assay is construed such that the results serve to evaluate whether a modified TAL effector is capable of binding a given target sequence included in the second plasmid. In this instance, a functional nuclease reporter domain would be fused to the modified TAL effector library and selection would identify those TAL effector nucleases with binding specificity for the given target sequence.

In a second embodiment, the assay may be construed such that the results serve to evaluate whether a modified nuclease domain is capable of cleaving a target sequence in the second plasmid to interfere with toxic gene expression. In this instance, a modified nuclease or nuclease domain library may be fused to a functional TAL repeat reporter domain and selection would identify those TAL effector nucleases with functional nuclease binding domains. In both instances functional fusion proteins would be characterized by the TAL effector binding to the target site in the second plasmid and nuclease domain cleaving and inactivating the toxic gene which results in survival of only those cells carrying a binding-site specific active TAL effector nucleases.

In a further aspect of the invention, the assay system can also be modified to allow for evaluation of TAL effector activity wherein the effector is a repressor such as, e.g., a lad repressor binding to a lac operon that controls expression of the selection marker gene. In yet another aspect of the invention the assay system can be modified to allow for evaluation of TAL effector activity wherein the effector is an activator such that the activation of another factor, e.g., neutralizes the toxic activity of the selection marker. One example of carrying out the invention would be a CcdA expressing cell wherein CcdA expression itself is regulated by the activity of the TAL effector, e.g., a TAL activator protein.

Thus, the invention refers to an assay system allowing for evaluation of modified TAL effector activity wherein either a modified TAL effector is combined with a functional reporter fusion or a functional reporter fusion is combined with a modified TAL effector and the TAL effector variant or a library of TAL effector variants are expressed in a host organism in the presence of a reporter system comprising at least one or more TAL binding sites and a selectable marker gene, wherein the expression of the selectable marker gene is regulated by the combined activity of the TAL effector and a functional effector fusion.

The assay may, e.g., be performed in a prokaryotic host such as *E. coli*. In some instances the effector fusion has nuclease, activator or repressor activity. In one embodiment the selection marker is a toxic gene such as, e.g., ccdB or tse2. In some embodiments the selection marker may be under control of an operon such as a lac operon and the expression of the selection marker may be repressed by an operon-specific repressor such as lad. In a specific embodiment the host cell may be a CcdA expressing cell and CcdA expression may be regulated by the activity of the tested TAL effector or TAL effector fusion.

Assays for Genomic Locus Modification and Off-Target Detection.

TAL effector nucleases as described above can be used to edit genomes by inducing double-strand breaks (DSB), which cells respond to with repair mechanisms. Non-homologous end joining (NHEJ) reconnects DNA from either side of a double-strand break where there is very little or no sequence overlap for annealing. This repair mechanism induces errors in the genome via insertion, deletion, or chromosomal rearrangement; any such errors may render the gene products coded at that location non-functional. Because this activity can vary depending on the species, cell type, target gene, and nuclease used, it should be monitored when designing new systems. In addition to detection of activity at specific target loci, it is and will therefore become more important to understand off-target activity of TAL effector nucleases. The invention provides solutions for this problem as described by the following approaches.

Mismatch-Detecting Enzymes Cleavage Assay.

To detect any difference between two alleles a simple heteroduplex cleavage assay can be performed. A first aspect of the invention takes advantage of mismatch-detecting enzymes, such as a mismatch-detecting enzymes derived from *Perkinsus marinus* nuclease PA3 (PM PA3) (see, e.g., GeneBank Accession Nos. XP_002788902, XP_002788899, and XP_002782582) and Cel1, Res1 or similar, to identify modifications in the genome. Thus, in one aspect the invention relates to a method to detect genomic locus modification wherein the method is characterized by the steps illustrated in FIG. 20. A detailed description of this assay is given in Example 9a.

A mismatch endonuclease is an endonuclease that recognizes mismatches within double-stranded DNA, including mispairing and unpaired mismatches, and cleaves the DNA (cuts both strands of the double-stranded DNA) at the site of the mismatch in order to excise the mismatch from the DNA. Depending on the mismatch endonuclease used, the endonuclease will cut the DNA either 5' or 3' to the mismatch. Apart from the above described enzymes, phage T4 endonuclease VII or T7 endonuclease I have been shown to bind to DNA mismatches and can therefore be used to efficiently detect genomic lesions caused by TAL nuclease cleavage. Both enzymes have similar properties (Babon et al. The use of resolvases T4 endonuclease VII and T7 endonuclease I in mutation detection. Mol. Biotechnol. 23:73-81. (2003)) and are capable of recognizing and cleaving all eight types of single base mismatches (AA, CC, GG, TT, AC, AG, TC and TG) and DNA loop structures resulting from insertions or deletions (indels). Example 9b illustrates an embodiment of a mismatch detecting enzymes cleavage assay according to the invention, wherein an efficient T7 endonuclease I enzyme mix was used to detect mismatches caused by TAL nuclease cleavage. The enzyme mix contains T7 endonuclease I in combination with a ligase such as, e.g., Taq ligase. The use of a ligase moderates the non-specific nicking activity of T7 endonuclease I by repairing spurious nicks before a double strand break occurs. This has the advantage of allowing higher T7 endonuclease I concentrations and a wider range of input DNA while still ensuring complete specific cutting of all DNA mismatches. In this respect, for example Taq ligase has also been shown to moderate the non specific nicking activity of other mismatch endonucleases, including T4 endonuclease VII.

Thus the invention relates, in part to an enzyme composition for detection of mismatch cleavage containing at least an endonuclease that is capable of recognizing and cleaving a mismatch in a DNA double strand and a ligase which is capable of repairing nicks generated by non-specific activity of the endonuclease. In one embodiment, the DNA ligase is Taq ligase. However, the DNA ligase may be any other ligase that repairs nicks in a single strand of a double-stranded DNA. Suitable DNA ligases include, without limitation, AMPLIGASE™ (Epicentre Biotechnologies, Madison, Wis., USA)—a thermostable DNA ligase derived from a thermophilic bacterium and catalyzes NAD-dependent ligation of adjacent 3'-hydroxylated and 5(r)-phosphorylated termini in duplex DNA; 9° N™ ligase (New England Biolabs, Ipswich, Me., USA)—a DNA ligase active at elevated temperatures (45-90° C.) that is isolated from a thermophilic archaea *Thermococcus* sp.; T4 DNA ligase, Taq DNA ligase, and *E. coli* DNA ligase. Apart from a mismatch cleaving endonuclease and a DNA ligase capable of repairing nicks, the composition does not require any further enzymatic activities. Thus, in one embodiment, the composition does not include any further enzymes or enzymatic activities.

To allow for complete cleavage of all mismatch DNA in a sample without leaving nicks due to non-specific endonuclease activity, two ratios are important: (i) the ratio of endonuclease to DNA substrate and (ii) the ratio of endonuclease to ligase. At high endonuclease concentrations, the DNA is rapidly degraded whereas too low concentrations would not allow complete cleavage of mismatch DNA which would result in an underestimation of TAL nuclease-mediated DNA editing. Most of the above referenced enzymes work at a broad temperature range. For example, T7 endonuclease I and Taq ligase may be used at various temperatures from 30° C. to 60° C. However the optimal temperature should be adjusted for each individual enzyme combination as each enzyme has different activity profiles across the temperature range. Also, the concentration of each enzyme must be thoroughly adjusted. Shorter incubation times may be achieved by increasing the concentrations of the enzymes. A skilled person can easily determine an appropriate amount of a particular endonuclease and DNA ligase required under certain reaction conditions by conducting a time course experiment for various amounts of DNA.

In certain instances, the DNA ligase may be added after the treatment with the mismatch endonuclease is completed. Chemical or heat inactivation of the mismatch endonuclease may be used to ensure the endonuclease reaction is completed, or the buffer containing the mismatch endonuclease may be exchanged, thus removing the mismatch endonuclease from the reaction. In other instances, it may be advantageous to incubate the mismatch-carrying DNA with both enzymes at the same time allowing the ligase to act for the whole period during which the mismatch endonuclease is acting on the double stranded DNA. For this purpose the inventors have developed a ready to use enzyme composition allowing for time-efficient treatment of DNA with both enzymes. Treatment of mismatch nucleic acid is performed in a suitable reaction buffer that contains any coenzymes or counterions that may be required for optimal endonuclease and DNA ligase activity. Where T7 endonuclease I is used with Taq ligase a ready to use enzyme composition according to the invention may, e.g., contain the following components: T7 endonuclease I and Taq ligase at a ratio of between 1:1 and 1:6 (e.g., at a ratio of from about 1:1 to about 1:5, from about 1:2 to about 1:5, from about 1:3 to about 1:5, from about 1:3.5 to about 1:5, from about 1:3.5 to about 1:4.5, etc.), in a Tris pH 7.4 buffer system supplied with KCl, EDTA, glycerol, BSA and Triton X-100. In one specific embodiment 100 µl of the enzyme composition contain 10 µl of T7 endonuclease I (10 U/µl) and 10 µl of Taq ligase (40 U/µl) (both New England Biolabs, Beverly, Mass.) and 80 µl of an enzyme dilution buffer consisting of 10 mM Tris pH 7.4 at 4° C., 50 mM KCl, 0.1 mM EDTA, 50% glycerol, 200 µg BSA/ml, 0.15% Triton X-100). A detailed description of a mismatch cleavage assay using such enzyme composition is given in Example 9b.

ChIP-seq Assays.

ChIP (chromatin immunoprecipitation) is an efficient method to selectively enrich for DNA sequences bound by a particular protein in living cells. The ChIP process enriches specific crosslinked DNA-protein complexes using an antibody against a protein of interest. Oligonucleotide adapters are then added to the small stretches of DNA that were bound to the protein of interest to enable massively parallel sequencing (ChIP Seq). After size selection, all the resulting ChIP-DNA fragments are sequenced simultaneously using a genome sequencer. A single sequencing run can scan for genome-wide associations with high resolution, meaning that features can be located precisely on the chromosomes.

The inventors have combined the ChIPSeq assay with the specific binding activity of DNA repair protein 53BP1 to map nucleotide lesions in TAL effector nuclease treated cells. Thus, in one aspect the invention relates to a method for mapping lesions wherein the method is characterized by the following steps: (i) subjecting cells treated with a TAL effector nuclease and untreated cells to immune chromatin immunoprecipitation with an anti-53BP1 antibody, (ii) crosslinking the complex with the DNA (iii) shearing the complex, and (iv) pulling down the complex with a second antibody, (v) optionally, separating the bound DNA from the antibody complex, (vi) performing a high throughput sequencing reaction, and (vii) comparing the sequence profiles with the predicted target site sequence by computer-aided homology analysis. The last step can help to exclude false results due to naturally occurring, spontaneous double stranded breaks or other DNA damage which recruit repair proteins that are present in the genome which would be scored as a lesion in this assay. Thus, the invention provides methods for assessing whether nucleotide sequence discrepancies are present in TAL effector coding sequences.

Site-Specific Integration.

One application of the invention relates the integration of desired nucleic acid segments or regions into cellular nucleic acid molecules (e.g., intracellular plasmids, chromosomes, plastid genomes, etc.). Nucleic acid integration may be site specific or random.

Site specific integration methods will typically involved the following: (1) The selection of a target site, (2) the design and/or production of a TAL effector fusion which interacts at or near the target site, and (3) a desired nucleic acid segment or region for integration into the target site.

Any number of criteria may be used for target site selection. As examples, the target site may be (1) known in the particular cell to be a region of open chromatin structure or (2) directly associated with cellular nucleic acid (e.g., a promoter and/or an enhancer) known to confer a particular function (e.g., transcriptional activation) upon nucleic acid at the integration site. Target site selection will vary with the particular cell, the specific application, information available about known potential integration sites, the desires to either disrupt or not disrupt cellular nucleic acid which confer upon the cell particular functional activities, and the nucleic acid segment or region for which integration is sought.

In some instances, it may be desirable to integrate nucleic acid at a location in cellular nucleic acid which is either known to not have open chromatin structure or where the chromatin structure is not know. One example of such a situation is where it is desirable to insert the same nucleic acid segment or region into the same location in cells of different types (e.g., cell of different tissues from the same plant or animal). In such instances, it may be desirable to employ an agent designed to alter chromatin regions. One example of a chromatin remodelling composition is a TAL effector fused to a chromatin remodeling complex protein.

A number of chromatin remodeling complexes are known. Chromatin remodeling complexes generally contain an enzymatic component, which is often an ATPase, a histone acetyl transferase or a histone deacetylase. ATPase components include, but are not limited to, the following polypeptides: SWI2/SNF2, Mi-2, ISWI, BRM, BRG/BAF, Chd-1, Chd-2, Chd-3, Chd-4 and Mot-1. Additional non-enzymatic components, involved in positioning the enzymatic component with respect to its substrate and/or for interaction with other proteins, are also present in chromatin remodeling complexes and can be used as a portion of a fusion molecule.

Modification of chromatin structure will facilitate many processes that require access to cellular DNA. In some embodiments, chromatin modification facilitates modulation of expression of a gene of interest. Modulation of expression comprises activation or repression of a gene of interest. In additional embodiments, chromatin modification facilitates recombination between an exogenous nucleic acid and cellular chromatin. In this way, targeted integration of transgenes is accomplished more efficiently.

Typically, when TAL effector fusions are designed to remodel chromatin, they will have a recognition sequence near the chromatin region for which remodelling is desired. In many instances, the chromatin remodelling TAL effector will bind to cellular nucleic acid within 500 nucleotides (e.g., from about 10 to about 500, from about 30 to about 500, from about 70 to about 500, from about 100 to about 500, from about 150 to about 500, from about 200 to about 500, from about 250 to about 500, from about 300 to about 500, from about 10 to about 400, from about 10 to about 300, from about 10 to about 200, from about 100 to about 200, from about 100 to about 400, etc.) the target site (e.g., double-stranded break site).

In many instances, methods of the invention will involve the use of a TAL effector fusion which creates a double-stranded break in a cellular nucleic acid molecule. Examples of such TAL effector fusion are provided elsewhere herein and will normally have a nuclease activity.

TAL effector nucleases of the invention allow for efficient site-specific integration of a gene or expression cassette of interest into a selected genetic locus of a cell. In those instances, where a reliable and predictable as well as safe expression of an integrated gene is to be achieved, the genetic target locus will often fulfill the following requirements: (i) locus disruption should not induce adverse effects or insertional oncogenesis on the engineered cell or organism and (ii) allow for active and steady transcription from the inserted gene or expression cassette. Genetic loci fulfilling those requirements across cell types are referred to as "safe harbor loci". Safe harbor loci are defined as genomic locations that maintain high levels of gene expression and are not appreciably silenced during development. Such loci have been identified in all sorts of organisms and can be targeted and used to express heterologous genes in a stable fashion. Heterologous genes inserted into intragenic loci can either be inserted in the absence of a promoter thus relying on the natural promoter of said locus or may be inserted in the context of additional components as described below such, as e.g., a heterologous promoter which may be a constitutive or an inducible promoter as outlined elsewhere herein. In the mouse, a locus known as Rosa26 locus meets these criteria because it is expressed in embryonic stem cells and many derivative tissues both in vitro and in vivo and genetic cargo can be easily integrated through homologous recombination why it is used as a standard locus for transgenesis in murine embryonic stem cells (Soriano P. Generalized lacZ expression with the ROSA26 Cre reporter strain. Nature Genetics, 21, 70-71 (1999)). Potential safe harbor loci in the human genome include, e.g., the ColA1 locus (Bead et al. Efficient method to generate single-copy transgenic mice by site-specific integration in embryonic stem cells Genesis, 44(1):23-28 (2006)) and the adeno-associated virus site 1 or so-called AAVS1 locus on chromosome 19 based on the observed repeated integration of wild-type adeno-associated virus into said locus. Integration into this locus disrupts the gene phosphate 1 regulatory subunit 12C (PPP1R12C) which encodes a protein of yet unclear function. Genes integrated into AAVS1 have been shown to be reliably transcribed in all primary human cells as well as common transformed cell lines such as HEK293, HeLa or Hep3B cells. Furthermore, embryonic stem cells and induced pluripotent stem cells retained pluripotency when targeted at the AAVS1 locus with Zn-finger nucleases (Hockemeyer et al. Efficient targeting of expressed and silent genes in human ESCs and iPSCs using zinc-finger nucleases. Nature Biotechnology 27, 851-857 (2009)). Other human loci that may qualify as safe harbor integration sites include CCR5 which encodes the major co-receptor of HIV-1 (Lombardo et al. Site-specific integration and tailoring of cassette design for sustainable gene transfer. Nature Methods 8, 861-869 (2011)), human ROSA 26 named after the homologous murine ROSA 26 locus (Irion et al. Identification and targeting of the ROSA26 locus in human embryonic stem cells. Nature Biotechnology 25, 1477-1482 (2007)) both of which are located on chromosome 3, the hypoxanthine phosphoribosyltransferase 1 (HPRT) locus on the X chromosome (Sakurai et al. Efficient integration of transgenes into a defined locus in human embryonic stem cells. Nucleic Acids Research 38(7):e96 (2010)) and a locus detected as a hotspot for phiC31 recombinase on chromosome 13 located in an intronic region of the CYLBL gene (Liu et al. Generation of Platform Human Embryonic Stem Cell Lines That Allow Efficient Targeting at a Predetermined Genomic Location. Stem Cells Dev, 18(10), 1459-1472 (2009)). Further loci in the human genome that may be safely targeted by TAL effector nucleases according to methods of the invention include loci 2p16.1 on chromosome 2, 3p12.2 or 3p24.1 on chromosome 3, 6p25.1 or 6p12.2 on chromosome 6, 7q31.2 on chromosome 7, 12q21.2 on chromosome 12, 13q34 on chromosome 13, 21q21.1 on chromosome 21.

The inventors have chosen some of the characterized human and murine safe harbor loci and have constructed and validated high efficiency TAL effector FokI nuclease pairs specifically targeting those loci. Genomic target sites for some of these TAL nuclease pairs are listed in TABLE 19 below:

TABLE 19

Exemplary target binding sites for TAL nuclease pairs

| Locus | Forward TAL nuclease target site | Reverse TAL nuclease target site |
|---|---|---|
| AAVS1 (human) | 5'-TTATCTCACAGGTAAAACT-3' (SEQ ID NO: 74) | 5'-TCTAGTCCCCAATTTATAT-3' (SEQ ID NO: 75) |
| HPRT (human) | 5'-TCTAGCCAGAGTCTTGCAT-3' (SEQ ID NO: 76) | 5'-TCAGCCCCAGTCCATTACC-3' (SEQ ID NO: 77) |
| CYLBL (human) | 5'-TGACTGCAATTTGCATCTT-3' (SEQ ID NO: 78) | 5'-TGAACATGAATCTCAGGGC-3' SEQ ID NO: 79 |
| ROSA26 (mouse) | 5'-TCGTGATCTGCAACTCCAG-3' (SEQ ID NO: 80) | 5'-TGCCCAGAAGACTCCCGCC-3' (SEQ ID NO: 81) |

Thus, in one aspect the invention relates to a TAL nuclease targeting a safe harbor locus. In certain embodiments, the safe harbor locus is selected from a mammalian or human safe harbor locus such as, e.g., AAVS1, HPRT, CYLBL or ROSA26 and the genomic target binding sites for the respective TAL nuclease pairs are defined by the forward and reverse target sites listed in TABLE 19.

In another aspect the invention relates to a kit or vector system allowing for targeted integration of a nucleic acid segment or region into a safe harbor locus of a mammalian or human cell, wherein said kit or vector system may comprise at least the following components:

(a) a first expression vector carrying a first TAL effector fused to a first nuclease cleavage half-domain wherein the first TAL effector binds a first target site within a safe harbor locus of a mammalian or human cell, (b) a second expression vector carrying a second TAL effector fused to a second nuclease cleavage half-domain wherein the second TAL effector binds a second target site within said safe harbor locus of a mammalian or human cell and wherein the second nuclease cleavage half-site is capable of dimerizing with said first nuclease cleavage-half site to form a functional dimer, and (c) a third vector carrying a nucleic acid segment, gene or expression cassette to be inserted into said safe harbor locus.

Alternatively, vectors (a) and (b) may be replaced by any of the vectors for TAL delivery described below or depicted in FIG. 22 allowing for co-expression of TAL nuclease cleavage half-domains from a single vector. The third vector of (c) carrying a nucleic acid segment, gene or expression cassette for integration may provide homology arms that match with the target sites of the genomic locus as further specified below. In certain instances, it may be desired that said third vector is a non-expression vector which does not allow for expression of the delivered nucleic acid segment or gene prior to integration into the safe harbor locus. The vector system of the invention may be used to co-transfect mammalian or human cells or cell lines according to standard techniques resulting in concurrent expression of the first and second TAL nuclease half-domains, The TAL nuclease half-domains will dimerize and create a double strand break at the safe harbor locus and the homology arm regions provided by the third vector will recombine specifically with homologous sequences juxtaposed to the break thereby inserting the nucleic acid segment, gene or expression cassette.

The nucleic acid segment or region for integration into the target site is sought may have any number of components.

Examples of such components include at least one promoter (e.g., a RNA polymerase I, II or III promoter), at least one enhancer, at least one selectable marker (e.g., a positive and/or negative selectable marker), and/or one of more region of sequence homology with cellular nucleic acid. The nucleic acid segment or region may encode a protein product or a functional RNA (e.g., a short hairpin RNA molecule or other short interfering RNA molecule, a microRNA, etc.).

In certain instances, the nucleic acid segment for integration may encode a fluorescent or other detectably labelled fusion protein. Expression of fluorescent or other detectably labelled fusion proteins may serve different purposes including, e.g., the labelling of cellular structures in living cells. Such fluorescent or other detectably labelled fusion proteins can be introduced into target cells by various means. For example, certain fluorescent cellular markers referred to as CELLLIGHT® (Life Technologies, Carlsbad, Calif.) are introduced into target cells via the BacMam technology. These baculo vectors encode a cellular marker protein (known to associate with specific cellular structures) fused to a fluorescent protein (such as GFP, RFP, CFP etc.). Following baculo-based transduction, the fusion protein is expressed and associates with its target structure allowing for live-cell imaging of the targeted cellular structure by means of the fused fluorescent moiety. One major drawback of baculovirus technology is transient and therefore limited expression of the transduced fusion protein. In certain instances, however, it may be desired to achieve a stable expression of a fluorescent marker protein, e.g., to allow longterm observation of cellular structures and associated developments. Stable expression of the respective fluorescent marker protein can be achieved by using TAL nuclease-mediated site-specific integration. A TAL nuclease according to the invention may be used to specifically integrate a single fluorescent or other detectably labelled fusion protein into a noncoding region or a safe harbor locus of the genome, eliminating undesired effects resulting from random insertion and variable copy number.

Examples of marker proteins known to associate with specific structures of human cells are indicated in TABLE 20 below. Any such marker protein can be combined with any fluorescent protein suitable for live-cell imaging to generate a fluorescent fusion protein for specific cell labeling.

TABLE 20

| Labeled Cellular Structure | Marker Protein |
|---|---|
| Actin | Human actin |
| Early endosomes | Rab5a |
| Late endosomes | Rab7a |

TABLE 20-continued

| Labeled Cellular Structure | Marker Protein |
| --- | --- |
| Endoplasmic reticulum (ER) | ER signal sequence of calreticulin and KDEL (ER retention signal) |
| Golgi | Human Golgi-resident enzyme N-acetylgalactosaminyltransferase 2 |
| Histones | Histone 2B |
| Lysosomes | Lamp1 (lysosomal associated membrane protein 1) |
| MAP4 | MAP4 |
| Mitochondria | Leader sequence of E1 alpha pyruvate dehydrogenase |
| Nucleus | SV40 nuclear localization sequence |
| Peroxisomes | Peroxisomal C-terminal targeting sequence |
| Plasma membrane | Myristolyation/palmitoylation sequence from Lck tyrosine kinase |
| Synaptic vesicles | Synaptophysin |
| Talin | Human c-terminus of talin |
| Tubulin | Human tubulin |

Such fluorescent fusion protein may be encoded on a plasmid vector co-delivered to the target cell with a TAL nuclease pair designed to introduce double-strand breaks at the target locus. Thus, in a first embodiment the invention relates, in part, to a vector carrying an expression cassette to be inserted into the genome of a mammalian or human cell, wherein the expression cassette encodes a fluorescent fusion protein and the vector further provides homology arms that match with the target sites of the genomic locus. A vector according to such first embodiment may encode one of the marker proteins listed in TABLE 20 fused to a sequence encoding a fluorescent protein selected from green fluorescent protein (GFP) or enhanced green fluorescent protein (EGFP), red fluorescent protein (RFP), blue fluorescent protein (BFP), cyan fluorescent protein (CFP), yellow fluorescent protein (YFP) or violet-excitable green fluorescent protein (Sapphire). Based on the folding requirements of the marker protein the fluorescent protein may either be fused to the marker's amino- or carboxylterminal end and may be separated by a flexible linker such as, e.g., a glycine-serine linker. In a second alternative embodiment, the vector encodes a fluorescent protein sequence and an engineered insertion site for insertion of a marker sequence of interest (e.g., encoding one of the markers listed in TABLE 20). The marker sequence may be inserted into a vector of such second embodiment by any of the various means described elsewhere herein including type II or type IIS restriction enzyme cleavage or recombination. Thus, such vector may for example be a Gateway vector allowing for insertion of the marker gene via att-site mediated recombination. Vector according to such first or second embodiment may further be provided as part of a kit or vector system.

Thus, the invention also relates to a kit or vector system allowing for targeted integration of an expression cassette encoding a fluorescent or other detectably labelled fusion protein into the genome of a mammalian or human cell, wherein said kit or vector system comprises at least the following components:
  (a) a first expression vector carrying a first TAL effector fused to a first nuclease cleavage half-domain wherein the first TAL effector binds a first target site within the genome of a mammalian or human cell,
  (b) a second expression vector carrying a second TAL effector fused to a second nuclease cleavage half-domain wherein the second TAL effector binds a second target site within the genome of said mammalian or human cell and wherein the second nuclease cleavage half-site is capable of dimerizing with said first nuclease cleavage-half site to form a functional dimer, and
  (c) a third vector according to the first or second embodiment described above.

Such kit or vector system may be used to create cell lines or whole organisms stably expressing a fluorescent or other detectably labelled protein fused to any desired marker gene. Vectors encoding fluorescent or other detectably labelled fusion proteins or any other nucleic acid segment subject to site-specific integration will be equipped with homology regions to allow for homologous recombination into the target locus of the cell.

Figure 21:
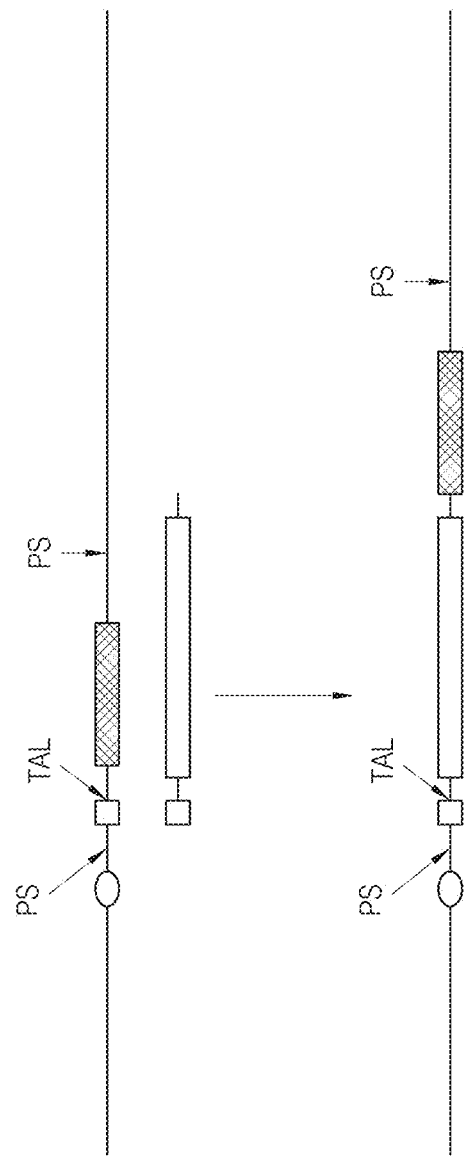
FIG. 21 shows one embodiment of a single-site, TAL effector fusion mediated homologous recombination process. The upper, long, thin horizontal line represents cellular nucleic acid (e.g., a region of a cellular chromosome). The line below containing the white box and the white rectangle represent nucleic acid which is to be integrated into the cellular nucleic acid. The white oval represents a cellular promoter, the white square represents an open reading frame which is to be integrated into the cellular nucleic acid. The black rectangle represents a cellular open reading from which is normally operable connected to the promoter. "TAL" represents a TAL effector nuclease cleavage site. "PS" represents primer binding sites.

FIG. 21 shows an example of a single-site homologous process. In this process, there is a region of homology between one end of the nucleic acid segment or region for integration and the cellular nucleic acid. Thus, homologous recombination occurs at one of the nucleic acid segment or region for integration and another joining method (e.g., non-homologous end joining) occurs between cellular nucleic acid and the other end of the nucleic acid segment or region.

The length region of shared sequence homology and the amount of sequence identity between the two regions may vary greatly. Typically, the higher the degree of sequence identity between two nucleic acid molecules, the shorter the regions of shared homology need to be for efficient homologous recombination. Thus, there are at least three parameters for consideration: (1) The degree of sequence identity between the homologous regions of the two nucleic acids, (2) the length of the shared region of sequence homology, and (3) the efficiency of the homologous recombination process.

In many instances, it will be desirable for homologous recombination to occur with high efficiency. However, if a selection marker is included in the nucleic acid segment or region for integration, then high levels of homologous recombination may not be needed. Further, lower levels of homologous recombination may be acceptable when a single construct is integrated into cellular nucleic acid of different cell types (e.g., cell from different species). In such instances, it may be desirable to have single integration construct, designed to be capable of undergoing homologous recombination with multiple cell types, and accept lower levels of homologous recombination in one or more of the cell types.

The lengths of the regions of shared homology may vary greatly but typically will be between 10 and 2,000 nucleotides (e.g., from about 10 to about 2,000, from about 50 to about 2,000, from about 100 to about 2,000, from about 200 to about 2,000, from about 400 to about 2,000, from about 500 to about 2,000, from about 10 to about 1,500, from about 10 to about 1,000, from about 10 to about 500, from about 50 to about 1,500, from about 100 to about 1,000, from about 200 to about 1,500, from about 200 to about 1,000, etc.) nucleotides. Also, the percent identity between the shared regions will typically be greater than 80% (e.g., from about 80% to about 99%, from about 80% to about 95%, from about 80% to about 90%, from about 85% to about 99%, from about 90% to about 99%, from about 90% to about 95%, etc.) sequence identity. Typically, there will be an inverse correlation between the level of identity and the amount of sequence identity of the shared sequences.

The invention also includes multiple site homologous recombination systems. Single-site homologous recombination systems generally result in the insertion of a nucleic acid segment or region into cellular nucleic acid and two site homologous recombination systems generally result in the replacement of cellular nucleic acid with the integrated nucleic acid segment or region.

Selection Systems for Enrichment of TAL-Nuclease Modified Cells.

Nucleases used to create double-stranded DNA breaks for site specific integration may be active as dimers as described above. Thus, TAL nucleases such as, e.g., TAL-FokI nuclease are designed in pairs, where each nuclease cleavage half domain is fused to a TAL effector with different binding specificity to allow simultaneous binding of both TAL moieties to opposing DNA target half-sites separated by a spacer. Binding of the TAL FokI nuclease to their DNA target allows the FokI monomers to dimerize resulting in a functional enzyme that will create a DNA double strand break. However, editing of the genome at specific loci in chromosomal DNA by a modifying agent such as a TAL nuclease can vary in efficiency in response to many factors. Delivery of the engineering agent into the cell (transfection), expression of the agent, and delivery into the nucleus are just the first steps. Engineering agents which are delivered to the nucleus must find and bind the specific loci in the genome, the efficiency of which is determined by the state of the locus (availability due to chromatin formation) and affinity of the agent for the binding site. TAL nucleases, for instance can have cleavage efficiency anywhere between 2% and 50% as a result of the combined effect of all these factors. One bottleneck in TAL nuclease-mediated cell engineering is the lack of systems to enrich or select modified cells. Based on the low cleavage efficiency it usually requires laborious screening of many clones in order to identify those cells that have been modified by the respective TAL nuclease which make only a minor fraction within a pool of cells.

Cells may be sorted or separated by various means. One popular method is cell sorting via flow cytometry which allows for physical separation of sub-populations of cells from a heterogeneous population. The advantage of cell sorting based on flow cytometry is that it is able to use multiparametric analysis to identify highly specific populations. Moreover, it is not just phenotypic characteristics (size, granularity etc.) that can be measured; but also possible to measure the content of nucleic acids within cells, or even assess functional characteristics such as ion flux or pH or altered cell states such as apoptosis and cell death. Flow cytometry may also be used to isolate or sort cells expressing fluorescent reporter proteins. Apart from the well-known green fluorescent protein derived from *Aequorea victoria*, many other engineered or improved fluorescent proteins are meanwhile available providing a broad spectrum of colors with distinct excitation and emission maxima. Examples of each of the main color classes include red fluorescent protein (RFP), blue fluorescent protein known as BFP (Heim et al. Wavelength mutations and posttranslational autoxidation of green fluorescent protein. Proc Natl Acad Sci USA. 91(26): 12501-4 (1994); Heim and Tsien. Engineering green fluorescent protein for improved brightness, longer wavelengths and fluorescence resonance energy transfer. Curr Biol. 6(2): 178-82 (1996)); cyan fluorescent protein known as CFP (Heim and Tsien. Engineering green fluorescent protein for improved brightness, longer wavelengths and fluorescence resonance energy transfer. Curr Biol. 6(2):178-82 (1996); Tsien R Y. The green fluorescent protein. Annu Rev Biochem. 67:509-44. Review. (1998)); yellow fluorescent protein known as YFP (Ormo et al. Crystal structure of the *Aequorea victoria* green fluorescent protein. Science. 273 (5280):1392-5. (1996); Wachter et al. Structural basis of spectral shifts in the yellow-emission variants of green fluorescent protein. Structure. 6(10):1267-77. (1998)); violet-excitable green fluorescent variant known as Sapphire (Tsien R Y. The green fluorescent protein. Annu Rev Biochem. 67:509-44. Review. (1998); Zapata-Hommer and Griesbeck. Efficiently folding and circularly permuted variants of the Sapphire mutant of GFP. BMC Biotechnol. 3:5. Epub (2003)); and cyan-excitable green fluorescent variant known as enhanced green fluorescent protein or EGFP (Yang et al. Optimized codon usage and chromophore mutations provide enhanced sensitivity with the green fluorescent protein. Nucleic Acids Res. 24(22):4592-3. (1996)). Besides sorting of cells expressing a particular fluorescent protein, the selection may also rely on the close co-localization or interaction of two proteins each fused to a different fluorescent protein by a technique referred to as FRET (fluorescence resonance energy transfer). FRET requires a distance- and orientation-dependent transfer of excitation energy from a donor fluorophore to an acceptor chromophore. Accordingly, by expressing the donor fluorescent protein as a fusion with one protein-of-interest and the acceptor fluorescent protein as a fusion with a second protein-of-interest, the distance between the two proteins-of-interest can be inferred from the FRET efficiency measured using, e.g., live cell fluorescence microscopy.

Another way to sort cells is to use magnetic beads. It is possible to positively select cells of interest by adding antibodies or other binding molecules (such as, e.g., a receptor) coupled to magnetic beads to specifically select the population of interest, or by negatively selecting cells by adding labeled antibodies specific for cells other than those of interest. Cells may then be passed through a column between a strong magnetic field to either elute or retard a population of interest. One example of magnetic separation known as magnetic-activated cell sorting (MACS® Technology, Miltenyi Biotec, Bisley, UK) is used to isolate transiently transfected cells expressing the gene of interest together with a cotransfected cell surface marker gene, The MACS® methodology allows the separation of cells expressing said surface marker from those lacking the marker. The cell surface marker could be either introduced into cells by DNA-mediated gene transfer techniques as disclosed elsewhere herein or be a surface protein that is endogenously expressed by the cell or cell type. Cells expressing said surface marker protein are then selected with specific antibodies attached to a magnetic matrix by applying a magnetic field under appropriate experimental conditions. The system can be used for any cell surface marker for which a suitable antibody is available. Typical surface markers of mammalian or human cells for which commercial antibodies are available include e.g. CD2, CD3, CD4, CCR5, CD8, CD11a/LFA-1, CD11b, CD11c, CD13, CD14, CD15, CD16, CD18, CD19, CD20, CD23, CD25, CD27, CD28, CD31, CD33, CD34, CD38, CD40, CD44, CD45, CD45RA, CD45RO, CD54, CD56, CD62L, CD69, CD79a, CD80, CD83, CD86, CD94, CD95, CD117, CD123, CD127, CD138, CD161, CD195, DC-SIGN, CTLA-4, or various MHC class I or MHC class II markers such as HLA-DR, HLA-F, If no labeled commercial antibody against a particular surface marker is available, cells may also be labeled with a primary unconjugated antibody or serum and then bound by a labelled secondary antibody directed to the Fc part of the primary antibody. Alternatively, the primary antibody may also by biotinylated or fluorochrome-conjugated and bound in a second step by an anti-fluorochrome antibody or streptavidin bound to magnetic particles.

Cell Enrichment Using Surrogate Reporters.

Cleavage of a specific locus is detected by the creation of a lesion (indel) which leaves a mutation in the genomic sequence and, if placed in an open reading frame, may often cause a frameshift gene knock out. In order to enrich for cells that have a high concentration of active TAL nucleases and thus, a high likelihood of carrying such lesions, the frameshifting activity of the error-prone nonhomologus end-joining (NHEJ)-mediated repair mechanism can be used to activate reporter genes in transiently expressed vectors. For this purpose, a TAL nuclease pair can be co-delivered into a cell with a "surrogate" reporter construct carrying an expression cassette, wherein said expression cassette contains in 5' to 3' direction at least a first selectable marker gene, a left and right TALE binding half site separated by a spacer and a second selectable marker gene, and wherein the first and second selectable marker genes are expressed under the control of a single promoter. The reading frame encoding the first selectable marker is different from the reading frame encoding the second selectable marker so that in the absence of a functional TAL nuclease only the first selectable marker is expressed. Those cells expressing a functional nuclease dimer will allow for introduction of nuclease-mediated double-strand breaks in the spacer region of the surrogate reporter's target sequence. The break will then be repaired by NHEJ, resulting in a frameshift mutation in approximately one third of cases which places the second selectable marker gene in the same reading frame with the first selectable marker gene and thus allows for the expression of both selectable markers. Cells carrying a modified surrogate reporter can therefore be selected via expression of the second selectable marker. The first and selectable marker genes may be of the same or different nature. In a first embodiment, both the first and selectable marker genes may encode different fluorescent proteins as described above. For example the first selectable marker may be GFP and the second selectable marker may be RFP or vice versa. In such embodiment, cells expressing the second selectable marker may be selected by flow cytometry or by fluorescence microscopy as described above. Alternatively, the first selectable marker gene may encode a fluorescent protein and the second selectable marker gene may encode a resistance marker such as, e.g., a hygromycin resistance. In this case, modified cells expressing the resistance marker can be put under selective pressure to grow in the presence of the respective antibiotic. In yet another embodiment, the first selectable marker may be a fluorescent protein and the second selectable marker may be one of the above described cell surface markers. To allow separation from the fusion protein and transport to the cell surface, the surface marker may be fused to a T2A translational cleavage site or other cleavage sites with similar function. Modified cells expressing a surface marker can then be sorted as described above, e.g., via magnetic beads carrying surface-marker specific antibodies. Because the surrogate reporter will be mainly modified in those cells exhibiting a high concentration of functional TAL nuclease pairs, this method allows for the efficient enrichment of cells that are likely carrying a nuclease-modified genome. Furthermore, the episomal surrogate reporter system is non invasive, does not interfere with TAL nuclease activity and will be diluted out after a few cell divisions which makes it an attractive and efficient tool for cell enrichment.

Tse2/Tsi2 Selectable Marker System for Enrichment of TAL Nuclease Modified Cells.

Apart from positive cell enrichment via fluorescence or surface marker expression, all of which require additional separation or isolation steps, cells may also be selected by negative selection, i.e., removing all cells that do not carry functional TAL nuclease pairs. The inventors have developed two expression systems which rely on the Tse2/Tsi2 selectable marker system which depends on the interaction between the toxin Tse2 and the antidote Tsi2. Whereas the expression of the cellular toxin Tse2 results in cell death (in many prokaryotic and eukaryotic cells) the co-expression of Tsi2 will restore cell viability (as described in detail elsewhere herein).

Figures 34A, 34B:
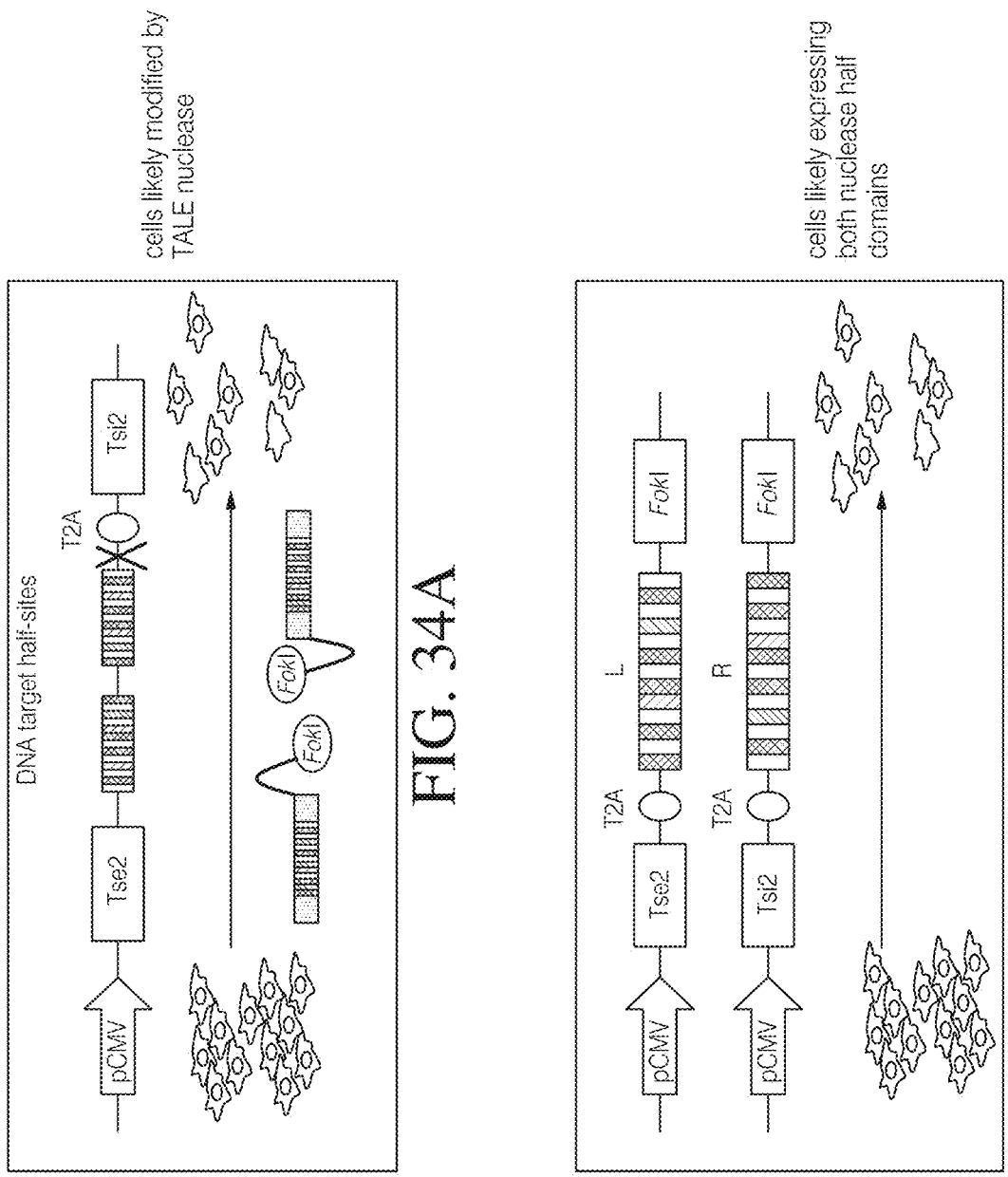
FIGS. 34A and 34B show expression systems based on the Tse2/Tsi2 toxin/antidote effect for the enrichment of TAL nuclease-modified cells.
Figure 36A:
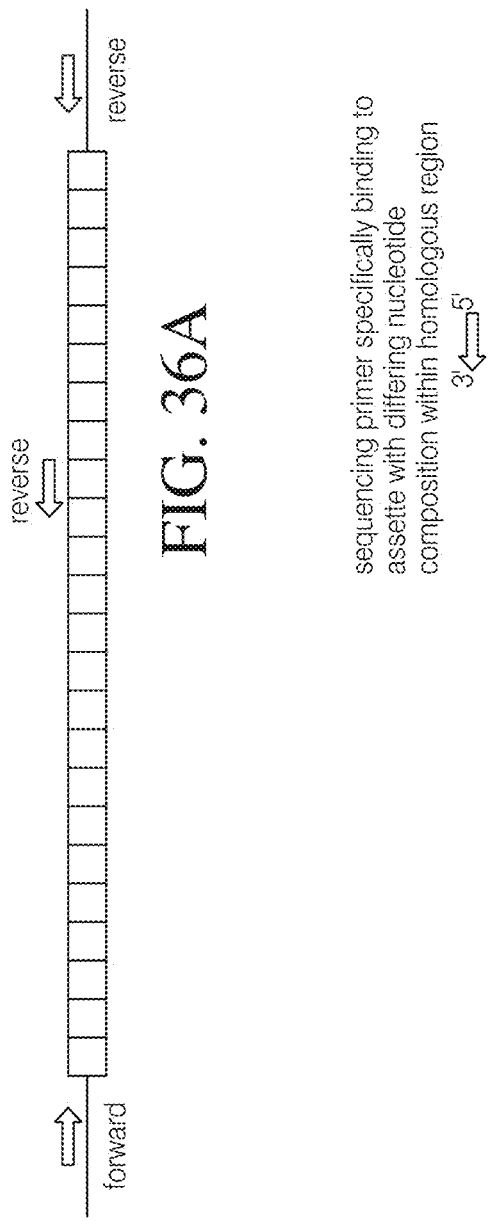
FIGS. 36A and 36B show an example of how a TAL effector sequence may be designed to allow for full-length sequencing of a repetitive TAL effector region.
Figure 36B:
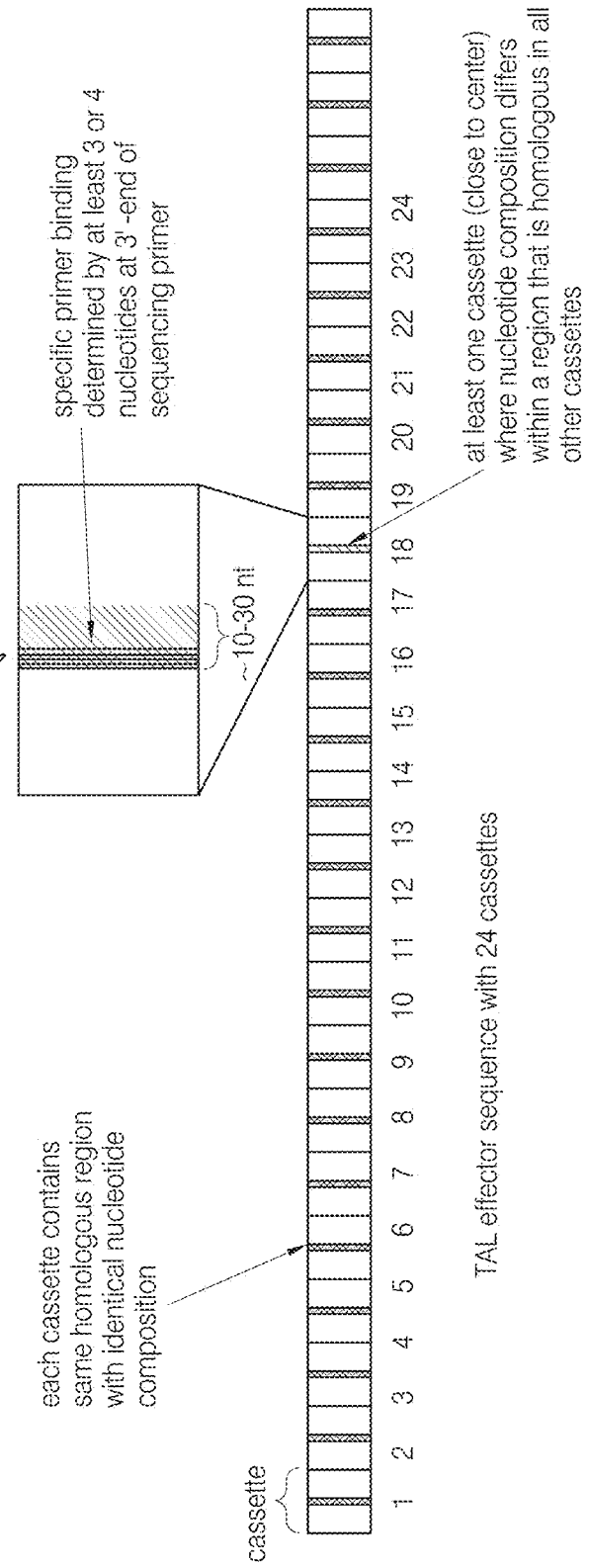

In a first embodiment, the invention relates to an expression system comprising at least a first and second vector expressing TAL nuclease cleavage half domains and a third vector functioning as a "surrogate reporter" as defined above. The surrogate reporter vector may comprise in a 5' to 3' direction a Tse2 coding sequence, both TALE effector target sites (left and right half-side) separated by a spacer, a self-cleavage sequence, and a Tsi2 coding sequence. An example of such surrogate reporter vector is shown in FIG. 34A. Whereas Tse2 is constitutively expressed (e.g., from a weak promoter such as PGK or SV40 etc,), the sequence encoding Tsi2 is placed out of frame so that no Tsi2 can be produced. Those cells expressing a functional nuclease dimer will allow for introduction of nuclease-mediated double-strand breaks into the target sequence of the surrogate reporter. The break will then be repaired by error-prone nonhomologus end-joining (NHEJ), which often causes frameshift mutation. Approximately one third of those mutations will place the Tsi2 coding sequence in frame with Tse2 and thus, allow for Tsi2 expression which will protect cells from Tse2-induced cell stasis. Such system allows only for the proliferation of those transfected cells which have a high likelihood of carrying a nuclease-modified genome. In most cases, co-transfection will deliver all three vectors into a single cell. However, to select against cells not carrying a surrogate reporter, the surrogate reporter vector may be equipped with an additional selection marker such as e.g. an antibiotic resistance gene and cells may be grown under selective pressure.

In a second embodiment, the invention relates to an expression system comprising a first and a second expression vector each encoding a TAL nuclease cleavage half domain, wherein the first TAL nuclease cleavage half domain in the first vector is fused to a Tse2 coding sequence via a self-cleavage site and wherein the second TAL nuclease cleavage half domain in the second vector is fused to a Tsi2 coding sequence via a self-cleavage site. One example of such first embodiment is illustrated in FIG. 34B which shows a vector set for coexpression of two TALE FokI nuclease cleavage half domains each of which is connected in a separate vector to either Tse2 or Tsi2 via a T2A self cleavage site. In this example, both fusion proteins are expressed under the control of a CMV promoter. However, any other promoter allowing for substantial expression in a given cell or tissue may be used instead as described elsewhere herein. As the modification of cells depends on the coexpression of both TAL nuclease cleavage half domains and the survival of cells depends on expression of Tsi2, only cells with balanced Tse2 and Tsi2 expression levels—which likely exhibit high nuclease activity—will survive and grow. The T2A self cleavage site can be replaced by another cleavage site of similar function. Alternatively, other vector setting may be used which allow for simultaneous expression of Tse2 with a first TAL nuclease cleavage half domain and simultaneous expression of Tsi2 with a second TAL nuclease cleavage half domain. For example, the Tse2 and Tsi2 sequences may be connected to the first and second TAL nuclease cleavage half domains via an IRES, a translational coupling sequence or an intein as indicated in FIG. 22. The two described embodiments allow for efficient non-invasive enrichment of cells expressing functional nuclease dimers without further cell separation or isolation which will facilitate the use of programmable nucleases in biotechnology and basic research.

Once a cell has been identified which potentially has integrated a nucleic acid segment or region into cellular nucleic acid, the integration site location may be confirmed by any number of methods. One method would be to sequence the integration site to determine whether the nucleic acid for which integration was desired is present. Another method is through the use of the polymerase chain reaction (PCR). FIG. 21 shows two primer sites. PCR using primers which binding to the indicated sites will generate PCR products of different lengths depending on whether nucleic acid in addition to the cellular nucleic acid is present. Such PCR reactions will give one of three results: (1) A relatively short PCR product, indicating that integration has not occurred at the locus, (2) a relatively long PCR product, indicating that integration has occurred at the locus, and (3) both relatively short and relatively long PCR products, indicating that the sample contains a mixture of (1) and (2). This can occur of there is a mixed population of cell (e.g., one cell type were integration has occurred and another cell type where integration has not occur) or the cell is either haploid or polyploid and integration has not occurred in all copies of the cellular nucleic acid. One instance of this would be if the target nucleic acid is *Chlamydomonas reinhardtii* chloroplast genome. The chloroplast genome of this organism contains rough 60 copies of the chloroplast chromosome.

Delivery and Transfection

Vectors for TAL Delivery.

In one aspect, the invention relates to novel vectors for delivery of TAL effectors to host cells. TAL effectors are generally delivered to cells in single expression vectors, wherein the TAL binding domain and the effector domain are provided in a single expression cassette expressed as a fusion protein from a single promoter. However, in embodiments where is desirable for TAL effectors to dimerize or multimerize to fulfil their effector function (such as, e.g., in the reconstitution of certain nucleases activities, including FokI or truncated or modified variants thereof), at least a pair of these single expression vectors may be delivered at to a given host cell. Co-delivery of two or more expression vectors may result in unequal uptake of the vectors and unequal expression and thus under- or overrepresentation of one or more of the interacting domains leading to a loss in enzymatic activity. Co-expression vectors may be used to resolve such issues. Such vectors may be constructed in a manner which allows for the simultaneous expression of two or more TAL effector domains from the same vector (e.g., plasmid). In some embodiments, co-expression vector used allow for simultaneous expression of at least one TAL effector pair from the same vector.

Vector produced by and/or used in the practice of the invention include those suitable for co-expression of at least two different TAL effector proteins may include, for example one or more of the following components: (i) a promoter operatively linked with a first open reading frame encoding a first TAL effector protein or a truncated or modified version thereof, (ii) a second open reading frame encoding a second TAL effector protein or a truncated or modified version thereof and (iii) a sequence element operatively linking at least the first and the second TAL effector open reading frame wherein the second TAL effector open reading frame contains at least one stop codon. These vectors may further comprise at least one second expression cassette encoding a resistance marker. In another aspect of the invention, at least one promoter of the aforementioned vector may be an algal, mammalian, yeast, bacterial, or plant promoter as disclosed elsewhere herein. In another aspect, the aforementioned vector may allow at least expression in microalgae and the promoter may be a synthetic promoter active in microalgae. In one aspect, the promoter of the aforementioned vector may be a CMV or EF1-α promoter, a tissue-specific mammalian promoter, or derivatives thereof.

In a first embodiment, the first open reading frame of the co-expression vector contains a stop codon and the second open reading frame contains a start codon and the sequence element operatively linking at least the first and the second TAL effector open reading frame contains an internal ribosome entry site (IRES) (FIG. 22A). Co-expression expression vectors containing an internal ribosomal entry site (IRES) element from the encephalomyocarditis virus (EMCV) allow for translation of two open reading frames (ORF 1 and ORF 2, respectively) from one message. IRESs are relatively short DNA sequences that can initiate RNA translation in a 5' cap-independent fashion. Placement of the IRES and a second gene of interest (ORF 2) downstream of the first target gene (ORF 1) allows co-expression of ORF 1 in a cap-dependent manner and ORF 2 in a cap-independent fashion, thus facilitating translation of two proteins from one mRNA transcript. In some instances the expression of the second open reading frame which is triggered by an IRES or related signal may be weaker than expression of the first open reading frame. This may be advantageous where more of the first protein is required or desirable. As an example, the second open reading frame could encode a selectable marker. In such an instance, stringent selection may be used to identify vectors and cells with high levels of expression of the first open reading frame.

Co-expression of two genes from the same promoter can also take place with the utilization of *Thosea asigna* virus 2A translational cleavage site or other cleavage sites with similar function. The T2A cleavage site is ~20 amino acids long and can be positioned in between the 2 open reading frames. Cotranslational cleavage occurs via a co-translational ribosome skipping mechanism between the C-terminal Glycine and Proline residues, leaving 17 residues attached to the end of the start of the second open reading frame. Thus, in another embodiment, the first open reading frame of the co-expression vector does not contain a stop codon and the second open reading frame does not contain a start codon and the sequence element operatively linking at least the first and the second open reading frame contains a translational cleavage site, such as, e.g., a T2A site (FIG. 22B). Thus, the invention further includes compositions and methods for the production polyproteins which are processed to generate two or more polypeptides from a initial translated product.

In a further embodiment, a sequence element operatively linking at least the first and the second open reading frame contains a translational coupler sequence. Translational coupling is achieved either by placing the stop codon of the first open reading frame in direct neighborhood of the start codon of the second open reading frame (e.g., UGAAUG) or causing an overlap between the stop codon of the first open reading frame and the start codon of the second open reading frame as, for example, represented by the sequence (UGAUG). Thus, in some embodiments, the translational coupler sequence may either be UGAAUG or UGAUG (FIG. 22C).

In yet another embodiment, the sequence element operatively linking at least the first and the second open reading frame contains an intein that is able to excise itself from the fusion protein. (FIG. 22D).

In an additional embodiment, the first and second open reading frames are located in the same vector at different insertion sites. The two open reading frames may be expressed from two separate expressing cassettes each under control of a separate promoter. In one aspect, the two separate promoters may be different promoters, such as, e.g., a constitute and an inducible promoter or a strong and a weak promoter or different combinations thereof. In certain instances at least one of the open reading frames has been codon-optimized with regard to a target host. The open reading frames of the vectors of the invention may, e.g., encode TAL effector nuclease cleavage domains. For example, a first open reading frame may encode a first TAL-FokI nuclease domain and a second open reading frame encode a second TAL-FokI nuclease domain. In some embodiments at least one open reading frame may encode a mutated, truncated or modified TAL-FokI nuclease domain. The mutated domain may, e.g., be a Sharkey domain or may carry at least one of the following mutations: E490K, I538K, H537R, Q486E, I499L, N496D, R487D, N496D, D483R, and/or H537R.

TAL Delivery Systems

An important factor in the administration of polypeptide compounds, such as TAL effector, is ensuring that the polypeptide has the ability to traverse the plasma membrane of a cell, or the membrane/matrix of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as TAL effectors across a cell membrane. For example, "membrane translocation polypeptides" have amphiphilic or hydrophobic amino acid subsequences that have the ability to act as membrane-translocating carriers. In one embodiment, homeodomain proteins have the ability to translocate across cell membranes. Examples of peptide sequences which can be linked to a protein, for facilitating uptake of the protein into cells, include, but are not limited to: an 11 amino acid peptide of the tat protein of HIV; a 20 residue peptide sequence which corresponds to amino acids 84-103 of the p16 protein (see Fahraeus et al., Current Biology 6:84 (1996)); the third helix of the 60-amino acid long homeodomain of Antennapedia (Derossi et al., J. Biol. Chem. 269:10444 (1994)); the h region of a signal peptide such as the Kaposi fibroblast growth factor (K-FGF) h region (Lin et al. "Identification, expression, and immunogenicity of Kaposi's sarcoma-associated herpesvirus-encoded small viral capsid antigen", J. Virol. 1997 April; 71(4):3069-76.) or the VP22 translocation domain from HSV (Elliot & O'Hare, Cell 88:223-233 (1997)). Other suitable chemical moieties that provide enhanced cellular uptake may also be chemically linked to ZFPs. Membrane translocation domains (i.e., internalization domains) can also be selected from libraries of randomized peptide sequences. See, for example, Yeh et al. (2003) Molecular Therapy 7(5):5461, Abstract #1191.

Many toxin molecules also have the ability to transport polypeptides across cell membranes. Often, such molecules (called "binary toxins") are composed of at least two parts: a translocation/binding domain or polypeptide and a separate toxin domain or polypeptide. Typically, the translocation domain or polypeptide binds to a cellular receptor, and then the toxin is transported into the cell. Several bacterial toxins, including Clostridium perfringens iota toxin, diphtheria toxin (DT), Pseudomonas exotoxin A (PE), pertussis toxin (PT), Bacillus anthracis toxin, and pertussis adenylate cyclase (CYA), have been used to deliver peptides to the cell cytosol as internal or amino-terminal fusions (Arora et al., J. Biol. Chem., 268:3334-3341 (1993); Perelle et al., Infect. Immun., 61:5147-5156 (1993); Stennark et al. J. Cell Biol. 113:1025-1032 (1991); Donnelly et al., Proc. Natl. Acad. Sci. USA 90:3530-3534 (1993); Carbonetti et al., Abstr. Annu. Meet. Am. Soc. Microbiol. 95:295 (1995); Sebo et al. Infect. Immun. 63:3851-3857 (1995); Klimpel et al., Proc. Natl. Acad. Sci. USA 89:10277-10281 (1992); and Novak et al., J. Biol. Chem. 267:17186-17193 1992)). Such peptide sequences can be used to translocate TAL-cleavage domain fusion proteins across a cell membrane. TAL effectors can be conveniently fused to or derivatized with such sequences. Typically, the translocation sequence is provided as part of a fusion protein. Optionally, a linker can be used to link the TAL effector and the translocation sequence. Any suitable linker can be used, e.g., a peptide linker.

TAL effectors can also be introduced into an animal cell, such as a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell. Liposome are believed to fuse with the plasma membrane, thereby releasing the drug into the cytosol. Alternatively, the liposome may be phagocytosed or taken up by the cell in a transport vesicle. Once in the endosome or phagosome, the liposome is believed to either degrades or fuses with the membrane of the transport vesicle and releases its contents. When liposomes are endocytosed by a target cell, for example, they become destabilized and release their contents. This destabilization is termed fusogenesis. Dioleoylphosphatidylethanolamine (DOPE) is the basis of many "fusogenic" systems. The invention thus include compositions and methods for the use of liposome to deliver TAL effectors to cells.

Conventional viral and non-viral based gene transfer methods can be used to introduce nucleic acids encoding engineered TAL effectors in animal cells (e.g., mammalian cells) and target tissues. Such methods can also be used to administer nucleic acids encoding TAL effectors to cells in vitro. In certain embodiments, nucleic acids encoding TAL effectors may be administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell.

Methods of non-viral delivery of nucleic acids encoding engineered TAL effectors include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids. Additional exemplary nucleic acid delivery systems include those provided by Amaxa Biosystems (Cologne, Germany), Maxcyte, Inc. (Rockville, Md.) and BTX Molecular Delivery Systems (Holliston, Mass.).

The use of RNA or DNA viral based systems for the delivery of nucleic acids encoding engineered TAL effectors take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of TAL effectors include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

In applications in which transient expression of a TAL effector is desirable, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *Proc. Natl. Acad. Sci. USA* 81:6466-6470 (1984); and Samulski et al., *J. Virol.* 63:03822-3828 (1989).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)).

Packaging cells are used to form virus particles that are capable of infecting a host cell. Such cells include 293 cells, which package adenovirus, and psi-2 packaging line (a retroviral packaging line created by stably introducing into NIH3T3 cells an engineered retroviral DNA genome from which the RNA packaging signal had been removed) cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. Missing viral functions are supplied in trans by the packaging cell line. The cell line is also infected with adenovirus as a helper. The helper virus promotes replication of the AAV vector and expression of AAV genes from the helper plasmid. In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In some embodiments, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-.gamma. and TNF-.alpha. are known (see Inaba et al., *J. Exp. Med.* 176:1693-1702 (1992)). Stem cells are isolated for transduction and differentiation using known methods. For example, stem cells are isolated from bone marrow cells by panning the bone marrow cells with antibodies which bind unwanted cells, such as CD4+ and CD8+(T cells), CD45+ (panB cells), GR-1 (granulocytes), and Iad (differentiated antigen presenting cells) (see Inaba et al., *J. Exp. Med.* 176:1693-1702 (1992)).

Vectors (e.g., retroviruses, adenoviruses, liposomes, etc.) containing therapeutic TAL effector nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Control of Transient TAL Effector Expression.

As described above, viral and non-viral based gene transfer methods can be used to introduce nucleic acids encoding TAL effectors into cells which will then be transcribed and translated by the cellular machinery. Following DNA transfection, detection of transient expression of the transgene generally lasts for 1 to 7 days. Only a fraction of DNA delivered to the cells makes it to the nucleus for transcription, with eventual export of the message to the cytoplasm for protein production. Within a few days most of the foreign DNA is degraded by nucleases or diluted by cell division; and after a week, its presence is no longer detected. However, even such short expression time may allow a TAL effector to interact with other potential genomic binding sites leading to unwanted off-target site manipulation. To avoid such additional interaction it may be desired in certain instances, to fine-tune the transient expression of a TAL effector function or even completely remove a TAL effector from the cell once the intended effect has been achieved. In principle, control of gene expression can be achieved at three different levels: at DNA, mRNA and protein level.

In a first embodiment, the activity of a TAL effector may be controlled at protein level by affecting its protein half-life. Long half-life proteins are accumulated over a very long period (days), such that any increase in production that occurs during a few to several hours has proportionally little impact on the very high steady-state levels already present. To reduce the half-life of a translated TAL effector protein, protein-destabilizing elements may be used. For example, the PEST sequence—a sequence rich in proline, glutamic acid, serine and threonine that acts as a signal peptide for protein degradation—may be fused to a TAL effector sequence (Rechsteiner and Rogers. PEST sequences and regulation by proteolysis. Trends Biochem Sci. 21(7):267-71 (1996)). The PEST sequence is associated with proteins that have a short intracellular half-life and was shown to efficiently destabilize transiently expressed reporter proteins when fused to their C-terminus (Li et al. Generation of destabilized green fluorescent protein as a transcription reporter J. Biol. Chem. 27334970-34975 (1998)). Other methods for destabilizing proteins utilize the N-end rule (Bachmair et al. In vivo half-life of a protein is a function of its amino-terminal residue Science 234179-186. (1986)) or ubiquitin fusion degradation pathways (Johnson et al. A proteolytic pathway that recognizes ubiquitin as a degradation signal. J. Biol. Chem. 27017442-17456 (1995)). For example it has been shown that the degree of destabilization of a protein can be controlled depending on the number of multimerized linear chains of ubiquitin coupled to the target protein (U.S. Pat. No. 7,262,005 incorporated herein by reference in its entirety). Alternatively, recognition sites for cleavage by cellular proteases (such as e.g. serine, threonine, cystein, aspartate or glutamic proteases) may be incorporated into the TAL effector sequence. Destabilizing the translated protein, however, only partly addresses the problem, since clearance rates are also dependent on the half-life of the TAL effector mRNA. As long as the pre-existing mRNA remains intact, it continues to produce new TAL effector proteins via translation.

Thus, in a second embodiment destabilizing elements may alternatively (or in addition) be provided at RNA level. For example, a PCR fragment or synthetic oligonucleotide containing an AU-rich sequence stretch known to destabilize cellular RNA may be fused to the 3'-UTR region (Zubiaga et al. The nonamer UUAUUUAUU is the key AU-rich sequence motif that mediates mRNA degradation Mol. Cell. Biol. 152219-2230. (1995)). RNA-destabilizing elements derived from myc orfos genes may also be suitable for this purpose. (Yeilding et al. Identification of sequences in c-myc mRNA that regulate its steady-state levels Mol. Cell. Biol. 163511-3522. (1996); Shyu et al. The c-fos transcript is targeted for rapid decay by two distinct mRNA degradation pathways Genes Dev. 360-72. (1989)). Alternatively, an artificial intron may be created within the coding region of a TAL effector sequence defined by a splice donor and a splice acceptor site that will cause splicing of TAL effector transcripts. The splice donor site includes an almost invariant sequence GU at the 5' end of the intron, within a larger, less highly conserved region. The splice acceptor site at the 3' end of the intron terminates the intron with an almost invariant AG sequence. Upstream from the AG there is a region high in pyrimidines (C and U), or a polypyrimidine tract that may be created based on the degeneracy of the genetic code. Upstream from the polypyrimidine tract is the branch point, which includes an adenine nucleotide. The artificial intron will induce splicing of at least a portion of the TAL effector transcripts which will then be translated into nonsense proteins.

In a third embodiment, TAL effector expression may also be controlled via temporary gene knockdown by treatment with short DNA or RNA molecules with a sequence complementary to the TAL effector mRNA transcript or gene. In a transient knockdown, the binding of a complementary oligonucleotide to the active TAL effector gene or its transcripts causes decreased expression through blocking of transcription (in the case of gene-binding), degradation of the mRNA transcript (e.g. by small interfering RNA (siRNA)) or blocking mRNA translation. An siRNA sequence targeting the TAL effector sequence may for example be delivered to the target host cell in a separate vector or may be provided with the vector containing the TAL effector, e.g. in the context of a separate expression cassette the promoter of which may be inducible.

Yet another possibility to fine-tune TAL effector expression in a given host cell is the introduction of a TAL effector binding site into the TAL effector coding sequence. If substantial amounts of TAL effector protein have been produced in a cell, the TAL effector will bind to its own DNA thereby inhibiting further transcription of the gene. Such negative feedback regulation has the advantage that expression control depends on the amount of functional protein in the cell. For example, if the TAL effector is a TAL nuclease, binding of the TAL nuclease to its own DNA will result in double strand breaks of the TAL nuclease encoding DNA. If the TAL effector is a repressor, binding of the TAL repressor to a TAL binding site inserted close to or overlapping the promoter region, may interfere with RNA polymerase's progress along the strand, thus impeding the expression of the gene. Thus, the invention relates, in part, to a TAL effector coding expression cassette comprising at least one target sequence for the TAL effector protein encoded by the expression cassette that allows binding of the TAL effector protein thereby interfering with TAL effector expression.

TAL Nucleic Acid Scaffolds.

As described elsewhere herein in more detail, TAL effectors can be fused to functional domains such as nucleases, activators, repressors or epigenetic modifiers thereby linking their inherent nucleic acid binding specificity to another nucleic acid binding or nucleic acid modifying activity. However, in one instance of the invention specific binding of TAL effectors to target nucleic acid can be used to arrange fused effector functions in predefined order on a nucleic acid scaffold designed to carry multiple TAL binding sites. A related approach was described by Conrado et al. ("DNA-guided assembly of biosynthetic pathways promotes improved catalytic efficiency. Nucleic Acids Res. 2012 Feb. 1; 40(4):1879-1889) for zinc-finger enzyme fusion proteins. By TAL nucleic acid (e.g., DNA) scaffold as used herein is meant a system comprising at least a nucleic acid scaffold with one or more TAL effector binding sites that can be bound by one or more engineered TAL effector fusions. In one embodiment of the invention TAL effectors may be fused to enzymes catalyzing reactions of a metabolic pathway to efficiently accumulate these enzymatic functions on a nucleic acid scaffold in predefined order. Such organized enzyme assembly may be used to increase or accelerate turn over of existing metabolic pathways or may be used to establish new biosynthetic pathways in a given host. In another embodiment, TAL effectors may be fused to signaling molecules to trigger signaling pathways or construct artificial communication or gene regulatory networks in a given host for applications in gene therapy, tissue engineering, biotechnology etc.

Thus, the invention also relates, in part, to TAL effector fusions organized on nucleic acid scaffolds. In one aspect TAL nucleic acid scaffolds are designed to harbor multiple target binding sites to assemble different TAL effector fusions. TAL effector binding sites may be located in one strand of the nucleic acid scaffold or may also be located in the opposite strand. Specific binding sites for different TAL effector fusions may be separated by spacers of same or different length. Spacer length between the binding sites determines the proximity of the bound fusion proteins on the nucleic acid scaffold and may critically influence protein interaction. In some embodiments, the spacers between two binding sites on the same nucleic acid strand may comprise between 2 and 5, between 4 and 10, between 6 and 20, between 15 and 30 nucleotides. In certain instances, nucleic acid scaffolds of the invention may only carry one unique binding site for each TAL effector fusion. In other instances, nucleic acid scaffolds of the invention may carry several copies of binding sites for a specific TAL effector fusion. The number of binding sites for different TAL effector fusions included in a nucleic acid scaffold may be equal or different. For example, the nucleic acid scaffold may contain one binding site for a first TAL effector, two binding sites for a second TAL effector, three or four binding sites for a third TAL effector etc. or the nucleic acid scaffold may contain two copies of a first binding site, one copy of a second binding site, two or four or more copies of a third binding site etc. The nucleic acid scaffold may for example consist of several units wherein one unit contains different binding sites for different TAL effectors and the nucleic acid scaffold contains many copies of the entire unit. For example, the nucleic acid scaffold may comprise TAL binding sites for TAL effectors 1, 2 and 3 in one unit and the nucleic acid scaffold may comprise 2, 3, 4, 5, 6, 7, 8, 9, 10, 11, 12, 13, 14, 15, 16, 17, 18, 19, 20 or more copies of this unit. The invention includes all combinations of repeats and/or ratios of binding sites or binding site units in a nucleic acid scaffold depending on the required concentration or activity of the binding TAL effector function. The order of binding sites for different TAL effectors in a nucleic acid scaffold may also vary in different embodiments of the invention. For example in a first embodiment one or several copies of a first TAL effector binding site in a nucleic acid scaffold may be followed by one or several copies of a second TAL effector binding site. In another embodiment several copies of a first TAL effector binding site may be interrupted by one or more copies of other TAL effector binding sites. The invention therefore includes all orders of single or multiple TAL effector binding sites in a nucleic acid scaffold depending on the required order of reactions or interactions mediated by same or different TAL effector functions. The TAL effector binding sites for different TAL effector fusions may have equal or different lengths. For example, the binding site for a first TAL effector may consist of 19 nucleotides whereas the binding site for another TAL effector may consist of 25 nucleotides, etc.

The invention further relates to methods of assembling nucleic acid scaffolds with multiple TAL binding sites. In some instances, nucleic acid scaffolds may be generated based on plasmid nucleic acid or vectors. For example, a series of TAL binding sites may be inserted into the multiple cleavage site of a plasmid or vector. Individual TAL binding sites maybe flanked by restriction enzyme cleavage sites to allow for insertion, deletion or replacement of binding sites. In other instances, nucleic acid scaffolds may be synthesized de novo from overlapping oligonucleotides, predesigned parts and/or PCR-based techniques as described elsewhere herein.

Figure 23A:
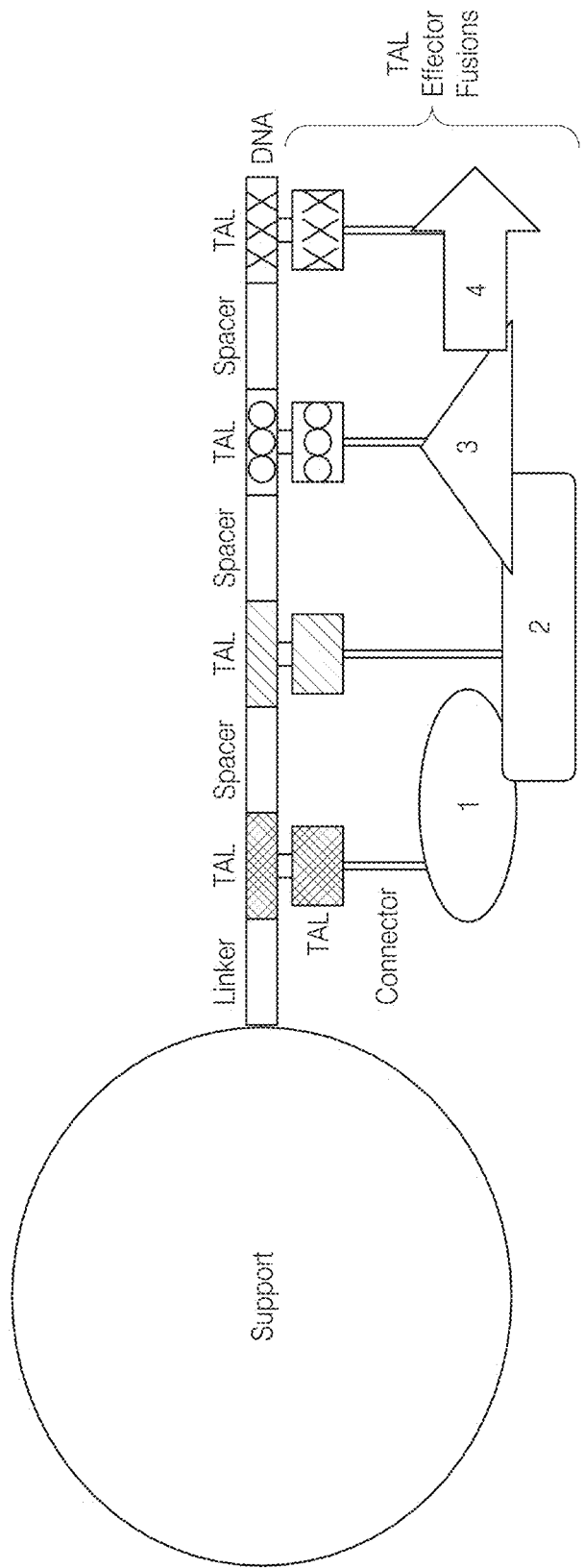
FIG. 23A shows a schematic of the use of TAL effector fusions for the assembly of a protein complex. In this figure, DNA with a series of TAL effector binding site (labeled "TAL") is connected to a solid support (labeled "Support") via a linker segment (labeled "Linker"). The DNA segment contains spacers (labeled "Spacers") between each TAL effector binding site. TAL effector fusions are shown interacting with the DNA. In addition to a TAL effector, these fusions contain an amino acid segment which connects the TAL effector to a fusion partner (labeled "Connector"). The DNA and the TAL effector fusions are designed in such a manner that, upon binding of the fusion to the DNA, the fusion partners form a protein complex.

In one aspect, TAL nucleic acid scaffolds of the invention are designed to assemble TAL effector enzyme fusions. The coding region of an enzyme or enzymatic domain may be fused either 5' or 3' to the TAL effector sequence depending on the structural requirements and/or accessibility of the enzymatic domain. Furthermore, a linker sequence such as, e.g., a sequence encoding a Gly-Ser linker may be included to separate the TAL effector from the enzymatic domain. In certain instances, the TAL effector fusions may be provided on a support as illustrated in FIG. 23A. The TAL effector enzyme fusions may harbor activities catalyzing defined steps of a metabolic pathway. By fusing pathway-associated enzymatic functions to TAL effectors which are organized to bind to a nucleic acid scaffold in a predicted order, the enzymatic functions can be concentrated in a defined region or compartment of a host thereby increasing pathway flux and turn-over rates of metabolic products. TAL nucleic acid scaffolds of the invention may be used, e.g., to establish non-native pathways in a given host. Any host or host cell including bacteria, yeast, fungi, plant, insect or mammalian cells suitable for genetic engineering may be used for this purpose. Thus, the invention relates in part to an engineered cell containing (i) at least one nucleic acid molecule with two or more distinct TAL effector binding sites, (ii) one or more nucleic acid sequences encoding at least a first and a second TAL effector fusion with enzymatic or signaling activity wherein the one or more TAL effector fusions are expressed in the cell and bind to the predicted target binding sites on the at least one nucleic acid molecule. The two or more TAL effector binding sites on the at least one nucleic acid molecule may be present at multiple copies and/or at different stoichiometric ratios.

Furthermore, the TAL nucleic acid scaffold may be episomal, stably integrated into the genome of said engineered cell or attached to the genome of said engineered cell, e.g., using scaffold matrix attachment regions. The engineered cell may be any cell including an algae or microalgae cell. In one aspect, the engineered cell is a microalgae and the TAL nucleic acid scaffold may be integrated into or attached to the nuclear or the chloroplast genome of said cell.

In one aspect, the nucleic acid sequences encoding the TAL effector, the linker and/or the fused enzymatic or signaling domain may be codon optimized with regard to the host cell. Different optimization strategies or parameters that may be taken into account are described in more detail elsewhere herein.

In one instance, TAL effector nucleic acid scaffolds may be used to engineer artificial pathways in plants or algae. Algae suitable for use in the present invention encompass both prokaryotic and eukaryotic algae, and in particular unicellular algae also known as microalgae. Non-limiting examples of microalgae that may be used to establish TAL effector nucleic acid scaffolds include *Chlamydomonas reinhardtii*, *Leptplyngbya*, *Synechococcus elongates*, diatoms, *Phaeodactylum tricornutum*, *Thalassiosira pseudonana*, *Cyanidioschyzon merolae*, *Ostreococcus lucimarinus*, *Ostreococcus tauri*, *Micromonas pusilla*, *Fragilariopsis cylindrus*, *Pseudo-nitzschia*, *Thalassiosira rotula*, *Botryococcus braunii*, *Chlorella vulgaris*, *Dunaliella salina*, *Micromonas pusilla*, *Galdieria sulphuraria*, *Porphyra purpurea*, *Volvox carteri* or *Aureococcus anophageferrens*. Microalgae systems provide rapid growth rates and inexpensive growth conditions and have the ability to product lipids and store significant amounts of energy-rich compounds such as triacylglycerides or starch making them an attractive source for production of biofuels such as biodiesel, green diesel, green gasoline, or green jet fuel. Thus, in one aspect the invention relates to TAL nucleic acid scaffolds for assembly of enzymatic activities involved in biofuel production. The enzymatic activities may be derived from different sources and may be, e.g., of bacterial, plant or yeast origin.

Figure 23B:
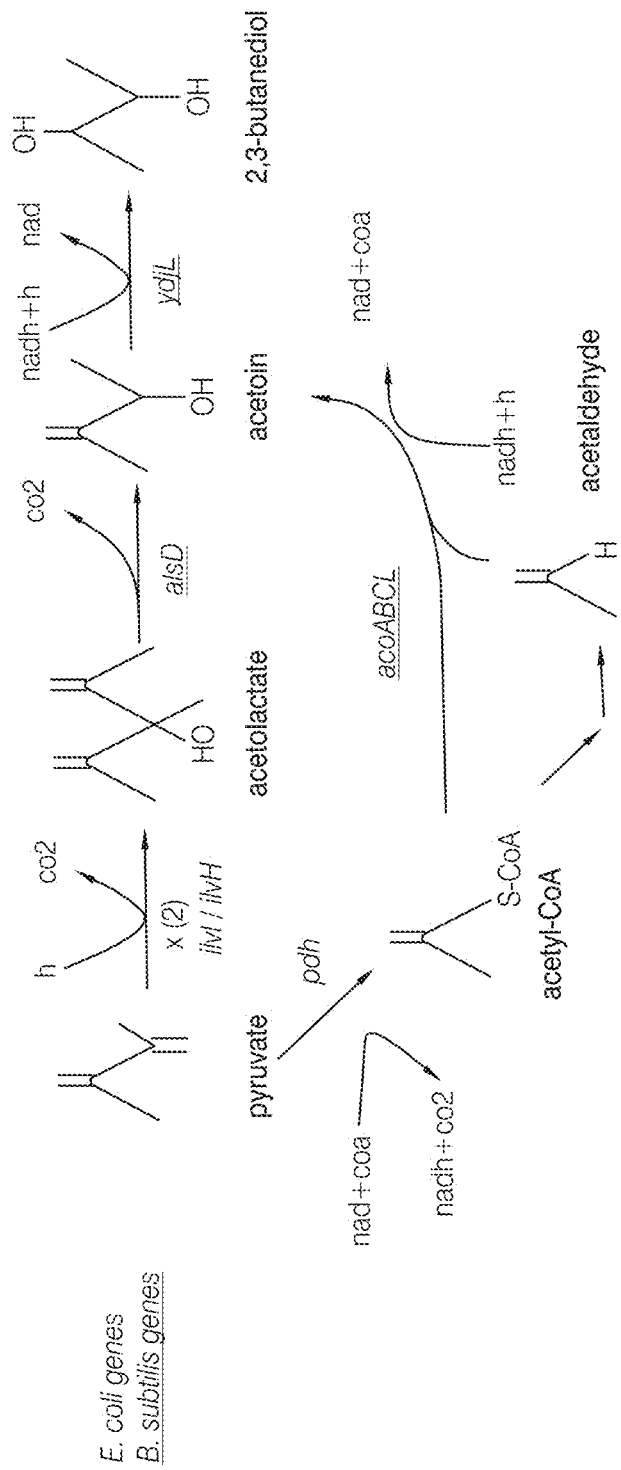
FIG. 23B illustrates two possible pathways for producing 2,3-butanediol using enzymes from *E. coli* and *B. subtilis*. *E. coli* gene products: ilvI, acetolactate synthase large subunit; ilvH, acetolactate synthase isozyme III small subunit; pdh, pyruvate dehydrogenase; *B. subtilis* gene products: alsD, acetolactate decarboxylase; ydjL, acetoin reductase/2,3-butanediol dehydrogenase; acoABCL operon, encodes the E1α, E1β, E2, and E3 subunits of the acetoin dehydrogenase complex.

In one example illustrated by FIG. 23, TAL nucleic acid scaffolds are designed for assembly of a pathway producing 2,3-butanediol in microalgae. 2,3-butanediol may be synthesized using enzymes of heterologous source (e.g., bacterial enzymes) in algae. In a first pathway, pyruvate is turned into acetolactate by *E. coli* acetolate synthase, an enzyme consisting of a large subunit (encoded by gene ilvI) and an isozyme III small subunit (encoded by gene ilvH). In a next step acetolactate is turned into acetoin by *B. subtilis* by acetolactate decarboxylase encoded by gene alsD. Finally acetoin is turned into 2,3-butanediol by *B. subtilis* acetoin reductase/2,3-butanediol dehydrogenase encoded by gene ydjL.

In an alternative pathway pyruvate is first turned into acetyl-CoA by *E. coli* pyruvate dehydrogenase encoded by gene pdh. Then acetyl-CoA is turned into acetoin and acetaldehyde by the concerted action of the E1α, E1β, E2, and E3 subunits of the acetoin dehydrogenase complex encoded by the acoABCL operon. The final step turning acetoin into 2,3-butanediol is again catalyzed by *B. subtilis* ydjL gene product (see FIG. 23B).

Figure 23C:
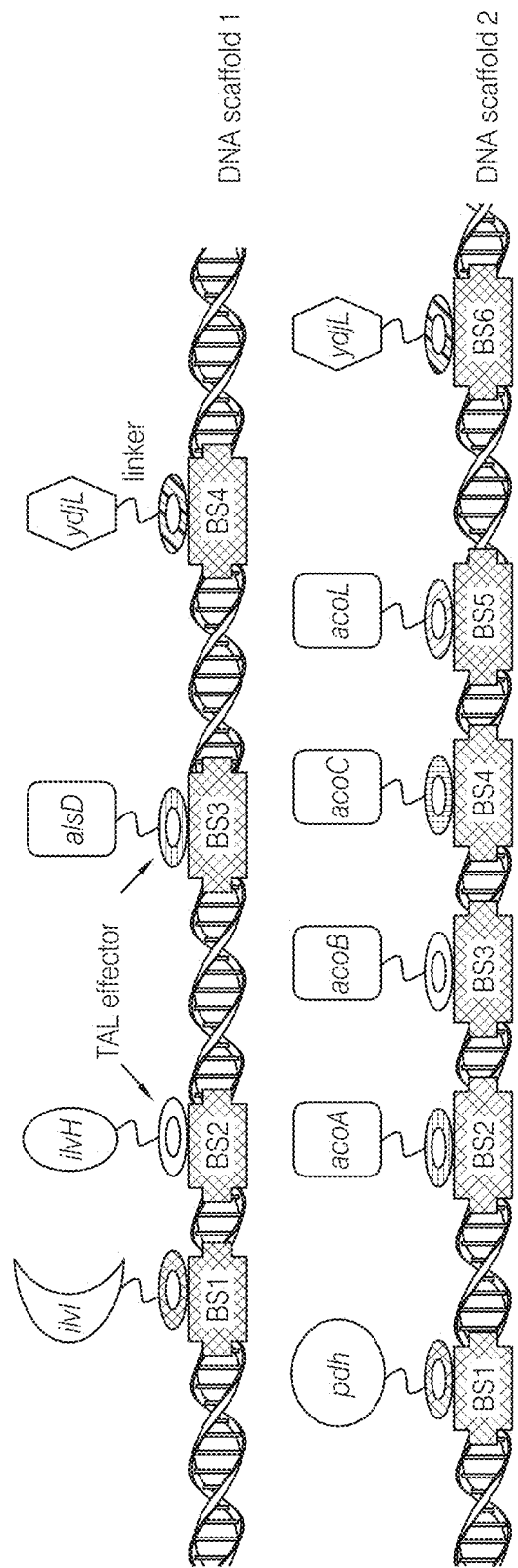
FIG. 23C shows an exemplary design of TAL DNA scaffold-assisted assembly of 2,3-butanediol pathways in microalgae. The genes encoding the different enzymatic activities required for 2,3-butanediol production are fused to different TAL effector sequences with specific binding sites (BS) on the DNA TAL scaffold. A flexible linker is inserted between the TAL effector and the enzymatic domain to allow for independent folding and accessibility of the fused enzymatic domains.

A possible arrangement of the TAL effector fusions on TAL nucleic acid scaffolds for assembly of the two described 2,3-butanediol pathways in microalgae is shown in FIG. 23C. The bacterial genes are fused to TAL effectors with different nucleic acid binding specificities. The bacterial genes may require codon optimization to achieve optimal expression rates in microalgae as described elsewhere herein and may be separated by a flexible linker from the TAL effector. The TAL effector fusion sequences are then cloned into one or more suitable vectors (e.g., a functional vector as described elsewhere herein) allowing for efficient expression of the fusion proteins in the target host. Depending on the length of the coding sequences and the amount of TAL effector fusions required to establish a given pathway, the TAL effector fusion sequences may be cloned into one single vector or may be provided in different vectors. The TAL effector fusion encoding vectors are then delivered to the host by methods known in the art. They may be delivered together with the TAL nucleic acid scaffolds carrying the TAL effector binding sites or may be delivered into host cells which have already been engineered to contain the TAL nucleic acid scaffolds (e.g., by stabile genomic integration). In some instances constitutive expression of the TAL effector fusions may be required whereas in other instances the expression of some or all TAL effector fusions may be inducible. Examples of inducible promoters that can be used in algae include copper-responsive elements or nitrate-responsive promoters. Furthermore, enzymatic activities from different pathways may be assembled or combined in the same host cell to achieve optimal titers of a required intermediate or end product.

To engineer pathways for biofuel production in algae, TAL effectors or TAL effector fusions with repressor or cleavage activity may further be used to induce gene knock-down or block metabolic pathways that lead to the accumulation of energy-rich storage compounds such as starch or decrease lipid catabolism to increase lipid accumulation in cells. In some instances it may be required to avoid one specific reaction catalyzed by a given enzyme whereas another reaction catalyzed by the same enzyme may be essential for cell survival. In such case, the enzyme may be knocked-down using a TAL effector fusion and may be replaced by an engineered enzyme or combination of enzymatic activities catalyzing only the desired reaction. The engineered enzymes may be provided via a TAL nucleic acid scaffold as described above. Thus, TAL effectors and TAL nucleic acid scaffolds of the invention can be used to specifically engineer hosts for improved or modified metabolic pathways.

TALs for Tethering Polymerase to DNA Templates

Single-stranded template DNA is sometimes prepared for DNA sequencing by attachment to beads by using emulsion PCR (e.g., 454, SOLiD™, and Ion Torrent™ Semiconductor Sequencing). This method creates a population of clonal single stranded DNA covalently attached to a bead. In some sequencing methods (e.g., 454 and Ion Torrent™ semiconductor sequencing) a primer is annealed to the single stranded DNA templates to form a suitable substrate for a DNA dependent DNA polymerase to perform nucleotide addition. It is important that every primer DNA on the bead is bound to a functional polymerase and that all of the DNA substrates on the bead are extended synchronously. If a DNA polymerase dissociates from the DNA (and the bead) the signal will be reduced because that DNA is no longer being extended. Furthermore, if a new polymerase molecule then associates with the free 3' substrate after the rest of the population on the bead is extended by at least one base, its extension will be asynchronous with the rest of the DNA population on the bead. Its extension products will then contribute noise to the signal. It is therefore normally important that DNA polymerases in these sequencing applications bind strongly to their target DNAs and remain bound through hundreds of nucleotide incorporation cycles. Thus, there is a need for improving the efficiency at which the polymerase functions while extending the template on a particular bead.

By tethering the polymerase to the short template, the polymerase would be restricted from diffusion, leading to more favorable kinetics for initiation of transcription. To solve this problem, the inventors have designed a TAL effector fused to a polymerase which efficiently binds to a double stranded target binding site at the end of a template thereby tethering the polymerase to its template DNA. The TAL polymerase fusion protein was produced by a two-step assembly process as described in detail elsewhere herein. The TAL effector domain was designed to bind to the double stranded DNA formed by annealing a primer to the single stranded DNA templates on a bead. For family A polymerases it is generally desirable (but not essential) that the TAL is fused to the amino terminus of the polymerase using a short linker sequence; for family B polymerases the carboxyl terminus may be desirable. Correct orientation and flexibility between the TAL effector and polymerase domains are important to allow independent folding of both domains to ensure efficient substrate binding and polymerase function at the same time. TAL polymerase fusion proteins can be expressed and purified by conventional methodologies well know to those skilled in the art. The purified TAL polymerase fusion proteins will bind to DNA templates on a bead with higher avidity than the polymerase alone. In the case of an amino fusion with a family A polymerase the TAL effector binds to the double stranded DNA formed by the primer annealing to the template and the polymerase binds to the free 3' end of the primer. The polymerase is freely capable of performing multiple nucleotide additions. During sequencing, the newly forming double stranded DNA forms a loop, but the substrate remains bound at two locations; the TAL effector moiety remains bound to the primer domain while the polymerase remains on the extending 3' end. If the polymerase dissociates from the substrate, the TAL prevents the polymerase from diffusing away. Because it is bound and localized, the polymerase has a greatly increased opportunity to rebind to the appropriate 3' end of its substrate and continue synchronous nucleotide synthesis.

Thus, the invention relates, in part, to a TAL polymerase fusion protein. In a first embodiment, the TAL effector binding domain is fused to the amino-terminal end of the polymerase domain. In a second embodiment the TAL binding domain is fused to the carboxyl-terminal end of the polymerase. In certain instances, the TAL and polymerase domains may be separated by a flexible peptide linker sequence such as, e.g., a glycine-serine linker. For some applications, the TAL polymerase fusion protein may be equipped with a tag for purification or detection purposes as described in more detail elsewhere herein. The TAL effector moiety may contain at least six (e.g., at least 8, at least 10, at least 12, at least 15, at least 17, from about 6 to about 25, from about 6 to about 35, from about 8 to about 25, from about 10 to about 25, from about 12 to about 25, from about 8 to about 22, from about 10 to about 22, from about 12 to about 22, from about 6 to about 20, from about 8 to about 20, from about 10 to about 22, from about 12 to about 20, from about 6 to about 18, from about 10 to about 18, from about 12 to about 18, etc.) TAL repeats. In some instances, the TAL effector moiety may contain 18 or 24 or 17.5 or 23.5 TAL nucleic acid binding cassettes. In additional instances, a TAL effector fused to a polymerase may contain 15.5, 16.5, 18.5, 19.5, 20.5, 21.5, 22.5 or 24.5 TAL nucleic acid binding cassettes.

The polymerase fused to the TAL effector may be any DNA polymerase known in the art that is capable of synthesizing single stranded template DNA. For example, the polymerase may be *Thermus aquaticus* DNA polymerase (Taq), *Thermus filiformis* (Tfi) DNA polymerase; *Thermococcus zilligi* (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase, Turbo Pfu DNA polymerase, *Thermococcus litoralis* (Tli) DNA polymerase, Vent DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase, *Sulfolobus acidocaldarius* DNA polymerase, *Thermococcus* sp. 9 deg. N-7 DNA polymerase, *Thermococcus* sp. NA1; *Pyrodictium occultum* DNA polymerase, *Methanococcus voltae* DNA polymerase, *Methanococcus thermoautotrophicum* DNA polymerase, *Methanococcus jannaschii* DNA polymerase, *Desulfurococcus* strain TOK DNA polymerase (D. Tok Pol), *Pyrococcus abyssi* DNA polymerase, *Pyrococcus horikoshii* DNA polymerase, *Pyrococcus islandicum* DNA polymerase, *Thermococcus fumicolans* DNA polymerase, *Aeropyrum pernix* DNA polymerase, or heterodimeric DNA polymerase DP1/DP. In some embodiments, the DNA polymerase may be a polymerase such as Deep Vent DNA polymerase (New England Biolabs), AMPLITAQ GOLD® DNA polymerase (Applied Biosciences), Stoffel fragment of AMPLITAQ® DNA Polymerase (Roche), KOD polymerase (EMD Biosciences), Klentaql polymerase (DNA Polymerase Technology, Inc), OMNI KLENTAQ™ DNA polymerase (DNA Polymerase Technology, Inc), OMNI KLENTAQ™ LA DNA polymerase (DNA Polymerase Technology, Inc), PHUSION® High Fidelity DNA polymerase (New England Biolabs), HEMO KLENTAQ™ (New England Biolabs), PLATINUM® Taq DNA Polymerase High Fidelity (Life Technologies), PLATINUM® Pfx (Life Technologies), ACCUPRIME™ Pfx (Life Technologies), or ACCUPRIME™ Taq DNA Polymerase High Fidelity (Life Technologies).

The polymerase fused to a TAL effector according to the invention can be any Family A DNA polymerase (also known as pol I family) or any Family B DNA polymerase. In some embodiments, the DNA polymerase can be a recombinant form capable of extending target-specific primers with superior accuracy and yield as compared to a non-recombinant DNA polymerase. For example, the polymerase can include one of the above listed high-fidelity polymerase or thermostable polymerase.

One example of a TAL polymerase fusion protein according to the invention is shown in FIG. 35. This example shows a TAL binding domain fused to the aminoterminal end of a Bst DNA polymerase via linker sequence GGGVTM (SEQ ID NO: 89). The amino acid sequence of this TAL-Bst1.0 polymerase fusion protein is referred to as SEQ ID NO: 82. Thus, in one specific embodiment the invention relates to a TAL polymerase fusion protein comprising the sequence of SEQ ID NO: 82 and its coding nucleic acid sequence which may be either a wildtype or codon-optimized sequence.

In another aspect, the invention relates to a method for tethering a DNA polymerase to a template DNA by using a TAL polymerase fusion protein as described above. In particular, the invention relates to a method for tethering a DNA polymerase to a primer for extension of singlestranded DNA templates in preparation of sequencing reactions (such as "emulsion PCR"), wherein the DNA polymerase is fused to a TAL effector domain as described above.

Furthermore, the invention also relates, in part, to the use of a TAL polymerase fusion protein in PCR amplification reactions, wherein the DNA template which is to be amplified by the polymerase portion of the TAL polymerase fusion protein is coupled to a bead.

The invention is further described by the following vector sequences:

pENTR221 Truncated TAL MCS Vector Sequence

SEQ ID NO: 30

```
  1 ctttcctgcg ttatccctg attctgtgga taaccgtatt accgcctttg agtgagctga 61 taccgctcgc cgcagccgaa cgaccgagcg cagcgagtca gtgagcgagg aagcggaaga
```

-continued

```
 121 gcgcccaata cgcaaaccgc ctctccccgc gcgttggccg attcattaat gcagctggca
 181 cgacaggttt cccgactgga aagcgggcag tgagcgcaac gcaattaata cgcgtaccgc
 241 tagccaggaa gagtttgtag aaacgcaaaa aggccatccg tcaggatggc cttctgctta
 301 gtttgatgcc tggcagttta tggcgggcgt cctgcccgcc accctccggg ccgttgcttc
 361 acaacgttca atccgctcc cggcggattt gtcctactca ggagagcgtt caccgacaaa
 421 caacagataa aacgaaaggc ccagtcttcc gactgagcct ttcgttttat ttgatgcctg
 481 gcagttccct actctcgcgt taacgctagc atggatgttt cccagtcac gacgttgtaa
 541 aacgacggcc agtcttaagc tcgggcccca aataatgatt ttatttttgac tgatagtgac
 601 ctgttcgttg caacaaattg atgagcaatg cttttttata atgccaactt tgtacaaaaa
 661 agcaggctgc ggccgcgcca ccatgggaaa acctattcct aatcctctgc tgggcctgga
 721 ttctaccgga ggcatggccc ctaagaaaaa gcggaaggtg gacggcggag tggacctgag
 781 aacactggga tattctcagc agcagcagga gaagatcaag cccaaggtga gatccacagt
 841 ggcccagcac cacgaagccc tggtgggaca cggatttaca cacgcccaca ttgtggccct
 901 gtctcagcac cctgccgccc tgggaacagt ggccgtgaaa tatcaggata tgattgccgc
 961 cctgcctgag gccacacacg aagccattgt gggagtggga aaacagtggt ctggagccag
1021 agccctggaa gccctgctga cagtggccgg agaactgaga ggacctcctc tgcagctgga
1081 tacaggacag ctgctgaaga ttgccaaaag gggcggagtg accgcggtgg aagccgtgca
1141 cgcctgagga aatgccctga caggagcccc tctgaaccct tgcaggtgcc ggaattgcca
1201 gctggggcgc cctctggtaa ggttgggaag ccctgcaaag taaactggat ggctttcttg
1261 ccgccaagga tctgatggcg caggggatca agctctgatc aagagacagg atgaggatcg
1321 tttcgcatgc agttcaaagt gtatacctac aaacgtgaaa gccgttatcg tctgtttgtg
1381 gatgtgcaga gcgatattat tgatacccc ggtcgtcgta tggtgattcc gctggcctct
1441 gcgcgtctgc tgtctgataa agtgagccgt gagctgtatc cggtggtgca tattggtgat
1501 gaaagctggc gtatgatgac caccgatatg gcgagcgtgc cggtgagcgt gattggcgaa
1561 gaagtggcgg atctgagcca tcgtgaaaac gatatcaaaa acgcgattaa cctgatgttt
1621 tggggcattt aataaatgtc aggctcccctt atacacagcc agtctgcagt cacctgcgga
1681 tagcattgtg gcccagctgt ctagacctga tcctgccctg gccgccctga caaatgatca
1741 cctggtggcc ctggcctgtc tgggaggcag acctgccctg gatgccgtga aaaaaggact
1801 gcctcacgcc cctgccctga tcaagagaac aaatagaaga atccccgagc ggacctctca
1861 cagagtggcc gatcacgccc aggtggtgag agtgctggga ttttttcagt gtcactctca
1921 ccctgcccag gcctttgatg atgccatgac acagtttggc atgagcagac acggactgct
1981 gcagctgttt agaagagtgg gagtgacaga actggaggcc agatccggaa ccctgcctcc
2041 tgcctctcag agatgggata ggattctgca gggttcccgt ttaaacaagc ttgtcgacgg
2101 taccgaattc atcgatagta ctctcgaggg atccgagctc aagatcttag ctaagtagac
2161 ccagcttttct tgtacaaagt tggcattata agaaagcatt gcttatcaat tgttgcaac
2221 gaacaggtca ctatcagtca aaataaaatc attatttgcc atccagctga tatccctat
2281 agtgagtcgt attacatggt catagctgtt tcctggcagc tctggcccgt gtctcaaaat
2341 ctctgatgtt acattgcaca agataaaaat atatcatcat gaacaataaa actgtctgct
2401 tacataaaca gtaatacaag gggtgttatg agccatattc aacgggaaac gtcgaggccg
2461 cgattaaatt ccaacatgga tgctgattta tatgggtata aatgggctcg cgataatgtc
```

```
2521 gggcaatcag gtgcgacaat ctatcgcttg tatgggaagc cgatgcgcc  agagttgttt
2581 ctgaaacatg gcaaaggtag cgttgccaat gatgttacag atgagatggt cagactaaac
2641 tggctgacgg aatttatgcc tcttccgacc atcaagcatt ttatccgtac tcctgatgat
2701 gcatggttac tcaccactgc gatccccgga aaaacagcat tccaggtatt agaagaatat
2761 cctgattcag gtgaaaatat tgttgatgcg ctggcagtgt tcctgcgccg gttgcattcg
2821 attcctgttt gtaattgtcc ttttaacagc gatcgcgtat ttcgtctcgc tcaggcgcaa
2881 tcacgaatga ataacggttt ggttgatgcg agtgattttg atgacgagcg taatggctgg
2941 cctgttgaac aagtctggaa agaaatgcat aaacttttgc cattctcacc ggattcagtc
3001 gtcactcatg gtgatttctc acttgataac cttattttg  acgaggggaa attaataggt
3061 tgtattgatg ttggacgagt cggaatcgca gaccgatacc aggatcttgc catcctatgg
3121 aactgcctcg gtgagttttc tccttcatta cagaaacggc ttttcaaaa  atatggtatt
3181 gataatcctg atatgaataa attgcagttt catttgatgc tcgatgagtt tttctaatca
3241 gaattggtta attggttgta acactggcag agcattacg  tgacttgacg ggacggcgca
3301 agctcatgac caaatcccct aacgtgagt  tacgcgtcgt tccactgagc gtcagacccc
3361 gtagaaaaga tcaaggatc  ttcttgagat cctttttttc tgcgcgtaat ctgctgcttg
3421 caaacaaaaa aaccaccgct accagcggtg tttgtttgc  cggatcaaga gctaccaact
3481 cttttccga  aggtaactgg cttcagcaga gcgcagatac caaatactgt ccttctagtg
3541 tagccgtagt taggccacca cttcaagaac tctgtagcac cgcctacata cctcgctctg
3601 ctaatcctgt taccagtggc tgctgccagt ggcgataagt cgtgtcttac cgggttggac
3661 tcaagacgat agttaccgga taaggcgcag cggtcgggct gaacggggggg ttcgtgcaca
3721 cagcccagct tggagcgaac gacctacacc gaactgagat acctacagcg tgagcattga
3781 gaaagcgcca cgcttcccga agggagaaag gcggacaggt atccggtaag cggcagggtc
3841 ggaacaggag agcgcacgag ggagcttcca ggggaaacg  cctggtatct ttatagtcct
3901 gtcgggtttc gccacctctg acttgagcgt cgatttttgt gatgctcgtc aggggggcgg
3961 agcctatgga aaaacgccag caacgcggcc ttttacggt  tcctggcctt tgctggcct
4021 tttgctcaca tgtt
``` pENTR221 Truncated TAL FokI Vector Sequence

SEQ ID NO: 31

```
  1 ctttcctgcg ttatcccctg attctgtgga taaccgtatt accgcctttg agtgagctga
 61 taccgctcgc cgcagccgaa cgaccgagcg cagcgagtca gtgagcgagg aagcggaaga
121 gcgcccaata cgcaaaccgc ctctccccgc gcgttggccg attcattaat gcagctggca
181 cgacaggttt cccgactgga aagcgggcag tgagcgcaac gcaattaata cgcgtaccgc
241 tagccaggaa gagtttgtag aaacgcaaaa aggccatccg tcaggatggc cttctgctta
301 gtttgatgcc tggcagttta tggcgggcgt cctgcccgcc accctccggg ccgttgcttc
361 acaacgttca aatccgctcc cggcggattt gtcctactca ggagagcgtt caccgacaaa
421 caacagataa aacgaaaggc ccagtcttcc gactgagcct tcgttttat  ttgatgcctg
481 gcagttccct actctcgcgt taacgctagc atggatgttt ccccagtcac gacgttgtaa
541 aacgacggcc agtcttaagc tcgggcccca ataatgatt  ttattttgac tgatagtgac
601 ctgttcgttg caacaaattg atgagcaatg cttttttata tgccaactt  tgtacaaaaa
661 agcaggctgc ggccgcgcca ccatgggaaa acctattcct aatcctctgc tgggcctgga
721 ttctaccgga ggcatggccc ctaagaaaaa gcggaaggtg acggcggag  tggacctgag
781 aacactggga tattctcagc agcagcagga gaagatcaag cccaaggtga gatctacagt
```

-continued

```
 841 ggcccagcac cacgaagccc tggtgggaca cggatttaca cacgcccaca ttgtggccct
 901 gtctcagcac cctgccgccc tgggaacagt ggccgtgaaa tatcaggata tgattgccgc
 961 cctgcctgag gccacacacg aagccattgt gggagtggga aaacagtggt ctggagccag
1021 agccctggaa gccctgctga cagtggccgg agaactgaga ggacctcctc tgcagctgga
1081 tacaggacag ctgctgaaga ttgccaaaag gggcggagtg accgcggtgg aagccgtgca
1141 cgcctggaga aatgccctga caggagcccc tctgaaccct tgcaggtgcc ggaattgcca
1201 gctggggcgc cctctggtaa ggttgggaag ccctgcaaag taaactggat ggctttcttg
1261 ccgccaagga tctgatggcg cagggatca agctctgatc aagagacagg atgaggatcg
1321 tttcgcatgc agttcaaagt gtatacctac aaacgtgaaa gccgttatcg tctgtttgtg
1381 gatgtgcaga gcgatattat tgataccccg gtcgtcgta tggtgattcc gctggcctct
1441 gcgcgtctgc tgtctgataa agtgagccgt gagctgtatc cggtggtgca tattggtgat
1501 gaaagctggc gtatgatgac caccgatatg gcgagcgtgc cggtgagcgt gattggcgaa
1561 gaagtggcgg atctgagcca tcgtgaaaac gatatcaaaa acgcgattaa cctgatgttt
1621 tggggcattt aataaatgtc aggctcccctt atacacagcc agtctgcagt cacctgcgga
1681 tagcattgtg gcccagctgt ctagacctga tcctgccctg gccgccctga caaatgatca
1741 cctggtggcc ctggcctgtc tgggaggcag acctgccctg gatgccgtga aaaaggact
1801 gcctcacgcc cctgccctga tcaagagaac aaatagaaga tccccgagc ggacctctca
1861 cagagtggcc ggatcccagc tggtgaaatc tgagctggag gagaagaagt ctgagctgag
1921 acacaagctg aagtacgtgc ctcacgagta catcgagctg atcgagatcg ccagaaatag
1981 cacccaggat agaatcctgg agatgaaggt gatggagttc ttcatgaagg tgtacggcta
2041 cagaggaaag cacctgggag gaagcagaaa acctgacgga gccatttata cagtgggcag
2101 ccctatcgat tatggcgtga tcgtggatac aaaggcctac agcggaggct acaatctgcc
2161 tattggacag gccgatgaga tgcagagata cgtggaggag aaccagacca ggaacaagca
2221 catcaaccct aacgagtggt ggaaggtgta cccttctagc gtgaccgagt tcaagttcct
2281 gtttgtgagc ggccacttca agggcaatta taaggcccag ctgaccaggc tgaaccacat
2341 cacaaattgt aatggcgccg tgctgtctgt ggaggaactg ctgattggag gagagatgat
2401 taaggccgga acactgacac tggaggaggt gagaagaaag ttcaacaacg gcgagatcaa
2461 cttctgaaag cttacccagc tttcttgtac aaagttggca ttataagaaa gcattgctta
2521 tcaatttgtt gcaacgaaca ggtcactatc agtcaaaata aaatcattat ttgccatcca
2581 gctgatatcc cctatagtga gtcgtattac atggtcatag ctgtttcctg gcagctctgg
2641 cccgtgtctc aaaatctctg atgttacatt gcacaagata aaaatatatc atcatgaaca
2701 ataaaactgt ctgcttacat aaacagtaat acaaggggtg ttatgagcca tattcaacgg
2761 gaaacgtcga ggccgcgatt aaattccaac atggatgctg atttatatgg gtataaatgg
2821 gctcgcgata atgtcgggca atcaggtgcg acaatctatc gcttgtatgg gaagcccgat
2881 gcgccagagt tgtttctgaa acatggcaaa ggtagcgttg ccaatgatgt tacagatgag
2941 atggtcagac taaactggct gacggaattt atgcctcttc cgaccatcaa gcattttatc
3001 cgtactcctg atgatgcatg gttactcacc actgcgatcc ccggaaaaac agcattccag
3061 gtattagaag aatatcctga ttcaggtgaa atattgttg atgcgctggc agtgttcctg
3121 cgccggttgc attcgattcc tgtttgtaat tgtccttta acagcgatcg cgtatttcgt
3181 ctcgctcagg cgcaatcacg aatgaataac ggtttggttg atgcgagtga ttttgatgac
```

```
3241 gagcgtaatg gctggcctgt tgaacaagtc tggaagaaa tgcataaact tttgccattc
3301 tcaccggatt cagtcgtcac tcatggtgat ttctcacttg ataaccttat ttttgacgag
3361 gggaaattaa taggttgtat tgatgttgga cgagtcggaa tcgcagaccg ataccaggat
3421 cttgccatcc tatggaactg cctcggtgag ttttctcctt cattacagaa acggcttttt
3481 caaaaatatg gtattgataa tcctgatatg aataaattgc agtttcattt gatgctcgat
3541 gagttttct aatcagaatt ggttaattgg ttgtaacact ggcagagcat acgctgact
3601 tgacgggacg gcgcaagctc atgaccaaaa tcccttaacg tgagttacgc gtcgttccac
3661 tgagcgtcag accccgtaga aaagatcaaa ggatcttctt gagatccttt ttttctgcgc
3721 gtaatctgct gcttgcaaac aaaaaaacca ccgctaccag cggtggtttg tttgccggat
3781 caagagctac caactctttt tccgaaggta actggcttca gcagagcgca gataccaaat
3841 actgtccttc tagtgtagcc gtagttaggc caccacttca agaactctgt agcaccgcct
3901 acatacctcg ctctgctaat cctgttacca gtggctgctg ccagtggcga taagtcgtgt
3961 cttaccgggt tggactcaag acgatagtta ccggataagg cgcagcggtc gggctgaacg
4021 gggggttcgt gcacacagcc cagcttggag cgaacgacct acaccgaact gagataccta
4081 cagcgtgagc attgagaaag cgccacgctt cccgaaggga gaaaggcgga caggtatccg
4141 gtaagcggca gggtcggaac aggagagcgc acgagggagc ttccaggggg aaacgcctgg
4201 tatctttata gtcctgtcgg gtttcgccac ctctgacttg agcgtcgatt tttgtgatgc
4261 tcgtcagggg ggcggagcct atggaaaaac gccagcaacg cggccttttt acggttcctg
4321 gccttttgct ggccttttgc tcacatgtt
``` pENTR221 Native TAL VP16 Activator Vector Sequence

SEQ ID NO: 32

```
   1 ctttcctgcg ttatccctg attctgtgga taaccgtatt accgcctttg agtgagctga
  61 taccgctcgc cgcagccgaa cgaccgagcg cagcgagtca gtgagcgagg aagcggaaga
 121 gcgcccaata cgcaaaccgc ctctccccgc gcgttggccg attcattaat gcagctggca
 181 cgacaggttt cccgactgga aagcgggcag tgagcgcaac gcaattaata cgcgtaccgc
 241 tagccaggaa gagtttgtag aaacgcaaaa aggccatccg tcaggatggc cttctgctta
 301 gtttgatgcc tggcagttta tggcgggcgt cctgcccgcc accctccggg ccgttgcttc
 361 acaacgttca atccgctcc cggcggattt gtcctactca ggagagcgtt caccgacaaa
 421 caacagataa aacgaaaggc ccagtcttcc gactgagcct ttcgttttat ttgatgcctg
 481 gcagttccct actctcgcgt taacgctagc atggatgttt tcccagtcac gacgttgtaa
 541 aacgacggcc agtcttaagc tcgggcccca ataatgatt ttatttgac tgatagtgac
 601 ctgttcgttg caacaaattg atgagcaatg cttttttata tgccaactt tgtacaaaaa
 661 agcaggctgc ggccgcgcca ccatgggaaa acctattcct aatcctctgc tgggcctgga
 721 ttctaccatg gaccctatta gaagcagaac ccctctcca gccagagaac tgctgtctgg
 781 acctcagcct gatggagtgc agcctacagc cgatagagga gtgtctcctc ctgccggagg
 841 acctctggat ggactgcctg cccggagaac aatgagcaga acaagactgc cttctcctcc
 901 agcccccatct cctgcctttt ctgccgattc ttttagcgac ctgctgagac agtttgaccc
 961 cagcctgttt aataccagcc tgttcgatag cctgcctcct tttggagccc accacacaga
1021 ggccgccaca ggcgaatggg atgaagtgca gtctggactg agagccgccg atgcccctcc
1081 tcctacaatg agagtggccg tgacagccgc cagacctcct agagccaaac ctgcccctag
1141 aaggagagcc gcccagcctt ctgatgcctc tcctgccgcc caggtggacc tgagaacact
1201 gggatattct cagcagcagc aggagaagat caagcccaag gtgaggtcta cagtgggcca
```

-continued

```
1261 gcaccacgaa gccctggtgg gacacggatt tacacacgcc cacattgtgg ccctgtctca 1321 gcaccctgcc gccctgggaa cagtggccgt gaaatatcag gatatgattg ccgccctgcc 1381 tgaggccaca cacgaagcca ttgtgggagt gggaaaacag tggtctggag ccagagccct 1441 ggaagccctg ctgacagtgg ccggagaact gagaggacct cctctgcagc tggatacagg 1501 acagctgctg aagattgcca aaaggggcgg agtgaccgcg gtggaagccg tgcacgcctg 1561 gagaaatgcc ctgacaggag cccctctgaa cccttgcagg tgccggaatt gccagctggg 1621 gcgccctctg gtaaggttgg gaagccctgc aaagtaaact ggatggcttt cttgccgcca 1681 aggatctgat ggcgcagggg atcaagctct gatcaagaga caggatgagg atcgtttcgc 1741 atgcagttca aagtgtatac ctacaaacgt gaaagccgtt atcgtctgtt tgtggatgtg 1801 cagagcgata ttattgatac ccctggtcgt cgtatggtga ttccgctggc ctctgcgcgt 1861 ctgctgtctg ataaagtgag ccgtgagctg tatccggtgg tgcatattgg tgatgaaagc 1921 tggcgtatga tgaccaccga tatggcgagc gtgccggtga gcgtgattgg cgaagaagtg 1981 gcggatctga gccatcgtga aaacgatatc aaaaacgcga ttaacctgat gttttggggc 2041 atttaataaa tgtcaggctc ccttatacac agccagtctg cagtcacctg cggatagcat 2101 tgtggcccag ctgtctagac ctgatcctgc cctggccgcc ctgacaaatg atcacctggt 2161 ggccctggcc tgtctgggag gcagaccgc cctggatgcc gtgaaaaaag gactgcctca 2221 cgcccctgcc ctgatcaaga gaacaaatag aagaatcccc gagcggacct ctcacagagt 2281 ggccgatcac gcccaggtgg tgagagtgct gggatttttt cagtgtcact ctcaccctgc 2341 ccaggccttt gatgatgcca tgacacagtt tggcatgagc agacacggac tgctgcagct 2401 gtttagaaga gtgggagtga cagaactgga ggccagaagc ggaacactgc ctccagcctc 2461 tcagagatgg gatagaattc tgcaggccag cggaatgaag agagccaaac cttctcctac 2521 cagcacccag acacctgatc aggccagcct gcacgccttt gccgattctc tggaacggga 2581 tctggacgcc ccttctccta tgcacgaagg agatcagaca agagccagca gcagaaagag 2641 aagcaggtct gatagagccg tgacaggacc ttctgcccag cagtcttttg aagtgagagt 2701 gcctgaacag agagatgccc tgcatctgcc tctgctgtct gggagtgaa aaagacctag 2761 aacaagaatc ggaggactgc tggaccctgg aacacctatg gatgccgatc tggtggcctc 2821 ttctacagtg gtgtgggaac aggatgccga tccttttgcc ggaacagccg atgatttccc 2881 tgccttaat gaggaagaac tggcctggct gatggaactg ctgcctcagg gatccgcccc 2941 tcctacagat gtgtctctgg gagatgagct ccacctggat ggagaagatg tggccatggc 3001 ccacgccgat gccctggatg attttgatct ggatatgctg ggagatggcg attctcctgg 3061 acctggattt acacctcacg attctgcccc ttatggagcc ctggatatgg ccgattttga 3121 gttcgagcag atgttcacag atgccctggg catcgacgag tatggcggct gaaagcttac 3181 ccagcttttct tgtacaaagt tggcattata gaaaagcatt gcttatcaat tgttgcaac 3241 gaacaggtca ctatcagtca aaataaaatc attatttgcc atccagctga tatccctat 3301 agtgagtcgt attacatggt catagctgtt tcctggcagc tctggcccgt gtctcaaaat 3361 ctctgatgtt acattgcaca agataaaaat atatcatcat gaacaataaa actgtctgct 3421 tacataaaca gtaatacaag gggtgttatg agccatattc aacgggaaac gtcgaggccg 3481 cgattaaatt ccaacatgga tgctgattta tatgggtata aatgggctcg cgataatgtc 3541 gggcaatcag gtgcgacaat ctatcgcttg tatgggaagc ccgatgcgcc agagttgttt 3601 ctgaaacatg gcaaaggtag cgttgccaat gatgttacag atgagatggt cagactaaac
```

```
3661 tggctgacgg aatttatgcc tcttccgacc atcaagcatt ttatccgtac tcctgatgat
3721 gcatggttac tcaccactgc gatccccgga aaaacagcat tccaggtatt agaagaatat
3781 cctgattcag gtgaaaatat tgttgatgcg ctggcagtgt tcctgcgccg gttgcattcg
3841 attcctgttt gtaattgtcc ttttaacagc gatcgcgtat ttcgtctcgc tcaggcgcaa
3901 tcacgaatga ataacggttt ggttgatgcg agtgattttg atgacgagcg taatggctgg
3961 cctgttgaac aagtctggaa agaaatgcat aaacttttgc cattctcacc ggattcagtc
4021 gtcactcatg gtgatttctc acttgataac cttatttttg acgagggaa attaataggt
4081 tgtattgatg ttggacgagt cggaatcgca gaccgatacc aggatcttgc catcctatgg
4141 aactgcctcg gtgagttttc tccttcatta cagaaacggc ttttcaaaa atatggtatt
4201 gataatcctg atatgaataa attgcagttt catttgatgc tcgatgagtt tttctaatca
4261 gaattggtta attggttgta acactggcag agcattacgc tgacttgacg ggacggcgca
4321 agctcatgac caaaatccct taacgtgagt tacgcgtcgt tccactgagc gtcagacccc
4381 gtagaaaaga tcaaaggatc ttcttgagat ccttttttc tgcgcgtaat ctgctgcttg
4441 caaacaaaaa aaccaccgct accagcggtg ttttgtttgc cggatcaaga gctaccaact
4501 ctttttccga aggtaactgg cttcagcaga gcgcagatac caaatactgt ccttctagtg
4561 tagccgtagt taggccacca cttcaagaac tctgtagcac cgcctacata cctcgctctg
4621 ctaatcctgt taccagtggc tgctgccagt ggcgataagt cgtgtcttac cgggttggac
4681 tcaagacgat agttaccgga taaggcgcag cggtcgggct gaacgggggg ttcgtgcaca
4741 cagcccagct tggagcgaac gacctacacc gaactgagat acctcagcg tgagcattga
4801 gaaagcgcca cgcttcccga agggagaaag gcggacaggt atccggtaag cggcagggtc
4861 ggaacaggag agcgcacgag ggagcttcca gggggaaacg cctggtatct ttatagtcct
4921 gtcgggtttc gccacctctg acttgagcgt cgatttttgt gatgctcgtc agggggggcgg
4981 agcctatgga aaaacgccag caacgcggcc ttttacggt tcctggcctt ttgctggcct
5041 tttgctcaca tgtt
``` pENTR221 Native TAL MCS Vector Sequence

SEQ ID NO: 33

```
   1 ctttcctgcg ttatcccctg attctgtgga taaccgtatt accgcctttg agtgagctga
  61 taccgctcgc cgcagccgaa cgaccgagcg cagcgagtca gtgagcgagg aagcggaaga
 121 gcgcccaata cgcaaaccgc ctctccccgc gcgttggccg attcattaat gcagctggca
 181 cgacaggttt cccgactgga aagcgggcag tgagcgcaac gcaattaata cgcgtaccgc
 241 tagccaggaa gagtttgtag aaacgcaaaa aggccatccg tcaggatggc cttctgctta
 301 gtttgatgcc tggcagttta tggcgggcgt cctgcccgcc accctccggg ccgttgcttc
 361 acaacgttca atccgctcc cggcggattt gtcctactca ggagagcgtt caccgacaaa
 421 caacagataa acgaaaggc ccagtcttcc gactgagcct ttcgttttat ttgatgcctg
 481 gcagttccct actctcgcgt taacgctagc atggatgttt cccagtcac gacgttgtaa
 541 aacgacggcc agtcttaagc tcgggcccca ataatgatt ttattttgac tgatagtgac
 601 ctgttcgttg caacaaattg atgagcaatg ctttttttata atgccaactt tgtacaaaaa
 661 agcaggctgc ggccgcgcca ccatgggaaa acctattcct aatcctctgc tgggcctgga
 721 ttctaccatg gaccctatta gaagcagaac accctctcca gccagagaac tgctgtctgg
 781 acctcagcct gatggagtgc agccctacag cgatagagga gtgtctcctc ctgccggagg
 841 acctctggat ggactgcctg cccggagaac aatgagcaga acaagactgc cttctcctcc
 901 agcccccatct cctgcctttt ctgccgattc ttttagcgac ctgctgagac agtttgaccc
```

```
 961 cagcctgttt aataccagcc tgttcgatag cctgcctcct tttggagccc accacacaga
1021 ggccgccaca ggcgaatggg atgaagtgca gtctggactg agagccgccg atgcccctcc
1081 tcctacaatg agagtggccg tgacagccgc cagacctcct agagccaaac ctgccsctag
1141 aaggagagcc gcccagcctt ctgatgcctc tcctgccgcc caggtggacc tgagaacact
1201 gggatattct cagcagcagc aggagaagat caagcccaag gtgaggtcta cagtggccca
1261 gcaccacgaa gccctggtgg acacggatt tacacacgcc cacattgtgg ccctgtctca
1321 gcaccctgcc gccctgggaa cagtggccgt gaaatatcag gatatgattg ccgccctgcc
1381 tgaggccaca cacgaagcca ttgtgggagt gggaaaacag tggtctggag ccagagccct
1441 ggaagccctg ctgacagtgg ccggagaact gagaggacct cctctgcagc tggatacagg
1501 acagctgctg aagattgcca aaaggggcgg agtgaccgcg gtggaagccg tgcacgcctg
1561 gagaaatgcc ctgacaggag cccctctgaa cccttgcagg tgccggaatt gccagctggg
1621 gcgccctctg gtaaggttgg gaagccctgc aaagtaaact ggatggcttt cttgccgcca
1681 aggatctgat ggcgcagggg atcaagctct gatcaagaga caggatgagg atcgtttcgc
1741 atgcagttca aagtgtatac ctacaaacgt gaaagccgtt atcgtctgtt tgtggatgtg
1801 cagagcgata ttattgatac ccctggtcgt cgtatggtga ttccgctggc ctctgcgcgt
1861 ctgctgtctg ataaagtgag ccgtgagctg tatccggtgg tgcatattgg tgatgaaagc
1921 tggcgtatga tgaccaccga tatggcgagc gtgccggtga gcgtgattgg cgaagaagtg
1981 gcggatctga gccatcgtga aaacgatatc aaaaacgcga ttaacctgat gttttgggc
2041 atttaataaa tgtcaggctc ccttatacac agccagtctg cagtcacctg cggatagcat
2101 tgtggcccag ctgtctagac ctgatcctgc cctggccgcc ctgacaaatg atcacctggt
2161 ggccctggcc tgtctgggag gcagacctgc cctggatgcc gtgaaaaaag gactgcctca
2221 cgcccctgcc ctgatcaaga gaacaaatag aagaatcccc gagcggacct ctcacagagt
2281 ggccgatcac gcccaggtgg tgagagtgct gggattttt cagtgtcact ctcaccctgc
2341 ccaggccttt gatgatgcca tgacacagtt tggcatgagc agacacggac tgctgcagct
2401 gtttagaaga gtgggagtga cagaactgga ggccagaagc ggaacactgc tccagccctc
2461 tcagagatgg gatagaatcc tgcaggccag cggaatgaag agagccaaac cttctcctac
2521 cagcacccag acacctgatc aggccagcct gcacgccttt gccgattctc tggaaaggga
2581 tctggacgcc ccttctccta tgcacgaagg agatcagaca agagccagca gcagaaagag
2641 aagcaggtct gatagagccg tgacaggacc ttctgcccag cagtcttttg aagtgagagt
2701 gcctgaacag agagatgccc tgcatctgcc tctgctgtct tggggagtga aaagacctag
2761 aacaagaatc ggaggactgc tggaccccgg gacacctatg gatgccgatc tggtggcctc
2821 ttctacagtg gtgtgggaac aggatgccga tccttttgcc ggaacagccg atgatttccc
2881 tgccttaat gaggaagaac tggcctggct gatggaactg ctgcctcagg ttcccgttt
2941 aaacaagctt gtcgacggta ccgaattcat cgatagtact ctcgagggat ccgagctcaa
3001 gatctagcta agtagaccca gctttcttgt acaaagttgg cattataaga aagcattgct
3061 tatcaatttg ttgcaacgaa caggtcacta tcagtcaaaa taaaatcatt atttgccatc
3121 cagctgatat cccctatagt gagtcgtatt acatggtcat agctgtttcc tggcagctct
3181 ggcccgtgtc tcaaaatctc tgatgttaca ttgcacaaga taaaaatata tcatcatgaa
3241 caataaaact gtctgcttac ataaacagta atacaagggg tgttatgagc catattcaac
3301 gggaaacgtc gaggccgcga ttaaattcca acatggatgc tgatttatat gggtataaat
```

```
3361 gggctcgcga taatgtcggg caatcaggtg cgacaatcta tcgcttgtat gggaagcccg 3421 atgcgccaga gttgtttctg aaacatggca aaggtagcgt tgccaatgat gttacagatg 3481 agatggtcag actaaactgg ctgacggaat ttatgcctct tccgaccatc aagcatttta 3541 tccgtactcc tgatgatgca tggttactca ccactgcgat ccccggaaaa acagcattcc 3601 aggtattaga agaatatcct gattcaggtg aaaatattgt tgatgcgctg gcagtgttcc 3661 tgcgccggtt gcattcgatt cctgtttgta attgtccttt taacagcgat cgcgtatttc 3721 gtctcgctca ggcgcaatca cgaatgaata acggtttggt tgatgcgagt gattttgatg 3781 acgagcgtaa tggctggcct gttgaacaag tctggaaaga atgcataaa cttttgccat 3841 tctcaccgga ttcagtcgtc actcatggtg atttctcact tgataacctt attttgacg 3901 agggaaatt aataggttgt attgatgttg gacgagtcgg aatcgcagac cgataccagg 3961 atcttgccat cctatggaac tgcctcggtg agttttctcc ttcattacag aaacggcttt 4021 ttcaaaaata tggtattgat aatcctgata tgaataaatt gcagtttcat ttgatgctcg 4081 atgagttttt ctaatcagaa ttggttaatt ggttgtaaca ctggcagagc attacgctga 4141 cttgacggga cggcgcaagc tcatgaccaa atcccttaa cgtgagttac gcgtcgttcc 4201 actgagcgtc agacccgta gaaaagatca aaggatcttc ttgagatcct ttttttctgc 4261 gcgtaatctg ctgcttgcaa acaaaaaaac caccgctacc agcggtggtt tgtttgccgg 4321 atcaagagct accaactctt tttccgaagg taactggctt cagcagagcg cagataccaa 4381 atactgtcct tctagtgtag ccgtagttag gccaccactt caagaactct gtagcaccgc 4441 ctacatacct cgctctgcta atcctgttac cagtggctgc tgccagtggc gataagtcgt 4501 gtcttaccgg gttggactca agacgatagt taccggataa ggcgcagcgg tcgggctgaa 4561 cggggggttc gtgcacacag cccagcttgg agcgaacgac ctacaccgaa ctgagatacc 4621 tacagcgtga gcattgagaa agcgccacgc ttcccgaagg gagaaaggcg gacaggtatc 4681 cggtaagcgg cagggtcgga acaggagagc gcacgaggga gcttccaggg ggaaacgcct 4741 ggtatcttta tagtcctgtc gggtttcgcc acctctgact tgagcgtcga ttttttgtgat 4801 gctcgtcagg gggggcggagc ctatggaaaa acgccagcaa cgcggccttt ttacggttcc 4861 tggccttttg ctggcctttt gctcacatgt t
``` pENTR221 Native TAL FokI Vector Sequence

SEQ ID NO: 34

```
   1 ctttcctgcg ttatcccctg attctgtgga taaccgtatt accgcctttg agtgagctga 61 taccgctcgc cgcagccgaa cgaccgagcg cagcgagtca gtgagcgagg aagcggaaga 121 gcgcccaata cgcaaaccgc ctctccccgc gcgttggccg attcattaat gcagctggca 181 cgacaggttt cccgactgga aagcgggcag tgagcgcaac gcaattaata cgcgtaccgc 241 tagccaggaa gagtttgtag aaacgcaaaa aggccatccg tcaggatggc cttctgctta 301 gtttgatgcc tggcagttta tggcgggcgt cctgcccgcc accctccggg ccgttgcttc 361 acaacgttca aatccgctcc cggcggattt gtcctactca ggagagcgtt caccgacaaa 421 caacagataa aacgaaaggc ccagtcttcc gactgagcct ttcgttttat ttgatgcctg 481 gcagttccct actctcgcgt taacgctagc atggatgttt tcccagtcac gacgttgtaa 541 aacgacggcc agtcttaagc tcgggcccca ataatgatt ttattttgac tgatagtgac 601 ctgttcgttg caacaaattg atgagcaatg ctttttata tgccaactt tgtacaaaaa 661 agcaggctgc ggccgcgcca ccatgggaaa acctattcct aatcctctgc tgggcctgga 721 ttctaccatg gaccctatta gaagcagaac accctctcca gccagagaac tgctgtctgg 781 acctcagcct gatggagtgc agcctacagc cgatagagga gtgtctcctc ctgccggagg
```

```
 841 acctctggat ggactgcctg cccggagaac aatgagcaga acaagactgc cttctcctcc
 901 agccccatct cctgccttt ctgccgattc ttttagcgac ctgctgagac agtttgaccc
 961 cagcctgttt aataccagcc tgttcgatag cctgcctcct tttggagccc accacacaga
1021 ggccgccaca ggcgaatggg atgaagtgca gtctggactg agagccgccg atgcccctcc
1081 tcctacaatg agagtggccg tgacagccgc cagacctcct agagccaaac ctgcccctag
1141 aaggagagcc gcccagcctt ctgatgcctc tcctgccgcc caggtggacc tgagaacact
1201 gggatattct cagcagcagc aggagaagat caagcccaag gtgaggtcta cagtggccca
1261 gcaccacgaa gccctggtgg acacggatt tacacacgcc cacattgtgg ccctgtctca
1321 gcaccctgcc gccctgggaa cagtggccgt gaaatatcag gatatgattg ccgccctgcc
1381 tgaggccaca cacgaagcca ttgtgggagt gggaaaacag tggtctggag ccagagccct
1441 ggaagccctg ctgacagtgg ccggagaact gagaggacct cctctgcagc tggatacagg
1501 acagctgctg aagattgcca aaggggcgg agtgaccgcg gtggaagccg tgcacgcctg
1561 gagaaatgcc ctgacaggag cccctctgaa cccttgcagg tgccggaatt gccagctggg
1621 gcgccctctg gtaaggttgg gaagccctgc aaagtaaact ggatggcttt cttgccgcca
1681 aggatctgat ggcgcagggg atcaagctct gatcaagaga caggatgagg atcgtttcgc
1741 atgcagttca aagtgtatac ctacaaacgt gaaagccgtt atcgtctgtt tgtggatgtg
1801 cagagcgata ttattgatac ccctggtcgt cgtatggtga ttccgctggc ctctgcgcgt
1861 ctgctgtctg ataaagtgag ccgtgagctg tatccggtgg tgcatattgg tgatgaaagc
1921 tggcgtatga tgaccaccga tatggcgagc gtgccggtga gcgtgattgg cgaagaagtg
1981 gcggatctga gccatcgtga aaacgatatc aaaaacgcga ttaacctgat gttttgggc
2041 atttaataaa tgtcaggctc ccttatacac agccagtctg cagtcacctg cggatagcat
2101 tgtggcccag ctgtctagac ctgatcctgc cctggccgcc ctgacaaatg atcacctggt
2161 ggccctggcc tgtctgggag gcagaccgc cctggatgcc gtgaaaaaag gactgcctca
2221 cgccctgcc ctgatcaaga gaacaaatag aagaatcccc gagcggacct ctcacagagt
2281 ggccgatcac gcccaggtgg tgagagtgct gggatttttt cagtgtcact ctcaccctgc
2341 ccaggccttt gatgatgcca tgacacagtt tggcatgagc agacacggac tgctgcagct
2401 gtttagaaga gtgggagtga cagaactgga ggccagaagc ggaacactgc ctccagcctc
2461 tcagagatgg gatagaattc tgcaggccag cggaatgaag agagccaaac cttctcctac
2521 cagcacccag acacctgatc aggccagcct gcacgccttt gccgattctc tggaacggga
2581 tctggacgcc ccttctccta tgcacgaagg agatcagaca agagccagca gcagaaagag
2641 aagcaggtct gatagagccg tgacaggacc ttctgcccag cagtctttg aagtgagagt
2701 gcctgaacag agagatgccc tgcatctgcc tctgctgtct tggggagtga aaagacctag
2761 aacaagaatc ggaggactgc tggacccctgg aacacctatg gatgccgatc tggtggcctc
2821 ttctacagtg gtgtgggaac aggatgccga tccttttgcc ggaacagccg atgatttccc
2881 tgcctttaat gaggaagaac tggcctggct gatggaactg ctgcctcagg atcccagct
2941 ggtgaaatct gagctggagg agaagaagtc tgagctgaga cacaagctga agtacgtgcc
3001 tcacagagtac atcgagctga tcgagatcgc cagaaatagc acccaggata gaatcctgga
3061 gatgaaggtg atggagttct tcatgaaggt gtacggctac agaggaaagc acctgggagg
3121 aagcagaaaa cctgacggag ccatttatac agtgggcagc cctatcgatt atggcgtgat
3181 cgtggataca aaggcctaca gcggaggcta caatctgcct attggacagg ccgatgagat
```

```
3241 gcagagatac gtggaggaga accagaccag gaacaagcac atcaacccta acgagtggtg 3301 gaaggtgtac ccttctagcg tgaccgagtt caagttcctg tttgtgagcg gccacttcaa 3361 gggcaattat aaggcccagc tgaccaggct gaaccacatc acaaattgta atggcgccgt 3421 gctgtctgtg gaggaactgc tgattggagg agagatgatt aaggccggaa cactgacact 3481 ggaggaggtg agaagaaagt tcaacaacgg cgagatcaac ttctgaaagc ttacccagct 3541 ttccttgtaca aagttggcat tataagaaag cattgcttat caatttgttg caacgaacag 3601 gtcactatca gtcaaaataa aatcattatt tgccatccag ctgatatccc ctatagtgag 3661 tcgtattaca tggtcatagc tgtttcctgg cagctctggc ccgtgtctca aaatctctga 3721 tgttacattg cacaagataa aaatatatca tcatgaacaa taaaactgtc tgcttacata 3781 aacagtaata caagggggtgt tatgagccat attcaacggg aaacgtcgag gccgcgatta 3841 aattccaaca tggatgctga tttatatggg tataaatggg ctcgcgataa tgtcgggcaa 3901 tcaggtgcga caatctatcg cttgtatggg aagcccgatg cgccagagtt gtttctgaaa 3961 catggcaaag gtagcgttgc caatgatgtt acagatgaga tggtcagact aaactggctg 4021 acggaattta tgcctcttcc gaccatcaag cattttatcc gtactcctga tgatgcatgg 4081 ttactcacca ctgcgatccc cggaaaaaca gcattccagg tattagaaga atatcctgat 4141 tcaggtgaaa atattgttga tgcgctggca gtgttcctgc gccggttgca ttcgattcct 4201 gtttgtaatt gtcctttaa cagcgatcgc gtatttcgtc tcgctcaggc gcaatcacga 4261 atgaataacg gtttggttga tgcgagtgat tttgatgacg agcgtaatgg ctggcctgtt 4321 gaacaagtct ggaaagaaat gcataaactt ttgccattct caccggattc agtcgtcact 4381 catggtgatt tctcacttga taaccttatt tttgacgagg ggaaattaat aggttgtatt 4441 gatgttggac gagtcggaat cgcagaccga taccaggatc ttgccatcct atggaactgc 4501 ctcggtgagt tttctccttc attacagaaa cggctttttc aaaaatatgg tattgataat 4561 cctgatatga ataaattgca gtttcatttg atgctcgatg agtttttcta atcagaattg 4621 gttaattggt tgtaacactg gcagagcatt acgctgactt gacgggacgg cgcaagctca 4681 tgaccaaaat cccttaacgt gagttacgcg tcgttccact gagcgtcaga ccccgtagaa 4741 aagatcaaag gatcttcttg agatcctttt tttctgcgcg taatctgctg cttgcaaaca 4801 aaaaaaccac cgctaccagc ggtggtttgt ttgccggatc aagagctacc aactcttttt 4861 ccgaaggtaa ctggcttcag cagagcgcag ataccaaata ctgtccttct agtgtagccg 4921 tagttaggcc accacttcaa gaactctgta gcaccgccta catacctcgc tctgctaatc 4981 ctgttaccag tggctgctgc cagtggcgat aagtcgtgtc ttaccgggtt ggactcaaga 5041 cgatagttac cggataaggc gcagcggtcg ggctgaacgg ggggttcgtg cacacagccc 5101 agcttggagc gaacgaccta caccgaactg agatacctac agcgtgagca ttgagaaagc 5161 gccacgcttc ccgaagggag aaaggcggac aggtatccgg taagcggcag gtcggaaca 5221 ggagagcgca cgagggagct tccaggggga aacgcctggt atctttatag tcctgtcggg 5281 tttcgccacc tctgacttga gcgtcgattt ttgtgatgct cgtcaggggg gcggagccta 5341 tggaaaaacg ccagcaacgc ggccttttta cggttcctgg ccttttgctg gccttttgct 5401 cacatgtt
``` pENTR221 Native TAL VP64 Activator Vector Sequence

SEQ ID NO: 35

```
  1 ctttcctgcg ttatcccctg attctgtgga taaccgtatt accgcctttg agtgagctga 61 taccgctcgc cgcagccgaa cgaccgagcg cagcgagtca gtgagcgagg aagcggaaga 121 gcgcccaata cgcaaaccgc ctctccccgc gcgttggccg attcattaat gcagctggca
```

```
 181 cgacaggttt cccgactgga aagcgggcag tgagcgcaac gcaattaata cgcgtaccgc
 241 tagccaggaa gagtttgtag aaacgcaaaa aggccatccg tcaggatggc cttctgctta
 301 gtttgatgcc tggcagttta tggcgggcgt cctgcccgcc accctccggg ccgttgcttc
 361 acaacgttca aatccgctcc cggcggattt gtcctactca ggagagcgtt caccgacaaa
 421 caacagataa aacgaaaggc ccagtcttcc gactgagcct ttcgttttat ttgatgcctg
 481 gcagttccct actctcgcgt taacgctagc atggatgttt tcccagtcac gacgttgtaa
 541 aacgacggcc agtcttaagc tcgggcccca ataatgatt ttattttgac tgatagtgac
 601 ctgttcgttg caacaaattg atgagcaatg cttttttata tgccaactt tgtacaaaaa
 661 agcaggctgc ggccgcgcca ccatgggaaa acctattcct aatcctctgc tgggcctgga
 721 ttctaccatg gaccctatta gaagcagaac ccctctcca gccagagaac tgctgtctgg
 781 acctcagcct gatggagtgc agcctacagc cgatagagga gtgtctcctc ctgccggagg
 841 acctctggat ggactgcctg cccggagaac aatgagcaga acaagactgc cttctcctcc
 901 agccccatct cctgcctttt ctgccgattc ttttagcgac ctgctgagac agtttgaccc
 961 cagcctgttt aataccagcc tgttcgatag cctgcctcct tttggagccc accacacaga
1021 ggccgccaca ggcgaatggg atgaagtgca gtctggactg agagccgccg atgcccctcc
1081 tcctacaatg agagtggccg tgacagccgc cagacctcct agagccaaac tgccccctag
1141 aaggagagcc gcccagcctt ctgatgcctc tcctgccgcc caggtggacc tgagaacact
1201 gggatattct cagcagcagc aggagaagat caagcccaag gtgaggtcta cagtggccca
1261 gcaccacgaa gccctggtgg gacacggatt tacacacgcc cacattgtgg ccctgtctca
1321 gcaccctgcc gccctgggaa cagtggccgt gaaatatcag gatatgattg ccgccctgcc
1381 tgaggccaca cacgaagcca ttgtgggagt gggaaaacag tggtctggag ccagagccct
1441 ggaagccctg ctgacagtgg ccggagaact gagaggacct cctctgcagc tggatacagg
1501 acagctgctg aagattgcca aaaggggcgg agtgaccgcg gtggaagccg tgcacgcctg
1561 gagaaatgcc ctgacaggag cccctctgaa cccttgcagg tgccggaatt gccagctggg
1621 gcgccctctg gtaaggttgg gaagccctgc aaagtaaact ggatggcttt cttgccgcca
1681 aggatctgat ggcgcagggg atcaagctct gatcaagaga caggatgagg atcgtttcgc
1741 atgcagttca aagtgtatac ctacaaacgt gaaagccgtt atcgtctgtt tgtggatgtg
1801 cagagcgata ttattgatac ccctggtcgt cgtatggtga ttccgctggc ctctgcgcgt
1861 ctgctgtctg ataaagtgag ccgtgagctg tatccggtgg tgcatattgg tgatgaaagc
1921 tggcgtatga tgaccaccga tatggcgagc gtgccggtga gcgtgattgg cgaagaagtg
1981 gcggatctga gccatcgtga aaacgatatc aaaaacgcga ttaacctgat gttttggggc
2041 atttaataaa tgtcaggctc ccttatacac agccagtctg cagtcacctg cggatagcat
2101 tgtgggccag ctgtctagac ctgatcctgc cctggccgcc ctgacaaatg atcacctggt
2161 ggccctggcc tgtctgggag gcagacctgc cctggatgcc gtgaaaaaag gactgcctca
2221 cgccctgcc ctgatcaaga aacaaatag aagaatcccc gagcggacct ctcacagagt
2281 ggccgatcac gcccaggtgg tgagagtgct gggattttt cagtgtcact ctcaccctgc
2341 ccaggccttt gatgatgcca tgacacagtt tggcatgagc agacacggac tgctgcagct
2401 gtttagaaga gtgggagtga cagaactgga ggccagaagc ggaacactgc tccagcctc
2461 tcagagatgg gatagaattc tgcaggccag cggaatgaag agagccaaac cttctcctac
2521 cagcacccag acacctgatc aggccagcct gcacgccttt gccgattctc tggaacggga
```

```
2581 tctggacgcc ccttctccta tgcacgaagg agatcagaca agagccagca gcagaaagag 2641 aagcaggtct gatagagccg tgacaggacc ttctgcccag cagtcttttg aagtgagagt 2701 gcctgaacag agagatgccc tgcatctgcc tctgctgtct tggggagtga aaagacctag 2761 aacaagaatc ggaggactgc tggacccctgg aacacctatg gatgccgatc tggtggcctc 2821 ttctacagtg gtgtgggaac aggatgccga tccttttgcc ggaacagccg atgatttccc 2881 tgcctttaat gaggaagaac tggcctggct gatggaactg ctgcctcagg gatcccctaa 2941 gaaaaagcgg aaagtggaag cctctggatc tggcagagcc gatgccctgg atgattttga 3001 tctggatatg ctgggaagcg acgccctgga tgatttcgat ctggatatgc tgggatctga 3061 cgccctggat gatttcgatc tggatatgct gggatctgac gccctggatg atttcgatct 3121 ggacatgctg atcaacagct gaaagcttac ccagctttct tgtacaaagt tggcattata 3181 agaaagcatt gcttatcaat ttgttgcaac gaacaggtca ctatcagtca aaataaaatc 3241 attatttgcc atccagctga tatcccctat agtgagtcgt attacatggt catagctgtt 3301 tcctggcagc tctggcccgt gtctcaaaat ctctgatgtt acattgcaca agataaaaat 3361 atatcatcat gaacaataaa actgtctgct tacataaaca gtaatacaag gggtgttatg 3421 agccatattc aacgggaaac gtcgaggccg cgattaaatt ccaacatgga tgctgattta 3481 tatgggtata aatgggctcg cgataatgtc gggcaatcag gtgcgacaat ctatcgcttg 3541 tatgggaagc ccgatgcgcc agagttgttt ctgaaacatg gcaaaggtag cgttgccaat 3601 gatgttacag atgagatggt cagactaaac tggctgacgg aatttatgcc tcttccgacc 3661 atcaagcatt ttatccgtac tcctgatgat gcatggttac tcaccactgc gatccccgga 3721 aaaacagcat tccaggtatt agaagaatat cctgattcag gtgaaaatat tgttgatgcg 3781 ctggcagtgt tcctgcgccg gttgcattcg attcctgttt gtaattgtcc ttttaacagc 3841 gatcgcgtat ttcgtctcgc tcaggcgcaa tcacgaatga ataacggttt ggttgatgcg 3901 agtgattttg atgacgagcg taatggctgg cctgttgaac aagtctggaa agaaatgcat 3961 aaacttttgc cattctcacc ggattcagtc gtcactcatg gtgatttctc acttgataac 4021 cttattttg acgagggga attaataggt tgtattgatg ttggacgagt cggaatcgca 4081 gaccgatacc aggatcttgc catcctatgg aactgcctcg gtgagttttc tccttcatta 4141 cagaaacggc tttttcaaaa atatggtatt gataatcctg atatgaataa attgcagttt 4201 catttgatgc tcgatgagtt tttctaatca gaattggtta attggttgta acactggcag 4261 agcattacgc tgacttgacg ggacggcgca agctcatgac caaaatccct taacgtgagt 4321 tacgcgtcgt tccactgagc gtcagacccc gtagaaaaga tcaaaggatc ttcttgagat 4381 ccttttttc tgcgcgtaat ctgctgcttg caaacaaaaa aaccaccgct accagcggtg 4441 gtttgtttgc cggatcaaga gctaccaact cttttccga aggtaactgg cttcagcaga 4501 gcgcagatac caaatactgt ccttctagtg tagccgtagt taggccacca cttcaagaac 4561 tctgtagcac cgcctacata cctcgctctg ctaatcctgt taccagtggc tgctgccagt 4621 ggcgataagt cgtgtcttac cgggttggac tcaagacgat agttaccgga taaggcgcag 4681 cggtcgggct gaacggggg ttcgtgcaca cagcccagct tggagcgaac gacctacacc 4741 gaactgagat acctacagcg tgagcattga gaaagcgcca cgcttcccga agggagaaag 4801 gcggacaggt atccggtaag cggcagggtc ggaacaggag agcgcacgag ggagcttcca 4861 gggggaaacg cctggtatct ttatagtcct gtcgggtttc gccacctctg acttgagcgt 4921 cgatttttgt gatgctcgtc aggggggcgg agcctatgga aaaacgccag caacgcggcc 4981 ttttttacggt tcctggcctt ttgctggcct tttgctcaca tgtt
``` pENTR221 Native TAL Repressor Vector Sequence

SEQ ID NO: 36

```
   1 CTTTCCTGCGTTATC CCCTGATTCTGTGGA TAACCGTATTACCGC CTTTGAGTGAGCTGA TACCGCTCGCCGCAG
  76 CCGAACGACCGAGCG CAGCGAGTCAGTGAG CGAGGAAGCGGAAGA GCGCCCAATACGCAA ACCGCCTCTCCCCGC
 151 GCGTTGGCCGATTCA TTAATGCAGCTGGCA CGACAGGTTTCCCGA CTGGAAAGCGGGCAG TGAGCGCAACGCAAT
 226 TAATACGCGTACCGC TAGCCAGGAAGAGTT TGTAGAAACGCAAAA AGGCCATCCGTCAGG ATGGCCTTCTGCTTA
 301 GTTTGATGCCTGGCA GTTTATGGCGGGCGT CCTGCCCGCCACCCT CCGGGCCGTTGCTTC ACAACGTTCAAATCC
 376 GCTCCCGGCGGATTT GTCCTACTCAGGAGA GCGTTCACCGACAAA CAACAGATAAAACGA AAGGCCCAGTCTTCC
 451 GACTGAGCCTTTCGT TTTATTTGATGCCTG GCAGTTCCCTACTCT CGCGTTAACGCTAGC ATGGATGTTTTCCCA
 526 GTCACGACGTTGTAA AACGACGGCCAGTCT TAAGCTCGGGCCCCA ATAATGATTTTATT TTGACTGATAGTGAC
 601 CTGTTCGTTGCAACA AATTGATGAGCAATG CTTTTTTATAATGCC AACTTTGTACAAAAA AGCAGGCTGCGGCCG
 676 CGCCACCATGGGAAA ACCTATTCCTAATCC TCTGCTGGGCCTGGA TTCTACCGACCCTAT TAGAAGCAGAACACC
 751 TTCTCCAGCCAGAGA GCTGCTGTCTGGACC TCAGCCTGATGGAGT GCAGCCTACAGCCGA TAGAGGAGTGTCTCC
 826 TCCTGCCGGAGGACC TCTGGATGGACTGCC TGCCCGGAGAACAAT GAGCAGAACAAGACT GCCTTCTCCTCCAGC
 901 CCCATCTCCTGCCTT TTCTGCCGATTCTTT TAGCGACCTGCTGAG ACAGTTTGACCCCAG CCTGTTTAATACCAG
 976 CCTGTTCGATAGCCT GCCTCCTTTTGGAGC CCACCACACAGAGGC CGCCACAGGCGAATG GGATGAAGTGCAGTC
1051 TGGACTGAGAGCCGC CGATGCCCCTCCTCC TACAATGAGAGTGGC CGTGACAGCCGCCAG ACCTCCTAGAGCCAA
1126 ACCTGCCCCTAGAAG GAGAGCCGCCCAGCC TTCTGATGCCTCTCC TGCCGCCCAGGTGGA TCTGAGAACACTGGG
1201 ATATTCTCAGCAGCA GCAGGAGAAGATCAA GCCCAAGGTGAGATC TACAGTGGCCCAGCA CCACGAAGCCCTGGT
1276 GGGACACGGATTTAC ACACGCCCACATTGT GGCCCTGTCTCAGCA CCCTGCCGCCCTGGG AACAGTGGCCGTGAA
1351 ATATCAGGATATGAT TGCCGCCCTGCCTGA GGCCACACACGAAGC CATTGTGGGAGTGGG AAAACAGTGGTCTGG
1426 AGCCAGAGCCCTGGA AGCCCTGCTGACAGT GGCCGGAGAACTGAG AGGACCTCCTCTGCA GCTGGATACAGGACA
1501 GCTGCTGAAGATTGC CAAAAGGGGCGGAGT GACCGCGGTGGAAGC CGTGCACGCCTGGAG AAATGCCCTGACAGG
1576 AGCCCCTCTGAACCC TTGCAGGTGCCGGAA TTGCCAGCTGGGGCG CCCTCTGGTAAGGTT GGGAAGCCCTGCAAA
1651 GTAAACTGGATGGCT TTCTTGCCGCCAAGG ATCTGATGGCGCAGG GGATCAAGCTCTGAT CAAGAGACAGGATGA
1726 GGATCGTTTCGCATG CAGTTCAAAGTGTAT ACCTACAAACGTGAA AGCCGTTATCGTCTG TTTGTGGATGTGCAG
1801 AGCGATATTATTGAT ACCCCGGGTCGTCGT ATGGTGATTCCGCTG GCCTCTGCGCGTCTG CTGTCTGATAAAGTG
1876 AGCCGTGAGCTGTAT CCGGTGGTGCATATT GGTGATGAAAGCTGG CGTATGATGACCACC GATATGGCGAGCGTG
1951 CCGGTGAGCGTGATT GGCGAAGAAGTGGCG GATCTGAGCCATCGT GAAAACGATATCAAA AACGCGATTAACCTG
2026 ATGTTTTGGGGCATT TAATAAATGTCAGGC TCCCTTATACACAGC CAGTCTGCAGTCACC TGCGGATAGCATTGT
2101 GGCCCAGCTGTCTAG ACCTGATCCTGCCCT GGCCGCCCTGACAAA TGATCACCTGGTGGC CCTGGCCTGTCTGGG
2176 AGGCAGACCTGCCCT GGATGCCGTGAAAAA AGGACTGCCTCACGC CCCTGCCCTGATCAA GAGAACAAATAGAAG
2251 AATCCCCGAGCGGAC CTCTCACAGAGTGGC CGATCACGCCCAGGT GGTGAGAGTGCTGGG ATTTTTTCAGTGTCA
2326 CTCTCACCCTGCCCA GGCCTTTGATGATGC CATGACACAGTTTGG CATGAGCAGACACGG ACTGCTGCAGCTGTT
2401 TAGAAGAGTGGGAGT GACAGAACTGGAGGC CAGATCTGGTACCCT GCCTCCTGCCTCTCA GAGATGGGATAGAAT
2476 TCTGCAGCTGAAGCT GCTGTCTAGCATTGA ACAGGCCTGCCCCAA GAAGAAGAGAAAAGT GGACGACGCCAAGAG
2551 CCTGACAGCCTGGAG CAGAACACTGGTGAC ATTCAAGGATGTGTT CGTGGACTTCACCAG GGAGGAATGGAAACT
2626 GCTGGATACAGCCCA GCAGATCGTGTACAG AAATGTGATGCTGGA AAACTACAAGAACCT GGTGTCTCTGGGCTA
2701 CCAGCTGACAAAGCC TGATGTGATTCTGAG ACTGGAGAAGGGCGA AGAACCTTGGCTGGT GGAAAGAGAGATCCA
2776 CTGAAAGCTTACCCA GCTTTCTTGTACAAA GTTGGCATTATAAGA AAGCATTGCTTATCA ATTTGTTGCAACGAA
2851 CAGGTCACTATCAGT CAAAATAAAATCATT ATTTGCCATCCAGCT GATATCCCCTATAGT GAGTCGTATTACATG
```

```
2926 GTCATAGCTGTTTCC TGGCAGCTCTGGCCC GTGTCTCAAAATCTC TGATGTTACATTGCA CAAGATAAAATATA

3001 TCATCATGAACAATA AAACTGTCTGCTTAC ATAAACAGTAATACA AGGGGTGTTATGAGC CATATTCAACGGGAA

3076 ACGTCGAGGCCGCGA TTAAATTCCAACATG GATGCTGATTTATAT GGGTATAAATGGGCT CGCGATAATGTCGGG

3151 CAATCAGGTGCGACA ATCTATCGCTTGTAT GGGAAGCCCGATGCG CCAGAGTTGTTTCTG AAACATGGCAAAGGT

3226 AGCGTTGCCAATGAT GTTACAGATGAGATG GTCAGACTAAACTGG CTGACGGAATTTATG CCTCTTCCGACCATC

3301 AAGCATTTTATCCGT ACTCCTGATGATGCA TGGTTACTCACCACT GCGATCCCCGGAAAA ACAGCATTCCAGGTA

3376 TTAGAAGAATATCCT GATTCAGGTGAAAAT ATTGTTGATGCGCTG GCAGTGTTCCTGCGC CGGTTGCATTCGATT

3451 CCTGTTTGTAATTGT CCTTTTAACAGCGAT CGCGTATTTCGTCTC GCTCAGGCGCAATCA CGAATGAATAACGGT

3526 TTGGTTGATGCGAGT GATTTTGATGACGAG CGTAATGGCTGGCCT GTTGAACAAGTCTGG AAAGAAATGCATAAA

3601 CTTTTGCCATTCTCA CCGGATTCAGTCGTC ACTCATGGTGATTTC TCACTTGATAACCTT ATTTTTGACGAGGGG

3676 AAATTAATAGGTTGT ATTGATGTTGGACGA GTCGGAATCGCAGAC CGATACCAGGATCTT GCCATCCTATGGAAC

3751 TGCCTCGGTGAGTTT TCTCCTTCATTACAG AAACGGCTTTTTCAA AAATATGGTATTGAT AATCCTGATATGAAT

3826 AAATTGCAGTTTCAT TTGATGCTCGATGAG TTTTTCTAATCAGAA TTGGTTAATTGGTTG TAACACTGGCAGAGC

3901 ATTACGCTGACTTGA CGGGACGGCGCAAGC TCATGACCAAAATCC CTTAACGTGAGTTAC GCGTCGTTCCACTGA

3976 GCGTCAGACCCCGTA GAAAAGATCAAAGGA TCTTCTTGAGATCCT TTTTTTCTGCGCGTA ATCTGCTGCTTGCAA

4051 ACAAAAAAACCACCG CTACCAGCGGTGGTT TGTTTGCCGGATCAA GAGCTACCAACTCTT TTTCCGAAGGTAACT

4126 GGCTTCAGCAGAGCG CAGATACCAAATACT GTCCTTCTAGTGTAG CCGTAGTTAGGCCAC CACTTCAAGAACTCT

4201 GTAGCACCGCCTACA TACCTCGCTCTGCTA ATCCTGTTACCAGTG GCTGCTGCCAGTGGC GATAAGTCGTGTCTT

4276 ACCGGGTTGGACTCA AGACGATAGTTACCG GATAAGGCGCAGCGG TCGGGCTGAACGGGG GGTTCGTGCACACAG

4351 CCCAGCTTGGAGCGA ACGACCTACACCGAA CTGAGATACCTACAG CGTGAGCATTGAGAA AGCGCCACGCTTCCC

4426 GAAGGGAGAAAGGCG GACAGGTATCCGGTA AGCGGCAGGGTCGGA ACAGGAGAGCGCACG AGGGAGCTTCCAGGG

4501 GGAAACGCCTGGTAT CTTTATAGTCCTGTC GGGTTTCGCCACCTC TGACTTGAGCGTCGA TTTTTGTGATGCTCG

4576 TCAGGGGGGCGGAGC CTATGGAAAAACGCC AGCAACGCGGCCTTT TTACGGTTCCTGGCC TTTTGCTGGCCTTTT

4651 GCTCACATG
```

EXAMPLES

Example 1: Placing an Order with a Service Provider Offering TAL-Related Services Via a Web-Based Platform This example describes one embodiment of a possible workflow underlying a customer order related to TAL-specific services. The order process begins with a customer inquiry or request. The request may be received directly via the portal or may be received otherwise, such as, e.g., by email, via the supplier's webpage, per phone or fax etc. The customer will be asked to create an account (if the customer is not already registered with the supplier) to be able to log in to the order portal of the service provider. After login, the customer encounters a TAL designer interface where the customer can choose from different options (see FIG. 1A). The customer is asked to enter a minimal TAL target sequence (e.g., a 24 base nucleotide sequence) and select a destination host from a drop-down menu. In this example, the customer wants to order a TAL expression construct for expression in human cells and will therefore select "human" as destination host. The selection of a destination host may influence the parameters chosen for gene optimization, the parts used for manufacturing (e.g., selected from a material repository) and the assembly strategy. Next, the customer is asked to select an effector domain from a drop-down menu. Alternatively, the customer can enter or paste the amino acid sequence of a desired effector domain in a "customized effector" field. The customer chooses a nuclease domain from the menu and additionally pastes the amino acid sequences of two mutated variants of the nuclease domain (which are not offered in the drop-down menu) into the customized effector field. As the selected nuclease domains only function as dimers, the system automatically generates a note that a pair of TAL effector nuclease constructs will be generated. In a next step, the customer chooses a target vector from one or more drop-down menus. The customer can choose, e.g., a cloning vector or an expression vector or both. In this example, the customer wishes the different TAL effector nuclease constructs to be subcloned into a pENTR GATEWAY® functional vector and selects a respective vector with a kanamycin resistance gene. Furthermore, the customer selects specific enzyme cleavage sites for the 5' and 3' ends of the genes and selects a His-Tag to be fused to the 3'-end of each construct for purification purposes. In a next step, the customer can choose from additional services and orders a TAL binding proof for the specified TAL effector nuclease. Finally, the customer requests a quote for manufacture of a stable TAL effector nuclease cell line where the cell line would be provided by the customer and adds material specifications in a comment box. To finalize the inquiry he presses a submit button and the specifications are analysed and processed by the service provider.

Example 2a: Development of a TAL Binding Plate Assay

To validate that engineered TAL effectors are capable of binding to their predicted target sites, we developed a plate binding assay. For this purpose, TAL effectors targeting Hax3 DNA binding box were cloned into a pDEST17 Gateway® vector containing a T7 promoter and placing a His tag at the N terminus of the proteins. TAL effectors were expressed using a rabbit reticulocyte in vitro transcription/translation system $TNT^R$ quick Coupled Transcription/Translation System (Life Technologies Corp., Carlsbad). The expressed TAL effectors where then captured by nickel coated 96-well plates Pierce Nickel Coated Plates (Pierce Biotechnology, Rockford, Ill.). Plates were washed with a buffer (30 mM KCl, 0.1 mM DDT, 0.1 mM EDTA, 10 mM Tris, pH7.4) to remove unbound components and where then incubated with a TAL DNA binding probe in binding buffer (30 mM KCl, 0.1 mM DDT, 0.1 mM EDTA, 10 mM Tris, pH 7.4). To generate the binding probe, DNA oligonucleotides containing the DNA binding sequence and between 5 and 10 extra nucleotides at each end were synthesized through Life Technologies (Carlsbad, Calif.). Binding probes were then generated by annealing two complimentary DNA oligonucleotides in a thermal cycler PCR machine. After incubation, unbound probe was removed by washing the plates. Next, the DNA bound to TAL effectors was labeled using QUANT-IT™ PICOGREEN® dsDNA reagent. After another washing step the fluorescence of the samples was measured at excitation 480 nM, emission 520 nM using a spectroflurometer. In the example illustrated in FIG. 4A specificity for a specific TAL protein (containing Hax3 binding repeats) was determined in the presence of increasing amounts of two different binding probes containing Hax3 and ArtX1 (negative control) binding sites. The results of this experiment demonstrate that the developed plate binding assay is a quick and reliable method to validate binding capacity of engineered TAL effectors to a given target sequence.

Example 2b: Development of a Bead-Based Binding Assay

As alternative, a bead-based assay for quantitative analysis of TAL binding was established as illustrated in FIG. 4B. In this assay format His-tagged TAL proteins expressed in a cell free system are covalently coupled to magnetic Ni-beads and incubated with target DNA. Beads are then washed and subject to quantitative PCR. In the illustrated example equal amounts of TAL protein were covalently coupled to activated DYNABEADS® and incubated with a 5-fold molar excess (Sample 1) and equimolar amount (Sample 2) of plasmid target DNA. Total bound DNA was then quantified by qPCR with plasmid specific primers and SYBR® Green. FIG. 4C shows another approach to determine TAL binding specificity (e.g., of Hax3) to target DNA by means of a gel-shift assay in the presence of increasing amounts of the expressed TAL protein.

Example 3: Design-Based Synthesis of TAL Effector Expression Constructs

The following is a protocol regarding how TAL effectors molecules can be designed and manufactured.

Sequence Design and Optimization:

A synthetic version of each TAL cassette and effector fusion wild-type sequences was generated reflecting the codon bias of the target organism (e.g., the codon usage of mammalian cells, bacteria, yeast, microalgae). Starting with a wild-type sequence, the target organism codon-preference as specified in a codon usage table (CUT, http://www.kazusa.or.jp/codon/) was transferred to the primary sequence based on the degeneracy of the genetic code. Basically, the amino acid sequence was back-translated into a nucleic acid sequence by exchanging codons with target organism-preferred codons wherever possible. For this purpose the GENE-OPTIMIZER® software tool was used. This multi-parameter optimization tool fulfils two functions: first, the software optimizes the nucleic acid sequence for a specific purpose taking multiple parameters into account, such as codon usage, GC content, repetitive sequences that may interfere with production, RNA secondary structure, cryptic splice sites or other inhibitory motifs or sequences relevant for specific hosts. In certain instances, it may be beneficial to harmonize the GC content if this results in more favourable production conditions or more balanced protein folding. Second, the oligonucleotide sequences for gene synthesis are determined which means that the full-length nucleic acid molecule that is to be synthesized will be fragmented into smaller subfragments that will again be assembled from oligonucleotides. For trimer and higher order assembly, TAL cassettes were designed as follows: 44 cassettes (monomers) were synthesized reflecting 11 discrete cassette positions within the final TAL effector for four nucleotides each.

Synthesis of Cassette Vectors:

The in silico designed coding sequences of 44 cassettes reflecting 11 discrete cassette positions in a TAL effector for 4 nucleotide binding categories were broken down into overlapping oligonucleotides. The sense strand sequence was then split into three sequential L-oligos of 50-60 nucleotides (nt) in length to cover the complete nucleic acid sequence without gaps. Likewise, the antisense strand was split into two shorter M-oligos of approximately 40 nt in length partially overlapping the corresponding, complementary L-oligos. For a second amplification step and in preparation for cloning, two terminal oligos, pf (primer forward) and pb (primer backward) were designed. These terminal oligos should provide a 25 nt overlap with the sequence and an additional 12 nt protruding sequence containing homologous regions with the destination vector for subsequent cloning. The designed oligonucleotides were then produced by conventional oligonucleotide synthesis procedures. The synthetic cassettes were then generated via stepwise PCR amplification, as follows: In a first amplification round referred to as SCR (Sequential Chain Reaction) for each fragment 5 μl of an oligo-pool containing all L- and M-oligos at a final concentration of 15 nM, 18 μl $H_2O$ and 27 μl PCR master-mix were mixed together and subjected to PCR using the protocol as outlined in TABLE 21. The SCR product cannot be used for cloning directly, but has to be further amplified using a method referred to as SPCR (Sequential PCR) to introduce the homologous with the terminal pf and pb primers. Seven μl of the SCR reaction were mixed with each 2 μl of pf and pb (at a concentration of 15 μM, each), 27 μl PCR master-mix and 14 μl $H_2O$, and were subjected to PCR using the protocol as specified in TABLE 22. The product of this PCR reaction was analysed on an agarose gel. The destination vector and the synthetic cassettes were then subject to an exonuclease based reaction as described in Aslanidis and de Jong (Ligation-independent cloning of PCR products (LIC-POR); Nucleic Acids Research, Vol. 18, No. 20 6069 (1990)) to generate single stranded overhangs for subsequent ligation-independent cloning. The annealed product was directly transformed into E. coli and correct clones were selected on kanamycin LB medium.

Generation of Trimer Library:

The resulting 44 cassette vectors (together a cassette library) were then used to generate a trimer library (see FIG. 7A). In order to produce each required trimer for each defined position three TAL cassettes were assembled to generate one trimer according to the type IIS assembly protocol following a library approach (according to the example, 8 libraries were produced). For the assembly of each three cassettes into one vector a 50 µl total volume approach was used. Two hundred ng of the target vector (containing ccdB as counter-selectable marker gene) and 50 ng of each cassette vector (a total of 12 TAL monomers) were mixed with 2 µl restriction enzyme BsaI and incubated for 1 hour at 37° C. Following addition of 1 µl buffer, 3 µl 10 mM ATP, 1 µl T4 ligase and 5 µl H$_2$O the mix was incubated for 1 h at 22° C. followed by an additional digestion step for 1 hour at 37° C. (no additional restriction enzyme added). The enzyme was inactivated for 10 minutes at 65° C. 2-5 µl of the reaction sample were directly used for transformation of competent E. coli cells. Finally, a sufficient amount of colonies was sequenced to ensure that every individual combination (64 per library) was recovered. In this example the final trimer library consisted of 512 trimer clones (8 libraries of 4$^3$ randomly assembled cassettes). The half cassettes (half repeats) are reflected by position 11 and allow for synthesis of TAL effectors with 17.5 and 23.5 cassettes. The trimer library was then used as a basis for all higher order TAL effector assembly projects which allows building a puzzle from less larger pieces thereby maximizing assembly efficiency.

Assembly of TAL Effector Fusions.

To build a TAL effector with 24 cassettes with desired binding specificity, trimer vectors were selected from the library for each position using a design tool described in more detail elsewhere herein and were assembled following a 2-step type IIS assembly method as described above (FIG. 7B). The desired TAL effector sequence was split into two sub-parts of similar length (two sets of 12-mers). Each sub-part was assembled into one capture vector using the 4 respective trimers. In a second step the two sub-parts of 12 cassettes each were assembled into a functional vector comprising the N- and C-terminal flanking sequences and a 3' located effector fusion (a FokI nuclease cleavage domain). In this example a Gateway entry clone was used as functional vector which may serve for further cloning and recombination.

TABLE 21

PCR protocol 1

| Cycle | Number | Step | ° C. | Time |
|---|---|---|---|---|
| 1 | 1 | 1 | 95 | 04:00 |
| 2 | 30 | 1 | 95 | 00:30 |
|  |  | 2 | 60 →40* | 00:30 |
|  |  | 3 | 72 | 01:00 |
| 3 | 1 | 1 | 72 | 04:00 |
| 4 | 1 | 1 | 4 | ∞ |

*use a touch down program starting with 60° C. and ending with 40° C.

TABLE 22

PCR protocol 2

| Cycle | Number | Step | ° C. | Time |
|---|---|---|---|---|
| 1 | 1 | 1 | 95 | 04:00 |
| 2 | 30 | 1 | 95 | 00:30 |
|  |  | 2 | 58 | 00:30 |
|  |  | 3 | 72 | 01:00 |
| 3 | 1 | 1 | 72 | 04:00 |
| 4 | 1 | 1 | 4 | ∞ |

Example 3a: TAL Effector Fusion Assembly According to a First Protocol

To clone four trimers (=12 cassettes) into each capture vector (step (i) assembly), two parallel assembly reactions were prepared on day 1. For each reaction, 50 ng of each of the four selected trimer vectors were mixed with 200 ng of the capture vector, 40 Units (2 µl) of type IIS restriction enzyme BsaI (New England Biolabs (NEB), Ipswich, Mass.) and incubated for 1 hour at 37° C. in a 20 µl reaction volume containing 2 µl of NEB4 buffer. Following addition of 1 µl buffer NEB4, 3 µl 10 mM ATP, 400 Units (1 µl) T4 ligase (NEB) and 5 µl H$_2$O, the reaction mixtures were incubated for 1 hour at 22° C. to allow for ligation of assembled capture vectors carrying 12 cassettes each followed by an optional additional digestion step for 1 hour at 37° C. (no additional restriction enzyme added). The enzymes were inactivated for 10 minutes at 65° C. before 5 µl of each reaction mixture was transformed separately into chemically competent E. coli which were plated overnight on selective media. On day 2, 8 cfu per assembled capture vector were screened for correct insert size by cPCR (PCR reaction in presence of two primers binding next to TAL repeat subsets in opposite direction in vector backbone) and 15 ml of LB-medium with spectinomycin (50 µg/ml final conc.) were inoculated with selected cfu and grown overnight at 37° C. On day 3 overnight cultures were harvested and plasmids were prepared using the PureYield™ Plasmid Midiprep System from Promega (Madison, Wis.) according to the manufacturer's instructions yielding ~100 µg plasmid DNA from 15-ml cultures.

Sequence verification of the assembled TAL repeat subsets was performed on an ABI Sequencer 3730 using primers binding next to the TAL repeat subsets in the vector backbones. On day 4, step (ii) assembly was performed to clone TAL repeat subsets (12 cassettes from each capture vector) into a functional vector containing the TAL N- and C-terminal domains. For this purpose 50 ng of each purified and sequence-verified capture vector and 200 ng of the functional vector were mixed and incubated with 4 Units (2 µl) of type IIS restriction enzyme AarI (Fermentas, Hanover, Md.) in the presence of 0.5 µM of oligonucleotides (as recommended by Fermentas) and incubated for 1 hour at 37° C. in a 20 µl reaction volume containing 2 µl of NEB4 buffer. Following addition of 1 µl buffer NEB4, 3 µl 10 mM ATP, 1µl T4 ligase (NEB) and 5 µl H2O, the reaction mixture was incubated for 1 hour at 22° C. to allow for ligation of assembled functional vector carrying 24 cassettes followed by an additional digestion step for 1 hour at 37° C. The enzymes were inactivated for 10 minutes at 65° C. before 5 µl of each reaction mixture was transformed into chemically competent E. coli which were plated overnight on selective media. On day 5 the same procedure as on day 2 was performed including cPCR of 8 cfu of functional vectors followed by inoculation of 15 ml LB-medium overnight cultures. On day 6, overnight cultures were harvested and plasmids were prepared according to the same protocol as outlined for day 3 resulting in ~100 μg amounts of purified functional vector. Finally, the full-length TAL effector fusion was subject to sequencing as described for day 3 above in the presence of additional primers binding to specific TAL repeats (as described in detail elsewhere herein).

Example 3b: TAL Effector Fusion Assembly According to a Second Protocol

On day 1 step (i) assembly of four trimers into each capture vector was performed as described for day 1 of Example 3a and 5 μl of each assembly reaction mixture were transformed into chemically competent *E. coli*. The bacteria were then regenerated in 500 μl LB medium for 1 hour at 37° C. Medium was added up to 2 ml and supplied with 50 μg/ml of spectinomycin for selection, and the cultures were grown at 37° C. over night. On day 2, plasmids were prepared from the 2-ml cultures each containing a pool of transformants using the Plasmid Mini Kit from Qiagen (Hilden, Germany) according to the manufacturer's instructions. The purified first and second capture vector plasmid preparations were subsequently used in the step (ii) assembly reaction without further sequence verification. For this purpose, 50 ng of each purified capture vector pool was mixed with 200 ng of the functional vector and incubated with 4 Units (2 μl) of type IIS restriction enzyme AarI (Fermentas, Hanover, Md.) in the presence of 0.5 μM of oligonucleotides (as recommended by Fermentas) for 1 hour at 37° C. in a 20 μl reaction volume containing 2 μl of NEB4 buffer. Following addition of 1 μl buffer NEB4, 3 μl 10 mM ATP, 1 μl T4 ligase (NEB) and 5 μl $H_2O$, the reaction mixture was incubated for 1 h at 22° C. to allow for ligation of assembled functional vector followed by an optional additional digestion step for 1 hour at 37° C. The enzymes were inactivated for 10 minutes at 65° C. before 5 μl of reaction mixture were transformed into chemically competent *E. coli* which were plated over night on selective media. On day 3, 8 cfu were screened for correct insert size by cPCR as outlined for day 2 of Example 3a and 15 ml of LB-medium with kanamycine (25 μg/ml) were inoculated with selected cfu and grown overnight at 37° C. On day 4 overnight cultures were harvested and plasmids were prepared and sequenced as outlined for day 3 in Example 3a resulting in ~100 μg amounts of purified sequence-verified functional vector.

Example 3c: TAL Effector Fusion Assembly According to a Third Protocol

On day 1, step (i) assembly of four trimers into each capture vector was performed as described for day 1 of Examples 3a and 3b. Twenty μl of each step (i) reaction mixture containing assembled and ligated first and second capture vectors carrying TAL repeat subsets were mixed with 200 ng of the functional vector and incubated with 8 Units (4 μl) of type IIS restriction enzyme AarI (Fermentas) in the presence of 0.5 μM of oligonucleotides (as recommended by Fermentas) for 1 hour at 37° C. in a 80 μl reaction volume containing 4 μl of NEB4 buffer. Following addition of 2 μl buffer NEB4, 6 μl 10 mM ATP, 2 μl T4 ligase (NEB) and 10 μl $H_2O$ the reaction mixture was incubated for 1 h at 22° C. to allow for ligation of assembled functional vector followed by an additional digestion step for 1 hour at 37° C. The enzymes were inactivated for 10 minutes at 65° C. before 10 μl of reaction mixture were transformed into chemically competent *E. coli* which were plated over night on selective media. On day 2, 8 cfu were screened for correct insert size by cPCR as outlined for day 2 of Example 3a and 15 ml of LB-medium with kanamycin (25 μg/ml) were inoculated with selected cfu and grown overnight at 37° C. On day 3 overnight cultures were harvested and plasmids were prepared and sequenced as outlined for day 3 in Example 3a resulting in ~100 μg amounts of purified sequence-verified functional vector.

Example 4: A Genetic Inverter System to Demonstrate TAL Effector Function in *E. coli*

Figure 13A:
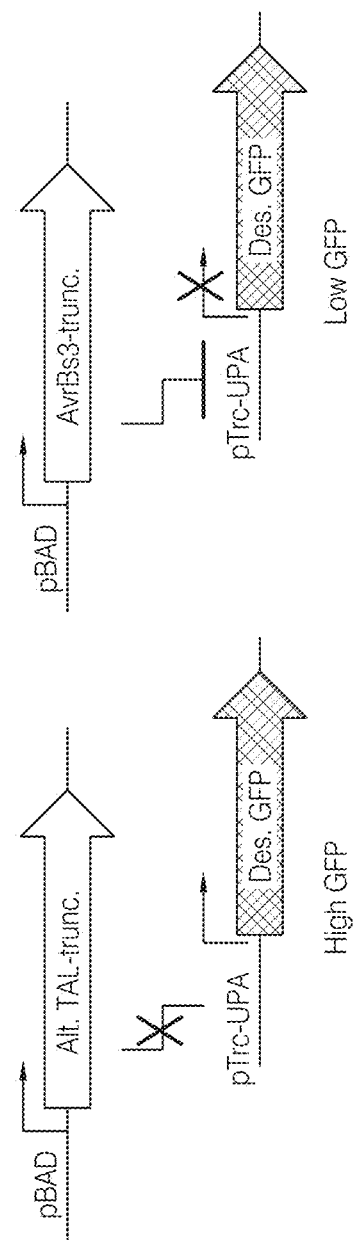
FIGS. 13A to 13C show an example of a reporter assay suitable to demonstrate TAL function in *E. coli*.
Figure 13B:
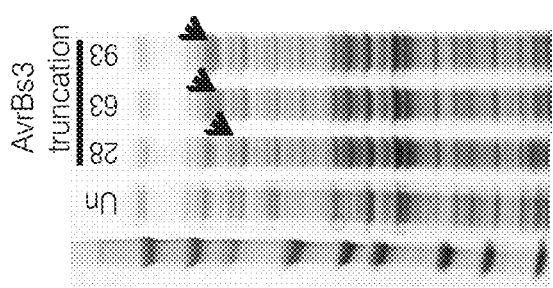
Figure 13C:
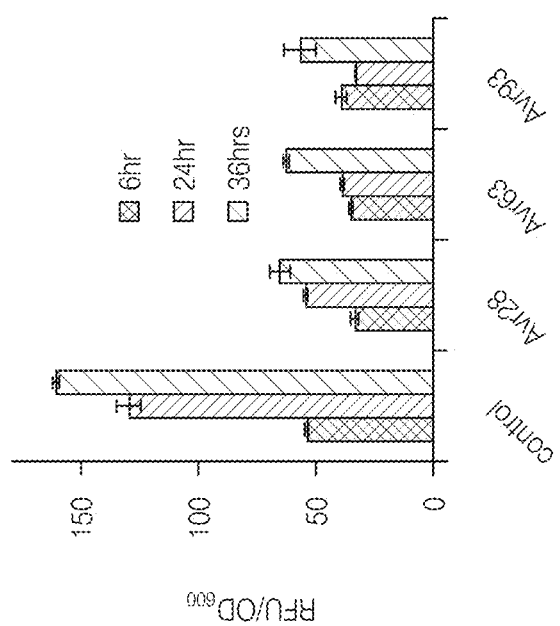
Figure 14A:
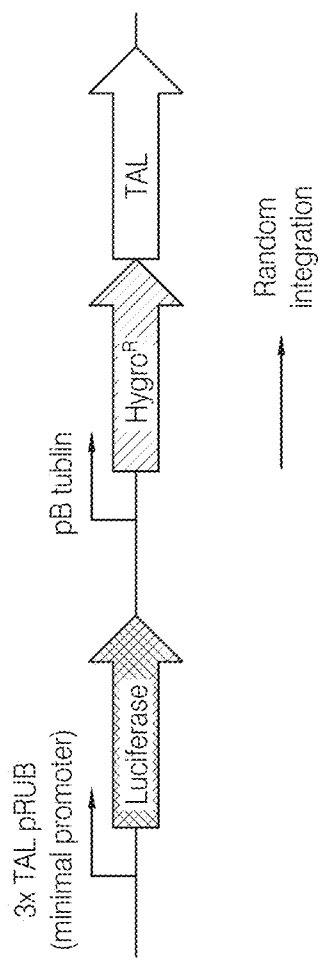
FIGS. 14A to 14C illustrate an example of TAL responsiveness in algae. A TAL genetic circuit for microalgae was constructed by placing a 3×TAL binding site in front of a minimal promoter driving expression of a luciferase reporter gene. A TAL effector was fused in frame to the N-terminus of hygromycin resistance gene (FIG. 14A). The genetic circuit with a Hsp70A-Rubisco promoter was used as a positive control and a circuit without TAL effector was used as a negative control. The constructs were transformed into algae, followed by Hygromycin B selection. The selected colonies were assayed for Luciferase expression (FIG. 14B) and TAL expression by Western blot analysis (FIG. 14C).
Figure 14B:
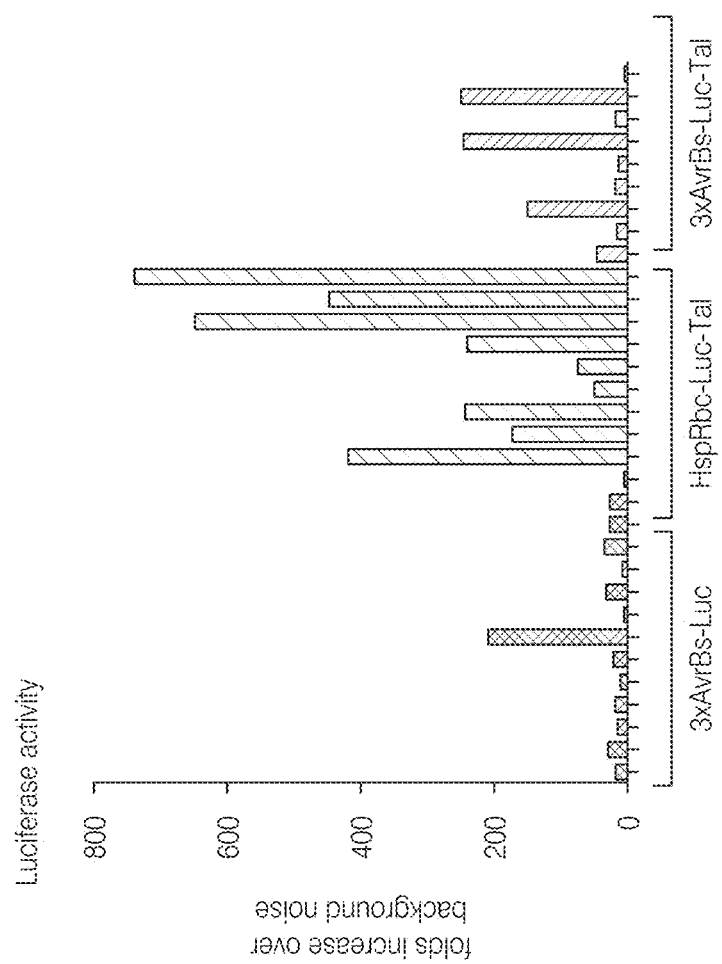
Figure 14C:
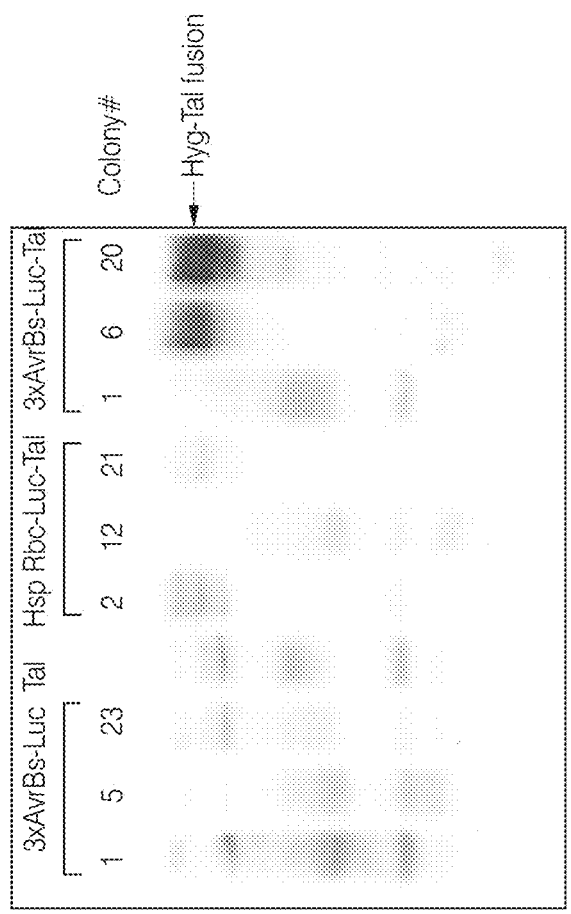

This example describes the development of a genetic inverter system created to test whether plant-derived AvrBs3 TAL proteins are active in *E. coli*. For this purpose a reporter plasmid encoding a destabilized GFP protein which has a short half-life in cells was designed wherein GFP expression is under the transcriptional control of a synthetic pTrc-UPA (upregulated by AvrBs3) promoter harboring the natural UPA20 TAL binding site (see FIG. 13A). Besides, arabinose-inducible TAL expression cassettes were constructed for expression of different C-terminally truncated variants of AvrBs3 TAL protein (Avr28, Avr63, Avr93) with binding specificity for the UPA20 target site. To validate correct TAL protein expression in *E. coli*, the three AvrBs3 truncation constructs were expressed separately as fusions to thioredoxin and protein extracts where analysed by SDS-PAGE (see. FIG. 13B) showing the calculated molecular weight for each TAL protein. Following co-transformation of the GFP reporter plasmid together with one of the AvrBs3 expression constructs into *E. coli* cells, TAL expression was induced by addition of arabinose. Reporter strains expressing AvrBs3 constructs showed significantly decreased fluorescence relative to control strains not induced with arabinose (FIG. 13C). These results demonstrate that TAL effectors are capable of repressing reporter gene activity in a non-natural bacterial host (*E. coli*).

Example 5: A TAL Genetic Circuit Developed for Microalgae

To test TAL function in microalgae, a TAL genetic circuit for microalgae was constructed by replacing the activation domain of Hsp70A with 3×AvrBs3 TAL binding site upstream of an RbcS2 minimal plant promoter that drives expression of a luciferase reporter gene at very low activity. Meanwhile, an AvrBs3 TAL effector was fused in frame to the N-terminus of a hygromycin resistance gene under control of a constitutive pB tublin promoter (see FIG. 14). As positive control the genetic circuit was expressed under control of a strong chimeric Hsp70A-RbcS2 promoter demonstrated to work well in algae. The Hsp70A promoter serves as a transcriptional activator when placed upstream of the RbcS2 promoter enhancing its efficiency. A circuit with a chimeric 3×AvrBs-RbcS2 promoter but without TAL effector was used as a negative control. One microgram of each construct (either circular or linearized DNA) was transformed into *Chlamydomonas* ($1×10^8$ cells) using electroporation followed by selection on TAP agar plates containing 10 ug/ml Hygromycin B. The selected colonies were assayed for Luciferase expression (A) and TAL expression by Western blot analysis (B). For this purpose the colonies were inoculated in 1 ml of TAP medium containing 10 μg/ml Hygromycin and incubated at Algal chamber for 4 days and then transferred to 9 ml TAP medium containing 10 μg/ml Hygromycin. The 10 ml cultures were grown for 3 days and then harvested by centrifugation. Cells were lysed in 300 µl of lysis buffer and cell lysate was obtained by centrifugation. The lysate was assayed for Luciferase activity using coelenterazine as substrate. 30 µl of the supernatants were mixed with SDS sample buffer containing 50 mM DTT. Upon heating at 95° C. for 5 minutes, the samples were loaded onto a NuPAGE gel. After electrophoresis, the proteins were transferred to a PVDF membrane using iBlot. The membrane was blocked for 1 hour and then incubated for 1 hour with primary mouse anti-His tag antibody at a final concentration of 0.2 µg/mL, followed by incubation for 1 hour with secondary goat anti-mouse HRP conjugate antibody at a 1:2000 dilution. The membrane was developed by ECL Chemiluminescent Substrate.

Example 6: TAL-Mediated Activation and Repression of Genes in Human Cells

Figure 15A:
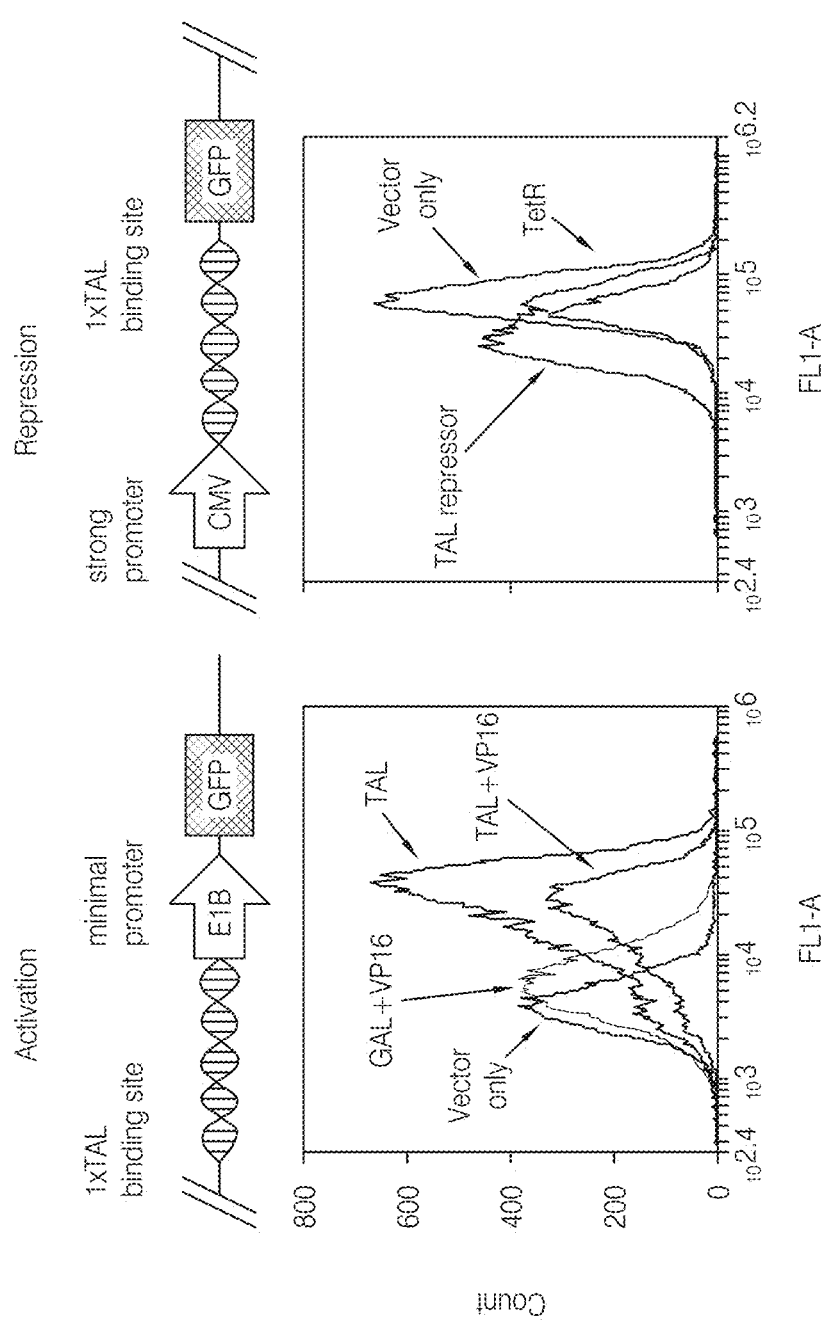
FIG. 15A shows FACS analyses of cells stably transfected with green fluorescent protein (GFP) reporter constructs. Two cell lines with stably integrated single copies of TAL response cassettes, wherein GFP reporter expression is either driven by an adenovirus E1b minimal promoter or a CMV promoter. The indicated plasmids were co-transfected with a red fluorescent protein (RFP) expression plasmid as transfection control into the TAL responsive cell lines. RFP positive cells were gated and analyzed by flow cytometry. Reporter gene expression was activated by TAL effectors and TAL-VP16 fusions but not by empty vector or an irrelevant activator (GAL-VP16) (left). Conversely, GFP protein expression was repressed by a TAL-KRAB repressor but not by vector control and an irrelevant Tet repressor (TetR) in the CMV-GFP reporter cell line (right).
Figure 15B:
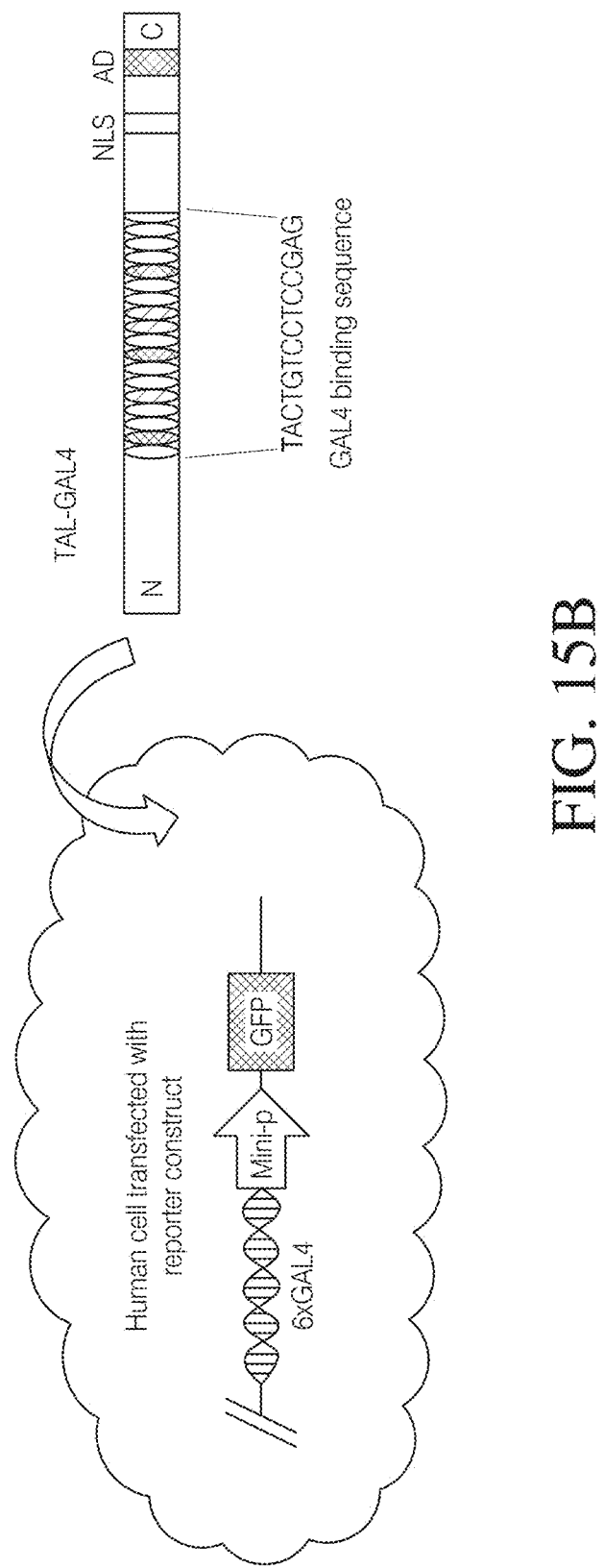
FIG. 15B illustrates how synthetic TAL effectors activate reporter gene expression. The repeat domain of wild-type TAL effector AvrBS3 was replaced with repeats designed to target the 13 base pairs of GAL4 DNA binding sequence. A Gal4 responsive reporter construct, which has 6 copies of GAL4 DNA binding sequences upstream and an adenovirus E1b minimal promoter, was used to demonstrate predicted binding of an engineered TAL effector to its co-responding DNA binding sequence and subsequent activation of gene expression.
Figure 15C:
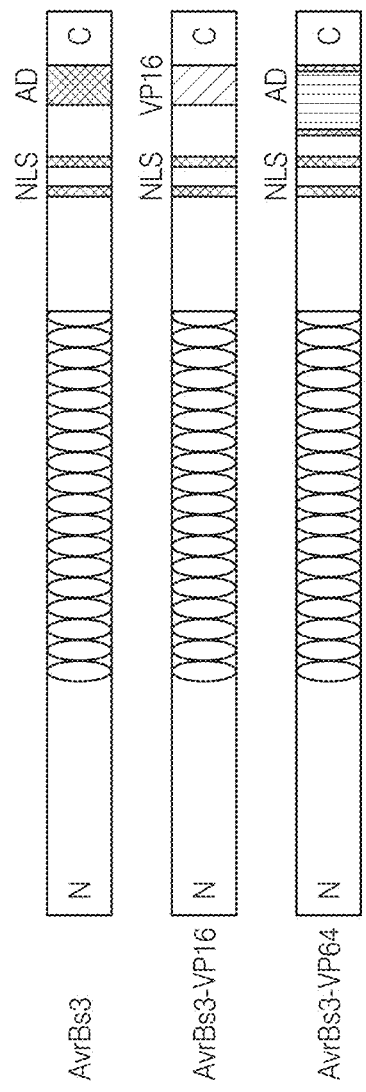
FIG. 15C shows an example of TAL-mediated activation in a dual luciferase assay. The endogenous NLS and activation domain of TAL effectors were replaced with NLS and VP16 or VP64 activation domains to create fusion activators TAL-VP16 and TAL-VP64. The reporter construct expresses luciferase from a CMV mini promoter harboring three copies of corresponding TAL DNA binding sequences. 293FT cells were co-transfected with indicated plasmids along with a *Renilla* luciferase expression plasmid.
Figure 15D:
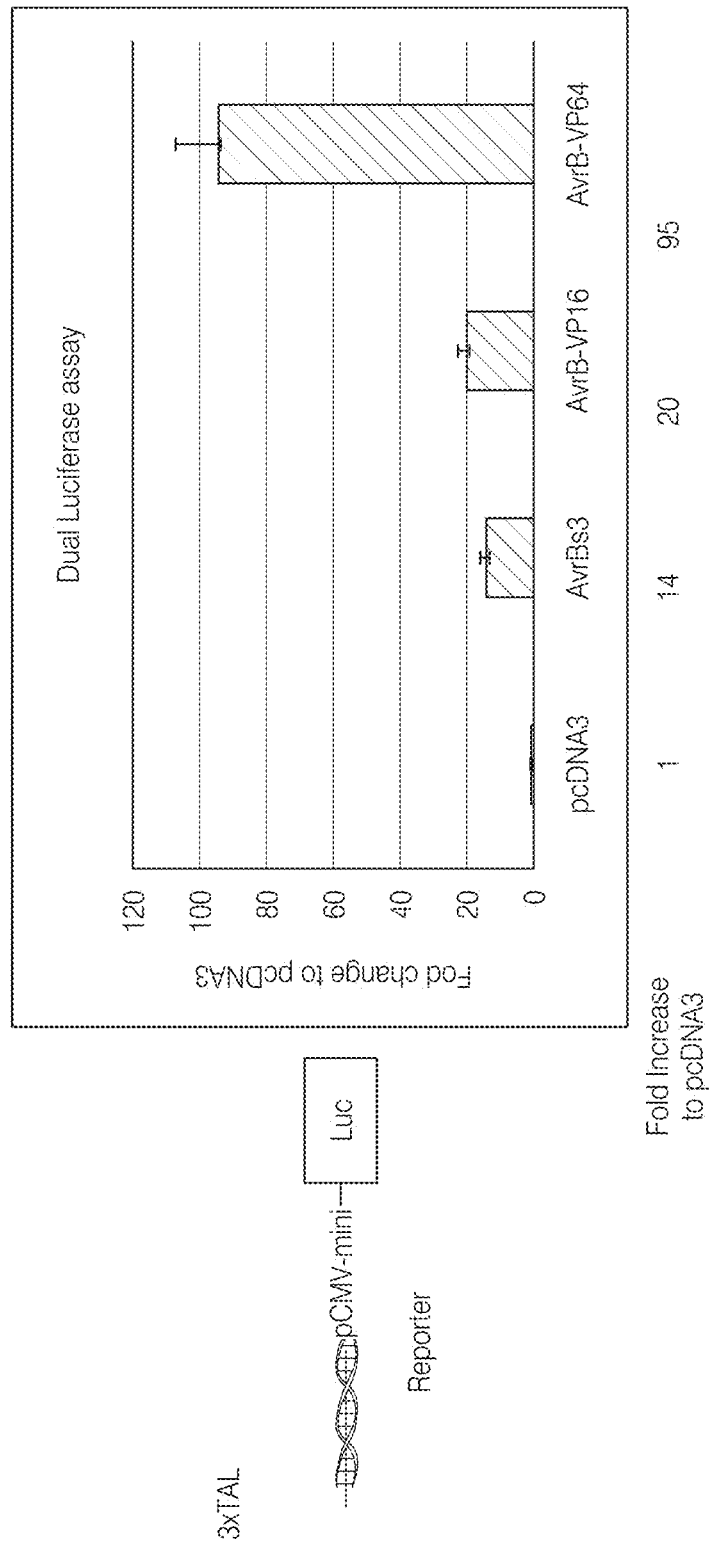
FIG. 15D shows a dual luciferase assay that was performed 48 h post-transfection.
Figure 16A:
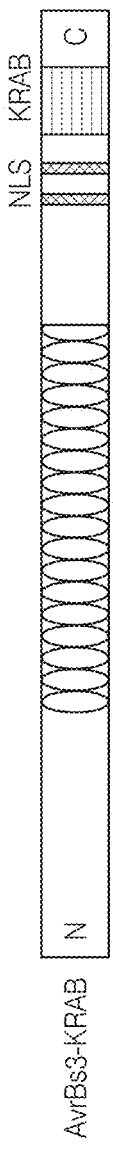
FIGS. 16A to 16C show TAL-mediated repression in a reporter assay.
Figure 16B:
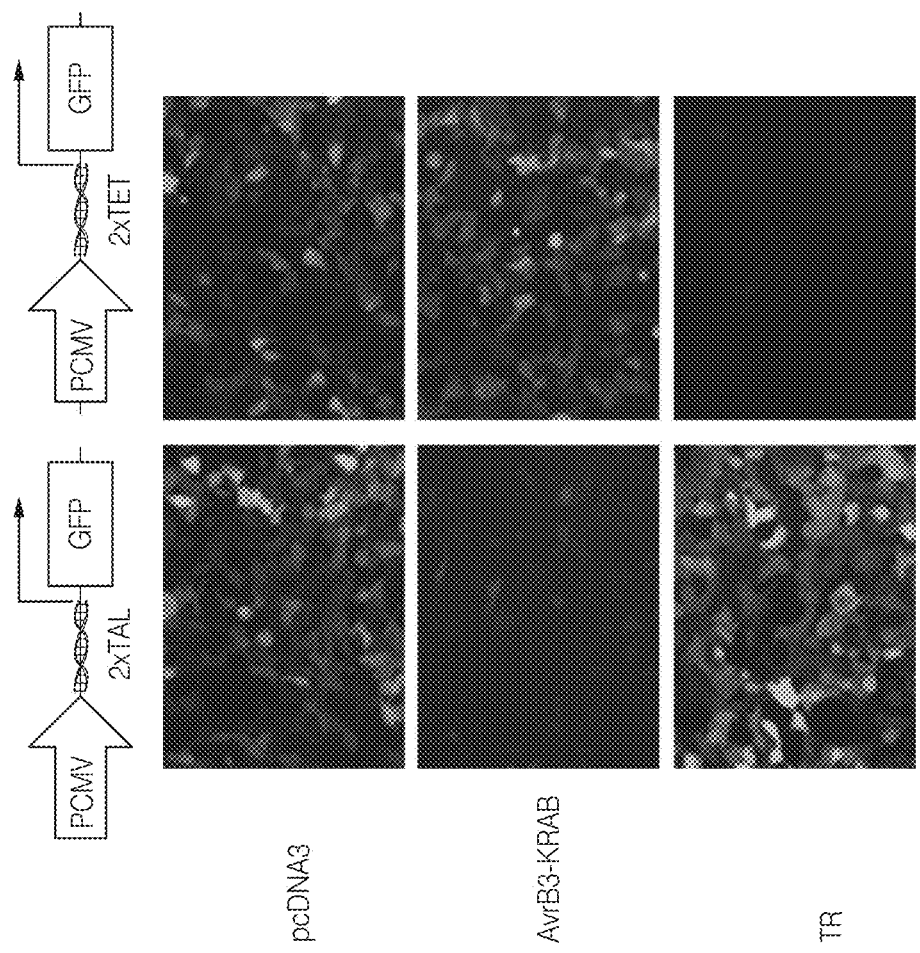
Figure 16C:
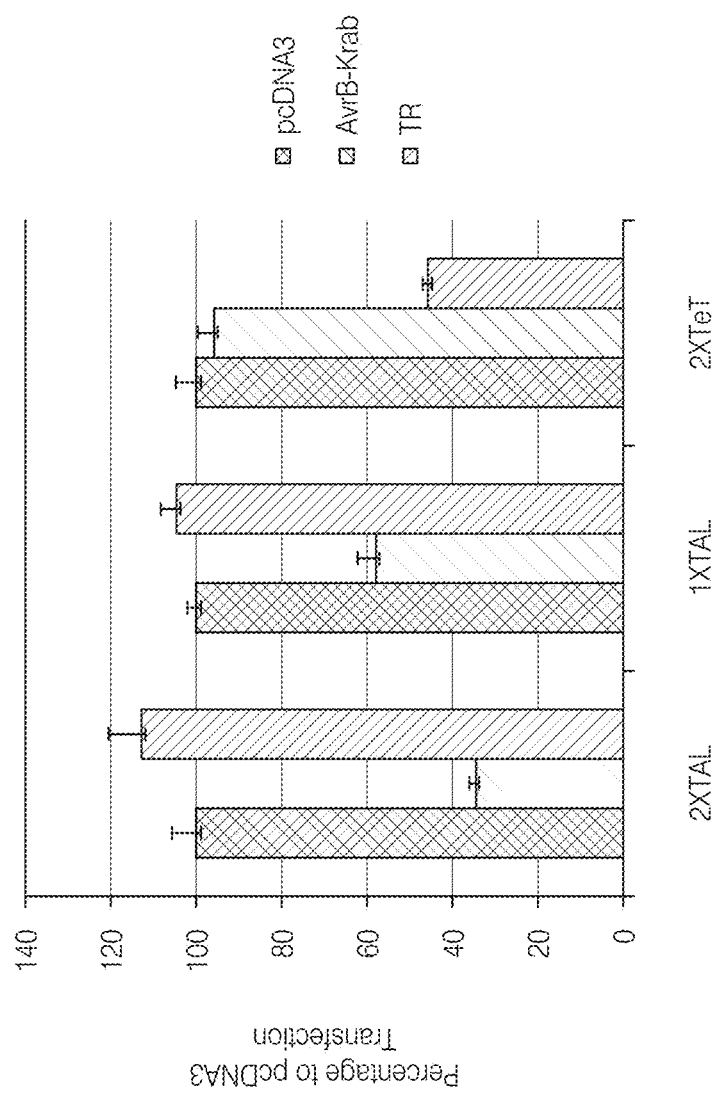
Figure 16H:
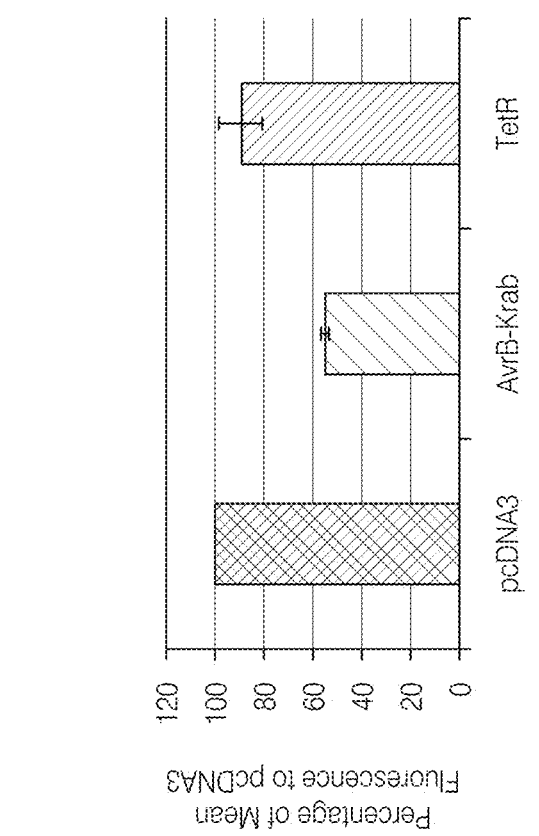
Figure 16G:
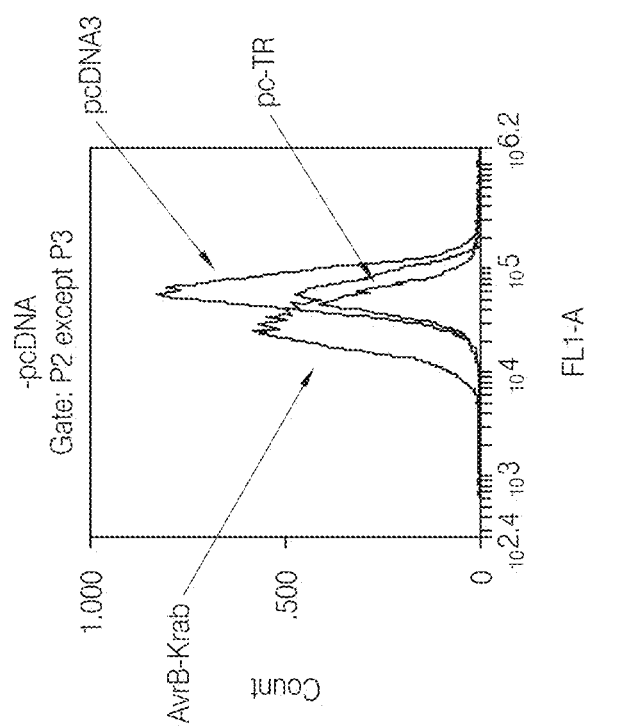
Figures 16I, 16J:
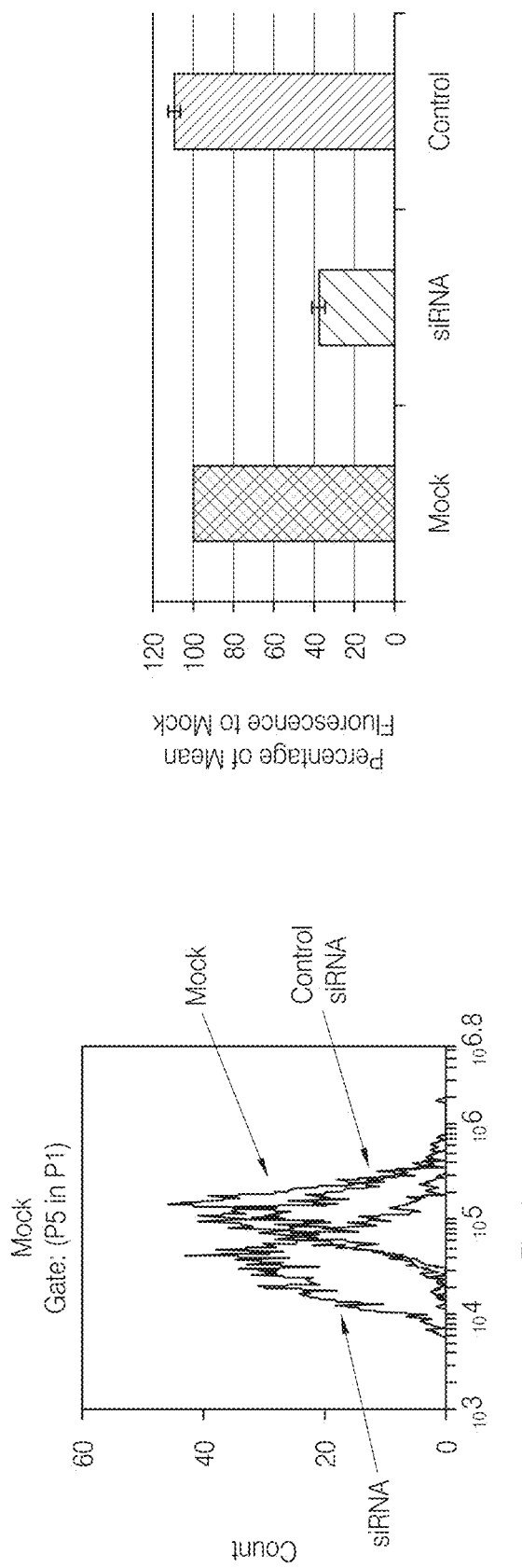
Figure 17A:
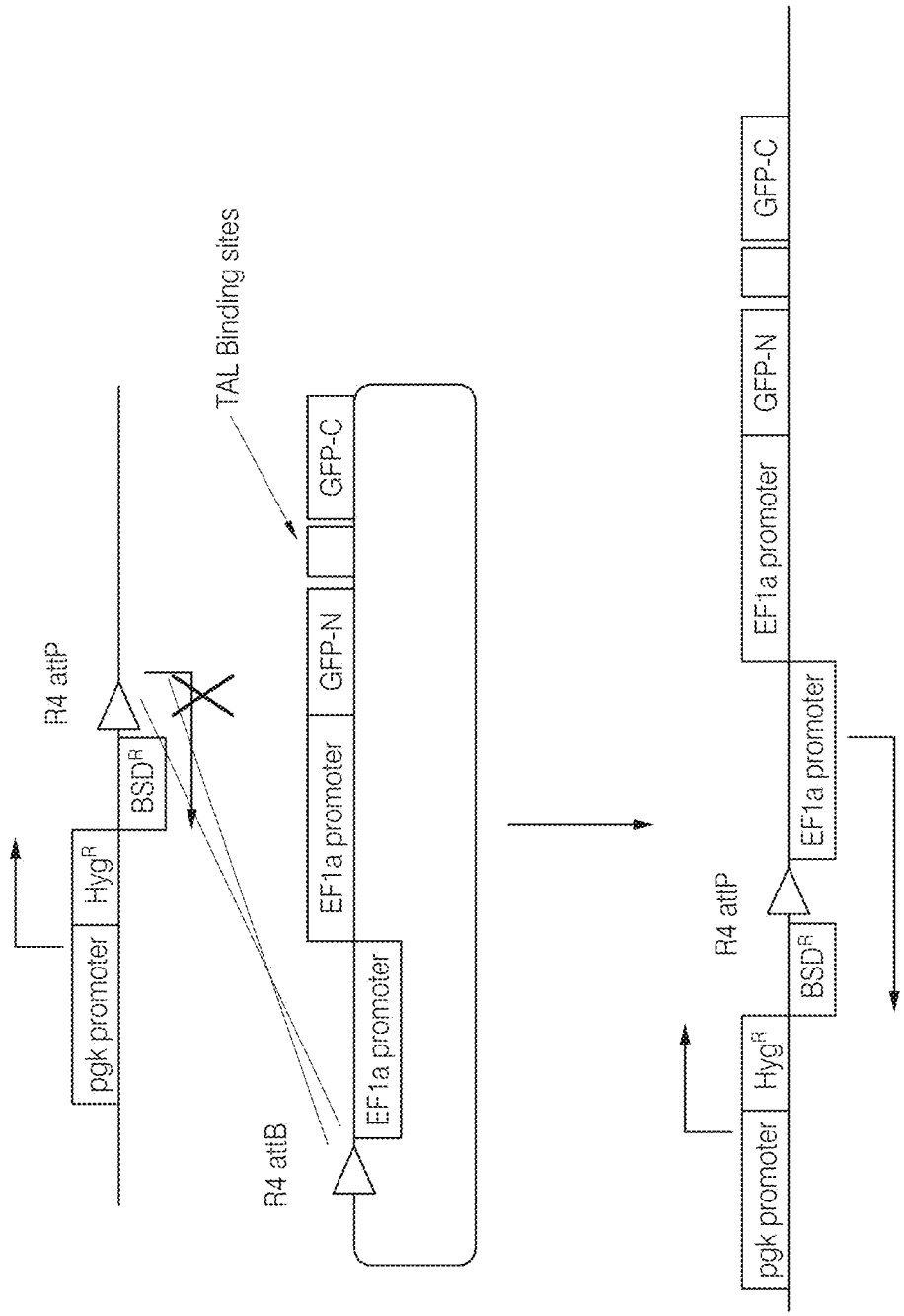
FIGS. 17A and 17B show a TAL effector GFP genomic cleavage assay designed to quantitatively assess the ability of a custom TAL nuclease pair to cleave a specific genomic DNA target. Spacers of different lengths were inserted into a GFP reporter gene to shift the open reading frame such that a non-functional protein is expressed. Reporter constructs were stably integrated in 293FT cells. The cells were transfected with TAL ArtX1-FokKK and ArtX2-FokEL nuclease pairs with TAL repeats directed to specific target sites flanking the spacers in the GFP open reading frame. Following nuclease cleavage within the spacer region, the DNA break is repaired by endogenous non-homologous end joining pathway leading to partial restoration of GFP expression and a respective shift in green cells.
Figure 17B:
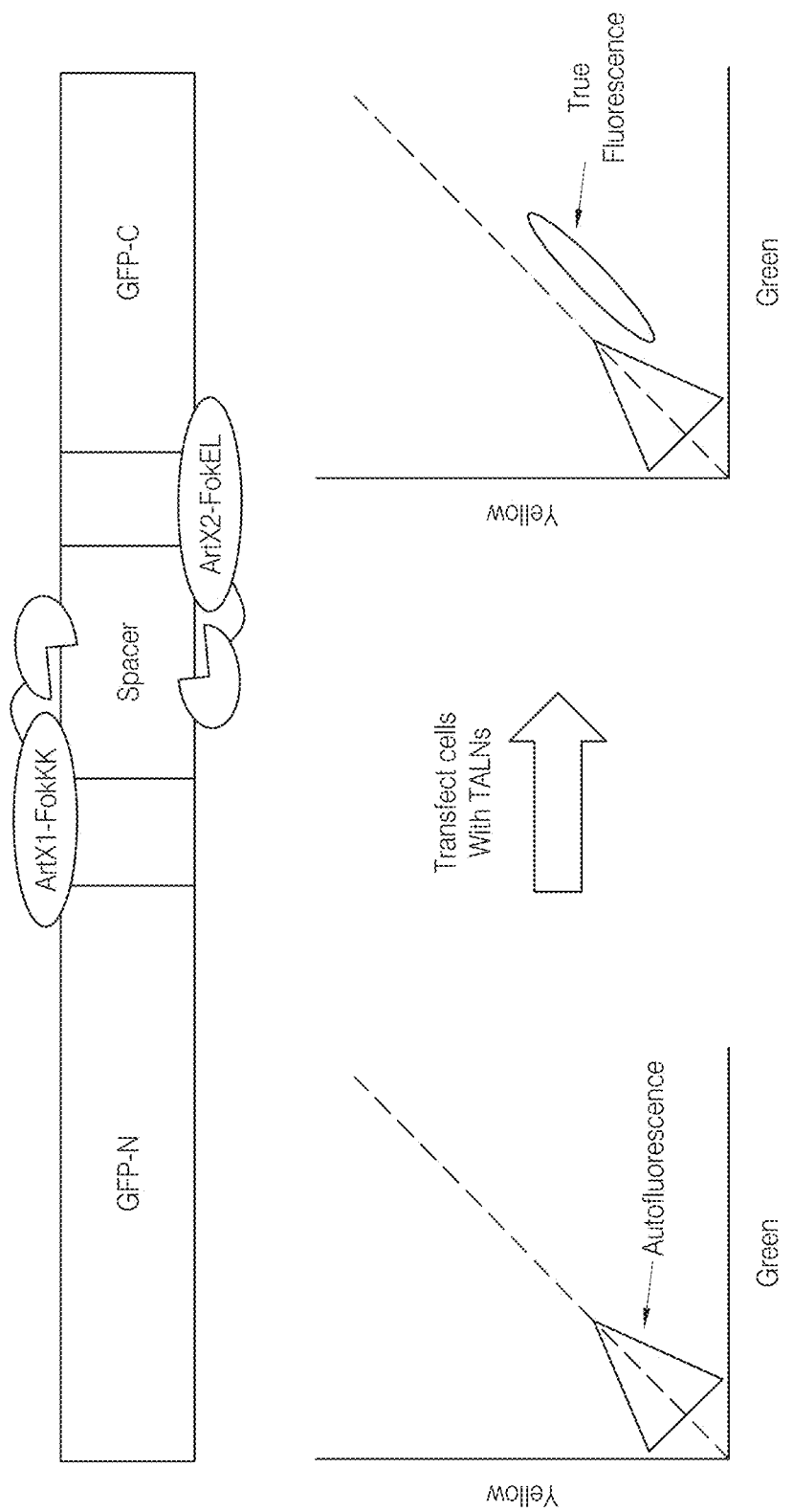

To analyze TAL-mediated activation or repression activities in human cells, two FLP-IN™ stable 293 cell lines in which a single copy TAL response cassette was integrated into the genome were established, one with a GFP reporter driven by an E1B mini promoter, another by a full-length CMV promoter (FIG. 16B). To demonstrate TAL-mediated activation, the TAL responsive cell line carrying the E1b-controlled gfp gene were co-transfected with a red fluorescence protein (RFP) expression plasmid as transfection control and one of the following vectors: pcDNA3.3-AvrBs3, expressing a wild-type TAL effector (TAL), pcDNA3.3-AvrBs3-VP16, expressing a TAL fused to a VP16 activation domain (TAL+VP16), pcDNA3.3-GAL-VP16, expressing a GAL4 binding domain fused to a VP16 domain (GAL+VP16) or an empty vector (Vector only). Cells were harvested after 48 hours post-transfection and RFP positive cells were gated and analyzed by flow cytometry. As shown in FIG. 15A (left panel) wild-type TAL effectors and TAL-VP16 fusions efficiently activated reporter gene expression whereas vector only or an irrelevant activator (GAL-VP16) had no effect.

To further demonstrate TAL-mediated repression, the TAL responsive cell line carrying the CMV-controlled GFO gene were co-transfected with a red fluorescence protein (RFP) expression plasmid as transfection control and one of the following vectors: a TAL fused to a KRAB repressor domain (TAL repressor), a Tet repressor (TetR) and an empty vector (FIG. 15A, right panel). Transfected cells were harvested and subject to FACS analysis. GFP protein expression was significantly reduced in the presence of the TAL-KRAB but was not impacted by empty vector or an irrelevant Tet repressor. In sum, these data demonstrate that TAL effectors can be specifically directed to target sites in the mammalian genome where they are capable of activate or repress gene activity.

Example 7: Transient TAL-Mediated Repression in Mammalian Cells

To evaluate the activity of an engineered TAL repressor in human cells, a TAL repressor was constructed by replacing the C-terminal activation domain of AvrBs3 with a KRAB domain, the repression domain of a zinc finger protein. A reporter construct harboring a Tet-responsive binding site was used as negative control to demonstrate TAL specificity. The reporter constructs express GFP or LacZ from a full-length CMV promoter harboring a TAL DNA binding sequence or a Tet binding sequence as a control. 293FT cells were co-transfected with the AvrBs3-KRAB construct or a Tet construct or empty vector and one of the GFP expression constructs harboring either the TAL binding or Tet binding site. Microscopic images of cells were taken 48 h post-transfection for GFP reporter expression (FIG. 16B, left panel). AvrB3-KRAB repressed its corresponding reporter gene expression but had no effect on Tet responsive reporter gene expression, suggesting that the repression of AvrBs3-KRAB is sequence specific.

293 FT cells were transfected with the indicated combination of plasmids in 96-well plates. Cells were lysed using 100 µl luciferase lysis buffer 72 hours post-transfection and the β-galactosidase activity was determined using FluoReporter LacZ/Galactosidase Quantitation kit (F-2905, Life Technologies). Briefly, 2-10 µl of cell lysate per well was added to 100 µl of reaction buffer (0.1 M NaPO4, pH7.3, 1 mM MgCL2, 45 mM β-mercaptoethanol, 1.1 mM CUG substrate). The reaction was incubated for 30 min followed by adding 50 µl of stop solution (0.2M $Na_2CO_3$) to each well. β-galactosidase activity was measured at the excitation 390 nM, emission 460 nm on Spectramx (FIG. 16B, right panel). The figure is graphed as the percentage of the signal to the pcDNA3 control transfection. Co-expression of AvrB3-KRAB specifically repressed the reporter gene expression about 70% with two copies of TAL DNA binding sites and around 40% repression with 1 copy of DNA binding sites, which is comparable with effect of Tet repressor.

Example 8: Assay for Demonstration of Cleavage of Genomic Target DNA by TAL Nucleases To quantitatively assess the ability of a custom TAL nuclease pair to cleave a specific genomic DNA target a GFP-based cleavage assay was developed. For this purpose spacers of different lengths (10, 15, 20 nucleotides) were inserted into a region of the GFP open reading frame that is known to result in a protein that is still partially functional (Guo et al., *J. Mol. Biol.*, 400:96-107 (2010). However, these spacers were designed to shift the open reading frame such that a non-functional protein is expressed. Three such constructs were generated and were each individually incorporated into a single defined location in 293FT cells using the Jump In™ targeted integration system (FIG. 17A) to make a panel of stable cell lines bearing a single defective GFP gene. These cell lines were created by inserting a mutated EmGFP gene with TAL binding site cassette placed in the loop region as described in Guo, et al. The GFP gene is expressed under the control of hte EF1alpha promoter in the pJTI-R4-Dest vector. This vector was then targeted to the Jump-In locus in HEK293 JI cells by cotransfection with a vector expressing R4 integrase, pJTI-R4-Int using Lipofectamin 2000. Targeted cells were then selected in the presence of neomycin. A TAL nuclease pair was then constructed (ArtXA-FokKK and ArtXB-FokEL) wherein the TAL repeats were designed to bind specific target sites ((T) CTTCT GCACC GGTAT GCG (SEQ ID NO: 113) and (T) ATTCT GGGAC GTTGT ACG (SEQ ID NO: 114), respectively) flanking the spacers in the mutated EmGFP open reading frame. The TAL nuclease constructs were LF2K-transfected into the 293FT cells containing the stably integrated GFP reporters. Binding of the TAL repeat domain was predicted to result in cleavage by the nuclease domain within the spacer region (see FIG. 17B, upper panel). Upon cleavage at the genomic site, the DNA break would be repaired by endogenous non-homologous end joining pathway which introduces or removes a small number of nucleotides at the repair site. Therefore it was expected that the correct translation frame would be restored for GFP expression in about one third of the cases. The partial re-establishment of the GFP ORF resulted in dim green cells that could be distinguished from background fluorescence by flow cytometry analysis (see FIG. 17B, lower panel).

Example 9: Sequence Mapping of TALE Nuclease Mediated Genomic Lesions

Example 9a

To evaluate successful TAL nuclease-mediated cleavage of genomic target sequence the following assay was developed: Genomic DNA was isolated from TAL nuclease-treated and untreated cells (FIGS. 20A and B) and was cleaved using a cocktail of common cutters to create ~100 bp fragments (FIG. 20C). The resulting fragments of both samples are then mixed, melted and cross-hybridized yielding a mixture of correct and mismatched double stranded fragments (FIG. 20D). The fragments are then ligated with specific sequencing primers containing a very rare restriction site at its 5' end referred to a 'P1*' adapter (FIG. 20E). After clean up, the mismatch (indicating the lesion to be identified) is cleaved by treatment with a PM (Perkinsus) mismatch nuclease (FIG. 20E). However, as understood by the skilled in the art any other suitable MME nuclease could be used for this purpose, such as, e.g., Cel1 or Res1 nucleases. The cleavage which is limited to the mismatched fragments results in a population containing new non-adapted ends (FIG. 20F). The entire population of fragments is then adapted with a second sequencing primer which does not contain the rare site in primer 1 referred to as 'A' adapter (FIG. 20G). The entire population is then treated with the rare cutting enzyme to release primer 2 ligated to primer 1 (FIG. 20H). This leaves a population of fragments appended with primer 1 on each end (non-lesion) and fragments with primer 1 on one end and primer 2 ligated to the lesion site. This population is then subjected to sequencing using primer 2 to identify the genomic lesion sites.

Example 9b

In a second embodiment genomic lesions were detected according to the following protocol. To extract genomic DNA from TAL nuclease-treated and untreated Vero E6 cells, two samples of $1 \times 10^6$ cells each were pelleted at 270×g for 5 min. The supernatants were gently removed and cells were resuspended vigorously in 50 µl of PicoPuro solution (Life Technologies, Carlsbad). The reaction was then transferred to PCR-compatible tubes and extraction of genomic DNA was finished by incubating the sample in a PCR Cycler at 68° C. for 15 min and 95° C. for 8 min followed by final storage at 4° C. Both samples were then subjected to a PCR amplification step in the presence of a primer mix to amplify amplicons containing the predicted genomic lesion. For this purpose 2 µl of each template genomic DNA sample were mixed in a 50 µl reaction volume with 25 µl of 2× GOLD 360 PCR mix (Life Technologies) and 1 µL of a 10 µM primer mix (yielding 400 bp amplicons) and were amplified under the PCR conditions provided in TABLE 23 in the presence of the PHUSION® High Fidelity DNA Polymerase (New England Biolabs, Beverly, Mass.):

TABLE 23 amplicon PCR protocol 1

| Cycle | Number | Step | ° C. | Time |
|---|---|---|---|---|
| 1 | 1 | 1 | 95 | 10:00 |
| 2 | 30 | 1 | 95 | 00:30 |
|   |    | 2 | 55* | 00:30 |
|   |    | 3 | 72 | 01:00 |
| 3 | 1 | 1 | 72 | 07:00 |
| 4 | 1 | 1 | 4 | ∞ |

*annealing temperature depends on choice of primers

The PCR products were then purified on spin columns and the OD260 was measured for each sample. Five µl of the PCR products were then run on a 1.2% SDS electrophoresis gel to determine whether the PCR was successful and provided only a single (400 bp) amplicon band.

Two 10-µl cleavage reactions were prepared for each sample (one containing an enzyme mix and the other as negative control) each containing 1 µl of a 10× endonuclease reaction buffer (200 mM Tris pH 8.3, 5 mM NAD, 250 mM KCl, 100 mM $MgCl_2$, 0.1% Triton x-100) and 100 ng of PCR product added up to a final volume of 9 µl $H_2O$. The samples were then incubated at 98° C. for 2 minutes to quantitatively denature all double stranded DNA before samples were cooled to 4° C. for 5 minutes to allow random reassortment of the single strands which causes random reannealing of the amplicons thereby converting any mutations into mismatched duplex DNA. Reannealing was allowed to finalize at 37° C. for 5 minutes and samples were cooled down to 4° C. and stored on ice.

For cleavage of mismatch positions in the reannealed amplicons test samples (but not control samples) were treated with an enzyme mix containing T7 endonuclease I and Taq ligase in an enzyme dilution buffer. To obtain 100 µl enzyme composition 10 µl of T7 endonuclease I (10 U/µl) and 10 µl of Taq ligase (40 U/µl) (both New England Biolabs, Beverly, Mass.) were mixed with 80 µl enzyme dilution buffer (10 mM Tris pH 7.4 at 4° C., 50 mM KCl, 0.1 mM EDTA, 50% glycerol, 200 ug BSA/ml, 0.15% Triton X-100) at 4° C. for 2 hours and subsequently stored at −20° C.

One µl of this enzyme composition was then added to the test samples and the reactions were incubated at 37° C. for 1 hour in a PCR cycler and then immediately moved to 4° C. before they were loaded on a 2% EX gel (Life Technologies). The gel was run for approximately 10 minutes before bands were measured by densitometry and analysed using a gel analysis software (IMAGEQUANT™ 5.1, GE Healthcare). To determine mismatch-mediated endonuclease cleavage in the test samples, intensities of cleaved bands were determined and divided by total intensity of all measured bands. Control reactions without enzyme mix served to determine background intensity.

Clause 1. A library of TAL nucleic acid binding cassettes for assembly of a TAL effector sequence, wherein the library of cassettes contains at least four different categories of cassettes encoding TAL repeats with all cassettes of one category binding to at least one of the bases adenine, guanine, thymidine, and cytosine in a nucleic acid target sequence, wherein each cassette is allocated to one or more distinct positions in the TAL effector sequence and wherein the library of cassettes contains at least one first cassette per category wherein the nucleotide composition of said first cassette differs from the nucleotide compositions of all other cassettes of the same category and wherein said first cassette is allocated to only one distinct position in the series of cassettes in the TAL effector sequence.

Clause 2. A library according to clause 1, wherein the library of cassettes contains at least one second cassette per category wherein the nucleotide composition of said second cassette differs from the nucleotide composition of the first cassette and from the nucleotide composition of all other cassettes of the same category and wherein said second cassette is allocated to only one distinct position in the series of cassettes in the TAL effector sequence which is different from the position of the first cassette.

Clause 3. A library according to clause 1 or 2 wherein the one or more distinct positions within the TAL effector sequence are determined by complementary terminal overhangs between cassettes.

Clause 4. A library according to any one of the preceding clauses wherein the TAL effector sequence comprises between 6 and 25 cassette positions.

Clause 5. A library according to any one of the preceding clauses wherein the TAL effector sequence comprises at least 9 cassette positions.

Clause 6. A library according to any one of the preceding clauses wherein the TAL effector sequence comprises 17.5 or 18 or 23.5 or 24 cassette positions.

Clause 7. A library according to any one of clauses 1 to 3 wherein the TAL effector sequence comprises more than 25 cassette positions.

Clause 8. A library according to any one of the preceding clauses wherein the nucleotide composition of the at least one first cassette and/or the at least one second cassette differs within a region that is homologous (i.e. contains an identical nucleotide composition) in all other cassettes of the library. Thus, said homologous region is located outside the terminal ends of the cassettes providing the compatible overhangs.

Clause 9. A library according to clause 8 wherein said homologous region has a length of at least 10, at least 15, or between 18 and 30 nucleotides.

Clause 10. A library according to clause 8 or 9 wherein the nucleotide composition of the at least one first cassette and/or the at least one second cassette differs within said homologous region by at least 3, preferably at least 4 nucleotides.

Clause 11. A library according to clause 10 wherein the at least 3, preferably at least 4 nucleotides are positioned near the 5'-end or 3'-end of said homologous region.

Clause 12. A library according to any one of the preceding clauses wherein said one distinct position of said first cassette is a position in the center or close to the center of the total amount of cassette positions (e.g. in a TAL effector sequence with 24 cassette positions a position in the center or close to the center may include one of positions 7 to 18; or in a TAL effector sequence with 18 positions a position in the center or close to the center may include one of positions 4 to 15).

Clause 13. A TAL effector sequence containing a series of TAL nucleic acid binding cassettes selected from one or more of at least four different categories of cassettes encoding TAL repeats with all cassettes of one category binding to at least one of the bases adenine, guanine, thymidine, and cytosine in a nucleic acid target sequence, wherein the nucleotide composition of at least one first cassette in the series of cassettes differs from the nucleotide composition of all other cassettes of the same category.

Clause 14. A TAL effector sequence according to clause 13 wherein the nucleotide composition of the at least one first cassette differs within a region of the cassette that is homologous (i.e., contains an identical nucleotide composition) in all other cassettes of said TAL effector sequence.

Clause 15. A TAL effector sequence according to clause 14 wherein said homologous region has a length of at least 10, at least 15, or between 18 and 30 nucleotides.

Clause 16. A TAL effector sequence according to clause 14 or 15, wherein the nucleotide composition of the at least one first cassette and/or the at least one second cassette differs within said homologous region by at least 3, preferably at least 4 nucleotides.

Clause 17. A TAL effector sequence according to any one of clauses 13 to 16 wherein the at least one first cassette is located in the center or close to the center of the series of cassettes. (e.g. in a TAL effector sequence with 24 cassettes the at least one first cassette may be located at one of positions 7 to 18; or in a TAL effector sequence with 18 positions the at least one first cassette may be located at one of positions 4 to 15).

Clause 18. A TAL effector sequence according to any one of clauses 13 to 16 wherein the TAL effector sequence comprises between 6 and 25 cassettes.

Clause 19. A TAL effector sequence according to any one of clauses 13 to 16 wherein the TAL effector sequence comprises at least 9 cassettes.

Clause 20. A TAL effector sequence according to any one of clauses 13 to 16 wherein the TAL effector sequence comprises more than 25 cassettes.

Clause 21. A TAL effector sequence according to any one of clauses 13 to 16 wherein the TAL effector sequence comprises 17.5 or 18 cassettes and wherein the at least one first cassette is located at one of positions 4 to 15.

Clause 22. A TAL effector sequence according to any one of clauses 13 to 16 wherein the TAL effector sequence comprises 23.5 or 24 cassettes and wherein the at least one first cassette is located at any one of positions 7 to 18.

Clause 23. A TAL effector fusion containing a TAL effector sequence according to any one of clauses 13 to 22.

Clause 24. A vector containing a TAL effector sequence according to clauses 13 to 22 or a TAL effector fusion according to clause 23.

Clause 24. A cell containing TAL effector sequence according to clauses 13 to 22 or a TAL effector fusion according to clause 23 or a vector according to clause 22.

Clause 25. A method of sequencing a TAL effector sequence according to any one of clauses 13 to 22 wherein said method comprises using at least one sequencing primer specifically binding to the at least one first cassette within the TAL effector sequence.

Clause 26. A method according to clause 25 wherein said at least one sequencing primer contains a 3'-end specifically binding to the at least one first cassette.

Clause 27. A method according to clause 26 wherein the 3'-end of the sequencing primer contains at at least 3, preferably 4 nucleotide positions determining the binding specificity for the at least one first cassette.

Clause 28. A method according to clause 27 wherein the 5' end of the at least one sequencing primer binds within a region that is homologous (i.e. contains an identical nucleotide composition) in all cassettes of the TAL effector sequence.

Another aspect of the invention is further described by the following set of clauses.

Clause 1. A method of detecting and identifying one or more genomic locus modifications comprising the steps of
a) isolating genomic DNA from (i) a cell treated with a TAL effector nuclease or a pair of TAL effector nucleases and (ii) an untreated cell, b) cleaving the isolated genomic DNA obtained from both samples with a mixture of restriction enzymes,
c) mixing the samples containing cleaved DNA fragments,
d) subjecting the double stranded DNA fragments to a melting an re-hybridizing procedure,
e) ligating the ends of the re-hybridized DNA fragments with a first double-stranded DNA adapter containing at least one restrictions enzyme cleavage site at its 5'-end,
f) optionally purifying the adapter containing DNA fragments,
g) treating the DNA fragments containing the first adapter with a mismatch cleaving enzyme thereby obtaining a pool of cleaved and uncleaved DNA fragments,
h) ligating the ends of the cleaved and uncleaved DNA fragments with a second double-stranded DNA adapter lacking the restriction enzyme cleavage site of the first adapter,
i) treating the population of DNA fragments containing the second adapter with a restriction enzyme specifically cleaving the at least one restriction enzyme cleavage site at the 5'-end of the first adapter resulting in the release of the second adapter,
j) optionally separating the population of DNA fragments containing only the first adapter from the population of DNA fragments containing a first and a second adapter,
k) subjecting at least the population of DNA fragments containing a first and a second adapter to a sequencing reaction using the second adapter as primer binding site, and
l) identifying the one or more genomic locus modifications.

Clause 2. A method according to clause 1 wherein the mixture of restriction enzymes in step b) contains one or more restriction enzymes having a four or six base pair recognition sequence.

Clause 3. A method according to clause 1 or 2, wherein the mismatch cleaving enzyme of step g) is selected from the group of *Perkinsus marinus* nuclease PA3, Cel1 or Res1.

Clause 4. A method according to any one of the preceding clauses wherein the restriction enzyme cleaving the restriction enzyme cleavage site in step i) has a seven or eight base pair recognition sequence.

Clause 5. A method according to any one of the preceding clauses wherein the sequencing reaction in step k) further comprises binding the population of DNA fragments containing a first and a second adapter to beads using the first adapter as an anchor.

Clause 6. A method according to any one of the preceding clauses wherein step 1) comprises mapping the sequences obtained in step k) against the genome of the cell.

Clause 7. A method according to any one of the preceding clauses wherein step k) comprises personal genome machine (PGM) sequencing.

Another aspect of the invention is further described by the following set of clauses.

Clause 1. A linear nucleic acid molecule comprising:
(a) a region encoding an N terminal portion of a TAL effector,
(b) a region encoding a C terminal portion of a TAL effector,
(c) at least one recombination site, and
(d) at least one covalently bound topoisomerase,
wherein the topoisomerase is located at one of the termini of the linear nucleic acid molecule and is within 100 nucleotides of the at least one recombination site, and wherein, when the nucleic acid molecule is circularized and contains a TAL repeat located between the termini of the nucleic acid molecule, the circularized nucleic acid molecule encode a TAL effector which is capable binding to a specified nucleic acid sequence.

Clause 2. The linear nucleic acid molecule according to clause 1, wherein the linear nucleic acid molecule contains an origin of replication.

Clause 3. The linear nucleic acid molecule according to any one of the preceding clauses, wherein the at least one recombination site is selected from the group consisting of:
(a) an att site,
(b) a lox site, and
(c) a frt site.

Clause 4. The linear nucleic acid molecule according to any one of the preceding clauses, wherein the at least one covalently bound topoisomerase is a Type IA, Type IB, Type IIA, or Type II topoisomerase.

Clause 5. The linear nucleic acid molecule according to any one of the preceding clauses, wherein the at least one covalently bound topoisomerase is a Vaccinia virus topoisomerase.

Another aspect of the invention is further described by the following set of clauses.

Clause 1. A method for preparing a TAL effector library, the method comprising:
(a) connecting a population of TAL nucleic acid binding cassettes that individually encode adenine, guanine, thymidine, or cytosine base binders, when the base is present in a nucleic acid molecule, and
(b) introducing the connected TAL nucleic acid binding cassettes generated in (a) into a vector to generate a TAL effector library, wherein the library encodes TAL effectors which bind to different nucleotide sequences.

Clause 2. The method according to clause 1, wherein TAL nucleic acid binding cassettes that encode adenine, guanine, thymidine, and cytosine binders are not all present in equimolar amounts.

Clause 3. The method according to any one of the preceding clauses, wherein TAL nucleic acid binding cassettes that encode adenine and thymine binders are present in equimolar amounts and represent from about 51% to about 75% of the total TAL nucleic acid binding cassettes present.

Clause 4. The method according to any one of the preceding clauses, wherein the TAL effector library encodes TAL effector fusions.

Clause 5. The method according to any one of the preceding clauses, wherein the TAL effector fusion have transcriptional activation activity.

Clause 6. The method according to any one of the preceding clauses, wherein the TAL effector fusion inhibits transcription.

Clause 7. The method according to any one of the preceding clauses, wherein the vector is a viral vector.

Clause 8. The method according to any one of the preceding clauses, wherein the vector contains at least one recombination site.

Clause 9. The method according to any one of the preceding clauses, wherein the at least one recombination site in an att site.

Clause 10. A TAL effector library prepared by the method according to any one of the preceding clauses.

Another aspect of the invention is further described by the following set of clauses.

Clause 1. A method for identifying TAL effectors that bind to specified nucleotide sequences, the method comprising:

(a) connecting a population TAL nucleic acid binding cassettes which individually encode TAL subunits that bind to one of the bases adenine, guanine, thymidine, and cytosine, when the base is present in a nucleic acid molecule, (b) introducing the connected TAL nucleic acid binding cassettes generated in (a) into a vector to generate a TAL effector library, wherein the library contains TAL effectors which bind to different nucleotide sequences, (c) introducing the TAL effector library into a cell under conditions which allow for the expression of TAL effectors, and (d) screening the cells generated in (c) to identify cells in which at least one cellular parameter is altered by expression of a TAL effector.

Clause 2. The method according to clause 1, wherein the cellular parameter is TAL effector induced transcriptional activation of a non-TAL effector gene.

Clause 3. The method according to any one of the preceding clauses, wherein the cell contains nucleic acid comprising a promoter operably linked to a reporter and wherein the cellular parameter is transcriptional activation of the reporter.

Clause 4. The method according to any one of the preceding clauses, wherein the reporter is green fluorescent protein.

Clause 5. The method according to any one of the preceding clauses, wherein a TAL effector library member is isolated from a cell in which at least one cellular parameter is altered by expression of a TAL effector.

Clause 6. A composition comprising a nucleic acid molecule encoding the TAL effector isolated by the method according to any one of the preceding clauses.

Another aspect of the invention is further described by the following set of clauses.

Clause 1. A non-naturally occurring protein comprising:

(a) an amine terminal region of between 25 and 500 amino acids, (b) a carboxyl terminal region of between 25 and 500 amino acids, and (c) a central region containing five or more amino acid segments which confer upon the non-naturally occurring protein sequence specific nucleic acid binding activity, wherein each of the individual amino acid segments in (c) are between 30 and 38 amino acid in length, and wherein at least one of the amino acid segments is at least 80% identical to one or more of the following amino acid sequences:

```
(1)
                                     (SEQ ID NO: 37)
FSQADIVKIAGN, (2)
                                     (SEQ ID NO: 38)
GGAQALQAVLDLEP, (3)
                                     (SEQ ID NO: 39)
GGAQALQAVLDLEPALRERG, (4)
                                     (SEQ ID NO: 40)
FRTEDIVQMVS, (5)
                                     (SEQ ID NO: 41)
GGSKNLAAVQA,
```

```
-continued
(6)
                                     (SEQ ID NO: 42)
GGSKNLEAVQA, (7)
                                     (SEQ ID NO: 43)
LEPKDIVSIAS, (8)
                                     (SEQ ID NO: 44)
GATQAITTLLNKW, (9)
                                     (SEQ ID NO: 45)
GATQAITTLLNKWDXLRAKG,
and

(10)
                                     (SEQ ID NO: 46)
GATQAITTLLNKWGXLRAKG;
``` wherein X is one of the following amino acids: aspartic acid, serine, alanine, or glutamic acid.

Clause 2. The non-naturally occurring protein according to clause 1, wherein none of the amino acid segments is identical to an amino acid sequence of a TAL protein which naturally occurs in a bacterium of the genera *Xanthamonas* or *Ralstonia*.

Clause 3. The non-naturally occurring protein according to any one of the preceding clauses, wherein at least one of the amino acid segments is not identical to an amino acid sequence shown in FIG. 30.

Clause 4. The non-naturally occurring protein according to any one of the preceding clauses, wherein at least one of the amino acid segments is not identical to one of the first eighteen amino acids sequence shown in FIG. 30.

Clause 5. The non-naturally occurring protein according to any one of the preceding clauses, wherein the protein is a fusion protein.

Clause 6. The non-naturally occurring fusion protein according to any one of the preceding clauses, wherein the fusion protein comprises a sequence specific nucleic acid binding activity and at least a second activity other than sequence specific nucleic acid binding activity.

Clause 7. A nucleic acid molecule comprising a sequence encoding the non-naturally occurring protein according to any one of the preceding clauses.

Clause 8. A vector comprising the nucleic acid molecule according to any one of the preceding clauses.

Clause 9. A host cell comprising the nucleic acid molecule according to clause 7 or the vector according to clause 8.

Another aspect of the invention is further described by the following set of clauses.

Clause 1. A method for generating a population of product cells, the method comprising:

(a) expressing a TAL-nuclease fusion in a population of starting cells to generate a sub-population of product cells that have undergone genetic recombination at a locus containing a detectable marker or selectable marker, wherein the TAL nuclease fusion is designed to bind to and cleave at least two nucleic acid loci in the population of starting cells and wherein at least one of the nucleic acid loci encodes the detectable marker or selectable marker, and (b) generating the population of product cells by separating the product cells from the population of starting cells or selecting for the product cells.

Clause 2. The method according to clause 1, wherein one of the at least two nucleic acid loci is present on a vector.

Clause 3. The method according to any one of the preceding clauses, wherein one of the at least two nucleic acid loci encodes a detectable marker.

Clause 4. The method according to any one of the preceding clauses, wherein the nucleic acid locus encoding the detectable marker encodes further encodes a selectable marker or a second detectable marker.

Clause 5. The method according to any one of the preceding clauses, wherein the two detectable markers are different fluorescent proteins.

Clause 6. The method according to any one of the preceding clauses, wherein one of the at least two nucleic acid loci encodes a selectable marker.

Clause 7. The method according to any one of the preceding clauses, wherein the nucleic acid locus encoding the selectable marker encodes further encodes a second selectable marker or a detectable marker.

Clause 8. The method according to any one of the preceding clauses, wherein the selectable marker is a negative selectable marker selectable from the group consisting of ccdB, Tse2, and Herpes simplex virus thymidine kinase.

Clause 9. The method according to any one of the preceding clauses, wherein the population of product cells is generated by collection of cells by fluorescence activated cells sorting.

Clause 10. The method according to any one of the preceding clauses, wherein the TAL nuclease fusion is designed to bind to and cleave a locus between a promoter and the detectable marker or selectable marker.

Another aspect of the invention is further described by the following set of clauses.

Clause 1. A method for the intracellular remodeling of chromatin, the method comprising expressing a TAL-chromatin modifier fusion in a cell, wherein the TAL nuclease fusion is designed to bind to a nucleic acid locus in the cell and modify the chromatin at the binding locus.

Clause 2. The method according to clause 1, wherein the chromatin modifier is a protein having at least one of ATPase, methylase, demethylase, acetylase, or deacetylase activities.

Clause 3. The method according to any one of the preceding clauses, wherein the TAL is fused to all or a portion of one of the following proteins: SWI2/SNF2, Mi-2, ISWI, BRM, BRG/BAF, Chd-1, Chd-2, Chd-3, Chd-4 and Mot-1.

Clause 4. The method according to any one of the preceding clauses, wherein the cell is an animal cell.

Clause 5. The method according to clause 4, wherein the animal cell is a mammalian cell.

While the invention has been described with reference to the specific embodiment thereof, it will be appreciated by those of ordinary skill in the art that modifications can be made to the structure and elements of the invention without departing from the spirit and scope of the invention as a whole.

U.S. Provisional Patent Application Nos. 61/620,228, filed Apr. 4, 2012, 61/644,975, filed May 9, 2012, and 61/784,658, filed Mar. 14, 2013, are incorporated herein by reference in their entireties.

The invention claimed is:

1. A nucleic acid molecule encoding a non-naturally occurring DNA binding protein, the non-naturally occurring DNA binding protein comprising:
   (a) an amine terminal region of between 25 and 500 amino acids,
   (b) a carboxyl terminal region of between 25 and 500 amino acids, and
   (c) a central region containing five or more amino acid segments which confer upon the non-naturally occurring protein sequence specific nucleic acid binding activity,
   wherein the individual amino acid segments comprise the amino acid sequence Leu Thr Pro Glu Gln Val Val Ala Ile Ala Ser Xaa1 Xaa2 Gly Gly Lys Gln Ala Leu Glu Thr Val Gln Arg Leu Leu Pro Val Leu Cys Gln Ala His Gly, wherein Xaa1 and Xaa2 are His Asp, Asn Ile, Asn Lys, or Asn Gly (SEQ ID NO: 234),
   wherein the N-terminus of the non-naturally occurring DNA binding protein comprises a V5 epitope,
   wherein the non-naturally occurring DNA binding protein comprises a nuclear localization sequence comprising the amino acid sequence of SEQ ID NO: 107, and
   wherein at least two of the individual amino acid segments are encoded by nucleic acids wherein different codons encode the same amino acids.

2. The nucleic acid molecule of claim 1, wherein the V5 epitope comprises the amino acid sequence of SEQ ID NO: 88.

3. The nucleic acid molecule of claim 2, wherein at least two of the individual amino acid segments encoded by nucleic wherein different codons encode the same amino acids comprise primer binding sites not present elsewhere in the nucleic acid molecule.

4. The nucleic acid molecule of claim 1, wherein one of the individual amino acid segments is encoded by nucleic acid comprising the nucleotide sequence of SEQ ID NO: 72.

5. The nucleic acid molecule of claim 1, wherein the non-naturally occurring DNA binding protein further comprises an effector domain.

6. The nucleic acid molecule of claim 5, wherein the effector domain is a nuclease domain.

7. A vector comprising the nucleic acid molecule of claim 1.

8. The vector of claim 7, wherein the nucleic acid molecule is operably connected to a Cytomegalovirus (CMV) promoter.

9. A host cell comprising the nucleic acid molecule of claim 1.

10. A protein encoded by the nucleic acid molecule of claim 1.

11. A method for genetic manipulation within a cell, the method comprising introducing the nucleic acid molecule of claim 1 into the cell under conditions that allow for intracellular production of the non-naturally occurring DNA binding protein.

* * * * *

UNITED STATES PATENT AND TRADEMARK OFFICE
CERTIFICATE OF CORRECTION

PATENT NO. : 10,745,695 B2
APPLICATION NO. : 15/951938
DATED : August 18, 2020
INVENTOR(S) : Chesnut et al.

Page 1 of 2

It is certified that error appears in the above-identified patent and that said Letters Patent is hereby corrected as shown below:

On the Title Page

The title page showing the item (12) correction should be deleted and replaced with the attached title page.

In Column 1, item (12), change:
"Chestnut et al."
To:
-- Chesnut et al. --.

In Column 1, item (72), change:
"Jonathan Chestnut"
To:
-- Jonathan Chesnut --.

In the Claims

In Claim 3, Column 352, Lines 1-5, change:
"3. The nucleic acid molecule of claim 2, wherein at least two of the individual amino acid segments encoded by nucleic wherein different codons encode the same amino acids comprise primer binding sites not present elsewhere in the nucleic acid molecule."
To:
-- 3. The nucleic acid molecule of claim 2, wherein at least two of the individual amino acid segments encoded by nucleic acids wherein different codons encoding the same amino acids comprise primer binding sites not present elsewhere in the nucleic acid molecule. --.

Signed and Sealed this
Second Day of March, 2021

Drew Hirshfeld
*Performing the Functions and Duties of the
Under Secretary of Commerce for Intellectual Property and
Director of the United States Patent and Trademark Office*

(12) United States Patent
Chesnut et al.

(10) Patent No.: US 10,745,695 B2
(45) Date of Patent: Aug. 18, 2020

(54) TAL-EFFECTOR ASSEMBLY PLATFORM, CUSTOMIZED SERVICES, KITS AND ASSAYS

(71) Applicants: LIFE TECHNOLOGIES CORPORATION, Carlsbad, CA (US); THERMO FISHER SCIENTIFIC GENEART GMBH, Regensburg (DE)

(72) Inventors: Jonathan Chesnut, Carlsbad, CA (US); Matthias Arnold, Regensburg (DE); Kevin Hoff, San Diego, CA (US)

(73) Assignees: LIFE TECHNOLOGIES CORPORATION, Carslbad, CA (US); THERMO FISHER SCIENTIFIC GENEART GMBH, Regensburg (DE)

(*) Notice: Subject to any disclaimer, the term of this patent is extended or adjusted under 35 U.S.C. 154(b) by 0 days.

(21) Appl. No.: 15/951,938

(22) Filed: Apr. 12, 2018

(65) Prior Publication Data

US 2019/0112596 A1    Apr. 18, 2019

Related U.S. Application Data

(60) Division of application No. 14/811,363, filed on Jul. 28, 2015, now abandoned, which is a continuation of application No. 13/856,978, filed on Apr. 4, 2013, now abandoned.

(60) Provisional application No. 61/784,658, filed on Mar. 14, 2013, provisional application No. 61/644,975, filed on May 9, 2012, provisional application No. 61/620,228, filed on Apr. 4, 2012.

(51) Int. Cl.
| | |
|---|---|
| *C12N 15/10* | (2006.01) |
| *C12N 9/96* | (2006.01) |
| *C07K 14/195* | (2006.01) |
| *C12N 15/66* | (2006.01) |
| *C12N 9/90* | (2006.01) |

(52) U.S. Cl.
CPC ........ *C12N 15/1082* (2013.01); *C07K 14/195* (2013.01); *C12N 9/90* (2013.01); *C12N 9/96* (2013.01); *C12N 15/102* (2013.01); *C12N 15/1086* (2013.01); *C12N 15/1093* (2013.01); *C12N 15/66* (2013.01); *C12Y 599/01002* (2013.01)

(58) Field of Classification Search
None
See application file for complete search history.

(56) References Cited

U.S. PATENT DOCUMENTS

| | | |
|---|---|---|
| 5,487,994 A | 1/1996 | Chandrasegaran |
| 5,786,464 A | 7/1998 | Seed |
| 5,888,732 A | 3/1999 | Hartley et al. |
| 6,114,148 A | 9/2000 | Seed et al. |
| 6,277,608 B1 | 8/2001 | Hartley et al. |
| 7,119,255 B2 * | 10/2006 | Betts ............... C07K 14/415 800/287 |
| 7,176,029 B2 | 2/2007 | Bernard et al. |
| 7,244,560 B2 | 7/2007 | Chestnut et al. |
| 7,393,623 B2 | 7/2008 | Conroy et al. |
| 7,670,823 B1 | 3/2010 | Hartley et al. |
| 7,820,412 B2 | 10/2010 | Belshaw et al. |
| 7,833,759 B2 | 11/2010 | Padgett et al. |
| 7,838,210 B2 | 11/2010 | Ludwig et al. |
| 8,030,066 B2 | 10/2011 | Chesnut et al. |
| 8,034,598 B2 | 10/2011 | Miller |
| 8,067,222 B2 | 11/2011 | Kerovuo et al. |
| 2006/0127920 A1 | 6/2006 | Church et al. |
| 2007/0141557 A1 | 6/2007 | Raab |
| 2007/0231805 A1 | 10/2007 | Baynes et al. |
| 2008/0145913 A1 | 6/2008 | Padgett |
| 2008/0216185 A1 | 9/2008 | Chesnut et al. |
| 2009/0324546 A1 | 12/2009 | Notka et al. |
| 2010/0216648 A1 | 8/2010 | Staehler et al. |
| 2010/0297642 A1 | 11/2010 | Liss et al. |
| 2011/0119778 A1 | 5/2011 | Liss |
| 2011/0124049 A1 | 5/2011 | Li et al. |
| 2011/0145940 A1 * | 6/2011 | Voytas ............... C12N 15/102 800/13 |
| 2011/0301073 A1 | 12/2011 | Gregory et al. |
| 2011/0311499 A1 | 12/2011 | Mougous et al. |
| 2012/0270271 A1 | 10/2012 | Mougous |

FOREIGN PATENT DOCUMENTS

| | | | |
|---|---|---|---|
| WO | WO2009/049359 | 4/2009 | |
| WO | WO2009/113794 | 9/2009 | |
| WO | WO2011/072246 | 6/2011 | |
| WO | WO-2011/102802 | 8/2011 | |
| WO | WO2011/146121 | 11/2011 | |
| WO | WO2011/154393 | 12/2011 | |
| WO | WO-2011154393 A1 * | 12/2011 | ......... A01K 67/0278 |
| WO | WO2013/152220 | 10/2013 | |

OTHER PUBLICATIONS

Aslanidis, et al., "Ligation-independent cloning of PCR products (LIC-PCR)" *Nucleic Acids Research*, vol. 18, No. 20, Oct. 25, 1990, 6069-6074.

Ayer, et al., "Mad proteins contain a dominant transcription repression domain", *Molecular and Cellular Biology*, vol. 16, No. 10, Oct. 1996, 5772-5781.

Babon, et al., "The use of resolvases T4 endonuclease VII and T7 endonuclease I in mutation detection", *Molecular Biotechnology*, vol. 23, No. 1, Jan. 2003, 73-81.

(Continued)

*Primary Examiner* — Tracy Vivlemore
*Assistant Examiner* — Sahana S Kaup
(74) *Attorney, Agent, or Firm* — Stephen G. Whiteside

(57) ABSTRACT

The invention generally relates to compositions and methods for designing and producing functional DNA binding effector molecules and associated customized services, tool kits and functional assays. In some aspects, the invention provides methods and tools for efficient assembly of customized TAL effector molecules. Furthermore, the invention relates to uses of TAL effector molecules and functional evaluation of such TAL by, for example, customized assays.

11 Claims, 74 Drawing Sheets

Specification includes a Sequence Listing.